US012187734B2

(12) United States Patent
Chu et al.

(10) Patent No.: US 12,187,734 B2
(45) Date of Patent: **\*Jan. 7, 2025**

(54) SUBSTITUTED PYRIDOTRIAZINE COMPOUNDS AND USES THEREOF

(71) Applicant: Gilead Sciences, Inc., Foster City, CA (US)

(72) Inventors: Hang Chu, San Mateo, CA (US); Ana Z. Gonzalez Buenrostro, San Mateo, CA (US); Hongyan Guo, San Mateo, CA (US); Xiaochun Han, San Jose, CA (US); Anna E. Hurtley, San Mateo, CA (US); Lan Jiang, Foster City, CA (US); Jiayao Li, Foster City, CA (US); David W. Lin, Berkeley, CA (US); Michael L. Mitchell, Castro Valley, CA (US); Devan Naduthambi, San Bruno, CA (US); Gregg M. Schwarzwalder, Redwood City, CA (US); Suzanne M. Szewczyk, San Mateo, CA (US); Matthew J. Von Bargen, Redwood City, CA (US); Qiaoyin Wu, Foster City, CA (US); Hong Yang, Fremont, CA (US); Jennifer R. Zhang, Union City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/393,778

(22) Filed: Dec. 22, 2023

(65) Prior Publication Data

US 2024/0300966 A1  Sep. 12, 2024

Related U.S. Application Data

(63) Continuation of application No. 18/164,317, filed on Feb. 3, 2023, now Pat. No. 11,897,892, which is a continuation of application No. 17/578,020, filed on Jan. 18, 2022, now Pat. No. 11,613,546.

(60) Provisional application No. 63/190,461, filed on May 19, 2021, provisional application No. 63/139,237, filed on Jan. 19, 2021.

(51) Int. Cl.
| | |
|---|---|
| C07D 487/18 | (2006.01) |
| A61P 31/18 | (2006.01) |
| C07D 487/22 | (2006.01) |
| C07D 491/22 | (2006.01) |

(52) U.S. Cl.
CPC ............ *C07D 487/18* (2013.01); *A61P 31/18* (2018.01); *C07D 487/22* (2013.01); *C07D 491/22* (2013.01)

(58) Field of Classification Search
CPC .. C07D 487/18; C07D 487/22; C07D 491/22; A61P 31/18

USPC ........................................................ 544/180
See application file for complete search history.

(56) References Cited

U.S. PATENT DOCUMENTS

| | | | |
|---|---|---|---|
| 9,522,912 B2 | 12/2016 | Bacon et al. | |
| 10,087,178 B2 | 10/2018 | Miyazaki et al. | |
| 11,084,832 B2 | 8/2021 | Chu et al. | |
| 11,492,352 B2 | 11/2022 | Ishii et al. | |
| 11,548,902 B1 | 1/2023 | Chu et al. | |
| 11,613,546 B2 | 3/2023 | Chu et al. | |
| 11,697,652 B2 | 7/2023 | Jiang et al. | |
| 11,884,683 B2 | 1/2024 | Yu et al. | |
| 11,897,892 B2 | 2/2024 | Chu et al. | |
| 12,024,528 B2 | 7/2024 | Chu et al. | |
| 12,054,496 B2 | 8/2024 | Chu et al. | |
| 2009/0253681 A1 | 10/2009 | Summa et al. | |
| 2009/0270412 A1 | 10/2009 | Hung et al. | |
| 2013/0171214 A1 | 7/2013 | Mundhra et al. | |
| 2018/0155365 A1 | 6/2018 | Graham et al. | |
| 2019/0284208 A1 | 9/2019 | Johns et al. | |
| 2019/0315769 A1 | 10/2019 | Graham et al. | |
| 2019/0322666 A1 | 10/2019 | Yu et al. | |
| 2020/0317689 A1 | 10/2020 | Chu et al. | |
| 2021/0284642 A1 | 9/2021 | Jiang et al. | |
| 2022/0135565 A1 | 5/2022 | Chu et al. | |
| 2022/0267343 A1 | 8/2022 | Chu et al. | |
| 2023/0058677 A1 | 2/2023 | Tomida et al. | |
| 2023/0203061 A1 | 6/2023 | Chu et al. | |
| 2023/0257389 A1 | 8/2023 | Chu et al. | |
| 2023/0339971 A1 | 10/2023 | Chu et al. | |
| 2023/0339972 A1 | 10/2023 | Chu et al. | |
| 2024/0010650 A1 | 1/2024 | Jiang et al. | |

(Continued)

FOREIGN PATENT DOCUMENTS

| | | |
|---|---|---|
| CN | 104995198 | 10/2015 |
| CN | 116390924 | 7/2023 |
| EP | 3938047 | 1/2022 |

(Continued)

OTHER PUBLICATIONS

Akiyama, T. et al. (2013) "Discovery of Novel HIV Integrase Inhibitors Part 2 Selection and Evaluation of an Azabicyclic Carbamoyl Pyridone as a Pre-clinical Candidate", 245th ACS National Meeting and Exposition, Poster MEDI 403.

(Continued)

*Primary Examiner* — Kristin A Vajda

(74) *Attorney, Agent, or Firm* — Fish & Richardson P.C.

(57) ABSTRACT

The present disclosure relates generally to certain tricyclic compounds, pharmaceutical compositions comprising said compounds, and methods of making said compounds and pharmaceutical compositions. The compounds of the disclosure are useful in treating or preventing human immunodeficiency virus (HIV) infection.

27 Claims, No Drawings

(56) References Cited

U.S. PATENT DOCUMENTS

2024/0246975 A1  7/2024  Chu et al.

FOREIGN PATENT DOCUMENTS

| | | |
|---|---|---|
| JP | 2006-342115 | 12/2006 |
| JP | 2011-515412 | 5/2011 |
| JP | 2012-516333 | 7/2012 |
| JP | 2016-508134 | 3/2016 |
| JP | 2018-510168 | 4/2018 |
| TW | 200716635 | 5/2007 |
| TW | 202106689 | 2/2021 |
| TW | 202120510 | 6/2021 |
| WO | WO 2006088173 | 8/2006 |
| WO | WO 2006116764 | 11/2006 |
| WO | WO 2007019098 | 2/2007 |
| WO | WO 2007049675 | 5/2007 |
| WO | WO 2007050510 | 5/2007 |
| WO | WO 2007148780 | 12/2007 |
| WO | WO 2008010964 | 1/2008 |
| WO | WO 2008048538 | 4/2008 |
| WO | WO 2009088729 | 7/2009 |
| WO | WO 2009117540 | 9/2009 |
| WO | WO 2009154870 | 12/2009 |
| WO | WO 2010000030 | 1/2010 |
| WO | WO 2010011812 | 1/2010 |
| WO | WO 2010011814 | 1/2010 |
| WO | WO 2010011815 | 1/2010 |
| WO | WO 2010011816 | 1/2010 |
| WO | WO 2010011818 | 1/2010 |
| WO | WO 2010011819 | 1/2010 |
| WO | WO 2010042391 | 4/2010 |
| WO | WO 2010068253 | 6/2010 |
| WO | WO 2010088167 | 8/2010 |
| WO | WO 2010147068 | 12/2010 |
| WO | WO 2011011483 | 1/2011 |
| WO | WO 2011025683 | 3/2011 |
| WO | WO 2011045330 | 4/2011 |
| WO | WO 2011094150 | 8/2011 |
| WO | WO 2011105590 | 9/2011 |
| WO | WO 2011121105 | 10/2011 |
| WO | WO 2011129095 | 10/2011 |
| WO | WO 2012018065 | 2/2012 |
| WO | WO 2012058173 | 5/2012 |
| WO | WO 2012078834 | 6/2012 |
| WO | WO 2013054862 | 4/2013 |
| WO | WO 2014008636 | 1/2014 |
| WO | WO 2014014933 | 1/2014 |
| WO | WO 2014028384 | 2/2014 |
| WO | WO 2014099586 | 6/2014 |
| WO | WO 2014100323 | 6/2014 |
| WO | WO 2014172188 | 10/2014 |
| WO | WO 2014183532 | 11/2014 |
| WO | WO 2014200880 | 12/2014 |
| WO | WO 2015006731 | 1/2015 |
| WO | WO 2015006733 | 1/2015 |
| WO | WO 2015039348 | 3/2015 |
| WO | WO 2015048363 | 4/2015 |
| WO | WO 2015089847 | 6/2015 |
| WO | WO 2015095258 | 6/2015 |
| WO | WO 2015196116 | 12/2015 |
| WO | WO 2016027879 | 2/2016 |
| WO | WO 2016033009 | 3/2016 |
| WO | WO 2016090545 | 6/2016 |
| WO | WO 2016094197 | 6/2016 |
| WO | WO 2016094198 | 6/2016 |
| WO | WO 2016106237 | 6/2016 |
| WO | WO 2016154527 | 9/2016 |
| WO | WO 2016161382 | 10/2016 |
| WO | WO 2016187788 | 12/2016 |
| WO | WO 2017087256 | 5/2017 |
| WO | WO 2017087257 | 5/2017 |
| WO | WO 2017106071 | 6/2017 |
| WO | WO 2017113288 | 7/2017 |
| WO | WO 2017116928 | 7/2017 |
| WO | WO 2017223280 | 12/2017 |
| WO | WO 2018102485 | 6/2018 |
| WO | WO 2018102634 | 6/2018 |
| WO | WO 2018109786 | 6/2018 |
| WO | WO 2018140368 | 8/2018 |
| WO | WO 2019058393 | 3/2019 |
| WO | WO 2019160783 | 8/2019 |
| WO | WO 2019209667 | 10/2019 |
| WO | WO 2019223408 | 11/2019 |
| WO | WO 2019230857 | 12/2019 |
| WO | WO 2019230858 | 12/2019 |
| WO | WO 2019232216 | 12/2019 |
| WO | WO 2019236396 | 12/2019 |
| WO | WO 2019244066 | 12/2019 |
| WO | WO 2020003093 | 1/2020 |
| WO | WO 2020075080 | 4/2020 |
| WO | WO 2020086555 | 4/2020 |
| WO | WO 2020112931 | 6/2020 |
| WO | WO 2020197991 | 10/2020 |
| WO | WO 2020221294 | 11/2020 |
| WO | WO 2020246910 | 12/2020 |
| WO | WO 2021007506 | 1/2021 |
| WO | WO 2021093846 | 5/2021 |
| WO | WO 2021107065 | 6/2021 |
| WO | WO 2021107066 | 6/2021 |
| WO | WO 2022089562 | 5/2022 |
| WO | WO 2022177840 | 8/2022 |

OTHER PUBLICATIONS

Andersson, V. et al. (2016) "Macrocyclic Prodrugs of a Selective Nonpeptidic Direct Thrombin Inhibitor Display High Permeability, Efficient Bioconversion but Low Bioavailability", J Med Chem, 59(14):6658-6670.

Anonymous (2013) "Thomson Reuters Drug News: Results from phase III trials of dolutegravir presented", Thomson Reuters. Retrieved from the Internet Jul. 5, 2013 <URL: http://drugnews.thomson-pharma.com/ddn/article.do?printerFriendlyFormat=true>.

Bari, H. (2010) "A Prolonged Release Parenteral Drug Delivery System—An Overview", Int J Pharm Sci Rev Res, 3(1):1-11.

Benn, P. et al. (2021) "Long-Acting Cabotegravir + Rilpivirine in Older Adults: Pooled Phase 3 Week 48 Results" CROI 2021, Science Spotlight, 1-11.

Bocedi, A. et al. (2004) "Binding of Anti-HIV Drugs to Human Serum Albumin" IUBMB Life, 56(10):609-614.

Bowers, G. et al. (2016) "Disposition and metabolism of cabotegravir: a comparison of biotransformation and excretion between different species and routes of administration in humans" Xenobiotica, 46(2):147-162.

Brinson, C. et al. (2013) "Dolutegravir Treatment Response and Safety by Key Subgroups in Treatment Naive HIV Infected Individuals", 20th CROI, Poster 554.

Brooks, K. et al. (2019) "Integrase Inhibitors: After 10 Years of Experience, Is the Best Yet to Come?" Pharmacotherapy, 1-23.

Burns, J. et al. (2020) "No overall change in the rate of weight gain after switching to an integrase-inhibitor in virologically suppressed adults with HIV" AIDS, 34:109-114.

Castellino, S. et al. (2013) "Metabolism, Excretion, and Mass Balance of the HIV-1 Integrase Inhibitor Dolutegravir in Humans" 57(8):3536-3546.

Cook, N. et al. (2019) "Structural basis of second-generation HIV Integrase inhibitor action and viral resistance" Science, 1-9.

Correll, C. et al. (2021) "Pharmacokinetic Characteristics of Long-Acting Injectable Antipsychotics for Schizophrenia: An Overview" CNS Drugs, 35: 39-59.

Cottrell, M. et al. (2013) "Clinical Pharmacokinetic, Pharmacodynamic and Drug-Interaction Profile of the Integrase Inhibitor Dolutegravir", Clin Pharmacokinet, 52(11):981-994.

Cottura, N. (2021) "In-Silico Prediction of Long-Acting Cabotegravir PK in Liver Impaired Patients" CROI 2021, Science Spotlight, 6 pages.

Curley, P. et al. (2019) "Long-Acting Emtricitabine Prodrugs Provide Protection From HIV Infection In Vivo" 2019 CROI, Poster 2262.

(56) References Cited

OTHER PUBLICATIONS

Del Mar Gutierrez, M. et al. (2014) "Drug safety profile of integrase strand transfer inhibitors", Expert Opin Drug Saf, 13(4):431-445.
Dicker, I. et al. (2011) "Simple and Accurate In Vitro Method for Predicting Serum Protein Binding of HIV Integrase Strand Transfer Inhibitors", HIV-1 Integrase: Mechanism and Inhibitor Design, First Edition.
EFSA (European Food Safety Authority), (2005) "Opinion of the Scientific Panel on Dietetic Products, Nutrition and Allergies on a request from the Commission related to the Tolerable Upper Intake Level of Potassium", EFSA Journal 2005, 3(3):193, 19 pp.
Flexner, C. (2020) "Novel Approaches to HIV Treatment and Prevention using Long Acting Drug Delivery" Johns Hopkins University, Division of Clinical Pharmacology, 45 pages.
Friedman, E. et al. (2016) "A Single Monotherapy Dose of MK-8591, a Novel NRTI, Suppresses HIV for 10 Days" CROI 2016, Poster, Abstract #437LB.
Gallant, J. et al. (2017) "Antiviral Activity, Safety, and Pharmacokinetics of Bictegravir as 10-Day Monotherapy in HIV-1-Infected Adults" J Acquir Immune Defic Syndr, 75(1):61-66.
Gelé, T. et al. (2020) "Characteristics of Dolutegravir and Bictegravir Plasma Protein Binding: a First Approach for the Study of Pharmacologic Sanctuaries", Antimicrob Agents Chemother, 64(11):e00895-20.
Grobler, J. et al. (2016) "Efficacy of once-weekly MK-8591 in SIV infected rhesus macaques", Merck & Co., Inc., 7th International Workshop on Clinical Pharmacology of HIV & Hepatitis Therapy.
Grobler, J. et al. (2019) "MK-8591 Potency and Pk Provide High Inhibitory Quotients at Low Doses QD and QQ" CROI 2019, Poster, Abstract #481.
Groseclose, M. et al. (2019) "Intramuscular and subcutaneous drug depot characterization of a long-acting abotegravir nanoformulation by MALDI IMS" International Journal of Mass Spectometry, 437:92-98.
Günthard, H. et al. (2016) "Antiretroviral Drugs for Treatment and Prevention of HIV Infection in Adults: 2016 Recommendations of the International Antiviral Society—USA Panel", JAMA, 316(2):191-210.
Gurevich, K. (2013) "Effect of blood protein concentrations on drug-dosing regimes: practical guidance", Theor Biol Med Model, 10:20.
Han, K. et al. (2021) "Cabotegravir Population Pharmacokinetic (PPK) Simulation to Inform Q2M Strategies Following Dosing Interruptions" CROI 2021, Science Spotlight, 9 pages.
Hare, S. et al. (2011) "Structural and Functional Analyses of the Second-Generation Integrase Stand Transfer Inhibitor Dolutegravir (S/GSK1349572)", Mol Pharmacol, 80(4):565-572.
Hill, L. et al. (2018) "Profile of bictegravir/emtricitabine/tenofovir alafenamide fixed dose combination and its potential in the treatment of HIV-1 infection: evidence to date" HIV/AIDS—Research and Palliative Care, 10:203-213.
Hughes, D. (2019) "Review of Synthetic Routes and Final Forms of Integrase Inhibitors Dolutegravir, Cabotegravir, and Bictegravir" Organic Process Research & Development, 23:716-729.
Hurt, C. et al. (2013) "Characterization and Resistance to Integrase Strand Transfer Inhibitors among Clinical Specimens in the United States, 2009-2012", 20th CROI, Poster 591.
Ivashchenko et al., "Synthesis, biological evaluation and in silico modeling of novel integrase strand transfer inhibitors (INSTIs)," European Journal of Medicinal Chemistry, Mar. 2, 2020, 189:112064.
Jaeger, H. et al. (2021) "Week 96 Efficacy and Safety of Long-Acting Cabotegravir + Rilpivirine Every 3 Months: ATLAS-2M" CROI 2021, Science Spotlight, 1-9.
Jiskoot, W. (2020) "Long-acting injectables & implantables: immunogenicity concerns" Third Long-Acting Injectables & Implantables Conference, 32 pages.
Jogiraju, V. (2021) "Pharmacokinetics of Lenacapavir, an HIV-1 Capsid Inhibitor, in Hepatic Impairment" CROI 2021, Science Spotlight, 6 pages.

Johns, B. et al. (2010) "The Discovery of S/GSK1349575: A Once Daily Next Generation Integrase Inhibitor with a Superior Resistance Profile", 17th CROI.
Johns, B. et al. (2013) "Carbamoyl Pyridone HIV?1 Integrase Inhibitors 3. A Diastereomeric Approach to Chiral Nonracemic Tricyclic Ring Systems and the Discovery of Dolutegravir (S/GSK1349572) and (S/GSK1265744)" J. Med. Chem., 56:5901-5916.
Jucker, B. et al. (2021) "Multiparametric magnetic resonance imaging to characterize cabotegravir long-acting formulation depot kinetics in healthy adult volunteers" Br J Clin Pharmacol., 1-12.
Kalicharan, R. et al. (2017) "New Insights Into Drug Absorption From Oil Depots" University Medical Center Utrecht, Utrecht, the Netherlands, Thesis, 152 pages.
Kalicharan, R. et al. (2016) "Fundamental understanding of drug absorption from a parenteral oil depot" European Journal of Pharmaceutical Sciences, 83: 19-27.
Kandala, B. et al. (2021) "Model-informed dose selection for Islatravir/MK-8507 oral once-weekly phase 2B study" CROI 2021, Science Spotlight, 6 pages.
Kandel, C. et al. (2015) "Dolutegravir—a review of the pharmacology, efficacy, and safety in the treatment of HIV" Drug Design, Development and Therapy, 9:3547-3555.
Kinvig, H. (2021) "In-Silico Prediction of Monthly Bictegravir Microneedle Array Patches" CROI 2021, Science Spotlight, 6 pages.
Klooster, G. et al. (2010) "Pharmacokinetics and Disposition of Rilpivirine (TMC278) Nanosuspension as a Long-Acting Injectable Antiretroviral Formulation" Antimicrobial Agents and Chemotherapy, 54(5): 2042-2050.
Kochansky, C. et al. (2008) "Impact of pH on Plasma Protein Binding in Equilibrium Dialysis" Mol Pharm, 5(3):438-448.
Kulkarni, T. et al. (2019) "Prodrugs extend the half life and potency of Cabotegravir", CROI, Poster 489.
Kulkarni, T. et al. (2020) "A Year-Long Extended Release Nanoformulated Cabotegravir Prodrug", Nat Mater, 19(8):910-920.
Lalezari, J. et al. (2009) "Potent Antiviral Activity of S/GSK1349572, A Next Generation Integrase Inhibitor (INI), in INI-Naïve HIV-1-Infected Patients: ING111521 Protocol" IAS 2009, 5th Conference on HIV Pathogenesis, Abstract TUAB105, 15 pages.
Landovitz, R. et al. (2018) "Safety, tolerability, and pharmacokinetics of long-acting injectable cabotegravir in low-risk HIV-uninfected individuals: HPTN 077, phase 2a randomized controlled trial" PLoS Med, 15(11):1-22.
Landovitz, R. et al. (2020) "Cabotegravir Is Not Associated With Weight Gain in Human Immunodeficiency Virus-uninfected Individuals in HPTN 077", Clin Infect Dis, 70(2):319-322.
Le Hingrat, Q. et al. (2018) "A New Mechanism of Resistance of Human Immunodeficiency Virus Type 2 to Integrase Inhibitors: A 5-Amino-Acid Insertion in the Integrase C-Terminal Domain" Clinical Infectious Diseases, 1-11.
Letendre, S. et al. (2013) "Distribution and Antiviral Activity in Cerebrospinal Fluid (CSF) of the Integrase Inhibitor, Dolutegravir (DTG): ING116070 Week 16 Results", 20th CROI, Poster 178LB.
Liu, S. et al. (2019) "Mechanistic Assessment of Extrahepatic Contributions to Glucuronidation of Integrase Strand Transfer Inhibitors" Drug Metabolism and Disposition, 47(5) 535-544.
Markowitz, M. (2017) "Weekly Oral MK-8591 Protects Male Rhesus Macaques against Repeated Low Dose Intrarectal Challenge with SHIV109CP3", 9th IAS Conference on HIV Science (IAS 2017), PowerPoint Presentation.
Martin, C. et al. (2021) "Bictegravir and Cabotegravir: In Vitro Phenotypic Susceptibility of HIV-1 Nongroup M" CROI 2021 Science Spotlight, 1-6.
Matthews, R. et al. (2017) "Single doses as low as 0.5 mg of the novel NRTTI MK-8591 suppress HIV for at least seven days", IAS 2017: Conference on HIV Pathogenesis, Poster.
McElnay, J. & D'arcy, P. (1983) "Protein Binding Displacement Interactions and their Clinical Importance", Drugs, 25(5):495-513.
McMillan, J. et al. (2019) "Pharmacokinetic testing of a first generation cabotegravir prodrug in rhesus macaques" AIDS, 33(3):585-588.

(56) References Cited

OTHER PUBLICATIONS

Menéndez-Arias, L. & Alvarez, M. (2014) "Antiretroviral therapy and drug resistance in human immunodeficiency virus type 2 infection", Antiviral Res, 102:70-86.

Métifiot, M. et al. (2013) "HIV Integrase Inhibitors: 20-Year Landmark and Challenges", Adv Pharmacol, 67:75-105.

Min, S. et al. (2011) "Antiviral activity, safety, and pharmacokinetics/pharmacodynamics of dolutegravir as 10-day monotherapy in HIV-1-infected adults" AIDS 25(14):1737-1745.

Muller, R. et al. (2011) "State of the art of nanocrystals—Special features, production, nanotoxicology aspects and intracellular delivery" European Journal of Pharmaceuticals and Biopharmaceutics, 78:1-9.

Mullokandov, E. et al. (2014) "Protein Binding Drug-Drug Interaction between Warfarin and Tizoxanide in Human Plasma", Austin J Pharmacol Ther, 2(7):id1038.

Nair, V. et al. (2014) "Pharmacokinetics and Dose-range Finding Toxicity of a Novel anti-HIV Active Integrase Inhibitor" Supplementary Materials.

Nair, V. et al. (2014) "Pharmacokinetics and Dose-range Finding Toxicity of a Novel anti-HIV Active Integrase Inhibitor", Antiviral Res, 108:25-29.

Neary, M. (2021) "In Vitro / In Vivo Development of Long Acting Biodegradable Emtricitabine Implants" CROI 2021, Science Spotlight, 6 pages.

Orkin, C. et al. (2019) "Long-Acting Cabotegravir + Rilpivirine for HIV Maintenance: Flair Week 48 Results", CROI 2019, PowerPoint Presentation.

Orkin, C. et al. (2020) "Long-Acting Cabotegravir + Rilpivirine for HIV Treatment: Flair Week 96 Results" Conference on Retroviruses and Opportunistic Infections, Poster 0482, 1 page.

Park, B. et al. (2001) "Metabolism of Fluorine-Containing Drugs" Annu. Rev. Pharmacol. Toxicol. 41:443-470.

Passos, D. et al. (2020) "Structural basis for strand transfer inhibitor binding to HIV intasomes" Science, 1-9.

Passos, D. et al. (2020) Supplementary Materials for "Structural basis for strand transfer inhibitor binding to HIV intasomes" Science, Supplementary Text, 38 pages.

Podany, A. et al. (2017) "Comparative Clinical Pharmacokinetics and Pharmacodynamics of HIV-1 Integrase Strand Transfer Inhibitors", Clin Pharmacokinet, 56(1):25-40.

Pozniak, A. et al. (2013) "Dolutegravir (DTG) Versus Raltegravir (RAL) in ART-Experienced, Integrase-Naive Subjects: 24-Week Interim Results From Sailing (ING111762)", 20th CROI.

Quashie, P. et al. (2013) "Evolution of HIV integrase resistance mutations", Curr Opin Infect Dis, 26(1):43-49.

Raffi, F. et al. (2013) "Once-daily dolutegravir versus raltegravir in antiretroviral-naive adults with HIV-1 infection: 48 week results from the randomised, double-blind, non-inferiority SPRING-2 study", Lancet, 381(9868):735-743.

Raheem, L. et al. (2015) "Discovery of 2-Pyridinone Aminals: A Prodrug Strategy to Advance a Second Generation of HIV-1 Integrase Strand Transfer Inhibitors," Med. Chem., 58:8154-8165.

Rahnfeld, L. et al. (2020) "Injectable Lipid-Based Depot Formulations: Where Do We Stand?" Pharmaceutics 12(0567):1-28.

Rajoli, R. et al. (2019) "In Silico Simulation Of Long-Acting Tenofovir Alafenamide Subcutaneous Implant", CROI 2019, Poster 487.

Rautio, J. et al. (2018), "The expanding role of prodrugs in contemporary drug design and development", Nat Rev Drug Discov, 17(8):559-587.

Reese, M. et al. (2013) "In Vitro Investigations into the Roles of Drug Transporters and Metabolizing Enzymes in the Disposition and Drug Interactions of Dolutegravir, a HIV Integrase Inhibitor" Drug Metab Dispos 41:353-361.

Rhodes, M. et al. (2012) "Assessing a Theoretical Risk of Dolutegravir-Induced Developmental Immunotoxicity in Juvenile Rats", Toxicol Sci, 130(1):70-81.

Roberts, J. et al. (2013) "The Clinical Relevance of Plasma Protein Binding Changes", Clin Pharmacokinet, 52(1):1-8.

Rossenu, S. et al. (2021) "Population PK Modeling of Every 2 Months im RPV LA for Managing Dosing Interruptions in HIV-1 Patients" CROI 2021, Science Spotlight, 1-7.

Rudd, D. et al. (2020) "Modeling-Supported Islatravir Dose Selection for Phase 3" CROI 2020, Poster, Abstract #462.

Scarsi, K. et al. (2020) "HIV-1 Integrase Inhibitors: A Comparative Review of Efficacy and Safety" Drugs, 80(16):1649-1676.

Shaik, J. et al. (2019) "A Phase 1 Study to Evaluate the Pharmacokinetics and Safety of Cabotegravir in Patients With Hepatic Impairment and Healthy Matched Controls" Clinical Pharmacology in Drug Development, 00(0):1-10.

Shi, Y. et al. (2021) "A review of existing strategies for designing long-acting parenteral formulations: Focus on underlying mechanisms, and future perspectives" Acta Pharmaceutica Sinica B, 11(8):2396-2415.

Song, I. et al. (2013) "Dolutegravir Has No Effect on the Pharmacokinetics of Methadone or Oral Contraceptives With Norgestimate and Ethinyl Estradiol", 20th CROI.

Spreen, W. et al. (2013) "Pharmacokinetics, Safety, and Monotherapy Antiviral Activity of GSK1265744, an HIV Integrase Strand Transfer Inhibitor" HIV Clinical Trials, 14(5):192-203.

Spreen, W. et al. (2014) "GSK1265744 Pharmacokinetics in Plasma and Tissue After Single-Dose Long-Acting Injectable Administration in Healthy Subjects" J Acquir Immune Defic Syndr, 67(5):481-486.

Taoada, Y. et al. (2013) "Discovery of Novel HIV Integrase Inhibitors Part 1; Molecular Design and SAR of Azabicyclic Carbamoyl Pyridone Inhibitors", 245th ACS National Meeting and Exposition, Poster MEDI 402.

Thenin-Houssier et al. Antimicrobial Agents and Chemotherapy 2016, 60, 2195-2208 (Year: 2016).

Thierry et al., "Different Pathways Leading to Integrase Inhibitors Resistance," Front. Microbiol., Jan. 11, 2017, 7:2165, 13 pages.

Tian, H. et al. (2018) "Effects of Plasma Albumin on the Pharmacokinetics of Esomeprazole in ICU Patients", Biomed Res Int, 2018:6374374.

Trezza, C. et al. (2015) "Formulation and pharmacology of long-acting cabotegravir" Current Opinion—HIV and AIDS, 10(4):239-245.

Van Der Galién, R. et al. (2019) "Pharmacokinetics of HIV-Integrase Inhibitors During Pregnancy: Mechanisms, Clinical Implications and Knowledge Gaps", Clin Pharmacokinet, 58(3):309-323.

ViiV Healthcare ULC, "Product Monograph Including Patient Medication Information," 2020, 51 pages.

Walji, A. et al. (2015) "Discovery of MK-8970: An Acetal Carbonate Prodrug of Raltegravir with Enhanced Colonic Absorption" ChemMedChem, 10:245-252.

Wang, Y. C. et al. (2002) "Switch in asymmetric induction sense in cycloadditions using camphor-based nitroso dienophiles", Tetrahedron: Asymmetry, 13(7):691-695.

Weaving, G. et al. (2016) "Age and sex variation in serum albumin concentration: an observational study", Ann Clin Biochem, 53(1):106-111.

Weller, S. et al. (2014) "Pharmacokinetics of dolutegravir in HIV-seronegative subjects with severe renal impairment" Eur J Clin Pharmacol 70:29-35.

Wilkinson, J. et al. (2022) "Lipid based intramuscular long-acting injectables: Current state of the art" European Journal of Pharmaceutical Sciences, 178(106253):1-20.

Williams, D. & Lemke, T. (2002), Foye's Principles of Medicinal Chemistry, 5th Ed., pp. 59-63.

Wolkowicz, U. et al. (2014) "Structural Basis of Mos1 Transposase Inhibition by the Anti-retroviral Drug Raltegravir", ACS Chem Biol, 9(3):743-751.

Wu, J. et al. (2012) "Implications of Plasma Protein Binding for Pharmacokinetics and Pharmacodynamics of the γ-Secretase Inhibitor RO4929097", Clin Cancer Res, 18(7):2066-2079.

Yoshinaga, T. et al. (2015) "Antiviral Characteristics of GSK1265744, an HIV Integrase Inhibitor Dosed Orally or by Long-Acting Injection" 59(1):397-406.

Yoshinaga, T. et al. (2018) "Novel secondary mutations C56S and G149A confer resistance to HIV-1 integrase strand transfer inhibitors" Antiviral Research, 152:1-9.

(56) References Cited

OTHER PUBLICATIONS

Zhang, W. et al. (2018) "Accumulation of Multiple Mutations In Vivo Confers Cross-Resistance to New and Existing Integrase Inhibitors" The Journal of Infectious Diseases, 218:1773-1776.
Zhao, X. et al. (2014) "4-Amino-1-hydroxy-2-oxo-1,8-naphthyridine-Containing Compounds Having High Potency against Raltegravir-Resistant Integrase Mutants of HIV-1", J Med Chem, 57(12):5190-5202.
Extended Search Report in European Appln. No. 23205202.7, dated Mar. 7, 2024, 6 pages.
International Preliminary Report on Patentability dated Aug. 3, 2023 for Intl. Appl. No. PCT/US2022/012773, 10 pages.
International Search Report and Written Opinion dated Jun. 2, 2022 for Intl. Appl. No. PCT/US2022/012773, 14 pages.
Office Action in Australian Appln. No. 2022210247, dated Jan. 8, 2024, 3 pages.
Office Action in Saudi Arabian Appln. No. 523441639, dated Mar. 8, 2024, 17 pages (with English translation).
Office Action in Taiwanese Appln. No. 111102065, mailed on Nov. 28, 2022 20 pages.
Opposition, by opponent Laboratorios Legrand S.A., dated Oct. 30, 2023 for Colombian Application No. NC2023/0009518, 44 pages (with English translation).
Boddy et al., "Stereoselective synthesis and applications of spirocyclic oxindoles," Organic Chemistry Frontiers, Jan. 6, 2021, 8(5):1026-1084.
Das et al., "Synthesis and biological evaluation of fluoro-substituted spiro-isoxazolines as potential anti-viral and anti-cancer agents," RSC Advances, Aug. 17, 2020, 10(50):30223-30237.
Zheng et al., "The use of spirocyclic scaffolds in drug discovery," Bioorganic & Medicinal Chemistry Letters, Aug. 15, 2014, 24(16):3673-3682.
Office Action in Japanese Appln. No. 2023-543136, mailed on Jun. 24, 2024, 7 pages (with English translation).

SUBSTITUTED PYRIDOTRIAZINE COMPOUNDS AND USES THEREOF

CROSS-REFERENCES TO RELATED APPLICATIONS

This application is a continuation of U.S. application Ser. No. 18/164,317, filed Feb. 3, 2023, which is a continuation of U.S. application Ser. No. 17/578,020, filed Jan. 18, 2022, now issued U.S. Pat. No. 11,613,546, which claims priority to U.S. Provisional Application No. 63/139,237, filed Jan. 19, 2021 and U.S. Provisional Application No. 63/190,461, filed May 19, 2021, each of which is incorporated herein in its entirety for all purposes.

FIELD

This disclosure relates generally to certain 2,3-dihydro-1H-pyrido[2,1-f][1,2,4]triazine compounds, pharmaceutical compositions comprising said compounds, and methods of making and using said compounds and pharmaceutical compositions.

BACKGROUND

Human immunodeficiency virus infection and related diseases are a major public health problem worldwide. Human immunodeficiency virus encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains may limit their usefulness (Palella, et al. N. Engl. J Med. (1998) 338:853-860; Richman, D. D. Nature (2001) 410:995-1001). Accordingly, there is a need for new agents that inhibit the replication of HIV.

A goal of antiretroviral therapy is to achieve viral suppression in the HIV infected patient. Current treatment guidelines published by the United States Department of Health and Human Services provide that achievement of viral suppression requires the use of combination therapies, i.e., several drugs from at least two or more drug classes (Panel on Antiretroviral Guidelines for Adults and Adolescents. Guidelines for the Use of Antiretroviral Agents in Adults and Adolescents Living with HIV. Department of Health and Human Services. Available at https://files.aidsinfo.nih.gov/contentfiles/lvguidelines/AdultandAdolescentGL.pdf Accessed Feb. 20, 2020). In addition, decisions regarding the treatment of HIV infected patients are complicated when the patient requires treatment for other medical conditions. Because the standard of care requires the use of multiple different drugs to suppress HIV, as well as to treat other conditions the patient may be experiencing, the potential for drug interaction is a criterion for selection of a drug regimen. As such, there is a need for antiretroviral therapies having a decreased potential for drug interactions.

In addition, the HIV virus is known to mutate in infected subjects (Tang, et al. Drugs (2012) 72 (9) e1-e25). Because of the proclivity of the HIV virus to mutate, there is a need for anti-HIV drugs to be effective against a range of known HIV variants (Hurt, et al. HIV/AIDS CID (2014) 58, 423-431).

For certain patients, for example, those with difficult or limited access to health care, adherence to daily oral treatment or prophylactic regimens can be challenging. Drugs that offer favorable pharmaceutical properties (for example, improved potency, long-acting pharmacokinetics, low solubility, low clearance, and/or other properties) are amenable to less frequent administration and provide for better patient compliance. Such improvements can, in turn, optimize drug exposure and limit the emergence of drug resistance.

SUMMARY

In some embodiments, disclosed herein are compounds of Formula I:

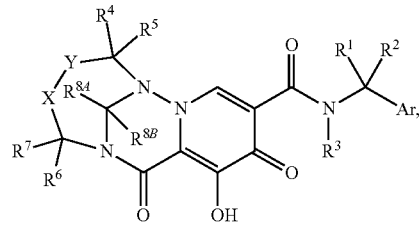

Formula I or a pharmaceutically acceptable salt thereof, wherein
Ar is $C_6$-$C_{10}$ aryl or six to ten membered heteroaryl containing one, two or three heteroatoms selected from N, O, and S; wherein the $C_6$-$C_{10}$ aryl or six to ten membered heteroaryl is optionally substituted with 1-4 substituents independently selected from the group consisting of halogen, $C_1$-$C_6$ alkyl, $C_1$-$C_6$ haloalkyl, and $C_1$-$C_6$ alkyloxy;

$R^1$ is H, $C_1$-$C_3$ alkyl or phenyl;

$R^2$ is H or $C_1$-$C_3$ alkyl;

$R^3$ is H or $C_1$-$C_3$ alkyl;

$R^4$ and $R^5$ are each independently H, halogen, cyano, $C_1$-$C_6$ alkyl, $C_1$-$C_6$ alkyloxy, $C_6$-$C_{10}$ aryl, or six to ten membered heteroaryl containing one, two or three heteroatoms selected from N, O, and S; wherein the $C_1$-$C_6$ alkyl, $C_1$-$C_6$ alkyloxy, $C_6$-$C_{10}$ aryl, or six to ten membered heteroaryl is optionally substituted with one two or three groups independently selected from halogen, $C_1$-$C_3$ alkyloxy, or $C_1$-$C_3$ haloalkyloxy; or $R^4$ and $R^5$ are joined together to form a 3-6 membered carbocyclic ring or 4-6 membered heterocyclic ring comprising one heteroatom selected from N, O, and S;

$R^6$ is H, halogen, $C_1$-$C_6$ alkyl, $C_1$-$C_6$ alkyloxy or $C_1$-$C_6$ haloalkyl;

$R^7$ is H, halogen, $C_1$-$C_6$ alkyl, $C_1$-$C_6$ alkyloxy, or $C_1$-$C_6$ haloalkyl;

$R^{8A}$ and $R^{8B}$ are independently H, $C_1$-$C_3$ alkyl or benzyl; and —X—Y— is —$(CR^{13A}R^{13B})_p$—$CR^9$=$CR^{10}$—, or —$(CR^{13A}R^{13B})_q$—$CR^{11A}R^{11B}$—$CR^{12A}R^{12B}$—; wherein $R^9$ is H, halogen, $C_1$-$C_6$ alkyl, $C_1$-$C_6$ haloalkyl or $C_1$-$C_6$ alkyloxy;

$R^{10}$ is H, halogen, $C_1$-$C_6$ alkyl, $C_1$-$C_6$ haloalkyl or $C_1$-$C_6$ alkyloxy; or $R^9$ and $R^{10}$ together with the carbons to which they are attached form a phenyl or a 5-6 membered heteroaromatic ring containing 1, 2, or 3 heteroatoms independently selected from N, O, and S; wherein the phenyl or the 5-6 membered heteroaromatic ring is optionally substituted with 1, 2, or 3 substituents independently selected from the group consisting of halogen, $C_1$-$C_3$ alkyl, $C_1$-$C_3$ haloalkyl, and $C_1$-$C_3$ alkyloxy; and $R^{11A}$, $R^{11B}$, $R^{12A}$, $R^{12B}$, $R^{13A}$, and $R^{13B}$ are each independently H, halogen, $C_1$-$C_6$ alkyl, $C_1$-$C_6$ alkyloxy; or $C_1$-$C_6$ haloalkyl; or $R^{11A}R^{12A}$, $R^{13A}$, and $R^{13B}$ are each independently H, halogen, $C_1$-$C_6$ alkyl, $C_1$-$C_6$ alkyloxy or $C_1$-$C_6$ haloalkyl; and $R^{11B}$ and $R^{12B}$ together with the carbons to which they are attached form a 3-6 membered carbocyclic ring; wherein the 3-6 membered carbocyclic ring is optionally substituted with 1, 2, or 3 substituents independently selected from the group consisting of halogen, $C_1$-$C_3$ alkyl, $C_1$-$C_3$ haloalkyl, and $C_1$-$C_3$ alkyloxy;

p is 0 or 1;
q is 0 or 1;
wherein when —X—Y— is —$(CR^{13A}R^{13B})_q CR^{11A}R^{11B}$—$CR^{12A}R^{12B}$-then:
  (i) $R^4$ is halogen, cyano, $C_1$-$C_6$ alkyl, $C_1$-$C_6$ alkyloxy, $C_6$-$C_{10}$ aryl, or six to ten membered heteroaryl containing one, two or three heteroatoms selected from N, O, and S; wherein the $C_1$-$C_6$ alkyl, $C_1$-$C_6$ alkyloxy, $C_6$-$C_{10}$ aryl, or six to ten membered heteroaryl is optionally substituted with one two or three groups independently selected from halogen, $C_1$-$C_3$ alkyloxy, or $C_1$-$C_3$ haloalkyloxy; and $R^5$ is H, halogen, cyano, $C_1$-$C_6$ alkyl, $C_1$-$C_6$ alkyloxy, $C_6$-$C_{10}$ aryl, or six to ten membered heteroaryl containing one, two or three heteroatoms selected from N, O, and S; wherein the $C_1$-$C_6$ alkyl, $C_1$-$C_6$ alkyloxy, $C_6$-$C_{10}$ aryl, or six to ten membered heteroaryl is optionally substituted with one two or three groups independently selected from halogen, $C_1$-$C_3$ alkyloxy, or $C_1$-$C_3$ haloalkyloxy; or
  (ii) $R^4$ and $R^5$ are joined together to form a 3-6 membered carbocyclic ring or 4-6 membered heterocyclic ring with one heteroatom; or
  (iii) $R^{8A}$ is $C_1$-$C_3$ alkyl or benzyl; or
  (iv) $R^6$ is halogen, $C_1$-$C_6$ alkyl, $C_1$-$C_6$ alkyloxy or $C_1$-$C_6$ haloalkyl.

In some embodiments, the disclosure provides pharmaceutical compositions comprising a therapeutically effective amount of a compound of Formula I, or pharmaceutically acceptable salt thereof, and a pharmaceutically acceptable excipient.

In some embodiments, the disclosure provides a kit comprising a compound of Formula I, or a pharmaceutically acceptable salt thereof, and instructions for use.

In some embodiments, the disclosure provides a method of treating an HIV infection in a human having or at risk of having the infection, comprising administering to the human a therapeutically effective amount of a compound of Formula I, a pharmaceutically acceptable salt thereof, or a pharmaceutical composition thereof.

In some embodiments, the disclosure provides a use of a compound of Formula I, pharmaceutically acceptable salt thereof, or a pharmaceutical composition thereof, for treating an HIV infection in a human having or at risk of having the infection.

In some embodiments, the disclosure provides a compound of Formula I, pharmaceutically acceptable salt thereof, or a pharmaceutical composition thereof any, for use in a medical therapy.

In some embodiments, the disclosure provides a compound of Formula I, pharmaceutically acceptable salt thereof, or a pharmaceutical composition thereof any, for use in treating an HIV infection.

In some embodiments, the disclosure provides use of a compound of Formula I, pharmaceutically acceptable salt thereof, or a pharmaceutical composition thereof, in the manufacture of a medicament for treating an HIV infection in a human having or at risk of having the infection.

DETAILED DESCRIPTION

In the following description, certain specific details are set forth in order to provide a thorough understanding of various embodiments disclosed herein. However, one skilled in the art will understand that the embodiments disclosed herein may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

I. Definitions

Unless the context requires otherwise, throughout the present disclosure and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment disclosed herein. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ radical.

"Hydroxy" or "hydroxyl" refers to the —OH radical.

"Oxo" refers to the =O substituent.

A prefix such as "$C_{u-v}$" or ($C_u$-$C_v$) indicates that the following group has from u to v carbon atoms. For example, "$C_{1-6}$alkyl" or ""$C_1$-$C_6$alkyl" indicates that the alkyl group has from 1 to 6 carbon atoms.

"Alkyl" refers to a straight or branched chain hydrocarbon radical consisting of carbon and hydrogen atoms, which is saturated, having from one to twelve carbon atoms ($C_{1-12}$alkyl), in certain embodiments one to eight carbon atoms ($C_{1-8}$alkyl) or one to six carbon atoms ($C_{1-6}$alkyl), or one to four carbon atoms ($C_{1-4}$alkyl), and which is attached to the rest of the molecule by a single bond, e.g., methyl, ethyl, n-propyl, 1-methylethyl (iso-propyl), n-butyl, 1-methylpropyl (sec-butyl), 2-methylpropyl (iso-butyl), 1,1-dimethylethyl (t-butyl), n-pentyl, hexyl, 3-methylhexyl, 2-methylhexyl, and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1 ethyl (—$CH(CH_3)$—), 1,2-ethyl (—$CH_2CH_2$—), 1,1-propyl (—$CH(CH_2CH_3)$—), 1,2- propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like.

"Aryl" or "aromatic ring" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., C$_6$-20 aryl), 6 to 12 carbon ring atoms (i.e., C$_{6-12}$ aryl), or 6 to 10 carbon ring atoms (i.e., C$_{6-10}$ aryl). Examples of aryl groups include, but are not limited to, phenyl, naphthyl, fluorenyl, and anthryl. Aryl, however, does not encompass or overlap in any way with heteroaryl defined below.

"Cyano" or "carbonitrile" refers to the group —CN.

"Cycloalkyl" or "carbocyclic ring" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_3$-10 cycloalkyl), 3 to 8 ring carbon atoms (i.e., C$_{3-8}$ cycloalkyl), or 3 to 6 ring carbon atoms (i.e., C$_{3-6}$ cycloalkyl). Examples of cycloalkyl groups include cyclopropyl, cyclobutyl, cyclopentyl, and cyclohexyl. "Halocycloalkyl" refers to a cycloalkyl substituted with one or more halogens.

"Halo" or "halogen" refers to bromo, chloro, fluoro or iodo.

"Haloalkyl" refers to an alkyl group, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heteroaryl" or "heteroaromatic ring" refers to an aromatic group having a single ring, multiple rings, or multiple fused rings, with one or more ring heteroatoms independently selected from nitrogen, oxygen, and sulfur. As used herein, heteroaryl includes 5 to 20 ring atoms (5 to 20 membered heteroaromatic ring), 5 to 12 ring atoms (5 to 12 membered heteroaromatic ring), 5 to 10 ring atoms (5 to 10 membered heteroaromatic ring) or 5 to 6 ring atoms (5 to 6 membered heteroaromatic ring); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" refers to a non-aromatic radical or ring having from three to fifteen atoms wherein from one to six atoms are heteroatoms selected from the group consisting of nitrogen, oxygen and sulfur and attached to the rest of the molecule by a single bond. In certain embodiments, "heterocyclyl" has from three to ten atoms, wherein from one to four atoms are heteroatoms selected from the group consisting of nitrogen, oxygen and sulfur, or from three to seven atoms, wherein from one to two atoms are heteroatoms selected from the group consisting of nitrogen, oxygen and sulfur. The nitrogen, carbon or sulfur atoms in the heterocyclyl may be optionally oxidized; the nitrogen atom may be optionally quaternized. As used herein, "heterocyclyl" or "heterocyclic ring" refers to rings that are saturated unless otherwise indicated, e.g., in some embodiments "heterocyclyl" or "heterocyclic ring" refers to rings that are saturated or partially saturated where specified. Examples of such heterocyclyl include, but are not limited to, dioxolanyl, imidazolidinyl, isothiazolidinyl, isoxazolidinyl, morpholinyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuranyl, trithianyl, tetrahydropyranyl, thiomorpholinyl, thiamorpholinyl, 1-oxo-thiomorpholinyl, and 1,1-dioxo-thiomorpholinyl.

The embodiments disclosed herein are also meant to encompass all pharmaceutically acceptable compounds of Formula I being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S $^{18}$F, $^{36}$Cl, $^{123}$I, and $^{125}$I, respectively. In certain embodiments, these radiolabeled compounds are useful to help determine or measure the effectiveness of the compounds, by characterizing, for example, the site or mode of action, or binding affinity to pharmacologically important site of action. Certain isotopically-labeled compounds of Formula I, Ia, Ib, II, IIa, IIb, III, IIIa, IIIb, IV, IVa, IVb, V, Va, or Vb, for example, those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

In certain embodiments, substitution with heavier isotopes such as deuterium, i.e., 2H, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}$C, $^{18}$F, $^{15}$O, and $^{13}$N, can be useful in Positron Emission Topography (PET) studies for examining substrate receptor occupancy. Isotopically-labeled compounds of Formula I, Ia, Ib, II, IIa, IIb, III, IIIa, IIIb, IV, IVa, IVb, V, Va, or Vb can be prepared by techniques known to those skilled in the art or by processes analogous to those described in the Examples as set out below using an appropriate isotopically-labeled reagent in place of the non-labeled reagent previously employed.

The methods, compositions, kits and articles of manufacture provided herein use or include compounds (e.g., a compound of Formula I, Ia, Ib, II, IIa, IIb, III, IIIa, IIIb, IV, IVa, IVb, V, Va, or Vb) or pharmaceutically acceptable salts thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds increase resistance to metabolism, and thus are useful for increasing the half-life of compounds or pharmaceutically acceptable salts thereof, when administered to a mammal. See, e.g., Foster, "Deuterium Isotope Effects in Studies of Drug Metabolism", Trends Pharmacol. Sci., 5(12):524-527 (1984). Such compounds can be synthesized by means known in the art, for example by employing starting materials in which one or more hydrogen atoms have been replaced by deuterium.

The embodiments disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the embodiments disclosed herein include compounds produced by a process comprising administering a compound according to the embodiments disclosed herein to a mammal for a period of time sufficient to yield a metabolic product thereof. Such products are typically identified by administering a radiolabeled compound according to the embodiments disclosed herein in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event or circumstances may or may not occur, and that the description includes instances where said event or circumstance occurs and instances in which it does not. For example, "optionally substituted heterocyclyl" means that the heterocyclyl radical may or may not be substituted and that the description includes both substituted heterocyclyl radicals and heterocyclyl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or other pharmacologically inactive substance that is formulated in combination with a pharmacologically active ingredient of a pharmaceutical composition and is compatible with the other ingredients of the formulation and suitable for use in humans or domestic animals without undue toxicity, irritation, allergic response, and the like.

Examples of "pharmaceutically acceptable salts" of the compounds disclosed herein include salts derived from an appropriate base, such as an alkali metal (for example, sodium), an alkaline earth metal (for example, magnesium), ammonium and $NX_4^+$ (wherein X is $C_{1-4}$alkyl). Pharmaceutically acceptable salts of a nitrogen atom or an amino group include, for example, salts of organic carboxylic acids such as acetic, trifluoroacetic, adipic, ascorbic, aspartic, butyric, camphoric, cinnamic, citric, digluconic, glutamic, glycolic, glycerophosphoric, formic, hexanoic, benzoic, lactic, fumaric, tartaric, maleic, hydroxymaleic, malonic, malic, mandelic, isethionic, lactobionic, nicotinic, oxalic, pamoic, pectinic, phenylacetic, 3-phenylpropionic, pivalic, propionic, pyruvic, salicylic, stearic, sulfanilic, tartaric, undecanoic, and succinic acids; organic sulfonic acids, such as methanesulfonic, ethanesulfonic, camphorsulfonic, mesitylenesulfonic, benzenesulfonic, p-toluenesulfonic acids, naphthalenesulfonic, and 2-naphthalenesulfonic; and inorganic acids, such as hydrochloric, hydrobromic, sulfuric, phosphoric, nitric, and sulfamic acids. Pharmaceutically acceptable salts of a compound of a hydroxy group include the anion of said compound in combination with a suitable cation such as $Na^+$ and $NX_4^+$ (wherein X is independently selected from H or a $C_{1-4}$alkyl group).

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of a compound of Formula I or another compound of the embodiments disclosed herein. All salts, whether or not derived from a physiologically acceptable acid or base, are within the scope of the embodiments disclosed herein.

Metal salts typically are prepared by reacting the metal hydroxide with a compound according to the embodiments disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines. Finally, it is to be understood that the compositions herein comprise compounds disclosed herein in their un-ionized, as well as zwitterionic form.

A "pharmaceutical composition" refers to a formulation of a compound of the embodiments disclosed herein and a medium generally accepted in the art for the delivery of the biologically active compound to mammals, e.g., humans. Such a medium includes all pharmaceutically acceptable excipients.

"Effective amount" or "therapeutically effective amount" refers to an amount of a compound according to the embodiments disclosed herein, which when administered to a patient in need thereof, is sufficient to effect treatment of disease-states, conditions, or disorders disclosed herein. Such an amount would be sufficient to elicit the biological or medical response of a tissue system, or patient that is sought by a researcher or clinician. The amount of a compound according to the embodiments disclosed herein which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination, or coincidentally, with the compounds of the embodiments disclosed herein, and the age, body weight, general health, sex and diet of the patient. Such a therapeutically effective amount can be determined by one of ordinary skill in the art having regard to their own knowledge, the state of the art, and this disclosure.

The terms "treating" and "treatment" as used herein are intended to mean the administration of a compound or composition according to the present embodiments disclosed herein to alleviate or eliminate one or more symptoms of HIV infection and/or to reduce viral load in a patient. In certain embodiments, the terms "treating" and "treatment" also encompass the administration of a compound or composition according to the present embodiments disclosed herein post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present embodiments disclosed herein to prevent perinatal transmission of HIV from mother to baby, by administration to the mother before giving birth and to the child within the first days of life. The terms "treating" and "treatment" also encompass the administration of a compound or composition according to the present embodiments disclosed herein before the exposure of the individual to the virus (also called pre-exposure prophylaxis or PrEP), to prevent HIV infection from taking hold if the individual is exposed to the virus and/or to keep the virus from establishing a permanent infection and/or to prevent the appearance of symptoms of the disease and/or to prevent the virus from reaching detectable levels in the blood. The terms "treating" and "treatment" also encompass the administration of a compound or composition according to the present embodiments disclosed herein both before and after the exposure of the individual to the virus.

As used herein, the terms "preventing" and "prevention" refer to the administration of a compound, composition, or pharmaceutically salt according to the present disclosure pre- or post-exposure of the human to the virus but before the appearance of symptoms of the disease, and/or prior to the detection of the virus in the blood. The terms also refer to prevention of the appearance of symptoms of the disease and/or to prevent the virus from reaching detectible levels in the blood. The terms include both pre-exposure prophylaxis (PrEP), as well as post-exposure prophylaxis (PEP) and event driven or "on demand" prophylaxis. The terms also refer to prevention of perinatal transmission of HIV from mother to baby, by administration to the mother before giving birth and to the child within the first days of life. The terms also refer to prevention of transmission of HIV through blood transfusion.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of HIV replication" as used herein is intended to mean an agent capable of reducing or eliminating the ability of HIV to replicate in a host cell, whether in vitro, ex vivo or in vivo.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic, scalemic, and optically pure forms. Optically active (+) and (−), (R)- and (S)-, or (D)- and (L)-isomers may be prepared using chiral synthons or chiral reagents, or resolved using methods such as chromatography and fractional crystallization. Techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another. In any of the embodiments disclosed herein, compounds disclosed herein may be in the form of a stereoisomer thereof.

"Partially unsaturated" refers to a cyclic group which contains at least one double bond but is not aromatic.

Substituents and multivalent groups can be attached to the remainder of the molecule at any position and in any orientation to produce a stable compound. For example, the compound of Formula I.

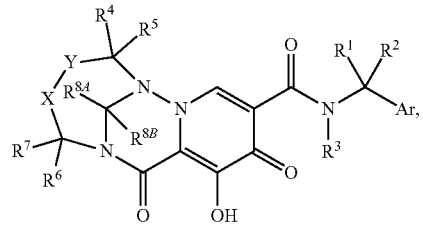

wherein —X—Y— is defined as —CR$^{13A}$R$^{13B}$—CR$^9$=CR$^{10}$— include compounds of Formula

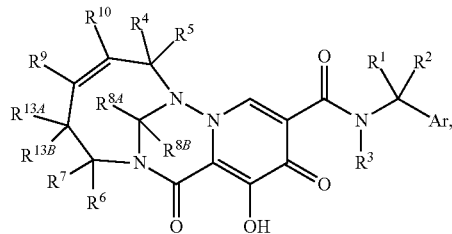

as well as compounds of Formula

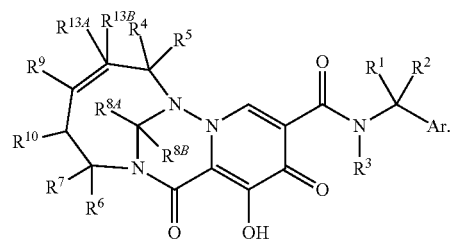

Similarly, compounds of Formula I, where —X—Y— is —CR$^{11A}$R$^{11B}$—CR$^{12A}$R$^{12B}$—, include compounds of Formula

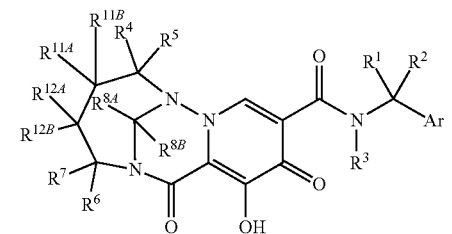

as well as compounds of Formula

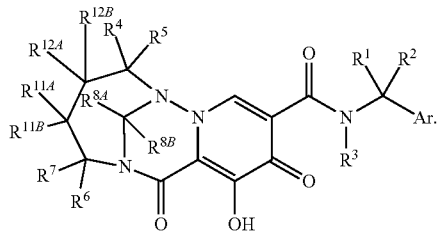

II. Compounds

Disclosed herein are compounds of Formula I:

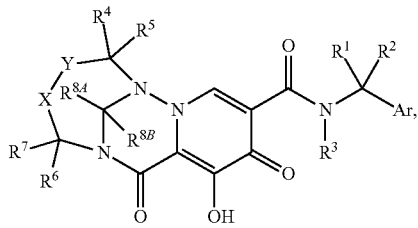

Formula I or a pharmaceutically acceptable salt thereof, wherein

Ar is $C_6$-$C_{10}$ aryl or six to ten membered heteroaryl containing one, two or three heteroatoms selected from N, O, and S; wherein the $C_6$-$C_{10}$ aryl or six to ten membered heteroaryl is optionally substituted with 1-4 substituents independently selected from the group consisting of halogen, $C_1$-$C_6$ alkyl, $C_1$-$C_6$ haloalkyl, and $C_1$-$C_6$ alkyloxy;

$R^1$ is H, $C_1$-$C_3$ alkyl or phenyl;

$R^2$ is H or $C_1$-$C_3$ alkyl;

$R^3$ is H or $C_1$-$C_3$ alkyl;

$R^4$ and $R^5$ are each independently H, halogen, cyano, $C_1$-$C_6$ alkyl, $C_1$-$C_6$ alkyloxy, $C_6$-$C_{10}$ aryl, or six to ten membered heteroaryl containing one, two or three heteroatoms selected from N, O, and S; wherein the $C_1$-$C_6$ alkyl, $C_1$-$C_6$ alkyloxy, $C_6$-$C_{10}$ aryl, or six to ten membered heteroaryl is optionally substituted with one two or three groups independently selected from halogen, $C_1$-$C_3$ alkyloxy, or $C_1$-$C_3$ haloalkyloxy; or $R^4$ and $R^5$ are joined together to form a 3-6 membered carbocyclic ring or 4-6 membered heterocyclic ring comprising one heteroatom selected from N, O, and S;

$R^6$ is H, halogen, $C_1$-$C_6$ alkyl, $C_1$-$C_6$ alkyloxy or $C_1$-$C_6$ haloalkyl;

$R^7$ is H, halogen, $C_1$-$C_6$ alkyl, $C_1$-$C_6$ alkyloxy, or $C_1$-$C_6$ haloalkyl;

$R^{8A}$ and $R^{8B}$ are each independently H, $C_1$-$C_3$ alkyl or benzyl; and —X—Y— is —(CR$^{13A}$R$^{13B}$)$_p$—CR$^9$=CR$^{10}$— or —(CR$^{13A}$R$^{13B}$)$_q$—CR$^{11A}$R$^{11B}$—CR$^{12A}$R$^{12B}$—; wherein $R^9$ is H, halogen, $C_1$-$C_6$ alkyl, $C_1$-$C_6$ haloalkyl or $C_1$-$C_6$ alkyloxy;

$R^{10}$ is H, halogen, $C_1$-$C_6$ alkyl, $C_1$-$C_6$ haloalkyl or $C_1$-$C_6$ alkyloxy; or $R^9$ and $R^{10}$ together with the carbons to which are attached form a phenyl or a 5-6 membered heteroaromatic ring containing 1, 2, or 3 heteroatoms independently selected from N, O, and S; wherein the phenyl or the 5-6 membered heteroaromatic ring is optionally substituted with 1, 2, or 3 substituents independently selected from the group consisting of halogen, $C_1$-$C_3$ alkyl, $C_1$-$C_3$ haloalkyl, and $C_1$-$C_3$ alkyloxy; and $R^{11A}$, $R^{11B}$, $R^{12A}$, $R^{12B}$, $R^{13A}$, and $R^{13B}$ are each independently H, halogen, $C_1$-$C_6$ alkyl, $C_1$-$C_6$ alkyloxy; or $C_1$-$C_6$ haloalkyl; or $R^{11A}$, $R^{12A}$, $R^{13A}$, and $R^{13B}$ are each independently H, halogen, $C_1$-$C_6$ alkyl, $C_1$-$C_6$ alkyloxy; or $C_1$-$C_6$ haloalkyl; and $R^{11B}$ and $R^{12B}$ together with the carbons to which they are attached form a 3-6 membered carbocyclic ring; wherein the 3-6 membered carbocyclic ring is optionally substituted with 1, 2, or 3 substituents independently selected from the group consisting of halogen, $C_1$-$C_3$ alkyl, $C_1$-$C_3$ haloalkyl, and $C_1$-$C_3$ alkyloxy;

p is 0 or 1; and q is 0 or 1;

wherein when —X—Y— is —(CR$^{13A}$R$^{13B}$)$_q$—CR$^{11A}$R$^{11B}$—CR$^{12A}$R$^{12B}$— then (i) $R^4$ is halogen, cyano, $C_1$-$C_6$ alkyl, $C_1$-$C_6$ alkyloxy, $C_6$-$C_{10}$ aryl, or six to ten membered heteroaryl containing one, two or three heteroatoms selected from N, O, and S; wherein the $C_1$-$C_6$ alkyl, $C_1$-$C_6$ alkyloxy, $C_6$-$C_{10}$ aryl, or six to ten membered heteroaryl is optionally substituted with one two or three groups independently selected from halogen, $C_1$-$C_3$ alkyloxy, or $C_1$-$C_3$ haloalkyloxy; and $R^5$ is H, halogen, cyano, $C_1$-$C_6$ alkyl, $C_1$-$C_6$ alkyloxy, $C_6$-$C_{10}$ aryl, or six to ten membered heteroaryl containing one, two or three heteroatoms selected from N, O, and S, wherein the $C_1$-$C_6$ alkyl, $C_1$-$C_6$ alkyloxy, $C_6$-$C_{10}$ aryl, or six to ten membered heteroaryl is optionally substituted with one two or three groups independently selected from halogen, $C_1$-$C_3$ alkyloxy, or $C_1$-$C_3$ haloalkyloxy; or (ii) $R^4$ and $R^5$ are joined together to form a 3-6 membered carbocyclic ring or 4-6 membered heterocyclic ring with one heteroatom; or (iii) $R^{8A}$ is $C_1$-$C_3$ alkyl or benzyl; or (iv) $R^6$ is halogen, $C_1$-$C_6$ alkyl, $C_1$-$C_6$ alkyloxy or $C_1$-$C_6$ haloalkyl.

In some embodiments, the compounds of Formula I provided herein have a Formula Ia:

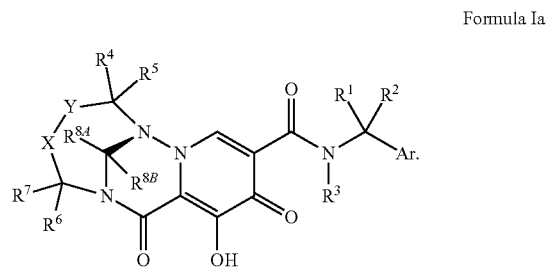

Formula Ia

In some embodiments, the compounds of Formula I provided herein have a Formula Ib:

Formula Ib

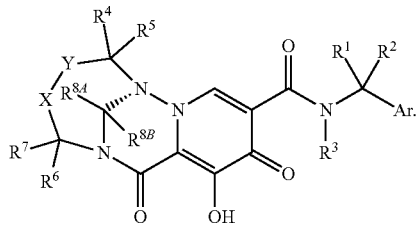

In some embodiments of the compound of Formula I, Formula Ia, and Formula Ib, Ar is $C_6$-$C_{10}$ aryl or six to ten membered heteroaryl containing one, two or three heteroatoms selected from N, O, and S; wherein the $C_6$-$C_{10}$ aryl or six to ten membered heteroaryl is optionally substituted with 1-4 halogens. In some embodiments, Ar is $C_6$-$C_{10}$ aryl or six to ten membered heteroaryl containing one, two or three heteroatoms selected from N, O, and S; wherein the $C_6$-$C_{10}$ aryl or six to ten membered heteroaryl is optionally substituted with 1-3 substituents independently selected from Cl and F.

In some embodiments of the compound of Formula I, Formula Ia, and Formula Ib, Ar is $C_6$-$C_{10}$ aryl or six to ten membered heteroaryl containing one heteroatom selected from N, O, and S; wherein the $C_6$-$C_{10}$ aryl or six to ten membered heteroaryl is optionally substituted with 1-4 substituents independently selected from the group consisting of halogen, $C_1$-$C_6$ alkyl, $C_1$-$C_6$ haloalkyl, and $C_1$-$C_6$ alkyloxy. In some embodiments, Ar is $C_6$-$C_{10}$ aryl or six to ten membered heteroaryl containing one heteroatom selected from N, O, and S; wherein the $C_6$-$C_{10}$ aryl or six to ten membered heteroaryl is optionally substituted with 1-4 substituents independently selected from the group consisting of halogen, $C_1$-$C_6$ alkyl, and $C_1$-$C_6$ alkyloxy. In some embodiments, Ar is $C_6$-$C_{10}$ aryl or six to ten membered heteroaryl containing one heteroatom selected from N, O, and S; wherein the $C_6$-$C_{10}$ aryl or six to ten membered heteroaryl is optionally substituted with 1-4 halogens. In some embodiments, Ar is $C_6$-$C_{10}$ aryl or six to ten membered heteroaryl containing one heteroatom selected from N, O, and S; wherein the $C_6$-$C_{10}$ aryl or six to ten membered heteroaryl is optionally substituted with 1-3 substituents independently selected from Cl and F.

In some embodiments of the compound of Formula I, Formula Ia, and Formula Ib, Ar is phenyl optionally substituted with 1-4 substituents independently selected from the group consisting of halogen, $C_1$-$C_6$ alkyl, $C_1$-$C_6$ haloalkyl, and $C_1$-$C_6$ alkyloxy. In some embodiments, Ar is phenyl optionally substituted with 1-4 substituents independently selected from the group consisting of halogen, $C_1$-$C_6$ alkyl, and $C_1$-$C_6$ alkyloxy. In some embodiments, Ar is phenyl optionally substituted with 1-4 halogens. In some embodiments, Ar is phenyl optionally substituted with 1-3 substituents independently selected from Cl and F.

In some embodiments of the compound of Formula I, Formula Ia, and Formula Ib, Ar is phenyl, optionally substituted with one, two, three, or four substituents independently selected from halogen and $C_1$-$C_6$ alkyloxy. In some embodiment, Ar is phenyl substituted with one, two, three, or four substituents independently selected from halo and $C_1$-$C_4$ alkyloxy. In some embodiment, Ar is phenyl substituted with one, two, three, or four substituents independently selected from Cl and F.

In some embodiments of the compound of Formula I, Formula Ia, and Formula Ib, Ar is:

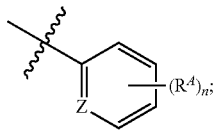

wherein Z is N or $CR^A$;
n is 0, 1, 2, 3, or 4; and
each $R^A$ is independently halogen, $C_1$-$C_6$ alkyl, $C_1$-$C_6$ haloalkyl, and $C_1$-$C_6$ alkyloxy.

In some embodiments of the compound of Formula I, Formula Ia, and Formula Ib, Z is CH or N. In some embodiments, Z is CH. In some embodiments, Z is N.

In some embodiments of the compound of Formula I, Formula Ia, and Formula Ib, Ar is

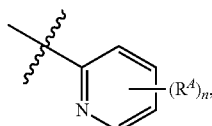

n is 1, 2, 3, or 4; and each $R^A$ is independently halogen, $C_1$-$C_6$ alkyl, $C_1$-$C_6$ haloalkyl and $C_1$-$C_6$ alkyloxy. In some embodiments of the compound of Formula I, Formula Ia, and Formula Ib, Ar is

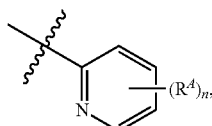

n is 1, 2, 3, or 4; and each $R^A$ is independently halogen, $C_1$-$C_6$ alkyl and $C_1$-$C_6$ alkyloxy. In some embodiments of the compound of Formula I, Formula Ia, and Formula Ib, Ar is

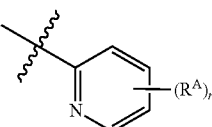

n is 1, 2, 3, or 4; and each $R^A$ is independently halogen and $C_1$-$C_6$ alkyloxy. In some embodiments, Ar is

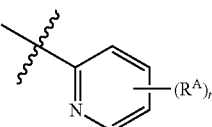

n is 1, 2, 3, or 4; and each $R^A$ is independently halogen and $C_1$-$C_4$ alkyloxy. In some embodiments, Ar is

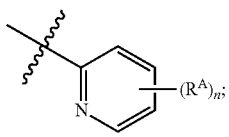

n is 1, 2, or 3; and each $R^A$ is independently fluoro or chloro.

In some embodiments of the compound of Formula I, Formula Ia, and Formula Ib, Ar is

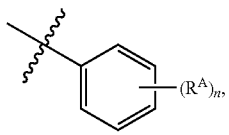

n is 1, 2, 3, or 4; and each $R^A$ is independently halogen, $C_1$-$C_6$ alkyl, $C_1$-$C_6$ haloalkyl and $C_1$-$C_6$ alkyloxy. In some embodiments of the compound of Formula I, Formula Ia, and Formula Ib, Ar is

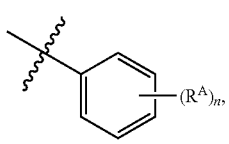

n is 1, 2, 3, or 4; and each $R^A$ is independently halogen, $C_1$-$C_6$ alkyl and $C_1$-$C_6$ alkyloxy. In some embodiments of the compound of Formula I, Formula Ia, and Formula Ib, Ar is

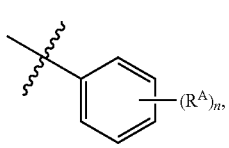

n is 1, 2, 3, or 4; and each $R^A$ is independently halogen and $C_1$-$C_6$ alkyloxy. In some embodiments, Ar is

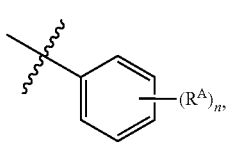

n is 1, 2, 3, or 4; and each $R^A$ is independently halogen and $C_1$-$C_4$ alkyloxy. In some embodiments, Ar is

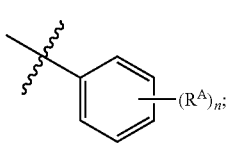

n is 1, 2, or 3; and each $R^A$ is independently fluoro or chloro.

In some embodiments of the compounds of Formula I, Formula Ia, and Formula Ib, Ar is

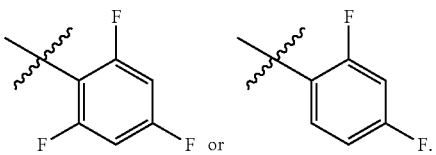 [SMILES: *c1c(F)cc(F)cc1F ; *c1ccc(F)cc1F]

In some embodiments, the compounds of Formula I, Formula Ia, and Formula Ib disclosed herein, have a Formula II:

Formula II

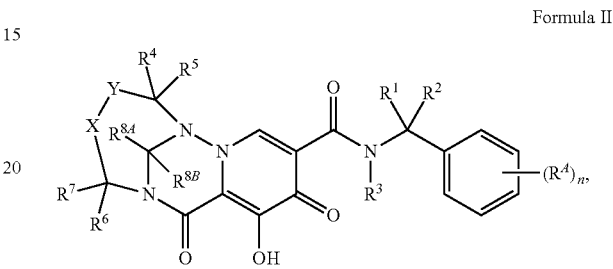

wherein n is 0, 1, 2, 3, or 4; and each $R^A$ is independently halogen, $C_1$-$C_6$ alkyl, $C_1$-$C_6$ haloalkyl, and $C_1$-$C_6$ alkyloxy.

In some embodiments, the compounds of Formula I, Formula Ia, Formula Ib, and Formula II disclosed herein, have a Formula IIa:

Formula IIa

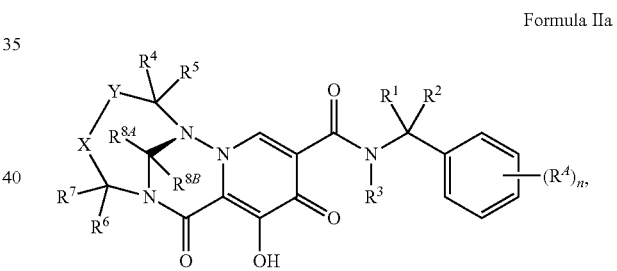

wherein n is 0, 1, 2, 3, or 4; and each $R^A$ is independently halogen, $C_1$-$C_6$ alkyl, $C_1$-$C_6$ haloalkyl, and $C_1$-$C_6$ alkyloxy.

In some embodiments, the compound of Formula I, Formula Ib, and Formula II disclosed herein, have a Formula IIb:

Formula IIb

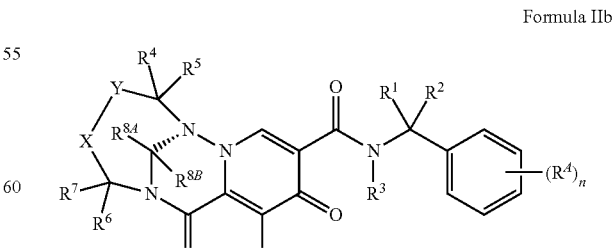

wherein n is 0, 1, 2, 3, or 4; and each $R^A$ is independently halogen, $C_1$-$C_6$ alkyl, $C_1$-$C_6$ haloalkyl, and $C_1$-$C_6$ alkyloxy.

In some embodiments of the compounds of Formula I, Ia, Ib, II, IIa, and IIb, —X—Y— is —CR$^{13A}$CR$^{13B}$—CR$^9$═CR$^{10}$—, wherein each R$^9$, R$^{10}$, R$^{13A}$ and R$^{13B}$ are each independently H, halogen, C$_1$-C$_6$ alkyl, C$_1$-C$_6$ haloalkyl or C$_1$-C$_6$ alkyloxy; or R$^{13A}$ and R$^{13B}$ are each independently H, halogen, C$_1$-C$_6$ alkyl, C$_1$-C$_6$ haloalkyl or C$_1$-C$_6$ alkyloxy; and R$^9$ and R$^{10}$ together with the carbons to which they are attached form a phenyl or a 5-6 membered heteroaromatic ring containing 1, 2, or 3 heteroatoms independently selected from N, O, and S; wherein the phenyl or the 5-6 membered heteroaromatic ring is optionally substituted with 1, 2, or 3 substituents independently selected from the group consisting of halogen, C$_1$-C$_3$ alkyl, C$_1$-C$_3$ haloalkyl, and C$_1$-C$_3$ alkyloxy.

In some embodiments of the compounds of Formula I, Ia, Ib, II, IIa, and IIb, —X—Y— is —CR$^9$═CR$^{10}$—, wherein each R$^9$ and R$^{10}$ is independently H, halogen, C$_1$-C$_6$ alkyl, C$_1$-C$_6$ haloalkyl or C$_1$-C$_6$ alkyloxy; or R$^9$ and R$^{10}$ together with the carbons to which they are attached form a phenyl or a 5-6 membered heteroaromatic ring containing 1, 2, or 3 heteroatoms independently selected from N, O, and S; wherein the phenyl or the 5-6 membered heteroaromatic ring is optionally substituted with 1, 2, or 3 substituents independently selected from the group consisting of halogen, C$_1$-C$_3$ alkyl, C$_1$-C$_3$ haloalkyl, and C$_1$-C$_3$ alkyloxy.

In some embodiments of the compounds of Formula I, Ia, Ib, II, IIa, and IIb, —X—Y— is —CH$_2$—CR$^9$═CR$^{10}$—, wherein R$^9$ and R$^{10}$ together with the carbons to which they are attached form a phenyl or a 5-6 membered heteroaromatic ring containing 1, 2, or 3 heteroatoms independently selected from N, O, and S; wherein the phenyl or the 5-6 membered heteroaromatic ring is optionally substituted with 1, 2, or 3 substituents independently selected from the group consisting of halogen, C$_1$-C$_3$ alkyl, C$_1$-C$_3$ haloalkyl, and C$_1$-C$_3$ alkyloxy. In some embodiments, —X—Y— is —CH$_2$—CR$^9$═CR$^{10}$—, wherein R$^9$ and R$^{10}$ together with the carbons to which they are attached form a 5-6 membered heteroaromatic ring containing 1, 2, or 3 heteroatoms independently selected from N, O, and S; wherein the 5-6 membered heteroaromatic ring is optionally substituted with 1, 2, or 3 substituents independently selected from the group consisting of halogen, C$_1$-C$_3$ alkyl, C$_1$-C$_3$ haloalkyl, and C$_1$-C$_3$ alkyloxy.

In some embodiments of the compounds of Formula I, Ia, Ib, II, IIa, and IIb, —X—Y— is —CR$^9$═CR$^{10}$—, wherein R$^9$ and R$^{10}$ together with the carbons to which they are attached form a phenyl or a 5-6 membered heteroaromatic ring containing 1, 2, or 3 heteroatoms independently selected from N, O, and S; wherein the phenyl or the 5-6 membered heteroaromatic ring is optionally substituted with 1, 2, or 3 substituents independently selected from the group consisting of halogen, C$_1$-C$_3$ alkyl, C$_1$-C$_3$ haloalkyl, and C$_1$-C$_3$ alkyloxy. In some embodiments, —X—Y— is —CR$^9$═CR$^{10}$—, wherein R$^9$ and R$^{10}$ together with the carbons to which they are attached form a 5-6 membered heteroaromatic ring containing 1, 2, or 3 heteroatoms independently selected from N, O, and S; wherein the 5-6 membered heteroaromatic ring is optionally substituted with 1, 2, or 3 substituents independently selected from the group consisting of halogen, C$_1$-C$_3$ alkyl, C$_1$-C$_3$ haloalkyl, and C$_1$-C$_3$ alkyloxy.

In some embodiments of the compounds of Formula I, Ia, Ib, II, IIa, and IIb, —X—Y— is —CH$_2$—CR$^9$═CR$^{10}$—, wherein R$^9$ and R$^{10}$ together with the carbons to which they are attached form a 5-6 membered heteroaromatic ring containing 1, 2, or 3 heteroatoms independently selected from N, O, and S; wherein the 5-6 membered heteroaromatic ring is optionally substituted with 1, 2, or 3 substituents independently selected from the group consisting of halogen, C$_1$-C$_3$ alkyl, C$_1$-C$_3$ haloalkyl, and C$_1$-C$_3$ alkyloxy.

In some embodiments of the compounds of Formula I, Ia, Ib, II, IIa, and IIb, —X—Y— is —CR$^9$═CR$^{10}$—, wherein R$^9$ and R$^{10}$ together with the carbons to which they are attached form a 5-6 membered heteroaromatic ring containing 1, 2, or 3 heteroatoms independently selected from N, O, and S; wherein the 5-6 membered heteroaromatic ring is optionally substituted with 1, 2, or 3 substituents independently selected from the group consisting of halogen, C$_1$-C$_3$ alkyl, C$_1$-C$_3$ haloalkyl, and C$_1$-C$_3$ alkyloxy.

In some embodiments of the compounds of Formula I, Ia, Ib, II, IIa, and IIb, —X—Y— is —CH$_2$—CR$^9$═CR$^{10}$—, R$^9$ and R$^{10}$ together with the carbons to which they are attached form a 5-6 membered heteroaromatic ring containing 1, 2, or 3 heteroatoms independently selected from N, and O; wherein the 5-6 membered heteroaromatic ring is optionally substituted with 1, 2, or 3 substituents independently selected from the group consisting of halogen, C$_1$-C$_3$ alkyl, C$_1$-C$_3$ haloalkyl, and C$_1$-C$_3$ alkyloxy.

In some embodiments of the compounds of Formula I, Ia, Ib, II, IIa, and IIb, —X—Y— is —CR$^9$═CR$^{10}$—, R$^9$ and R$^{10}$ together with the carbons to which they are attached form a 5-6 membered heteroaromatic ring containing 1, 2, or 3 heteroatoms independently selected from N, and O; wherein the 5-6 membered heteroaromatic ring is optionally substituted with 1, 2, or 3 substituents independently selected from the group consisting of halogen, C$_1$-C$_3$ alkyl, C$_1$-C$_3$ haloalkyl, and C$_1$-C$_3$ alkyloxy.

In some embodiments of the compounds of Formula I, Ia, Ib, II, IIa, and IIb, R$^{11A}$, R$^{11B}$, R$^{12A}$, R$^{12B}$, R$^{13A}$, and R$^{13B}$ are each independently H, halogen, C$_1$-C$_6$ alkyl, or C$_1$-C$_6$ alkyloxy. In some embodiments, R$^{11A}$, R$^{1B}$, R$^{12A}$, R$^{12B}$, R$^{13A}$, and R$^{13B}$ are each independently H, halogen, or C$_1$-C$_6$ alkyloxy. In some embodiments, R$^{11A}$, R$^{11B}$, R$^{12A}$, R$^{12B}$, R$^{13A}$, and R$^{13B}$ are each independently H, halogen, or methoxy. In some embodiments, R$^{11A}$, R$^{1B}$, R$^{12A}$, R$^{12B}$, R$^{13A}$ and R$^{13B}$ are each independently H, fluoro, or methoxy.

In some embodiments of the compounds of Formula I, Ia, Ib, II, IIa, and IIb, have a Formula III:

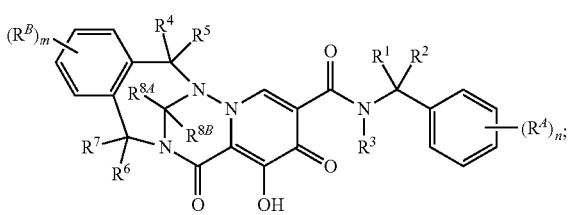

Formula III wherein m is 0, 1, 2, or 3; and each R$^B$ is independently halogen, C$_1$-C$_3$ alkyl, C$_1$-C$_3$ haloalkyl, or C$_1$-C$_3$ alkyloxy.

In some embodiments of the compounds of Formula I, Ia, II, IIa, and III, have a Formula IIIa:

Formula IIIa

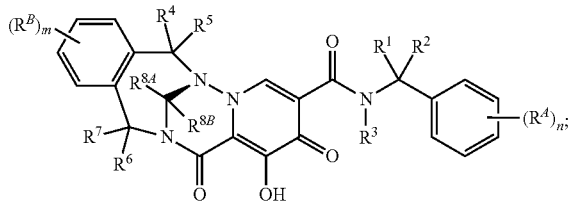

wherein
m is 0, 1, 2, or 3; and
each $R^B$ is independently halogen, $C_1$-$C_3$ alkyl, $C_1$-$C_3$ haloalkyl, or $C_1$-$C_3$ alkyloxy.

In some embodiments of the compounds of Formula I, Ib, II, IIb, and III, have a Formula IIIb:

Formula IIIb

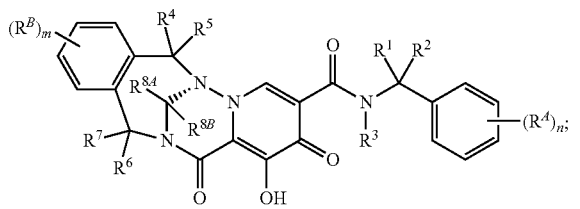

wherein
m is 0, 1, 2, or 3; and
each $R^B$ is independently halogen, $C_1$-$C_3$ alkyl, $C_1$-$C_3$ haloalkyl, or $C_1$-$C_3$ alkyloxy.

In some embodiments of the compounds of Formula III, IIIa, and IIIb, m is 0, 1, or 2. In some embodiments, m is 0 or 1. In some embodiments, m is 1 or 2. In some embodiments, m is 0. In some embodiments, m is 1. In some embodiments, m is 2. In some embodiments, m is 3.

In some embodiments of the compounds of Formula III, IIIa, and IIIb, each $R^B$ is independently halogen, $C_1$-$C_3$ alkyl, $C_1$-$C_3$ haloalkyl, and $C_1$-$C_3$ alkyloxy. In some embodiments, each $R^B$ is independently halogen, $C_1$-$C_3$ alkyl or $C_1$-$C_3$ haloalkyl. In some embodiments, each $R^B$ is independently halogen or $C_1$-$C_3$ alkyl. In some embodiments, each $R^B$ is independently halogen.

In some embodiments of the compounds of Formula III, IIIa, and IIIb, m is 0, 1, or 2, and each $R^B$ is independently halogen, $C_1$-$C_3$ alkyl, $C_1$-$C_3$ haloalkyl, and $C_1$-$C_3$ alkyloxy. In some embodiments, m is 0, 1, or 2, and each $R^B$ is independently halogen, $C_1$-$C_3$ alkyl or $C_1$-$C_3$ haloalkyl. In some embodiments, m is 0, 1, or 2, and each $R^B$ is independently halogen or $C_1$-$C_3$ alkyl. In some embodiments, m is 0, 1, or 2, and each $R^B$ is independently halogen.

In some embodiments of the compounds of Formula III, IIIa, and IIIb, m is 0 or 1, and each $R^B$ is independently halogen, $C_1$-$C_3$ alkyl, $C_1$-$C_3$ haloalkyl, and $C_1$-$C_3$ alkyloxy. In some embodiments, m is 0 or 1, and each $R^B$ is independently halogen, $C_1$-$C_3$ alkyl or $C_1$-$C_3$ haloalkyl. In some embodiments, m is 0 or 1, and each $R^B$ is independently halogen or $C_1$-$C_3$ alkyl. In some embodiments, m is 0 or 1, and each $R^B$ is independently halogen.

In some embodiments of the compounds of Formula III, IIIa, and IIIb, m is 1 or 2, and each $R^B$ is independently halogen, $C_1$-$C_3$ alkyl, $C_1$-$C_3$ haloalkyl, and $C_1$-$C_3$ alkyloxy. In some embodiments, m is 1 or 2, and each $R^B$ is independently halogen, $C_1$-$C_3$ alkyl or $C_1$-$C_3$ haloalkyl. In some embodiments, m is 1 or 2, and each $R^B$ is independently halogen or $C_1$-$C_3$ alkyl. In some embodiments, m is 1 or 2, and each $R^B$ is independently halogen.

In some embodiments of the compounds of Formula III, IIIa, and IIIb, m is 1, and $R^B$ is halogen, $C_1$-$C_3$ alkyl, $C_1$-$C_3$ haloalkyl, and $C_1$-$C_3$ alkyloxy. In some embodiments, m is, and $R^B$ is halogen, $C_1$-$C_3$ alkyl or $C_1$-$C_3$ haloalkyl. In some embodiments, m is 1, and $R^B$ is halogen or $C_1$-$C_3$ alkyl. In some embodiments, m is 1, and $R^B$ is halogen.

In some embodiments of the compounds of Formula III, IIIa, and IIIb, m is 2, and each $R^B$ is independently halogen, $C_1$-$C_3$ alkyl, $C_1$-$C_3$ haloalkyl, and $C_1$-$C_3$ alkyloxy. In some embodiments, m is 2, and each $R^B$ is independently halogen, $C_1$-$C_3$ alkyl or $C_1$-$C_3$ haloalkyl. In some embodiments, m is 2, and each $R^B$ is independently halogen or $C_1$-$C_3$ alkyl. In some embodiments, m is 2, and each $R^B$ is independently halogen.

In some embodiments of the compounds of Formula I, Ia, Ib, II, IIa, and IIb, have a Formula IV:

Formula IV

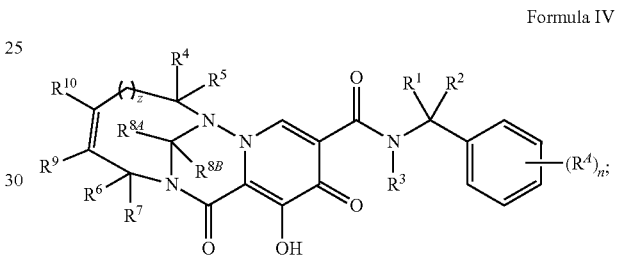

wherein z is 0 or 1.

In some embodiments of the compounds of Formula I, Ia, II, IIa, and IV, have a Formula IVa:

Formula IVa

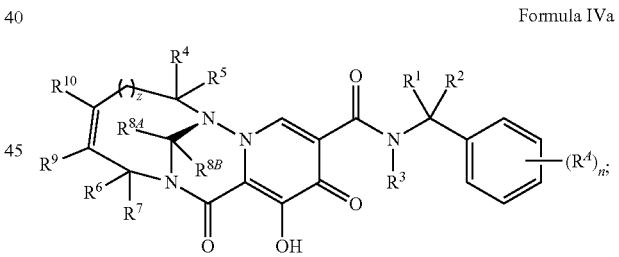

wherein z is 0 or 1.

In some embodiments of the compounds of Formula I, Ib, II, IIb, and IV, have a Formula IVb:

Formula IVb

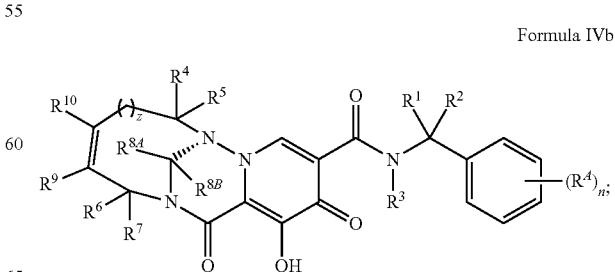

wherein z is 0 or 1.

In some embodiments of the compounds of Formula I, Ia, Ib, II, IIa, and IIb, —X—Y— is —CR$^9$=CR$^{10}$—, wherein each R$^9$ and R$^{10}$ is independently H, halogen, C$_1$-C$_6$ alkyl, C$_1$-C$_6$ haloalkyl or C$_1$-C$_6$ alkyloxy. In some embodiments, —X—Y— is —CR$^9$=CR$^{10}$—, wherein each R$^9$ and R$^{10}$ is independently H, halogen, C$_1$-C$_6$ alkyl, or C$_1$-C$_6$ haloalkyl. In some embodiments, —X—Y— is —CR$^9$=CR$^{10}$—, wherein each R$^9$ and R$^{10}$ is independently H, halogen, or C$_1$-C$_6$ alkyl. In some embodiments, —X—Y— is —CR$^9$=CR$^{10}$—, wherein each R$^9$ and R$^{10}$ is independently H or halogen. In some embodiments, —X—Y— is —CR$^9$=CR$^{10}$—, wherein each R$^9$ and R$^{10}$ is independently H or F.

In some embodiments of the compounds of Formula I, Ia, Ib, II, IIa, and IIb, —X—Y— is —CR$^{11A}$R$^{11B}$—CR$^{12A}$R$^{12B}$—, wherein each R$^{11A}$, R$^{11B}$, R$^{12A}$, and R$^{12B}$ is independently H, halogen, C$_1$-C$_6$ alkyl, C$_1$-C$_6$ alkyloxy or C$_1$-C$_6$ haloalkyl; or each R$^{1A}$ and R$^{12A}$ is independently H, halogen, C$_1$-C$_6$ alkyl, C$_1$-C$_6$ alkyloxy, or C$_1$-C$_6$ haloalkyl; and R$^{11B}$ and R$^{12B}$ together with the carbons to which they are attached form a 3-6 membered carbocyclic ring; wherein the 3-6 membered carbocyclic ring is optionally substituted with 1, 2, or 3 substituents independently selected from the group consisting of halogen, C$_1$-C$_3$ alkyl, C$_1$-C$_3$ haloalkyl, and C$_1$-C$_3$ alkyloxy.

In some embodiments of the compounds of Formula I, Ia, Ib, II, IIa, and IIb, —X—Y— is —CR$^{11A}$R$^{11B}$—CR$^{12A}$R$^{12B}$—, wherein each R$^{11A}$, R$^{11B}$, R$^{12A}$, and R$^{12B}$ is independently H, halogen, C$_1$-C$_6$ alkyl, C$_1$-C$_6$ alkyloxy or C$_1$-C$_6$ haloalkyl. In some embodiments, —X—Y— is —CR$^{11A}$R$^{11B}$—CR$^{12A}$R$^{12B}$—, wherein each R$^{11A}$, R$^{11B}$, R$^{12A}$, and R$^{12B}$ is independently H, halogen, C$_1$-C$_6$ alkyl, or C$_1$-C$_6$ haloalkyl. In some embodiments, —X—Y— is —CR$^{11A}$R$^{11B}$—CR$^{12A}$R$^{12B}$—, wherein each R$^{11A}$, R$^{11B}$, R$^{12A}$, and R$^{12B}$ is independently H, halogen or C$_1$-C$_6$ alkyl. In some embodiments, —X—Y— is —CR$^{11A}$R$^{11B}$—CR$^{12A}$R$^{12B}$—, wherein each R$^{11A}$, R$^{11B}$, R$^{12A}$, and R$^{12B}$ is independently H or halogen. In some embodiments, —X—Y— is —CR$^{11A}$R$^{11B}$—CR$^{12A}$R$^{12B}$—, wherein each R$^{11A}$, R$^{11B}$, R$^{12A}$, and R$^{12B}$ is independently H or F. In some embodiments, —X—Y— is —CR$^{11A}$R$^{11B}$—CR$^{12A}$R$^{12B}$—, wherein each R$^{11A}$, R$^{11B}$, R$^{12A}$, and R$^{12B}$ is H.

In some embodiments of the compounds of Formula I, Ia, Ib, II, IIa, and IIb, —X—Y— is —CR$^{11A}$R$^{11B}$—CR$^{12A}$R$^{12B}$—, wherein each R$^{11A}$ and R$^{12A}$ is independently H, halogen, C$_1$-C$_6$ alkyl, C$_1$-C$_6$ alkyloxy, or C$_1$-C$_6$ haloalkyl; and R$^{11B}$ and R$^{12B}$ together with the carbons to which they are attached form a 3-6 membered carbocyclic ring; wherein the 3-6 membered carbocyclic ring is optionally substituted with 1, 2, or 3 substituents independently selected from the group consisting of halogen, C$_1$-C$_3$ alkyl, C$_1$-C$_3$ haloalkyl, and C$_1$-C$_3$ alkyloxy.

In some embodiments of the compounds of Formula I, Ia, Ib, II, IIa, and IIb, have a Formula V:

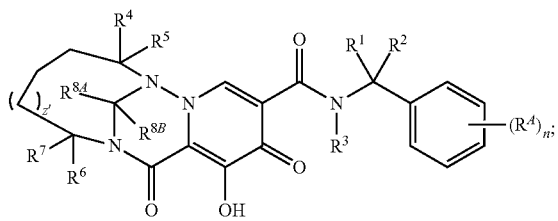

Formula V wherein z' is 1 or 2.

In some embodiments of the compounds of Formula I, Ia, II, IIa, and V, have a Formula Va:

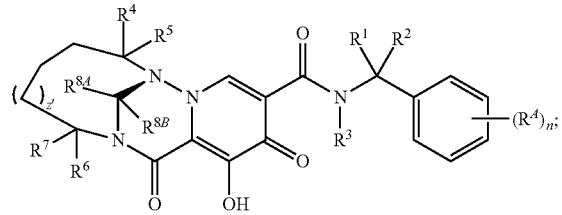

Formula Va wherein z' is 1 or 2.

In some embodiments of the compounds of Formula I, Ib, II, IIb, and V, have a Formula Vb:

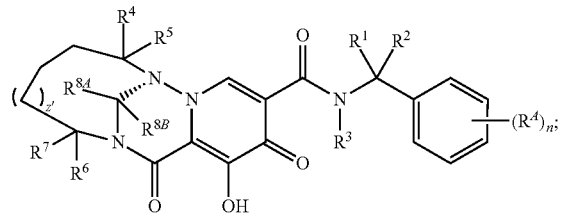

Formula Vb wherein z' is 1 or 2.

In some embodiments of the compound of Formula V, Va, and Vb described herein, z' is 1. In some embodiments z' is 2.

In some embodiments of the compounds of Formula I, Ia, Ib, II, IIa, IIb, III, IIIa, IIIb, IV, IVa, IVb, V, Va, and Vb described herein, R$^{8A}$ is H and R$^{8B}$ is H, C$_1$-C$_3$ alkyl or benzyl. In some embodiments, R$^{8A}$ is H and R$^{8B}$ is H or C$_1$-C$_3$ alkyl. In some embodiments, R$^{8A}$ is H and R$^{8B}$ is H or benzyl. In some embodiments, R$^{8A}$ is H and R$^{8B}$ is C$_1$-C$_3$ alkyl or benzyl. In some embodiments, R$^{8A}$ is H and R$^{8B}$ is C$_1$-C$_3$ alkyl. In some embodiments, R$^{8A}$ is H and R$^{8B}$ is benzyl. In some embodiments, both R$^{8A}$ and R$^{8B}$ are H.

In some embodiments of the compounds of Formula I, Ia, Ib, II, IIa, IIb, III, IIIa, IIIb, IV, IVa, IVb, V, Va, and Vb described herein, R$^{8A}$ is C$_1$-C$_3$ alkyl and R$^{8B}$ is H, C$_1$-C$_3$ alkyl or benzyl. In some embodiments, R$^{8A}$ is C$_1$-C$_3$ alkyl and R$^{8B}$ is H or C$_1$-C$_3$ alkyl. In some embodiments, R$^{8A}$ is C$_1$-C$_3$ alkyl and R$^{8B}$ is H or benzyl. In some embodiments, R$^{8A}$ is C$_1$-C$_3$ alkyl and R$^{8B}$ is C$_1$-C$_3$ alkyl or benzyl. In some embodiments, R$^{8A}$ is C$_1$-C$_3$ alkyl and R$^{8B}$ is H. In some embodiments, R$^{8A}$ is C$_1$-C$_3$ alkyl and R$^{8B}$ is benzyl. In some embodiments, both R$^{8A}$ and R$^{8B}$ are independently C$_1$-C$_3$ alkyl.

In some embodiments of the compounds of Formula I, Ia, Ib, II, IIa, IIb, III, IIIa, IIIb, IV, IVa, IVb, V, Va, and Vb described herein, R$^{8A}$ is benzyl and R$^{8B}$ is H, C$_1$-C$_3$ alkyl or benzyl. In some embodiments, R$^{8A}$ is benzyl and R$^{8B}$ is H or C$_1$-C$_3$ alkyl. In some embodiments, R$^{8A}$ is benzyl and R$^{8B}$ is H or benzyl. In some embodiments, R$^{8A}$ is benzyl and R$^{8B}$ is C$_1$-C$_3$ alkyl or benzyl. In some embodiments, R$^{8A}$ is benzyl and R$^{8B}$ is C$_1$-C$_3$ alkyl. In some embodiments, R$^{8A}$ is benzyl and R$^{8B}$ is H. In some embodiments, both R$^{8A}$ and R$^{8B}$ are benzyl.

In some embodiments of the compounds of Formula I, Ia, Ib, II, IIa, IIb, III, IIIa, IIIb, IV, IVa, IVb, V, Va, and Vb described herein, $R^1$ is H, $C_1$-$C_3$ alkyl or phenyl and $R^2$ is H. In some embodiments, $R^1$ is H or phenyl and $R^2$ is H. In some embodiments, $R^1$ is H or $C_1$-$C_3$ alkyl and $R^2$ is H. In some embodiments, $R^1$ is $C_1$-$C_3$ alkyl or phenyl and $R^2$ is H. In some embodiments, both $R^1$ and $R^2$ are H. In some embodiments, $R^1$ is $C_1$-$C_3$ alkyl and $R^2$ is H. In some embodiments, $R^1$ is phenyl and $R^2$ is H.

In some embodiments of the compounds of Formula I, Ia, Ib, II, IIa, IIb, III, IIIa, IIIb, IV, IVa, IVb, V, Va, and Vb described herein, $R^1$ is H, $C_1$-$C_3$ alkyl or phenyl and $R^2$ is $C_1$-$C_3$ alkyl. In some embodiments, $R^1$ is H or phenyl and $R^2$ is $C_1$-$C_3$ alkyl. In some embodiments, $R^1$ is H or $C_1$-$C_3$ alkyl and $R^2$ is $C_1$-$C_3$ alkyl. In some embodiments, $R^1$ is $C_1$-$C_3$ alkyl or phenyl and $R^2$ is $C_1$-$C_3$ alkyl. In some embodiments, $R^1$ is H and $R^2$ is $C_1$-$C_3$ alkyl. In some embodiments, each $R^1$ and $R^2$ is independently $C_1$-$C_3$ alkyl. In some embodiments, $R^1$ is phenyl and $R^2$ is $C_1$-$C_3$ alkyl. In some embodiments, each $R^1$ and $R^2$ is independently H or $C_1$-$C_3$ alkyl.

In some embodiments of the compounds of Formula I, Ia, Ib, II, IIa, IIb, III, IIIa, IIIb, IV, IVa, and IVb, described herein, each $R^4$ and $R^5$ is independently H, or $C_1$-$C_6$ alkyl, wherein the $C_1$-$C_6$ alkyl is optionally substituted with one two or three groups independently selected from halogen, $C_1$-$C_3$ alkyloxy, or $C_1$-$C_3$ haloalkyloxy. In some embodiments, $R^4$ is H or $C_1$-$C_6$ alkyl, wherein the $C_1$-$C_6$ alkyl is optionally substituted with one two or three groups independently selected from halogen, $C_1$-$C_3$ alkyloxy, or $C_1$-$C_3$ haloalkyloxy; and $R^5$ is H or $C_1$-$C_6$ alkyl. In some embodiments, $R^4$ is H or $C_1$-$C_6$ alkyl, wherein the $C_1$-$C_6$ alkyl is optionally substituted with one two or three groups independently selected from halogen, $C_1$-$C_3$ alkyloxy, or $C_1$-$C_3$ haloalkyloxy; and $R^5$ is H.

In some embodiments of the compounds of Formula IV, IVa, and IVb, described herein, $R^4$ is halogen or $C_1$-$C_6$ alkyl wherein the $C_1$-$C_6$ alkyl is optionally substituted with one two or three groups independently selected from halogen, $C_1$-$C_3$ alkyloxy, or $C_1$-$C_3$ haloalkyloxy; and $R^5$ is H, halogen, or $C_1$-$C_6$ alkyl wherein the $C_1$-$C_6$ alkyl is optionally substituted with one two or three groups independently selected from halogen, $C_1$-$C_3$ alkyloxy, or $C_1$-$C_3$ haloalkyloxy. In some embodiments, $R^4$ is halogen or $C_1$-$C_6$ alkyl wherein the $C_1$-$C_6$ alkyl is optionally substituted with one two or three groups independently selected from halogen, $C_1$-$C_3$ alkyloxy, or $C_1$-$C_3$ haloalkyloxy; and $R^5$ is H, halogen, or $C_1$-$C_6$ alkyl. In some embodiments, $R^4$ is halogen or $C_1$-$C_6$ alkyl wherein the $C_1$-$C_6$ alkyl is optionally substituted with one two or three groups independently selected from halogen, $C_1$-$C_3$ alkyloxy, or $C_1$-$C_3$ haloalkyloxy; and $R^5$ is H.

In some embodiments of the compounds of Formula I, Ia, Ib, II, IIa, IIb, III, IIIa, IIIb, IV, IVa, and IVb, described herein, each $R^4$ and $R^5$ is independently H, Me, OMe, or $CH_2F$. In some embodiments, $R^4$ is H, Me, OMe, or $CH_2F$ and $R^5$ is H.

In some embodiments of the compounds of Formula I, Ia, Ib, II, IIa, IIb, III, IIIa, IIIb, IV, IVa, IVb, V, Va, and Vb described herein, $R^4$ and $R^5$ are joined together to form a 4-6 membered heterocyclic ring comprising one heteroatom selected from N, O, and S.

In some embodiments of the compounds of Formula I, Ia, Ib, II, IIa, IIb, III, IIIa, IIIb, IV, IVa, IVb, V, Va, and Vb described herein, $R^4$ and $R^5$ are joined together to form a 3-6 membered carbocyclic ring.

In some embodiments of the compounds of Formula I, Ia, Ib, II, IIa, IIb, III, IIIa, IIIb, IV, IVa, IVb, V, Va, and Vb described herein, $R^6$ is H, halogen, $C_1$-$C_6$ alkyl, or $C_1$-$C_6$ haloalkyl. In some embodiments, $R^6$ is H, halogen or $C_1$-$C_6$ alkyl. In some embodiments, $R^6$ is halogen or $C_1$-$C_6$ alkyl. In some embodiments, $R^6$ is $C_1$-$C_6$ alkyl. In some embodiments, $R^6$ is H.

In some embodiments of the compounds of Formula I, Ia, Ib, II, IIa, IIb, III, IIIa, IIIb, IV, IVa, and IVb, described herein, $R^7$ is H, halogen, $C_1$-$C_6$ alkyl, or $C_1$-$C_6$ haloalkyl. In some embodiments, $R^7$ is H, halogen, or $C_1$-$C_6$ alkyl. In some embodiments, $R^7$ is halogen or $C_1$-$C_6$ alkyl. In some embodiments, $R^7$ is $C_1$-$C_6$ alkyl. In some embodiments, $R^7$ is H.

In some embodiments, the compounds of Formula I, Ia, Ib, II, IIa, IIb, III, IIIa, IIIb, IV, IVa, IVb, V, Va, or Vb is selected from the group consisting of.

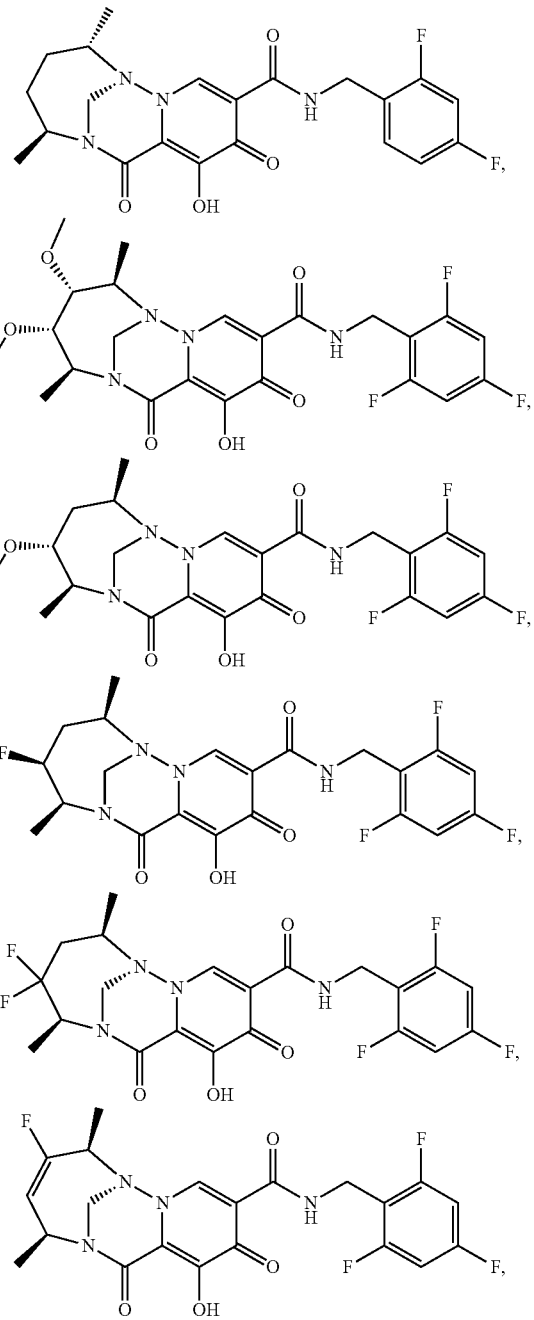

25
-continued
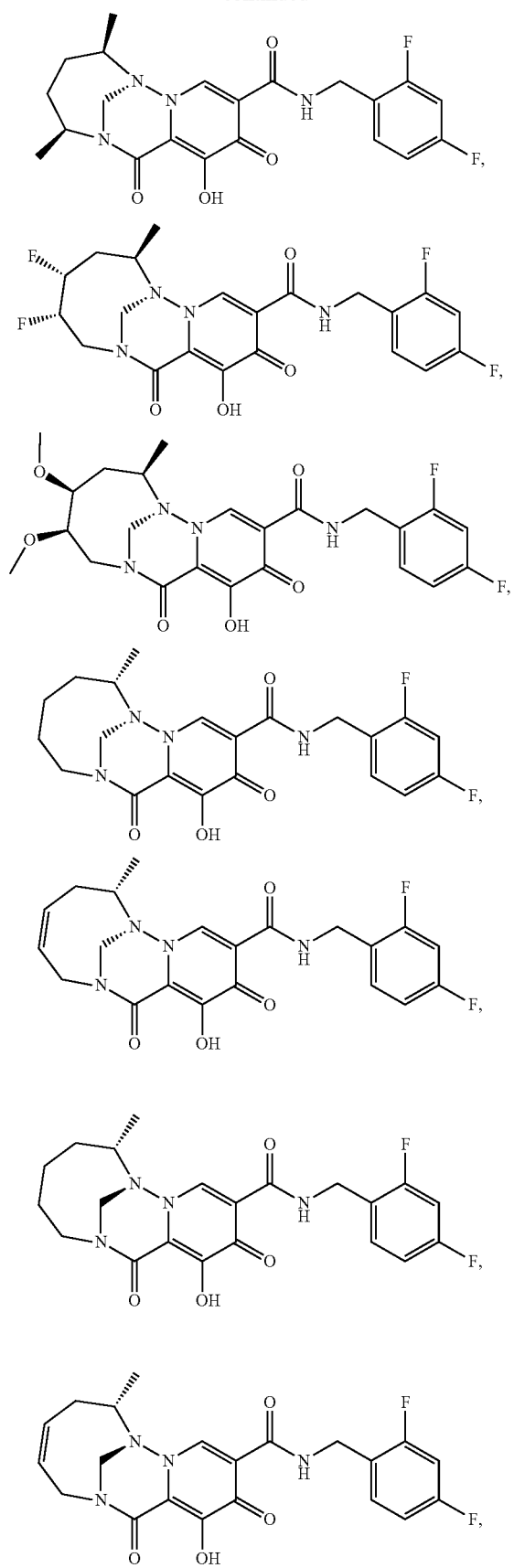
26
-continued
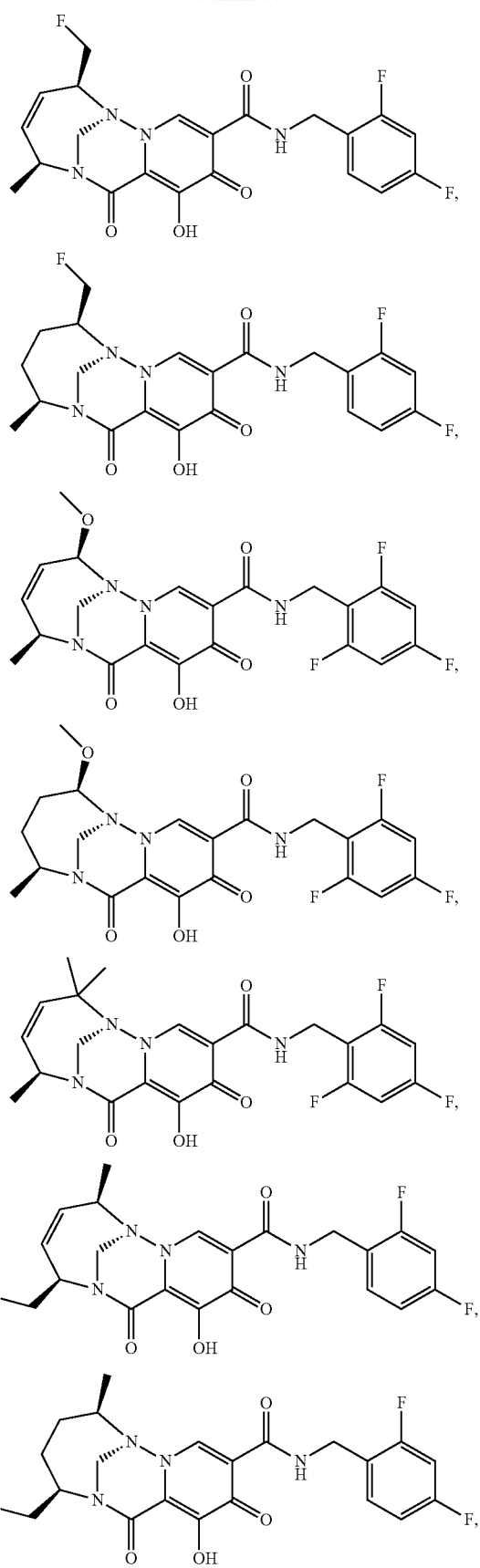

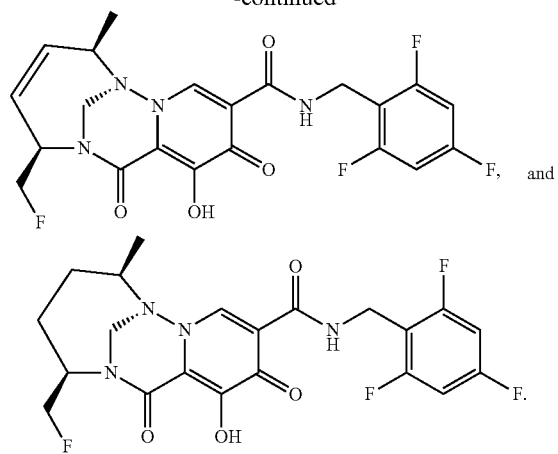
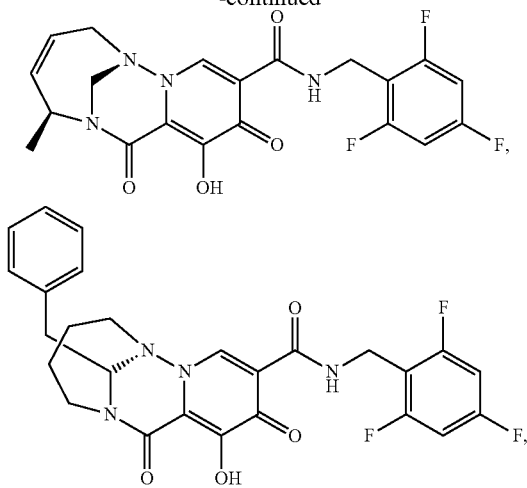
In some embodiments, the compounds of Formula I, Ia, Ib, II, IIa, IIb, III, IIIa, IIIb, IV, IVa, IVb, V, Va, or Vb is selected from the group consisting of:
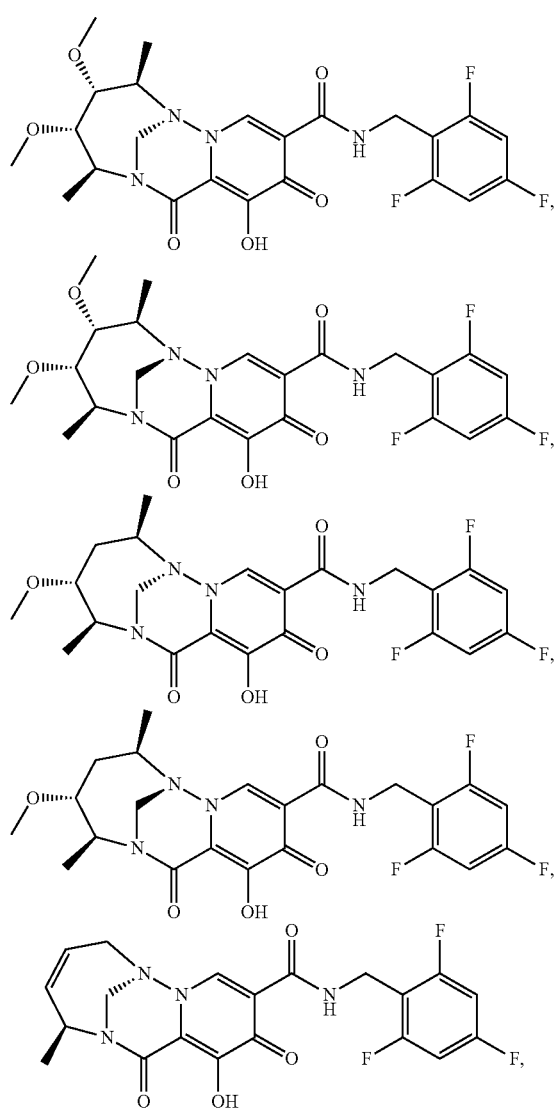
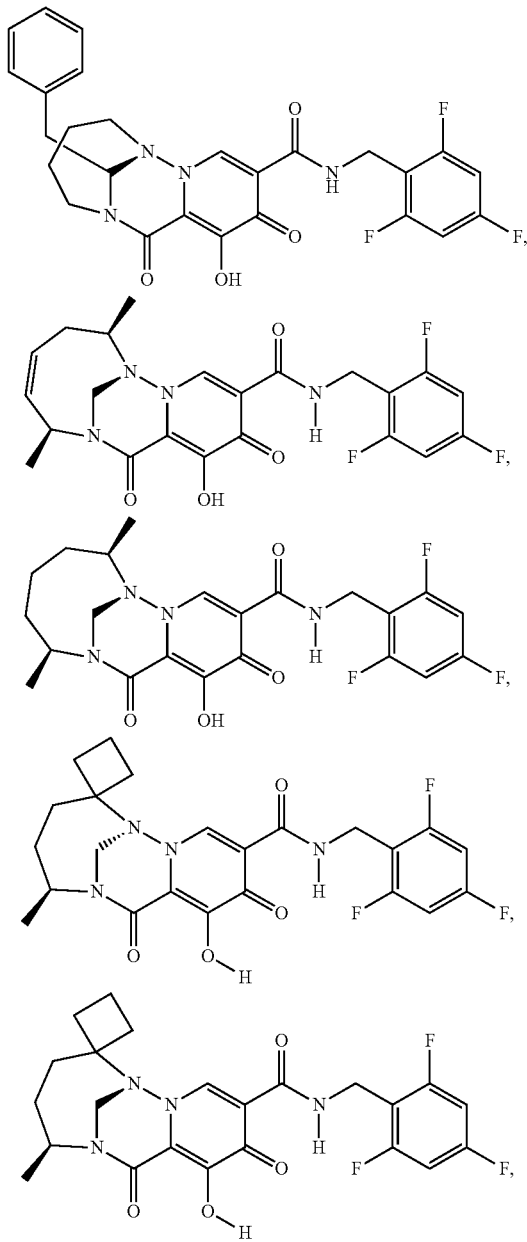

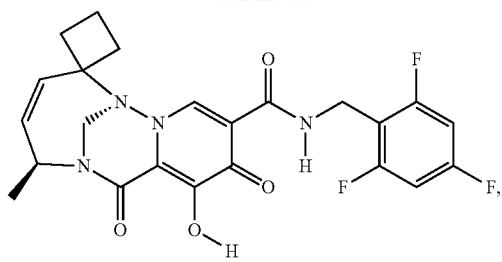
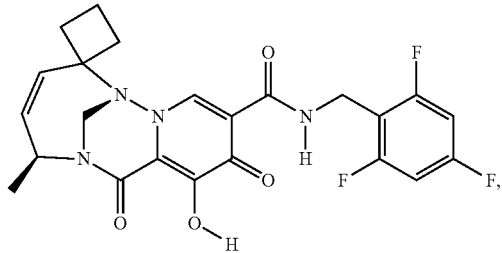
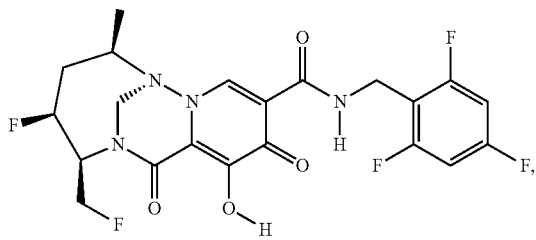
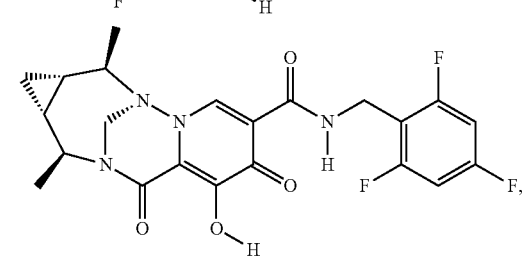
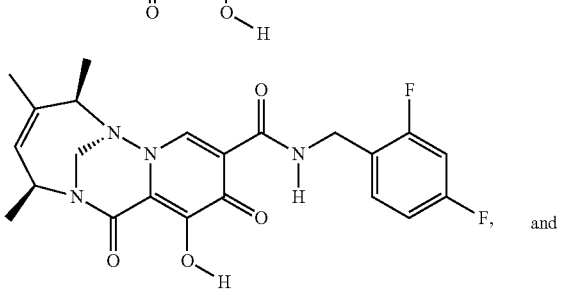
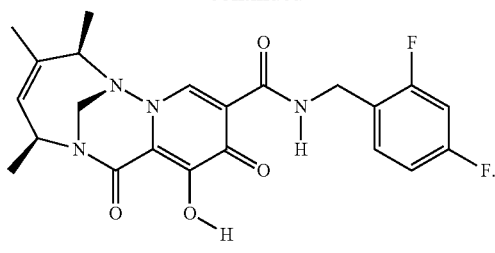
In some embodiments, the compounds of Formula I, Ia, Ib, II, IIa, IIb, III, IIIa, IIIb, IV, IVa, IVb, V, Va, or Vb is selected from the group consisting of:
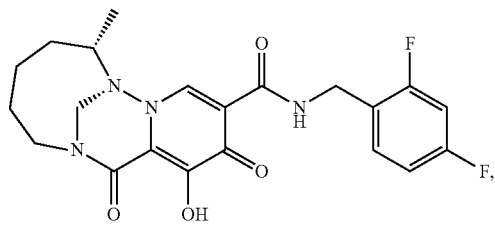
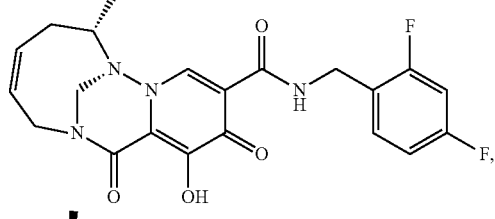
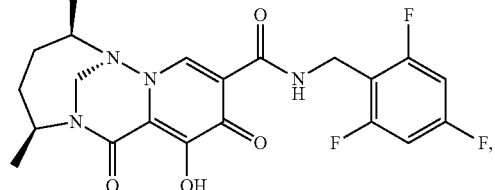
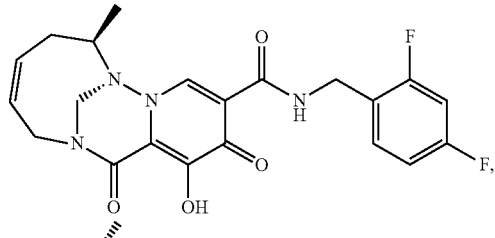
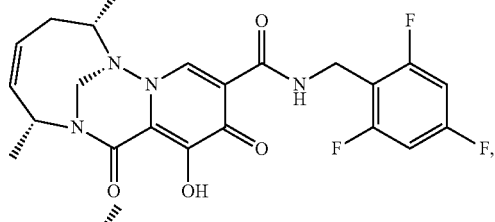
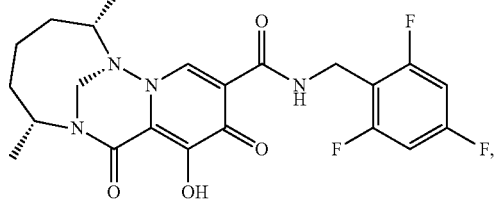

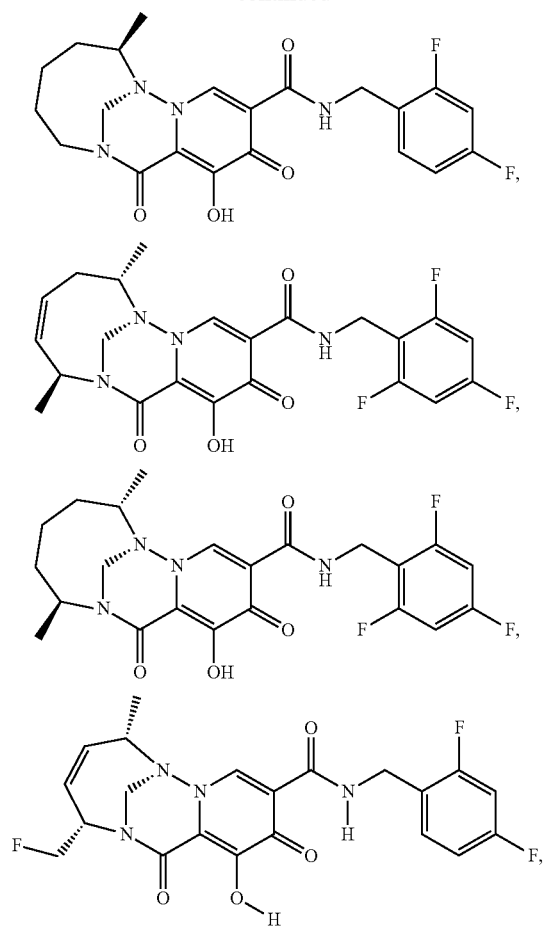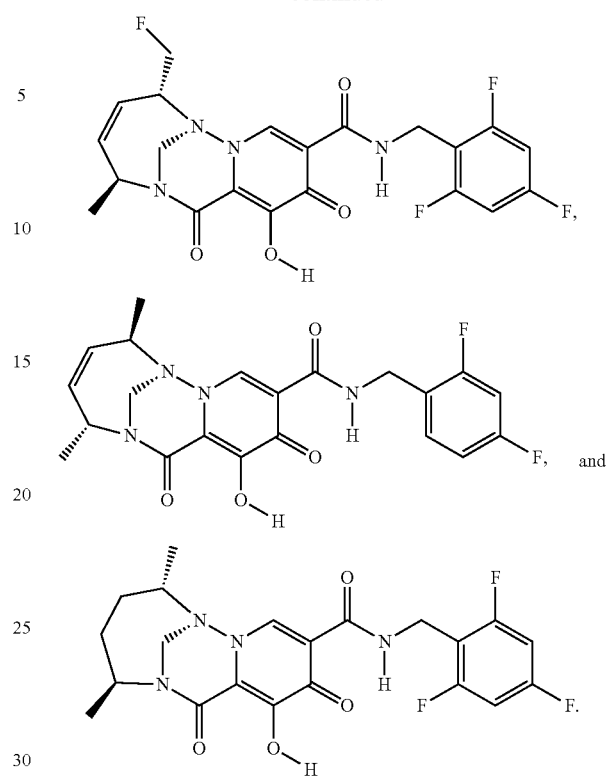
In some embodiments, the compounds of Formula I, Ia, Ib, II, IIa, IIb, III, IIIa, IIIb, IV, IVa, IVb, V, Va, or Vb is selected from the group consisting of:
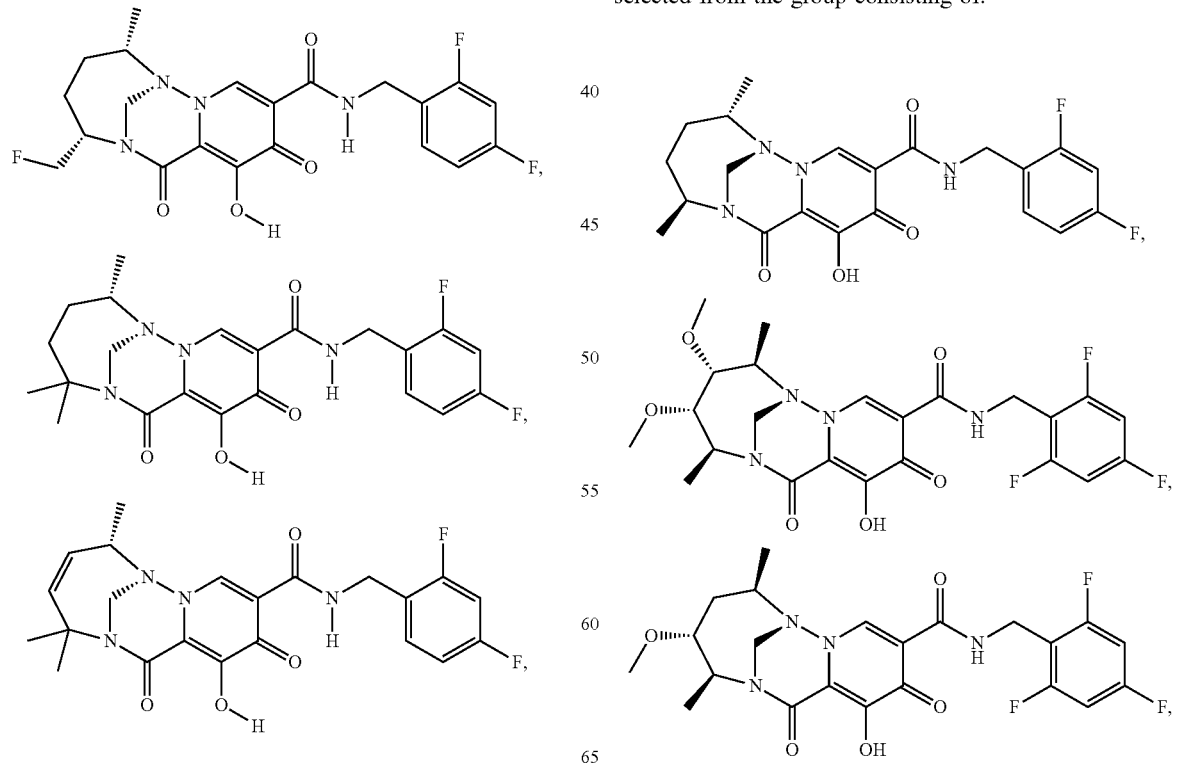

33
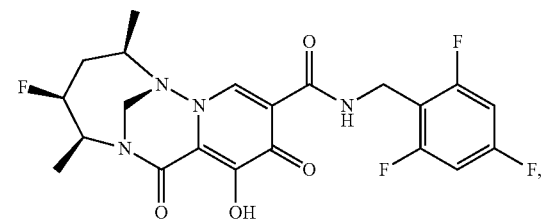
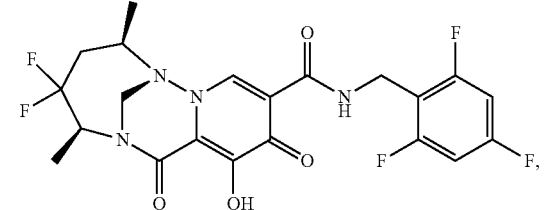
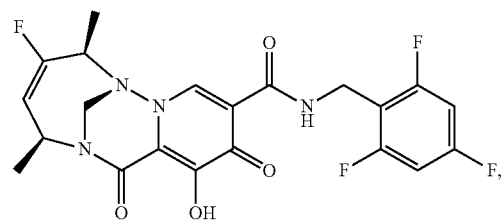
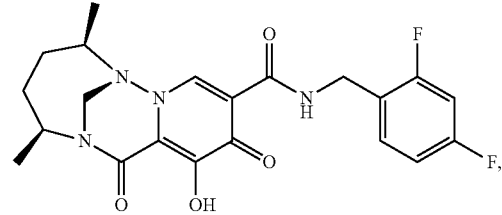
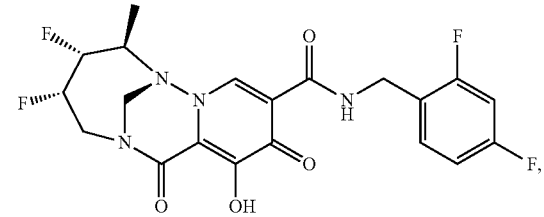
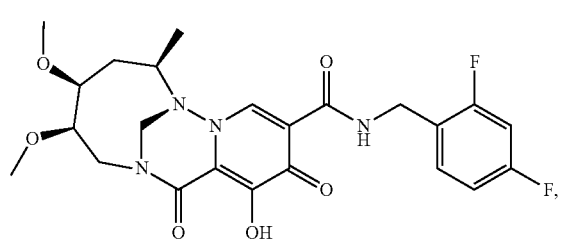
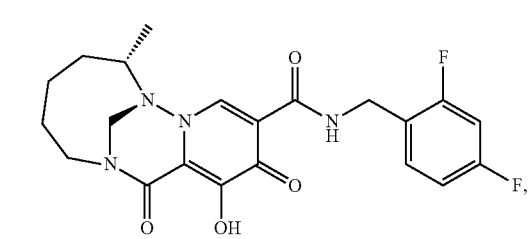
34
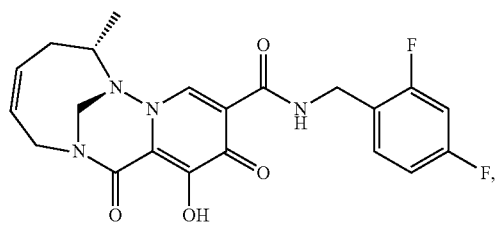
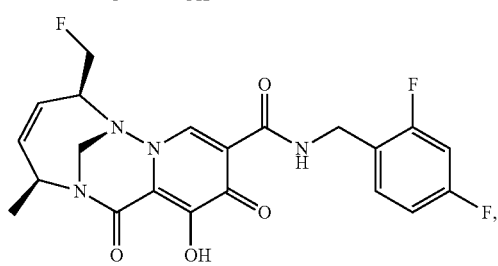
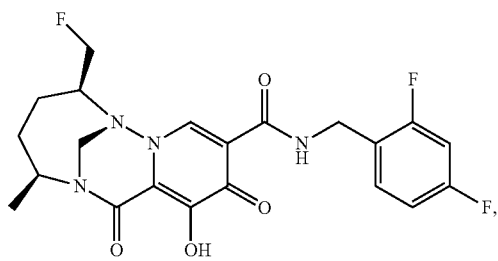
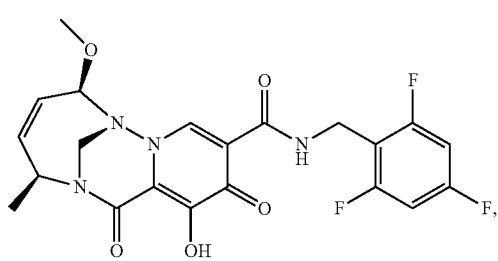
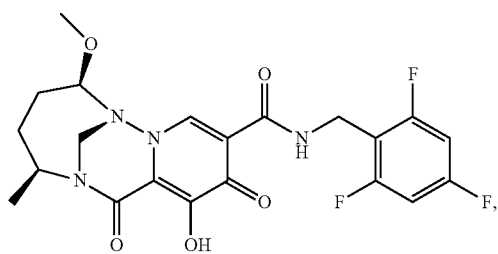
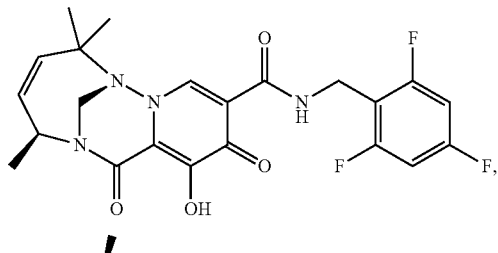
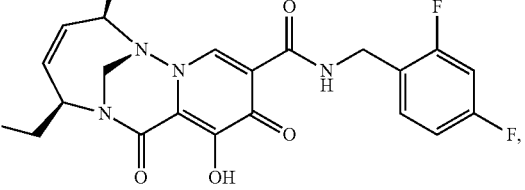

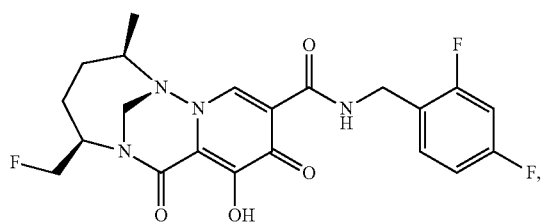
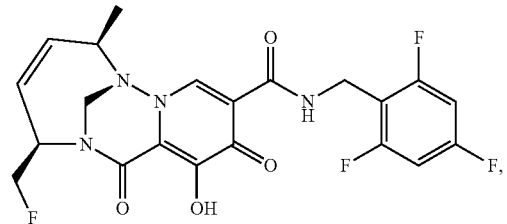
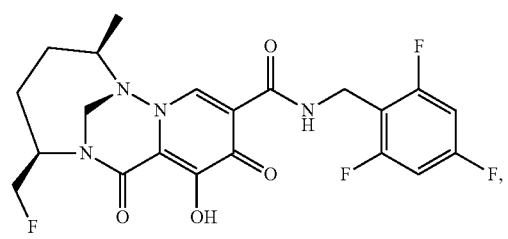
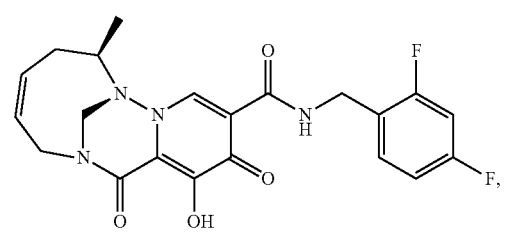
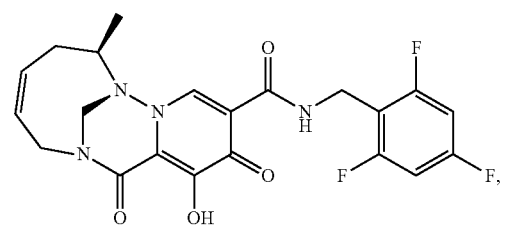
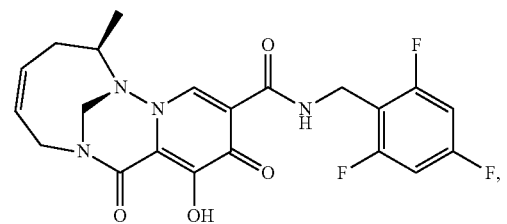
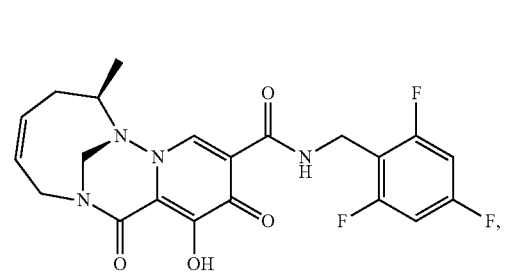
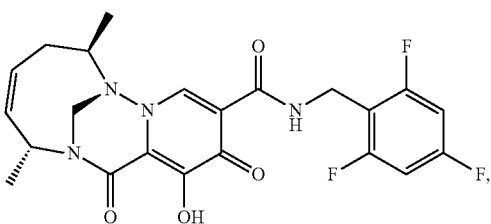
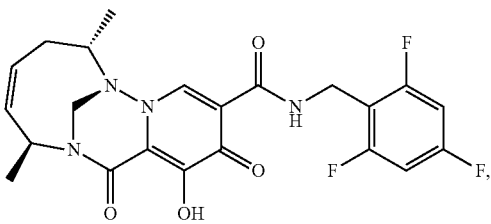
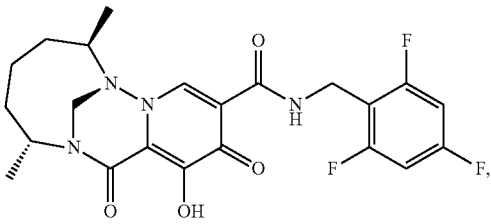
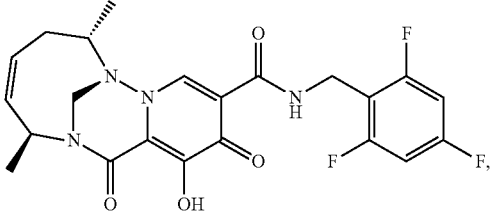
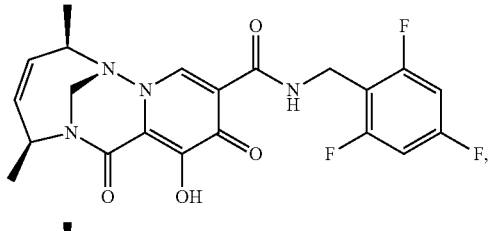
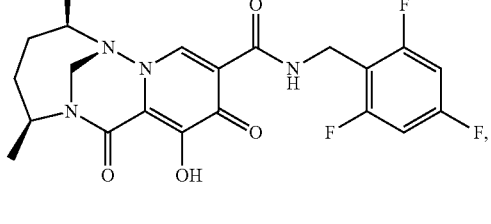
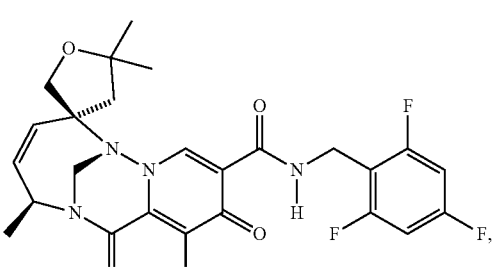

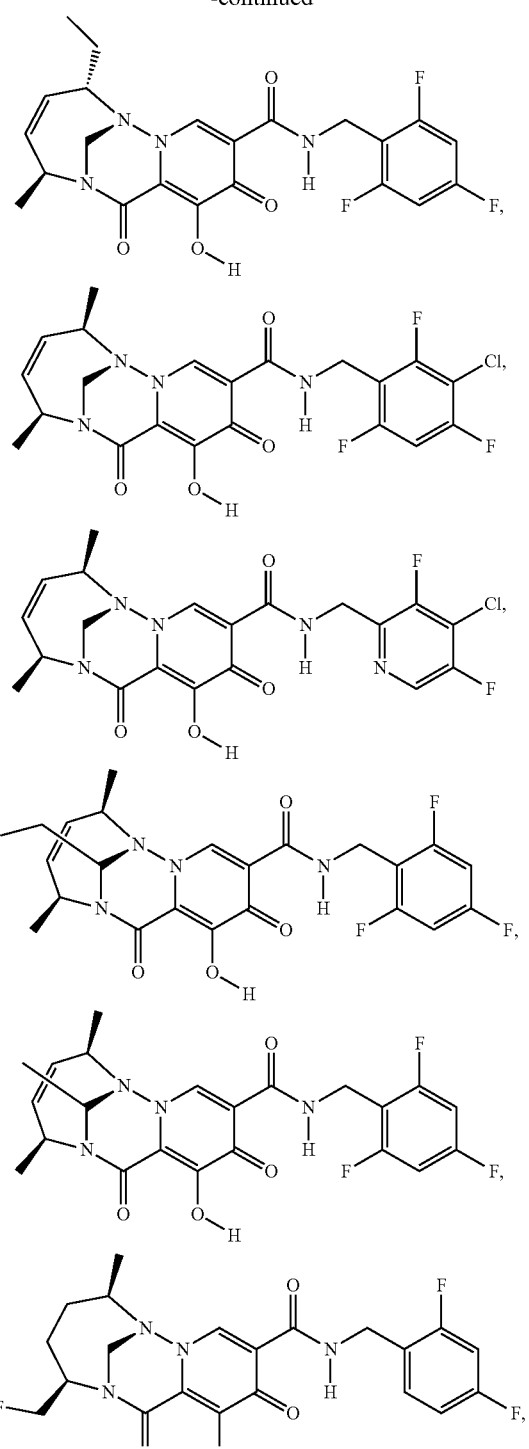
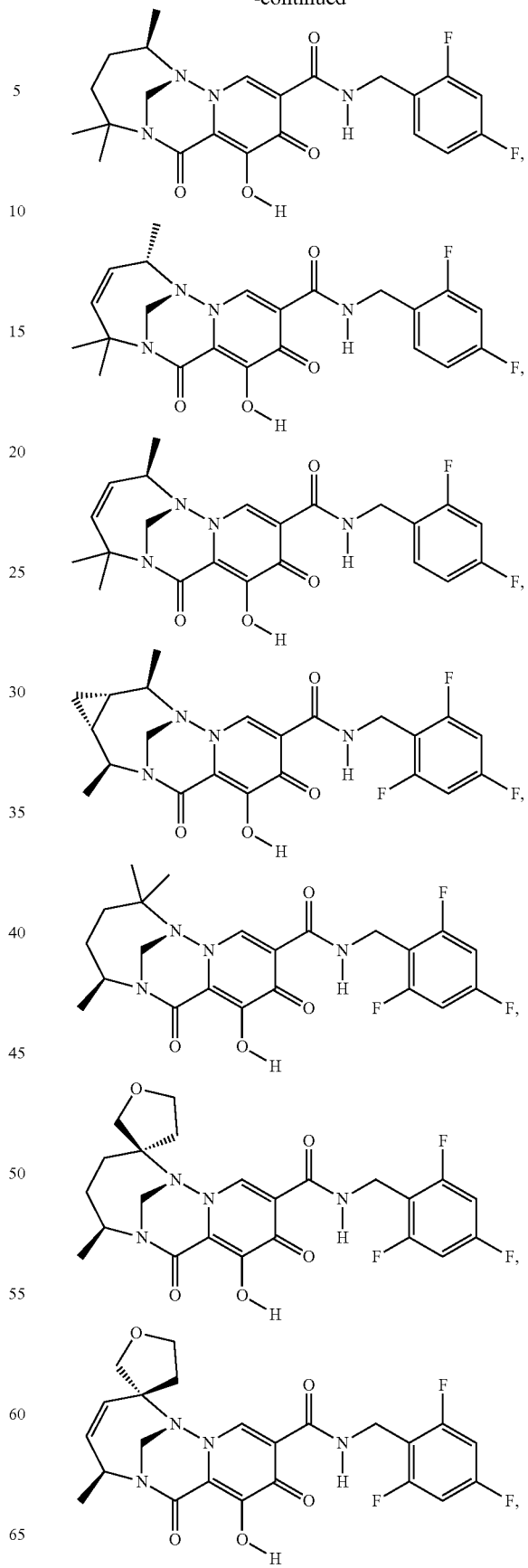

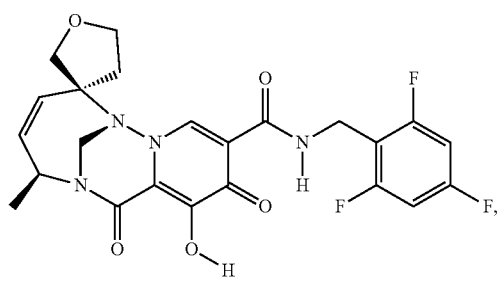
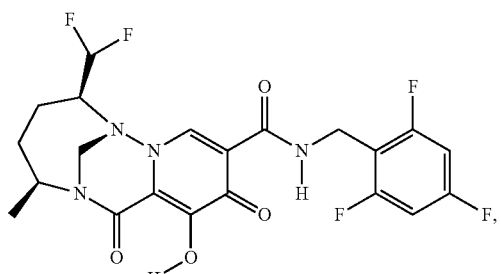
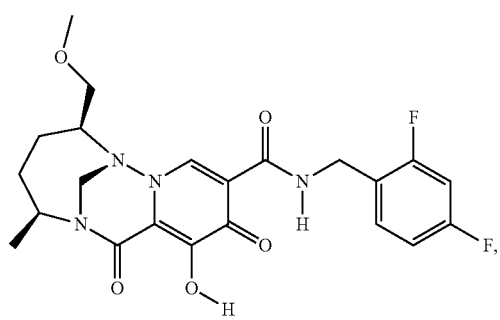
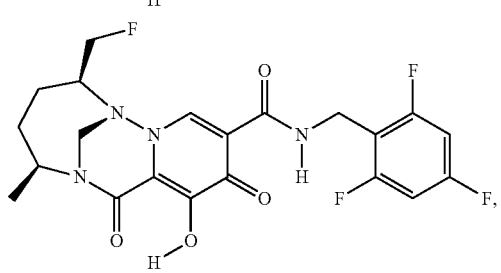
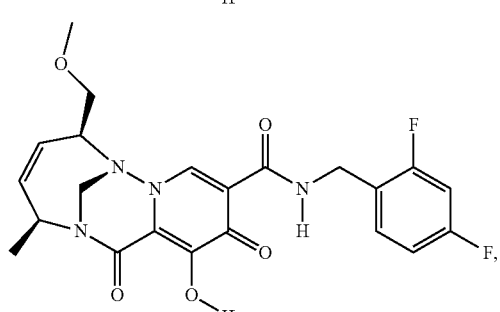
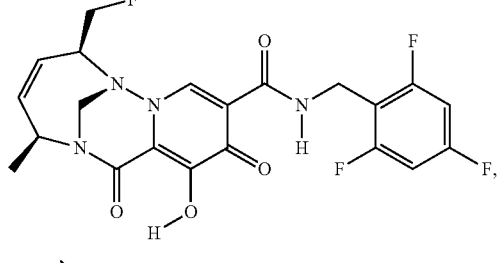
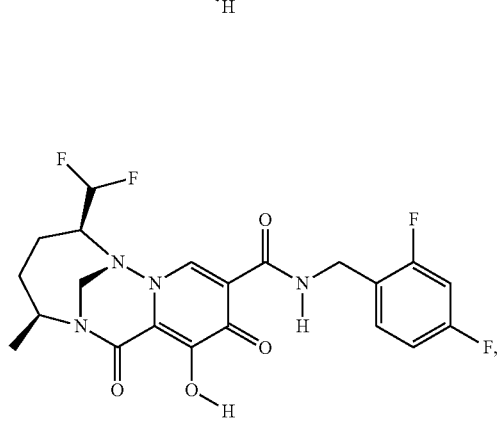
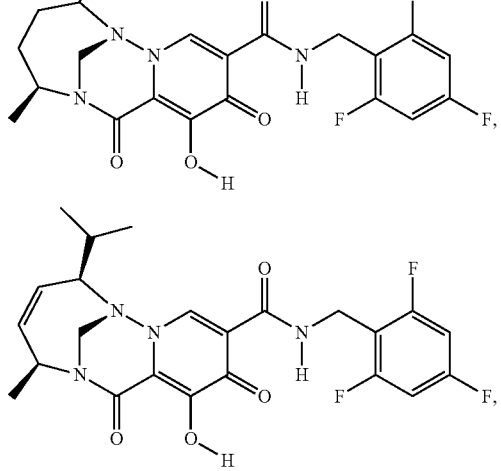
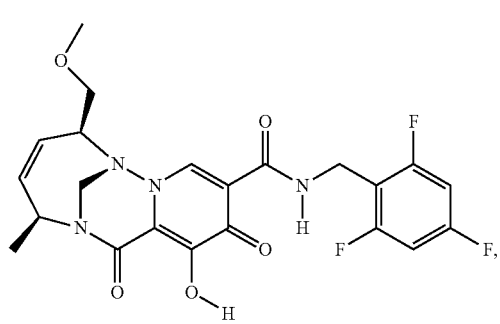
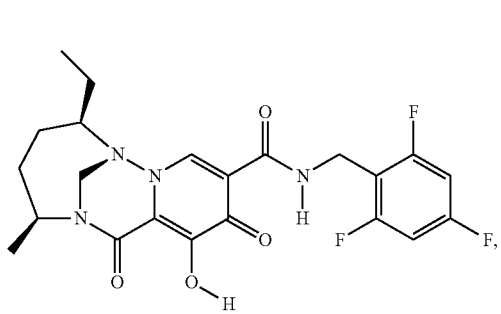

41
-continued
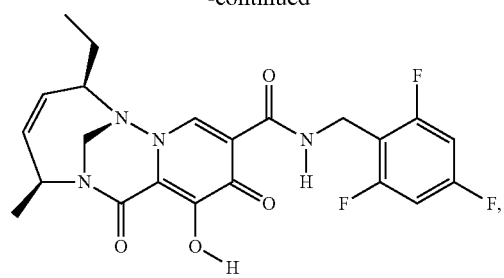
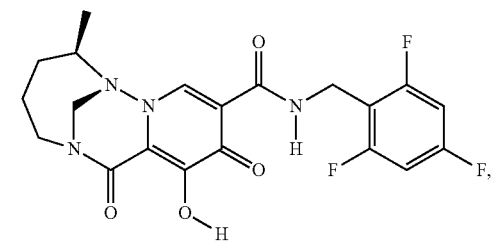
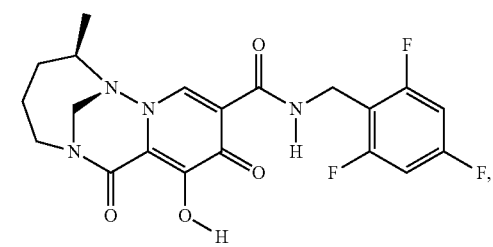
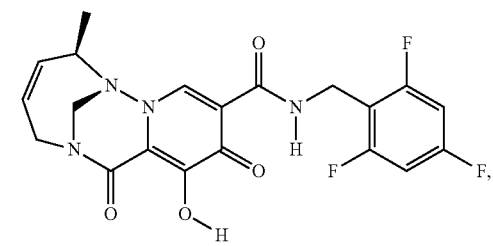
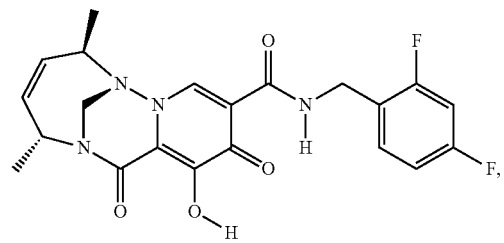
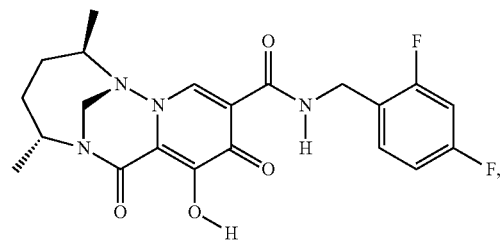
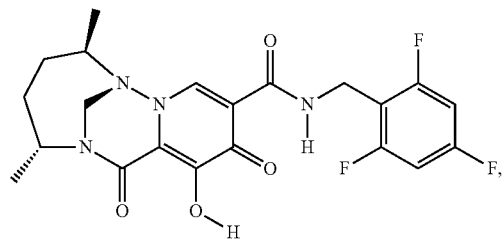
42
-continued
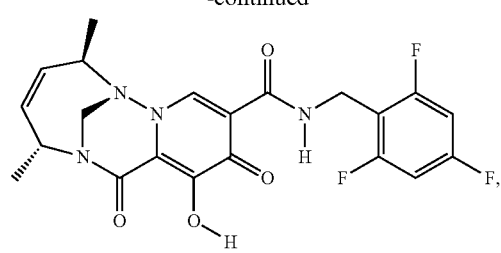
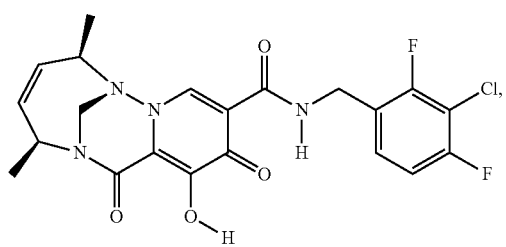
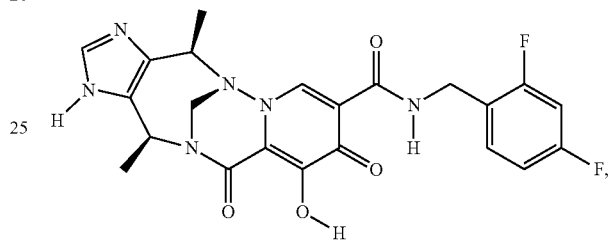
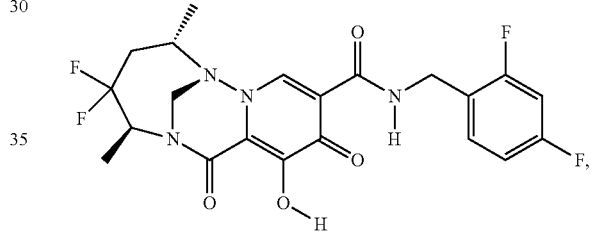
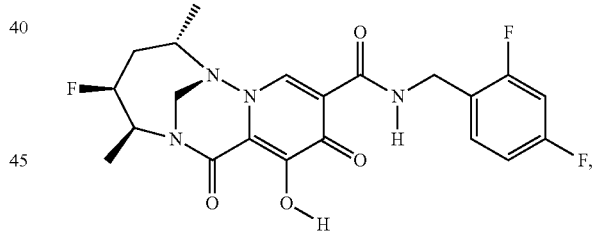
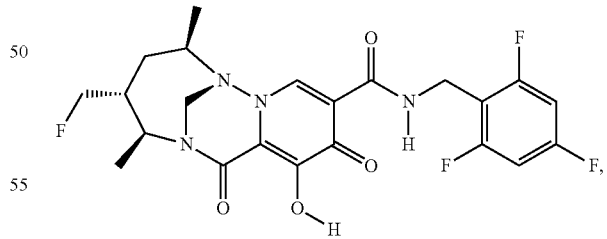
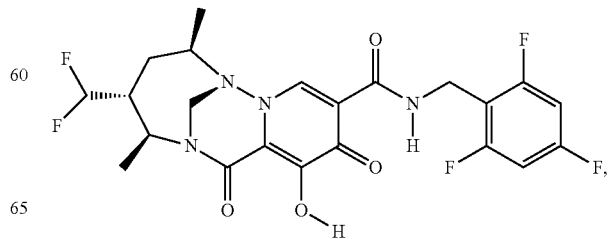

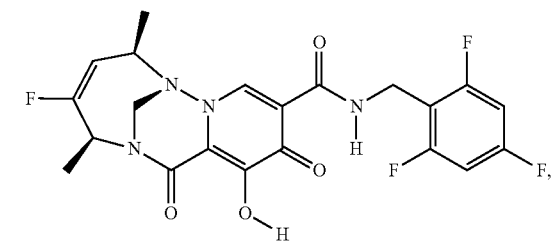
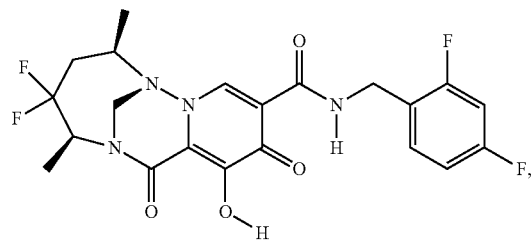
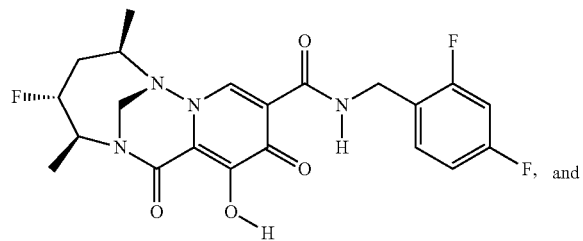
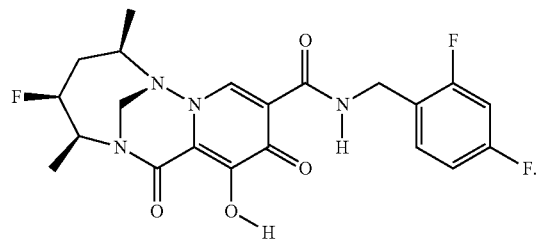
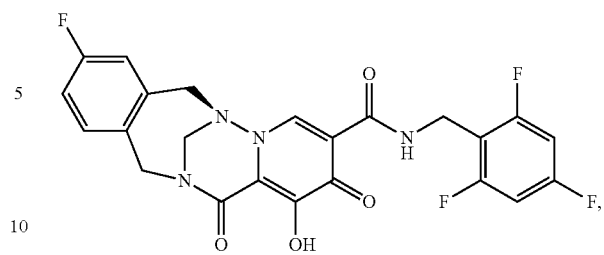
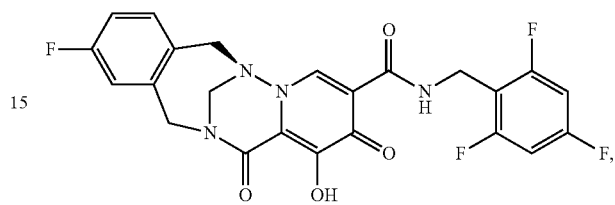
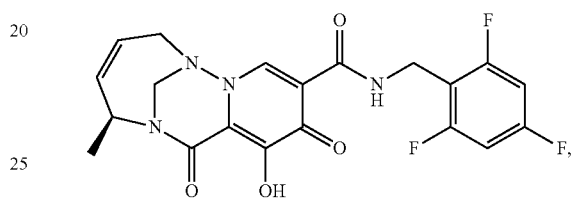
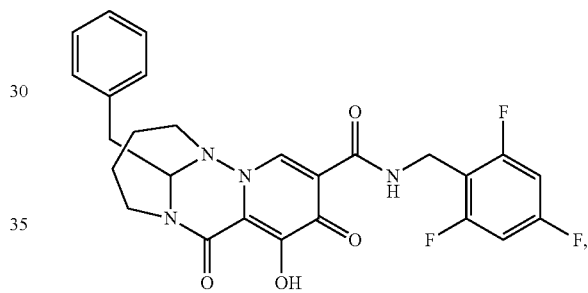
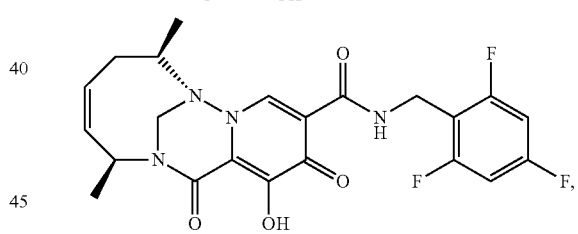
In some embodiments, the compounds of Formula I, Ia, Ib, II, IIa, IIb, III, IIIa, IIIb, IV, IVa, IVb, V, Va, or Vb is selected from the group consisting of:
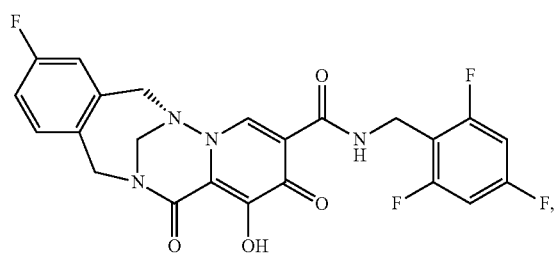
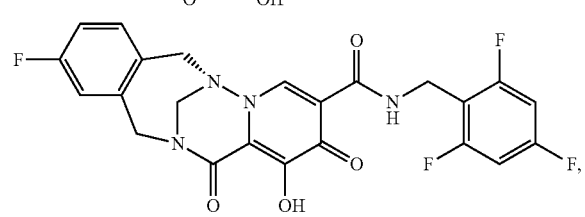
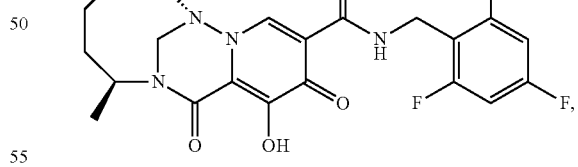
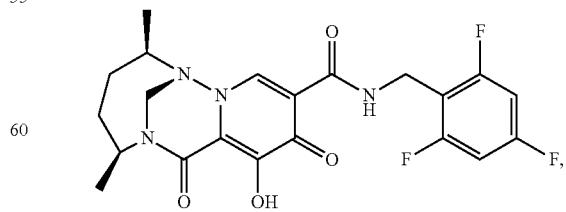

45
-continued
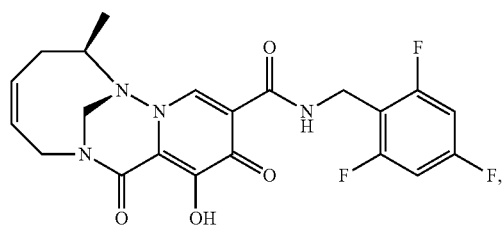
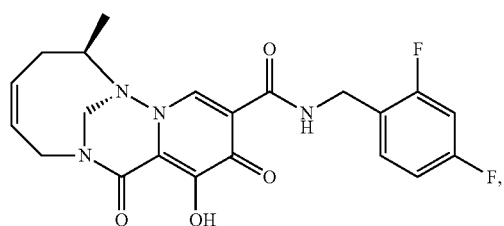
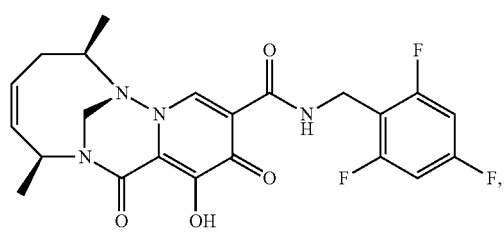
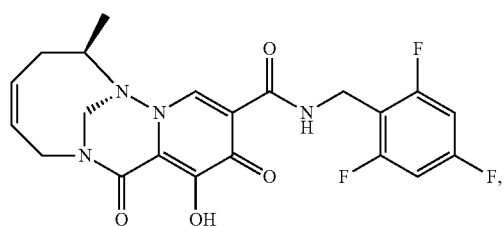
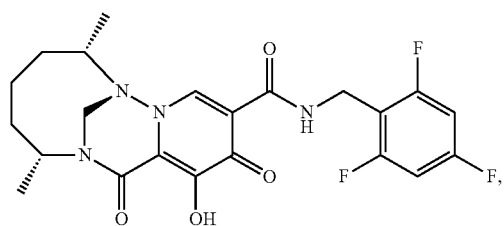
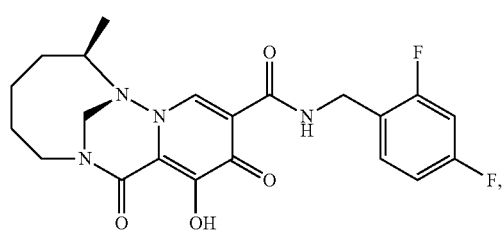
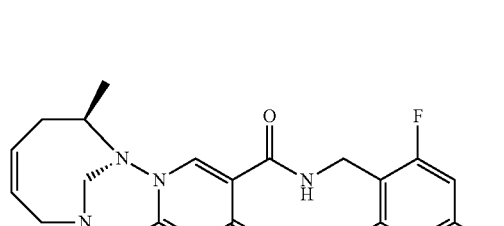
46
-continued
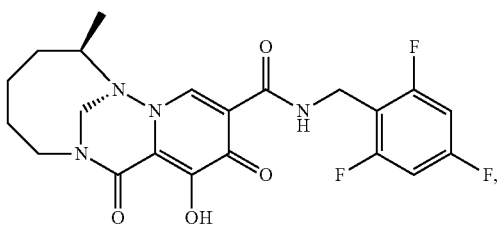
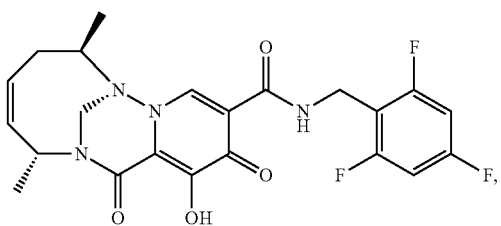
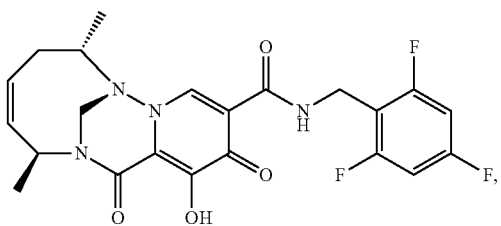
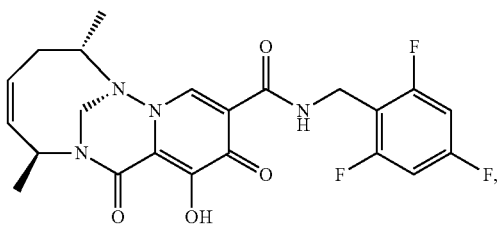
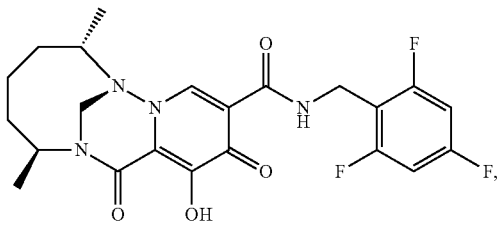
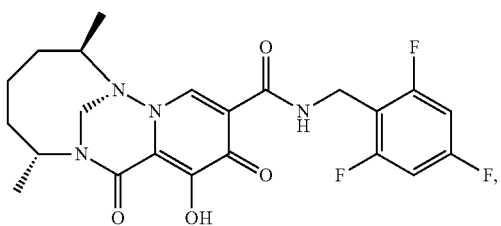
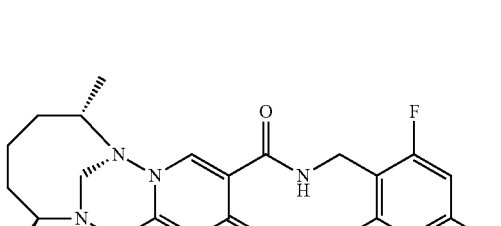

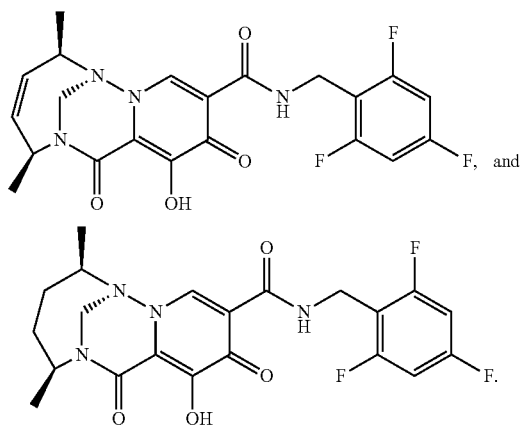
In some embodiments, the compounds of Formula I, Ia, Ib, II, IIa, IIb, III, IIIa, IIIb, IV, IVa, IVb, V, Va, or Vb is selected from the group consisting of:
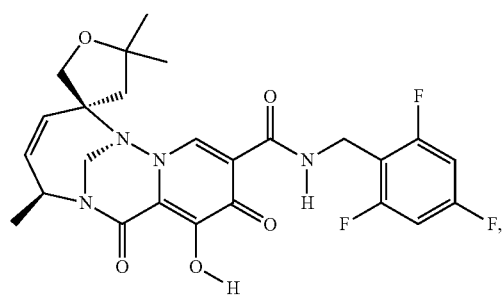
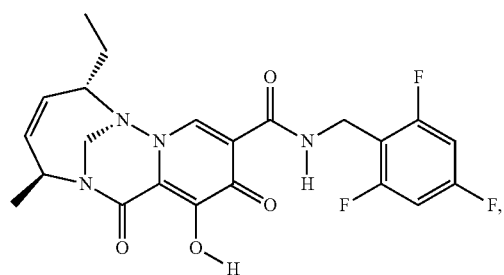
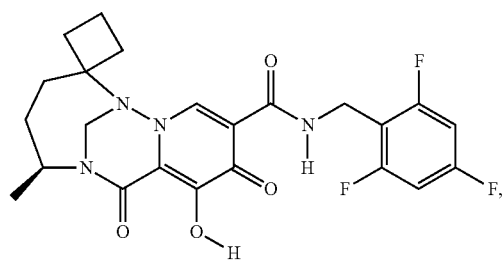
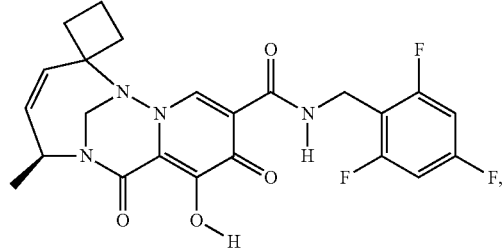
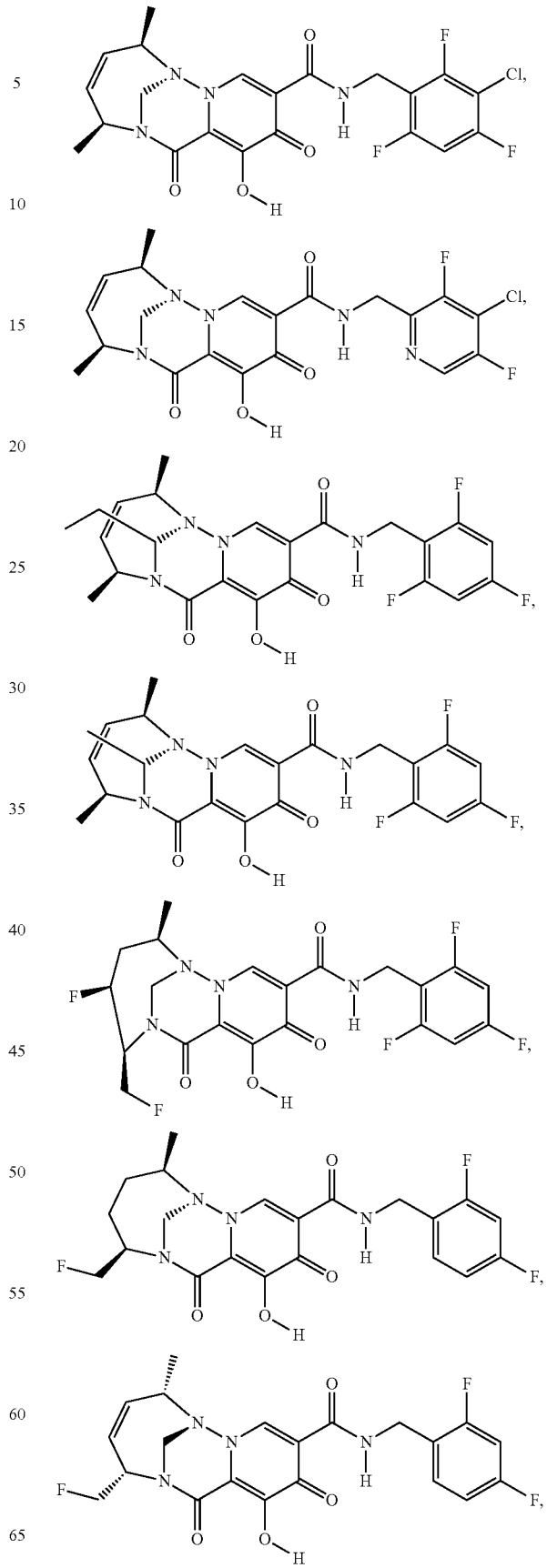

49
-continued
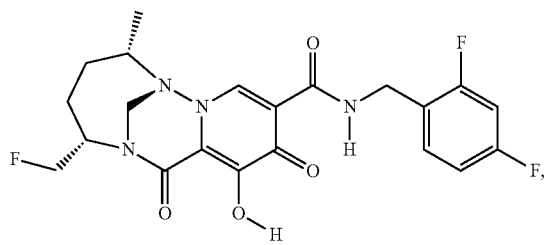
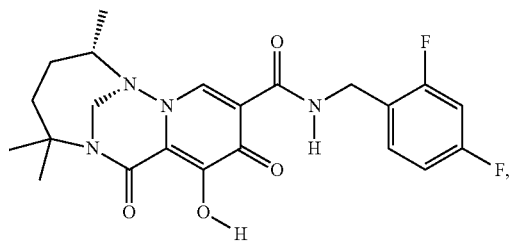
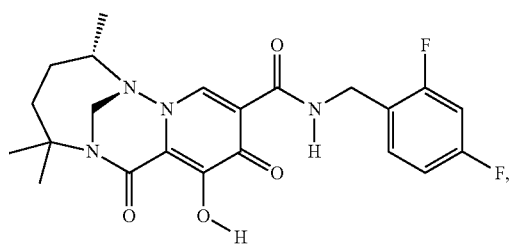
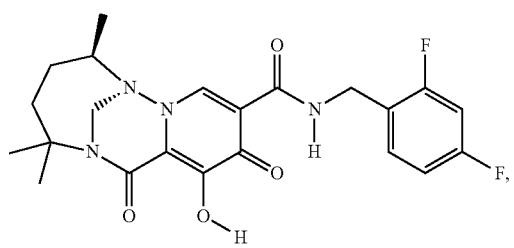
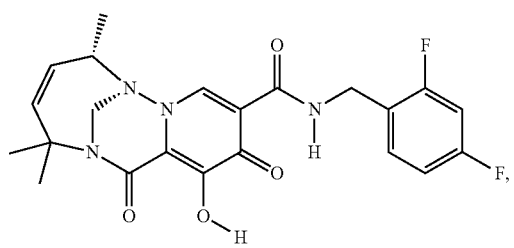
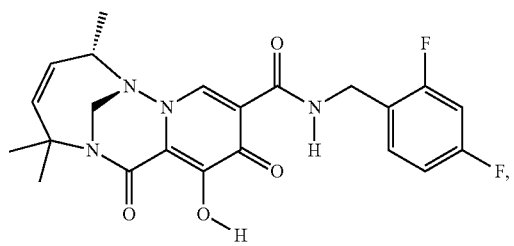
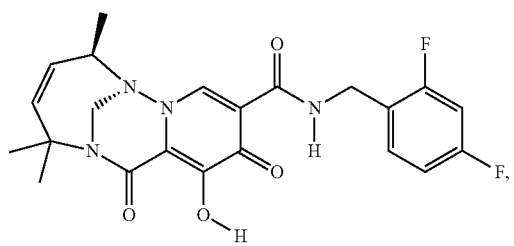
50
-continued
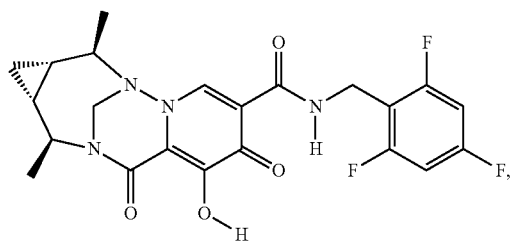
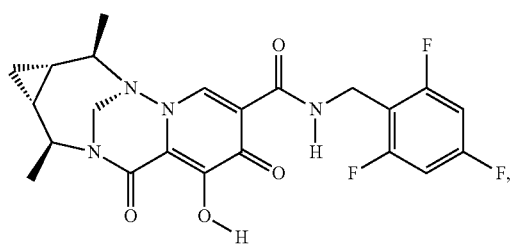
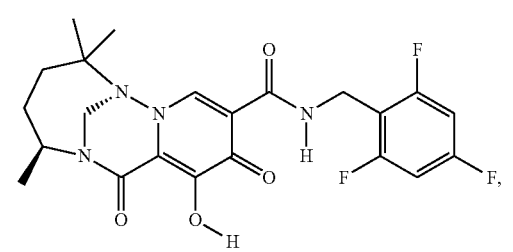
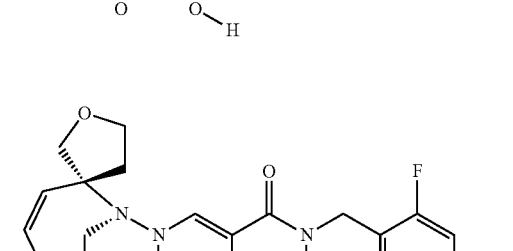
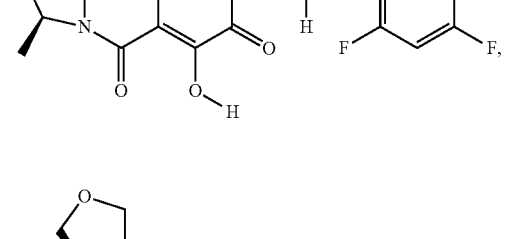
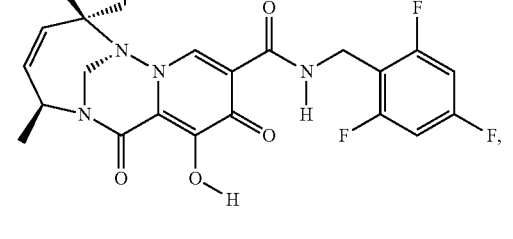

51
-continued
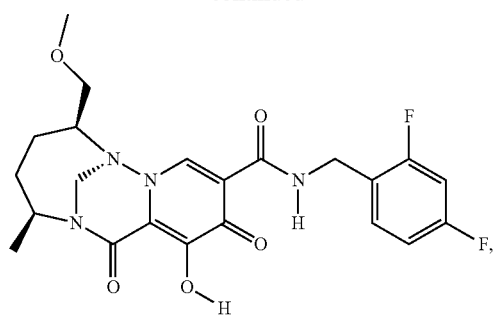
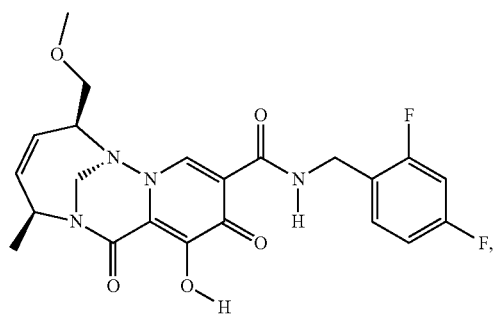
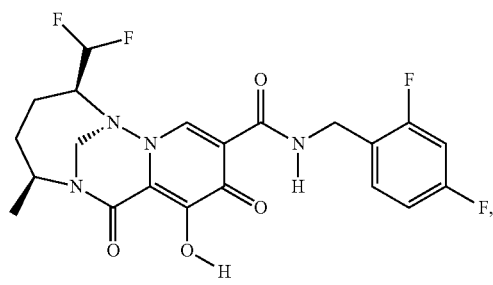
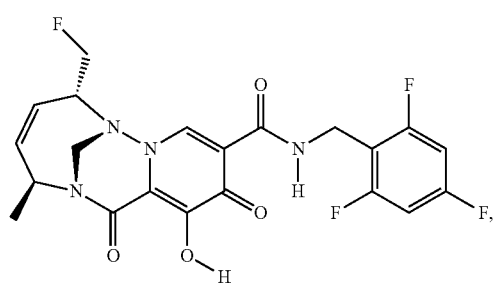
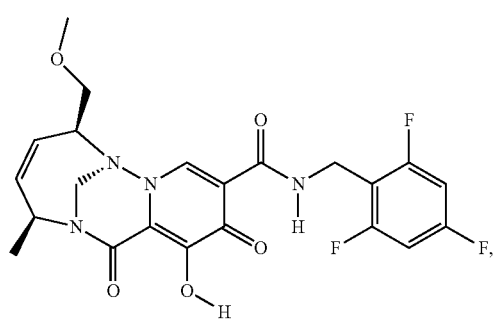
52
-continued
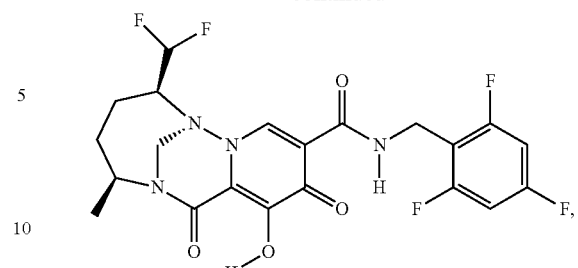
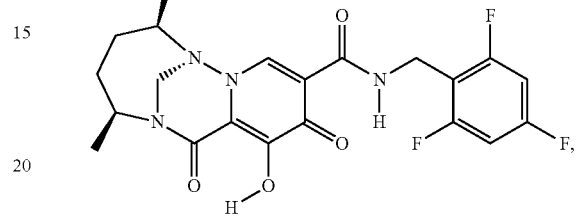
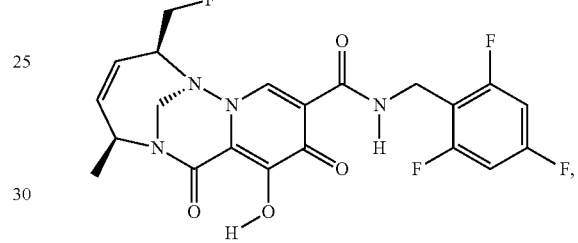
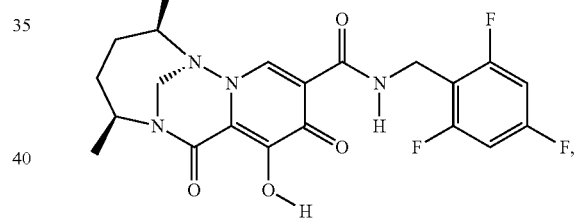
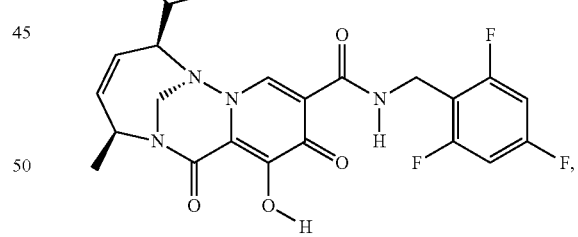
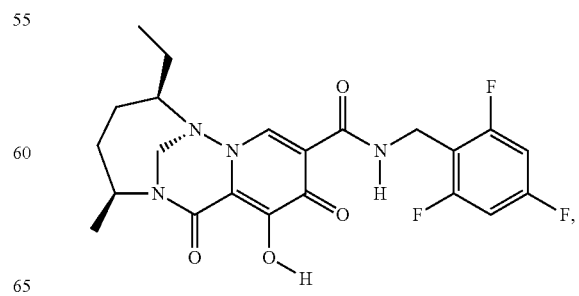

53
-continued
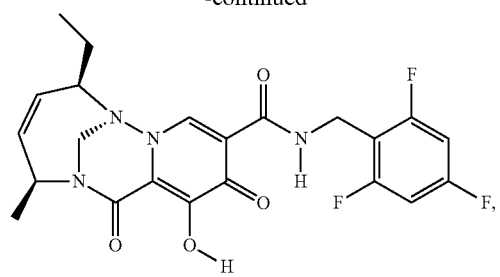
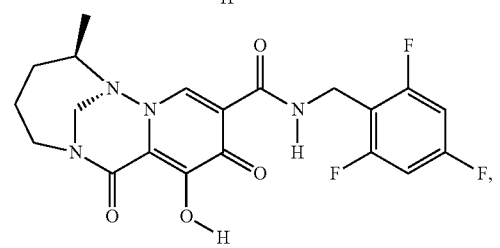
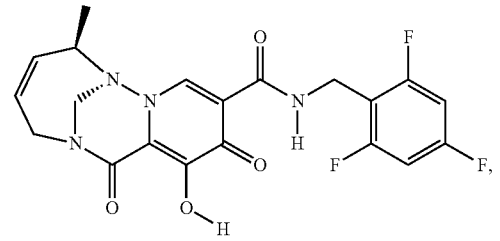
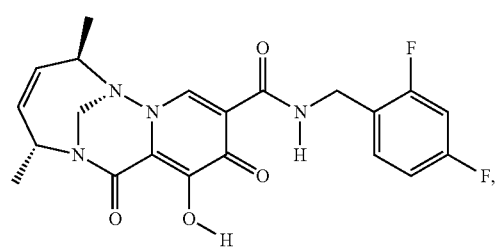
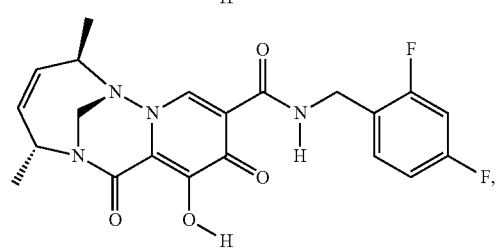
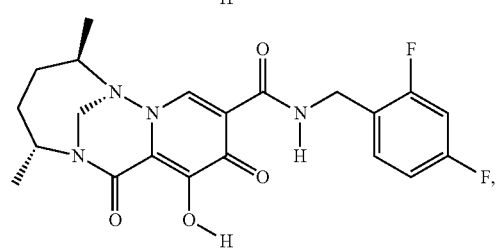
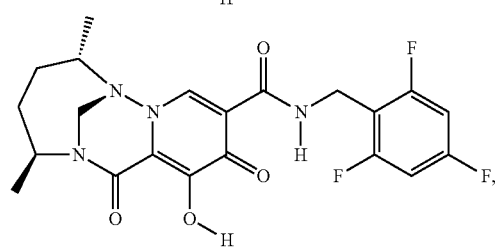
54
-continued
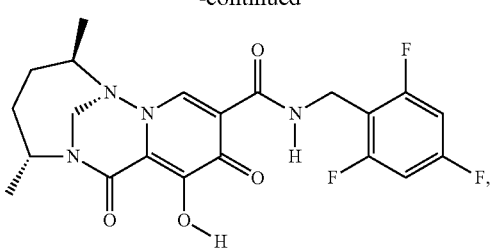
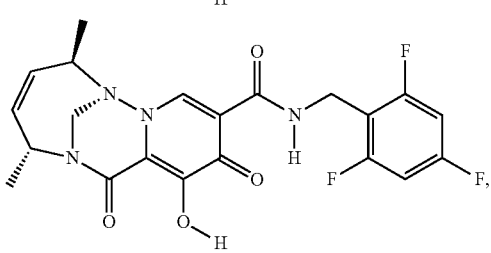
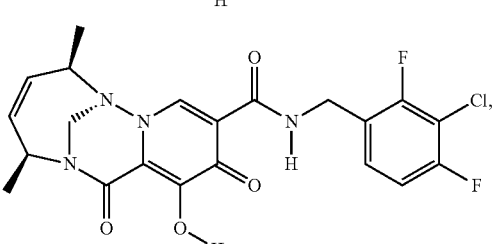
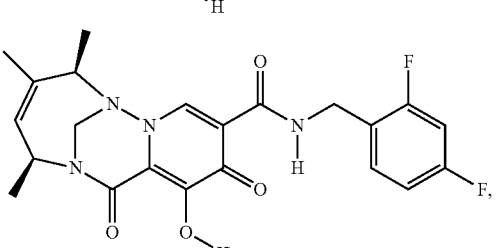
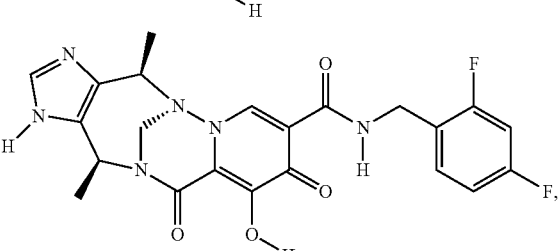
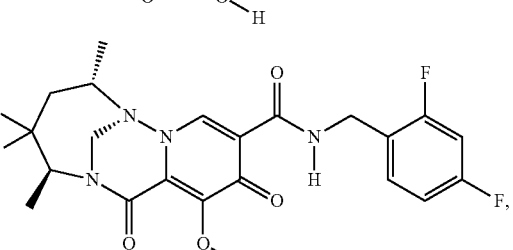
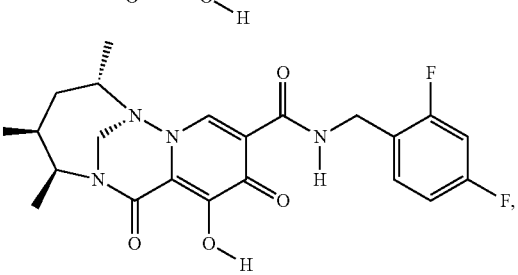

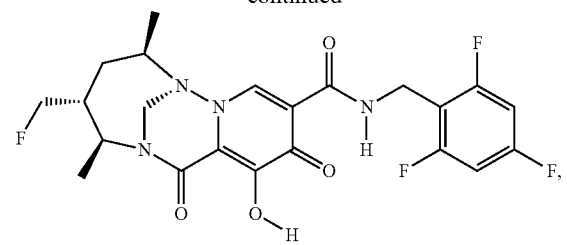
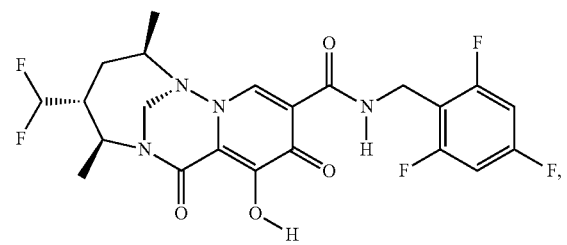
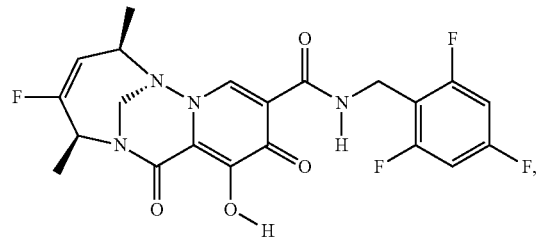
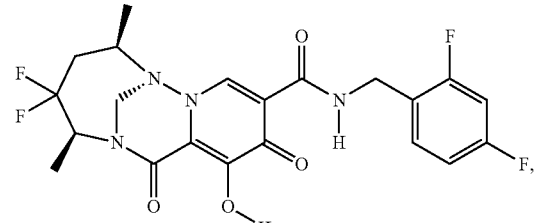
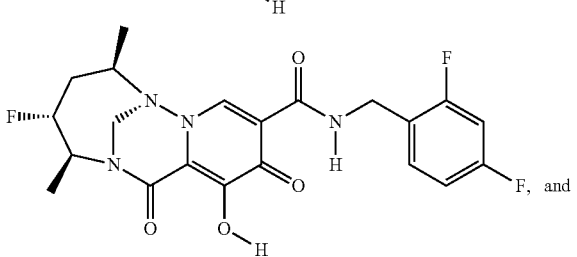
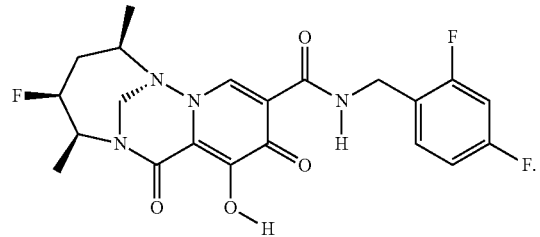, and
In some embodiments, the compounds of Formula I, Ia, Ib, II, IIa, IIb, III, IIIa, IIIb, IV, IVa, IVb, V, Va, or Vb is selected from the group consisting of:
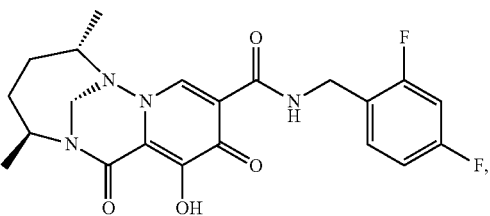
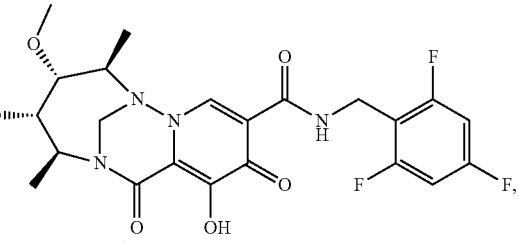
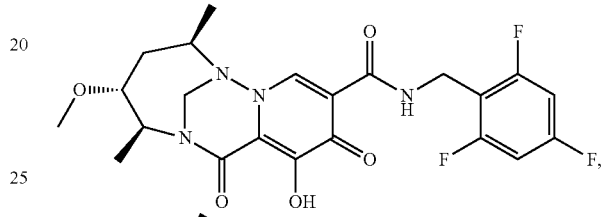
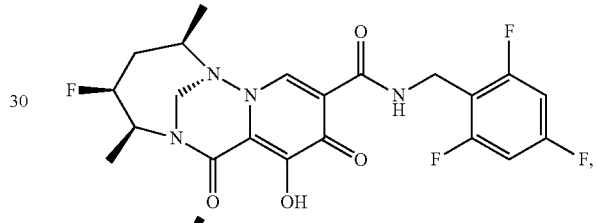
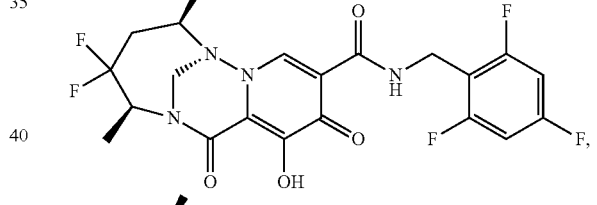
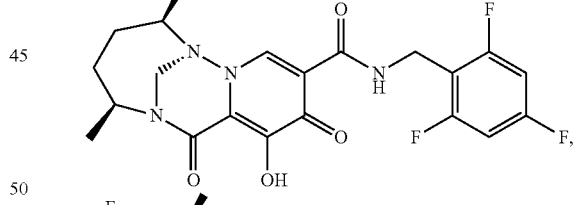
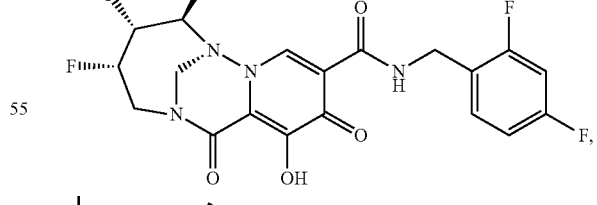
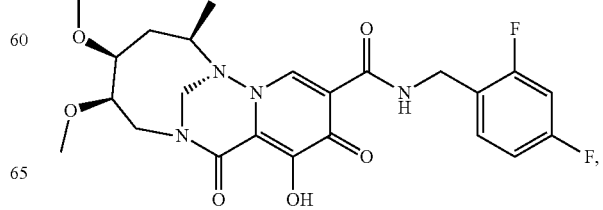

57
-continued
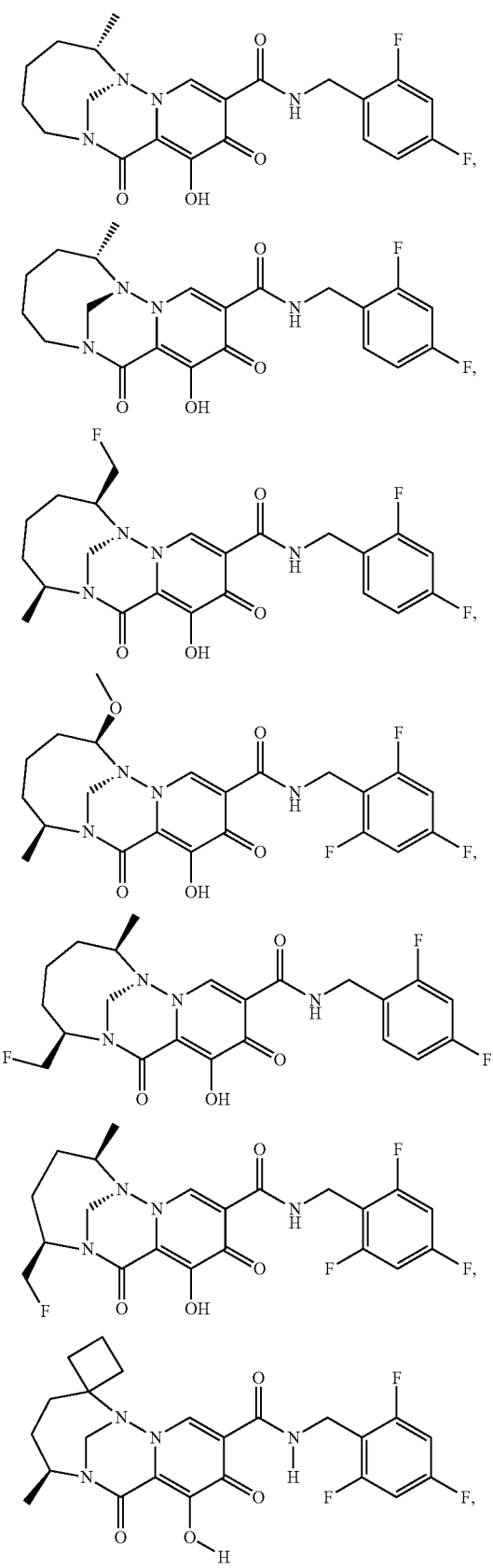
58
-continued
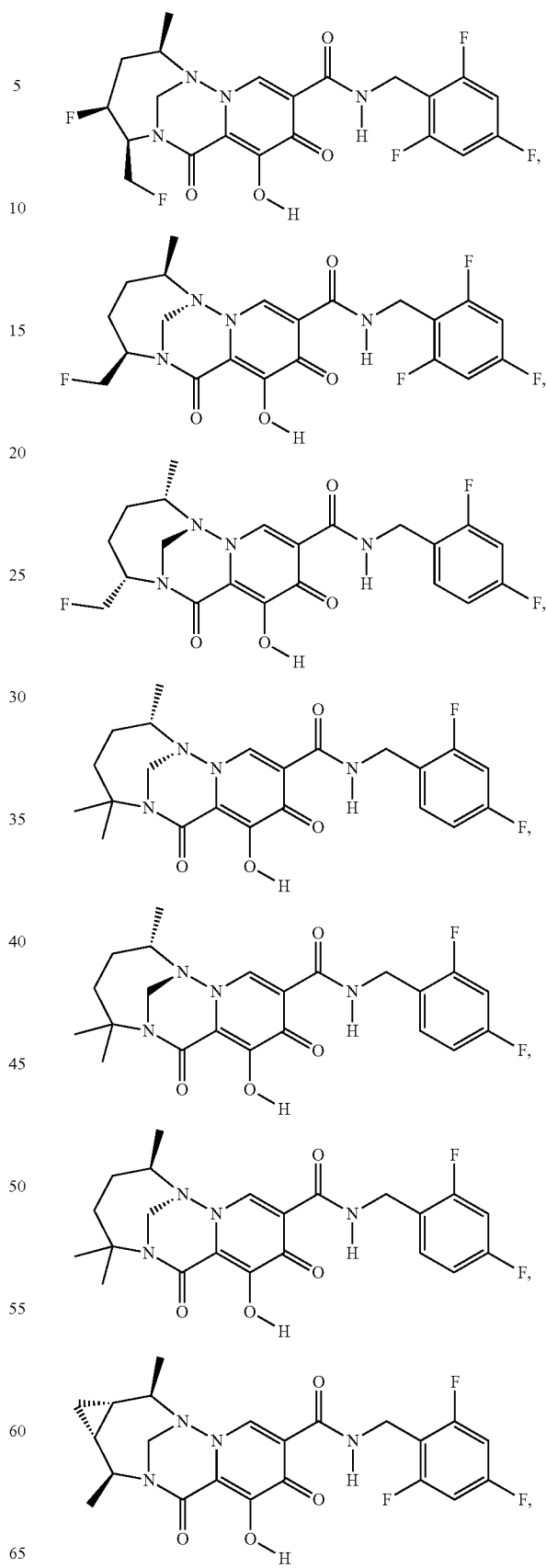

59
-continued
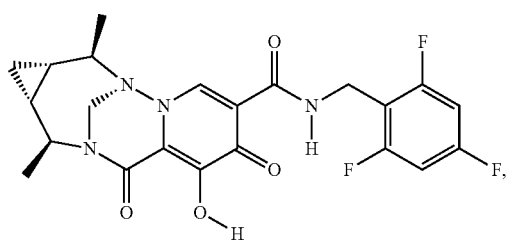
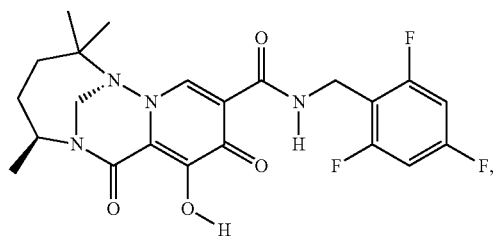
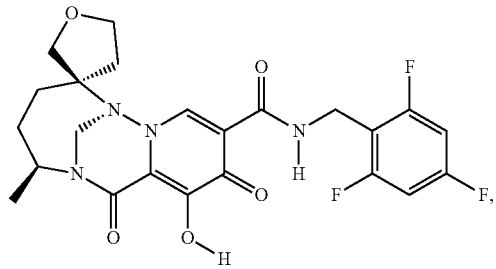
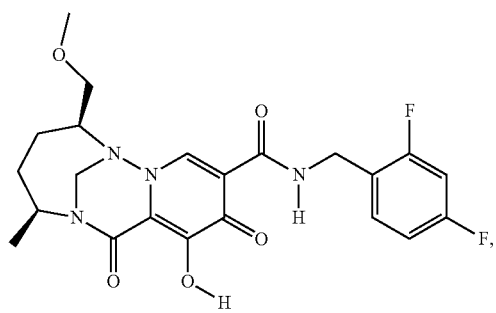
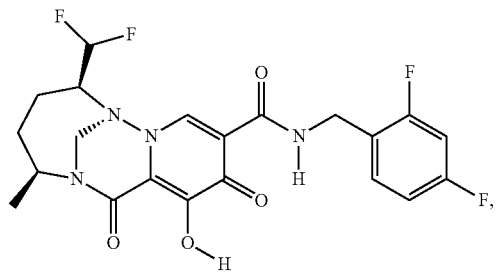
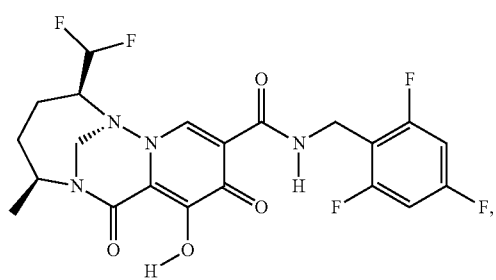
60
-continued
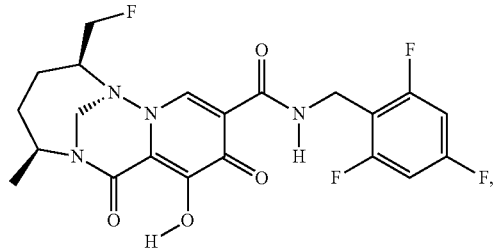
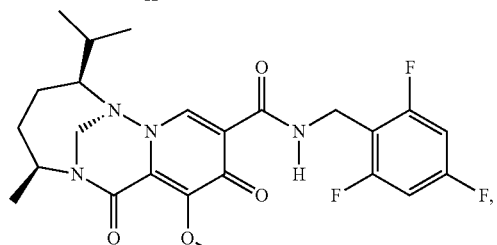
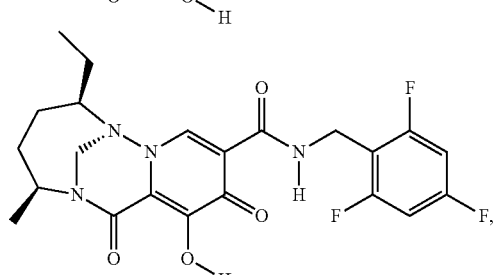
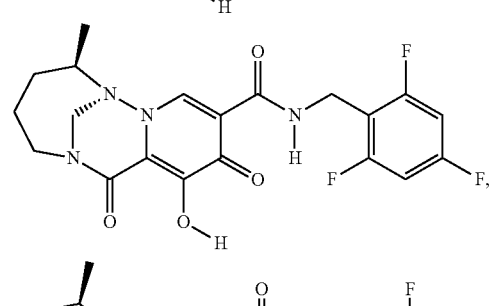
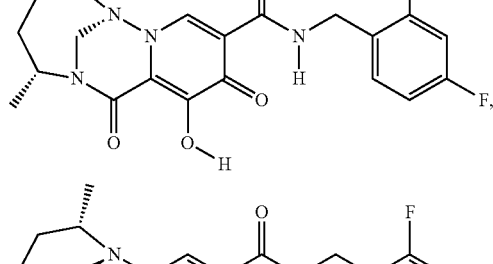
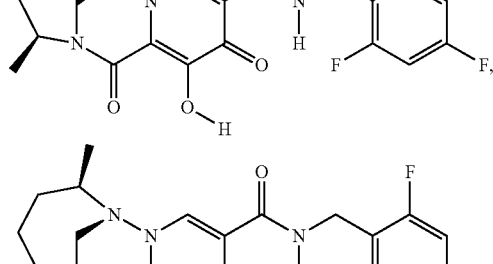

61
-continued
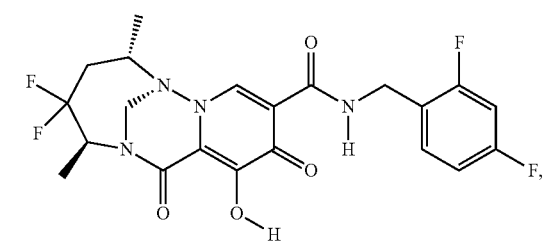
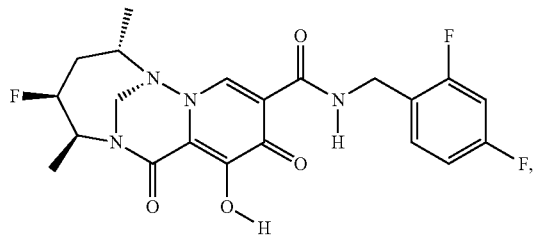
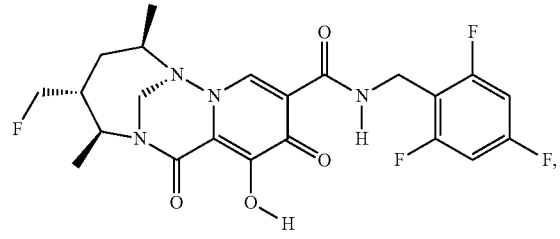
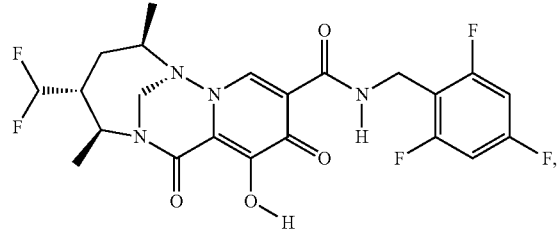
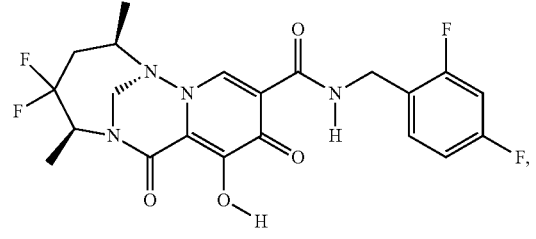
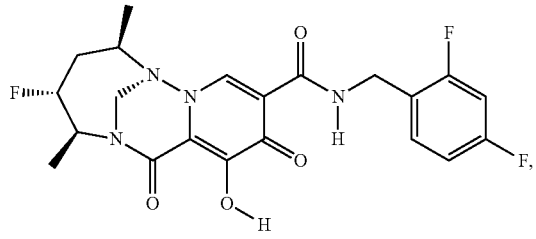
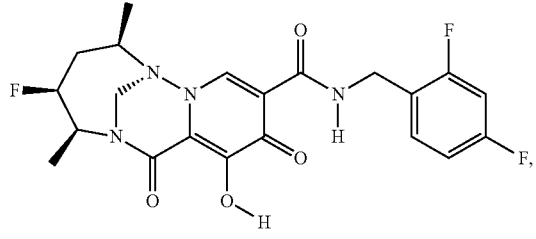
62
-continued
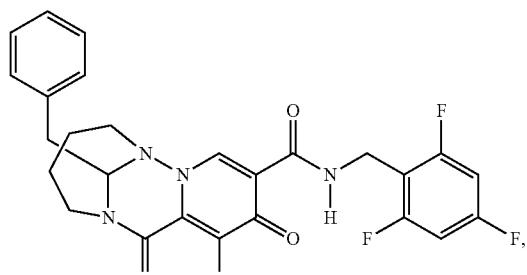
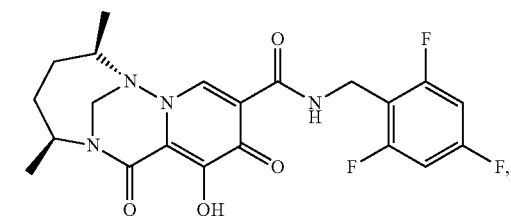
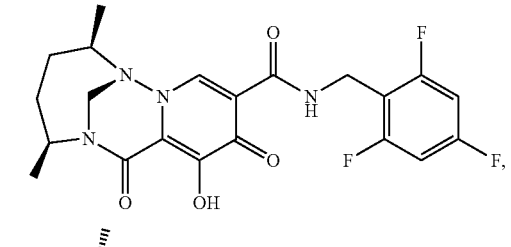
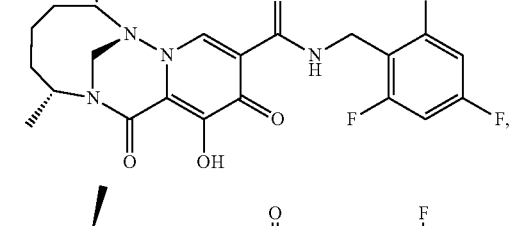
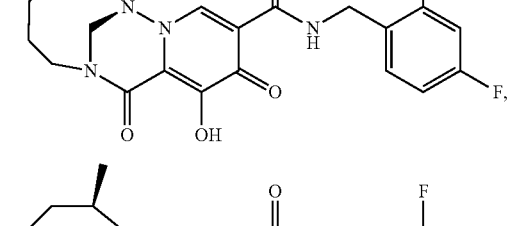
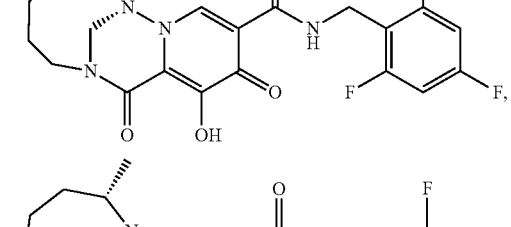
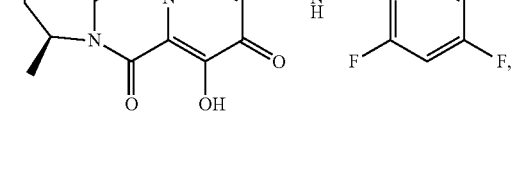

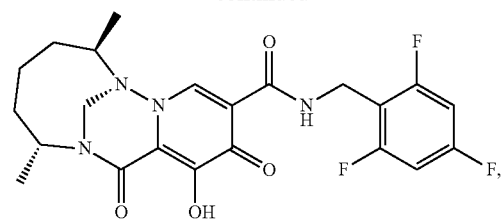
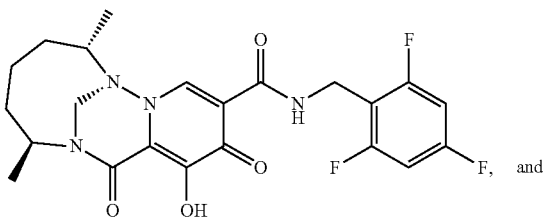 and
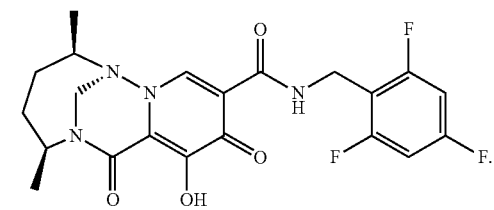
In some embodiments, the compounds of Formula I, Ia, Ib, II, IIa, IIb, III, IIIa, IIIb, IV, IVa, IVb, V, Va, or Vb is selected from the group consisting of:
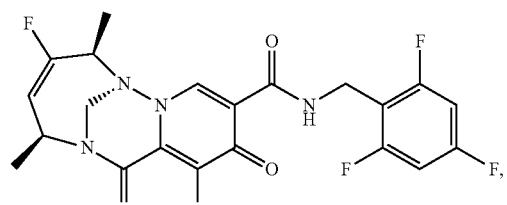
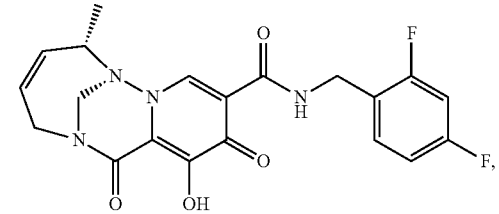
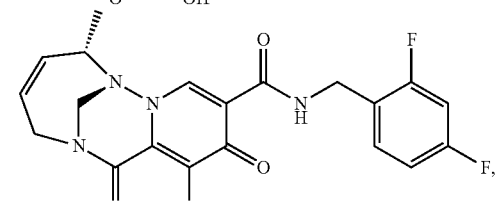
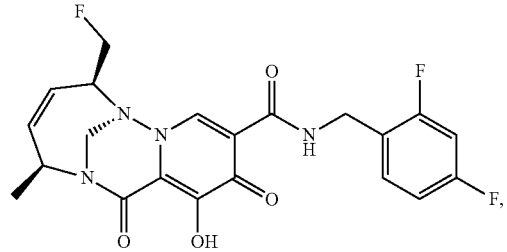
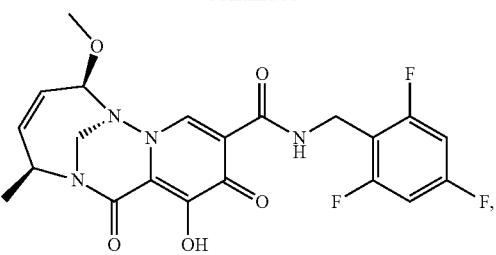
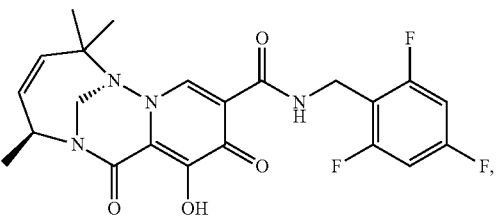
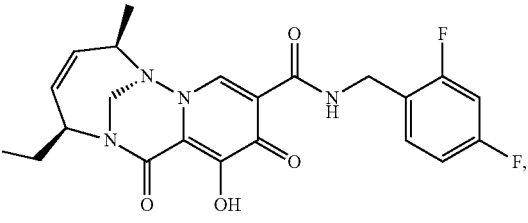
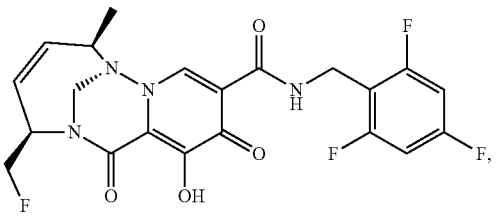
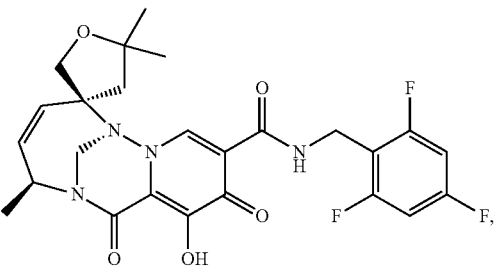
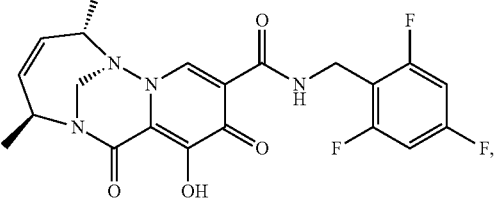
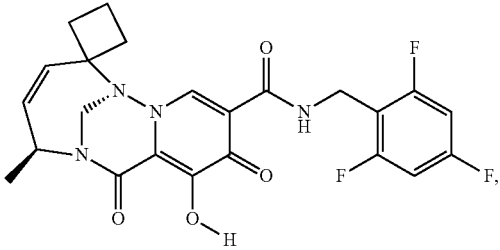

65
-continued
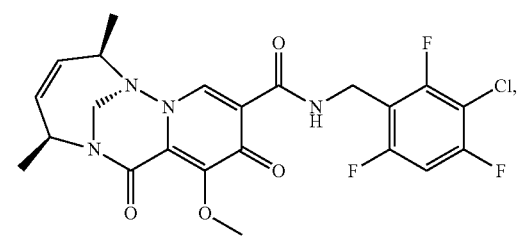
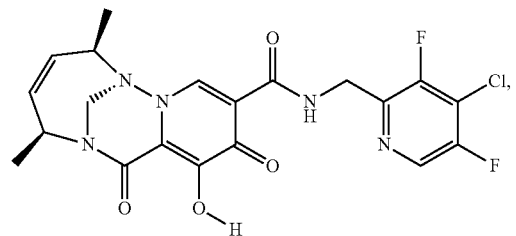
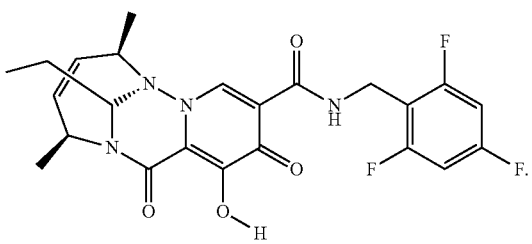
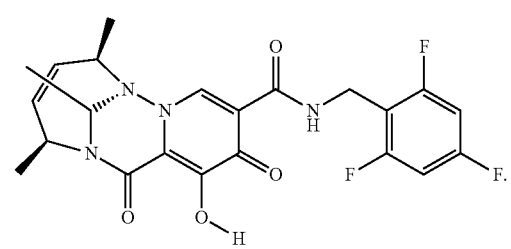
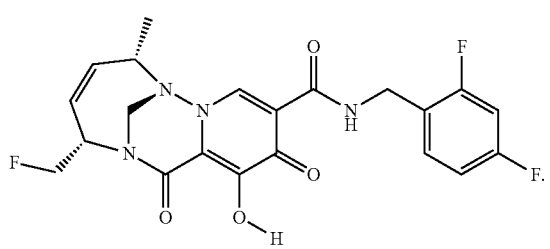
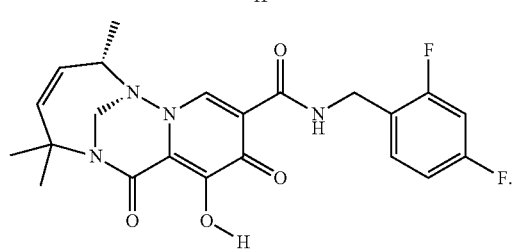
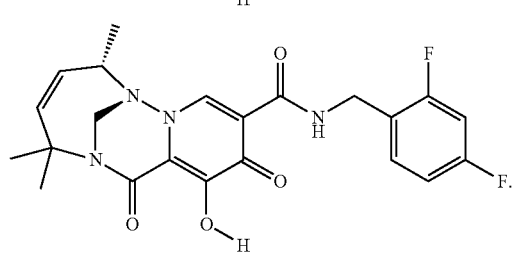
66
-continued
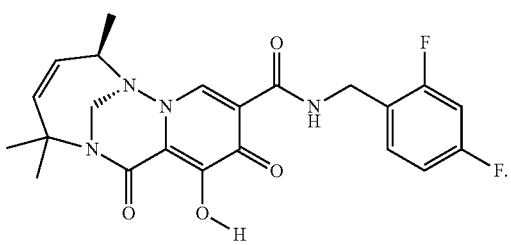
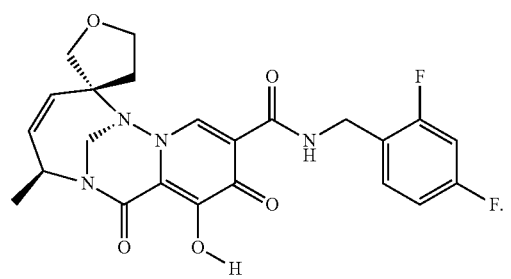
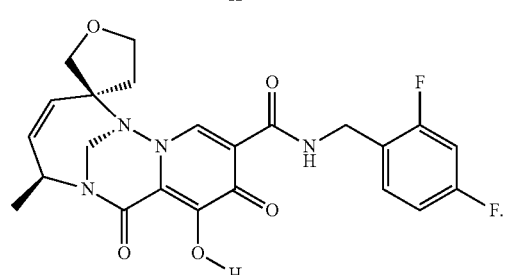
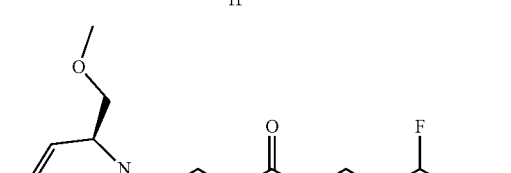
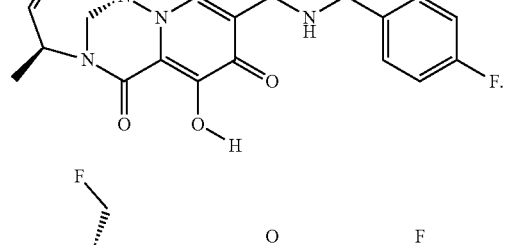
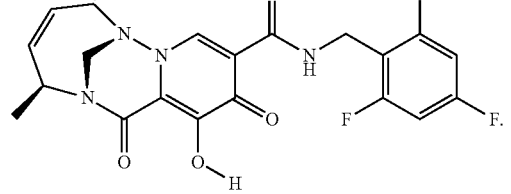
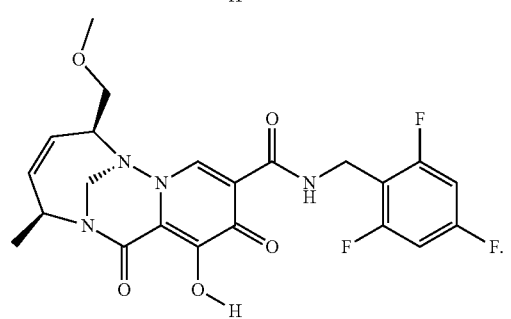

67
-continued
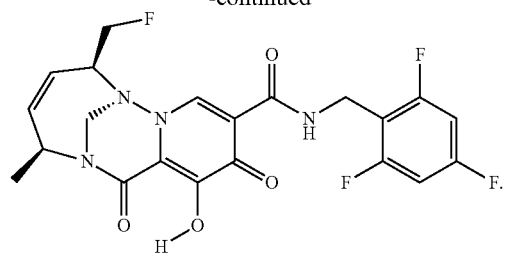
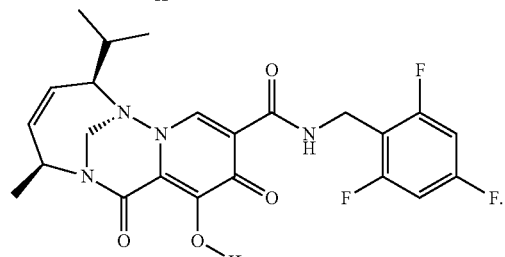
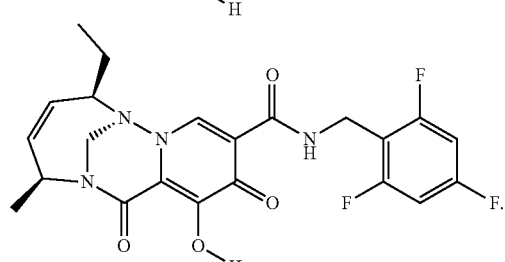
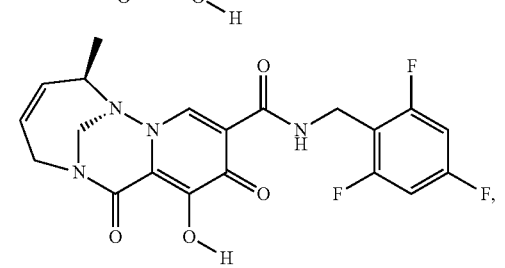
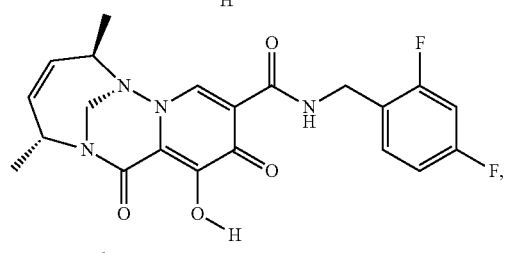
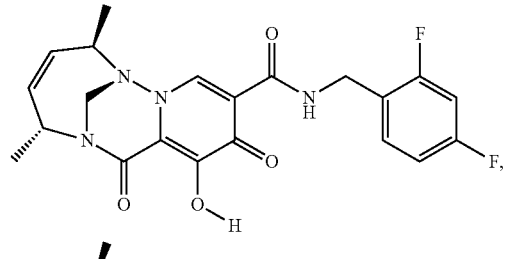
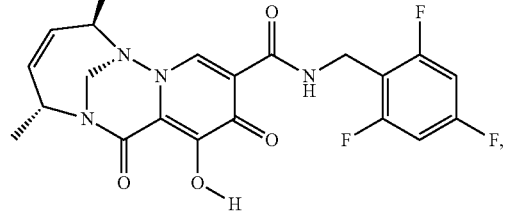
68
-continued
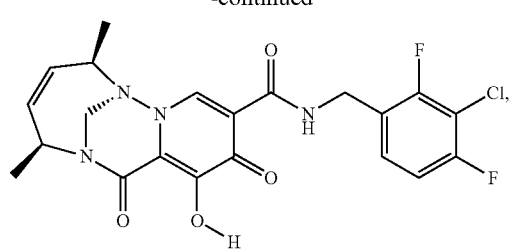
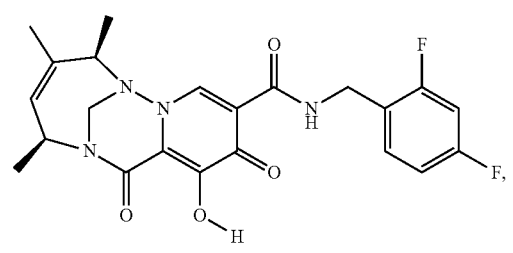
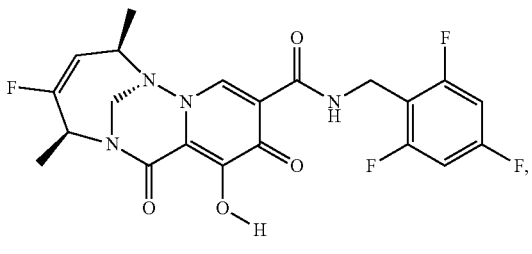
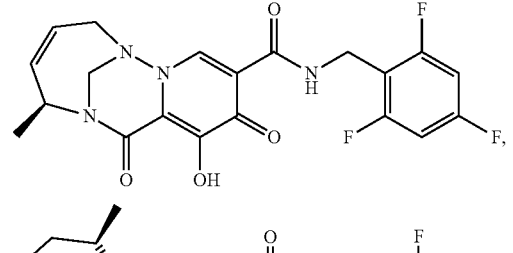
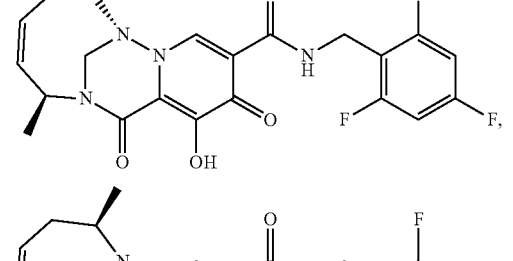
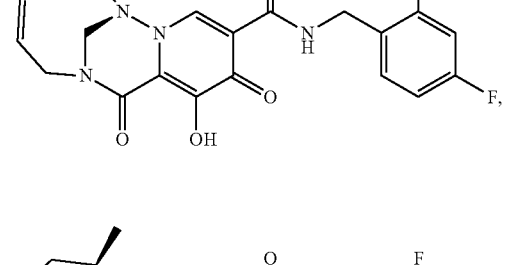
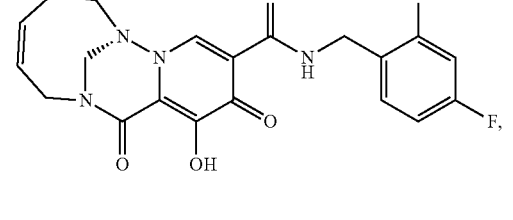

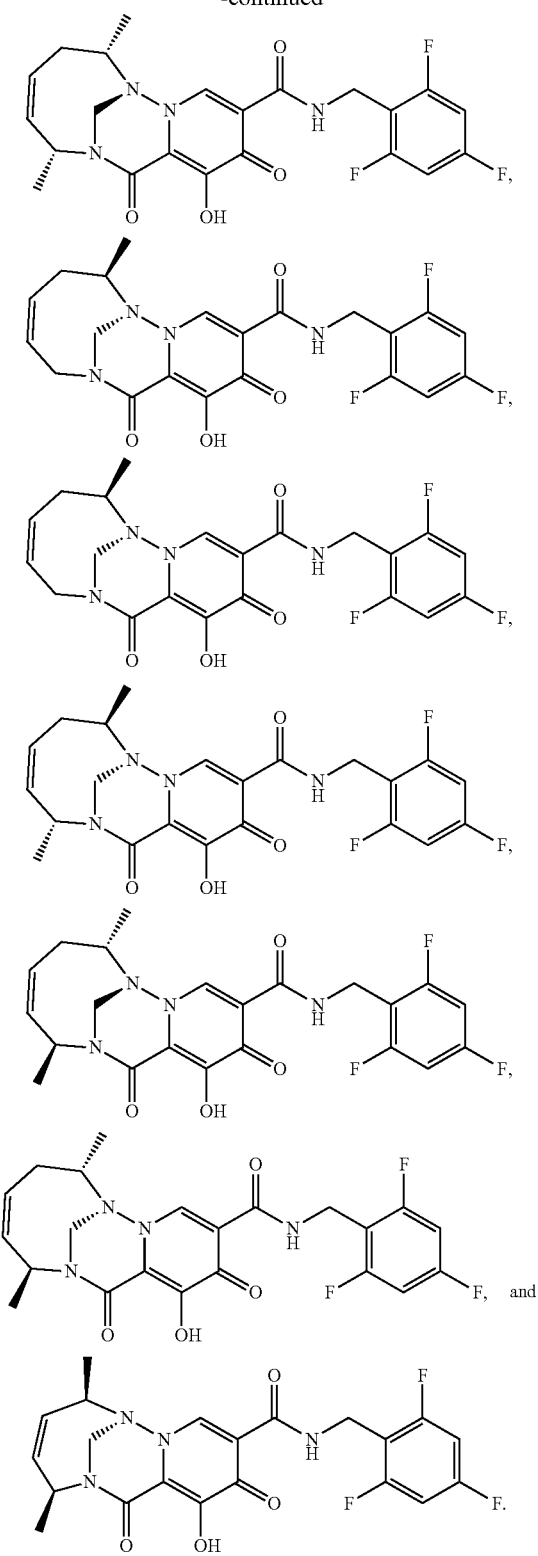
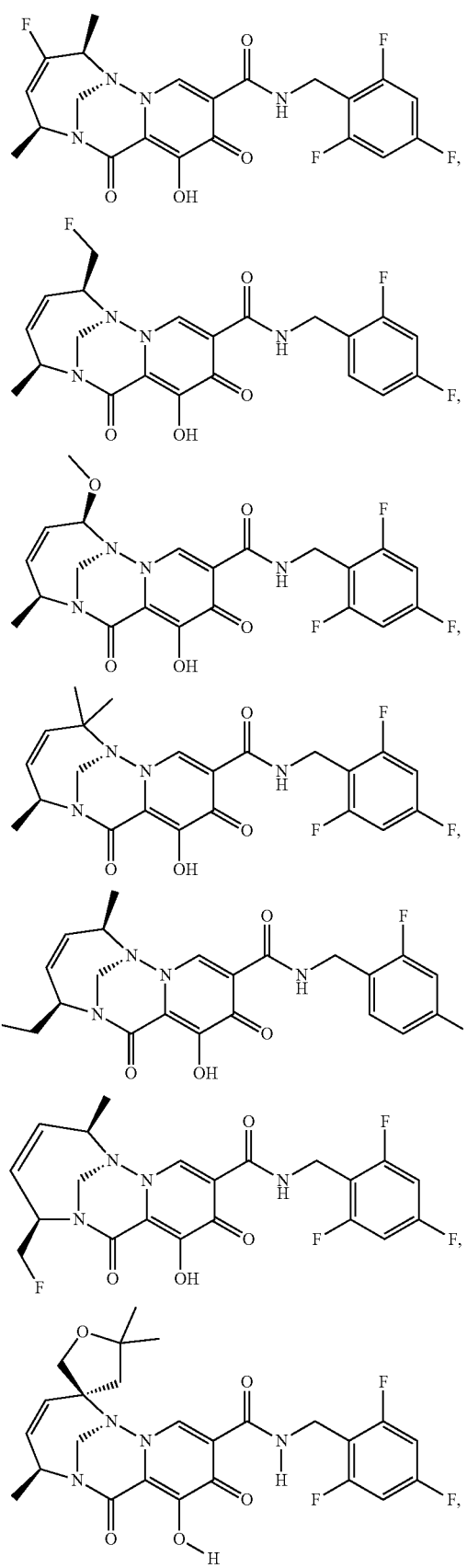
In some embodiments, the compounds of Formula I, Ia, Ib, II, IIa, IIb, III, IIIa, IIIb, IV, IVa, IVb, V, Va, or Vb is selected from the group consisting of:

71
-continued
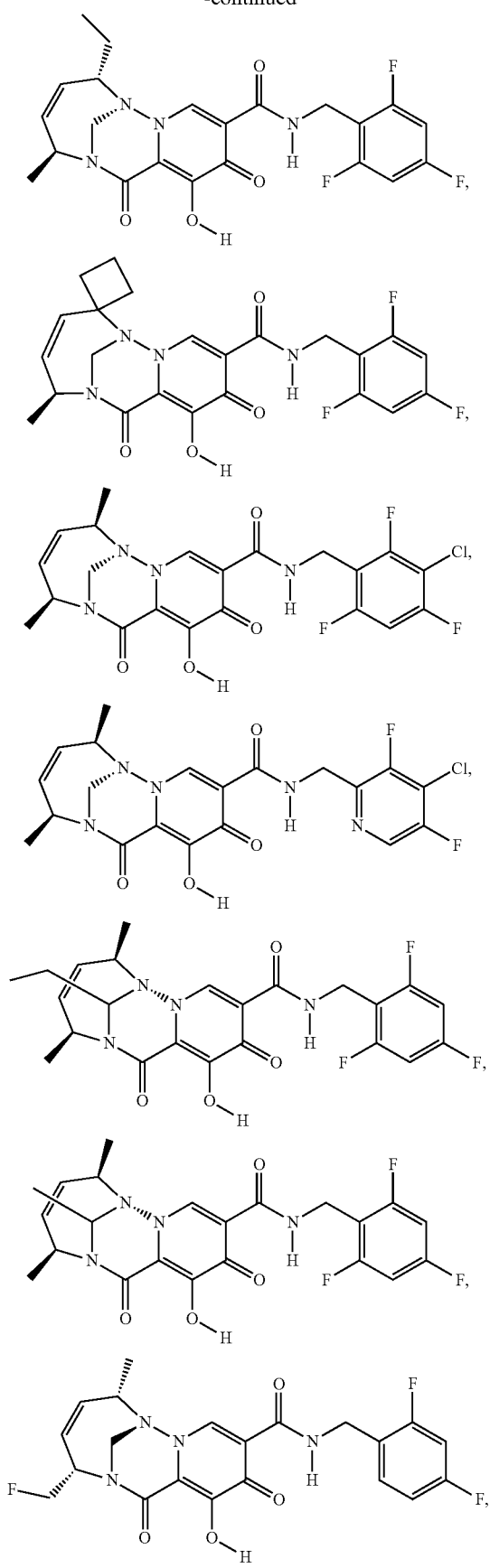
72
-continued
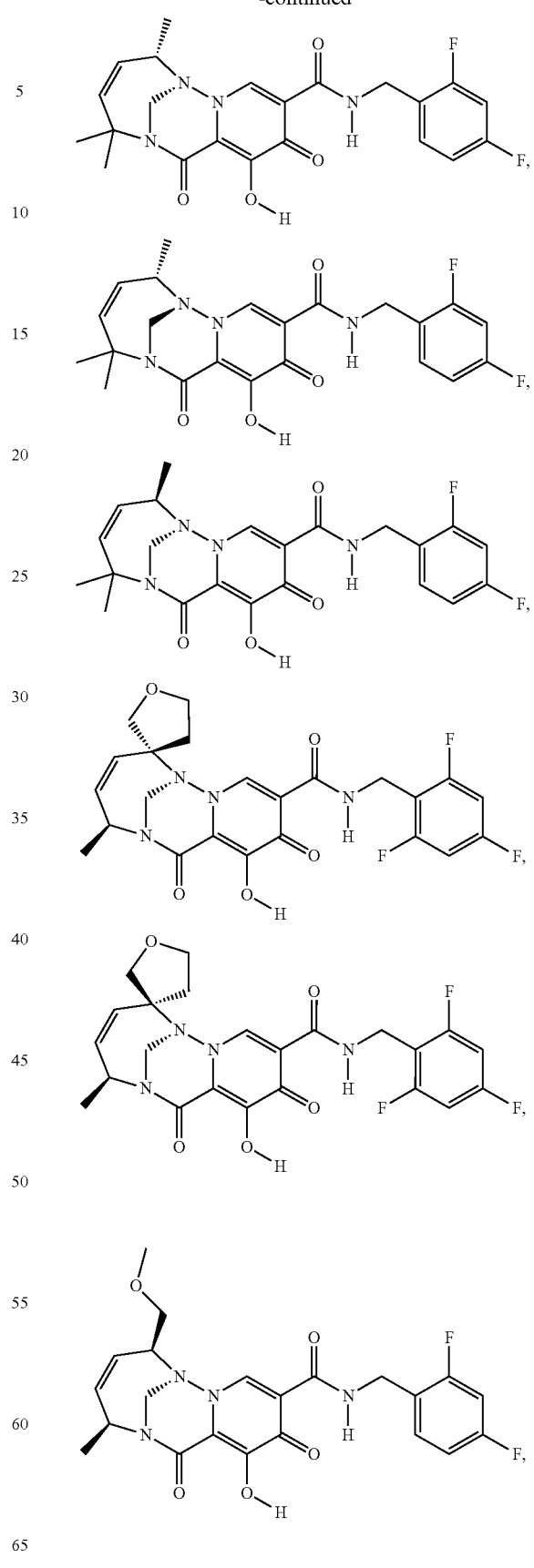

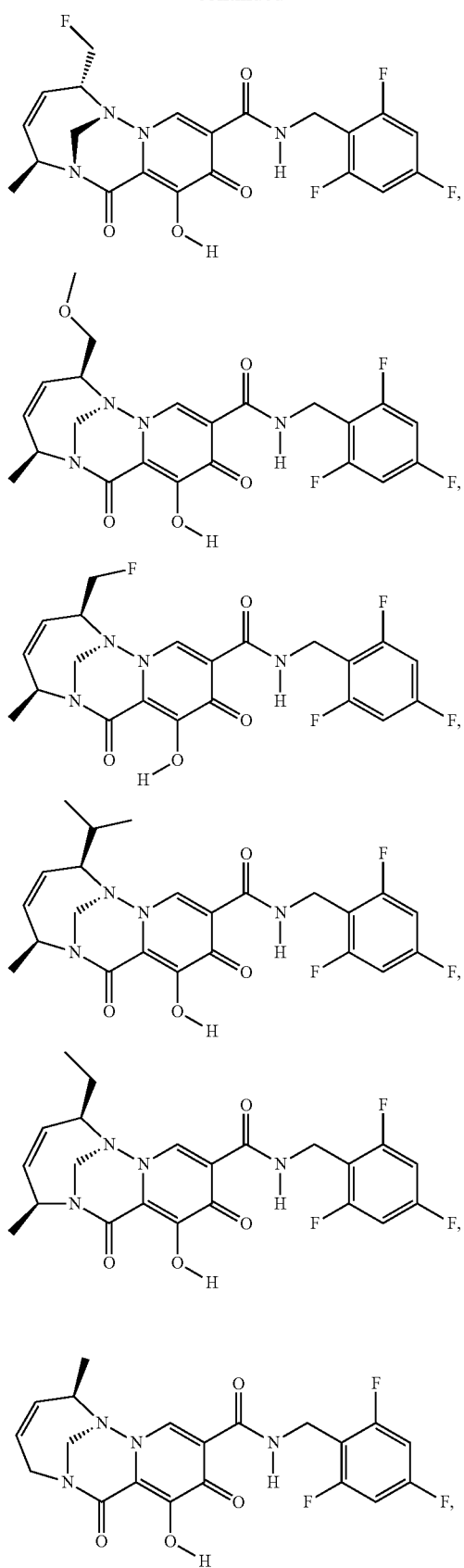
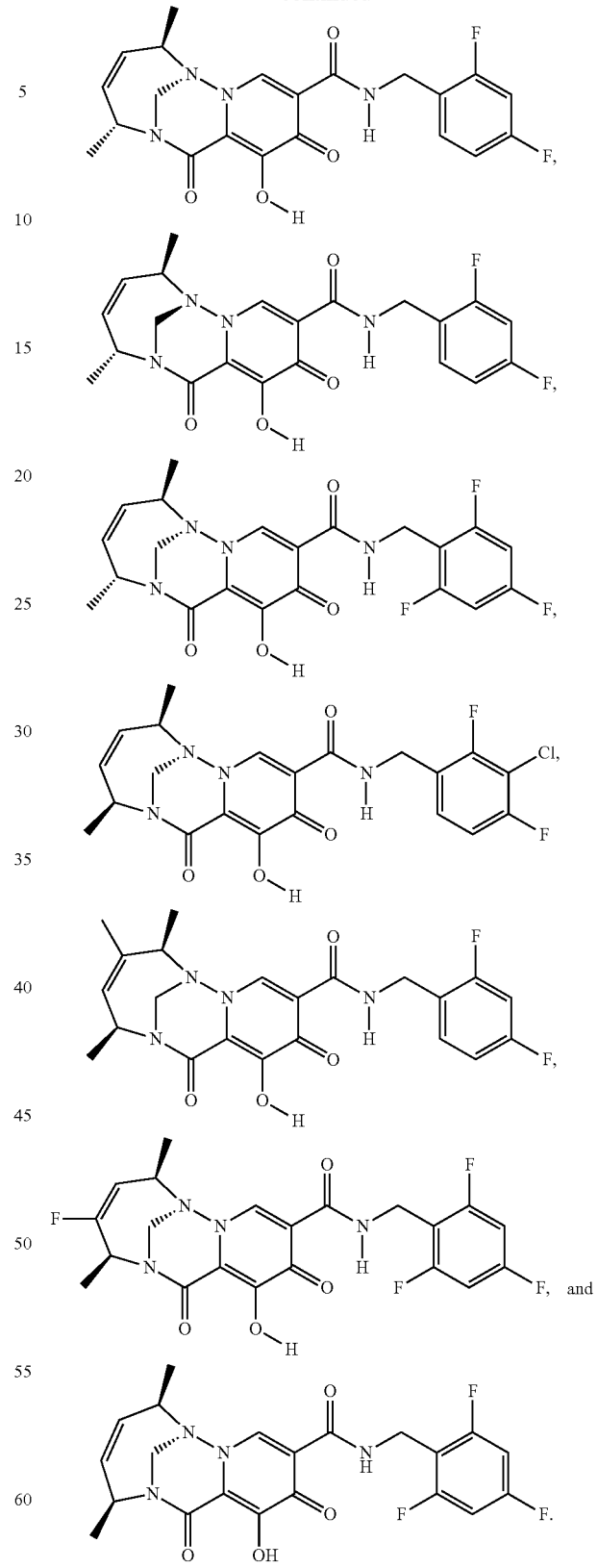
In some embodiments, the compounds of Formula I, Ia, Ib, II, IIa, IIb, III, IIIa, IIIb, IV, IVa, IVb, V, Va, or Vb is selected from the group consisting of:

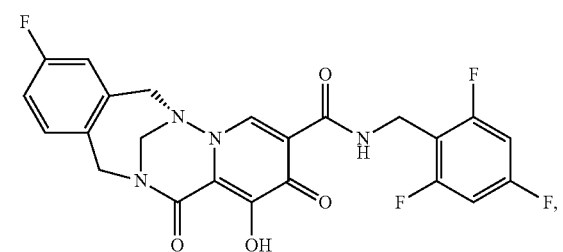

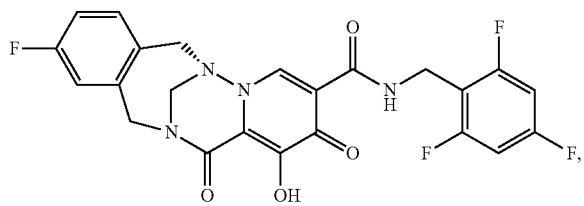

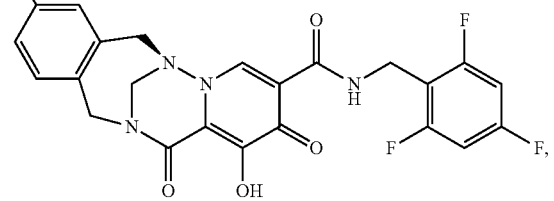

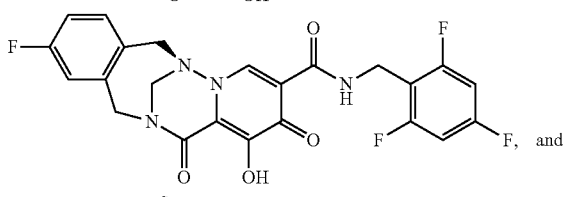

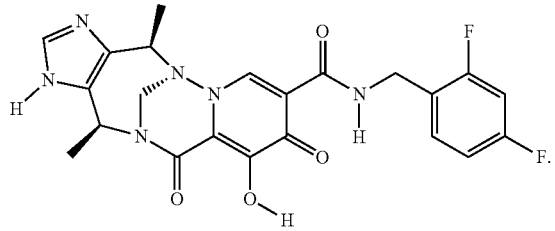, and

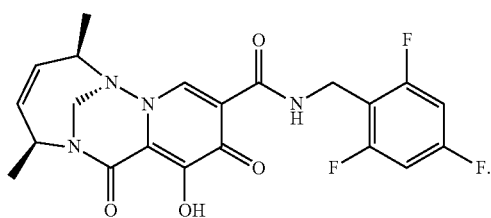

In some embodiments, the compounds of Formula I, Ia, Ib, II, IIa, IIb, III, IIIa, IIIb, IV, IVa, IVb, V, Va, or Vb is:

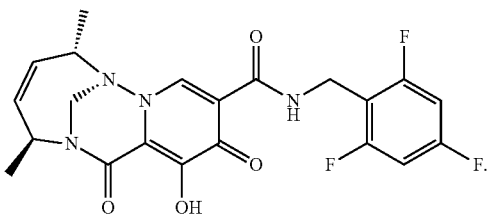

In some embodiments, the compounds of Formula I, Ia, Ib, II, IIa, IIb, III, IIIa, IIIb, IV, IVa, IVb, V, Va, or Vb is:

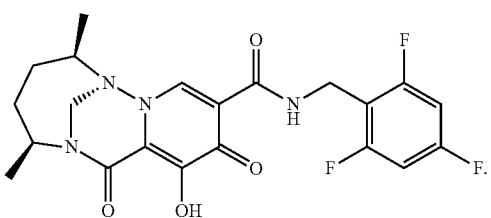

In some embodiments, the compounds of Formula I, Ia, Ib, II, IIa, IIb, III, IIIa, IIIb, IV, IVa, IVb, V, Va, or Vb is:

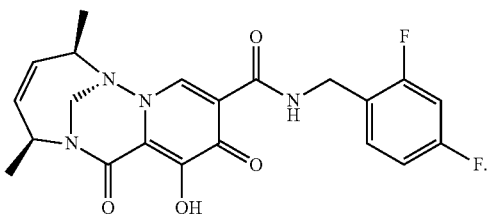

In some embodiments, the compounds of Formula I, Ia, Ib, II, IIa, IIb, III, IIIa, IIIb, IV, IVa, IVb, V, Va, or Vb is:

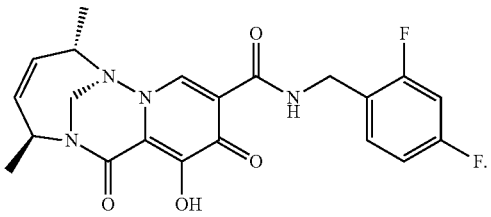

In some embodiments, the compounds of Formula I, Ia, Ib, II, IIa, IIb, III, IIIa, IIIb, IV, IVa, IVb, V, Va, or Vb is:

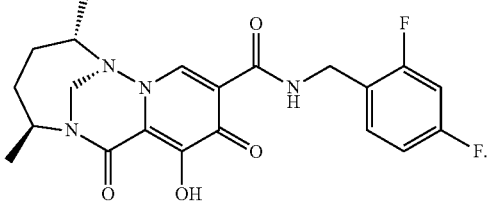

In some embodiments, the compounds of Formula I, Ia, Ib, II, IIa, IIb, III, IIIa, IIIb, IV, IVa, IVb, V, Va, or Vb is:

In some embodiments, the compounds of Formula I, Ia, Ib, II, IIa, IIb, III, IIIa, IIIb, IV, IVa, IVb, V, Va, or Vb is:

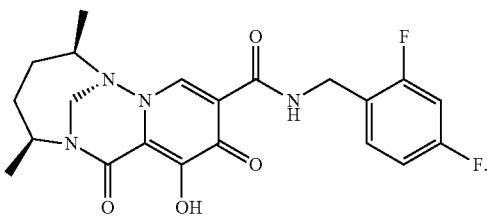

In some embodiments, the compounds of Formula I, Ia, Ib, II, IIa, IIb, III, IIIa, IIIb, IV, IVa, IVb, V, Va, or Vb is:

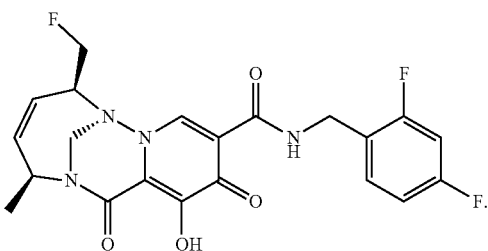

In some embodiments, the compounds of Formula I, Ia, Ib, II, IIa, IIb, III, IIIa, IIIb, IV, IVa, IVb, V, Va, or Vb is:

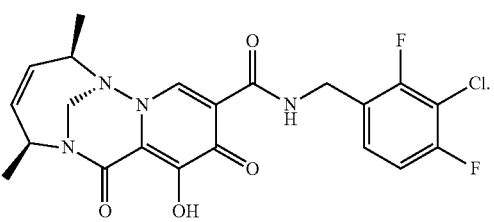

In some embodiments, the compounds of Formula I, Ia, Ib, II, IIa, IIb, III, IIIa, IIIb, IV, IVa, IVb, V, Va, or Vb is:

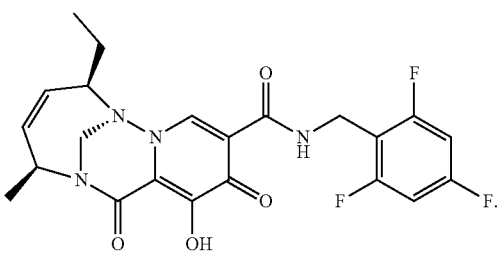

In some embodiments, the compounds of Formula I, Ia, Ib, II, IIa, IIb, III, IIIa, IIIb, IV, IVa, IVb, V, Va, or Vb is:

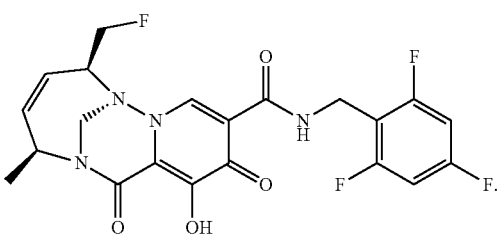

III. Compositions and Kits

Compounds provided herein are usually administered in the form of pharmaceutical compositions. Thus, provided herein are also pharmaceutical compositions that comprise one or more of the compounds provided herein or pharmaceutically acceptable salts, isomer, or a mixture thereof and one or more pharmaceutically acceptable vehicles selected from carriers, adjuvants and excipients. The compounds provided herein may be the sole active ingredient or one of the active ingredients of the pharmaceutical compositions. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

In one aspect, provided herein are pharmaceutical compositions comprising a compound provided herein (e.g., a compound of Formula I, Ia, Ib, II, IIa, IIb, III, IIIa, IIIb, IV, IVa, IVb, V, Va, or Vb), or a pharmaceutically acceptable salt thereof, and a pharmaceutically acceptable excipient or carrier. In some embodiments, the pharmaceutical compositions comprise a therapeutically effective amount of a compound provided herein, or a pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or a pharmaceutically acceptable salt thereof. In some embodiments, the pharmaceutical compositions further comprise a therapeutically effective amount of the one or more (e.g., one, two, three, four, one or two, one to three, or one to four) additional therapeutic agents, or a pharmaceutically acceptable salt thereof.

The pharmaceutical compositions may be administered in either single or multiple doses. The pharmaceutical compositions may be administered by various methods including, for example, rectal, buccal, intranasal and transdermal routes. In some embodiments, the pharmaceutical compositions may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds provided herein. Administration may be via, for example, capsule or enteric coated tablets. In making the pharmaceutical compositions that include at least one compound provided herein or pharmaceutically acceptable salts, isomer, or a mixture thereof, the active ingredient (such as a compound provided herein) is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient.

Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose or any combinations thereof. The pharmaceutical compositions can additionally include lubricating agents such as talc, magnesium stearate, and mineral oil; wetting agents; emulsifying and suspending agents; preserving agents such as methyl and propylhydroxy-benzoates; sweetening agents; and flavoring agents; or any combinations thereof.

The pharmaceutical compositions that include at least one compound described herein or pharmaceutically acceptable salts, isomer, or a mixture thereof can be formulated so as to provide quick, sustained or delayed release of the active ingredient (such as a compound provided herein) after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds provided herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with materials such as shellac, cetyl alcohol, and cellulose acetate.

Pharmaceutical compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In one aspect, provided herein are kits that comprise a compound provided herein, (e.g., a compound of Formula I, Ia, Ib, II, IIa, IIb, III, IIIa, IIIb, IV, IVa, IVb, V, Va, or Vb), or a pharmaceutically acceptable salt, stereoisomer, prodrug, or solvate thereof, and suitable packaging. In some embodiments, the kit further comprises instructions for use. In some embodiments, the kit comprises a compound provided herein (e.g., a compound of Formula I, Ia, Ib, II, IIa, IIb, III, IIIa, IIIb, IV, IVa, IVb, V, Va, or Vb), or a pharmaceutically acceptable salt, stereoisomer, prodrug, or solvate thereof, and a label and/or instructions for use of the compounds in the treatment of the indications, including the diseases or conditions, described herein.

In some embodiments, the kits further comprise one or more (e.g., one, two, three, four, one or two, one to three, or one to four) additional therapeutic agents, or a pharmaceutically acceptable salt thereof.

In one aspect, provided herein are articles of manufacture that comprise a compound described herein or pharmaceutically acceptable salts, isomer, or a mixture thereof in a suitable container. In some embodiments, the container may be a vial, jar, ampoule, preloaded syringe, or intravenous bag.

IV. Methods

In one embodiment, methods of treating an HIV (e.g., HIV-1 and/or HIV-2) infection in a human having or at risk of having the infection comprising administering to the human a therapeutically effective amount of a compound of Formula I, Ia, Ib, II, IIa, IIb, III, IIIa, IIIb, IV, IVa, IVb, V, Va, or Vb, or a pharmaceutically acceptable salt thereof, or a pharmaceutical composition of a compound of Formula I, Ia, Ib, II, IIa, IIb, III, IIIa, IIIb, IV, IVa, IVb, V, Va, or Vb, or a pharmaceutically acceptable salt thereof, are provided.

In some embodiments, the methods further comprise administering to the human a therapeutically effective amount of one, two, three, or four additional therapeutic agents. In certain embodiments, the additional therapeutic agent or agents are anti-HIV agents. In particular embodiments, the additional therapeutic agent or agents are HIV protease inhibitors, HIV non-nucleoside or non-nucleotide inhibitors of reverse transcriptase, HIV nucleoside or nucleotide inhibitors of reverse transcriptase, HIV capsid inhibitors, gp41 inhibitors, CXCR4 inhibitors, gp120 inhibitors, CCR5 inhibitors, latency reversing agents, capsid polymerization inhibitors, HIV bNAbs (broadly neutralizing HIV antibodies), TLR7 agonists, pharmacokinetic enhancers, other drugs for treating HIV, or combinations thereof. In one embodiment, the additional therapeutic agent or agents are abacavir, tenofovir alafenamide, tenofovir disoproxil, lenacapavir, or a pharmaceutically acceptable salt thereof. In one embodiment, the additional therapeutic agent or agents are abacavir, tenofovir alafenamide, tenofovir disoproxil, lenacapavir, GS-5894, islatravir, or a pharmaceutically acceptable salt thereof. In some embodiments, the additional therapeutic agent or agents are lenacapavir, islatravir. In some embodiments, the additional therapeutic agent is lenacapavir. In some embodiments, the additional therapeutic agent is islatravir.

In another embodiment, a use of a compound of Formula I, Ia, Ib, II, IIa, IIb, III, IIIa, IIIb, IV, IVa, IVb, V, Va, or Vb, or a pharmaceutically acceptable salt thereof, or a pharmaceutical composition of a compound of Formula I, Ia, Ib, II, IIa, IIb, III, IIIa, IIIb, IV, IVa, IVb, V, Va, or Vb, or a pharmaceutically acceptable salt thereof, for treating an HIV (e.g., HIV-1 and/or HIV-2) infection in a human having or at risk of having the infection is provided.

In another embodiment, a compound of Formula I, Ia, Ib, II, IIa, IIb, III, IIIa, IIIb, IV, IVa, IVb, V, Va, or Vb, or a pharmaceutically acceptable salt thereof, or a pharmaceutical composition of a compound of Formula I, Ia, Ib, II, IIa, IIb, III, IIIa, IIIb, IV, IVa, IVb, V, Va, or Vb, or a pharmaceutically acceptable salt thereof, for use in medical therapy is provided.

In another embodiment, a compound of Formula I, Ia, Ib, II, IIa, IIb, III, IIIa, IIIb, IV, IVa, IVb, V, Va, or Vb, or a pharmaceutically acceptable salt thereof, or a pharmaceutical composition of Formula I, Ia, Ib, II, IIa, IIb, III, IIIa, IIIb, IV, IVa, IVb, V, Va, or Vb, or pharmaceutically acceptable salt thereof, for use in treating an HIV infection is provided.

In another embodiment, a compound of Formula I, Ia, Ib, II, IIa, IIb, III, IIIa, IIIb, IV, IVa, IVb, V, Va, or Vb, or a pharmaceutically acceptable salt thereof, or a pharmaceutical composition of a compound of Formula I, Ia, Ib, II, IIa, IIb, III, IIIa, IIIb, IV, IVa, IVb, V, Va, or Vb, or a pharmaceutically acceptable salt thereof for use in a method of treating an HIV infection in a human having or at risk of having the infection, is provided.

In another embodiment, a compound of Formula I, Ia, Ib, II, IIa, IIb, III, IIIa, IIIb, IV, IVa, IVb, V, Va, or Vb, or a pharmaceutically acceptable salt thereof, or a pharmaceutical composition of a compound of Formula I, Ia, Ib, II, IIa, IIb, III, IIIa, IIIb, IV, IVa, IVb, V, Va, or Vb, or a pharmaceutically acceptable salt thereof for use in a method of treating an HIV infection in a human having or at risk of having the infection, is provided wherein said method further comprises administering to the human one, two, three, or four additional therapeutic agents.

In another embodiment, a compound of Formula I, Ia, Ib, II, IIa, IIb, III, IIIa, IIIb, IV, IVa, IVb, V, Va, or Vb, or a pharmaceutically acceptable salt thereof, or a pharmaceutical composition of a compound of Formula I, Ia, Ib, II, IIa, IIb, III, IIIa, IIIb, IV, IVa, IVb, V, Va, or Vb, or a pharmaceutically acceptable salt thereof for use in a method of treating an HIV infection in a human having or at risk of having the infection, is provided wherein said method further comprises administering to the human one, two, three, or four additional therapeutic agents selected from the group consisting of HIV protease inhibitors, HIV non-nucleoside or non-nucleotide inhibitors of reverse transcriptase, HIV nucleoside or nucleotide inhibitors of reverse transcriptase, HIV capsid inhibitors, gp41 inhibitors, CXCR4 inhibitors, gp120 inhibitors, CCR5 inhibitors, latency reversing agents, capsid polymerization inhibitors, HIV bNAbs, TLR7 agonists, pharmacokinetic enhancers, other drugs for treating HIV, or combinations thereof. In one embodiment, the one, two, three, or four additional therapeutic agents are selected from HIV protease inhibitors, HIV non-nucleoside inhibitors of reverse transcriptase, HIV nucleoside or nucleotide inhibitors of reverse transcriptase, latency reversing agents, HIV capsid inhibitors, HIV bNAbs, TLR7 agonists, and combinations thereof.

In another embodiment, a compound of Formula I, Ia, Ib, II, IIa, IIb, III, IIIa, IIIb, IV, IVa, IVb, V, Va, or Vb, or a pharmaceutically acceptable salt thereof, or a pharmaceutical composition of a compound of Formula I, Ia, Ib, II, IIa, IIb, III, IIIa, IIIb, IV, IVa, IVb, V, Va, or Vb, or a pharmaceutically acceptable salt thereof for use in a method of treating an HIV infection in a human having or at risk of having the infection, is provided wherein said method further comprises administering to the human a therapeutically effective amount of tenofovir disoproxil and emtricitabine.

In another embodiment, a compound of Formula I, Ia, Ib, II, IIa, IIb, III, IIIa, IIIb, IV, IVa, IVb, V, Va, or Vb, or a pharmaceutically acceptable salt thereof, or a pharmaceutical composition of a compound of Formula I, Ia, Ib, II, IIa, IIb, III, IIIa, IIIb, IV, IVa, IVb, V, Va, or Vb, or a pharmaceutically acceptable salt thereof for use in a method of treating an HIV infection in a human having or at risk of having the infection, is provided wherein said method further comprises administering to the human a therapeutically effective amount of tenofovir alafenamide and emtricitabine.

In another embodiment, a compound of Formula I, Ia, Ib, II, IIa, IIb, III, IIIa, IIIb, IV, IVa, IVb, V, Va, or Vb, or a pharmaceutically acceptable salt thereof, or a pharmaceutical composition of a compound of Formula I, Ia, Ib, II, IIa, IIb, III, IIIa, IIIb, IV, IVa, IVb, V, Va, or Vb, or a pharmaceutically acceptable salt thereof for use in a method of treating an HIV infection in a human having or at risk of having the infection, is provided wherein said method further comprises administering to the human a therapeutically effective amount of tenofovir disoproxil.

In another embodiment, a compound of Formula I, Ia, Ib, II, IIa, IIb, III, IIIa, IIIb, IV, IVa, IVb, V, Va, or Vb, or a pharmaceutically acceptable salt thereof, or a pharmaceutical composition of a compound of Formula I, Ia, Ib, II, IIa, IIb, III, IIIa, IIIb, IV, IVa, IVb, V, Va, or Vb, or a pharmaceutically acceptable salt thereof for use in a method of treating an HIV infection in a human having or at risk of having the infection, is provided wherein said method further comprises administering to the human a therapeutically effective amount of tenofovir alafenamide.

In another embodiment, a method of using a compound of Formula I, Ia, Ib, II, IIa, IIb, III, IIIa, IIIb, IV, IVa, IVb, V, Va, or Vb in therapy is provided. In particular, a method of treating the proliferation of the HIV virus, treating AIDS, or delaying the onset of AIDS or ARC symptoms in a mammal (e.g., a human) is provided, comprising administering to the mammal a compound of Formula I, Ia, Ib, II, IIa, IIb, III, IIIa, IIIb, IV, IVa, IVb, V, Va, or Vb, or a pharmaceutically acceptable salt thereof, and a pharmaceutically acceptable excipient.

In another embodiment, a composition comprising a compound of Formula I, Ia, Ib, II, IIa, IIb, III, IIIa, IIIb, IV, IVa, IVb, V, Va, or Vb, or pharmaceutically acceptable salt thereof, and a pharmaceutically acceptable excipient, for use in a method of treating the proliferation of the HIV virus, treating AIDS, or delaying the onset of AIDS or ARC symptoms in a mammal (e.g., a human) is provided.

In one embodiment, a compound of Formula I, Ia, Ib, II, IIa, IIb, III, IIIa, IIIb, IV, IVa, IVb, V, Va, or Vb, or a pharmaceutically acceptable salt thereof, or a pharmaceutical composition of a compound of Formula I, Ia, Ib, II, IIa, IIb, III, IIIa, IIIb, IV, IVa, IVb, V, Va, or Vb, or a pharmaceutically acceptable salt thereof, is provided for use in preventing HIV infection.

For example, in one embodiment, a compound of Formula I, Ia, Ib, II, IIa, IIb, III, IIIa, IIIb, IV, IVa, IVb, V, Va, or Vb, or a pharmaceutically acceptable salt thereof, or a pharmaceutical composition of a compound of Formula I, Ia, Ib, II, IIa, IIb, III, IIIa, IIIb, IV, IVa, IVb, V, Va, or Vb, or a pharmaceutically acceptable salt thereof, is provided for use in pre-exposure prophylaxis (PrEP), i.e., before the exposure of the individual to the HIV virus to prevent HIV infection from taking hold if the individual is exposed to the virus and/or to keep the virus from establishing a permanent infection and/or to prevent the appearance of symptoms of the disease and/or to prevent the virus from reaching detectable levels in the blood.

In another embodiment, the use of a compound of Formula I, Ia, Ib, II, IIa, IIb, III, IIIa, IIIb, IV, IVa, IVb, V, Va, or Vb, or a pharmaceutically acceptable salt thereof, for the manufacture of a medicament for treating an HIV infection in a human being having or at risk of having the infection is disclosed.

In another embodiment, the use of a compound of Formula I, Ia, Ib, II, IIa, IIb, III, IIIa, IIIb, IV, IVa, IVb, V, Va, or Vb, or a pharmaceutically acceptable salt thereof, as a research tool is disclosed.

In another embodiment, an article of manufacture comprising a composition effective to treat an HIV infection; and packaging material comprising a label which indicates that the composition can be used to treat infection by HIV is disclosed. Exemplary compositions comprise a compound of Formula I, Ia, Ib, II, IIa, IIb, III, IIIa, IIIb, IV, IVa, IVb, V, Va, or Vb, or a pharmaceutically acceptable salt thereof.

In still another embodiment, a method of inhibiting the replication of HIV is disclosed. The method comprises exposing the virus to an effective amount of the compound of Formula I, Ia, Ib, II, IIa, IIb, III, IIIa, IIIb, IV, IVa, IVb, V, Va, or Vb, or a salt thereof, under conditions where replication of HIV is inhibited.

In another embodiment, the use of a compound of Formula I, Ia, Ib, II, IIa, IIb, III, IIIa, IIIb, IV, IVa, IVb, V, Va, or Vb, to inhibit the activity of the HIV integrase enzyme is disclosed.

In another embodiment, the use of a compound of Formula I, Ia, Ib, II, IIa, IIb, III, IIIa, IIIb, IV, IVa, IVb, V, Va, or Vb, or a salt thereof, to inhibit the replication of HIV is disclosed.

V. Administration

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In some embodiments, the compound is administered on a daily or intermittent schedule for the duration of the individual's life.

The specific dose level of a compound of the present disclosure for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I, Ia, Ib, II, IIa, IIb, III, IIIa, IIIb, IV, IVa, IVb, V, Va, or Vb, or a pharmaceutically acceptable salt or pharmaceutically acceptable tautomer thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

The dosage or dosing frequency of a compound of the present disclosure may be adjusted over the course of the treatment, based on the judgment of the administering physician.

The compounds of the present disclosure may be administered to an individual (e.g., a human) in a therapeutically effective amount. In some embodiments, the compound is administered once daily.

The compounds provided herein can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the compounds provided herein include from about 0.3 mg to about 30 mg per day, or from about 30 mg to about 300 mg per day, or from about 0.3 μg to about 30 mg per day, or from about 30 μg to about 300 μg per day.

A compound of the present disclosure may be combined with one or more additional therapeutic agents in any dosage amount of the compound of the present disclosure (e.g., from 1 mg to 1000 mg of compound). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amounts of the compound of Formula I, Ia, Ib, II, IIa, IIb, III, IIIa, IIIb, IV, IVa, IVb, V, Va, or Vb are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of the present disclosure are about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, the methods described herein comprise administering to the subject an initial daily dose of about 1 to 500 mg of a compound p herein and increasing the dose by increments until clinical efficacy is achieved. Increments of about 5, 10, 25, 50, or 100 mg can be used to increase the dose. The dosage can be increased daily, every other day, twice per week, once per week, once every two weeks, once every three weeks, or once a month.

When administered orally, the total daily dosage for a human subject may be between about 1 mg and 1,000 mg, between about 10-500 mg/day, between about 50-300 mg/day, between about 75-200 mg/day, or between about 100-150 mg/day. In some embodiments, the total daily dosage for a human subject may be about 100, 200, 300, 400, 500, 600, 700, 800, 900, or 1000 mg/day administered in a single dose. In some embodiments, the total daily dosage for a human subject may be about 200, 300, 400, 500, 600, 700, or 800 mg/day administered in a single dose. In some embodiments, the total daily dosage for a human subject may be about 300, 400, 500, or 600 mg/day administered in a single dose.

In some embodiments, the total daily dosage for a human subject may be about 100 mg/day administered in a single dose. In some embodiments, the total daily dosage for a human subject may be about 150 mg/day administered in a single dose. In some embodiments, the total daily dosage for a human subject may be about 200 mg/day administered in a single dose. In some embodiments, the total daily dosage for a human subject may be about 250 mg/day administered in a single dose. In some embodiments, the total daily dosage for a human subject may be about 300 mg/day administered in a single dose. In some embodiments, the total daily dosage for a human subject may be about 350 mg/day administered in a single dose. In some embodiments, the total daily dosage for a human subject may be about 400 mg/day administered in a single dose. In some embodiments, the total daily dosage for a human subject may be about 450 mg/day administered in a single dose. In some embodiments, the total daily dosage for a human subject may be about 500 mg/day administered in a single dose. In some embodiments, the total daily dosage for a human subject may be about 550 mg/day administered in a single dose. In some embodiments, the total daily dosage for a human subject may be about 600 mg/day administered in a single dose. In some embodiments, the total daily dosage for a human subject may be about 650 mg/day administered in a single dose. In some embodiments, the total daily dosage for a human subject may be about 700 mg/day administered in a single dose. In some embodiments, the total daily dosage for a human subject may be about 750 mg/day administered in a single dose. In some embodiments, the total daily dosage for a human subject may be about 800 mg/day administered in a single dose. In some embodiments, the total daily dosage for a human subject may be about 850 mg/day administered in a single dose. In some embodiments, the total daily dosage for a human subject may be about 900 mg/day administered in a single dose. In some embodiments, the total daily dosage for a human subject may be about 950 mg/day administered in a single dose. In some embodiments, the total daily dosage for a human subject may be about 1000 mg/day administered in a single dose.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound disclosed herein is administered once daily in a method disclosed herein. In some embodiments, a compound disclosed herein is administered twice daily in a method disclosed herein.

In some embodiments, a compound disclosed herein is administered once every 10 days. In some embodiments, a compound disclosed herein is administered once every 15 days. In some embodiments, a compound disclosed herein is administered once every 20 days. In some embodiments, a compound disclosed herein is administered once every 10-15 days. In some embodiments, a compound disclosed herein is administered once every 15-20 days. In some embodiments, a compound disclosed herein is administered once every 10-20 days. In some embodiments, a compound disclosed herein is administered once every month. In some embodiments, a compound disclosed herein is administered once every 2 months. In some embodiments, a compound disclosed herein is administered once every 3 months. In some embodiments, a compound disclosed herein is administered once every 4 months. In some embodiments, a compound disclosed herein is administered once every 5 months. In some embodiments, a compound disclosed herein is administered once every 6 months. In some embodiments, a compound disclosed herein is administered once every 8 months. In some embodiments, a compound disclosed herein is administered once every 10 months. In some embodiments, a compound disclosed herein is administered once every year.

The frequency of dosage of the compound of the present disclosure will be determined by the needs of the individual patient and can be, for example, once per day or twice, or more times, per day. Administration of the compound continues for as long as necessary to treat the HBV infection, HIV infection, cancer, hyper-proliferative disease, or any other indication described herein. For example, a compound can be administered to a human being infected with HBV for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

The compounds of the present disclosure or the pharmaceutical compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

VI. Combination Therapy

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient. When administered sequentially, the combination may be administered in two or more administrations.

Co-administration includes administration of unit dosages of the compounds disclosed herein before or after administration of unit dosages of one or more additional therapeutic agents. For example, the compound disclosed herein may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments, a compound of Formula I is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.

HIV Combination Therapy

In the above embodiments, the additional therapeutic agent may be an anti-HIV agent. HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T, autologous T cell therapies), latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement $C_5$a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, CD4 modulators, CD4 antagonists, HIV ribonuclease H inhibitors, retrocyclin modulators, CDK-9 inhibitors, CCR5 chemokine antagonists, CCR5 gene modulators, dendritic ICAM-3 grabbing nonintegrin 1 inhibitors, HIV GAG protein inhibitors, HIV POL protein inhibitors, hyaluronidase inhibitors, Nef antagonists, Nef inhibitors, Protease-activated receptor-1 antagonists, TNF alpha ligand inhibitors, PDE4 inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine); BIKTARVY® (bictegravir, emtricitabine, and tenofovir alafenamide); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMDU™ (lamivudine and tenofovir disoproxil fumarate); tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

Other HIV Drugs

Examples of other drugs for treating HIV include acemannan, alisporivir, astodrimer, BanLec, CC-11050, deferiprone, Gamimune, griffithsin, metenkefalin, naltrexone, Prolastin, REP 9, RPI-MN, Vorapaxar, VSSP, H1viral, SB-728-T, 1,5-dicaffeoylquinic acid, rHIV7-shl-TAR-CCR5RZ, MazF gene therapy, MK-8527, BlockAide, PSC-RANTES, ABX-464, AG-1105, APH-0812, BIT-225, CYT-107, HGTV-43, HPH-116, HS-10234, IMO-3100, IND-02, MK-1376, MK-2048, MK-4250, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, and elsulfavirine (VM-1500).

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fozivudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500 and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC- 48240, NSC-642710, NSC-699171, NSC-699172, NSC-699173, NSC-699174, stilbenedisulfonic acid, T-169, VM-3500 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, DS-003 (BMS-599793), gp120 inhibitors, and CXCR4 inhibitors.

Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs.

Examples of gp120 inhibitors include Radha-108 (receptol) 3B3-PE38, BanLec, bentonite-based nanomedicine, fostemsavir tromethamine, IQP-0831, and BMS-663068.

Examples of CXCR4 inhibitors include plerixafor, ALT-1188, N15 peptide, and vMIP (Haimipu).

HIV Maturation Inhibitors

Examples of HIV maturation inhibitors include BMS-955176, BMS-986197, GSK-3640254 and GSK-2838232.

Latency Reversing Agents

Examples of latency reversing agents include histone deacetylase (HDAC) inhibitors, proteasome inhibitors such as velcade, and ixazomib citrate, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), IL-15 modulating antibodies, JQ1, disulfiram, amphotericin B, and ubiquitin inhibitors such as largazole analogs, APH-0812, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, GS-6207, AVI-621, AVI-101, AVI-201, AVI-301, and AVI-CAN1-15 series.

Immune-Based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, interleukin-15/Fc fusion protein, AM-0015, ALT-803, NIZ-985, NKTR-255, NKTR-262, NKTR-214, normferon, peginterferon alfa-2a, peginterferon alfa-2b, recombinant interleukin-15, Xmab-24306, RPI-MN, STING modulators, RIG-I modulators, NOD2 modulators, SB-9200, and IR-103.

Examples of TLR agonists: vesatolimod (GS-9620), GS-986, IR-103, lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.RO-7020531.

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4 Beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bispecific antibodies, trispecific antibodies, multivalent antibodies, bnABs (broadly neutralizing HIV-1 antibodies), BMS-936559, TMB-360, and those targeting HIV gp120 or gp41, antibody-recruiting Molecules targeting HIV, anti-CD63 monoclonal antibodies, CD3 bispecific antibodies, CD16 bispecific antibodies, anti-GB virus C antibodies, anti-GP120/CD4, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66.

Examples of those targeting HIV in such a manner include bavituximab, UB-421, $C_2F5$, 2G12, $C_4E10$, $C_2F5+C_2G12+C_4E10$, 8ANC195, 3BNC117, 3BNC117-LS, 3BNC60, D1D2, 10-1074, 10-1074-LS, GS-9722, DH411-2, BG18, PGT145, PGT121, PGT122, PGT-151, PGT-133, PGT-135, PGT-128, MDX010 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PG9, PG16, 8ANC195, 2Dm2m, 4Dm2m, 6Dm2m, VRC-01, VRC-01-LS, PGDM1400, A32, 7B2, 10E8, 10E8VLS, 3810109, 10E8v4, 10E8.4/iMab, VRC-01/PGDM-1400/10E8v4, IMC-HIV, iMabm36, 10E8v4/PGT121-VRC01, eCD4-Ig, IOMA, CAP256-VRC26.25, DRVIA7, SAR-441236, VRC-07-523, VRC07-523LS, VRC-HIVMAB080-00-AB, VRC-HIVMAB060-00-AB, P2G12, and VRC07. Examples of HIV bispecific antibodies include MGD014, TMB-bispecific.

Example of in vivo delivered bnABs such as AAV8-VRC07; mRNA encoding anti-HIV antibody VRC01.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/

145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include peptide vaccines, recombinant subunit protein vaccines, live vector vaccines using viral vectors such as arenavirus, lymphocytic choriomeningitis virus (LCMV), pichinde virus, modified vaccinia Ankara virus (MVA), adenovirus, adeno-associated virus (AAV), vesicular stomatitis virus (VSV) and Chimpanzee adenovirus (ChAd), DNA vaccines, CD4-derived peptide vaccines, vaccine combinations, BG505 SOSIP.664 gp140, rgp120 (AIDSVAX), ALVAC HIV, (vCP1521)/AIDSVAX B/E (gpl20) (RV144), monomeric gp120 HIV-1 subtype C vaccine, Remune, ITV-1, Contre Vir, Ad4-Env145NFL, Ad5-ENVA-48, HB-500, DCVax-001 (CDX-2401), Vacc-4x, Vacc-C$_5$, Vacc-CRX, VVX-004, VAC-3S, multiclade DNA recombinant adenovirus-5 (rAd5), rAd5 gag-pol env A/B/C vaccine, Pennvax-G, Pennvax-GP/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gpl40 [delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), Paxvax, EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, arenavirus vector-based immunotherapies (Vaxwave, TheraT), MVA-BN HIV-1 vaccine regimen, MVA.tHIVconsv4, MVA.tHIVconsv3, UBI HIV gp120, mRNA based prophylactic vaccines, TBL-1203HI, VRC-HIVRGP096-00-VP, VAX-3S, HIV MAG DNA vaccine, HIV Combination Therapy In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

A compound as disclosed herein (e.g., any compound of Formula I) may be combined with one or more additional therapeutic agents in any dosage amount of the compound of Formula I (e.g., from 1 mg to 500 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of Formula I) may be combined with the agents provided herein in any dosage amount of the compound (e.g., from 1 mg to 500 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of Formula I) may be combined with the agents provided herein in any dosage amount of the compound (e.g., from 1 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, one or two, or one to three) additional therapeutic agents are provided.

Birth Control (Contraceptive) Combination Therapy

Therapeutic agents used for birth control (contraceptive) include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Examples of dendritic cell therapy include AGS-004.

Example of CCR5 gene editing drugs such as SB-728T.

Example of CCR5 gene inhibitors such as Cal-1.

C34-CCR5/C34-CXCR4 expressing CD4-positive T cells.

AGT-103-transduced autologous T cell therapy.

AAV-eCD4-Ig gene therapy.

Gene Editors

The genome editing system is selected from the group consisting of: a CRISPR/Cas9 system, a zinc finger nuclease system, a TALEN system, a homing endonucleases system, and a meganuclease system.

Examples of HIV targeting CRISPR/Cas9 systems include EBT-101.

CAR-T Cell Therapy

A population of immune effector cells engineered to express a chimeric antigen receptor (CAR), wherein the CAR comprises an HIV antigen-binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T cell or an NK cell. In some embodiments, the T cell is a CD4+ T cell, a CD8+ T cell, or a combination thereof. Cells can be autologous or allogeneic.

Examples of HIV CAR-T include VC-CAR-T, anti-CD4 CART cell therapy, autologous hematopoietic stem cells genetically engineered to express a CD4 CAR and the $C_{46}$ peptide.

TCR-T Cell Therapy

TCR-T cells are engineered to target HIV derived peptides present on the surface of virus-infected cells.

VI. EXAMPLES

Exemplary chemical entities of the present disclosure are provided in the specific examples that follow. Those skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

Example 1-4: Preparation of (6R)-10-fluoro-1-hydroxy-2,14-dioxo-N-(2,4,6-trifluorobenzyl)-2,7,12,14-tetrahydro-6,13-methanobenzo[g]pyrido[1,2-b][1,2,5]triazonine-3-carboxamide (C1)

(6R)-9-fluoro-1-hydroxy-2,14-dioxo-N-(2,4,6-trifluorobenzyl)-2,7,12,14-tetrahydro-6,13-methanobenzo[g]pyrido[1,2-b][1,2,5]triazonine-3-carboxamide (C2)

(6S)-10-fluoro-1-hydroxy-2,14-dioxo-N-(2,4,6-trifluorobenzyl)-2,7,12,14-tetrahydro-6,13-methanobenzo[g]pyrido[1,2-b][1,2,5]triazonine-3-carboxamide (C3)

(6S)-9-fluoro-1-hydroxy-2,14-dioxo-N-(2,4,6-trifluorobenzyl)-2,7,12,14-tetrahydro-6,13-methanobenzo[g]pyrido[1,2-b][1,2,5]triazonine-3-carboxamide (C4)

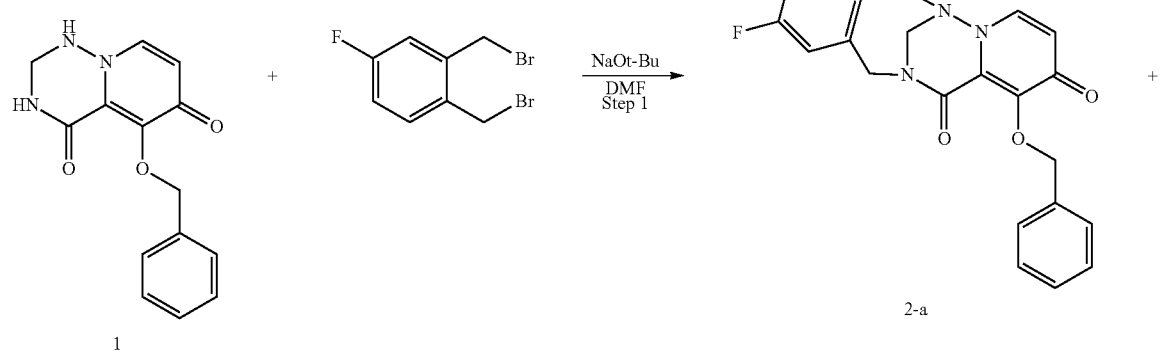

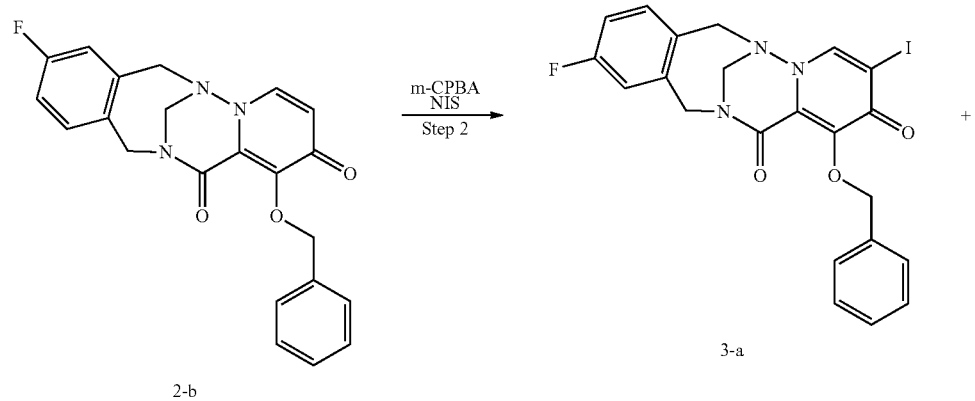

-continued
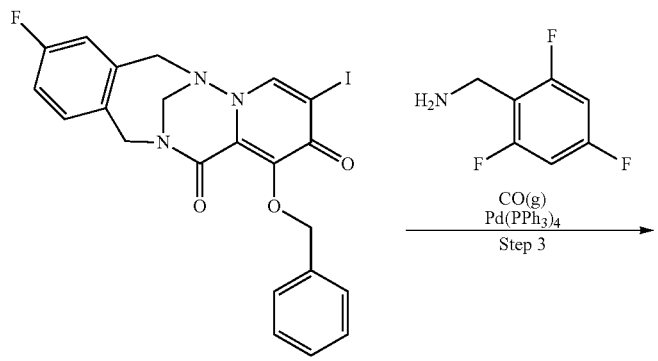
3-b
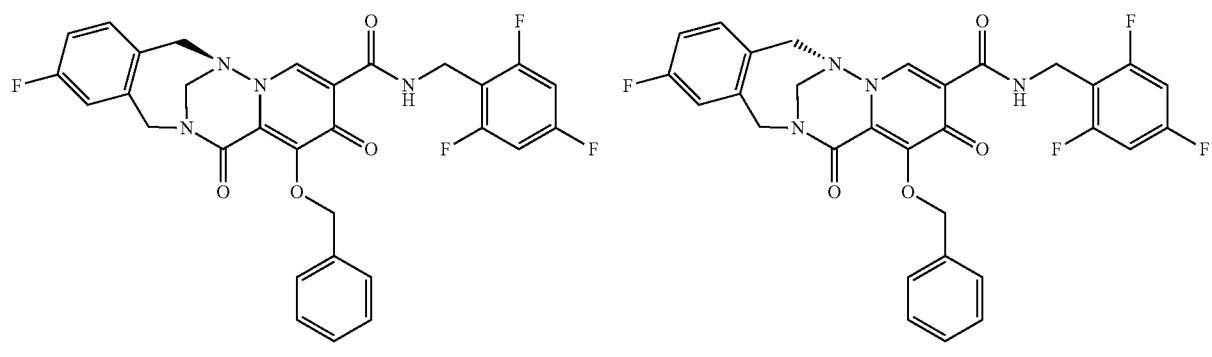
4-a
4-c
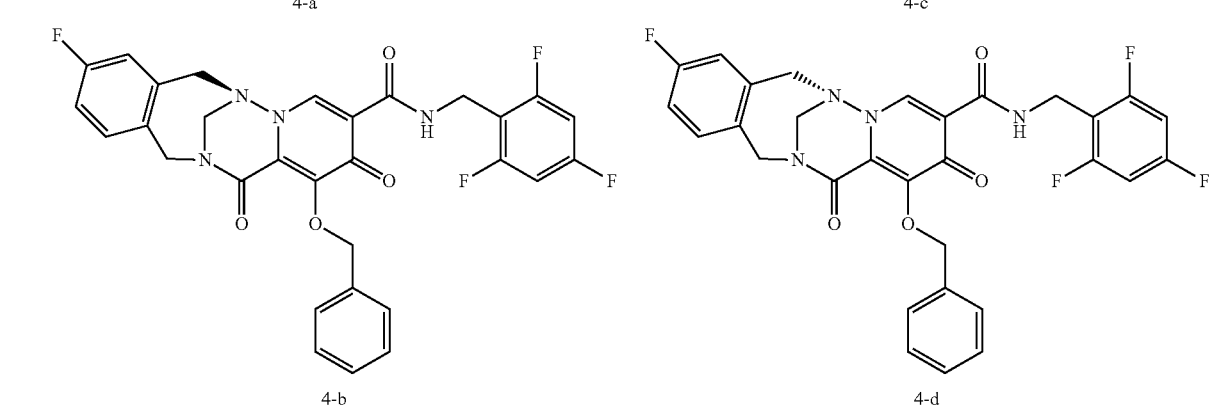
4-b
4-d
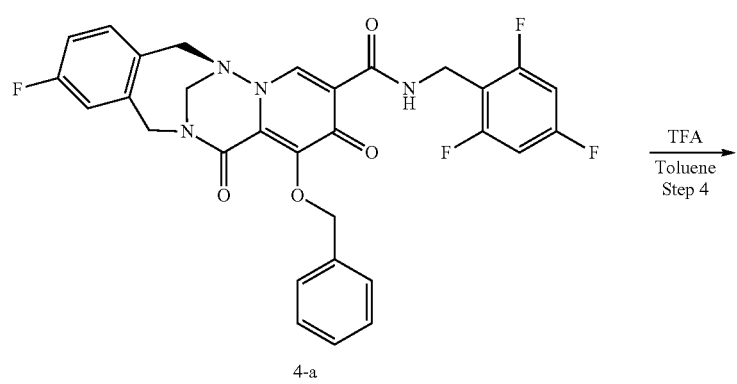
4-a -continued
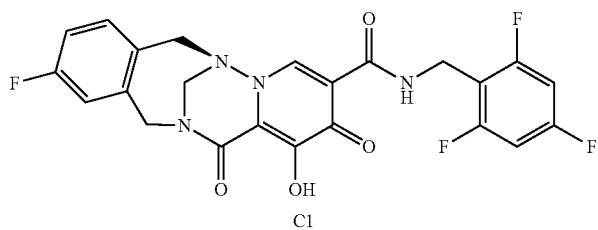
C1
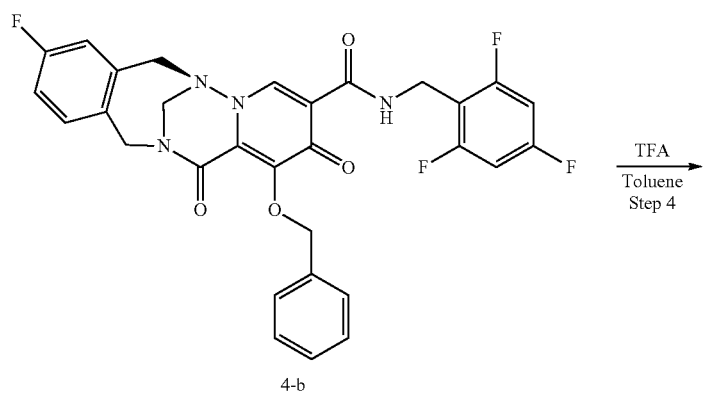
4-b
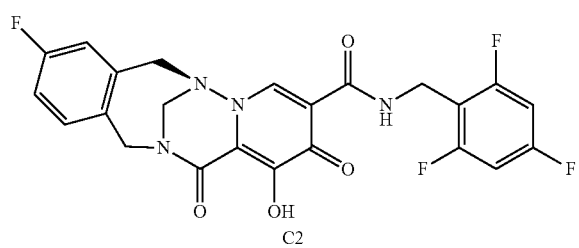
C2
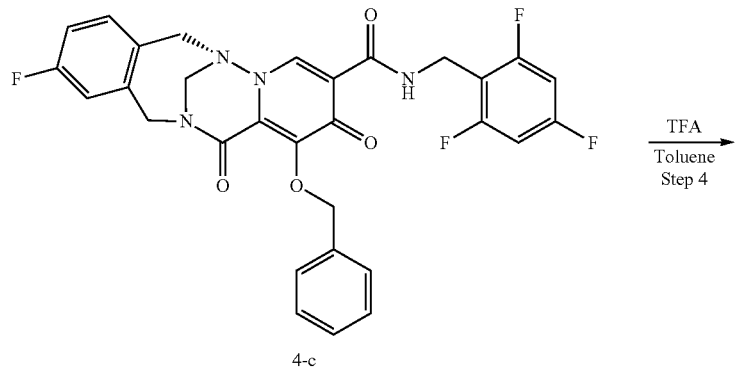
4-c
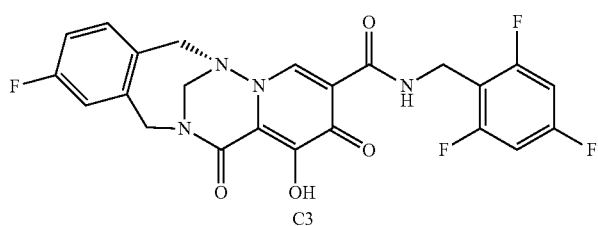
C3

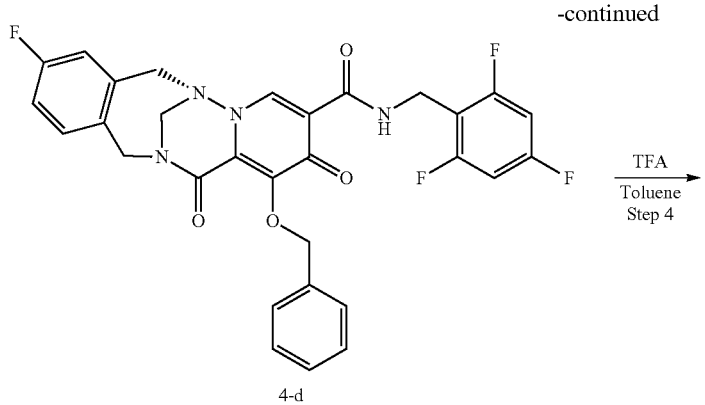

4-d

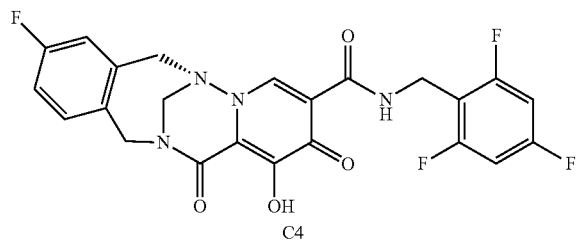

C4

5-(Benzyloxy)-2,3-dihydro-1H-pyrido[2,1-f][1,2,4]triazine-4,6-dione (1) was prepared according to published procedure for "intermediate A" in WO 20191160883 A1.

Step 1: Preparation of 1-(benzyloxy)-10-fluoro-7,12-dihydro-6,13-methanobenzo[g]pyrido[1,2-b][1,2,5]triazonine-2,14-dione (2-a) and 1-(benzyloxy)-9-fluoro-7,12-dihydro-6,13-methanobenzo[g]pyrido[1,2-b][1,2,5]triazonine-2,14-dione (2-b)

5-(Benzyloxy)-2,3-dihydro-1H-pyrido[2,1-f][1,2,4]triazine-4,6-dione (1) (200 mg, 0.737 mmol) and 1,2-bis(bromomethyl)-4-fluorobenzene (229 mg, 0.811 mmol) were mixed with DMF (5 ml) and the mixture was cooled down to 0° C. NaOt-Bu (159 mg, 1.66 mmol) was added over 1 hr. The reaction mixture was the allowed to be stirred without recharged cold bath overnight. The reaction mixture was then diluted with EtOAc and was treated with NH$_4$Cl/water. Organic phase was separated and concentrated. The residue was purified with silica gel chromatography with 0-100% EtOAc in Heptane and then 10% MeOH in EtOAc to afford the mixture of two regio-isomers of products (2-a and 2-b). MS (m/z): 392.1 [M+H]. These two regio-isomers were not separated and were carried over to next step.

Step 2: Preparation of 1-(benzyloxy)-10-fluoro-3-iodo-7,12-dihydro-6,13-methanobenzo[g]pyrido[1,2-b][1,2,5]triazonine-2,14-dione (3-a) and 1-(benzyloxy)-9-fluoro-3-iodo-7,12-dihydro-6,13-methanobenzo[g]pyrido[1,2-b][1,2,5]triazonine-2,14-dione (3-b)

A mixture of 1-(benzyloxy)-10-fluoro-7,12-dihydro-6,13-methanobenzo[g]pyrido[1,2-b][1,2,5]triazonine-2,14-dione (2-a) and 1-(benzyloxy)-9-fluoro-7,12-dihydro-6,13-methanobenzo[g]pyrido[1,2-b][1,2,5]triazonine-2,14-dione (2-b) (50 mg, 0.128 mmol) was mixed with MeOH (0.8 ml) at rt. m-CPBA (77%) (114 mg, 0.51 mmol) and NIS (114 mg, 0.51 mmol) were added sequentially. Reaction vial was sealed and heated from rt to 80° C. for 30 min. Additional m-CPBA (77%) (114 mg, 0.51 mmol) and NIS (114 mg, 0.51 mmol) were added sequentially. Reaction mixture was heated again at 80° C. for 30 min. Reaction mixture was then diluted with EtOAc and treated with NaHCO$_3$/water and Na$_2$S$_2$O$_3$ (10%) in water. Organic phase was separated and concentrated. The residue was purified with silica gel column with 0-100% EtOAc/Heptane to afford product as a mixture of two regio-isomers (3-a and 3-b) 60 mg. MS (m/z): 518.06 [M+H]. These two regio-isomers were not separated and carried over to next step.

Step 3: Preparation of (6R)-1-(benzyloxy)-10-fluoro-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-a)

(6R)-1-(benzyloxy)-9-fluoro-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-b)

(6S)-1-(benzyloxy)-10-fluoro-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-c)

(6S)-1-(benzyloxy)-9-fluoro-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-d)

To a solution of the mixture of 1-(benzyloxy)-10-fluoro-3-iodo-7,12-dihydro-6,13-methanobenzo[g]pyrido[1,2-b][1,2,5]triazonine-2,14-dione (3-a) and 1-(benzyloxy)-9-fluoro-3-iodo-7,12-dihydro-6,13-methanobenzo[g]pyrido[1,2-b][1,2,5]triazonine-2,14-dione (3-b) (32 mg, 0.062 mmol) in DMSO (2 ml) was added 2,4,6-trifluorobenzylamine (50 mg, 0.309 mmol), DIPEA (40 mg, 0.309 mmol), and Pd(PPh$_3$)$_4$ (3.57 mg, 0.00309 mmol). Reaction mixture was bubbled with CO (g) for 10 min. The reaction mixture was then heated at 80° C. under CO atmosphere for 17 hours. Reaction mixture was cooled to room temperature and was diluted with ethyl acetate. The resulting mixture was treated with 0.05N HCl. Organic phase was separated and was treated with saturated sodium bicarbonate solution and brine. Organic phase was then dried with Na$_2$SO$_4$ and was concentrated. The residue was purified by silica gel column with 0-100% EtOAc in heptane to afford desired product. This mixture of four isomers were subject to SFC separation method (ADH 50 IPA-NH$_3$) to afford 4 isomers in the order of ascending retention time: (6R)-1-(benzyloxy)-10-fluoro-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-a) 10 mg. MS (m/z): 579.08 [M+H]; (6R)-1-(benzyloxy)-9-fluoro-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-b) 6 mg. MS (m/z): 579.08 [M+H]; (6S)-1-(benzyloxy)-10-fluoro-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-c) 7 mg. MS (m/z): 579.03 [M+H]; and (6S)-1-(benzyloxy)-9-fluoro-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-d) 4 mg. MS (m/z): 579.02 [M+H].

Step 4: Preparation of (6R)-10-fluoro-1-hydroxy-2,14-dioxo-N-(2,4,6-trifluorobenzyl)-2,7,12,14-tetrahydro-6,13-methanobenzo[g]pyrido[1,2-b][1,2,5]triazonine-3-carboxamide (C1)

(6R)-1-(Benzyloxy)-10-fluoro-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-a) (10 mg, 0.0173 mmol) was dissolved in toluene (0.5 ml) at rt. TFA (0.5 ml) was added in one portion. Reaction mixture was stirred at rt for 17 hrs. Reaction mixture was concentrated to dryness. The residue was taken up in MeOH and purified with reverse phase prep-HPLC with 0-100% CH$_3$CN in water with 0.1% TFA to afford the desired product. Lyophilization afforded the product as TFA salt. MS (m/z): 489.26 [M+H]+. $^1$H NMR (400 MHz, Acetonitrile-d3) δ 10.13 (s, 1H), 8.52 (s, 1H), 7.41-7.22 (m, 1H), 7.13 (d, J=9.3 Hz, 1H), 7.04 (t, J=8.6 Hz, 1H), 6.88 (t, J=8.6 Hz, 2H), 5.56 (d, J=16.7 Hz, 1H), 4.87-4.69 (m, 2H), 4.64 (d, J=5.7 Hz, 2H), 4.55 (d, J=15.3 Hz, 2H), 4.13 (d, J=13.2 Hz, 1H).

Preparation of (6R)-9-fluoro-1-hydroxy-2,14-dioxo-N-(2,4,6-trifluorobenzyl)-2,7,12,14-tetrahydro-6,13-methanobenzo[g]pyrido[1,2-b][1,2,5]triazonine-3-carboxamide (C2)

The synthesis of title product was taken in the same way as (C1) except using (6R)-9-fluoro-1-hydroxy-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-b) as starting material instead of (6R)-1-(Benzyloxy)-10-fluoro-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-a). Product was obtained as TFA salt. MS (m/z): 489.14 [M+H]+. $^1$H NMR (400 MHz, Acetonitrile-d3) δ 10.14 (s, 1H), 8.54 (d, J=17.3 Hz, 1H), 7.36 (dd, J=8.4, 5.7 Hz, 1H), 7.23-6.98 (m, 2H), 6.88 (t, J=8.5 Hz, 2H), 5.51 (d, J=16.5 Hz, 1H), 4.81 (p, J=14.7, 14.0 Hz, 2H), 4.64 (d, J=5.4 Hz, 2H), 4.56 (dd, J=15.0, 10.4 Hz, 2H), 4.20 (d, J=13.6 Hz, 1H).

Preparation of (6S)-10-fluoro-1-hydroxy-2,14-dioxo-N-(2,4,6-trifluorobenzyl)-2,7,12,14-tetrahydro-6,13-methanobenzo[g]pyrido[, 2-b][1,2,5]triazonine-3-carboxamide (C3)

The synthesis of title product was taken in the same way as (C1) except using (6S)-10-fluoro-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-c) as starting material instead of (6R)-1-(Benzyloxy)-10-fluoro-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-a). Product was obtained as TFA salt. MS (m/z): 489.18 [M+H]+. $^1$H NMR (400 MHz, Acetonitrile-d3) δ 10.13 (s, 1H), 8.52 (s, 1H), 7.32 (dd, J=8.4, 5.8 Hz, 1H), 7.23-7.08 (m, 1H), 7.08-6.97 (m, 1H), 6.88 (t, J=8.5 Hz, 2H), 5.56 (d, J=16.7 Hz, 1H), 4.83-4.69 (m, 2H), 4.64 (d, J=5.7 Hz, 2H), 4.58-4.49 (m, 2H), 4.13 (d, J=13.3 Hz, 1H).

Preparation of (6S)-9-fluoro-1-hydroxy-2,14-dioxo-N-(2,4,6-trifluorobenzyl)-2,7,12,14-tetrahydro-6,13-methanobenzo[g]pyrido[,2-b][1,2,5]triazonine-3-carboxamide (C4)

The synthesis of title product was taken in the same way as (C1) except using (6S)-9-fluoro-1-hydroxy-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-d) as starting material instead of (6R)-1-(Benzyloxy)-10-fluoro-2,14-dioxo-N-(2,4,6-trifluorobenzyl)-2,7,12,14-tetrahydro-6,13-methanobenzo[g]pyrido[1,2-b][1,2,5]triazonine-3-carboxamide (4-a). Product was obtained as TFA salt. MS (m/z): 489.19 [M+H]+. $^1$H NMR (400 MHz, Acetonitrile-d3) δ 10.14 (s, 1H), 8.53 (d, J=14.2 Hz, 1H), 7.36 (dd, J=8.5, 5.7 Hz, 1H), 7.28-7.01 (m, 2H), 6.88 (t, J=8.6 Hz, 2H), 5.51 (d, J=16.3 Hz, 1H), 4.79 (q, J=14.5 Hz, 2H), 4.71-4.60 (m, 2H), 4.56 (dd, J=15.0, 10.3 Hz, 2H), 4.20 (d, J=13.6 Hz, 1H).

Example 5: Preparation of (10S)-6-hydroxy-10-methyl-5,8-dioxo-N-[(2,4,6-trifluorophenyl)methyl]-1,2,9-triazatricyclo[7.4.1.0²,⁷]tetradeca-3,6,11-triene-4-carboxamide (C5)
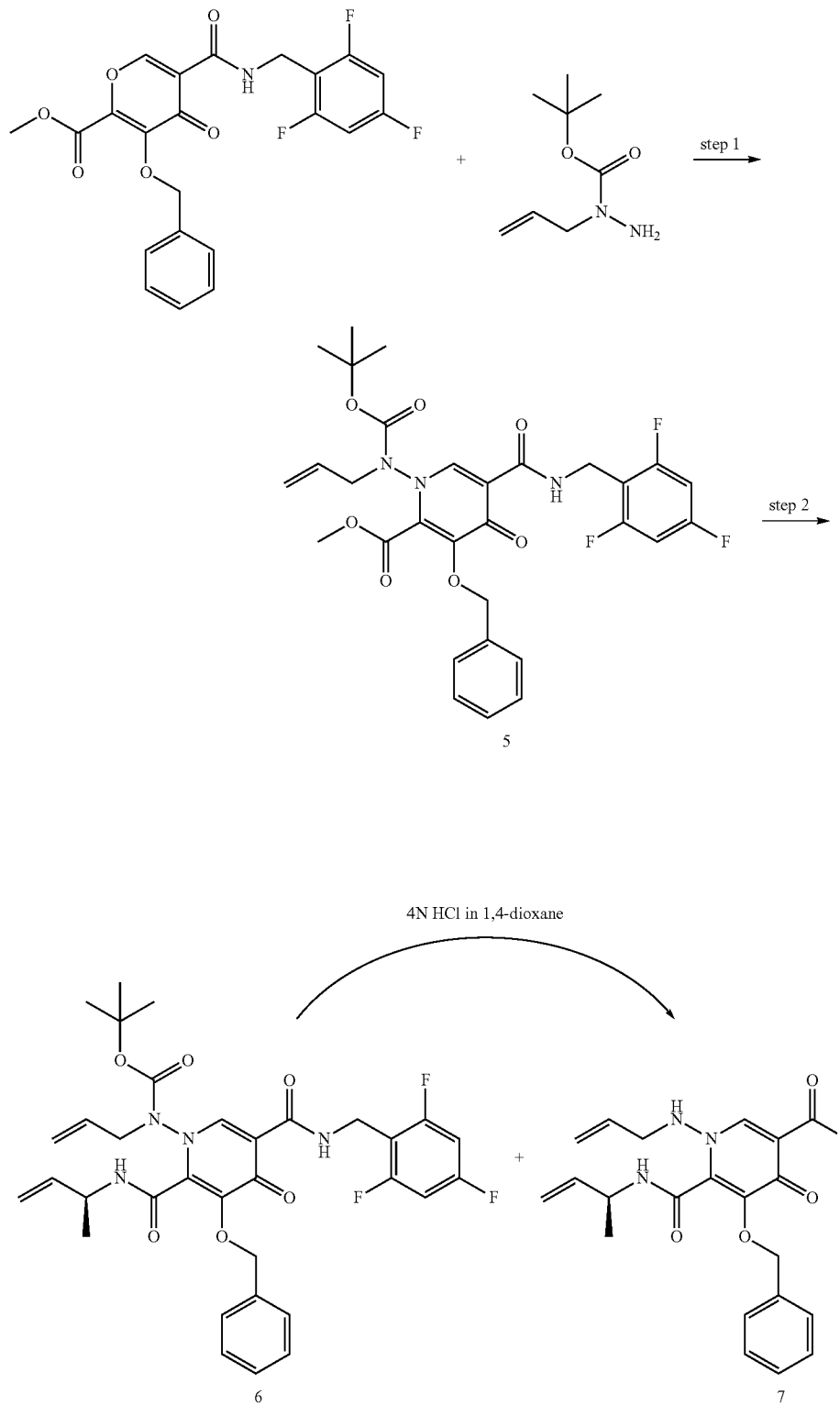

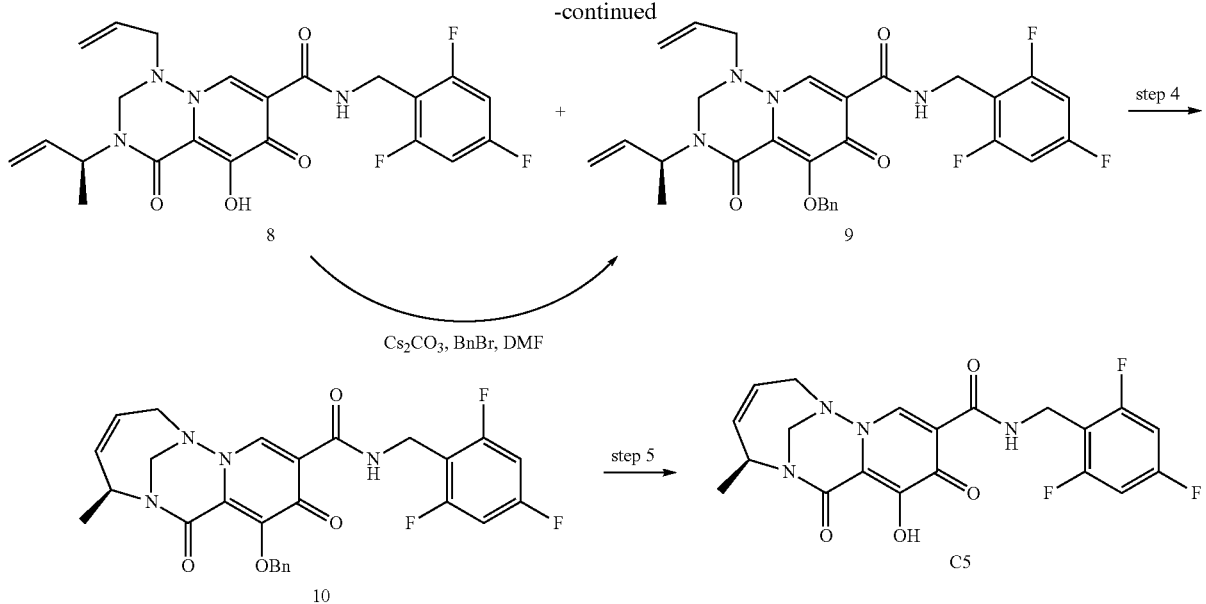

Step 1: Synthesis of methyl 1-(allyl(tert-butoxycarbonyl)amino)-3-(benzyloxy)-4-oxo-5-((2,4,6-trifluorobenzyl)carbamoyl)-1,4-dihydropyridine-2-carboxylate (5)

To a suspension of methyl 3-benzyloxy-4-oxo-5-[(2,4,6-trifluorophenyl)methylcarbamoyl]pyran-2-carboxylate (2.0 g, 4.47 mmol) in a mixture of MeOH (48.0 mL) and water (8.0 mL) was added tert-butyl N-allyl-N-amino-carbamate (0.77 g, 4.47 mmol) and sodium bicarbonate (3.76 g, 44.7 mmol). The resulting mixture was stirred overnight at room temperature. Water (15.0 mL) was added to the reaction and the mixture was stirred for 10 minutes. The suspension was filtered, filter cake was then partitioned between ethyl acetate and water. Aqueous layer was extracted with EtOAc (×2), combined organic layers was washed with brine, dried over sodium sulfate, filtered and concentrated to give the desired product which was directly in next step. LCMS-ESI+(m/z): calcd H+ for $C_{30}H_{30}F_3N_3O_7$, Theoretical: 601.20, Found: 601.99.

Step 2: Synthesis of tert-butyl N-allyl-N-[3-benzyloxy-2-[[(1S)-1-methylallyl]carbamoyl]-4-oxo-5-[(2,4,6-trifluorophenyl)methylcarbamoyl]-1-pyridyl]carbamate (443-int-2) and 1-(allylamino)-3-benzyloxy-N2-[(1S)-1-methylallyl]-4-oxo-N5-[(2,4,6-trifluorophenyl)methyl]pyridine-2,5-dicarboxamide (6)

Methyl 1-(allyl(tert-butoxycarbonyl)amino)-3-(benzyloxy)-4-oxo-5-((2,4,6-trifluorophenyl)carbamoyl)-1,4-dihydropyridine-2-carboxylate (5, 2.3 g, 3.82 mmol) was dissolved in a mixture of MeOH (24.0 mL), THF (12.0 mL) and water (12.0 mL). To this mixture was added Lithium hydroxide monohydrate (1.28 g, 30.6 mmol). The resulting mixture was heated to 60° C. with stirring for 3 hrs. The reaction was cooled to room temperature and concentrated. The residue was diluted with EtOAc, acidified to pH-4 with 1N aq HCl, organic layer was washed with brine, dried over sodium sulfate, filtered and concentrated.

The residue was then dissolved in DCM (17.0 mL) at room temperature and treated with EDCI·HCl (975 mg, 5.11 mmol) followed by HOAt (695 mg, 5.11 mmol) and DIEA (1.76 g, 13.6 mmol). (2S)-but-3-en-2-amine HCl (315 mg, 4.43 mmol) was added afterwards. The newly formed mixture was stirred at room temperature for overnight. The reaction was then diluted with DCM, washed with sat. NH4Cl, brine, dried over sodium sulfate, filtered and concentrated, the residue was mixed with silica gel, concentrated to dryness, purified by combiflash (24 g silica gel, 0-100% EtOAc/Hexanes). Desired fractions were combined and concentrated to give tert-butyl N-allyl-N-[3-benzyloxy-2-[[(1S)-1-methylallyl]carbamoyl]-4-oxo-5-[(2,4,6-trifluorophenyl)methylcarbamoyl]-1-pyridyl]carbamate (6) (LCMS-ESI+(m/z): calcd H+ for $C_{33}H_{35}F_3N_4O_6$, Theoretical: 640.25, Found: 641.05) and 1-(allylamino)-3-benzyloxy-N2-[(1S)-1-methylallyl]-4-oxo-N5-[(2,4,6-trifluorophenyl)methyl]pyridine-2,5-dicarboxamide (7) (LCMS-ESI+(m/z): calcd H+ for C28H27F3N4O4, Theoretical: 540.20, Found: 541.02).

Compound 6 was then converted to compound 7 by treating the solution of 6 (1.0 g) in DCM (10.0 mL) at room temperature with 4N HCl in 1,4-dioxane (10.0 mL, 40.0 mmol) at room temperature for 1 hour. The reaction was concentrated, coevaporated with EtOAc×3. The residue was then dissolved in MeOH (20 mL), NaHCO3 (solid) was added, stirred for 15 min, filtered, and filtrate was concentrated and repurified by combiflash to give compound 7.

Step 3: Synthesis of 1-allyl-5-hydroxy-3-[(1S)-1-methylallyl]-4,6-dioxo-N-[(2,4,6-trifluorophenyl)methyl]-2H-pyrido[2,1-f][1,2,4]triazine-7-carboxamide (8) and 1-allyl-5-benzyloxy-3-[(1S)-1-methylallyl]-4,6-dioxo-N-[(2,4,6-trifluorophenyl)methyl]-2H-pyrido[2,1-f][1,2,4]triazine-7-carboxamide (9)

1-(allylamino)-3-benzyloxy-N2-[(1S)-1-methylallyl]-4-oxo-N5-[(2,4,6-trifluorophenyl)methyl]pyridine-2,5-dicarboxamide (7) (350 mg, 0.647 mmol) was dissolved in a mixture of ACN (3.5 mL) and DCE (3.5 mL) at room temperature. To this mixture was added paraformaldehyde (58.4 mg, 0.647 mmol). The resulting mixture was then heated to 88° C. To this hot mixture was added acetic acid (0.35 mL) dropwise followed by TFA (0.15 mL) dropwise. The reaction was capped and heated for another 30 min. The reaction was cooled to rt, diluted with EtOAc, basified to pH-7 with sat. NaHCO₃, organic layer was washed with brine, dried over sodium sulfate, filtered and concentrated. The residue was purified by combiflash (12 g silica gel, 0-100% EtOAc, dry loading) to obtain the desired 1-allyl-5-benzyloxy-3-[(1S)-1-methylallyl]-4,6-dioxo-N-[(2,4,6-trifluorophenyl)methyl]-2H-pyrido[2,1-f][1,2,4]triazine-7-carboxamide (9) LCMS-ESI+(m/z): calcd H+ for C29H27F3N4O4, Theoretical: 552.20, Found: 552.93. De-benzylated form (8) was also isolated. LCMS-ESI+(m/z): calcd H+ for C22H21F3N4O4, Theoretical: 462.15, Found: 463.02.

Compound 8 was converted back to compound 9 by treating compound 8 (120 mg, 0.26 mmol) in DMF (2.6 mL) with benzyl bromide (46.6 mg, 0.272 mmol) and cesium carbonate (101 mg, 0.31 mmol) at room temperature overnight. The reaction was diluted with EtOAc, washed with water, brine, dried over sodium sulfate, filtered, mixed with silica gel, concentrated to dryness, purified by combiflash (4 g silica gel, 0-100% EtOAc/Hexanes) to give 9. LCMS-ESI+(m/z): calcd H+ for C29H27F3N4O4, Theoretical: 552.20, Found: 552.92.

Step 4: Synthesis of (10S)-6-benzyloxy-10-methyl-5,8-dioxo-N-[(2,4,6-trifluorophenyl)methyl]-1,2,9-triazatricyclo[7.4.1.0²,⁷]tetradeca-3,6,11-triene-4-carboxamide (10)

Compound 9 (130 mg, 0.23 mmol) was dissolved in DCM (29 mL), to this mixture was added Hoveyda-Grubbs II catalyst (36.9 mg, 0.059 mmol). The resulting mixture was sparged with nitrogen for 5 minutes before it was capped and heated at 70° C. for overnight. The reaction was then cooled to room temperature, concentrated, purified by normal phase chromatography (12 g silica gel, 0-100% EtOAc/Hexanes). LCMS-ESI+(m/z): calcd H+ for C27H23F3N4O4, Theoretical: 524.17, Found: 524.91.

Step 5: Synthesis of (10S)-6-hydroxy-10-methyl-5,8-dioxo-N-[(2,4,6-trifluorophenyl)methyl]-1,2,9-triazatricyclo[7.4.1.0²,⁷]tetradeca-3,6,11-triene-4-carboxamide (C5)

Compound 10 (8 mg, 0.015 mmol) was dissolved in DCM (1.0 mL) at room temperature and treated with TFA (1.0 mL) at room temperature for 3 hours. The reaction was concentrated, redissolved in DMF, filtered and purified by reverse phase prep HPLC. LCMS-ESI+(m/z): calcd H+ for C20H17F3N4O4, Theoretical: 434.12, Found: 435.19. 1H NMR (400 MHz, DMSO-d6) δ 10.34 (t, J=5.8 Hz, 1H), 8.32 (s, 1H), 7.26-7.17 (m, 2H), 5.75-5.66 (m, 1H), 5.46 (ddt, J=12.0, 6.2, 3.3 Hz, 1H), 5.34-5.22 (m, 1H), 4.92 (d, J=14.4 Hz, 1H), 4.72 (d, J=14.4 Hz, 1H), 4.65-4.50 (m, 3H), 4.27-4.17 (m, 1H), 3.70-3.62 (m, 1H), 1.29 (d, J=7.3 Hz, 3H).

Example 6: Preparation of 13-benzyl-8-hydroxy-7,9-dioxo-N-(2,4,6-trifluorobenzyl)-2,3,4,5,7,9-hexahydro-1,6-methanopyrido[1,2-b][1,2,5]triazonine-10-carboxamide (C6)

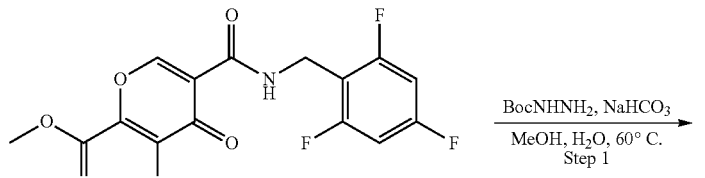

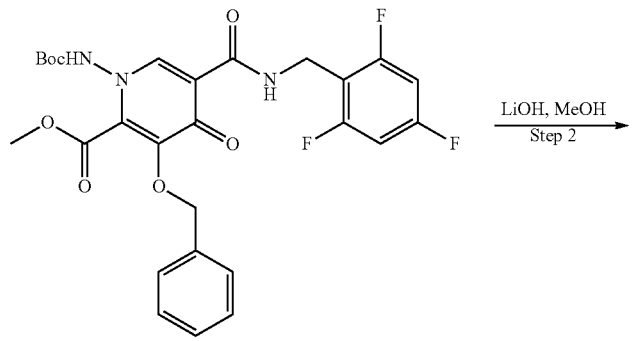

-continued
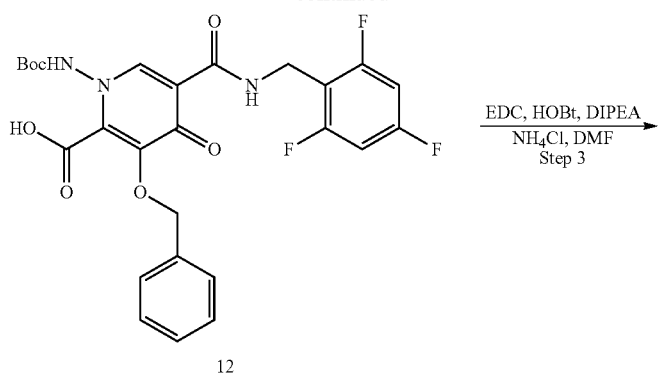
12
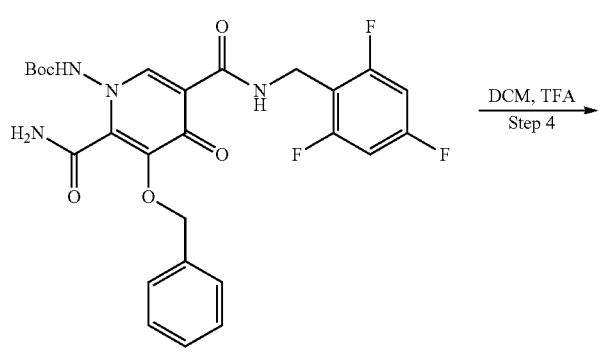
13
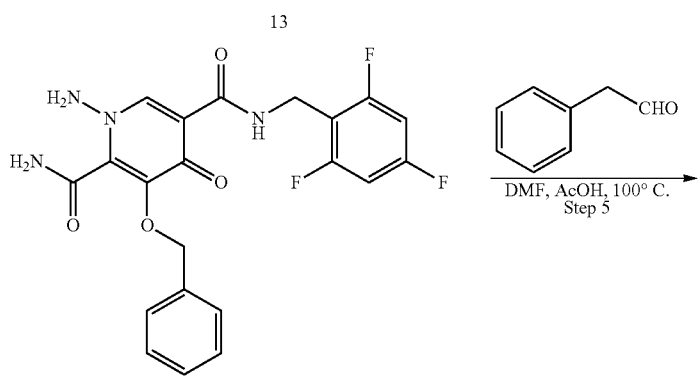
14
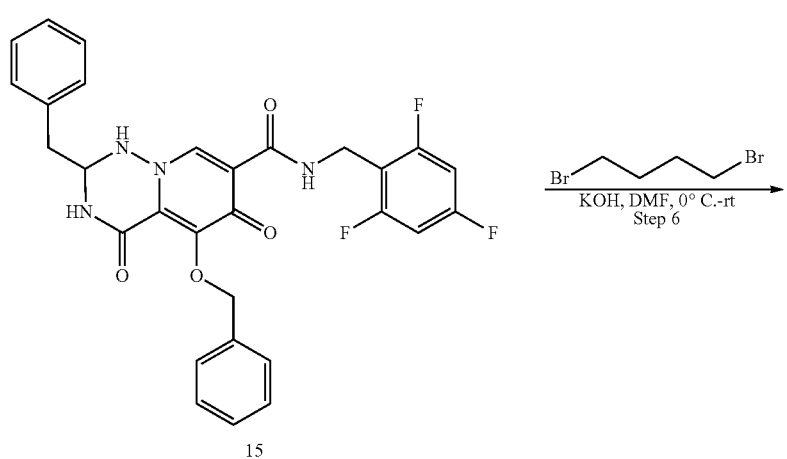
15

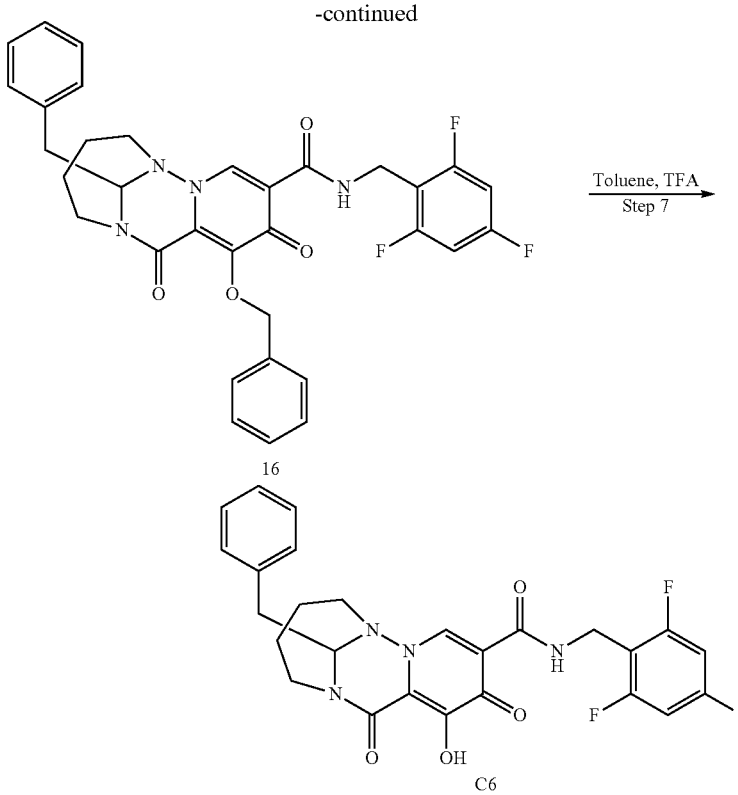

Step 1: Synthesis of methyl 3-(benzyloxy)-1-((tert-butoxycarbonyl)amino)-4-oxo-5-((2,4,6-trifluorobenzyl)carbamoyl)-1,4-dihydropyridine-2-carboxylate A reactor was charged with tert-butyl N-aminocarbamate (390 mg 2.95 mmol), NaHCO$_3$ (451 mg, 5.4 mmol) in MeOH/Water (9 ml/6 ml), Then added methyl 3-(benzyloxy)-4-oxo-5-((2,4,6-trifluorobenzyl)carbamoyl)-4H-pyran-2-carboxylate (1200 mg, 2.68 mmol). The reaction mixture was heated to 60° C. for overnight. The reaction was cooled to room temperature, and extracted with Ethyl Acetate (100 ml). The organic layer was concentrated under vacuum. The residue was used for next step reaction without purification. MS (m/z) 562.064 [M+H]$^+$.

Step 2: Synthesis of 3-(benzyloxy)-1-((tert-butoxycarbonyl)amino)-4-oxo-5-((2,4,6-trifluorobenzyl)carbamoyl)-1,4-dihydropyridine-2-carboxylic acid Into the above residue in MeOH (6 ml), was added 2.5N solution of LiOH (2 ml) at rt. After 2 hours at room temperature, the reaction was acidified by 2N HCl and extracted with Ethyl Acetate (100 ml). The organic layer was concentrated under vacuum. The residue was used for next step reaction without purification. MS (m/z) 547.96 [M+H]+.

Step 3: Synthesis of tert-butyl (3-(benzyloxy)-2-carbamoyl-4-oxo-5-((2,4,6-trifluorobenzyl)carbamoyl)pyridin-1(4H)-yl)carbamate Into the solution of 3-(benzyloxy)-1-((tert-butoxycarbonyl)amino)-4-oxo-5-((2,4,6-trifluorobenzyl)carbamoyl)-1,4-dihydropyridine-2-carboxylic acid (1720 mg, 3.14 mmol) in DMF (12 ml) was, added EDC (1205 mg, 6.28 mmol), HOBt (722 mg, 4.7 mmol), DIPEA (4060 mg, 31.4 mmol) and ammonium chloride (1680 mg. 31.4 mmol) at rt. After overnight stirring at rt, the reaction was diluted with ethyl acetate (100 ml) and wash with brine. The organic layer was dried over MgSO$_4$, and concentrated under vacuum. The resulting residue was purified by column chromatography. MS (m/z) 547.029 [M+H]+. 1H NMR (400 MHz, Chloroform-d) δ 10.12 (t, J=5.7 Hz, 1H), 8.58 (s, 1H), 8.50 (s, 1H), 7.37 (dq, J=4.1, 3.0, 2.4 Hz, 5H), 6.70 (dd, J=8.7, 7.5 Hz, 3H), 5.84 (s, 1H), 5.33 (d, J=4.5 Hz, 3H), 4.68 (d, J=5.7 Hz, 2H), 1.45 (s, 9H).

Step 4: Synthesis of 1-amino-3-(benzyloxy)-4-oxo-N5-(2,4,6-trifluorobenzyl)-1,4-dihydropyridine-2,5-dicarboxamide Into the solution of 1-amino-3-(benzyloxy)-4-oxo-N5-(2,4,6-trifluorobenzyl)-1,4-dihydropyridine-2,5-dicarboxamide (200 mg, 0.366 mmol) in DCM (6 ml), was added TFA (0.5 ml) at rt. After 2 hr stirring at rt, remove the solvent and excess TFA under vacuum. The resulting residue was used for next step reaction without purification. MS (m/z) 447.075 [M+H]$^+$.

Step 5: Synthesis of 2-benzyl-5-(benzyloxy)-4,6-dioxo-N-(2,4,6-trifluorobenzyl)-2,3,4,6-tetrahydro-1H-pyrido[2,1-f][1,2,4]triazine-7-carboxamide Into the solution of 1-amino-3-(benzyloxy)-4-oxo-N5-(2,4,6-trifluorobenzyl)-1,4-dihydropyridine-2,5-dicarboxamide (165 mg, 0.37 mmol) in DMF (2 ml), was added AcOH (2 ml) and 2-phenylacetaldehyde (44 mg, 0.37 mmol) at rt. After heated to 100° C. for 2 h, remove DMF and excess AcOH under vacuum. The residue left over was purified by column chromatography. MS (m/z) 549.065 [M+H]+.

Step 6: Synthesis of 13-benzyl-8-(benzyloxy)-7,9-dioxo-N-(2,4,6-trifluorobenzyl)-2,3,4,5,7,9-hexahydro-1,6-methanopyrido[1,2-b][1,2,5]triazonine-10-carboxamide Solid KOH (106 mg, 1.9 mmol) was suspended in DMF (12 ml), the mixture solution of 2-benzyl-5-(benzyloxy)-4,6-dioxo-N-(2,4,6-trifluorobenzyl)-2,3,4,6-tetrahydro-1H-pyrido[2,1-f][1,2,4]triazine-7-carboxamide (129 mg, 0.235 mmol) and 1,4-dibromobutane (56 mg, 0.26 mmol) in DMF (10 ml) was added by syringe pump in 2 h at 0° C. The reaction mixture was extracted with Ethyl Acetate (100 ml). The organic layer was concentrated under vacuum. The residue was used for next step reaction without purification. MS (m/z) 601.033 [M−H]+.

Step 7: Synthesis of 13-benzyl-8-hydroxy-7,9-dioxo-N-(2,4,6-trifluorobenzyl)-2,3,4,5,7,9-hexahydro-1,6-methanopyrido[1,2-b][1,2,5]triazonine-10-carboxamide (C6)

Into the solution of crude 13-benzyl-8-(benzyloxy)-7,9-dioxo-N-(2,4,6-trifluorobenzyl)-2,3,4,5,7,9-hexahydro-1,6-methanopyrido[1,2-b][1,2,5]triazonine-10-carboxamide (129 mg, 0.225 mmol) in Toluene (5 ml), was added TFA (1 ml) at rt. After overnight stirring at rt, the solvent and excess TFA was removed. The resulting residue was purified by prep HPLC to provide title compound TFA salt. MS (m/z) 513.253 [M+H]+. $^1$H NMR (400 MHz, Chloroform-d) δ 10.37 (d, J=5.9 Hz, 1H), 9.13 (s, 1H), 8.57 (s, 1H), 7.28 (s, 5H), 7.11 (d, J=7.0 Hz, 1H), 6.69 (t, J=8.3 Hz, 2H), 4.90-4.60 (m, 2H), 4.56-4.22 (m, 2H), 3.58-3.24 (m, 2H), 3.06-2.74 (m, 2H).

Example 7: Preparation of (1S,2R,6S,Z)-9-hydroxy-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (C7)

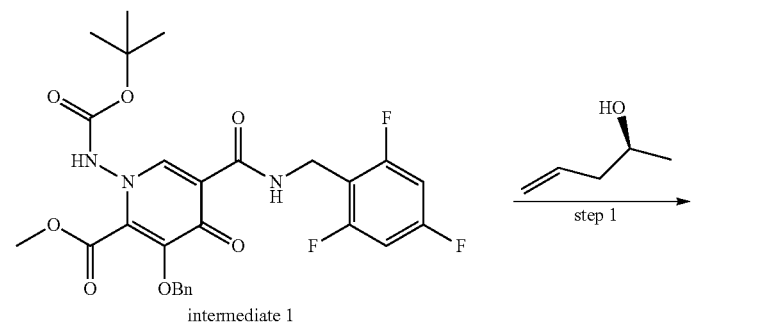

intermediate 1

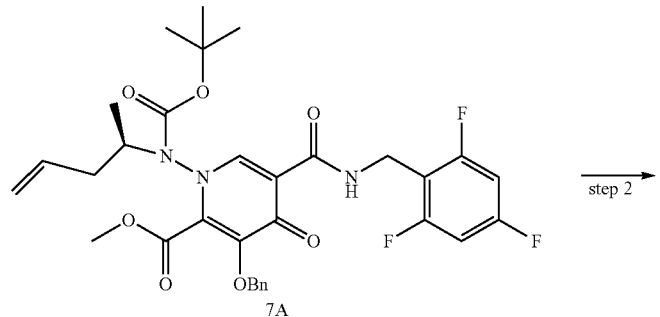

7A

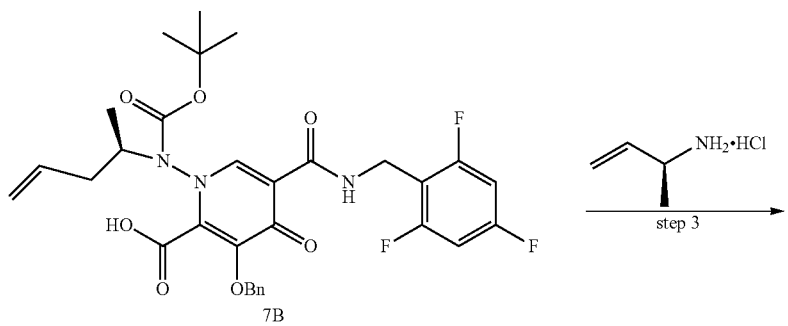

7B

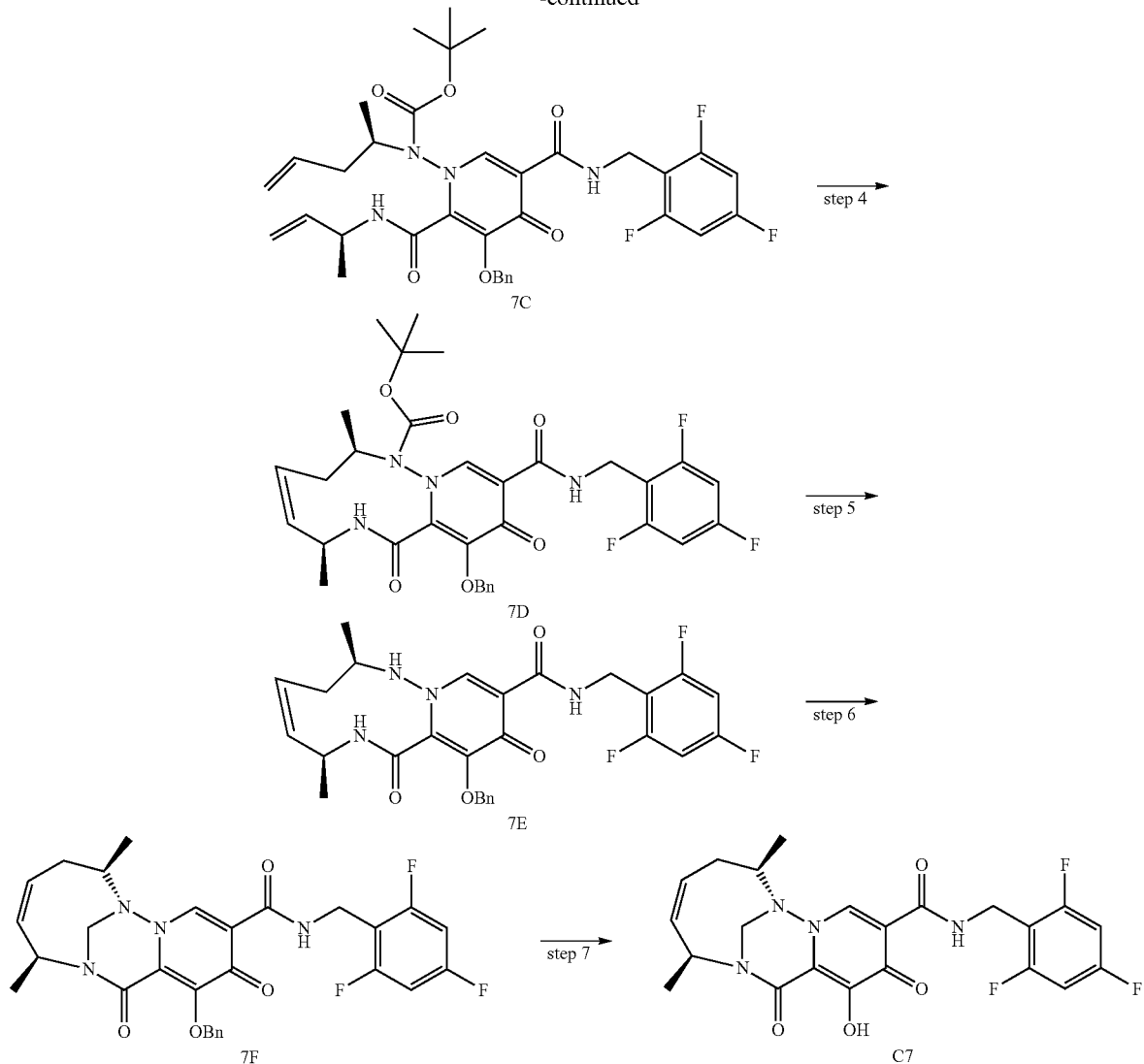

Step: Synthesis of methyl (R)-3-(benzyloxy)-1-((tert-butoxycarbonyl)(pent-4-en-2 yl)amino)-4-oxo-5-((2,4,6-trifluorobenzyl)carbamoyl)-1,4-dihydropyridine-2-carboxylate (7A)

To a reaction mixture of methyl 3-(benzyloxy)-1-((tert-butoxycarbonyl)amino)-4-oxo-5-((2,4,6-trifluorobenzyl)carbamoyl)-1,4-dihydropyridine-2-carboxylate (3.5 g, 6.23 mmol), (2S)-pent-4-en-2-ol (805 mg, 9.35 mmol) and triphenylphosphine (3.27 g, 12.5 mmol) in 7 mL of THF was added Diisopropylazodicarboxylate (2.45 mL, 12.5 mmol). The resulting reaction mixture was stirred at room temperature for 30 min and concentrated in vacuo. The residue was chromatographed on silica gel eluting with EtOAc/hexane to afford the title product. MS (m/z) 630.10 [M+H]⁺.

Step 2: Synthesis of (R)-3-(benzyloxy)-1-((tert-butoxycarbonyl)(pent-4-en-2-yl)amino)-4-oxo-5-((2,4,6-trifluorobenzyl)carbamoyl)-1,4-dihydropyridine-2-carboxylic acid (7B)

Methyl (R)-3-(benzyloxy)-1-((tert-butoxycarbonyl)(pent-4-en-2-yl)amino)-4-oxo-5-((2,4,6-trifluorobenzyl)carbamoyl)-1,4-dihydropyridine-2-carboxylate (7A, 3.17 g, 5.04 mmol) was dissolved in MeOH (20 mL), THF (30 mL) and water (10 mL). Lithium hydroxide monohydrate (1.05 g, 25.2 mmol) was added. The reaction mixture was stirred at room temperature for overnight. It was diluted with EtOAc, acidified to pH~4 with 1N HCl, organic layer was washed with brine, dried over sodium sulfate, filtered and concentrated to afford the title product. MS (m/z) 616.20 [M+H]⁺.

Step 3: Synthesis of tert-butyl (3-(benzyloxy)-2-(((S)-but-3-en-2-yl)carbamoyl)-4-oxo-5-((2,4,6-trifluorobenzyl)carbamoyl)pyridin-1(4H)-yl)((R)-pent-4-en-2-yl)carbamate (7C)

To a reaction mixture of (R)-3-(benzyloxy)-1-((tert-butoxycarbonyl)(pent-4-en-2-yl)amino)-4-oxo-5-((2,4,6-trifluorobenzyl)carbamoyl)-1,4-dihydropyridine-2-carboxylic acid (7B, 2.1 g, 3.41 mmol), (2S)-but-3-en-2-amine; hydrochloride (477 mg, 4.43 mmol), EDCI·HCl (977 mg, 5.12 mmol) and HOAt (696 mg, 5.12 mmol) in DCM (34 mL) was added N,N-diisopropylethylamine (2.38 mL, 13.6 mmol). The reaction mixture was stirred at room temperature for 30 min, diluted with DCM, washed with sat. NH$_4$Cl and brine, dried over sodium sulfate, filtered and concentrated. The residue was chromatographed on silica gel eluting with EtOAc/hexane to afford the title product. MS (m/z) 669.83 [M+H]$^+$.

Step 4: Synthesis of tert-butyl (2R,6S,Z)-9-(benzyloxy)-2,6-dimethyl-8,10-dioxo-11-((2,4,6-trifluorobenzyl)carbamoyl)-2,3,6,7,8,10-hexahydro-1H-pyrido[1,2-b][1,2,5]triazecine-1-carboxylate (7D)

A solution of tert-butyl (3-(benzyloxy)-2-(((S)-but-3-en-2-yl)carbamoyl)-4-oxo-5-((2,4,6-trifluorobenzyl)carbamoyl)pyridin-1(4H)-yl)((R)-pent-4-en-2-yl)carbamate (7C, 1.0 g, 1.5 mmol) and Grubbs catalyst 2nd generation (63.5 mg, 0.075 mmol) in 500 ml of toluene was purged with Ar gas for 30 min. The resulting solution was heated at 80° C. oil bath for 5 hours. The reaction mixture was concentrated, and the residue was purified by column chromatography on silica gel eluting EtOAc in hexane to afford the title product. MS (m/z) 641.29 [M+H]+.

Step 5: Synthesis of (2R,6S,Z)-9-(benzyloxy)-2,6-dimethyl-8,10-dioxo-N-(2,4,6-trifluorobenzyl)-2,3,6,7,8,10-hexahydro-1H-pyrido[1,2-b][1,2,5]triazecine-11-carboxamide (7E)

Tert-butyl (2R,6S,Z)-9-(benzyloxy)-2,6-dimethyl-8,10-dioxo-11-((2,4,6-trifluorobenzyl)carbamoyl)-2,3,6,7,8,10-hexahydro-1H-pyrido[1,2-b][1,2,5]triazecine-1-carboxylate (7D, 170 mg, 0.265 mmol) was dissolved in DCM (5 ml), and treated with 4N HCl in 1,4-dioxane (3 ml) at room temperature for 3 hours. Then added more 4N HCl in 1,4-dioxane (2 mL) stirred at room temperature for 2 hours. After concentrated to dryness, the residue was dissolved in EtOAc and washed with saturated NaHCO$_3$ and brine. the organic layer was dried over MgSO$_4$, filtered and concentrated to dryness followed by high vacuum dried to afford the title product. MS (m/z) 541.24 [M+H]$^+$.

Step 6: Synthesis of (1S,2R,6S)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (7F)

In a 8 mL sample vial, (2R,6S,Z)-9-(benzyloxy)-2,6-dimethyl-8,10-dioxo-N-(2,4,6-trifluorobenzyl)-2,3,6,7,8,10-hexahydro-1H-pyrido[1,2-b][1,2,5]triazecine-11-carboxamide (7E, 50 mg, 0.093) and paraformaldehyde (6.1 mg, 2.2 eq based on MW: 30) mixed with Acetonitrile (1.25 mL) and DCE (1.25 mL) at room temperature, caped and placed right away on pre-heated hot plate at 88° C. To it was add AcOH (0.25 mL, 10% in Acetonitrile) dropwise followed by TFA (0.25 mL, 10% in DCE) dropwise. The resulting reaction mixture was then continued to be heated for 30 min. Cooled to room temperature and poured onto well-stirred two-phase mixture of EtOAc-NaHCO$_3$ (aq). Organic phase was separated. Aqueous layer was extracted once with EtOAc. Combined Organic phase was washed with brine, dried over Na$_2$SO$_4$ and filtered. Residue was concentrated to dryness and purified by RP-HPLC to afford the title product. MS (m/z) 553.17 [M+H]+.

Step 7: Synthesis (1S,2R,6S,Z)-9-hydroxy-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (C7)

(1S,2R,6S,Z)-9-(benzyloxy)-2,6-dimethyl-8,10-dioxo-N-(2,4,6-trifluorobenzyl)-3,6,8,10-tetrahydro-2H-1,7-metha-nopyrido[1,2-b][1,2,5]triazecine-11-carboxamide (7F, 30 mg, 0.054 mmol) dissolved in 2 mL of Toluene, to it was added 2 mL of TFA. The mixture was stirred at room temperature for 40 minutes. Removed the solvent and purified by RP-HPLC to afford the title product. The structure was confirmed by X-Ray Crystallography. MS (m/z): 463.20 [M+H]$^+$. $^1$H NMR (400 MHz, Acetonitrile-d3) δ 10.42 (s, 1H), 8.42 (s, 1H), 6.94-6.81 (m, 2H), 5.75-5.60 (m, 2H), 5.20 (q, J=7.1, 6.7 Hz, 1H), 4.82-4.56 (m, 4H), 3.59 (p, J=6.9 Hz, 1H), 2.39 (dd, J=15.5, 7.3 Hz, 1H), 2.06 (ddd, J=16.7, 7.9, 5.5 Hz, 1H), 1.29 (t, J=7.3 Hz, 6H).

Example 8: Preparation of (1S,2R,6S)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (C8)

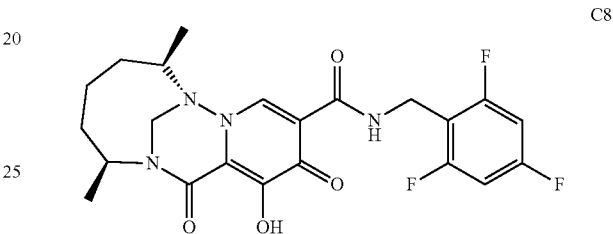

C8

(1S,2R,6S,Z)-9-(benzyloxy)-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (7F, 35 mg, 0.063 mmol) was dissolved in 3 mL of ethanol and 3 mL of EtOAc and was sparged under an argon atmosphere. Palladium on carbon (10 wt %, wet) (13.5 mg) was added and the mixture was sparged under a hydrogen atmosphere (1 atm, balloon). The mixture was stirred vigorously for two hours and then sparged under an argon atmosphere. It was filtered through a pad of Celite®. The Celite® was washed with absolute ethanol and the filtrate was concentrated to dryness and the residue was purified by RP-HPLC to afford the title product. MS (m/z): 465.200 [M+H]+. $^1$H NMR (400 MHz, Acetonitrile-d3) δ 10.37 (s, 1H), 8.32 (s, 1H), 6.94-6.81 (m, 2H), 4.87 (d, J=14.3 Hz, 1H), 4.71-4.59 (m, 3H), 4.39 (tt, J=11.5, 6.6 Hz, 1H), 2.95 (dq, J=8.6, 6.3 Hz, 1H), 2.10-1.97 (m, 2H), 1.87-1.72 (m, 2H), 1.63-1.49 (m, 1H), 1.30 (q, J=12.0 Hz, 1H), 1.13 (dd, J=14.3, 6.5 Hz, 6H).

Example 9: Preparation of (1'S,5'S)-8'-hydroxy-5,5,5'-trimethyl-7',9'-dioxo-N-(2,4,6-trifluorobenzyl)-4,5,7',9'-tetrahydro-2H,5'H-spiro[furan-3,2'-[1,6]methanopyrido[1,2-b][1,2,5]triazonine]-10'-carboxamide (C9)

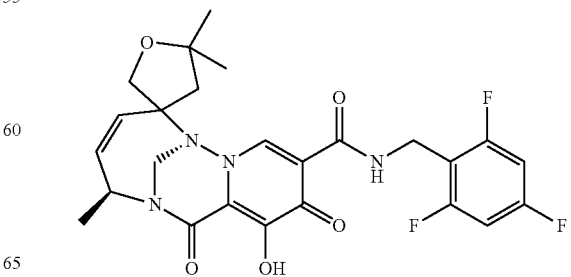

(1'S,5'S)-8'-hydroxy-5,5,5'-trimethyl-7',9'-dioxo-N-(2,4,6-trifluorobenzyl)-4,5,7',9'-tetrahydro-2H,5'H-spiro[furan-3,2'-[1,6]methanopyrido[1,2-b][1,2,5]triazonine]-10'-carboxamide was prepared using a similar method as Example 84, except that 5,5-dimethyltetrahydrofuran-3-carbaldehyde was used instead of tetrahydrofuran-3-carbaldehyde in Step 1 and only one product was isolated from the ring closing metathesis reaction in Step 9. MS (m/z) 519.24 [M+H]⁺. 1H NMR (400 MHz, Methanol-d4) δ 8.79 (s, 1H), 6.91 (t, J=8.4 Hz, 2H), 6.01 (dd, J=11.9, 2.3 Hz, 1H), 5.49 (dd, J=12.0, 2.8 Hz, 1H), 5.19 (d, J=14.7 Hz, 1H), 5.01 (d, J=14.7 Hz, 1H), 4.67 (s, 2H), 4.37 (dt, J=7.5, 2.6 Hz, 1H), 3.73-3.61 (m, 2H), 2.52 (dd, J=13.5, 1.6 Hz, 1H), 2.07-1.94 (m, 1H), 1.87 (d, J=7.4 Hz, 3H), 1.56 (s, 3H), 1.34 (s, 3H).

Example 10 and 11: Preparation of (1R,2R,Z)—N-(2,4-difluorobenzyl)-9-hydroxy-2-methyl-8,10-dioxo-3,6,8,10-tetrahydro-2H-1,7-methanopyrido[1,2-b][1,2,5]triazecine-11-carboxamide (C10) and (1S,2R,Z)—N-(2,4-difluorobenzyl)-9-hydroxy-2-methyl-8,10-dioxo-3,6,8,10-terahydro-2H-1,7-methanopyrido[1,2-b][1,2,5]triazecine-11-carboxamide (C11)

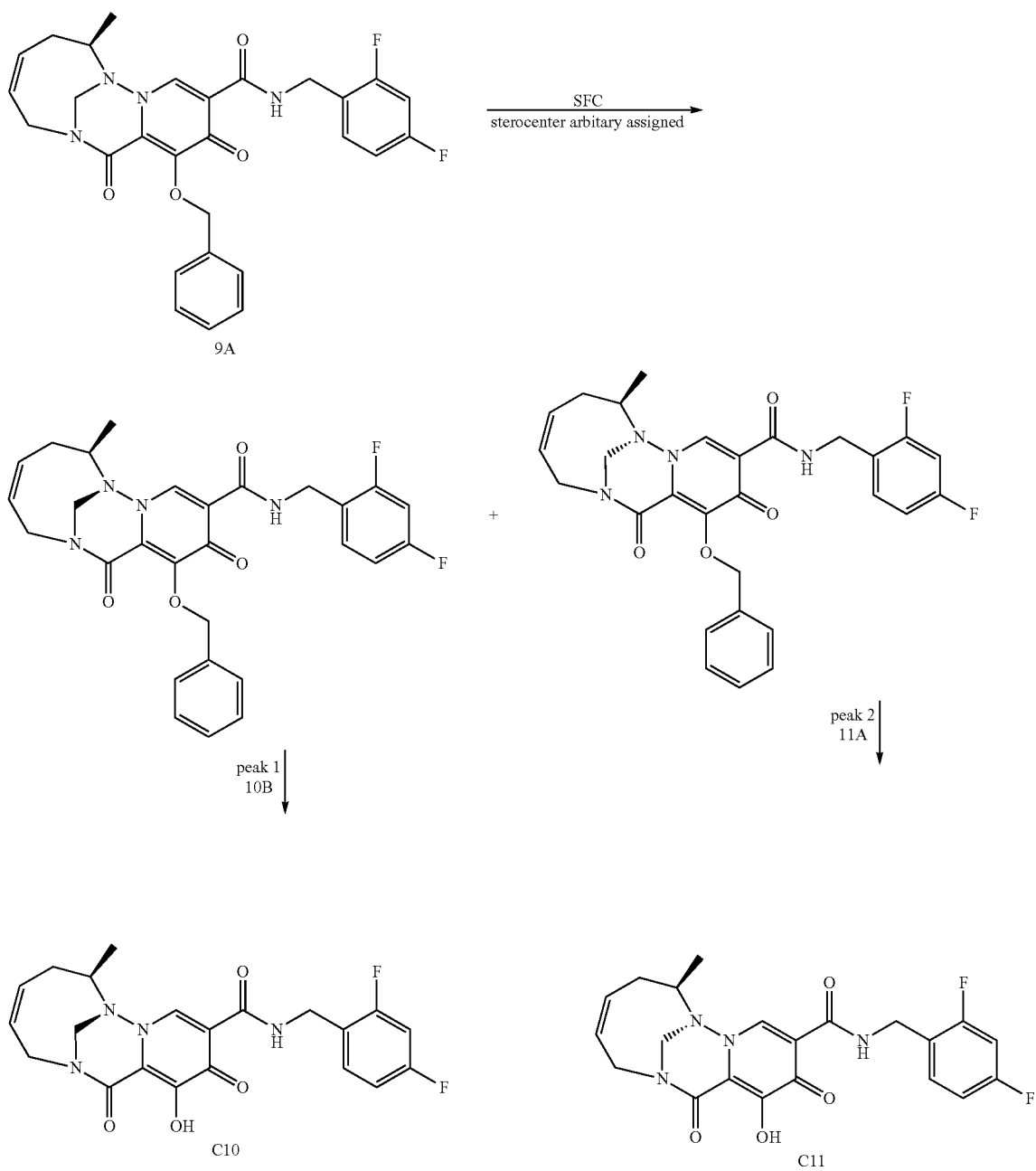

(2R,Z)-9-(benzyloxy)-N-(2,4-difluorobenzyl)-2-methyl-8,10-dioxo-3,6,8,10-tetrahydro-2H-1,7-methanopyrido[1,2-b][1,2,5]triazecine-11-carboxamide (9A) was prepared in a manner similar to (1S,2R,6S)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (7F in example 7) using methyl 3-(benzyloxy)-1-((tert-butoxycarbonyl)amino)-5-((2,4-difluorobenzyl)carbamoyl)-4-oxo-1,4-dihydropyridine-2-carboxylate instead of methyl 3-(benzyloxy)-1-((tert-butoxycarbonyl)amino)-4-oxo-5-((2,4,6-trifluorobenzyl)carbamoyl)-1,4-dihydropyridine-2-carboxylate in step 1 and using allylamine; hydrochloride instead of (2S)-but-3-en-2-amine; hydrochloride in step 3. MS (m/z): 521.20 [M+H]+.

It was separated into its individual diastereomers (10B and 11A) by preparative SFC chromatography on an IA column using ethanol as co-solvent. The separated diastereomers were dissolved in 1 mL of Toluene and 1 mL of TFA and stirred at room temperature for 1 h. after concentration, purified by RP-HPLC eluting with ACN/water (0.1% TFA) to provide the title compounds C10 and C11.

Peak 1: (1R,2R,Z)—N-(2,4-difluorobenzyl)-9-hydroxy-2-methyl-8,10-dioxo-3,6,8,10-tetrahydro-2H-1,7-methanopyrido[1,2-b][1,2,5]triazecine-11-carboxamide (C10): MS (m/z): 431.20 [M+H]+. $^1$H NMR (400 MHz, Acetonitrile-d3) δ 10.37 (s, 1H), 8.35 (s, 1H), 7.44 (d, J=7.4 Hz, 1H), 6.96 (d, J=9.8 Hz, 2H), 5.83 (q, J=9.7, 8.6 Hz, 1H), 5.66-5.58 (m, 1H), 5.15 (d, J=13.8 Hz, 1H), 4.94 (d, J=17.8 Hz, 1H), 4.68-4.57 (m, 3H), 3.55-3.38 (m, 2H), 2.25 (dt, J=16.7, 8.5 Hz, 1H), 1.97-1.86 (m, 1H), 1.15 (d, J=6.9 Hz, 3H).

Peak 2: (1S,2R,Z)—N-(2,4-difluorobenzyl)-9-hydroxy-2-methyl-8,10-dioxo-3,6,8,10-tetrahydro-2H-1,7-methanopyrido[1,2-b][1,2,5]triazecine-11-carboxamide (C11): MS (m/z): 431.20 [M+H]+. $^1$H NMR (400 MHz, Acetonitrile-d3) δ 10.41 (s, 1H), 8.44 (s, 1H), 7.44 (q, J=8.8, 8.3 Hz, 1H), 6.97 (tt, J=10.8, 3.1 Hz, 2H), 5.79-5.64 (m, 2H), 4.98-4.88 (m, 2H), 4.69-4.58 (m, 3H), 3.61 (t, J=6.7 Hz, 1H), 3.53 (dd, J=18.0, 4.0 Hz, 1H), 2.42 (dd, J=15.4, 7.1 Hz, 1H), 2.16-2.03 (m, 1H), 1.29 (d, J=7.1 Hz, 3H).

Example 12: Preparation of (1R,2S,6R,Z)-9-hydroxy-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (C12)

Acetonitrile-d3) δ 10.43 (s, 1H), 8.42 (s, 1H), 6.94-6.81 (m, 2H), 5.75-5.60 (m, 2H), 5.20 (q, J=7.5 Hz, 1H), 4.84-4.53 (m, 4H), 3.58 (q, J=6.9 Hz, 1H), 2.39 (dd, J=15.2, 7.2 Hz, 1H), 2.12-2.00 (m, 1H), 1.29 (t, J=7.3 Hz, 6H).

Example 13: Preparation of (1S,2R)—N-(2,4-difluorobenzyl)-9-hydroxy-2-methyl-8,10-dioxo-3,4,5,6,8,10-hexahydro-2H-1,7-methanopyrido[1,2-b][1,2,5]triazecine-11-carboxamide (C13)

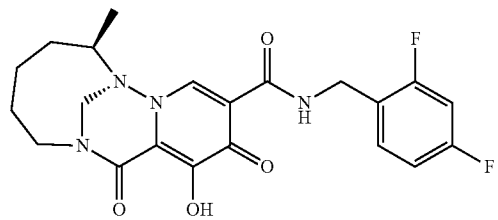

C13

Compound 13 was prepared in a manner similar to (1S,2R,6S)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (C8) in example 8 using (1S,2R,Z)—N-(2,4-difluorobenzyl)-9-hydroxy-2-methyl-8,10-dioxo-3,6,8,10-tetrahydro-2H-1,7-methanopyrido[1,2-b][1,2,5]triazecine-11-carboxamide (11) instead of (2R,6S,Z)-9-(benzyloxy)-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (7F). MS (m/z): 433.20 [M+H]+. $^1$H NMR (400 MHz, Acetonitrile-d3) δ 10.39 (s, 1H), 8.34 (s, 1H), 7.57-7.20 (m, 1H), 7.03-6.91 (m, 2H), 4.86 (d, J=14.3 Hz, 1H), 4.78 (d, J=14.6 Hz, 1H), 4.60 (d, J=5.6 Hz, 2H), 4.14 (dd, J=13.4, 5.9 Hz, 1H), 3.39-2.97 (m, 2H), 1.97-1.87 (m, 2H), 1.75 (d, J=6.5 Hz, 1H), 1.63 (dt, J=16.9, 9.1 Hz, 1H), 1.55-1.20 (m, 2H), 1.17 (d, J=6.5 Hz, 3H).

Example 14: Preparation of (1R,2S,6R)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (C14)

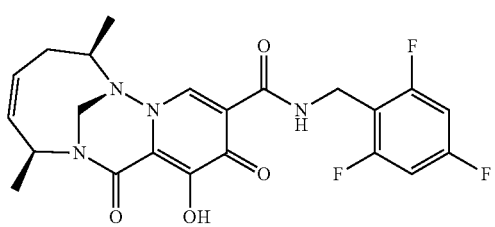

C12

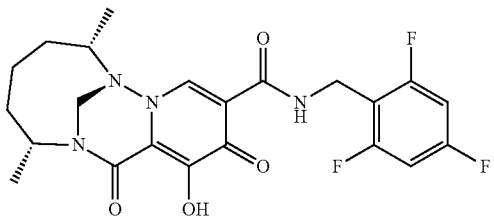

C14

Compound 12 was prepared in a manner similar to (1S,2R,6S,Z)-9-hydroxy-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (C7 in example 7) using (2R)-pent-4-en-2-ol instead of (2S)-pent-4-en-2-ol in step 1 and using (2R)-but-3-en-2-amine; hydrochloride instead of (2S)-but-3-en-2-amine; hydrochloride in step 3. MS (m/z): 431.20 [M+H]+. $^1$H NMR (400 MHz, Compound 14 was prepared in a manner similar to (1S,2R,6S)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (C8) in example 8 using (1R,2S,6R,Z)-9-(benzyloxy)-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide instead of (2R,6S,Z)-9-(benzyloxy)-2,6-dimethyl-8, 10-dioxo-N-(2,4,6-trifluorobenzyl)-3,6,8,10-tetrahydro-2H-1,7-methanopyrido[1,2-b][1,2,5]triazecine-11-carboxamide (7F). MS (m/z): 465.20 [M+H]+. ¹H NMR (400 MHz, Acetonitrile-d3) δ 10.37 (s, 1H), 8.32 (s, 1H), 6.94-6.81 (m, 2H), 4.87 (d, J=14.3 Hz, 1H), 4.74-4.58 (m, 3H), 4.39 (ddd, J=11.8, 6.7, 4.8 Hz, 1H), 3.01-2.89 (m, 1H), 2.07-1.97 (m, 1H), 1.87-1.72 (m, 2H), 1.56 (dt, J=16.6, 10.1 Hz, 1H), 1.30 (q, J=12.0 Hz, 1H), 1.13 (dd, J=14.5, 6.5 Hz, 6H).

Example 15: Preparation of (1R,2R)—N-(2,4-difluorobenzyl)-9-hydroxy-2-methyl-8,10-dioxo-3,4,5,6,8,10-hexahydro-2H-1,7-methanopyrido[1,2,5]triazecine-11-carboxamide (C15)

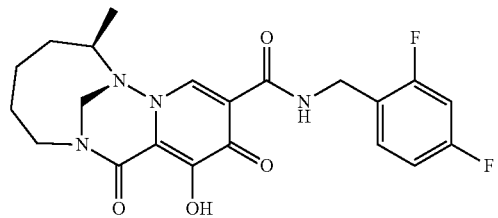

C15

Compound 15 was prepared in a manner similar to (1R,2R,Z)—N-(2,4-difluorobenzyl)-9-hydroxy-2-methyl-8,10-dioxo-3,6,8,10-tetrahydro-2H-1,7-methanopyrido[1,2-b][1,2,5]triazecine-11-carboxamide (C8) in example 8 using (1R,2R,Z)—N-(2,4-difluorobenzyl)-9-hydroxy-2-methyl-8,10-dioxo-3,6,8,10-tetrahydro-2H-1,7-methanopyrido[1,2-b][1,2,5]triazecine-11-carboxamide (10) instead of (2R,6S,Z)-9-(benzyloxy)-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (7F). MS (m/z): 433.20 [M+H]⁺. ¹H NMR (400 MHz, Acetonitrile-d3) δ 11.50 (s, 1H), 10.41 (s, 1H), 8.32 (d, J=16.7 Hz, 1H), 7.49-7.38 (m, 1H), 6.97 (ddt, J=13.4, 8.5, 3.0 Hz, 2H), 5.13 (d, J=14.1 Hz, 1H), 4.80 (t, J=14.9 Hz, 1H), 4.60 (d, J=6.0 Hz, 2H), 4.22 (dt, J=13.8, 4.6 Hz, 1H), 3.57 (p, J=7.2 Hz, 1H), 3.02 (ddd, J=14.0, 10.1, 4.2 Hz, 1H), 1.96 (d, J=2.5 Hz, 3H), 1.70-1.55 (m, 1H), 1.53-1.16 (m, 2H), 1.13 (d, J=7.0 Hz, 3H).

Example 16: Preparation of (1S,2R,Z)-9-hydroxy-2-methyl-8,10-dioxo-N-(2,4,6-trifluorobenzyl)-3,6,8,10-tetrahydro-2H-1,7-methanopyrido[1,2-b][1,2,5]triazecine-11-carboxamide (C16)

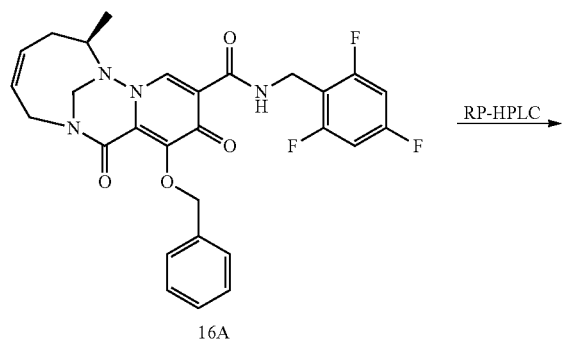

16A

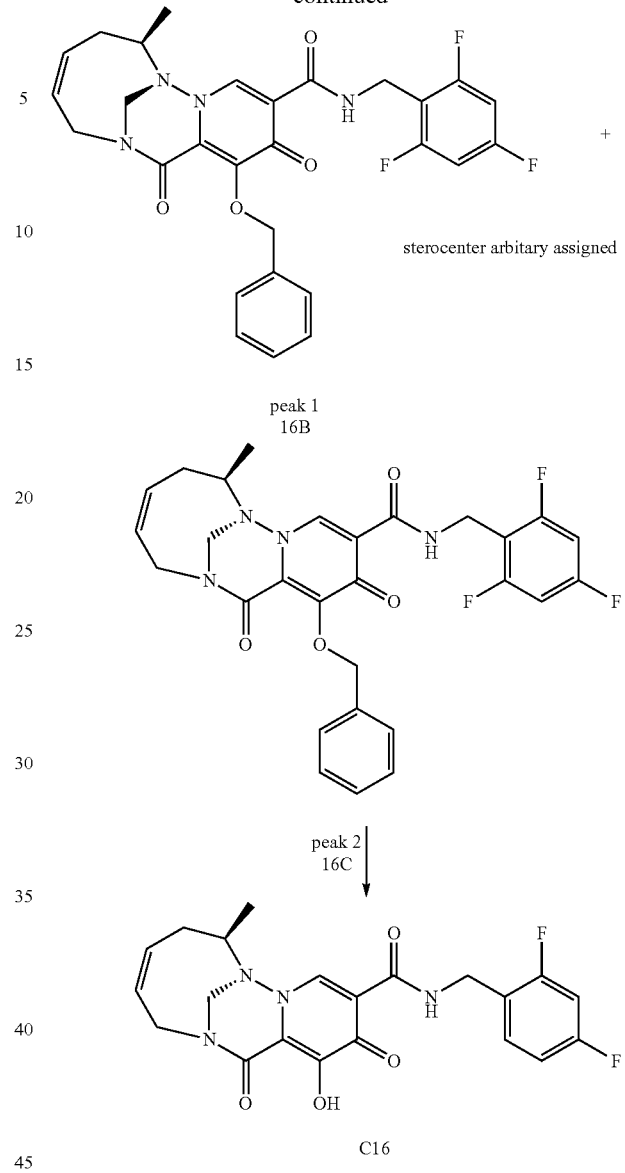

(2R,Z)-9-(benzyloxy)-2-methyl-8,10-dioxo-N-(2,4,6-trifluorobenzyl)-3,6,8,10-tetrahydro-2H-1,7-methanopyrido[1,2-b][1,2,5]triazecine-11-carboxamide (16A) was prepared in a manner similar to (1S,2R,6S)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (7F in example 7) using allylamine; hydrochloride instead of (2S)-but-3-en-2-amine; hydrochloride in step 3. MS (m/z): 539.20 [M+H]+.

It was separated into its individual diastereomers (peak 1 and peak 2) by RP-HPLC eluting with acetonitrile and water (with 0.1% TFA). Take peak 2 (23 mg, 0.043 mmol) dissolved in 0.5 mL of Toluene and 0.5 mL of TFA and stirred at room temperature for 1 hour. After concentration, purified by RP-HPLC eluting with ACN/water (0.1% TFA) to provide the title compound. MS (m/z): 449.10 [M+H]+. ¹H NMR (400 MHz, Acetonitrile-d₃) δ 10.41 (s, 1H), 8.42 (s, 1H), 6.87 (t, J=8.7 Hz, 2H), 5.72 (q, J=11.7, 9.1 Hz, 2H), 4.92 (d, J=15.7 Hz, 2H), 4.64 (d, J=14.6 Hz, 3H), 3.82-3.11 (m, 2H), 2.46-2.35 (m, 1H), 2.08 (dt, J=13.7, 6.3 Hz, 1H), 1.28 (d, J=7.2 Hz, 3H).

Example 17: Preparation of (1S,2R)-9-hydroxy-2-methyl-8,10-dioxo-N-(2,4,6-trifluorobenzyl)-3,4,5,6,8,10-hexahydro-2H-1,7-methanopyrido[1,2-b][1,2,5]triazecine-11-carboxamide (C17)

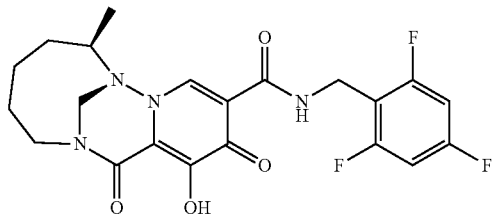

C17

Compound 17 was prepared in a manner similar to (1S,2R,6S)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (C8) in example 8 using (1S,2R,Z)-9-hydroxy-2-methyl-8,10-dioxo-N-(2,4,6-trifluorobenzyl)-3,6,8,10-tetrahydro-2H-1,7-methanopyrido[1,2-b][1,2,5]triazecine-11-carboxamide (16) instead of (2R,6S,Z)-9-(benzyloxy)-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (7F). MS (m/z): 451.20 [M+H]+. $^1$H NMR (400 MHz, Acetonitrile-d3) δ 10.38 (s, 1H), 8.33 (s, 1H), 6.94-6.81 (m, 2H), 4.85 (d, J=14.4 Hz, 1H), 4.76 (d, J=14.5 Hz, 1H), 4.62 (d, J=5.6 Hz, 2H), 4.14 (dt, J=14.0, 7.0 Hz, 1H), 3.06 (dt, J=13.8, 4.4 Hz, 2H), 1.93 (d, J=14.4 Hz, 3H), 1.75 (t, J=8.3 Hz, 1H), 1.63 (dt, J=16.9, 8.9 Hz, 1H), 1.44 (q, J=10.1 Hz, 1H), 1.16 (d, J=6.5 Hz, 3H).

Example 18: Preparation of (1S,2R,6R,Z)-9-hydroxy-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (C18)

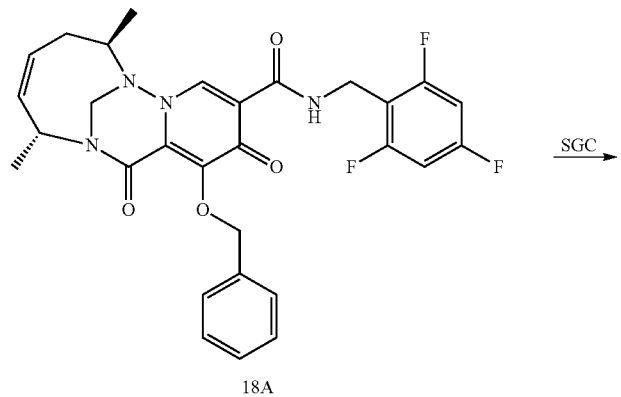

18A

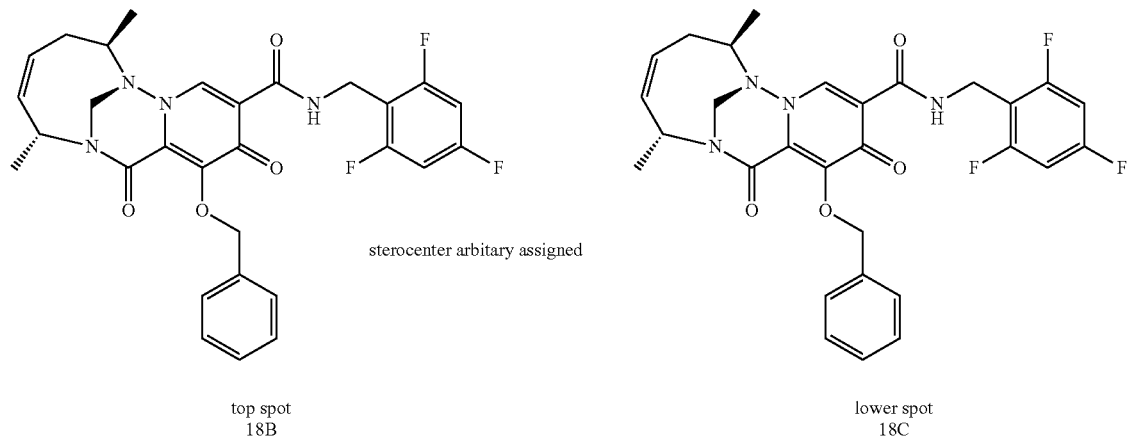

sterocenter arbitary assigned top spot
18B lower spot
18C

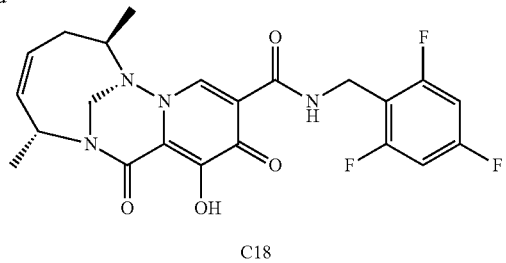

C18

(2R,6R,Z)-9-(benzyloxy)-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (18A) was prepared in a manner similar to (1S,2R,6S)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (7F in example 7) using (2R)-but-3-en-2-amine; hydrochloride instead of (2S)-but-3-en-2-amine; hydrochloride in step 3. MS (m/z): 553.30 [M+H]+.

It was separated into its individual diastereomers top spot and lower spot) by silica gel chromatography eluting with EtOAc/hexane. Took lower spot (15 mg, 0.027 mmol), dissolved in 0.5 mL of Toluene and 0.5 mL of TFA and stirred at room temperature for 1 hour. After concentration, purified by RP-HPLC eluting with ACN/water (0.1% TFA) to provide the title compound (18). MS (m/z): 463.20 [M+H]+. $^1$H NMR (400 MHz, Acetonitrile-d$_3$) δ 10.38 (s, 1H), 8.34 (s, 1H), 6.94-6.81 (m, 2H), 5.85-5.72 (m, 1H), 5.53 (dt, J=11.6, 1.6 Hz, 1H), 5.27 (d, J=7.9 Hz, 1H), 4.96 (d, J=13.7 Hz, 1H), 4.73 (d, J=13.7 Hz, 1H), 4.62 (d, J=5.7 Hz, 2H), 3.48-3.35 (m, 1H), 2.29-2.15 (m, 1H), 1.96-1.87 (m, 1H), 1.27 (d, J=7.4 Hz, 3H), 1.12 (d, J=7.0 Hz, 3H).

Example 19 and 20: Preparation of (1R,2S,6S,Z)-9-hydroxy-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (C19) and (1S,2S,6S,Z)-9-hydroxy-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (C20)

(2S,6S,Z)-9-hydroxy-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (19A) was prepared in a manner similar to (1S,2R,6S,Z)-9-hydroxy-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (7 in example 7) using (2R)-pent-4-en-2-ol instead of (2S)-pent-4-en-2-ol in step 1. MS (m/z): 463.20 [M+H]+.

It was separated into its individual diastereomers (peak 1 and peak 2) by preparative SFC chromatography on an AZ-H column using methanol as co-solvent.

Peak 1: (1R,2S,6S,Z)-9-hydroxy-2,6-dimethyl-8,10-dioxo-N-(2,4,6-trifluorobenzyl)-3,6,8,10-tetrahydro-2H-1,7-methanopyrido[12-b][1,2,5]triazecine-11-carboxamide (19): MS (m/z): 463.20 [M+H]+. $^1$H NMR (400 MHz, Acetonitrile-d3) δ 11.45 (s, 1H), 10.38 (s, 1H), 8.33 (s, 1H), 6.94-6.81 (m, 2H), 5.85-5.72 (m, 1H), 5.53 (dt, J=11.5, 1.6 Hz, 1H), 5.27 (d, J=8.0 Hz, 1H), 4.96 (d, J=13.7 Hz, 1H), 4.72 (d, J=13.6 Hz, 1H), 4.62 (d, J=5.7 Hz, 2H), 3.48-3.35 (m, 1H), 2.29-2.15 (m, 1H), 1.97-1.85 (m, 1H), 1.27 (d, J=7.4 Hz, 3H), 1.12 (d, J=7.0 Hz, 3H).

Peak 2: (1S,2S,6S,Z)-9-hydroxy-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (20): MS (m/z): 463.20 [M+H]+. $^1$H NMR (400 MHz, Acetonitrile-d3) δ 10.44 (s, 1H), 8.39 (s, 1H), 6.87 (t, J=8.5 Hz, 2H), 5.69 (d, J=12.1 Hz, 1H), 5.59 (dd, J=18.9, 9.5 Hz, 1H), 4.93 (d, J=14.2 Hz, 1H), 4.76-4.42 (m, 3H), 4.06 (s, 1H), 3.55 (s, 1H), 2.60 (s, 1H), 2.07 (t, J=7.4 Hz, 1H), 1.81 (d, J=7.4 Hz, 3H), 1.29 (d, J=7.1 Hz, 3H).

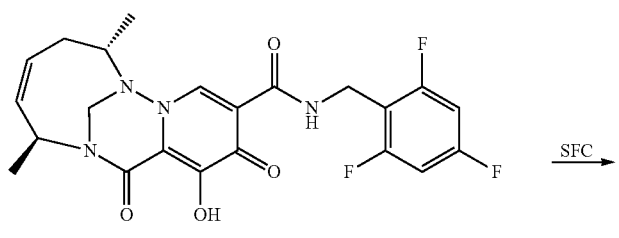

19A

→ SFC

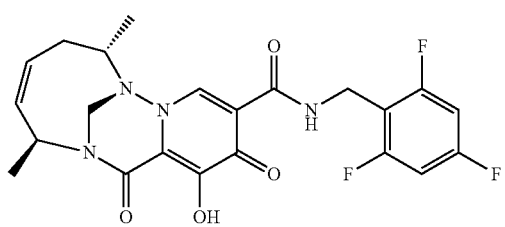

peak 1
C19 sterocenter arbitary assigned

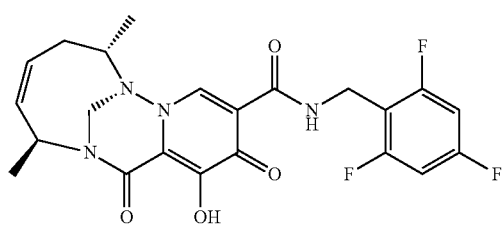

peak 2
C20

Example 21: Preparation of (1R,2S,6S)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (C21)

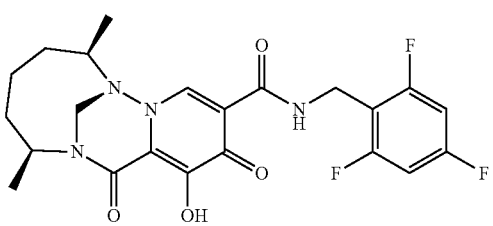

C21

Prepared in a manner similar to (1S,2R,6S)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (C8) in example 8 using (1R,2S,6S,Z)-9-hydroxy-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (C19) instead of (2R,6S,Z)-9-(benzyloxy)-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (7F). MS (m/z): 465.20 [M+H]+. $^1$H NMR (400 MHz, Acetonitrile-d3) δ 10.40 (s, 1H), 8.29 (s, 1H), 6.91-6.83 (m, 2H), 4.84 (d, J=14.4 Hz, 1H), 4.77 (d, J=14.5 Hz, 1H), 4.69-4.51 (m, 3H), 3.57 (q, J=7.1 Hz, 1H), 1.96-1.83 (m, 2H), 1.80-1.54 (m, 3H), 1.39 (dd, J=13.0, 6.2 Hz, 1H), 1.18 (dd, J=7.0, 2.3 Hz, 6H).

Example 22: Preparation of (1S,2R,6R)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (C22)

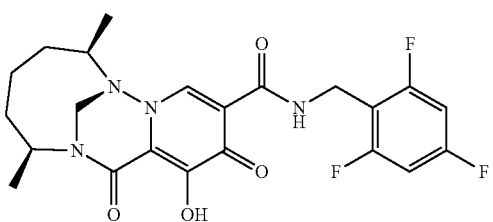

C22

Prepared in a manner similar to (1S,2R,6S)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (C8) in example 8 using (1S,2R,6R,Z)-9-hydroxy-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (C18) instead of (2R,6S,Z)-9-(benzyloxy)-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (7F). MS (m/z): 465.20 [M+H]+. $^1$H NMR (400 MHz, Acetonitrile-d$_3$) δ 10.41 (s, 1H), 8.28 (s, 1H), 6.87 (t, J=8.5 Hz, 2H), 4.84 (d, J=14.4 Hz, 1H), 4.77 (d, J=14.4 Hz, 1H), 4.65-4.52 (m, 3H), 3.55 (q, J=7.0 Hz, 1H), 1.95-1.84 (m, 1H), 1.79-1.54 (m, 3H), 1.44-1.34 (m, 1H), 1.18 (dd, J=6.9, 2.5 Hz, 7H).

Example 23: Preparation of (1S,2S,6S)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (C23)

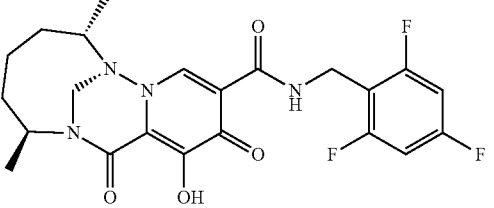

C23

Compound 23 was prepared in a manner similar to (1S,2R,6S)-9-hydroxy-2,6-dimethyl-8,10-dioxo-N-(2,4,6-trifluorobenzyl)-3,4,5,6,8,10-hexahydro-2H-1,7-methanopyrido[1,2-b][1,2,5]triazecine-11-carboxamide (C8) in example 8 using (1S,2S,6S,Z)-9-hydroxy-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (C20): instead of (2R,6S,Z)-9-(benzyloxy)-2,6-dimethyl-8,10-dioxo-N-(2,4,6-trifluorobenzyl)-3,6,8,10-tetrahydro-2H-1,7-methanopyrido[1,2-b][1,2,5]triazecine-11-carboxamide (7F). MS (m/z): 465.20 [M+H]+. $^1$H NMR (400 MHz, DMSO-d$_6$) δ 11.10 (s, 1H), 10.41 (t, J=5.8 Hz, 1H), 8.28 (s, 1H), 7.21 (t, J=8.6 Hz, 2H), 6.53 (s, OH), 5.00 (d, J=14.4 Hz, 1H), 4.88 (d, J=14.6 Hz, 1H), 4.60 (dd, J=14.6, 6.0 Hz, 1H), 4.51 (dd, J=14.6, 5.7 Hz, 1H), 3.53-3.50 (m, 2H), 2.11-1.96 (m, 1H), 1.76 (q, J=12.1 Hz, 1H), 1.70-1.61 (m, 2H), 1.53 (d, J=6.9 Hz, 5H), 1.32 (d, J=7.1 Hz, 3H).

Example 24. Preparation of (1S,2R,5S)-8-hydroxy-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (C24)

Step 1: Preparation of methyl 3-(benzyloxy)-1-((tert-butoxycarbonyl)amino)-4-oxo-5-((2,4,6-trifluorobenzyl)carbamoyl)-1,4-dihydropyridine-2-carboxylate

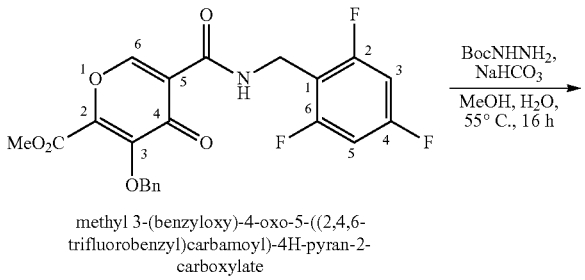

methyl 3-(benzyloxy)-4-oxo-5-((2,4,6-trifluorobenzyl)carbamoyl)-4H-pyran-2-carboxylate

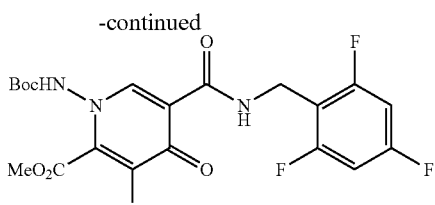

methyl 3-(benzyloxy)-1-((tert-butoxycarbonyl)amino)-4-oxo-5-((2,4,6-trifluorobenzyl)carbamoyl)-1,4-dihydropyridine-2-carboxylate Methyl 3-(benzyloxy)-4-oxo-5-((2,4,6-trifluorobenzyl)carbamoyl)-4H-pyran-2-carboxylate (60.0 g, 134 mmol, 1.00 eq) was mixed with MeOH (300 mL) and H$_2$O (60.0 mL). BocNHNH$_2$ (19.5 g, 147 mmol, 1.10 eq) and NaHCO$_3$ (22.5 g, 268 mmol, 10.4 mL, 2.00 eq) were added at room temperature. Reaction mixture was then stirred at 55° C. for 16 hours. The reaction mixture was placed under vacuum to remove most of the MeOH. The resulting residue was diluted with H$_2$O (200 mL) and the crude product was extracted with EtOAc (1500 mL). The organic layer was washed with brine (500 mL), dried with Na$_2$SO$_4$ and was concentrated in vacuum. The resulting slurry was purified with silica gel chromatography with Petroleum ether:Ethyl acetate=5:1 to afford product. MS (m/z): 562.5 [M+H].

Step 2: Preparation of methyl 3-(benzyloxy)-1-(but-3-en-2-yl(tert-butoxycarbonyl)amino)-4-oxo-5-((2,4,6-trifluorobenzyl)carbamoyl)-1,4-dihydropyridine-2-carboxylate

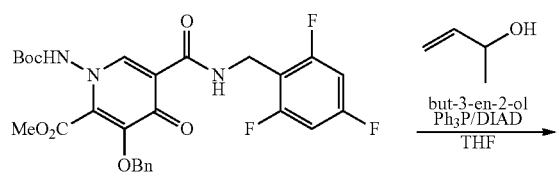

methyl 3-(benzyloxy)-1-((tert-butoxycarbonyl)amino)-4-oxo-5-((2,4,6-trifluorobenzyl)carbamoyl)-1,4-dihydropyridine-2-carboxylate

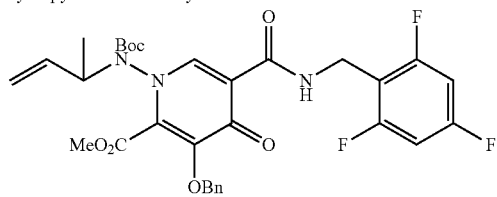

methyl 3-(benzyloxy)-1-(but-3-en-2-yl(tert-butoxycarbonyl)amino)-4-oxo-5-((2,4,6-trifluorobenzyl)carbamoyl)-1,4-dihydropyridine-2-carboxylate Methyl 3-(benzyloxy)-1-((tert-butoxycarbonyl)amino)-4-oxo-5-((2,4,6-trifluorobenzyl)carbamoyl)-1,4-dihydropyridine-2-carboxylate (5 g, 8.9 mmol) was dissolved in THF (100 mL) at rt. The solution was cooled down to 0° C. under argon. But-3-en-2-ol (963 mg, 13.4 mmol) and Ph$_3$P (3.5 g, 13.4 mmol) were added sequentially. Then DIAD (2.7 g, 13.4 mmol) was added drop-wise over 5 min. The resulting reaction was stirred at 0° C. for 5 min. The cold bath was removed. The reaction mixture was stirred at rt for 17 hr. The reaction mixture was concentrated to dryness. Residue was purified on silica gel column with 0-100% EtOAc/Hex to obtain the product. MS (m/z): 616.0 [M+H].

Step 3: Preparation of 3-(benzyloxy)-1-(but-3-en-2-yl(tert-butoxycarbonyl)amino)-4-oxo-5-((2,4,6-trifluorobenzyl)carbamoyl)-1,4-dihydropyridine-2-carboxylic acid

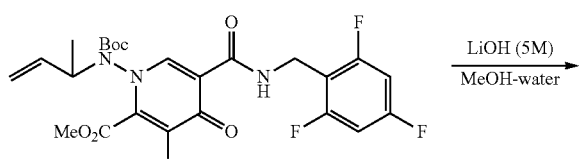

methyl 3-(benzyloxy)-1-(but-3-en-2-yl(tert-butoxycarbonyl)amino)-4-oxo-5-((2,4,6-trifluorobenzyl)carbamoyl)-1,4-dihydropyridine-2-carboxylate

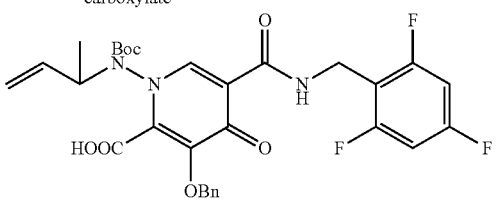

3-(benzyloxy)-1-(but-3-en-2-yl(tert-butoxycarbonyl)amino)-4-oxo-5-((2,4,6-trifluorobenzyl)carbamoyl)-1,4-dihydropyridine-2-carboxylic acid Methyl 3-(benzyloxy)-1-(but-3-en-2-yl(tert-butoxycarbonyl)amino)-4-oxo-5-((2,4,6-trifluorobenzyl)carbamoyl)-1,4-dihydropyridine-2-carboxylate (5.4 g, 8.9 mmol) was mixed with MeOH (125 mL) and water (100 mL) at rt. LiOH (5 M in water) (11 ml) was added. Fitted with air condenser, reaction mixture was heated to 73° C. with stirring for 3.5 hr. Added more LiOH (5 M) (2 mL). Reaction mixture was then stirred at 40° C. for 17 hr. Reaction mixture was concentrated carefully for removal of MeOH. The residue was diluted and rinsed with some water and was acidified with 1N HCl to pH=3. EtOAc (200 mL) was added for extraction. Organic phase was separated. Aqueous layer was extracted with more EtOAc (100 mL). The combined organic phases were washed with water and brine, separated, dried over Na$_2$SO$_4$, filtered, and concentrated to afford the product. MS (m/z): 602.0 [M+H].

Step 4: Preparation of tert-butyl (3-(benzyloxy)-2-(((S)-but-3-en-2-yl)carbamoyl)-4-oxo-5-((2,4,6-trifluorobenzyl)carbamoyl)pyridin-1(4H)-yl)(but-3-en-2-yl)carbamate

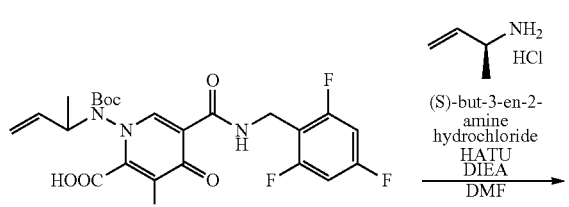

3-(benzyloxy)-1-(but-3-en-2-yl(tert-butoxycarbonyl)amino)-4-oxo-5-((2,4,6-trifluorobenzyl)carbamoyl)-1,4-dihydropyridine-2-carboxylic acid

137

-continued

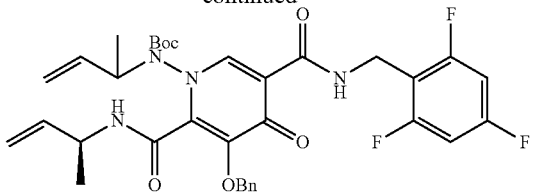

tert-butyl (3-(benzyloxy)-2-(((S)-but-3-en-2-yl)carbamoyl)-4-oxo-5-((2,4,6-trifluorobenzyl)carbamoyl)pyridin-1(4H)-yl)(but-3-en-2-yl)carbamate 3-(Benzyloxy)-1-(but-3-en-2-yl(tert-butoxycarbonyl)amino)-4-oxo-5-((2,4,6-trifluorobenzyl)carbamoyl)-1,4-dihydropyridine-2-carboxylic acid (4.75 g, 7.9 mmol) was dissolved in DMF (20 mL) at rt. DIEA (6.1 g, 47.4 mmol) was added. Then (S)-but-3-en-2-amine hydrochloride (1.27 g, 11.8 mmol) and HATU (4.5 g, 11.8 mmol) were added sequentially. The resulting reaction mixture was stirred at rt for 17 hrs. The reaction mixture was diluted with EtOAc (100 mL) and was then treated with NaHCO₃ (saturated aqueous solution, 100 mL) and water (100 mL). Organic phase was separated and washed with water (50 mL) and brine (50 mL). The final organic phase was concentrated to remove solvents. The residue was purified on silica gel column with 0-100% EtOAc/Hex to afford product. MS (m/z): 655.0 [M+H].

Step 5: Preparation of 3-(benzyloxy)-N2-((S)-but-3-en-2-yl)-1-(but-3-en-2-ylamino)-4-oxo-N5-(2,4,6-trifluorobenzyl)-1,4-dihydropyridine-2,5-dicarboxamide

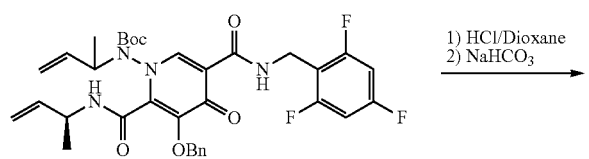

tert-butyl (3-(benzyloxy)-2-(((S)-but-3-en-2-yl)carbamoyl)-4-oxo-5-((2,4,6-trifluorobenzyl)carbamoyl)pyridin-1(4H)-yl)(but-3-en-2-yl)carbamate 1) HCl/Dioxane
2) NaHCO₃
→

138

-continued

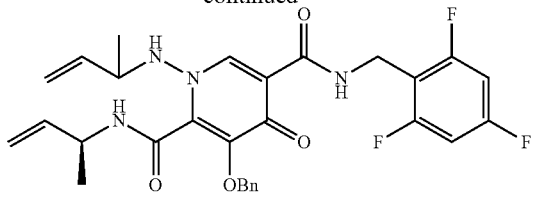

3-(benzyloxy)-N²-((S)-but-3-en-2-yl)-1-(but-3-en-2-ylamino)-4-oxo-N⁵-(2,4,6-trifluorobenzyl)-1,4-dihydropyridine-2,5-dicarboxamide Tert-butyl (3-(benzyloxy)-2-(((S)-but-3-en-2-yl)carbamoyl)-4-oxo-5-((2,4,6-trifluorobenzyl)carbamoyl)pyridin-1(4H)-yl)(but-3-en-2-yl)carbamate (4.42 g, 6.75 mmol) was dissolved in DCM (10 mL) at rt. HCl (4 M in dioxane) (10 mL) was added. Reaction mixture was stirred at rt for 6 hrs. Reaction mixture was then concentrated to dryness. The residue was partitioned between EtOAc (100 mL) and NaHCO₃ (saturated aqueous solution, 100 mL). Organic phase was separated, washed with brine and was dried over Na₂SO₄. The solvent was removed to afford the product. MS (m/z): 555.3 [M+H].

Step 6: Preparation of 5-(benzyloxy)-3-((S)-but-3-en-2-yl)-1-(but-3-en-2-yl)-4,6-dioxo-N-(2,4,6-trifluorobenzyl)-2,3,4,6-tetrahydro-1H-pyrido[2,1-f][1,2,4]triazine-7-carboxamide

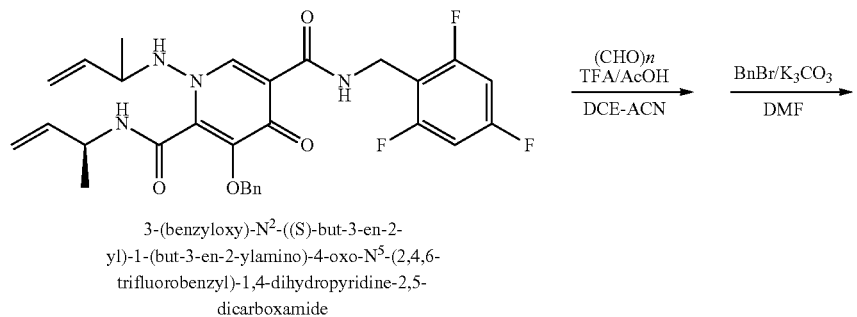

3-(benzyloxy)-N²-((S)-but-3-en-2-yl)-1-(but-3-en-2-ylamino)-4-oxo-N⁵-(2,4,6-trifluorobenzyl)-1,4-dihydropyridine-2,5-dicarboxamide (CHO)n
TFA/AcOH
─────────→
DCE-ACN BnBr/K₃CO₃
─────────→
DMF

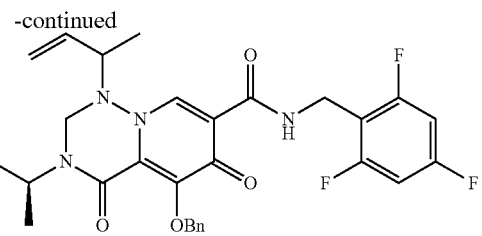

5-(benzyloxy)-3-((S)-but-3-en-2-yl)-1-(but-3-en-2-yl)-4,6-dioxo-N-(2,4,6-trifluorobenzyl)-2,3,4,6-tetrahydro-1H-pyrido[2,1-f][1,2,4]triazine-7-carboxamide

15

3-(Benzyloxy)-N2-((S)-but-3-en-2-yl)-1-(but-3-en-2-ylamino)-4-oxo-N5-(2,4,6-trifluorobenzyl)-1,4-dihydropyridine-2,5-dicarboxamide (1.845 g, 3.33 mmol) was dissolved in acetonitrile (18.45 mL) and dichloroethane (18.45 mL) at rt. Paraformaldehyde (200 mg, 6.66 mmol) was added. The resulting mixture was placed onto pre-heated hot bath at 88° C. Then AcOH (0.9 mL) and TFA (0.9 mL) were added sequentially into the pre-heated reaction mixture within 5 min. The resulting reaction mixture was then sealed and heated with stirring for 30 min. The resulting reaction mixture was then concentrated to dryness to remove all solvents and acids. The resulting crude material was then dissolved in DMF (17 mL). $K_2CO_3$ (2.76 g, 20 mmol) and benzyl bromide (2.56 g, 15 mmol) were added sequentially. The reaction mixture was then heated at 100° C. for 3 hrs. Reaction mixture was then diluted with EtOAc (100 mL) and was then treated with $NaHCO_3$ (saturated aqueous solution) (100 mL) and water (100 mL). The organic phase was separated and washed with water (50 mL) and brine (50 mL). The solvent was removed in vacuum. The residual crude product was purified on silica gel column with 0-100% EtOAc/Hex to afford the product. MS (m/z): 567.2 [M+H].

Step 7: Preparation of (1S,2R,5S)-8-(benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (A), (1S,2S,5S)-8-(benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (B) and (1R,2S,5S)-8-(benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (C)

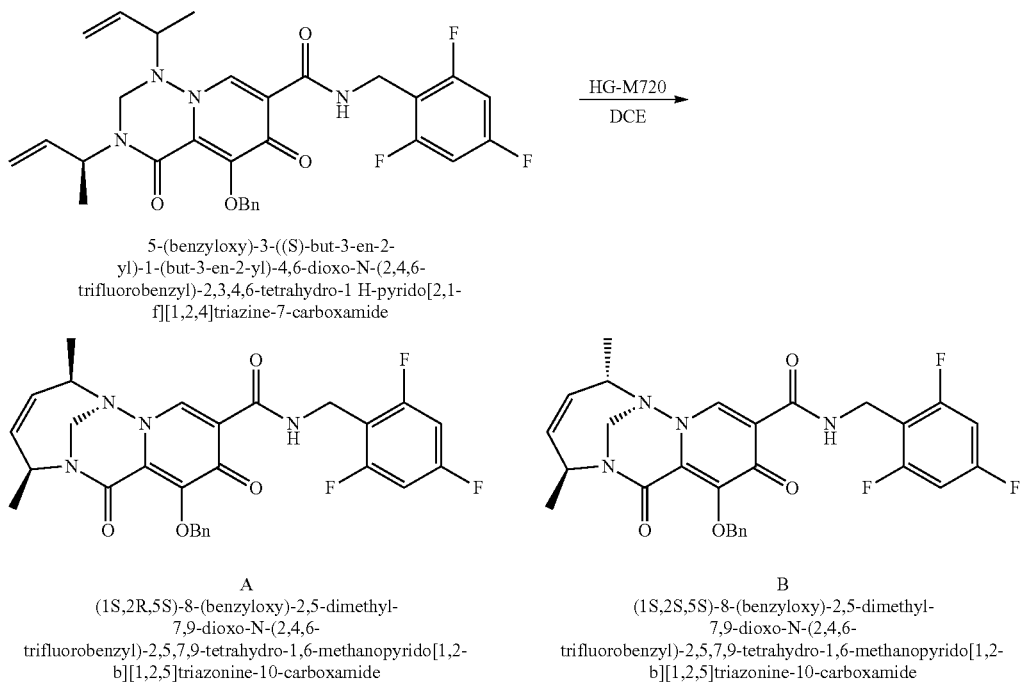

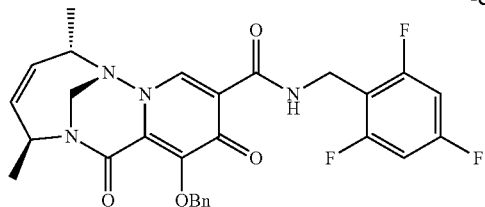

C
(1R,2S,5S)-8-(benzyloxy)-2,5-dimethyl-
7,9-dioxo-N-(2,4,6-
trifluorobenzyl)-2,5,7,9-tetrahydro-1,6-methanopyrido[1,2-
b][1,2,5]triazonine-10-carboxamide 5-(Benzyloxy)-3-((S)-but-3-en-2-yl)-1-(but-3-en-2-yl)-4,6-dioxo-N-(2,4,6-trifluorobenzyl)-2,3,4,6-tetrahydro-1H-pyrido[2,1-f][1,2,4]triazine-7-carboxamide (931 mg, 1.64 mmol) was dissolved in dichloroethane (88 mL) at rt. Argon was bubbled through the reaction solution for 5 min. HG-M720 catalyst (103.4 mg, 0.164 mmol) was then added with stirring. The purging with argon was continued for 10 min. The reaction mixture was then heated with stirring under argon atmosphere for 48 hrs. The resulting reaction mixture was then concentrated to dryness. The crude material was purified on silica gel column with 0-100% EtOAc/Hex to afford three diastereomers there can be separated: (1S,2R,5S)-8-(benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (A), 334 mg. MS (m/z): 539.2 [M+H] and (1S,2S,5S)-8-(benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (B), 96 mg. MS (m/z): 539.2 [M+H] and (1R,2S,5S)-8-(benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (C), 16 mg, MS (m/z): 539.2 [M+H]. The absolute configurations of those two compounds are yet to be determined.

Preparation of (1S,2R,5S)-8-hydroxy-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (C24)

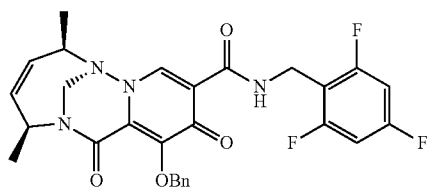

(1S,2R,5S)-8-(benzyloxy)-2,5-dimethyl-
7,9-dioxo-N-(2,4,6-
trifluorobenzyl)-2,5,7,9-tetrahydro-1,
6-methanopyrido[1,2-
b][1,2,5]triazonine-10-carboxamide → TFA / Toluene →

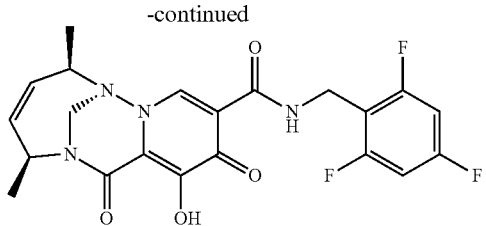

(1S,2R,5S)-8-hydroxy-2,5-dimethyl-
7,9-dioxo-N-(2,4,6-
trifluorobenzyl)-2,5,7,9-tetrahydro-1,6-methanopyrido[1,2-
b][1,2,5]triazonine-10-carboxamide (1S,2R,5S)-8-(Benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (110 mg, 0.188 mmol) was dissolved in toluene (1 mL) at rt. TFA (1 mL) was added carefully with stirring. The resulting reaction mixture was stirred at rt for 17 hrs. Reaction mixture was then concentrated to dryness. The residue was taken up in MeOH and was purified with reverse phase prep-HPLC with 0-100% $CH_3CN$ in water with 0.1% TFA to afford the desired product. Lyophilization afford product as mono TFA salt. 50 mg. MS (m/z): 449.2 [M+H]. 1H NMR (400 MHz, Acetonitrile-d3) δ 10.21 (t, J=5.9 Hz, 1H), 8.38 (s, 1H), 6.87 (t, J=8.5 Hz, 2H), 5.65 (dt, J=11.4, 2.4 Hz, 1H), 5.47-5.27 (m, 2H), 5.01 (d, J=14.4 Hz, 1H), 4.62 (d, J=5.8 Hz, 2H), 4.57 (d, J=14.3 Hz, 1H), 3.82 (tp, J=6.6, 3.3 Hz, 1H), 1.35 (d, J=2.0 Hz, 3H), 1.33 (d, J=2.6 Hz, 3H).

Example 25: Preparation of (1S,2S,5S)-8-hydroxy-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (C25)

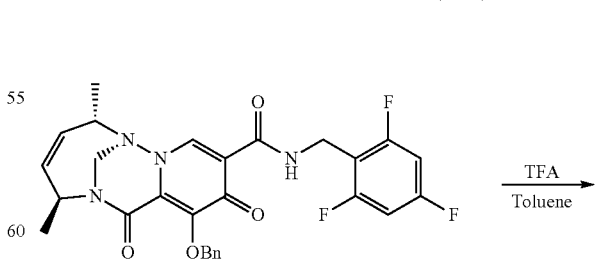

(1S,2S,5S)-8-(benzyloxy)-2,5-dimethyl-
7,9-dioxo-N-(2,4,6-
trifluorobenzyl)-2,5,7,9-tetrahydro-1,
6-methanopyrido[1,2-
b][1,2,5]triazonine-10-carboxamide → TFA / Toluene →

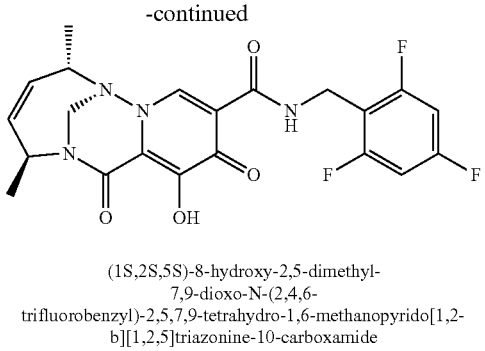

(1S,2S,5S)-8-hydroxy-2,5-dimethyl-
7,9-dioxo-N-(2,4,6-
trifluorobenzyl)-2,5,7,9-tetrahydro-1,6-methanopyrido[1,2-
b][1,2,5]triazonine-10-carboxamide (1S,2S,5S)-8-(Benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (78 mg, 0.145 mmol) was dissolved in toluene (1 mL) at rt. TFA (1 mL) was added carefully with stirring. The resulting reaction mixture was stirred at rt for 17 hrs. Reaction mixture was then concentrated to dryness. The residue was taken up in MeOH and was purified with reverse phase prep-HPLC with 0-100% CH$_3$CN in water with 0.1% TFA to afford the desired product. Lyophilization afford product as mono TFA salt. 34 mg. MS (m/z): 449.2 [M+H]. 1H NMR (400 MHz, Acetonitrile-d3) δ 10.28 (s, 1H), 8.44 (s, 1H), 7.11-6.61 (m, 2H), 5.61 (ddd, J=12.3, 3.3, 2.1 Hz, 1H), 5.50-5.27 (m, 2H), 4.93 (d, J=14.4 Hz, 1H), 4.72 (d, J=14.4 Hz, 1H), 4.66-4.53 (m, 3H), 1.35 (d, J=7.2 Hz, 3H), 1.01 (d, J=7.4 Hz, 3H).

Example 26: Preparation of (1R,2S,5S)-8-hydroxy-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (C26)

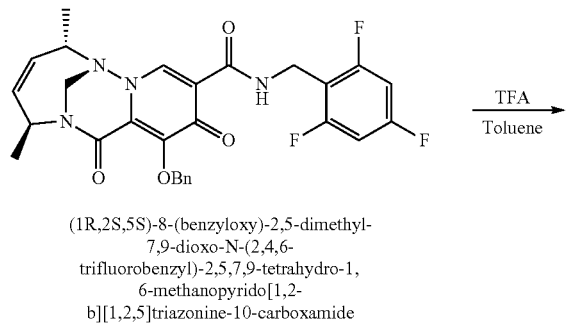

(1R,2S,5S)-8-(benzyloxy)-2,5-dimethyl-
7,9-dioxo-N-(2,4,6-
trifluorobenzyl)-2,5,7,9-tetrahydro-1,
6-methanopyrido[1,2-
b][1,2,5]triazonine-10-carboxamide

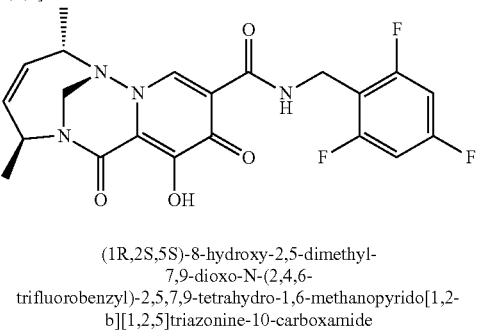

(1R,2S,5S)-8-hydroxy-2,5-dimethyl-
7,9-dioxo-N-(2,4,6-
trifluorobenzyl)-2,5,7,9-tetrahydro-1,6-methanopyrido[1,2-
b][1,2,5]triazonine-10-carboxamide (1R,2S,5S)-8-(Benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (16 mg, mmol) was dissolved in toluene (1 mL) at rt. TFA (1 mL) was added carefully with stirring. The resulting reaction mixture was stirred at rt for 17 hrs. Reaction mixture was then concentrated to dryness. The residue was purified with 0-100% EtOAc in Hexane to afford product as neural form. 8 mg. MS (m/z): 449.2 [M+H]. 1H NMR (400 MHz, Acetonitrile-d3) δ 10.30 (s, 1H), 8.40 (s, 1H), 6.97-6.77 (m, 2H), 5.80 (ddd, J=11.7, 2.7, 1.9 Hz, 1H), 5.45 (ddd, J=11.7, 4.2, 2.4 Hz, 1H), 4.81-4.69 (m, 2H), 4.65-4.59 (m, 2H), 4.32 (dtt, J=7.5, 5.0, 2.5 Hz, 1H), 4.01 (ddq, J=7.0, 4.8, 2.4 Hz, 1H), 1.79 (d, J=7.5 Hz, 3H), 1.40 (d, J=7.0 Hz, 3H).

Example 27: Preparation of (1S,2R,5S)-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (C27)

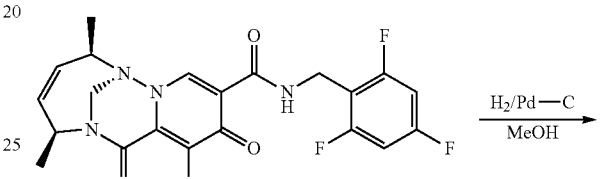

(1S,2R,5S)-8-(benzyloxy)-2,5-dimethyl-
7,9-dioxo-N-(2,4,6-
trifluorobenzyl)-2,5,7,9-tetrahydro-1,
6-methanopyrido[1,2-
b][1,2,5]triazonine-10-carboxamide

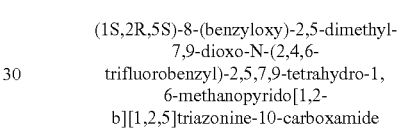

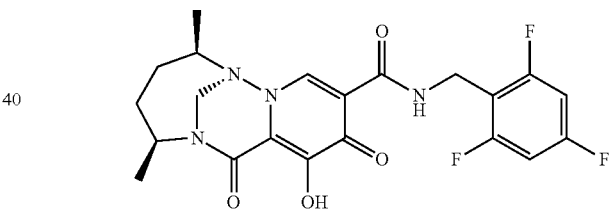

(1S,2R,5S)-8-hydroxy-2,5-dimethyl-
7,9-dioxo-N-(2,4,6-
trifluorobenzyl)-2,3,4,5,7,9-
hexahydro-1,6-methanopyrido[1,2-
b][1,2,5]triazonine-10-carboxamide (1S,2R,5S)-8-(Benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (92.8 mg, 0.172 mmol) was dissolved in MeOH (10 mL). Pd—C(10%) (23 mg) was added. Hydrogenolysis was taken with H$_2$ balloon at rt for 7 hrs. Reaction mixture was filtered through celite. Filtrate was collected and concentrated to dryness. The residue was taken up in MeOH and was purified with reverse phase prep-HPLC with 0-100% CH$_3$CN in water with 0.1% TFA to afford the desired product. Lyophilization afford product as mono TFA salt. 34 mg. MS (m/z): 451.3 [M+H]. 1H NMR (400 MHz, Acetonitrile-d3) δ 10.37 (s, 1H), 8.43 (s, 1H), 7.02-6.78 (m, 2H), 4.71-4.45 (m, 5H), 3.51 (dq, J=7.2, 3.6 Hz, 1H), 2.02 (ddd, J=8.2, 6.1, 3.3 Hz, 1H), 1.78-1.66 (m, 1H), 1.55 (dt, J=8.6, 3.3 Hz, 2H), 1.31 (d, J=7.2 Hz, 3H), 1.27 (d, J=6.8 Hz, 3H).

Example 28: Preparation of (1S,2S,5S)-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (C28)

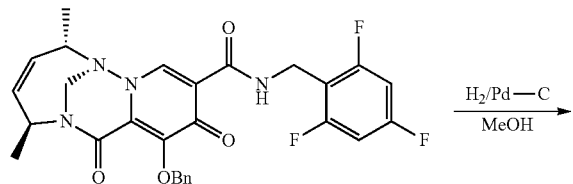

(1S,2S,5S)-8-(benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide

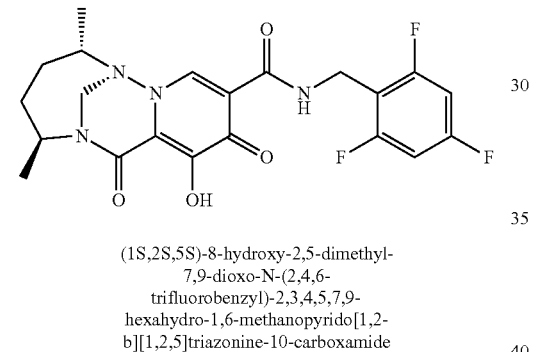

(1S,2S,5S)-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (1S,2S,5S)-8-(Benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (18 mg, 0.172 mmol) was dissolved in MeOH (8 mL). Pd—C(10%) (10 mg) was added. Hydrogenolysis was taken with $H_2$ balloon at rt for 7 hrs. Reaction mixture was filtered through celite. Filtrate was collected and concentrated to dryness. The residue was taken up in MeOH and was purified with reverse phase prep-HPLC with 0-100% $CH_3CN$ in water with 0.1% TFA to afford the desired product. Lyophilization afford product as mono TFA salt. 7 mg. MS (m/z): 451.3 [M+H]. 1H NMR (400 MHz, Acetonitrile-d3) δ 10.36 (s, 1H), 8.34 (s, 1H), 6.98-6.77 (m, 2H), 4.76-4.59 (m, 5H), 3.41 (dd, J=11.6, 6.3 Hz, 1H), 2.20 (dt, J=14.2, 6.8 Hz, 1H), 1.80-1.49 (m, 2H), 1.26 (d, J=6.7 Hz, 3H), 1.30-1.17 (m, 1H), 1.08 (d, J=6.9 Hz, 3H).

Example 29: Preparation of (1S,2R,5S)—N-(2,4-difluorobenzyl)-8-hydroxy-2,5-dimethyl-7,9-dioxo-2,5,7,9-tetrahydro-1,6-methanopyrido[1,2-b][1,2,5]triazonine-10-carboxamide (C29)

Step 1: Preparation of methyl 3-(benzyloxy)-1-((tert-butoxycarbonyl)amino)-5-((2,4-difluorobenzyl)carbamoyl)-4-oxo-1,4-dihydropyridine-2-carboxylate

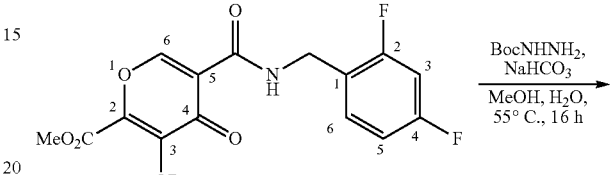

methyl 3-(benzyloxy)-5-((2,4-difluorobenzyl)carbamoyl)-4-oxo-4H-pyran-2-carboxylate

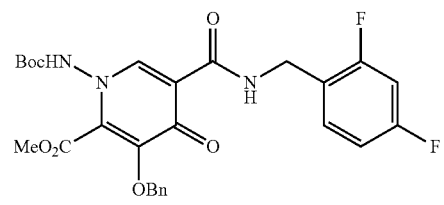

methyl 3-(benzyloxy)-1-((tert-butoxycarbonyl)amino)-5-((2,4-difluorobenzyl)carbamoyl)-4-oxo-1,4-dihydropyridine-2-carboxylate Methyl 3-(benzyloxy)-5-((2,4-difluorobenzyl)carbamoyl)-4-oxo-4H-pyran-2-carboxylate (15 g, 34.9 mmol) was mixed with MeOH (100 mL) and $H_2O$ (30.0 mL). Boc-NHNH$_2$ (5 g, 37.8 mmol) and NaHCO$_3$ (5.87 g, 69.9 mmol) were added at room temperature. Reaction mixture was then stirred at 55° C. for 16 hours. The reaction mixture was placed under vacuum to remove the most MeOH. The resulting residue was diluted with $H_2O$ (200 mL) and the crude product was extracted with EtOAc (500 mL). The organic layer was washed with brine (500 mL), dried with Na$_2$SO$_4$ and was concentrated in vacuum. The resulting slurry was purified with silica gel chromatography with Hexane:Ethyl acetate=5:1 to afford product 18 g as white solid. MS (m/z): 543.95 [M+H].

Step 2: Preparation of methyl 3-(benzyloxy)-1-(but-3-en-2-yl(tert-butoxycarbonyl)amino)-4-oxo-5-((2,4-difluorobenzyl)carbamoyl)-1,4-dihydropyridine-2-carboxylate

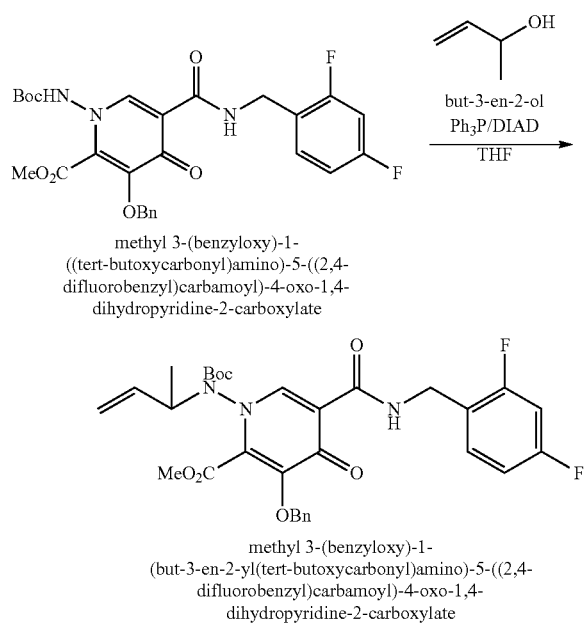

methyl 3-(benzyloxy)-1-((tert-butoxycarbonyl)amino)-5-((2,4-difluorobenzyl)carbamoyl)-4-oxo-1,4-dihydropyridine-2-carboxylate methyl 3-(benzyloxy)-1-(but-3-en-2-yl(tert-butoxycarbonyl)amino)-5-((2,4-difluorobenzyl)carbamoyl)-4-oxo-1,4-dihydropyridine-2-carboxylate Methyl 3-(benzyloxy)-1-((tert-butoxycarbonyl)amino)-4-oxo-5-((2,4-difluorobenzyl)carbamoyl)-1,4-dihydropyridine-2-carboxylate (10.5 g, 19.3 mmol) was dissolved in THF (200 mL) at rt. The solution was cooled down to 0° C. under argon. But-3-en-2-ol (2.37 g, 32.8 mmol) and Ph₃P (8.6 g, 32.8 mmol) were added sequentially. Then DIAD (6.64 g, 32.8 mmol) was added drop-wise over 5 min. The resulting reaction mixture was slightly orange solution. Let it be stirred at 0° C. for 5 min. The cold bath was removed. Let reaction mixture be stirred at rt for 17 hr. The reaction mixture was concentrated to dryness. Residue was purified on silica gel column with 0-100% EtOAc/Hex to obtained product 10 g. MS (m/z): 598.04 [M+H].

Step 3: Preparation of 3-(benzyloxy)-1-(but-3-en-2-yl(tert-butoxycarbonyl)amino)-4-oxo-5-((2,4-difluorobenzyl)carbamoyl)-1,4-dihydropyridine-2-carboxylic acid

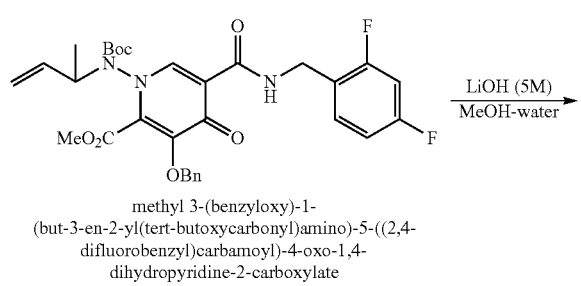

methyl 3-(benzyloxy)-1-(but-3-en-2-yl(tert-butoxycarbonyl)amino)-5-((2,4-difluorobenzyl)carbamoyl)-4-oxo-1,4-dihydropyridine-2-carboxylate

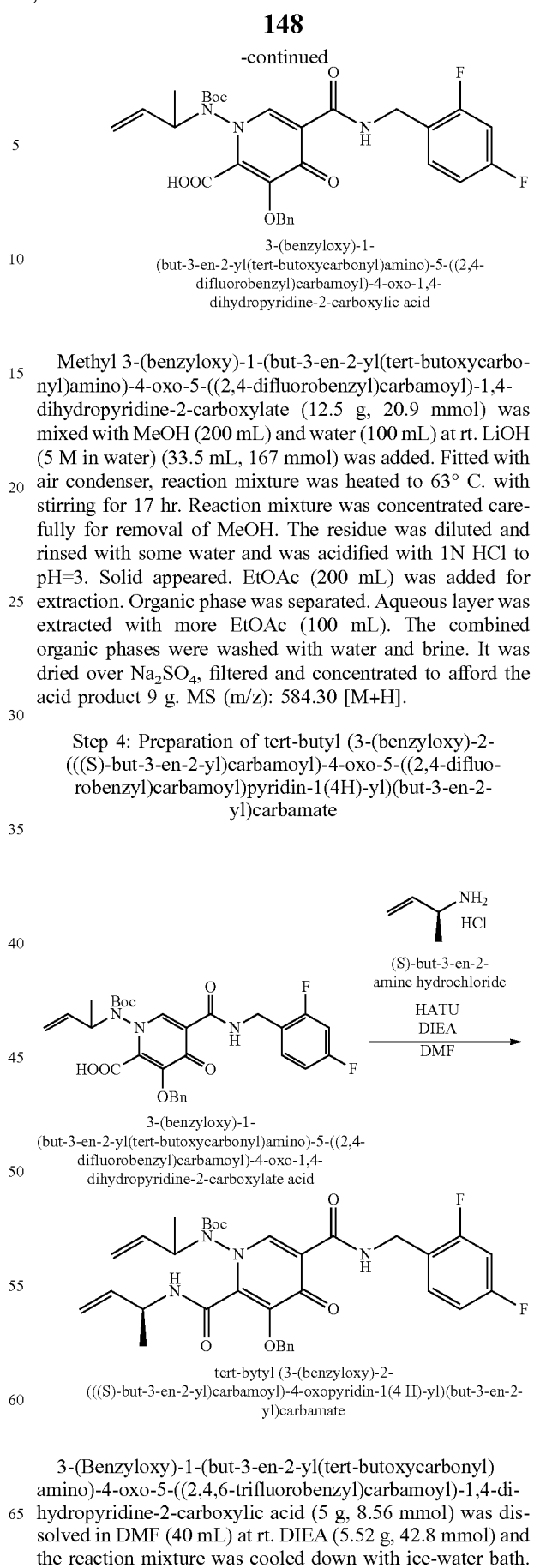

3-(benzyloxy)-1-(but-3-en-2-yl(tert-butoxycarbonyl)amino)-5-((2,4-difluorobenzyl)carbamoyl)-4-oxo-1,4-dihydropyridine-2-carboxylic acid Methyl 3-(benzyloxy)-1-(but-3-en-2-yl(tert-butoxycarbonyl)amino)-4-oxo-5-((2,4-difluorobenzyl)carbamoyl)-1,4-dihydropyridine-2-carboxylate (12.5 g, 20.9 mmol) was mixed with MeOH (200 mL) and water (100 mL) at rt. LiOH (5 M in water) (33.5 mL, 167 mmol) was added. Fitted with air condenser, reaction mixture was heated to 63° C. with stirring for 17 hr. Reaction mixture was concentrated carefully for removal of MeOH. The residue was diluted and rinsed with some water and was acidified with 1N HCl to pH=3. Solid appeared. EtOAc (200 mL) was added for extraction. Organic phase was separated. Aqueous layer was extracted with more EtOAc (100 mL). The combined organic phases were washed with water and brine. It was dried over Na₂SO₄, filtered and concentrated to afford the acid product 9 g. MS (m/z): 584.30 [M+H].

Step 4: Preparation of tert-butyl (3-(benzyloxy)-2-(((S)-but-3-en-2-yl)carbamoyl)-4-oxo-5-((2,4-difluorobenzyl)carbamoyl)pyridin-1(4H)-yl)(but-3-en-2-yl)carbamate 3-(benzyloxy)-1-(but-3-en-2-yl(tert-butoxycarbonyl)amino)-5-((2,4-difluorobenzyl)carbamoyl)-4-oxo-1,4-dihydropyridine-2-carboxylate acid tert-bytyl (3-(benzyloxy)-2-(((S)-but-3-en-2-yl)carbamoyl)-4-oxopyridin-1(4 H)-yl)(but-3-en-2-yl)carbamate 3-(Benzyloxy)-1-(but-3-en-2-yl(tert-butoxycarbonyl)amino)-4-oxo-5-((2,4,6-trifluorobenzyl)carbamoyl)-1,4-dihydropyridine-2-carboxylic acid (5 g, 8.56 mmol) was dissolved in DMF (40 mL) at rt. DIEA (5.52 g, 42.8 mmol) and the reaction mixture was cooled down with ice-water bath.

HATU (6.52 g, 17.14 mmol) was added in one portion. Then the reaction mixture was warmed up to rt with stirring for 1 h. Then (S)-but-3-en-2-amine hydrochloride (2.3 g, 21.4 mmol) was added. The resulting reaction mixture was stirred at rt for 17 hrs. The reaction mixture was diluted with EtOAc (200 mL) and was then treated with NaHCO$_3$ (saturated aqueous solution, 100 mL) and water (100 mL). Organic phase was separated and washed with water (50 mL) and brine (50 mL). The final organic phase was concentrated to remove solvents. The residue was pure enough for next step. 4 g. MS (m/z): 637.03 [M+H].

Step 5: Preparation of 3-(benzyloxy)-N2-((S)-but-3-en-2-yl)-1-(but-3-en-2-ylamino)-4-oxo-N5-(2,4-difluorobenzyl)-1,4-dihydropyridine-2,5-dicarboxamide

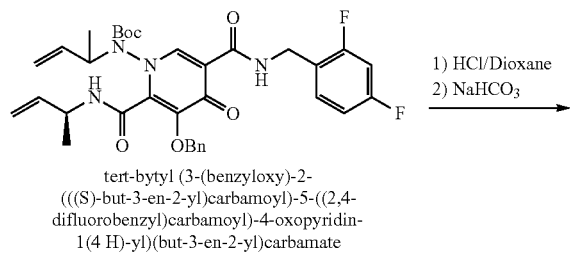

tert-bytyl (3-(benzyloxy)-2-(((S)-but-3-en-2-yl)carbamoyl)-5-((2,4-difluorobenzyl)carbamoyl)-4-oxopyridin-1(4H)-yl)(but-3-en-2-yl)carbamate 1) HCl/Dioxane
2) NaHCO$_3$

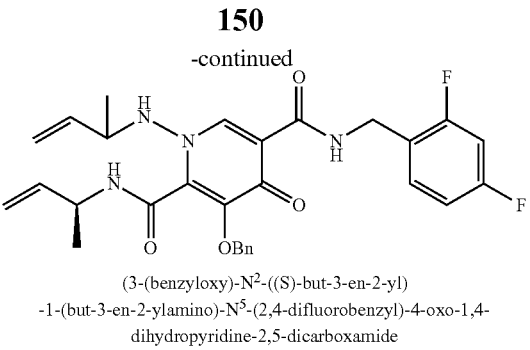

(3-(benzyloxy)-N$^2$-((S)-but-3-en-2-yl)-1-(but-3-en-2-ylamino)-N$^5$-(2,4-difluorobenzyl)-4-oxo-1,4-dihydropyridine-2,5-dicarboxamide Tert-butyl (3-(benzyloxy)-2-(((S)-but-3-en-2-yl)carbamoyl)-4-oxo-5-((2,4-difluorobenzyl)carbamoyl)pyridin-1(4H)-yl)(but-3-en-2-yl)carbamate (4 g, 6.29 mmol) was dissolved in DCM (10 mL) at rt. HCl (4 M in dioxane) (10 mL) was added. Reaction mixture was stirred at rt for 6 hrs. Reaction mixture was then concentrated to dryness. The residue was partitioned between EtOAc (100 mL) and NaHCO$_3$ (saturated aqueous solution, 100 mL). Organic phase was separated, washed with brine and was dried over Na$_2$SO$_4$. The solvent was removed to afford the product 3 g. MS (m/z): 537.17 [M+H].

Step 6: Preparation of 5-(benzyloxy)-3-((S)-but-3-en-2-yl)-1-(but-3-en-2-yl)-4,6-dioxo-N-(2,4-difluorobenzyl)-2,3,4,6-tetrahydro-1H-pyrido[2,1-f][1,2,4]triazine-7-carboxamide

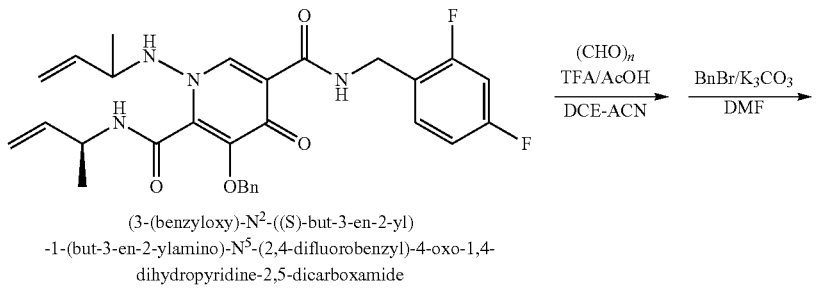

(3-(benzyloxy)-N$^2$-((S)-but-3-en-2-yl)-1-(but-3-en-2-ylamino)-N$^5$-(2,4-difluorobenzyl)-4-oxo-1,4-dihydropyridine-2,5-dicarboxamide (CHO)$_n$
TFA/AcOH
DCE-ACN BnBr/K$_3$CO$_3$
DMF

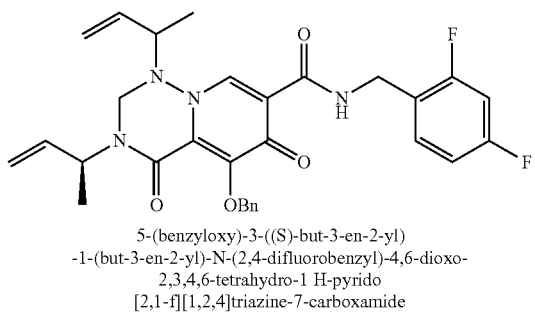

5-(benzyloxy)-3-((S)-but-3-en-2-yl)-1-(but-3-en-2-yl)-N-(2,4-difluorobenzyl)-4,6-dioxo-2,3,4,6-tetrahydro-1H-pyrido[2,1-f][1,2,4]triazine-7-carboxamide 3-(Benzyloxy)-N2-((S)-but-3-en-2-yl)-1-(but-3-en-2-ylamino)-4-oxo-N5-(2,4-difluorobenzyl)-1,4-dihydropyridine-2,5-dicarboxamide (2.52 g, 4.7 mmol) was dissolved in acetonitrile (25 mL) and dichloroethane (25 mL) at rt. Paraformaldehyde (278 mg, 9.25 mmol) was added. The resulting slurry was placed onto pre-heated hot bath at 88° C. Then AcOH (1.15 mL) and TFA (1.15 mL) were added sequentially into the pre-heated reaction mixture within 5 min. The resulting reaction mixture was then sealed and heated with stirring for 30 min. The resulting reaction mixture was then concentrated to dryness to remove all solvents and acids. The resulting crude material was then dissolved in DMF (17 mL). K$_2$CO$_3$ (10 g, 72.4 mmol) and benzyl bromide (6.63 g, 38.8 mmol) were added sequentially. The reaction mixture was then heated at 100° C. for 3 hrs. Reaction mixture was then diluted with EtOAc (100 mL) and was then treated with NaHCO$_3$ (saturated aqueous solution) (100 mL) and water (100 mL). The organic phase was separated and washed with water (50 mL) and brine (50 mL). The solvent was removed in vacuum. The residual crude product was purified on silica gel column with 0-100% EtOAc/Hex to afford product 1 g. MS (m/z): 549.2 [M+H].

Step 7: Preparation of (1S,2R,5S)-8-(benzyloxy)-2,5-dimethyl-7,9-dioxo-N-(2,4-difluorobenzyl)-2,5,7,9-tetrahydro-1,6-methanopyrido[1,2-b][1,2,5]triazonine-10-carboxamide and (1S,2S,5S)-8-(benzyloxy)-2,5-dimethyl-7,9-dioxo-N-(2,4-difluorobenzyl)-2,5,7,9-tetrahydro-1,6-methanopyrido[1,2-b][1,2,5]triazonine-10-carboxamide

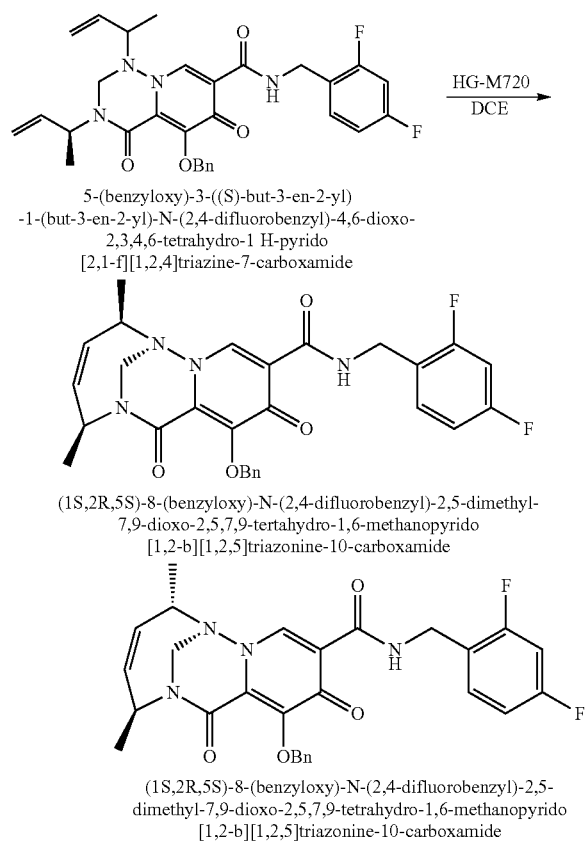

5-(Benzyloxy)-3-((S)-but-3-en-2-yl)-1-(but-3-en-2-yl)-4,6-dioxo-N-(2,4-difluorobenzyl)-2,3,4,6-tetrahydro-1H-pyrido[2,1-f][1,2,4]triazine-7-carboxamide (753 mg, 1.37 mmol) was dissolved in dichloroethane (83 mL) at rt. Argon was bubbled through the reaction solution for 5 min. HG-M720 catalyst (146.4 mg, 0.233 mmol) was then added with stirring. The purging with argon was continued for 10 min. The reaction mixture was then heated with stirring under argon atmosphere for 48 hrs. The resulting reaction mixture was then concentrated to dryness. The crude material was purified on silica gel column with 0-100% EtOAc/Hex to afford two products as single diastereomers: (1S,2R,5S)-8-(benzyloxy)-2,5-dimethyl-7,9-dioxo-N-(2,4-difluorobenzyl)-2,5,7,9-tetrahydro-1,6-methanopyrido[1,2-b][1,2,5]triazonine-10-carboxamide, 230 mg. MS (m/z): 521.2 [M+H] and (1S,2S,5S)-8-(benzyloxy)-2,5-dimethyl-7,9-dioxo-N-(2,4-difluorobenzyl)-2,5,7,9-tetrahydro-1,6-methanopyrido[1,2-b][1,2,5]triazonine-10-carboxamide, 15 mg. MS (m/z): 521.2 [M+H]. The absolute configurations of those two compounds are yet to be determined.

Step 8: Preparation of (1S,2R,5S)-8-hydroxy-2,5-dimethyl-7,9-dioxo-N-(2,4-difluorobenzyl)-2,5,7,9-tetrahydro-1,6-methanopyrido[1,2-b][1,2,5]triazonine-10-carboxamide

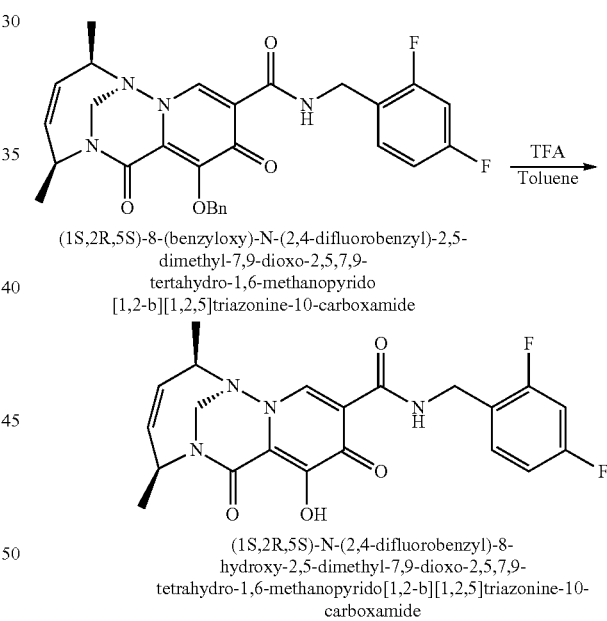

(1S,2R,5S)-8-(Benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (230 mg, 0.188 mmol) was dissolved in toluene (1 mL) at rt. TFA (1 mL) was added carefully with stirring. The resulting reaction mixture was stirred at rt for 17 hrs. Reaction mixture was then concentrated to dryness. The residue was taken up in MeOH and was purified with reverse phase prep-HPLC with 0-100% CH$_3$CN in water with 0.1% TFA to afford the desired product. Lyophilization afford product as mono TFA salt. 150 mg. MS (m/z): 431.2 [M+H]. 1H NMR (400 MHz, Acetonitrile-d3) δ 10.21 (s, 1H), 8.39 (s, 1H), 7.44 (td, J=8.8, 6.5 Hz, 1H), 7.21-6.84 (m, 2H), 5.66 (dt, J=11.4, 2.4

Hz, 1H), 5.46-5.32 (m, 2H), 5.02 (d, J=14.4 Hz, 1H), 4.67-4.50 (m, 3H), 3.84 (qq, J=6.6, 3.0 Hz, 1H), 1.35 (dd, J=7.1, 4.1 Hz, 6H).

Example 30: Preparation of (1S,2S,5S)-8-hydroxy-2,5-dimethyl-7,9-dioxo-N-(2,4-difluorobenzyl)-2,5,7,9-tetrahydro-1,6-methanopyrido[1,2-b][1,2,5]triazonine-10-carboxamide (C30)

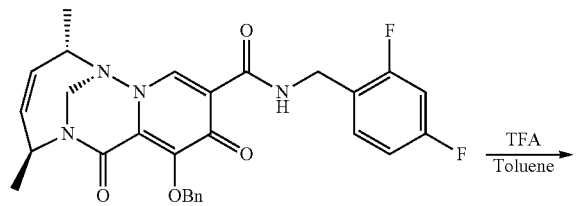

(1S,2S,5S)-8-(benzyloxy)-N-(2,4-difluorobenzyl)-2,5-dimethyl-7,9-dioxo-2,5,7,9-tetrahydro-1,6-methanopyrido[1,2-b][1,2,5]triazonine-10-carboxamide TFA / Toluene

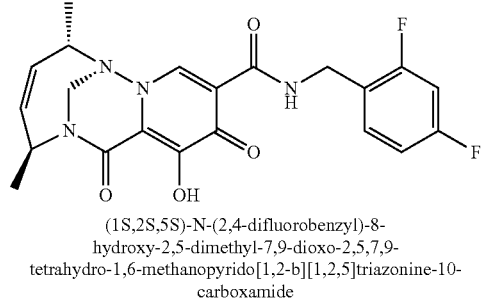

(1S,2S,5S)-N-(2,4-difluorobenzyl)-8-hydroxy-2,5-dimethyl-7,9-dioxo-2,5,7,9-tetrahydro-1,6-methanopyrido[1,2-b][1,2,5]triazonine-10-carboxamide (1S,2S,5S)-8-(Benzyloxy)-2,5-dimethyl-7,9-dioxo-N-(2,4-difluorobenzyl)-2,5,7,9-tetrahydro-1,6-methanopyrido[1,2-b][1,2,5]triazonine-10-carboxamide (15 mg, 0.0288 mmol) was dissolved in toluene (1 mL) at rt. TFA (1 mL) was added carefully with stirring. The resulting reaction mixture was stirred at rt for 17 hrs. Reaction mixture was then concentrated to dryness. The residue was taken up in MeOH and was purified with reverse phase prep-HPLC with 0-100% CH$_3$CN in water with 0.1% TFA to afford the desired product. Lyophilization afford product as mono TFA salt. 5 mg. MS (m/z): 431.2 [M+H]. 1H NMR (400 MHz, Acetonitrile-d3) δ 10.27 (s, 1H), 8.45 (s, 1H), 7.44 (td, J=8.8, 6.5 Hz, 1H), 6.97 (dddd, J=10.7, 5.2, 4.3, 2.5 Hz, 2H), 5.62 (ddd, J=12.2, 3.3, 2.1 Hz, 1H), 5.46-5.31 (m, 2H), 4.94 (d, J=14.4 Hz, 1H), 4.73 (d, J=14.4 Hz, 1H), 4.61 (d, J=6.1 Hz, 3H), 1.36 (d, J=7.2 Hz, 3H), 1.03 (d, J=7.4 Hz, 3H).

Example 31: Preparation of (1S,2S,5S)—N-(2,4-difluorobenzyl)-8-hydroxy-2,5-dimethyl-7,9-dioxo-2,3,4,5,7,9-hexahydro-1,6-methanopyrido[1,2-b][1,2,5]triazonine-10-carboxamide (C31)

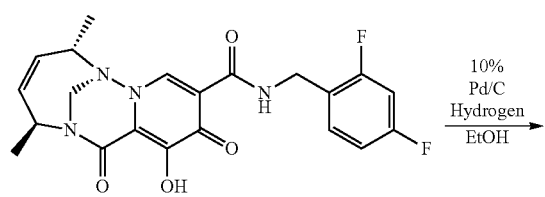

10% Pd/C Hydrogen EtOH

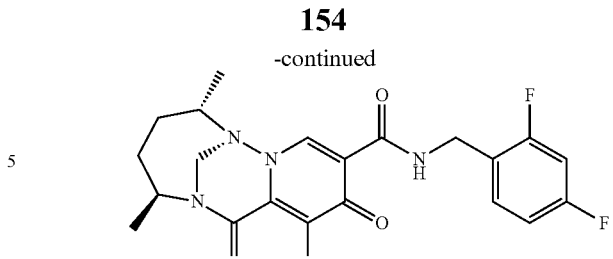

A solution of (1S,2S,5S)—N-(2,4-difluorobenzyl)-8-hydroxy-2,5-dimethyl-7,9-dioxo-2,5,7,9-tetrahydro-1,6-methanopyrido[1,2-b][1,2,5]triazonine-10-carboxamide (Example 30, 0.291 mmol, 125 mg) in EtOH (9 mL) was evacuated and back-filled with argon (5× cycles) then treated with 10% Pd/C (25 mg) and further evacuated and back-filled with argon (5× cycles) followed by hydrogen (5× cycles). The reaction mixture was stirred at room temperature under a hydrogen balloon overnight then filtered across Celite, washed with EtOH and concentrated. The resulting residue was dissolved again in EtOH (22 mL) and treated with 10% Pd/C (50 mg) and hydrogen per above. After 4 hours, the reaction mixture was filtered across Celite, washed with EtOH and concentrated then purified by preparative HPLC (10-100% MeCN in water with 0.10% TFA) and lyophilized to afford the title compound as the trifluoroacetic acid salt (62 mg, 39% yield). MS (m/z) 433.25 [M+H]$^+$. $^1$H NMR (400 MHz, Methanol-d4) δ 8.43 (s, 1H), 7.43 (td, J=8.5, 6.4 Hz, 1H), 7.02-6.88 (m, 2H), 4.85-4.76 (m, 2H), 4.69 (dt, J=10.6, 6.7 Hz, 1H), 4.63 (s, 2H), 3.55-3.44 (m, 1H), 2.22 (dt, J=14.2, 6.8 Hz, 1H), 1.75 (dt, J=15.0, 11.3 Hz, 1H), 1.66 (dd, J=15.7, 6.9 Hz, 1H), 1.30 (d, J=6.7 Hz, 3H), 1.36-1.20 (m, 1H), 1.11 (d, J=6.8 Hz, 3H).

Example 32: Preparation of (1S,2R,3R,4S,5S)-8-hydroxy-3,4-dimethoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide: (C32)

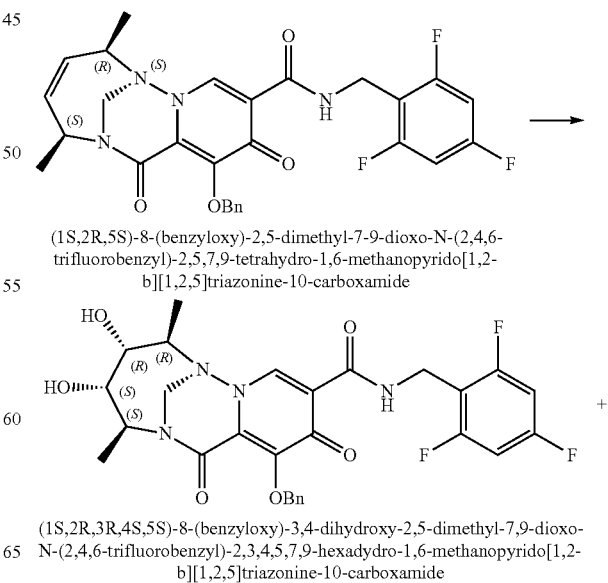

(1S,2R,5S)-8-(benzyloxy)-2,5-dimethyl-7-9-dioxo-N-(2,4,6-trifluorobenzyl)-2,5,7,9-tetrahydro-1,6-methanopyrido[1,2-b][1,2,5]triazonine-10-carboxamide (1S,2R,3R,4S,5S)-8-(benzyloxy)-3,4-dihydroxy-2,5-dimethyl-7,9-dioxo-N-(2,4,6-trifluorobenzyl)-2,3,4,5,7,9-hexaydro-1,6-methanopyrido[1,2-b][1,2,5]triazonine-10-carboxamide -continued

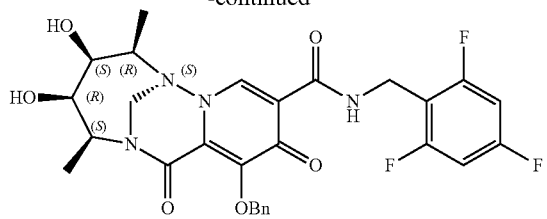

(1S,2R,3S,4R,5S)-8-(benzyloxy)-3,4-dihydroxy-2,5-dimethyl-7,9-dioxo-N-(2,4,6-trifluorobenzyl)-2,3,4,5,7,9-hexadydro-1,6-methanopyrido[1,2-b][1,2,5]triazonine-10-carboxamide Preparation of (1S,2R,3R,4S,5S)-8-(benzyloxy)-3,4-dihydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide In a 50-mL flask, (1S,2R,5S)-8-(benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (Example 24, step 7, A) (140 mg, 0.26 mmol) was dissolved in acetone (8 mL) and water (1 mL) mixture, then was cooled down to 0° C. in ice-water bath. 4-Methylmorpholine N-oxide (50% in water, 0.1 mL, 2 eq.) was slowly added into above reaction solution. Then 2.5% osmium tetroxide (0.01 mL, 4% eq.) was added. The mixture was stirred at 0° C. and warm up to r.t. for 2 days. The reaction was quenched by adding aqueous 10% sodium sulfite solution. The reaction mixture was extracted using (1:1) EtOAc: n-BnOH. The organic layer was concentrate down, and purified via silica column (eluting with 0-10% MeOH/DCM) to give (1S,2R,3S,4R,5S)-8-(benzyloxy)-3,4-dihydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (non-polar, minor product) and (1S,2R,3R,4S,5S)-8-(benzyloxy)-3,4-dihydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (polar, major product). MS (m/z) 573.3 [M+H]$^+$.

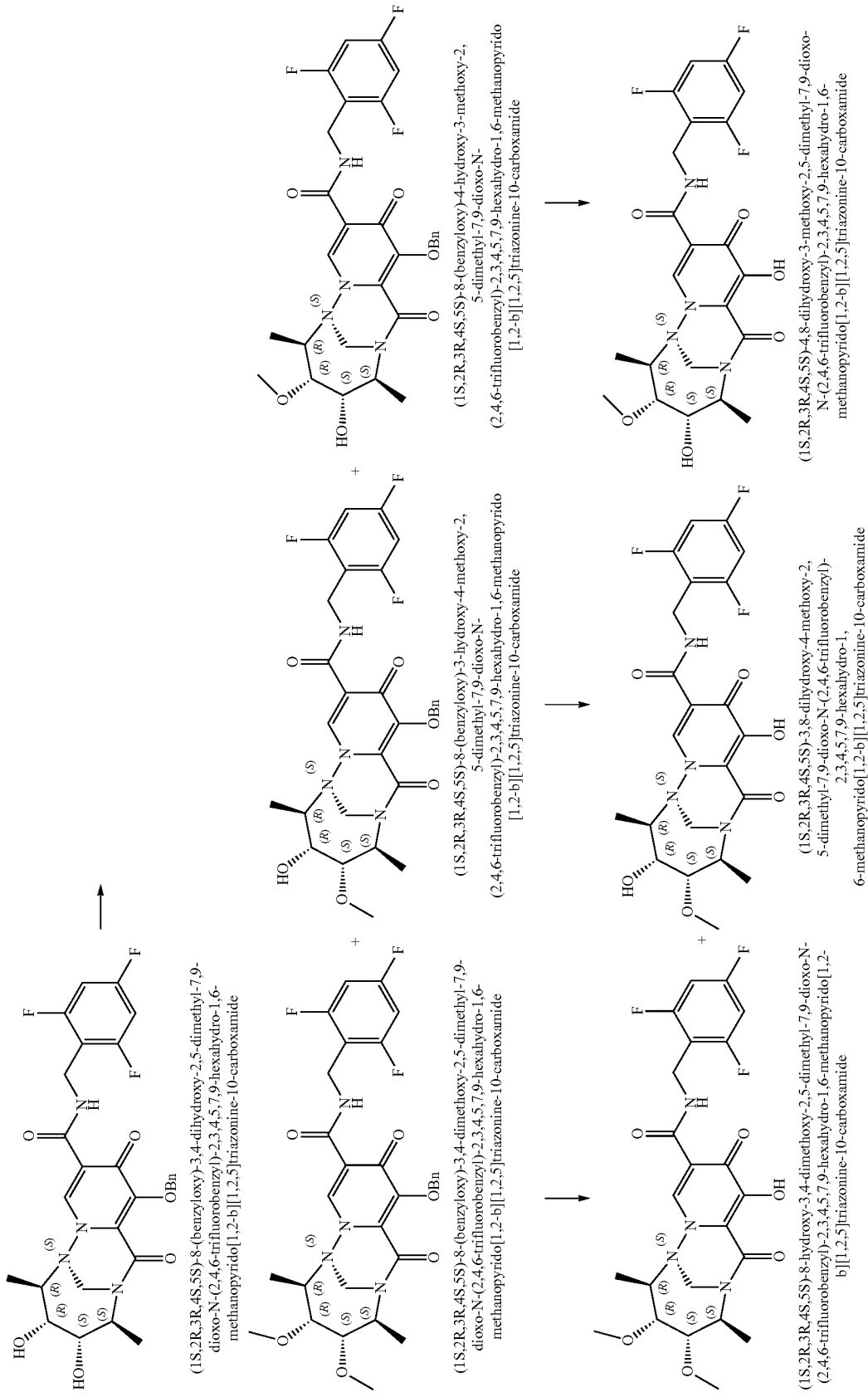

Preparation of (1S,2R,3R,4S,5S)-8-(benzyloxy)-3,4-dimethoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide, (1S,2R,3R,4S,5S)-8-(benzyloxy)-3-hydroxy-4-methoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide, and (1S,2R,3R,4S,5S)-8-(benzyloxy)-4-hydroxy-3-methoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide In a 50-mL flask, (1S,2R,3R,4S,5S)-8-(benzyloxy)-3,4-dihydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (77 mg, 0.134 mmol) was dissolved in DMF (3 mL), then was cooled down to 0° C. in ice-water bath. Sodium hydride (60%, 11 mg, 2.2 eq.) was added into above reaction solution. After 10 minutes, methyl iodide (diluted with DCM to 100 times dilute, 1 mL, 1.3 eq.) was added. The mixture was stirred at 0° C. for 30 minutes. LC-MS showed bis-Me product, and two mono-Me products, and some starting material. The reaction was quenched by adding aqueous saturated sodium bicarbonate solution. The reaction mixture was extract using ethyl acetate. The organic layer was concentrated down, and purified via preparative HPLC, eluting 10-100% acetonitrile (0.1% TFA) in water (0.1% TFA) to give (1S,2R,3R,4S,5S)-8-(benzyloxy)-3,4-dimethoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide MS (m/z) 601.3 [M+H]$^+$) and (1S,2R,3R,4S,5S)-8-(benzyloxy)-3-hydroxy-4-methoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (polar, major mono-Me product MS (m/z) 587.3 [M+H]$^+$) and (1S,2R,3R,4S,5S)-8-(benzyloxy)-4-hydroxy-3-methoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (nonpolar, minor mono-Me product MS (m/z) 587.3 [M+H]$^+$)

Preparation of (1S,2R,3R,4S,5S)-8-hydroxy-3,4-dimethoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (C32)

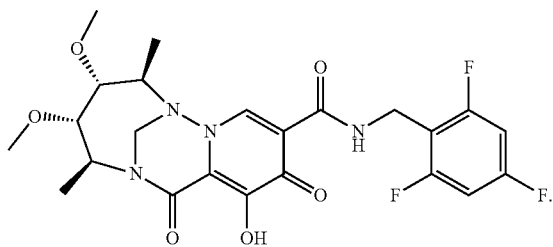 [SMILES: CO[C@@H]1[C@H](OC)[C@@H](C)N2CN(C(=O)c3c(O)c(=O)c(C(=O)NCc4c(F)cc(F)cc4F)cn32)[C@H]1C]

(1S,2R,3R,4S,5S)-8-(benzyloxy)-3,4-dimethoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (15 mg) was dissolved in toluene (0.5 mL), trifluoroacetic acid (1 mL) was added. The reaction was stirred at r.t. for 2 hours. The reaction was concentrated down and purified via preparative HPLC, eluting 10-100% acetonitrile (0.1% TFA) in water (0.1% TFA) to give to 7.2 mg the title compound. MS (m/z) 511.3 [M+H]$^+$. 1H NMR (400 MHz, Acetonitrile-d3) δ 10.40 (s, 1H), 8.45 (s, 1H), 6.99-6.80 (m, 2H), 4.70-4.59 (m, 2H), 4.52 (t, J=14.8 Hz, 2H), 4.26-4.12 (m, 1H), 3.81 (d, J=7.6 Hz, 1H), 3.61 (d, J=3.1 Hz, 1H), 3.47 (d, J=8.8 Hz, 1H), 3.36 (s, 3H), 3.09 (s, 3H), 1.48-1.25 (m, 6H).

Example 33: Preparation of (1S,2R,4R,5S)-8-hydroxy-4-methoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (C33)

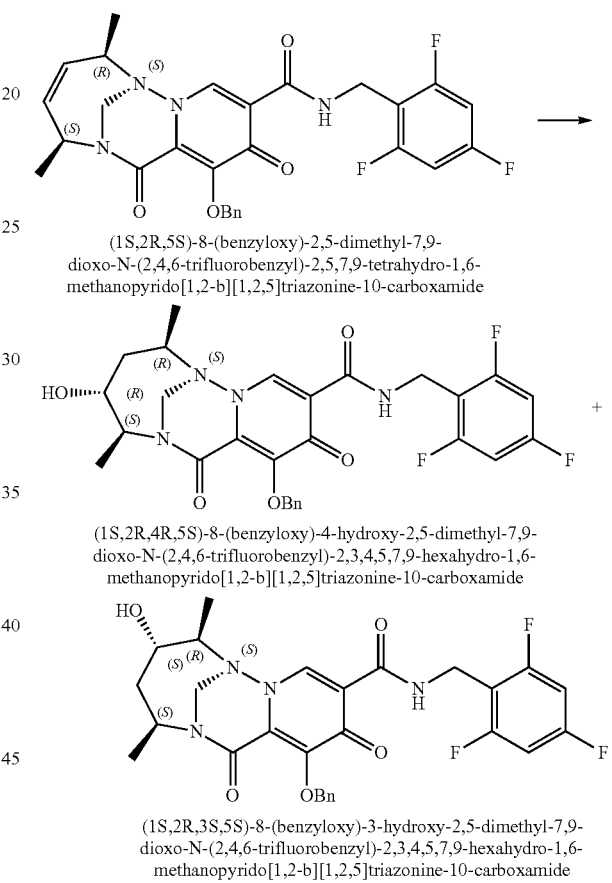

Preparation of (1S,2R,4R,5S)-8-(benzyloxy)-4-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide and (1S,2R,3S,5S)-8-(benzyloxy)-3-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide In a 100-mL flask, (1S,2R,5S)-8-(benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (Example 24, step 7, A) (384 mg, 0.71 mmol) was dissolved in isopropanol (15 mL) and purged argon. Phenylsilane (2 eq.) and Shenvi's catalyst (tris[(Z)-1-tert-butyl- 4,4-dimethyl-3-oxo-pent-1-enoxy]manganese) (3%) was added into above reaction solution. An oxygen balloon was applied. The mixture was stirred at r.t. for one day. LC-MS shows products, still starting material. The reaction was quenched by adding aqueous 10% sodium thiosulfate solution. The reaction mixture was extracted using ethyl acetate. The organic layer was concentrated down, and purified via silica column (eluting with 0-10% MeOH/DCM) to give (1S,2R,4R,5S)-8-(benzyloxy)-4-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (polar product, MS (m/z) 573.3 [M+H]+, NMR HMBC, COSY, NOE studies confirmed the structure) and (1S,2R,3S,5S)-8-(benzyloxy)-3-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (nonpolar, MS (m/z) MS (m/z) 573.3 [M+H]+).

(4 mg) was dissolved in toluene (0.2 mL), trifluoroacetic acid (0.4 mL) was added. The reaction was stirred at r.t. for 2 hours. The reaction was concentrated down and purified via preparative HPLC, eluting 10-100% acetonitrile (0.1% TFA) in water (0.1% TFA) to give the title compound. MS (m/z) 467.2 [M+H]+. 1H NMR (400 MHz, Acetonitrile-d3) δ 10.35 (s, 1H), 8.40 (s, 1H), 6.87 (t, J=8.5 Hz, 2H), 4.71-4.43 (m, 4H), 4.36 (p, J=6.8 Hz, 1H), 3.88 (dd, J=9.2, 6.0 Hz, 1H), 3.49 (m, 1H), 1.87-1.69 (m, 1H), 1.51-1.19 (m, 7H).

Preparation of (1S,2R,4R,5S)-8-(benzyloxy)-4-methoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide In a 50-mL flask, (1S,2R,4R,5S)-8-(benzyloxy)-4-hydroxy-2,5-dimethyl-7,9-dioxo-N-(2,4,6-trifluorobenzyl)-2,

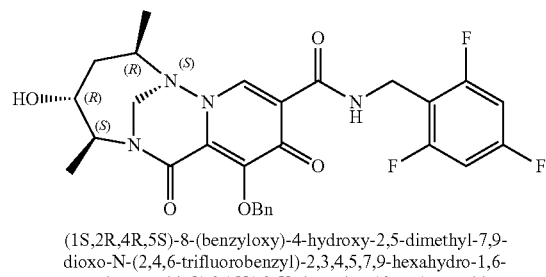

(1S,2R,4R,5S)-8-(benzyloxy)-4-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide

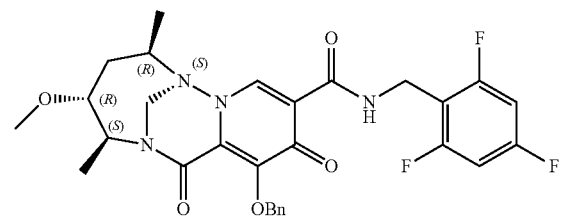

(1S,2R,4R,5S)-8-(benzyloxy)-4-methoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide

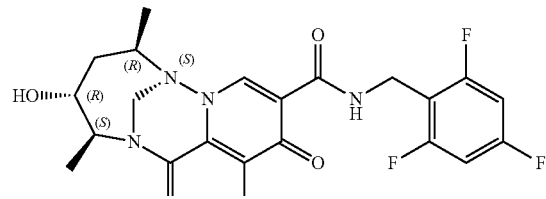

(1S,2R,4R,5S)-4,8-dihydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide

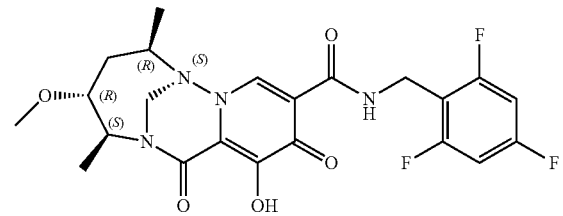

(1S,2R,4R,5S)-8-hydroxy-4-methoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide Preparation of (1S,2R,4R,5S)-4,8-dihydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide

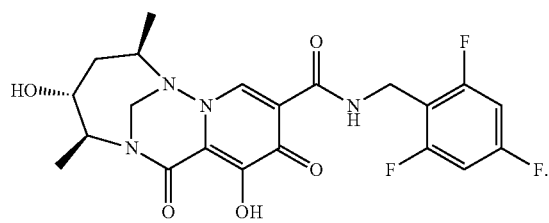 [SMILES: C[C@@H]1C[C@@H](O)[C@H](C)N2CN1n1cc(C(=O)NCc3c(F)cc(F)cc3F)c(=O)c(O)c1C2=O]

(1S,2R,4R,5S)-8-(benzyloxy)-4-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide 3,4,5,7,9-hexahydro-1,6-methanopyrido[1,2-b][1,2,5]triazonine-10-carboxamide (10 mg, 0.018 mmol) was dissolved in DMF (1 mL), then was cooled down to 0° C. in ice-water bath. Sodium hydride (60%, 1.4 mg, 2 eq.) was added into above reaction solution. After 10 minutes, methyl iodide (diluted with DCM to 100 times dilute, 0.11 mL, 1 eq.) was added. The mixture was stirred at 0° C. for 30 minutes. LC-MS showed bis-Me product, major was mono-Me product. The reaction was quenched by adding aqueous saturated sodium bicarbonate solution. The reaction mixture was extracted using ethyl acetate. The organic layer was concentrate down, and purified via preparative HPLC, eluting 10-100% acetonitrile (0.10% TFA) in water (0.1% TFA) to give the titled compound. MS (m/z) 571.3 [M+H]+.

Preparation of (1S,2R,4R,5S)-8-hydroxy-4-methoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (C33)

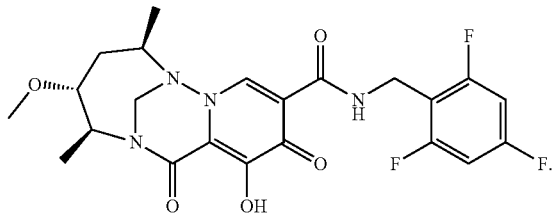 [SMILES: CO[C@@H]1C[C@@H](C)N2CN(C(=O)c3c(O)c(=O)c(C(=O)NCc4c(F)cc(F)cc4F)cn32)[C@H]1C]

(1S,2R,4R,5S)-8-(benzyloxy)-4-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (4 mg) was dissolved in toluene (0.2 mL), trifluoroacetic acid (0.4 mL) was added. The reaction was stirred at r.t. for 2 hours. The reaction was concentrated down and purified via preparative HPLC, eluting 10-100% acetonitrile (0.1% TFA) in water (0.1% TFA) to give to 1.6 mg the title compound. MS (m/z) 481.2 [M+H]$^+$. $^1$H NMR (400 MHz, Acetonitrile-d3) δ 10.33 (s, 1H), 8.42 (d, J=8.2 Hz, 1H), 6.87 (t, J=8.5 Hz, 2H), 4.76-4.46 (m, 4H), 3.45 (dd, J=9.0, 5.4 Hz, 2H), 3.30 (s, 3H), 1.90-1.74 (m, 2H), 1.55-1.21 (m, 7H).

Example 34: Preparation of (1S,2R,4S,5S)-4-fluoro-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (C34)

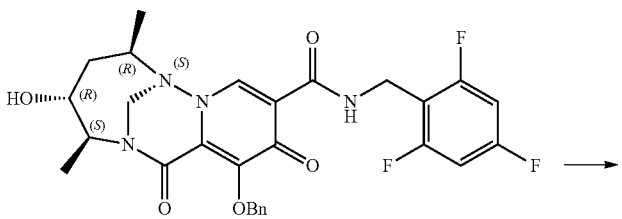

(1S,2R,4R,5S)-8-(benzyloxy)-4-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide

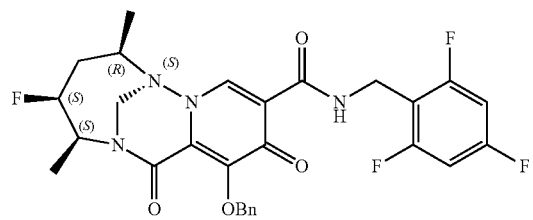 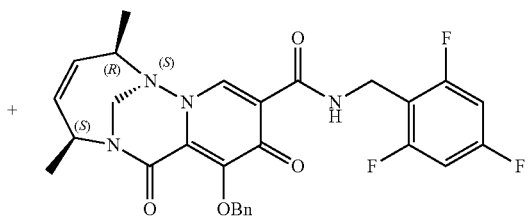

(1S,2R,4S,5S)-8-(benzyloxy)-4-fluoro-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (1S,2R,5S)-8-(benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide

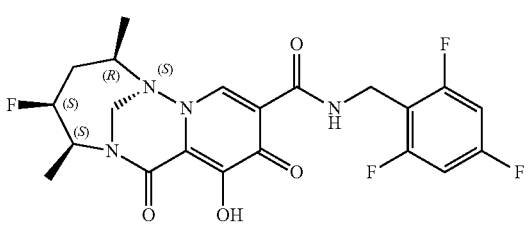 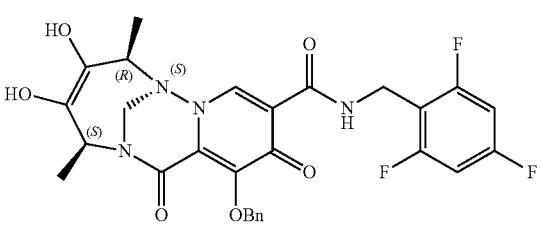

(1S,2R,4S,5S)-4-fluoro-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (1S,2R,5S)-8-(benzyloxy)-3,4-dihydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide Preparation of (1S,2R,4S,5S)-8-(benzyloxy)-4-fluoro-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide In a 50-mL flask, (1S,2R,4R,5S)-8-(benzyloxy)-4-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (28 mg, 0.05 mmol) was dissolved in DCM (1.5 mL), then was cooled down to 0° C. in ice-water bath. Bis(2-methoxyethyl)aminosulfur trifluoride (50% in toluene, 2.7 M, 0.037 mL, 2 eq.) was added into above reaction solution. The mixture was stirred at 0° C. for 30 minutes. LC-MS showed fluorination product and elimination product. The reaction was quenched by adding aqueous saturated sodium bicarbonate solution. The reaction mixture was extracted using ethyl acetate. The organic layer was concentrate down, tried purification via normal phase silica column and preparative HPLC, no separation. The mixture was dissolved in acetone (4 mL) and water (0.5 mL) mixture, cooled down to 0° C. in ice-water bath. 4-Methylmorpholine N-oxide (50% in water, 0.017 mL, 1.5 eq.) was slowly added into above reaction solution. Then 2.5% osmium tetroxide (0.023 mL, 4% eq.) was added. The mixture was stirred at 0° C. and warm up to r.t. for 2 days. The reaction was quenched by adding aqueous 10% sodium sulfite solution. The reaction mixture was extracted using ethyl acetate. The organic layer was concentrate down, and purified via preparative HPLC, eluting 10-100% acetonitrile (0.1% TFA) in water (0.1% TFA), collected the non-polar product to give (1S,2R,4S,5S)-8-(benzyloxy)-4-fluoro-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (non-polar). MS (m/z) 559.3 [M+H]$^+$.

Preparation of (1S,2R,4S,5S)-4-fluoro-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (C34)

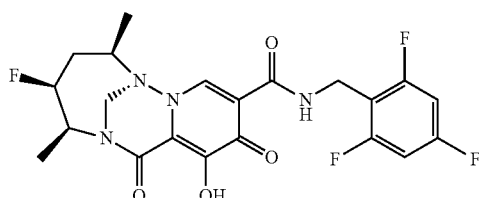

(1S,2R,4S,5S)-8-(benzyloxy)-4-fluoro-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (8 mg) was dissolved in toluene (0.2 mL), trifluoroacetic acid (0.4 mL) was added. The reaction was stirred at r.t. for 2 hours. The reaction was concentrated down and purified via preparative HPLC, eluting 10-100% acetonitrile (0.1% TFA) in water (0.1% TFA) to give the title compound. MS (m/z) 469.2 [M+H]$^+$. $^1$H NMR (400 MHz, Acetonitrile-d3) δ 10.26 (s, 1H), 8.41 (s, 1H), 7.01-6.75 (m, 2H), 5.11-4.92 (m, 1H), 4.91-4.81 (m, 2H), 4.66-4.59 (m, 2H), 3.49-3.34 (m, 1H), 2.39-2.23 (m, 1H), 1.95-1.79 (m, 1H), 1.51, 1.30 (m, 1H), 1.45 (dd, J=7.1, 2.0 Hz, 3H), 1.35 (dd, J=7.2, 2.9 Hz, 3H).

Example 35: Preparation of (1S,2R,5S)-4,4-difluoro-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide: (C35)

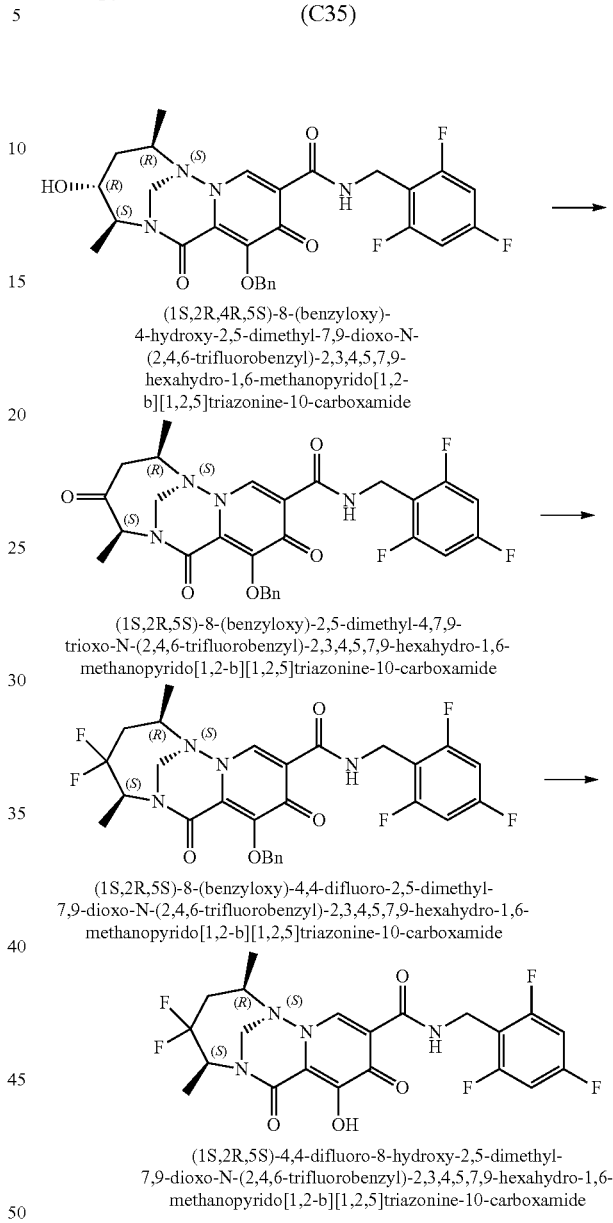

(1S,2R,4R,5S)-8-(benzyloxy)-4-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (1S,2R,5S)-8-(benzyloxy)-2,5-dimethyl-4,7,9-trioxo-N-(2,4,6-trifluorobenzyl)-2,3,4,5,7,9-hexahydro-1,6-methanopyrido[1,2-b][1,2,5]triazonine-10-carboxamide (1S,2R,5S)-8-(benzyloxy)-4,4-difluoro-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (1S,2R,5S)-4,4-difluoro-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide Preparation of (1S,2R,5S)-8-(benzyloxy)-2,5-dimethyl-4,7,9-trioxo-N-(2,4,6-trifluorobenzyl)-2,3,4,5,7,9-hexahydro-1,6-methanopyrido[1,2-b][1,2,5]triazonine-10-carboxamide In a 50-mL flask, (1S,2R,4R,5S)-8-(benzyloxy)-4-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (127 mg, 0.228 mmol) was dissolved in DCM (3 mL), then was cooled down to 0° C. in ice-water bath. Dess-Martin periodinane (194 mg, 2 eq.) was added into above reaction solution. The mixture was stirred at 0° C. and warm up to room temperature for 2 hours. The reaction was quenched by adding aqueous 10% sodium thiosulfate solution. The reaction mixture was extracted using ethyl acetate. The organic layer was concentrated down, purified via silica column (eluting with 0-10% MeOH/DCM) to give (1S,2R,5S)-8-(benzyloxy)-2, 5-dimethyl-4,7,9-trioxo-N-(2,4,6-trifluorobenzyl)-2,3,4,5,7, 9-hexahydro-1,6-methanopyrido[1,2-b][1,2,5]triazonine-10-carboxamide (93 mg). MS (m/z) 555.3 [M+H]+.

Preparation of (1S,2R,5S)-8-(benzyloxy)-4,4-difluoro-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide In a 50-mL flask, (1S,2R,5S)-8-(benzyloxy)-2,5-dimethyl-4,7,9-trioxo-N-(2,4,6-trifluorobenzyl)-2,3,4,5,7,9-hexahydro-1,6-methanopyrido[1,2-b][1,2,5]triazonine-10-carboxamide (110 mg, 0.2 mmol) was dissolved in DCM (5 mL), then was cooled down to 0° C. in ice-water bath. Bis(2-methoxyethyl)aminosulfur trifluoride (50% in toluene, 2.7 M, 0.147 mL, 2 eq.) was added into above reaction solution. The mixture was stirred at 0° C., and warmed up to room temperature overnight. The reaction was quenched by adding aqueous saturated sodium bicarbonate solution. The reaction mixture was extracted using ethyl acetate. The organic layer was concentrated down and purified via silica column (eluting with 0-10% MeOH/DCM) to give (1S,2R, 5S)-8-(benzyloxy)-4,4-difluoro-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide. MS (m/z) 577.2 [M+H]+.

Preparation of (1S,2R,5S)-4,4-di fluoro-8-hydroxy-2,5-dimethyl-7,9-dioxo-N-(2,4,6-trifluorobenzyl)-2, 3,4,5,7,9-hexahydro-1,6-methanopyrido[1,2-b][1,2, 5]triazonine-10-carboxamide (C35)

(1S,2R,5S)-8-(benzyloxy)-4,4-difluoro-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (25 mg) was dissolved in toluene (0.5 mL) and trifluoroacetic acid (2 mL) was added. The reaction was stirred at r.t. for 2 hours. The reaction was concentrated down and purified via preparative HPLC, eluting 10-100% acetonitrile (0.1% TFA) in water (0.1% TFA) to give the title compound. MS (m/z) 487.2 [M+H]+. 1H NMR (400 MHz, DMSO-d6) δ 10.47 (s, 1H), 10.29 (t, J=5.8 Hz, 1H), 8.24 (s, 1H), 7.31-7.16 (m, 2H), 5.76 (s, 1H), 5.07 (d, J=15.2 Hz, 1H), 4.91 (dq, J=15.0, 7.2 Hz, 1H), 4.76 (d, J=15.2 Hz, 1H), 4.57 (d, J=5.8 Hz, 2H), 3.21 (t, J=8.3 Hz, 1H), 2.83 (ddd, J=32.9, 16.3, 10.1 Hz, 2H), 1.33 (dd, J=7.0, 3.1 Hz, 6H).

Example 36: Preparation of (1S,2R,5S)-3-fluoro-8-hydroxy-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide: (C36)

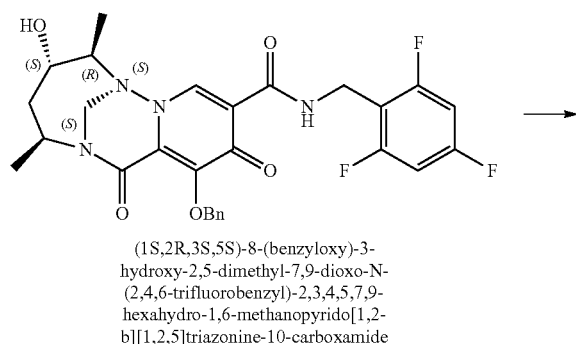

(1S,2R,3S,5S)-8-(benzyloxy)-3-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide

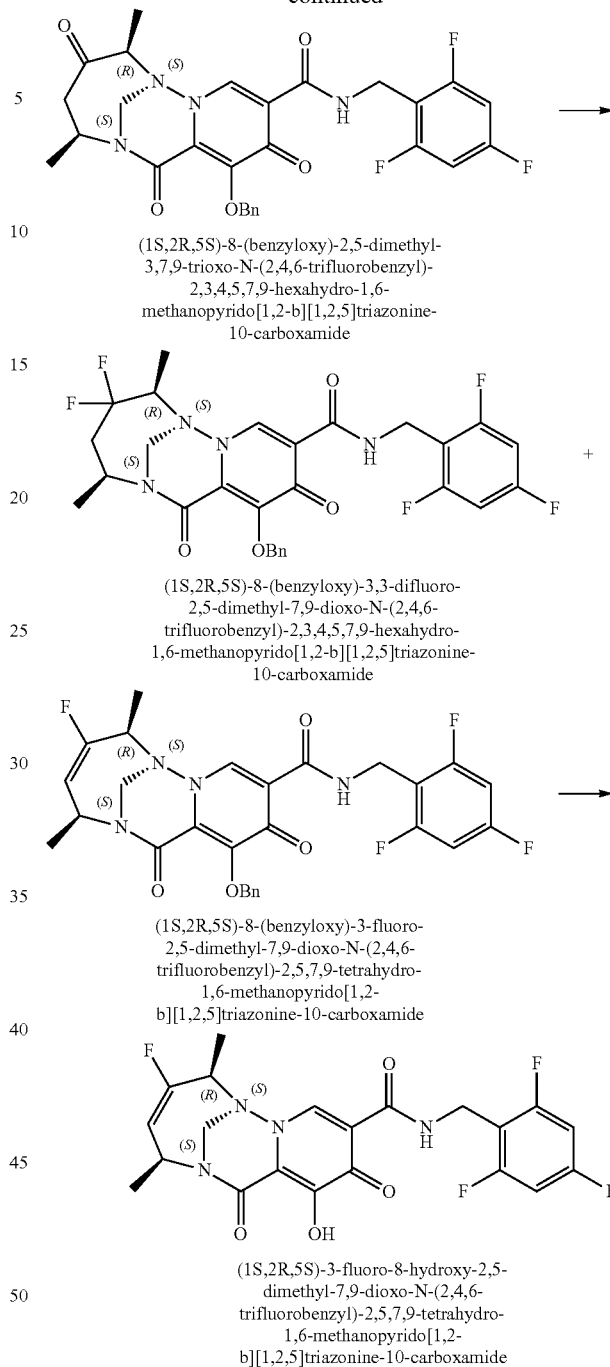

Preparation of (1S,2R,5S)-8-(benzyloxy)-2,5-dimethyl-3,7,9-trioxo-N-(2,4,6-trifluorobenzyl)-2,3,4,5, 7,9-hexahydro-1,6-methanopyrido[1,2-b][1,2,5]triazonine-10-carboxamide In a 25-mL flask, (1S,2R,3S,5S)-8-(benzyloxy)-3-hydroxy-2,5-dimethyl-7,9-dioxo-N-(2,4,6-trifluorobenzyl)-2, 3,4,5,7,9-hexahydro-1,6-methanopyrido[1,2-b][1,2,5]triazonine-10-carboxamide (16 mg, 0.028 mmol) was dissolved in DCM (1 mL), then was cooled down to 0° C. in ice-water bath. Dess-Martin Periodinane (11 mg, 2 eq.) was added into above reaction solution. The mixture was stirred at 0° C. and warm up to room temperature for 2 hours. The reaction was quenched by adding aqueous 10% sodium thiosulfate solution. The reaction mixture was extracted using ethyl acetate. The organic layer was concentrated down, purified via silica column (eluting with 0-10% MeOH/DCM) to give (1S,2R,5S)-8-(benzyloxy)-2,5-dimethyl-3,7,9-trioxo-N-(2,4,6-trifluorobenzyl)-2,3,4,5,7,9-hexahydro-1,6-methanopyrido[1,2-b][1,2,5]triazonine-10-carboxamide. MS (m/z) 555.3 [M+H]+.

Preparation of (1S,2R,5S)-8-(benzyloxy)-3-fluoro-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide In a 50-mL flask, (1S,2R,5S)-8-(benzyloxy)-2,5-dimethyl-3,7,9-trioxo-N-(2,4,6-trifluorobenzyl)-2,3,4,5,7,9-hexahydro-1,6-methanopyrido[1,2-b][1,2,5]triazonine-10-carboxamide (12 mg, 0.2 mmol) was dissolved in DCM (2 mL), then was cooled down to 0° C. in ice-water bath. Bis(2-methoxyethyl)aminosulfur Trifluoride (50% in toluene, 2.7 M, 0.018 mL, 2 eq.) was added into above reaction solution. The mixture was stirred at 0° C., and warmed up to room temperature for 3 hours. LC-MS showed elimination product and di-F product. The reaction was quenched by adding aqueous saturated sodium bicarbonate solution. The reaction mixture was extracted using ethyl acetate. The organic layer was concentrated down, and purified via preparative HPLC, eluting 10-100% acetonitrile (0.1% TFA) in water (0.1% TFA) to give (1S,2R,5S)-8-(benzyloxy)-3-fluoro-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide. MS (m/z) 557.3 [M+H]+.

Preparation of (1S,2R,5S)-3-fluoro-8-hydroxy-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (C36)

(1S,2R,5S)-8-(benzyloxy)-3-fluoro-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (6 mg) was dissolved in toluene (0.2 mL) and trifluoroacetic acid (0.5 mL) was added. The reaction was stirred at r.t. for 2 hours. The reaction was concentrated down and purified via preparative HPLC, eluting 10-100% acetonitrile (0.1% TFA) in water (0.1% TFA) to give to the title compound. MS (m/z) 467.2 [M+H]+. 1H NMR (400 MHz, Acetonitrile-d3) δ 10.20 (s, 1H), 8.43 (s, 1H), 6.87 (t, J=8.5 Hz, 2H), 5.70-5.48 (m, 1H), 5.32-5.17 (m, 1H), 5.00 (d, J=14.8 Hz, 1H), 4.78-4.57 (m, 3H), 4.22-4.08 (m, 1H), 1.52 (dd, J=6.9, 3.0 Hz, 3H), 1.37 (d, J=7.2 Hz, 3H).

Example 37: Preparation of (1S,2R,5S)—N-(2,4-difluorobenzyl)-8-hydroxy-2,5-dimethyl-7,9-dioxo-2,3,4,5,7,9-hexahydro-1,6-methanopyrido[1,2-b][1,2,5]triazonine-10-carboxamide (C37)

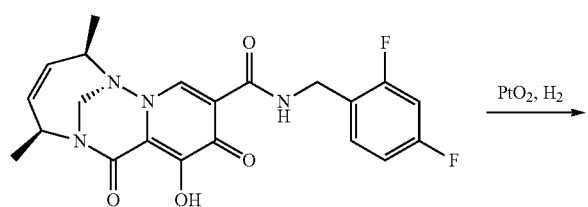

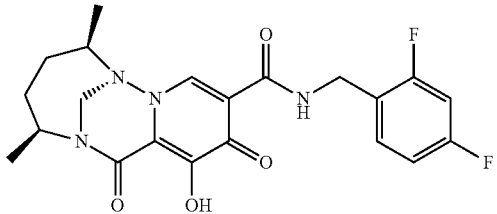

To a solution of (1S,2R,5S)—N-(2,4-difluorobenzyl)-8-hydroxy-2,5-dimethyl-7,9-dioxo-2,5,7,9-tetrahydro-1,6-methanopyrido[1,2-b][1,2,5]triazonine-10-carboxamide (10.2 mg, 0.023 mmol) in EtOH (5 mL), was added PtO2 (2 mg, 0.009 mmol). The reaction was stirred at rt under H2 balloon for 2 h. The reaction mixture was filtered through celite, the filtrate was concentrated down and the residue was purified by reverse phase HPLC, eluting with 5-100% acetonitrile in water to give the desired product. MS (m/z): 433.11 [M+H]+. 1H NMR (400 MHz, Methanol-d4) δ 8.50 (s, 1H), 7.51-7.38 (m, 1H), 6.97 (q, J=10.0, 9.5 Hz, 2H), 4.78 (d, J=14.3 Hz, 1H), 4.65 (s, 4H), 3.57 (s, 1H), 2.05 (dd, J=15.0, 7.6 Hz, 1H), 1.82 (dd, J=15.1, 9.4 Hz, 1H), 1.62 (d, J=12.2 Hz, 2H), 1.40 (d, J=7.0 Hz, 3H), 1.33 (d, J=6.7 Hz, 3H).

Example 38: Preparation of (1S,2R,4R,5S)—N-(2,4-difluorobenzyl)-4,5-difluoro-9-hydroxy-2-methyl-8,10-dioxo-3,4,5,6,8,10-hexahydro-2H-1,7-methanopyrido[1,2-b][1,2,5]triazecine-11-carboxamide (C38)

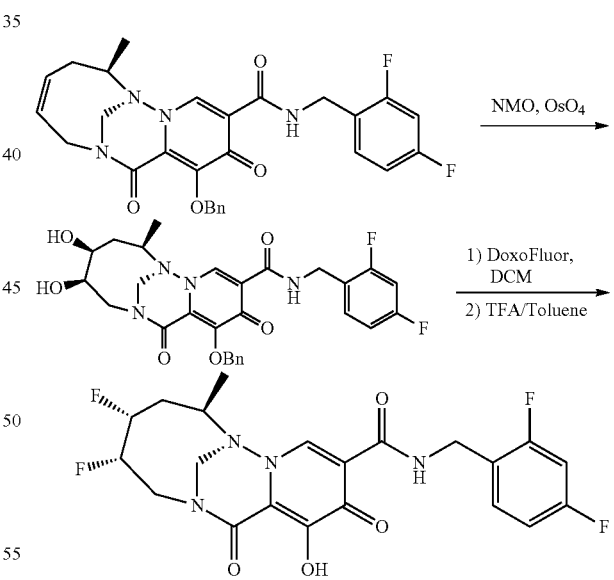

Step 1: Synthesis of (1S,2R,4S,5R)-9-(benzyloxy)-N-(2,4-difluorobenzyl)-4,5-dihydroxy-2-methyl-8,10-dioxo-3,4,5,6,8,10-hexahydro-2H-1,7-methanopyrido[1,2-b][1,2,5]triazecine-11-carboxamide (15A)

(1S,2R,Z)-9-(benzyloxy)-N-(2,4-difluorobenzyl)-2-methyl-8,10-dioxo-3,6,8,10-tetrahydro-2H-1,7-methanopyrido[1,2-b][1,2,5]triazecine-11-carboxamide (11A, 190 mg, 0.36 mmol) in 3 mL acetone and 0.45 mL water was cool to 0° C. To it was added 4-methylmorpholine n-oxide (50% in water, 0.076 ml, 0.36 mmol) and osmium tetroxide (2.5% in t-BuOH, 0.15 ml, 0.0014 mmol). The reaction was stirred at room temperature for 2 days. Added 10% Sodium sulfite aqueous solution (3 mL) to reaction and stirred for 15 minutes. Extracted it with ethyl acetate three times. Combined organic layers were washed with brine, dried over magnesium sulfate, filtered and concentrated to dryness. The residue was purified by silica gel chromatography eluting with methanol in dichloromethane to afford the title product. Both hydroxy stereocenter were arbitrarily assigned. MS (m/z) 555.300 [M+H]$^+$.

Step 2: Synthesis of (1S,2R,4R,5S)—N-(2,4-difluorobenzyl)-4,5-difluoro-9-hydroxy-2-methyl-8,10-dioxo-3,4,5,6,8,10-hexahydro-2H-1,7-methanopyrido[1,2-b][1,2,5]triazecine-11-carboxamide (C38)

(1S,2R,4S,5R)-9-(benzyloxy)-N-(2,4-difluorobenzyl)-4,5-dihydroxy-2-methyl-8,10-dioxo-3,4,5,6,8,10-hexahydro-2H-1,7-methanopyrido[1,2-b][1,2,5]triazecine-11-carboxamide (10 mg, 0.018 mmol) in dichloromethane (2 mL) was cooled to 0° C. under argon. To it was added Deoxo-fluoro (50% in toluene, 0.02 ml, 0.054 mmol). The resulting mixture was stirred at 0° C. for three hours. The reaction mixture was diluted with dichloromethane, cooled in an ice/water bath and quenched by dropwise addition of saturated aqueous sodium bicarbonate. The resulting mixture was stirred for 20 minutes, added more saturated aqueous sodium bicarbonate until no more bubbling. The organic layer was separated, dried over magnesium sulfate and the solvent removed under reduced pressure. The residue was purified by RP-HPLC eluting with acetonitrile/water (with 0.1% TFA) to afford (1S,2R,4R,5S)-9-(benzyloxy)-N-(2,4-difluorobenzyl)-4,5-difluoro-2-methyl-8,10-dioxo-3,4,5,6,8,10-hexahydro-2H-1,7-methanopyrido[1,2-b][1,2,5]triazecine-11-carboxamide which was dissolved in 0.5 ml of Toluene and 0.5 ml of TFA. The reaction was stirred at room temperature for one hour. The solvent removed under reduced pressure and the residue was purified by RP-HPLC eluting with acetonitrile/water (with 0.1% TFA) to afford the title product. MS (m/z) 469.200 [M+H]$^+$. $^1$H NMR (400 MHz, Acetonitrile-d3) δ 10.32 (s, 1H), 8.33 (s, 1H), 7.43 (q, J=9.1, 8.4 Hz, 1H), 7.00-6.95 (m, 2H), 4.82 (s, 2H), 4.69 (s, OH), 4.60 (d, J=6.0 Hz, 2H), 4.37 (dq, J=8.5, 4.4 Hz, 1H), 4.19 (dd, J=14.2, 7.9 Hz, 1H), 3.45 (t, J=7.3 Hz, 1H), 3.39-3.31 (m, 1H), 2.29-2.06 (m, 2H), 1.20 (d, J=6.5 Hz, 3H).

Example 39: Preparation of (1S,2R,4S,5R)—N-(2,4-difluorobenzyl)-9-hydroxy-4,5-dimethoxy-2-methyl-8,10-dioxo-3,4,5,6,8,10-hexahydro-2H-1,7-methanopyrido[1,2-b][1,2,5]triazecine-11-carboxamide (C39)

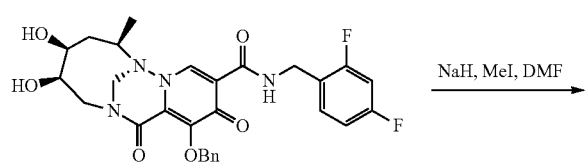

NaH, MeI, DMF

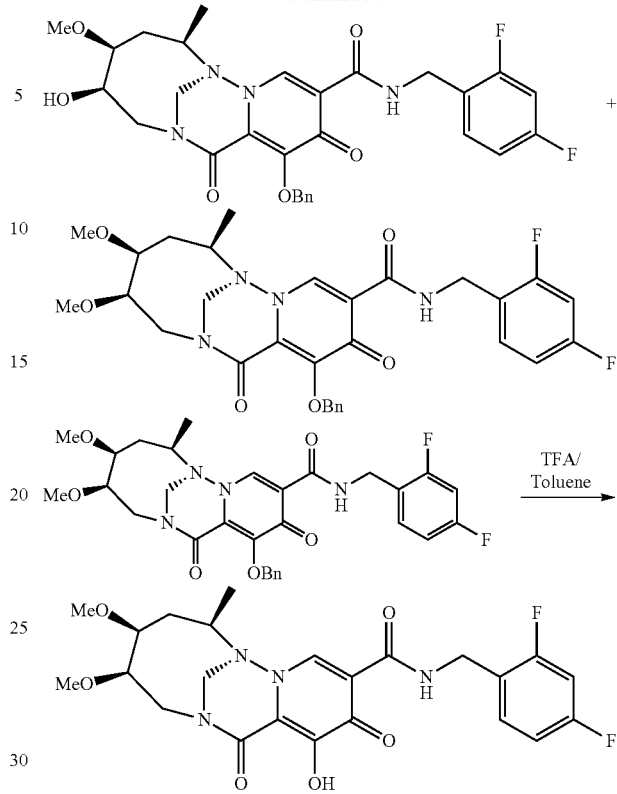

Step 1: Synthesis of (1S,2R,4S,5R)-9-(benzyloxy)-N-(2,4-difluorobenzyl)-5-hydroxy-4-methoxy-2-methyl-8,10-dioxo-3,4,5,6,8,10-hexahydro-2H-1,7-methanopyrido[1,2-b][1,2,5]triazecine-11-carboxamide and (1S,2R,4S,5R)-9-(benzyloxy)-N-(2,4-difluorobenzyl)-4,5-dimethoxy-2-methyl-8,10-dioxo-3,4,5,6,8,10-hexahydro-2H-1,7-methanopyrido[1,2-b][1,2,5]triazecine-11-carboxamide (1S,2R,4S,5R)-9-(benzyloxy)-N-(2,4-difluorobenzyl)-4,5-dihydroxy-2-methyl-8,10-dioxo-3,4,5,6,8,10-hexahydro-2H-1,7-methanopyrido[1,2-b][1,2,5]triazecine-11-carboxamide (40 mg, 0.072 mmol) was dissolved in 2 ml of dry DMF and cooled to 0° C. using ice-water bath. Sodium hydride (3.8 mg of 60 weight % in oil, 0.094 mmol) was added, and the mixture was stirred at 0° C. for 30 minutes. To it was added iodomethane (0.0056 ml, 0.09 mmol), the mixture was stirred at 0° C. for 10 min, quenched the reaction with saturated ammonium chloride aqueous solution and extracted it with ethyl acetate three times. The combined organic extracts were washed with 5% lithium chloride aqueous solution and brine, dried over magnesium sulfate, filtered and concentrated. The residue was purified by silica gel chromatography eluting with ethyl acetate in hexane to afford the title products.

(1S,2R,4S,5R)-9-(benzyloxy)-N-(2,4-difluorobenzyl)-5-hydroxy-4-methoxy-2-methyl-8,10-dioxo-3,4,5,6,8,10-hexahydro-2H-1,7-methanopyrido[1,2-b][1,2,5]triazecine-11-carboxamide: (m/z): 569.300 [M+H]+.

(1S,2R,4S,5R)-9-(benzyloxy)-N-(2,4-difluorobenzyl)-4,5-dimethoxy-2-methyl-8,10-dioxo-3,4,5,6,8,10-hexahydro-2H-1,7-methanopyrido[1,2-b][1,2,5]triazecine-11-carboxamide: (m/z): 583.300 [M+H]+.

Step 2: Synthesis of (1S,2R,4S,5R)—N-(2,4-difluorobenzyl)-9-hydroxy-4,5-dimethoxy-2-methyl-8,10-dioxo-3,4,5,6,8,10-hexahydro-2H-1,7-methanopyrido[1,2-b][1,2,5]triazecine-11-carboxamide (C39)

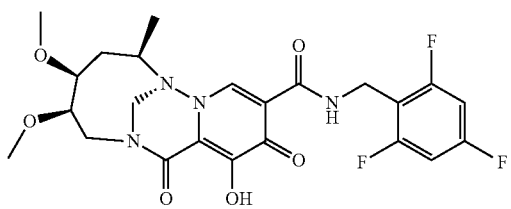

(1S,2R,4S,5R)-9-(benzyloxy)-N-(2,4-difluorobenzyl)-4,5-dimethoxy-2-methyl-8,10-dioxo-3,4,5,6,8,10-hexahydro-2H-1,7-methanopyrido[1,2-b][1,2,5]triazecine-11-carboxamide (10 mg, 0.017 mmol) was dissolved in 0.5 ml of toluene and 0.5 ml of TFA and stirred at room temperature for 20 minutes. The solvent removed under reduced pressure and the residue was purified by RP-HPLC eluting with acetonitrile/water (with 0.1% TFA) to afford the title product. MS (m/z) 493.200 [M+H]$^+$. $^1$H NMR (400 MHz, Acetonitrile-d$_3$) δ 10.37 (s, 1H), 8.32 (s, 1H), 7.49-7.38 (m, 1H), 6.97 (ddt, J=14.4, 8.4, 3.0 Hz, 2H), 4.81 (d, J=15.0 Hz, 1H), 4.59 (d, J=6.2 Hz, 3H), 3.79 (dd, J=7.0, 3.6 Hz, 2H), 3.46-3.37 (m, OH), 3.41 (s, 3H), 3.33 (s, 3H), 3.32 (d, J=13.2 Hz, 1H), 3.19 (d, J=33.1 Hz, 1H), 3.20-3.08 (m, 1H), 2.18 (s, 1H), 1.94 (d, J=2.5 Hz, OH), 1.89-1.74 (m, OH), 1.18 (d, J=6.5 Hz, 3H).

Example 40: Preparation of (1S,2S)—N-(2,4-difluorobenzyl)-9-hydroxy-2-methyl-8,10-dioxo-3,4,5,6,8,10-hexahydro-2H-1,7-methanopyrido[1,2-b][1,2,5]triazecine-11-carboxamide (C40)

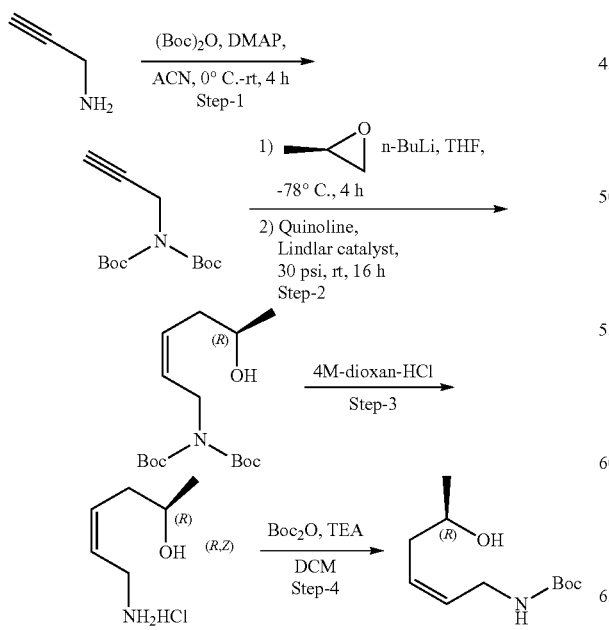

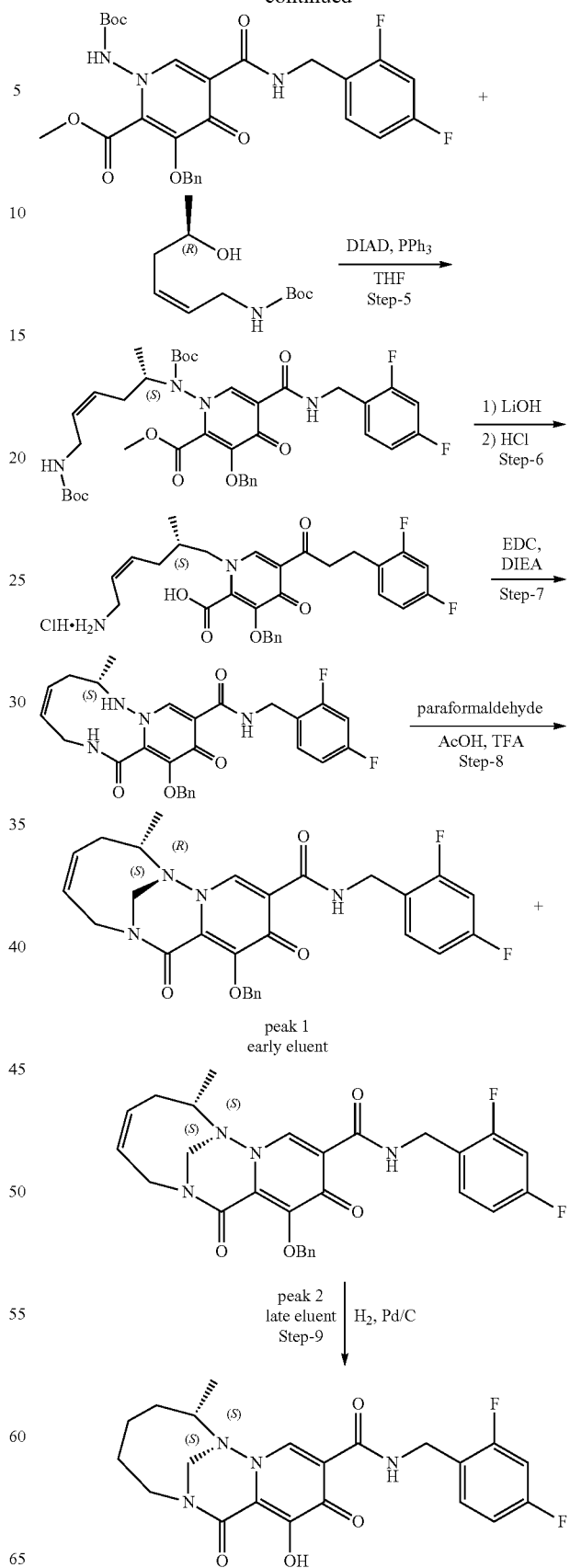

Step 1: Synthesis of tert-butyl (tert-butoxycarbonyl)(prop-2-yn-1-yl)carbamate To a stirred solution of prop-2-yn-1-amine (100 g, 181.65 mmol) in acetonitrile (2 L) was added Di-tert-butyl dicarbonate (991 g, 4541 mmol) followed by DMAP (221.9 g, 181.65 mmol) portion wise at room temperature then stirred for 4 h at room temperature. After completion of the reaction, the reaction mixture was quenched with water and extracted with ethyl acetate. The combined organic layer was washed with brine, dried over $Na_2SO_4$ and evaporated under reduced pressure to obtain crude compound which was purified by silica gel column chromatography eluting with ethyl acetate in hexane to obtain the title product as a colorless liquid. MS (m/z): 256.31[M+H]+.

Step 2: Synthesis of tert-butyl (R,Z)-(tert-butoxycarbonyl)(5-hydroxyhex-2-en-1-yl)carbamate To a stirred solution of tert-butyl (tert-butoxycarbonyl) (prop-2-yn-1-yl)carbamate (100 g, 390.6 mmol) in THF (1 L) was added n-BuLi (1.6 M in hexane, 244.14 ml, 390.6 mmol) dropwise at −78° C. for 30 minutes. To this was added $BF_3$ etherate (119.7 g, 390.6 mmol) followed by a solution of (R)-2-methyloxirane (21.51 g, 390.6 mmol) in THF (0.5 L) dropwise. The reaction mixture was stirred at this temperature for 4 h. After completion, the reaction mixture was quenched with saturated ammonium chloride solution and water. The reaction mixture was extracted with ethyl acetate. The combined organic layer was washed with saturated $NaHCO_3$ solution and brine, dried over $Na_2SO_4$ and evaporated to obtain crude which was purified by silica gel column chromatography eluting with ethyl acetate in hexane to obtain tert-butyl (R)-(tert-butoxycarbonyl)(5-hydroxyhex-2-yn-1-yl)carbamate as a colorless liquid. Took 20 g (63.89 mmol), charged in a parr apparatus, and added 400 ml of ethyl acetate. Lindlar catalyst (4.4 g) was added under inert atmosphere followed by quinoline and hydrogenated under 30 Psi at room temperature for 16 h. After completion, the reaction mixture was filtered through a pad of celite. The celite pad was washed with ethyl acetate. The filtrate was washed with 1N HCl and concentrated under reduced pressure to obtain crude which was purified by silica gel column chromatography eluting with ethyl acetate in hexane to obtain the title product. MS (m/z): 316.29 [M+H]$^+$.

Step 3: Synthesis of (R,Z)-6-aminohex-4-en-2-ol hydrochloride

A solution of tert-butyl (R,Z)-(tert-butoxycarbonyl)(5-hydroxyhex-2-en-1-yl)carbamate (14 g, 44.44 mmol) and 4 M HCl in dioxane (210 ml) was stirred at room temperature for 1 h. After completion, the reaction mixture was concentrated under reduced pressure and crude was washed with diethyl ether, filtered, and dried under vacuum to afford the title product. MS (m/z): 116.3 [M+H]$^+$.

Step 4: Synthesis of tert-butyl (R,Z)-(5-hydroxyhex-2-en-1-yl)carbamate

To a stirred solution of (R,Z)-6-aminohex-4-en-2-ol hydrochloride (2 g, 13.2 mmol) in 30 ml of DCM was added di-tert-butyl dicarbonate (4.3 g, 19.8 mmol) followed by triethylamine (5.52 ml, 39.6 mmol) at room temperature. The reaction mixture was stirred for overnight and concentrated to dryness. The crude compound was purified by silica gel column chromatography eluting with ethyl acetate in hexane to obtain the title product. $^1$H NMR (400 MHz, Chloroform-d) δ 5.59 (dq, J=10.4, 5.4 Hz, 2H), 4.67 (s, 1H), 3.94-3.78 (m, 2H), 3.71 (dd, J=15.0, 5.0 Hz, 1H), 2.44-2.18 (m, 2H), 1.46 (s, 9H), 1.25 (d, J=6.3 Hz, 3H).

Step 5: Synthesis of methyl (S,Z)-3-(benzyloxy)-1-((tert-butoxycarbonyl)(6-((tert-butoxycarbonyl)amino)hex-4-en-2-yl)amino)-5-((2,4-difluorobenzyl)carbamoyl)-4-oxo-1,4-dihydropyridine-2-carboxylate (26E)

Prepared in a manner similar to methyl (R)-3-(benzyloxy)-1-((tert-butoxycarbonyl)(pent-4-en-2-yl)amino)-4-oxo-5-((2,4,6-trifluorobenzyl)carbamoyl)-1,4-dihydropyridine-2-carboxylate (7A) using methyl 3-(benzyloxy)-1-((tert-butoxycarbonyl)amino)-5-((2,4-difluorobenzyl)carbamoyl)-4-oxo-1,4-dihydropyridine-2-carboxylate and tert-butyl (R,Z)-(5-hydroxyhex-2-en-1-yl)carbamate instead of methyl 3-(benzyloxy)-1-((tert-butoxycarbonyl)amino)-4-oxo-5-((2,4,6-trifluorobenzyl)carbamoyl)-1,4-dihydropyridine-2-carboxylate and (2S)-pent-4-en-2-ol. MS (m/z): 741.400 [M+H]$^+$.

Step 6: Synthesis of (S,Z)-1-((6-aminohex-4-en-2-yl)amino)-3-(benzyloxy)-5-((2,4-difluorobenzyl)carbamoyl)-4-oxo-1,4-dihydropyridine-2-carboxylic acid hydrochloride (26F)

To a solution of Methyl (S,Z)-3-(benzyloxy)-1-((tert-butoxycarbonyl)(6-((tert-butoxycarbonyl)amino)hex-4-en-2-yl)amino)-5-((2,4-difluorobenzyl)carbamoyl)-4-oxo-1,4-dihydropyridine-2-carboxylate (5.4 g, 7.29 mmol) in 140 ml of THF/MeOH/$H_2O$ (3/2/1) was added lithium hydroxide (698 mg, 29.2 mmol). The reaction mixture was stirred at 60° C. for 2 hours. LCMS showed high conversion to the carboxylic acid. The reaction mixture was diluted with ethyl acetate, acidified to pH-4 with 1N HCl. Organic layer was washed with brine, dried over sodium sulfate, filtered and concentrated to afford (S,Z)-3-(benzyloxy)-1-((tert-butoxycarbonyl)(6-((tert-butoxycarbonyl)amino)hex-4-en-2-yl)amino)-5-((2,4-difluorobenzyl)carbamoyl)-4-oxo-1,4-dihydropyridine-2-carboxylic acid which was dissolved in 50 ml of DCM, treated with 4N HCl in 1,4-dioxane (7.3 mL) at room temperature for overnight, concentrated to dryness. High vacuum dried to afford the title product. MS (m/z): 527.300 [M+H]$^+$.

Step 7: Synthesis of (S,Z)-9-(benzyloxy)-N-(2,4-difluorobenzyl)-2-methyl-8,10-dioxo-2,3,6,7,8,10-hexahydro-1H-pyrido[1,2-b][1,2,5]triazecine-11-carboxamide (S,Z)-1-((6-aminohex-4-en-2-yl)amino)-3-(benzyloxy)-5-((2,4-difluorobenzyl)carbamoyl)-4-oxo-1,4-dihydropyridine-2-carboxylic acid hydrochloride (5.29 g, 8.8 mmol) was dissolved in 500 ml of DCM. To it was added EDCI·HCl (2.5 g, 13.2 mmol), HOAt (1.8 g, 13.2 mmol) followed by N,N-diisopropylethylamine (7.69 ml, 44.1 mmol). The reaction mixture was stirred at room temperature for 10 minutes, washed with water and brine. The organic layer was separated, dried over magnesium sulfate, filtered and concentrated. The residue was purified by silica gel chromatography eluting with EtOAc/hexane to afford the title product. MS (m/z): 509.300 [M+H]+.

Step 8: Synthesis of (R,2S,Z)-9-(benzyloxy)-N-(2,4-difluorobenzyl)-2-methyl-8,10-dioxo-3,6,8,10-tetrahydro-2H-1,7-methanopyrido[1,2-b][1,2,5]triazecine-11-carboxamide (26H) and (1S,2S,Z)-9-(benzyloxy)-N-(2,4-difluorobenzyl)-2-methyl-8,10-dioxo-3,6,8,10-tetrahydro-2H-1,7-methanopyrido[1,2-b][1,2,5]triazecine-11-carboxamide Prepared in a manner similar to (1S,2R,6S)-9-hydroxy-2,6-dimethyl-8,10-dioxo-N-(2,4,6-trifluorobenzyl) 3,4,5,6,8,10-hexahydro-2H-1,7-methanopyrido[1,2-b][1,2,5]triazecine-11-carboxamide (7F) using (S,Z)-9-(benzyloxy)-N-(2,4-difluorobenzyl)-2-methyl-8,10-dioxo-2,3,6,7,8,10-hexahydro-1H-pyrido[1,2-b][1,2,5]triazecine-11-carboxamide instead of (2R,6S,Z)-9-(benzyloxy)-2,6-dimethyl-8,10-dioxo-N-(2,4,6-trifluorobenzyl)-2,3,6,7,8,10-hexahydro-1H-pyrido[1,2-b][1,2,5]triazecine-11-carboxamide (7E). After silica gel chromatography eluting with ethyl acetate in hexane to afford two products:

Peak 1: (1R,2S,Z)-9-(benzyloxy)-N-(2,4-difluorobenzyl)-2-methyl-8,10-dioxo-3,6,8,10-tetrahydro-2H-1,7-methanopyrido[1,2-b][1,2,5]triazecine-11-carboxamide: MS (m/z): 521.300 [M+H]+.

Peak 2: (1S,2S,Z)-9-(benzyloxy)-N-(2,4-difluorobenzyl)-2-methyl-8,10-dioxo-3,6,8,10-tetrahydro-2H-1,7-methanopyrido[1,2-b][1,2,5]triazecine-11-carboxamide: MS (m/z): 521.300 [M+H]+.

Step 9: Synthesis of (1S,2S)—N-(2,4-difluorobenzyl)-9-hydroxy-2-methyl-8,10-dioxo-3,4,5,6,8,10-hexahydro-2H-1,7-methanopyrido[1,2-b][1,2,5]triazecine-11-carboxamide (C40)

Prepared in a manner similar to (1S,2R,6S)-9-hydroxy-2,6-dimethyl-8,10-dioxo-N-(2,4,6 trifluorobenzyl)-3,4,5,6,8,10-hexahydro-2H-1,7-methanopyrido[1,2-b][1,2,5]triazecine-11 carboxamide (C8) using (1S,2S,Z)-9-(benzyloxy)-N-(2,4-difluorobenzyl)-2-methyl-8,10-dioxo-3,6,8,10-tetrahydro-2H-1,7-methanopyrido[1,2-b][1,2,5]triazecine-11-carboxamide instead of (2R,6S,Z)-9-(benzyloxy)-2,6-dimethyl-8,10-dioxo-N-(2,4,6-trifluorobenzyl) 3,6,8,10-tetrahydro-2H-1,7-methanopyrido[1,2-b][1,2,5]triazecine-11-carboxamide (7F). MS (m/z): 433.200 [M+H]+. $^1$H NMR (400 MHz, Acetonitrile-d$_3$) δ 11.45 (s, 1H), 10.40 (s, 1H), 8.29 (s, 1H), 7.49-7.38 (m, 1H), 7.04-6.91 (m, 2H), 5.12 (d, J=14.1 Hz, 1H), 4.80 (d, J=14.2 Hz, 1H), 4.59 (d, J=5.9 Hz, 2H), 4.21 (dt, J=13.8, 4.7 Hz, 1H), 3.57 (p, J=7.2 Hz, 1H), 3.02 (ddd, J=14.1, 10.1, 4.2 Hz, 1H), 1.97 (p, J=2.5 Hz, 3H), 1.84-1.70 (m, 1H), 1.71-1.54 (m, 2H), 1.50-1.25 (m, 1H), 1.12 (d, J=7.0 Hz, 3H).

Example 41: Preparation of (1S,2S,Z)—N-(2,4-difluorobenzyl)-9-hydroxy-2-methyl-8,10-dioxo-3,6,8,10-tetrahydro-2H-1,7-methanopyrido[1,2-b][1,2,5]triazecine-11-carboxamide (C41)

Prepared in a manner similar to (2R,6S,Z)-9-hydroxy-2,6-dimethyl-8,10-dioxo-N-(2,4,6 trifluorobenzyl)-3,6,8,10-tetrahydro-2H-1,7-methanopyrido[1,2-b][1,2,5]triazecine-11 carboxamide (C7) using (1S,2S,Z)-9-(benzyloxy)-N-(2,4-difluorobenzyl)-2-methyl-8,10-dioxo-3,6,8,10-tetrahydro-2H-1,7-methanopyrido[1,2-b][1,2,5]triazecine-11-carboxamide instead of (1S,2R,6S,Z)-9-(benzyloxy)-2,6-dimethyl-8,10-dioxo-N-(2,4,6-trifluorobenzyl) 3,6,8,10-tetrahydro-2H-1,7-methanopyrido[1,2-b][1,2,5]triazecine-11-carboxamide (7F). MS (m/z): 431.200 [M+H]+. $^1$H NMR (400 MHz, Acetonitrile-d$_3$) δ 10.37 (s, 1H), 8.35 (s, 1H), 7.50-7.39 (m, 1H), 6.97 (ddt, J=12.9, 8.4, 3.0 Hz, 2H), 5.89-5.77 (m, 1H), 5.62 (ddt, J=11.8, 4.3, 1.8 Hz, 1H), 5.14 (d, J=13.8 Hz, 1H), 4.94 (d, J=18.1 Hz, 1H), 4.68-4.57 (m, 3H), 3.55-3.38 (m, 2H), 2.26 (dt, J=16.1, 8.4 Hz, 1H), 1.97-1.86 (m, 1H), 1.15 (d, J=7.0 Hz, 3H).

Example 42: Preparation of (1R,2S)—N-(2,4-difluorobenzyl)-9-hydroxy-2-methyl-8,10-dioxo-3,4,5,6,8,10-hexahydro-2H-1,7-methanopyrido[1,2-b][1,2,5]triazecine-11-carboxamide (C42)

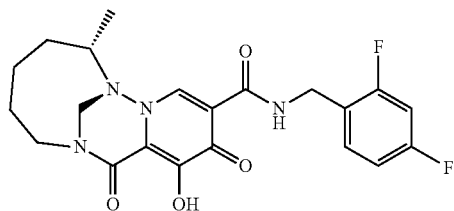

Prepared in a manner similar to (1S,2R,6S)-9-hydroxy-2,6-dimethyl-8,10-dioxo-N-(2,4,6 trifluorobenzyl)-3,4,5,6,8,10-hexahydro-2H-1,7-methanopyrido[1,2-b][1,2,5]triazecine-11 carboxamide (C8) using (1R,2S,Z)-9-(benzyloxy)-N-(2,4-difluorobenzyl)-2-methyl-8,10-dioxo-3,6,8,10-tetrahydro-2H-1,7-methanopyrido[1,2-b][1,2,5]triazecine-11-carboxamide instead of (2R,6S,Z)-9-(benzyloxy)-2,6-dimethyl-8,10-dioxo-N-(2,4,6-trifluorobenzyl) 3,6,8,10-tetrahydro-2H-1,7-methanopyrido[1,2-b][1,2,5]triazecine-11-carboxamide (7F). MS (m/z): 433.200 [M+H]+. $^1$H NMR (400 MHz, Acetonitrile-d3) δ 10.38 (s, 1H), 8.35 (s, 1H), 7.44 (td, J=9.2, 8.8, 6.5 Hz, 1H), 7.03-6.91 (m, 2H), 4.86 (d, J=14.5 Hz, 1H), 4.78 (d, J=14.5 Hz, 1H), 4.60 (d, J=5.8 Hz, 2H), 4.15 (ddd, J=14.1, 7.4, 5.2 Hz, 1H), 3.14-3.02 (m, 2H), 1.96-1.91 (m, 1H), 1.77 (dd, J=16.7, 7.1 Hz, 1H), 1.71-1.57 (m, 1H), 1.45 (q, J=10.3 Hz, 2H), 1.17 (d, J=6.5 Hz, 3H).

Example 43: Preparation of (1R,2S,Z)—N-(2,4-difluorobenzyl)-9-hydroxy-2-methyl-8,10-dioxo-3,6,8,10-tetrahydro-2H-1,7-methanopyrido[1,2-b][1,2,5]triazecine-11-carboxamide (C43)

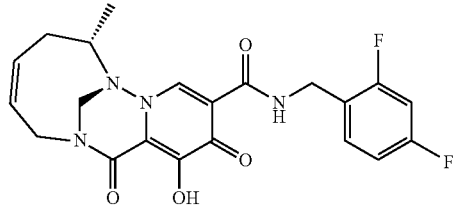

Prepared in a manner similar to (2R,6S,Z)-9-hydroxy-2,6-dimethyl-8,10-dioxo-N-(2,4,6 trifluorobenzyl)-3,6,8,10-tetrahydro-2H-1,7-methanopyrido[1,2-b][1,2,5]triazecine-11 carboxamide (C7) using (1R,2S,Z)-9-(benzyloxy)-N-(2,4-difluorobenzyl)-2-methyl-8,10-dioxo-3,6,8,10-tetrahydro-2H-1,7-methanopyrido[1,2-b][1,2,5]triazecine-11-carboxamide instead of (2R,6S,Z)-9-(benzyloxy)-2,6-dimethyl-8,10-dioxo-N-(2,4,6-trifluorobenzyl) 3,6,8,10-tetrahydro-2H-1,7-methanopyrido[1,2-b][1,2,5]triazecine-11-carboxamide (7F). MS (m/z): 431.200 [M+H]$^+$. $^1$H NMR (400 MHz, Acetonitrile-d$_3$) δ 10.41 (s, 1H), 8.44 (s, 1H), 7.44 (td, J=8.8, 6.5 Hz, 1H), 6.97 (ddt, J=10.8, 8.2, 3.0 Hz, 2H), 5.79-5.63 (m, 2H), 5.00-4.88 (m, 2H), 4.69-4.57 (m, 3H), 3.61 (p, J=6.8 Hz, 1H), 3.58-3.48 (m, 1H), 2.42 (dd, J=15.5, 7.1 Hz, 1H), 2.10 (ddd, J=14.7, 8.4, 5.5 Hz, 1H), 1.29 (d, J=7.1 Hz, 3H).

Example 44: Preparation of (2S,5S)—N-(2,4-difluorobenzyl)-2-(fluoromethyl)-8-hydroxy-5-methyl-7,9-dioxo-2,5,7,9-tetrahydro-1,6-methanopyrido[1,2-b][1,2,5]triazonine-10-carboxamide (C44)

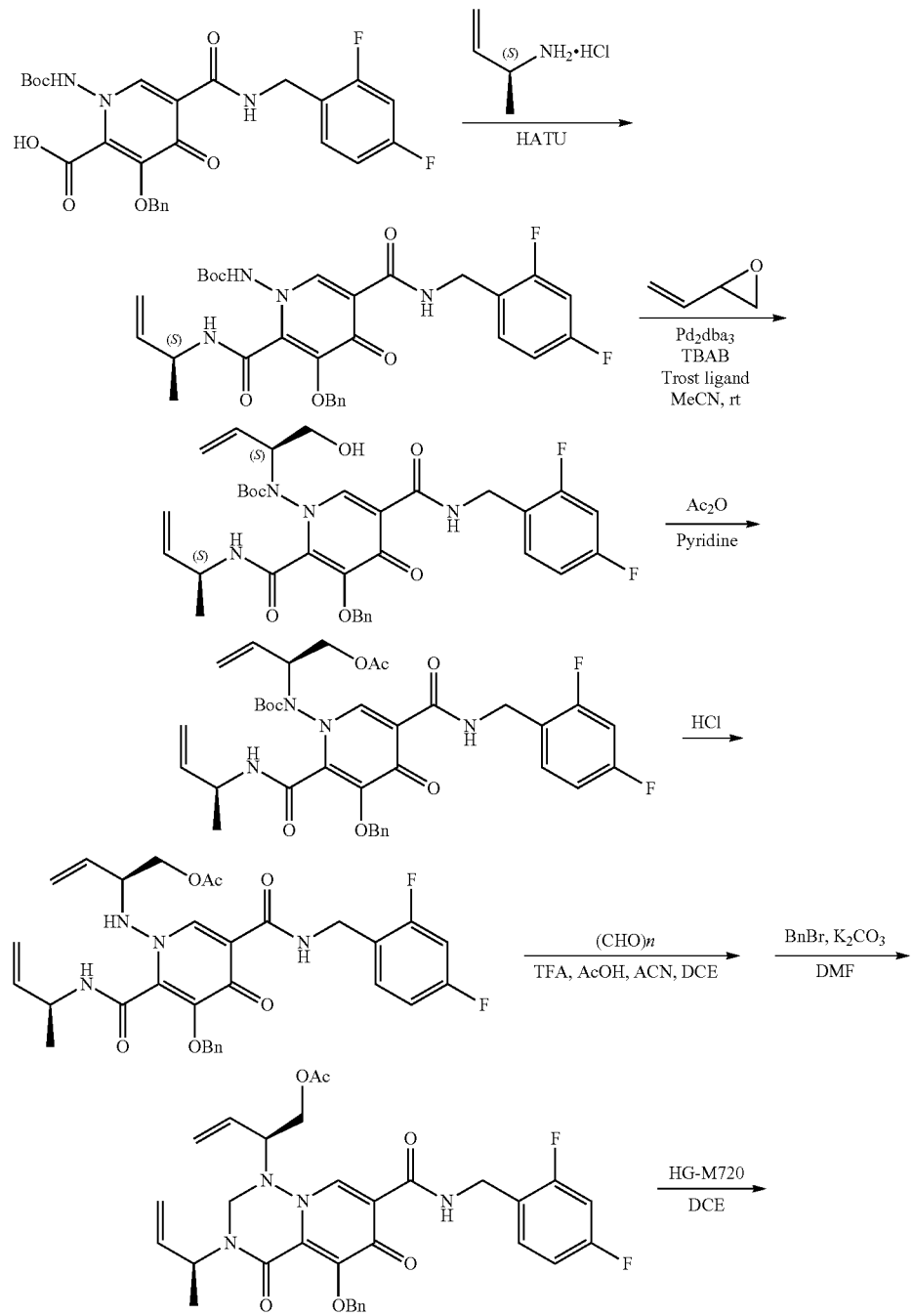

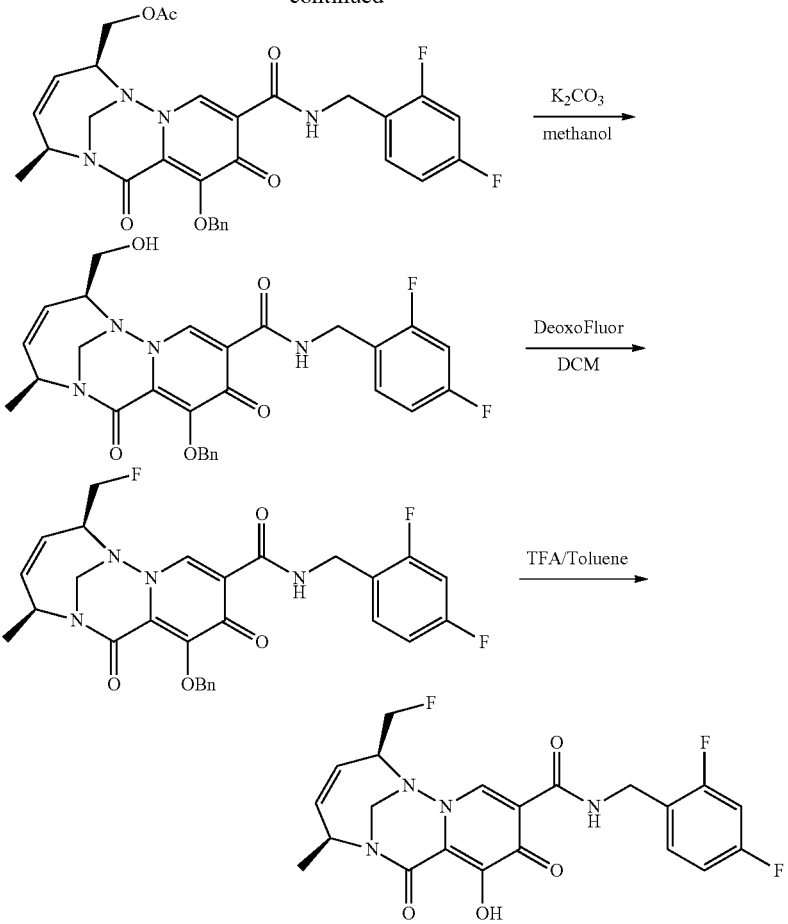

Synthesis of 3-(benzyloxy)-1-((tert-butoxycarbonyl) amino)-5-((2,4-difluorobenzyl)carbamoyl)-4-oxo-1, 4-dihydropyridine-2-carboxylic acid Prepared in a manner similar to 3-(benzyloxy)-1-((tert-butoxycarbonyl)amino)-4-oxo-5-((2,4,6-trifluorobenzyl) carbamoyl)-1,4-dihydropyridine-2-carboxylic acid(12) in example 6 using methyl 3-(benzyloxy)-1-((tert-butoxycarbonyl)amino)-5-((2,4-difluorobenzyl)carbamoyl)-4-oxo-1, 4-dihydropyridine-2-carboxylate instead of methyl 3-(benzyloxy)-1-((tert-butoxycarbonyl)amino)-4-oxo-5-((2,4,6-trifluorobenzyl)carbamoyl)-1,4-dihydropyridine-2-carboxylate. MS (m/z): 530.200[M+H]$^+$.

Synthesis of tert-butyl (S)-(3-(benzyloxy)-2-(but-3-en-2-ylcarbamoyl)-5-((2,4-difluorobenzyl)carbamoyl)-4-oxopyridin-1(4H)-yl)carbamate A reaction mixture of 3-(benzyloxy)-1-((tert-butoxycarbonyl)amino)-5-((2,4-difluorobenzyl)carbamoyl)-4-oxo-1, 4-dihydropyridine-2-carboxylic acid (200 mg, 0.378 mmol), (2S)-but-3-en-2-amine hydrochloride (61 mg, 0.567 mmol), HATU (172 mg, 0.453 mmol) and HOAt (61.7 mg, 0.453 mmol) in 10 ml of DMF was cooled to 0° C. DIPEA (0.2 ml, 1.13 mmol) was added dropwise. The reaction mixture was allowed to stir for 10 minutes, and then poured into water. Extracted it with ethyl acetate three times. Combined organic layers were washed with 5% lithium chloride aqueous solution and brine. The organic layer was dried over MgSO$_4$ and concentrated under vacuum. The residue was purified by silica gel column chromatography. MS (m/z) 583.300 [M+H]$^+$.

Synthesis of tert-butyl (3-(benzyloxy)-2-(((S)-but-3-en-2-yl)carbamoyl)-5-((2,4-difluorobenzyl)carbamoyl)-4-oxopyridin-1(4H)-yl)((S)-1-hydroxybut-3-en-2-yl)carbamate Tert-butyl (S)-(3-(benzyloxy)-2-(but-3-en-2-ylcarbamoyl)-5-((2,4-difluorobenzyl)carbamoyl)-4-oxopyridin-1 (4H)-yl)carbamate (430 mg, 0.738 mmol) and tetrabutyl ammonium bromide (476 mg, 1.48 mmol) was charged to a round bottom flask then acetonitrile (20 ml, degassed immediately prior to use by bubbling through argon) followed by (R,R)-DACH naphthyl Trost ligand (58.4 mg, 0.0738 mmol) and tris(dibenzylideneacetone)dipalladium-chloroform adduct (22.9 mg, 0.0221 mmol). The solution was stirred under argon at room temperature for 20 minutes. Butadiene monoxide (0.149 ml, 1.85 mmol) was added. The reaction mixture was stirred at room temperature for 2 hours. The reactant mixture was concentrated in vacuo and purified by column chromatography eluting with ethyl acetate in hexane to afford the title product. MS (m/z) 653.300 [M+H]$^+$

Synthesis of (S)-2-((3-(benzyloxy)-2-(((S)-but-3-en-2-yl)carbamoyl)-5-((2,4-difluorobenzyl)carbamoyl)-4-oxopyridin-1(4H)-yl)(tert-butoxycarbonyl)amino)but-3-en-1-yl acetate Tert-butyl (3-(benzyloxy)-2-(((S)-but-3-en-2-yl)carbamoyl)-5-((2,4-difluorobenzyl)carbamoyl)-4-oxopyridin-1 (4H)-yl)((S)-1-hydroxybut-3-en-2-yl)carbamate (280 mg, 0.429 mmol) was dissolved in 14 ml of pyridine. To it was added DMAP (105 mg, 0.858 mmol) and acetic anhydride (0.40 ml, 4.29 mmol). The reaction was heated to 60° C. for 2 days, cooled to room temperature, and concentrated to dryness. The reaction mixture was partitioned between ethyl acetate and 1N HCl, washed organic phase with more 1N HCl, then saturated aqueous NaHCO$_3$ and brine. Dried organic phase over MgSO$_4$, filtered and concentrated in vacuo. Purified by Silica gel column chromatography eluting with ethyl acetate in hexane to afford the title product. MS (m/z) 695.400 [M+H]$^+$.

Synthesis of (S)-2-((3-(benzyloxy)-2-(((S)-but-3-en-2-yl)carbamoyl)-5-((2,4-difluorobenzyl)carbamoyl)-4-oxopyridin-1(4H)-yl)amino)but-3-en-1-yl acetate (S)-2-((3-(benzyloxy)-2-(((S)-but-3-en-2-yl)carbamoyl)-5-((2,4-difluorobenzyl)carbamoyl)-4-oxopyridin-1(4H)-yl)(tert-butoxycarbonyl)amino)but-3-en-1-yl acetate (202 mg, 0.29 mmol) was dissolved in 4 ml of DCM, to it was added hydrogen chloride, 4.0 M solution in 1,4-dioxane (0.73 ml, 2.9 mmol). It was stirred at room temperature for 2 hours. The reaction mixture was concentrated in vacuo and high vacuum dried to afford the title product. MS (m/z) 595.300 [M+H]$^+$.

Synthesis of (S)-2-(5-(benzyloxy)-3-((S)-but-3-en-2-yl)-7-((2,4-difluorobenzyl)carbamoyl)-4,6-dioxo-2,3,4,6-tetrahydro-1H-pyrido[2,1-f][1,2,4]triazin-1-yl)but-3-en-1-yl acetate Prepared in a manner similar to 5-(benzyloxy)-3-((S)-but-3-en-2-yl)-1-(but-3-en-2-yl)-4,6-dioxo-N-(2,4,6-trifluorobenzyl)-2,3,4,6-tetrahydro-1H-pyrido[2,1-f][1,2,4]triazine-7-carboxamide in example 24 using (S)-2-((3-(benzyloxy)-2-(((S)-but-3-en-2-yl)carbamoyl)-5-((2,4-difluorobenzyl)carbamoyl)-4-oxopyridin-1(4H)-yl)amino)but-3-en-1-yl acetate instead of 3-(Benzyloxy)-N2-((S)-but-3-en-2-yl)-1-(but-3-en-2-ylamino)-4-oxo-N5-(2,4,6-trifluorobenzyl)-1,4-dihydropyridine-2,5-dicarboxamide. MS (m/z) 607.300 [M+H]$^+$.

Synthesis of ((2S,5S)-8-(benzyloxy)-10-((2,4-difluorobenzyl)carbamoyl)-5-methyl-7,9-dioxo-2,5,7,9-tetrahydro-1,6-methanopyrido[1,2-b][1,2,5]triazonin-2-yl)methyl acetate Prepared in a manner similar to (1R,2R,5S)-8-(benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide in example 24 using (S)-2-(5-(benzyloxy)-3-((S)-but-3-en-2-yl)-7-((2,4-difluorobenzyl)carbamoyl)-4,6-dioxo-2,3,4,6-tetrahydro-1H-pyrido[2,1-f][1,2,4]triazin-1-yl)but-3-en-1-yl acetate instead of 5-(Benzyloxy)-3-((S)-but-3-en-2-yl)-1-(but-3-en-2-yl)-4,6-dioxo-N-(2,4,6-trifluorobenzyl)-2,3,4,6-tetrahydro-1H-pyrido[2,1-f][1,2,4]triazine-7-carboxamide. MS (m/z) 579.300 [M+H]$^+$.

Synthesis of (2S,5S)-8-(benzyloxy)-N-(2,4-difluorobenzyl)-2-(hydroxymethyl)-5-methyl-7,9-dioxo-2,5,7,9-tetrahydro-1,6-methanopyrido[1,2-b][1,2,5]triazonine-10-carboxamide ((2S,5S)-8-(benzyloxy)-10-((2,4-difluorobenzyl)carbamoyl)-5-methyl-7,9-dioxo-2,5,7,9-tetrahydro-1,6-methanopyrido[1,2-b][1,2,5]triazonin-2-yl)methyl acetate (46 mg, 0.79 mmol) was dissolved in 2 ml of methanol. To it was added potassium carbonate (22 mg, 0.16 mmol). The reaction was stirred at room temperature for 10 minutes, then partitioned between ethyl acetate and water. The organic layer was separated, washed with brine, dried over MgSO$_4$ and concentrated to dryness to afford the title product. MS (m/z) 537.300 [M+H]$^+$.

Synthesis of (2S,5S)-8-(benzyloxy)-N-(2,4-difluorobenzyl)-2-(fluoromethyl)-5-methyl-7,9-dioxo-2,5,7,9-tetrahydro-1,6-methanopyrido[1,2-b][1,2,5]triazonine-10-carboxamide (2S,5S)-8-(benzyloxy)-N-(2,4-difluorobenzyl)-2-(hydroxymethyl)-5-methyl-7,9-dioxo-2,5,7,9-tetrahydro-1,6-methanopyrido[1,2-b][1,2,5]triazonine-10-carboxamide (xxH, 15 mg, 0.028 mmol) in DCM (2 mL) was cooled at 0° C. under argon. to it was added Deoxo-fluro (50% in toluene, 0.031 ml, 0.084 mmol). The resulting mixture was stirred at 0° C. for 2 h. The reaction mixture was diluted with DCM, cooled in an ice/water bath and quenched by dropwise addition of saturated aqueous NaHCO$_3$. The resulting mixture was stirred for 20 min, added more saturated aqueous NaHCO$_3$ and stirred for 10 min until no more bubbling. The organic layer was separated, dried over Na$_2$SO$_4$ and the solvent removed under reduced pressure. The residue was purified by silica gel chromatography eluting with EtOAc/hexane to afford the title product. MS (m/z) 539.200 [M+H]$^+$.

Synthesis of (2S,5S)—N-(2,4-difluorobenzyl)-2-(fluoromethyl)-8-hydroxy-5-methyl-7,9-dioxo-2,5,7,9-tetrahydro-1,6-methanopyrido[1,2-b][1,2,5]triazonine-10-carboxamide (C44)

(2S,5S)-8-(benzyloxy)-N-(2,4-difluorobenzyl)-2-(fluoromethyl)-5-methyl-7,9-dioxo-2,5,7,9-tetrahydro-1,6-methanopyrido[1,2-b][1,2,5]triazonine-10-carboxamide (11 mg, 0.02 mmol) was dissolved in 0.5 ml of toluene and 0.5 ml of TFA and stirred at room temperature for 3 hours. The solvent removed under reduced pressure and the residue was purified by RP-HPLC eluting with acetonitrile/water (with 0.1% TFA) to afford the title product. MS (m/z) 449.200 [M+H]$^+$. $^1$H NMR (400 MHz, Acetonitrile-d$_3$) δ 10.19 (s, 1H), 8.47 (s, 1H), 7.44 (td, J=9.2, 8.7, 6.4 Hz, 1H), 6.97 (ddt, J=11.1, 8.5, 3.0 Hz, 2H), 5.83 (dt, J=11.8, 2.7 Hz, 1H), 5.39 (ddt, J=14.5, 12.0, 2.9 Hz, 2H), 4.96 (d, J=14.4 Hz, 1H), 4.70-4.57 (m, 4H), 4.52 (d, J=5.5 Hz, 1H), 4.10 (ddq, J=20.0, 5.7, 2.9 Hz, 1H), 1.36 (d, J=7.3 Hz, 3H).

Example 45: Preparation of (1S,2S,5S)—N-(2,4-difluorobenzyl)-2-(fluoromethyl)-8-hydroxy-5-methyl-7,9-dioxo-2,3,4,5,7,9-hexahydro-1,6-methanopyrido[1,2-b][1,2,5]triazonine-10-carboxamide (C45)

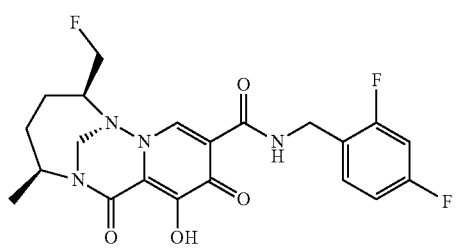

(1S,2S,5S)-8-(benzyloxy)-N-(2,4-difluorobenzyl)-2-(fluoromethyl)-5-methyl-7,9-dioxo-2,5,7,9-tetrahydro-1,6-methanopyrido[1,2-b][1,2,5]triazonine-10-carboxamide (10 mg, 0.19 mmol) was dissolved in 3 ml of ethanol and 3 ml of ethyl acetate, and was sparged under an argon atmosphere. Palladium on carbon (10 wt %, wet) E101 NE/W (2 mg) was added and the mixture was sparged under a hydrogen atmosphere (1 atm, balloon). The mixture was stirred vigorously for one hour and then sparged under an argon atmosphere. It was filtered through a pad of Celite®. The Celite® was washed with absolute ethanol and the filtrate was concentrated to dryness. the residue was purified by RP-HPLC to afford the title product. MS (m/z) 451.200 [M+H]+. 1H NMR (400 MHz, Acetonitrile-d3) δ 10.31 (s, 1H), 8.41 (s, 1H), 7.44 (td, J=9.2, 8.7, 6.3 Hz, 1H), 7.03-6.91 (m, 2H), 5.05-4.26 (m, 7H), 3.62-3.51 (m, 1H), 2.13-2.00 (m, 1H), 1.84 (ddd, J=15.6, 8.0, 4.1 Hz, 1H), 1.77-1.57 (m, 2H), 1.26 (d, J=6.8 Hz, 3H).

Example 46: Preparation of (1R,2R,5S)-8-hydroxy-2-methoxy-5-methyl-7,9-dioxo-N-(2,4,6-trifluorobenzyl)-2,5,7,9-tetrahydro-1,6-methanopyrido[1,2-b][1,2,5]triazonine-10-carboxamide (C46)

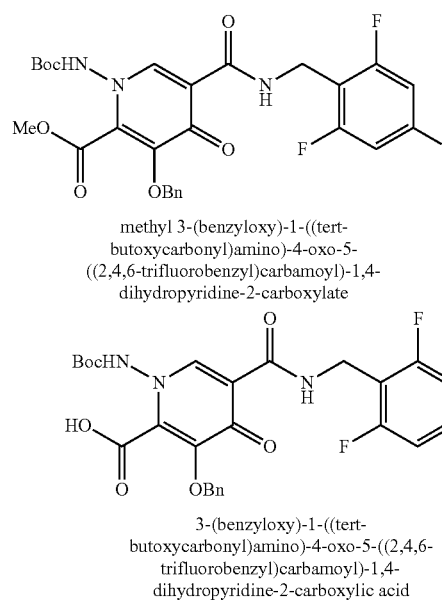

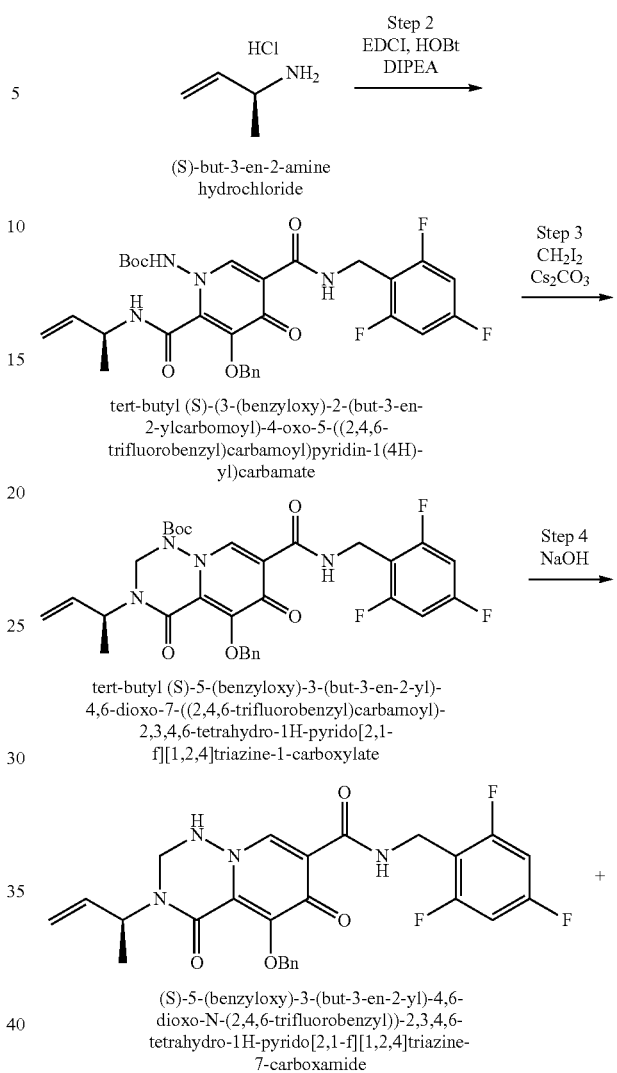

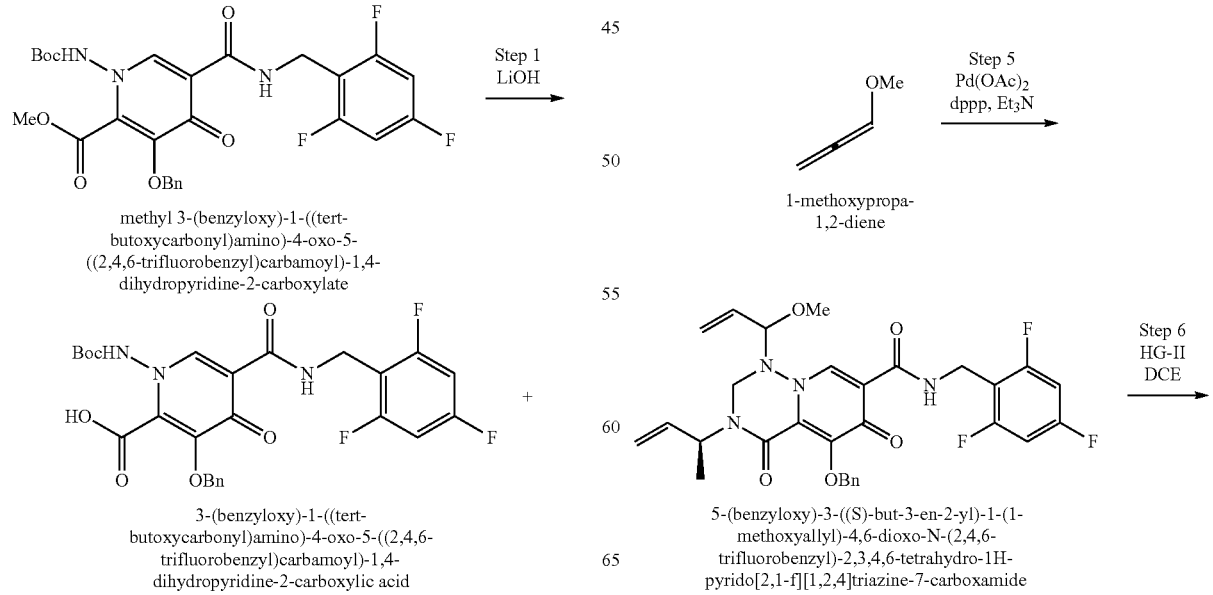

-continued

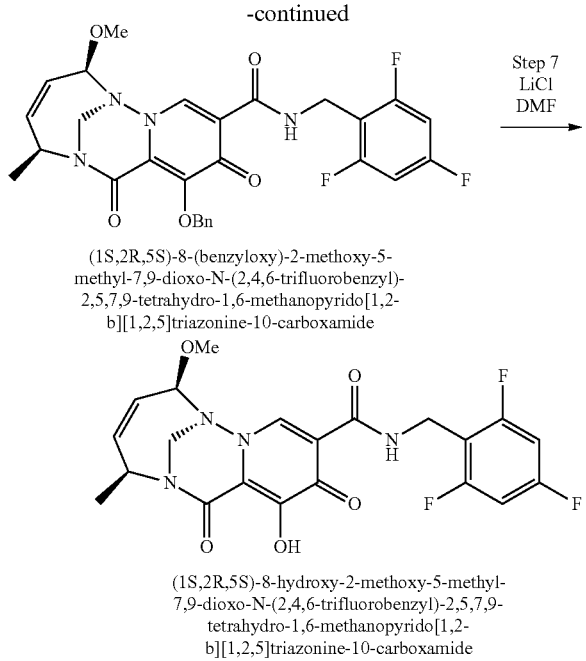

(1S,2R,5S)-8-(benzyloxy)-2-methoxy-5-methyl-7,9-dioxo-N-(2,4,6-trifluorobenzyl)-2,5,7,9-tetrahydro-1,6-methanopyrido[1,2-b][1,2,5]triazonine-10-carboxamide Step 7
LiCl
DMF (1S,2R,5S)-8-hydroxy-2-methoxy-5-methyl-7,9-dioxo-N-(2,4,6-trifluorobenzyl)-2,5,7,9-tetrahydro-1,6-methanopyrido[1,2-b][1,2,5]triazonine-10-carboxamide

Step 1: Synthesis of 3-(benzyloxy)-1-((tert-butoxycarbonyl)amino)-4-oxo-5-((2,4,6-trifluorobenzyl)carbamoyl)-1,4-dihydropyridine-2-carboxylic acid To a suspension of methyl 3-(benzyloxy)-1-((tert-butoxycarbonyl)amino)-4-oxo-5-((2,4,6-trifluorobenzyl)carbamoyl)-1,4-dihydropyridine-2-carboxylate (10.0 g, 17.8 mmol, 1 equiv.), prepared according to Example 24, step 3, in methanol (200 mL) and water (100 mL) was added lithium hydroxide monohydrate (5.979 g, 142 mmol, 8 equiv.). The reaction mixture was heated to 50° C. for 18 h, diluted with water, and acidified with 1N HCl (aq). The slurry was extracted with EtOAc (2×) and the combined organic phase was washed with brine, dried over Na$_2$SO$_4$, filtered, and concentrated to afford 3-(benzyloxy)-1-((tert-butoxycarbonyl)amino)-4-oxo-5-((2,4,6-trifluorobenzyl)carbamoyl)-1,4-dihydropyridine-2-carboxylic acid. MS (m/z) 547.82 [M+H]$^+$.

Step 2: Synthesis of tert-butyl (S)-(3-(benzyloxy)-2-(but-3-en-2-ylcarbamoyl)-4-oxo-5-((2,4,6-trifluorobenzyl)carbamoyl)pyridin-1(4H)-yl)carbamate To a solution of 3-(benzyloxy)-1-((tert-butoxycarbonyl)amino)-4-oxo-5-((2,4,6-trifluorobenzyl)carbamoyl)-1,4-dihydropyridine-2-carboxylic acid (6.00 g, 11.0 mmol, 1 equiv.), (S)-but-3-en-2-amine hydrochloride (1.769 g, 16.4 mmol, 1.5 equiv.), and HOBt (2.221 g, 16.4 mmol, 1.5 equiv.) in CH$_2$Cl$_2$ (120 mL) at 0° C. was added DIPEA (9.54 mL, 54.8 mmol, 5 equiv.) and EDCI (3.151 g, 16.4 mmol, 1.5 equiv.). The reaction mixture was warmed to rt and left to stir for 18 h. The reaction mixture was quenched with water and 1 M HCl and extracted with CH$_2$Cl$_2$ (3×). The combined organic phase was dried over N$_{a2}$SO$_4$, filtered, and concentrated. The crude residue was purified by column chromatography (0-100% EtOAc/hexanes) and concentrated to afford tert-butyl (S)-(3-(benzyloxy)-2-(but-3-en-2-ylcarbamoyl)-4-oxo-5-((2,4,6-trifluorobenzyl)carbamoyl)pyridin-1(4H)-yl)carbamate. MS (m/z) 600.90 [M+H]$^+$.

Step 3: Synthesis of tert-butyl (S)-5-(benzyloxy)-3-(but-3-en-2-yl)-4,6-dioxo-7-((2,4,6-trifluorobenzyl)carbamoyl)-2,3,4,6-tetrahydro-1H-pyrido[2,1-f][1,2,4]triazine-1-carboxylate To a suspension of tert-butyl (S)-(3-(benzyloxy)-2-(but-3-en-2-ylcarbamoyl)-4-oxo-5-((2,4,6-trifluorobenzyl)carbamoyl)pyridin-1(4H)-yl)carbamate (2.20 g, 3.66 mmol, 1 equiv.) and cesium carbonate (4.77 g, 14.7 mmol, 4 equiv.) in MeCN (55 mL) was added diiodomethane (0.59 mL, 7.33 mmol, 2 equiv.). The reaction mixture was heated to 70° C. for 8 h and quenched with NH$_4$Cl (aq). The mixture was extracted with EtOAc (2×) and the combined organic phase was dried over Na$_2$SO$_4$, filtered, and concentrated. The residue was purified by column chromatography (0-100% EtOAc/hexanes) to afford tert-butyl (S)-5-(benzyloxy)-3-(but-3-en-2-yl)-4,6-dioxo-7-((2,4,6-trifluorobenzyl)carbamoyl)-2,3,4,6-tetrahydro-1H-pyrido[2,1-f][1,2,4]triazine-1-carboxylate. MS (m/z) 612.79 [M+H]$^+$.

Step 4: Synthesis of (S)-5-(benzyloxy)-3-(but-3-en-2-yl)-4,6-dioxo-N-(2,4,6-trifluorobenzyl)-2,3,4,6-tetrahydro-1H-pyrido[2,1-f][1,2,4]triazine-7-carboxamide To a solution of tert-butyl (S)-5-(benzyloxy)-3-(but-3-en-2-yl)-4,6-dioxo-7-((2,4,6-trifluorobenzyl)carbamoyl)-2,3,4,6-tetrahydro-1H-pyrido[2,1-f][1,2,4]triazine-1-carboxylate (2.00 g, 3.26 mmol, 1 equiv.) in methanol (55 mL) was added 2N aqueous NaOH (2.45 mL, 4.90 mmol, 1.5 equiv.). The reaction mixture was heated to 40° C. for 1 h, quenched with 10% citric acid solution, and diluted with CH$_2$Cl$_2$. The phases were separated, and the aqueous phase was extracted with CH$_2$Cl$_2$. The combined organic phase was dried over Na$_2$SO$_4$, filtered, and concentrated. The residue was suspended in 1:1 EtOAc/hexanes and the precipitate was collected by filtration to afford (S)-5-(benzyloxy)-3-(but-3-en-2-yl)-4,6-dioxo-N-(2,4,6-trifluorobenzyl)-2,3,4,6-tetrahydro-1H-pyrido[2,1-f][1,2,4]triazine-7-carboxamide. MS (m/z) 512.96 [M+H]$^+$.

Step 5: Synthesis of 5-(benzyloxy)-3-((S)-but-3-en-2-yl)-1-(1-methoxyallyl)-4,6-dioxo-N-(2,4,6-trifluorobenzyl)-2,3,4,6-tetrahydro-1H-pyrido[2,1-f][1,2,4]triazine-7-carboxamide To a solution of (S)-5-(benzyloxy)-3-(but-3-en-2-yl)-4,6-dioxo-N-(2,4,6-trifluorobenzyl)-2,3,4,6-tetrahydro-1H-pyrido[2,1-f][1,2,4]triazine-7-carboxamide (0.122 g, 0.237 mmol, 1 equiv.) in acetonitrile (5 mL) was added Pd(OAc)$_2$ (0.0027 g, 0.012 mmol, 0.05 equiv.), 1,3-bis(diphenylphosphino)propane (dppp) (0.0049 g, 0.012 mmol, 0.05 equiv.), triethylamine (0.050 mL, 0.356 mmol, 1.5 equiv.), and methoxyallene (0.100 mL, 1.19 mmol, 5 equiv.). The reaction mixture was heated to 100° C. for 20 min. Water and brine were added and the aqueous phase was extracted with EtOAc (2×). The combined organic phase was dried over Na$_2$SO$_4$, filtered, and concentrated. The residue was purified by column chromatography (0-100% EtOAc/hexanes) to provide 5-(benzyloxy)-3-((S)-but-3-en-2-yl)-1-(1-methoxyallyl)-4,6-dioxo-N-(2,4,6-trifluorobenzyl)-2,3,4,6-tetrahydro-1H-pyrido[2,1-f][1,2,4]triazine-7-carboxamide. MS (m/z) 583.00 [M+H]$^+$.

Step 6: Synthesis of (R,2R,5S)-8-(benzyloxy)-2-methoxy-5-methyl-7,9-dioxo-N-(2,4,6-trifluorobenzyl)-2,5,7,9-tetrahydro-1,6-methanopyrido[1,2-b][1,2,5]triazonine-10-carboxamide To a solution of 5-(benzyloxy)-3-((S)-but-3-en-2-yl)-1-(1-methoxyallyl)-4,6-dioxo-N-(2,4,6-trifluorobenzyl)-2,3,4, 6-tetrahydro-1H-pyrido[2,1-f][1,2,4]triazine-7-carboxamide (0.112 g, 0.192 mmol, 1 equiv.) in 1,2-dichloroethane (5 mL) was added Hoveyda-Grubbs II catalyst (0.024 g, 0.038 mmol, 0.2 equiv.). The reaction mixture was heated to 70° C. for 24 h and concentrated. The residue was purified by preparative HPLC (column, Gemini 10p C18 110A, AXI/; 250×21.2 mm) eluting 5-100% acetonitrile (0.1% TFA) in water (0.1% TFA) over 20 minutes. Combined fractions were lyophilized to afford (1R,2R,5S)-8-(benzyloxy)-2-methoxy-5-methyl-7,9-dioxo-N-(2,4,6-trifluorobenzyl)-2,5,7,9-tetrahydro-1,6-methanopyrido[1,2-b][1,2,5]triazonine-10-carboxamide. MS (m/z) 554.98.

Step 7: Synthesis of (1R,2R,5S)-8-hydroxy-2-methoxy-5-methyl-7,9-dioxo-N-(2,4,6-trifluorobenzyl)-2,5,7,9-tetrahydro-1,6-methanopyrido[1,2-b][1,2,5]triazonine-10-carboxamide (C46)

To a solution of (1R,2R,5S)-8-(benzyloxy)-2-methoxy-5-methyl-7,9-dioxo-N-(2,4,6-trifluorobenzyl)-2,5,7,9-tetrahydro-1,6-methanopyrido[1,2-b][1,2,5]triazonine-10-carboxamide (0.0455 g, 0.0821 mmol, 1 equiv.) in DMF (2 mL) was added lithium chloride (0.0348 g, 0.821 mmol, 10 equiv.). The reaction mixture was heated to 100° C. for 1 h and filtered. The filtrate was purified by preparative HPLC (column, Gemini 10μ C18 110A, AXI/; 250×21.2 mm) eluting 5-100% acetonitrile (0.1% TFA) in water (0.1% TFA) over 20 minutes. Combined fractions were lyophilized to afford (1R,2R,5S)-8-hydroxy-2-methoxy-5-methyl-7,9-dioxo-N-(2,4,6-trifluorobenzyl)-2,5,7,9-tetrahydro-1,6-methanopyrido[1,2-b][1,2,5]triazonine-10-carboxamide. MS (m/z) 465.02 [M+H]$^+$. $^1$H NMR (400 MHz, DMSO-$d_6$) δ 10.31 (t, J=5.8 Hz, 1H), 8.21 (s, 1H), 7.20 (t, J=8.6 Hz, 2H), 5.76 (dt, J=12.1, 2.3 Hz, 1H), 5.55 (dt, J=12.0, 2.4 Hz, 1H), 5.29-5.17 (m, 2H), 5.06 (d, J=14.6 Hz, 1H), 4.75 (d, J=14.6 Hz, 1H), 4.57 (d, J=5.8 Hz, 2H), 3.39 (s, 3H), 1.28 (d, J=7.2 Hz, 3H). $^{19}$F NMR (376 MHz, DMSO-$d_6$) δ−109.25 (ddd, J=15.5, 9.3, 6.2 Hz), −112.45-−112.69 (m).

Example 47: Preparation of (1R,2R,5S)-8-hydroxy-2-methoxy-5-methyl-7,9-dioxo-N-(2,4,6-trifluorobenzyl)-2,3,4,5,7,9-hexahydro-1,6-methanopyrido[1,2-b][1,2,5]triazonine-10-carboxamide (C47)

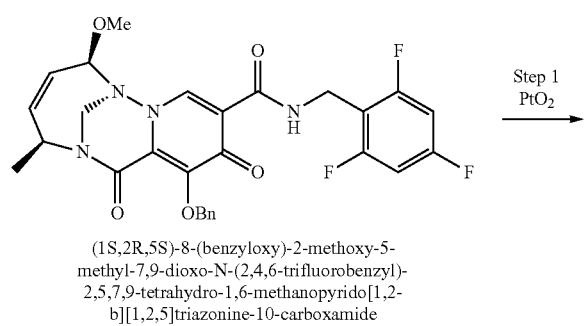

(1S,2R,5S)-8-(benzyloxy)-2-methoxy-5-methyl-7,9-dioxo-N-(2,4,6-trifluorobenzyl)-2,5,7,9-tetrahydro-1,6-methanopyrido[1,2-b][1,2,5]triazonine-10-carboxamide Step 1
PtO₂
→

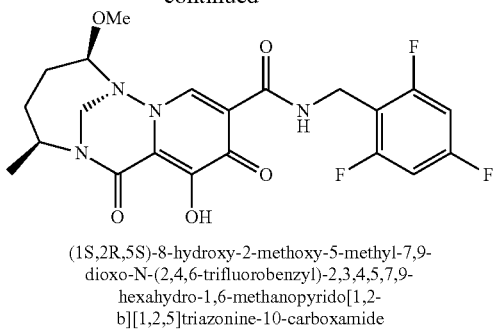

(1S,2R,5S)-8-hydroxy-2-methoxy-5-methyl-7,9-dioxo-N-(2,4,6-trifluorobenzyl)-2,3,4,5,7,9-hexahydro-1,6-methanopyrido[1,2-b][1,2,5]triazonine-10-carboxamide Step 1: Synthesis of (1R,2R,5S)-8-hydroxy-2-methoxy-5-methyl-7,9-dioxo-N-(2,4,6-trifluorobenzyl)-2,3,4,5,7,9-hexahydro-1,6-methanopyrido[1,2-b][1,2,5]triazonine-10-carboxamide)

To a solution of (1R,2R,5S)-8-(benzyloxy)-2-methoxy-5-methyl-7,9-dioxo-N-(2,4,6-trifluorobenzyl)-2,5,7,9-tetrahydro-1,6-methanopyrido[1,2-b][1,2,5]triazonine-10-carboxamide (0.008 g, 0.0144 mmol, 1 equiv.), prepared according to Example 46, in methanol (1 mL) was added platinum(IV) oxide (0.0003 g, 0.0014 equiv. 0.1 equiv). The reaction mixture was evacuated and backfilled with hydrogen gas (2×), sparged with hydrogen gas for 5 min, and left to stir under hydrogen balloon atmosphere for 1 h. The reaction mixture was filtered, concentrated, and purified by preparative HPLC (column, Gemini 10μ C18 110A, AXI/; 250×21.2 mm) eluting 5-100% acetonitrile (0.1% TFA) in water (0.1% TFA) over 20 minutes. Combined fractions were lyophilized to afford (1R,2R,5S)-8-hydroxy-2-methoxy-5-methyl-7,9-dioxo-N-(2,4,6-trifluorobenzyl)-2,3,4,5,7,9-hexahydro-1,6-methanopyrido[1,2-b][1,2,5]triazonine-10-carboxamide. MS (m/z) 467.07 [M+H]$^+$. $^1$H NMR (400 MHz, DMSO-$d_6$) δ 10.37 (t, J=5.9 Hz, 1H), 8.25 (s, 1H), 7.20 (t, J=8.6 Hz, 2H), 4.69-4.59 (m, 2H), 4.59-4.49 (m, 2H), 4.45 (s, 1H), 4.44-4.35 (m, 1H), 3.53 (s, 3H), 1.91-1.72 (m, 3H), 1.34-1.22 (m, 1H), 1.17 (d, J=6.7 Hz, 3H). $^{19}$F NMR (376 MHz, DMSO-$d_6$) δ−109.32 (ddd, J=15.5, 9.4, 6.4 Hz), −112.55 (t, J=7.2 Hz).

Example 48: Preparation of (1S,5S)-8-hydroxy-2,2,5-trimethyl-7,9-dioxo-N-(2,4,6-trifluorobenzyl)-2,5,7,9-tetrahydro-1,6-methanopyrido[1,2-b][1,2,5]triazonine-10-carboxamide (C48)

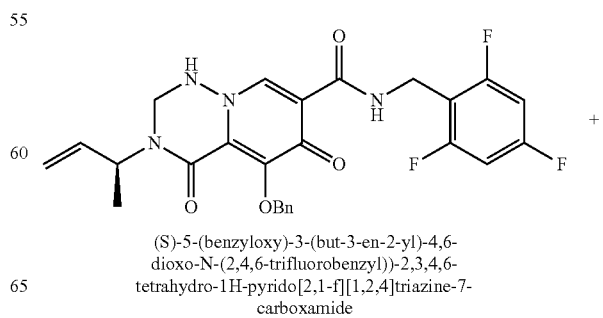

(S)-5-(benzyloxy)-3-(but-3-en-2-yl)-4,6-dioxo-N-(2,4,6-trifluorobenzyl))-2,3,4,6-tetrahydro-1H-pyrido[2,1-f][1,2,4]triazine-7-carboxamide

+

-continued

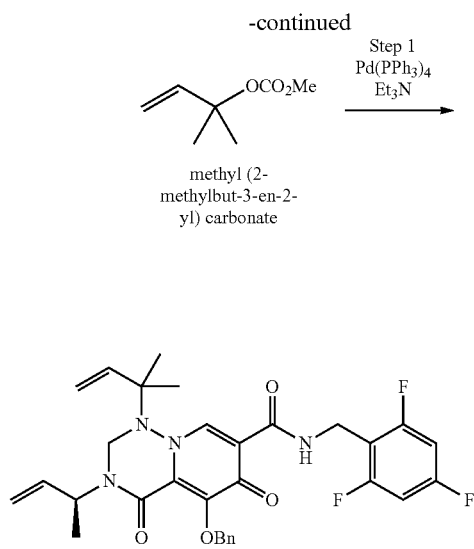

methyl (2-methylbut-3-en-2-yl) carbonate

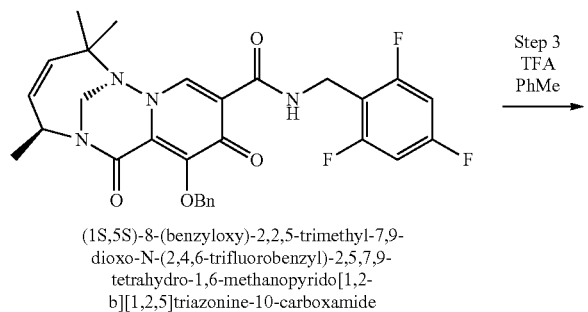

(S)-5-(benzyloxy)-3-(but-3-en-2-yl)-1-(2-methylbut-3-en-2-yl)-4,6-dioxo-N-(2,4,6-trifluorobenzyl)-2,3,4,6-tetrahydro-1H-pyrido[2,1-f][1,2,4]triazine-7-carboxamide

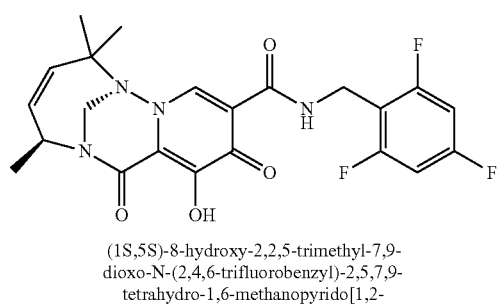

(1S,5S)-8-(benzyloxy)-2,2,5-trimethyl-7,9-dioxo-N-(2,4,6-trifluorobenzyl)-2,5,7,9-tetrahydro-1,6-methanopyrido[1,2-b][1,2,5]triazonine-10-carboxamide (1S,5S)-8-hydroxy-2,2,5-trimethyl-7,9-dioxo-N-(2,4,6-trifluorobenzyl)-2,5,7,9-tetrahydro-1,6-methanopyrido[1,2-b][1,2,5]triazonine-10-carboxamide Step 1: Synthesis of (S)-5-(benzyloxy)-3-(but-3-en-2-yl)-1-(2-methylbut-3-en-2-yl)-4,6-dioxo-N-(2,4,6-trifluorobenzyl)-2,3,4,6-tetrahydro-1H-pyrido[2,1-f][1,2,4]triazine-7-carboxamide To a solution of (S)-5-(benzyloxy)-3-(but-3-en-2-yl)-4,6-dioxo-N-(2,4,6-trifluorobenzyl)-2,3,4,6-tetrahydro-1H-pyrido[2,1-f][1,2,4]triazine-7-carboxamide (0.150 g, 0.293 mmol, 1 equiv.), prepared according to Example 46, (S)-5-(benzyloxy)-3-(but-3-en-2-yl)-4,6-dioxo-N-(2,4,6-trifluorobenzyl)-2,3,4,6-tetrahydro-1H-pyrido[2,1-f][1,2,4]triazine-7-carboxamide and Pd(PPh$_3$)$_4$ (0.0338 g, 0.029 mmol, 0.1 equiv.) in THF (3 mL) and DMF (0.15 mL) was added methyl (2-methylbut-3-en-2-yl) carbonate (0.0633 g, 0.439 mmol, 1.5 equiv.). The reaction mixture was heated to 60° C. for 2 h and concentrated. The residue was purified by column chromatography (0-100% EtOAc/hexanes) and the pure fractions were collected and concentrated to afford (S)-5-(benzyloxy)-3-(but-3-en-2-yl)-1-(2-methylbut-3-en-2-yl)-4,6-dioxo-N-(2,4,6-trifluorobenzyl)-2,3,4,6-tetrahydro-1H-pyrido[2,1-f][1,2,4]triazine-7-carboxamide. MS (m/z) 581.02 [M+H]$^+$.

Step 2: Synthesis of (1S,5S)-8-(benzyloxy)-2,2,5-trimethyl-7,9-dioxo-N-(2,4,6-trifluorobenzyl)-2,5,7,9-tetrahydro-1,6-methanopyrido[1,2-b][1,2,5]triazonine-10-carboxamide To a solution of (0.019 g, 0.033 mmol, 1 equiv.) in 1,2-dichloroethane (1 mL) was added Hoveyda-Grubbs II catalyst (0.004 g, 0.006 mmol, 0.2 equiv.). The reaction mixture was sparged with Ar (g) for 10 min and heated to 75° C. for 18 h. The mixture was concentrated and purified by column chromatography (0-100% EtOAc/hexanes) to afford (1S,5S)-8-(benzyloxy)-2,2,5-trimethyl-7,9-dioxo-N-(2,4,6-trifluorobenzyl)-2,5,7,9-tetrahydro-1,6-methanopyrido[1,2-b][1,2,5]triazonine-10-carboxamide. MS (m/z) 553.00 [M+H]$^+$.

Step 3: Synthesis of (1S,5S)-8-hydroxy-2,2,5-trimethyl-7,9-dioxo-N-(2,4,6-trifluorobenzyl)-2,5,7,9-tetrahydro-1,6-methanopyrido[1,2-b][1,2,5]triazonine-10-carboxamide (C49)

(1S,5S)-8-(benzyloxy)-2,2,5-trimethyl-7,9-dioxo-N-(2,4,6-trifluorobenzyl)-2,5,7,9-tetrahydro-1,6-methanopyrido[1,2-b][1,2,5]triazonine-10-carboxamide (0.011 g, 0.020 mmol, 1 equiv.) was dissolved in 1:1 TFA/toluene (2 mL) and stirred at rt for 5 h. The reaction mixture was concentrated, dissolved in MeCN, filtered, and purified by preparative HPLC (column, Gemini 10µ C18 110A, AXI/; 250×21.2 mm) eluting 5-100% acetonitrile (0.1% TFA) in water (0.1% TFA) over 20 minutes. Combined fractions were lyophilized to afford (1S,5S)-8-hydroxy-2,2,5-trimethyl-7,9-dioxo-N-(2,4,6-trifluorobenzyl)-2,5,7,9-tetrahydro-1,6-methanopyrido[1,2-b][1,2,5]triazonine-10-carboxamide. MS (m/z) 463.10 [M+H]$^+$. $^1$H NMR (400 MHz, DMSO-d$_6$) δ 10.33 (t, J=5.7 Hz, 1H), 8.25 (s, 1H), 7.23-7.17 (m, 2H), 5.41 (td, J=11.8, 11.3, 2.9 Hz, 1H), 5.33 (dd, J=12.4, 2.0 Hz, 1H), 5.29-5.18 (m, 1H), 5.06-4.98 (m, 1H), 4.72 (d, J=14.5 Hz, 1H), 4.56 (d, J=5.6 Hz, 2H), 1.49 (s, 3H), 1.28 (d, J=7.2 Hz, 3H), 0.93 (s, 3H). $^{19}$F NMR (376 MHz, DMSO-d$_6$) δ −109.19 (ddd, J=15.6, 9.3, 6.3 Hz), −112.52 (q, J=7.3, 5.9 Hz).

Example 49: Preparation of (1S,10R,13R)—N-[(2,4-difluorophenyl)methyl]-10-(fluoromethyl)-6-hydroxy-13-methyl-5,8-dioxo-1,2,9-triazatricyclo[7.4.1.02,7]tetradeca-3,6,11-triene-4-carboxamide (C49a) and (1S,10R,13R)—N-[(2,4-difluorophenyl)methyl]-10-(fluoromethyl)-6-hydroxy-13-methyl-5,8-dioxo-1,2,9-triazatricyclo[7.4.1.02,7]tetradeca-3,6-diene-4-carboxamide (C49b)
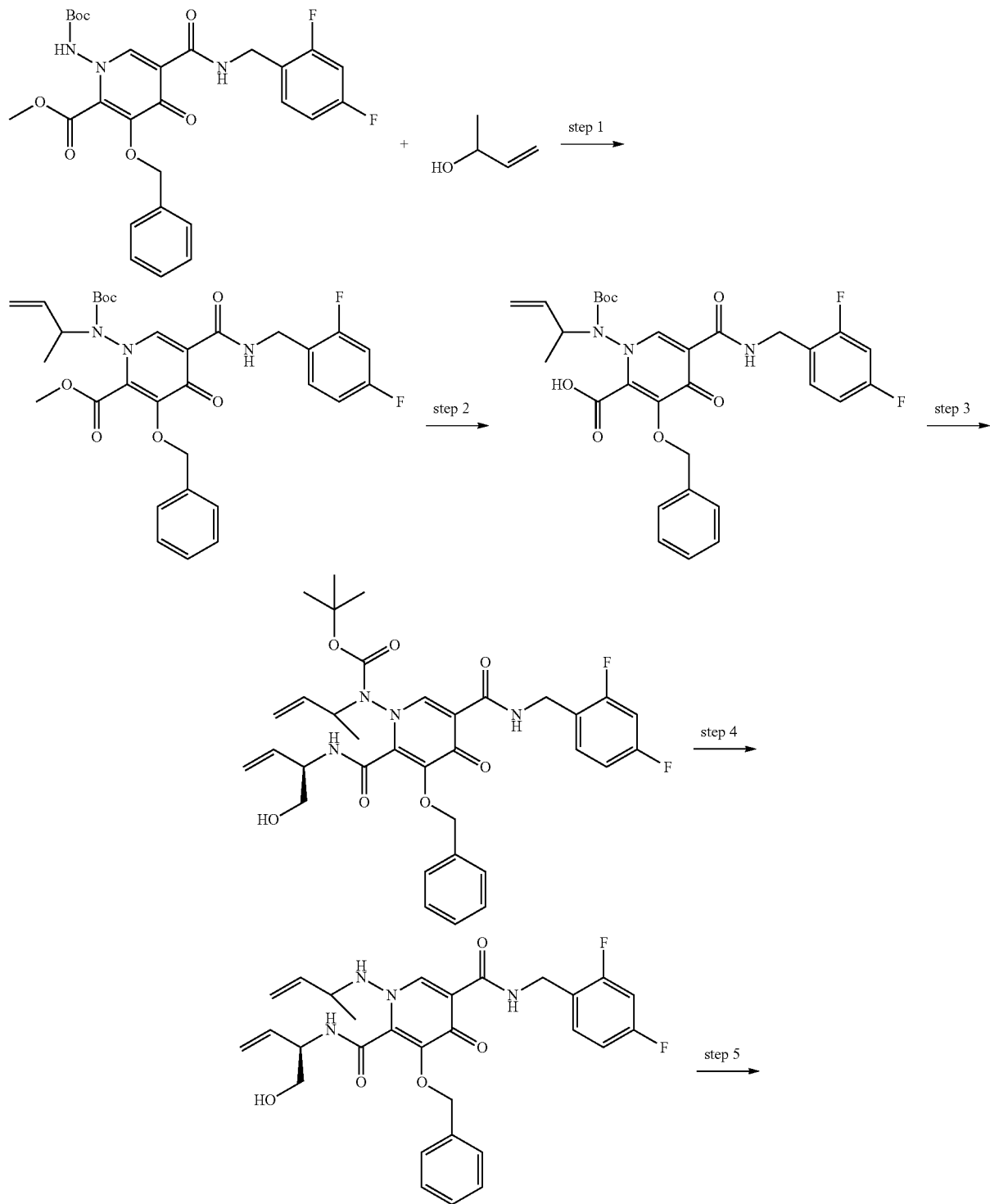

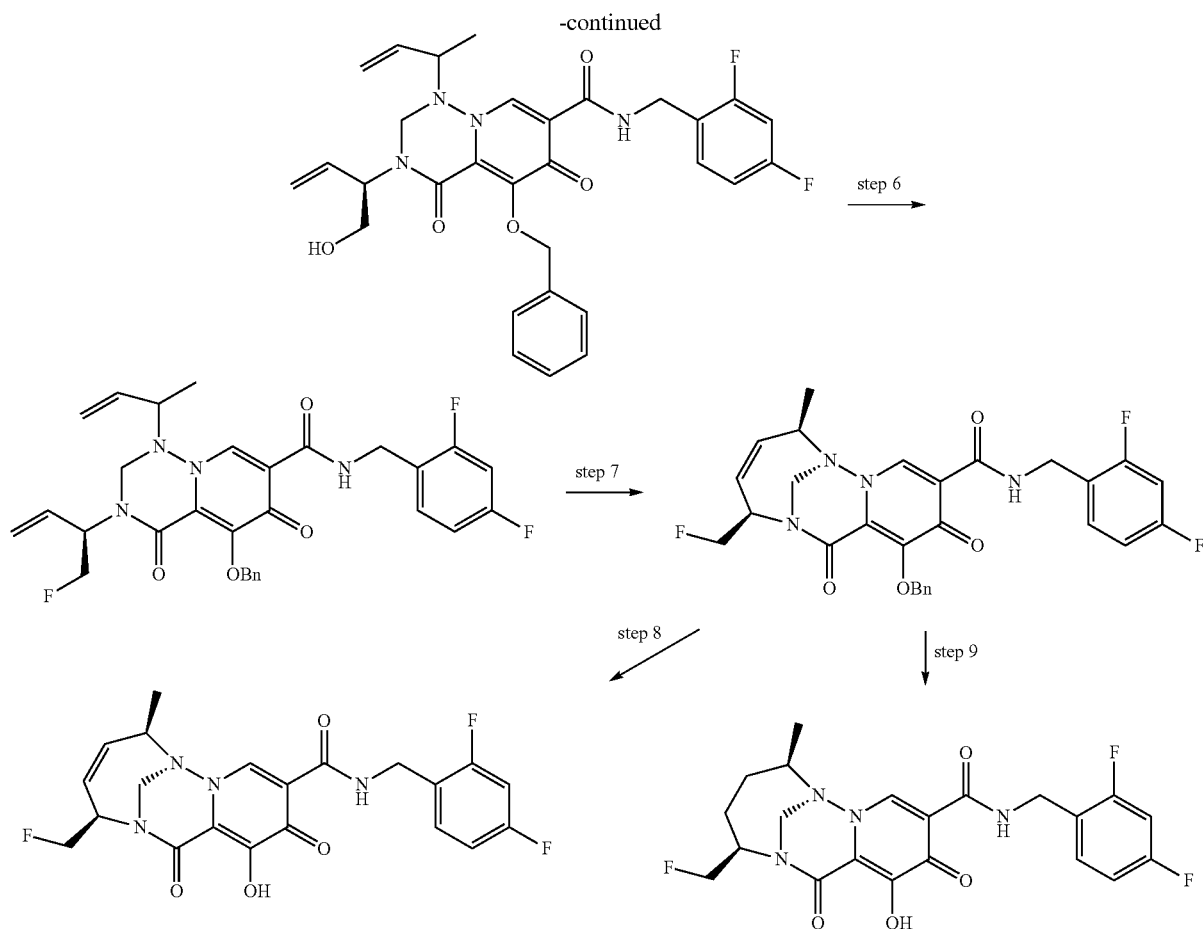

Step 1: Synthesis of methyl 3-benzyloxy-1-[tert-butoxycarbonyl(1-methylallyl)amino]-5-[(2,4-difluorophenyl)methylcarbamoyl]-4-oxo-pyridine-2-carboxylate To a mixture of methyl 3-benzyloxy-1-(tert-butoxycarbonylamino)-5-[(2,4-difluorophenyl)methylcarbamoyl]-4-oxo-pyridine-2-carboxylate (8 g, 14.7 mmol) in THF (75 mL) at 0° C. was added but-3-en-2-ol (1.59 g, 22.1 mmol), triphenyl phosphine (5.79 g, 22.1 mmol). Diisopropyl azodicarboxylate (4.46 g, 22.1 mmol) was then added dropwise. The resulting mixture was stirred at 0° C. for 5 minutes before it was removed from the cooling bath and stirred at room temperature for 2 hours. The reaction was mixed with silica gel, concentrated and purified by normal phase chromatography. LCMS-ESI+(m/z): calcd H+ for C31H33F2N3O7, Theoretical: 597.23, Found: 597.88.

Step 2: Synthesis of 3-benzyloxy-1-[tert-butoxycarbonyl(1-methylallyl)amino]-5-[(2,4-difluorophenyl)methylcarbamoyl]-4-oxo-pyridine-2-carboxylic acid Methyl 3-benzyloxy-1-[tert-butoxycarbonyl(1-methylallyl)amino]-5-[(2,4-difluorophenyl)methylcarbamoyl]-4-oxo-pyridine-2-carboxylate (10 g, 16.7 mmol) was dissolved in a mixture of MeOH (96 mL), THF (48 mL) and water (48 mL). Lithium hydroxide monohydrate (4.2 g, 41.96 mmol) was added. The resulting mixture was heated to 60° C. for 6 hrs. The reaction was then cooled to rt, concentrated, residue was diluted with EtOAc, acidified to pH-4 with 1N HCl, organic layer was washed with brine, dried over sodium sulfate, filtered and concentrated to give a light pinkish solid. The resulting product was used directly in next step. LCMS-ESI+(m/z): calcd H+ for C30H31F2N3O7, Theoretical: 583.21, Found: 583.87.

Step 3: Synthesis of tert-butyl N-13-benzyloxy-5-[(2,4-difluorophenyl)methylcarbamoyl]-2-[[[(1R)-1-(hydroxymethyl)allyl]carbamoyl]-4-oxo-1-pyridyl]-N-(1-methylallyl)carbamate The residue from previous step (7 g, 12.0 mmol) was dissolved in DCM (60 mL) at room temperature. To this stirred mixture was added (2R)-2-aminobut-3-en-1-ol (1.57 g, 18.0 mmol) followed by EDCI. HCl (4.12 g, 21.6 mmol), HOAt (2.94 g, 21.6 mmol) and DIEA (6.2 g, 48 mmol). The newly formed mixture was stirred for one hour. The reaction was then diluted with DCM, washed with 10% citric acid, brine, dried over sodium sulfate, filtered and concentrated and used directly in next step. LCMS-ESI+(m/z): calcd H+ for C34H38F2N4O7, Theoretical: 652.27, Found: 653.03.

Step 4: Synthesis of 3-benzyloxy N5-[(2,4-difluorophenyl)methyl]-N2-[(1R)-1-(hydroxymethyl)allyl]-1-(1-methylallylamino)-4-oxo pyridine-2,5-dicarboxamide Tert-butyl N-[3-benzyloxy-5-[(2,4-difluorophenyl)methylcarbamoyl]-2-[[(1R)-1-(hydroxymethyl)allyl]carbamoyl]-

4-oxo-1-pyridyl]-N-(1-methylallyl)carbamate (7.8 g, 12 mmol) was dissolved in DCM (70 mL) at room temperature and treated with 4N HCl in 1,4-dioxane (70 mL) at room temperature for 1 hour. The reaction was concentrated, diluted with EtOAc, basified with sat. sodium bicarbonate slowly till no bubbling, then solid sodium bicarbonate was added to saturate the aqeuous layer. Extracted with EtOAc, washed organic layer with brine, dried over sodium sulfate, filtered and concentrated to give a brownish oil. The resulting product was used directly in next step. LCMS-ESI+(m/z): calcd H+ for C29H30F2N4O5, Theoretical: 552.22, Found: 553.09.

Step 5: Synthesis of 5-benzyloxy-N-[(2,4-difluorophenyl)methyl]-3-[(1R)-1-(hydroxymethyl)allyl]-1-(1-methylallyl)-4,6-dioxo-2H-pyrido[2,1-f][1,2,4]triazine-7-carboxamide 3-Benzyloxy-N5-[(2,4-difluorophenyl)methyl]-N2-[(1R)-1-(hydroxymethyl)allyl]-1-(1-methylallylamino)-4-oxo-pyridine-2,5-dicarboxamide (1.57 g, 2.84 mmol) was dispensed in a mixture of DCE (5.3 mL) and acetonitrile (5.3 mL) at room temperature, paraformaldehyde (224 mg) was added. The resulting mixture was then heated to 88° C., a mixture of AcOH (0.79 mL) and TFA (0.79 mL) was added in one portion quickly. The reaction was sealed and stirred for 1 hr. The reaction was then cooled to room temperature, concentrated, redissolved in EtOAc, washed with saturated sodium bicarbonate, brine, dried over sodium sulfate, filtered and concentrated to give a brownish oil. The residue was then dissolved in DMF (5 mL) and treated with potassium carbonate (392 mg, 2.84 mmol) and benzyl bromide (485 mg, 2.84 mmol). The reaction was then heated at 70° C. for 2 hours before it was cooled to room temperature, partitioned between EtOAc and water. The organic layer was washed with brine, dried over sodium sulfate, filtered and concentrated, purified by normal phase chromatography. LCMS-ESI+(m/z): calcd H+ for C30H30F2N4O5, Theoretical: 564.22, Found: 565.02.

Step 6: Synthesis of 5-benzyloxy-N-[(2,4-difluorophenyl)methyl]-3-[(1R)-1-(fluoromethyl)allyl]-1-(1-methylallyl)-4,6-dioxo-2H pyrido[2,1-f][1,2,4]triazine-7-carboxamide 5-Benzyloxy-N-[(2,4-difluorophenyl)methyl]-3-[(1R)-1-(hydroxymethyl)allyl]-1-(1-methylallyl)-4,6-dioxo-2H-pyrido[2,1-f][1,2,4]triazine-7-carboxamide (851 mg, 1.51 mmol) was dissolved in DCM (12.0 mL) at 0° C. Bis(2-methoxyethyl)aminosulfur trifluoride (1.33 g, 6.03 mmol) was added. The reaction was removed from cooling bath after addition and stirred at ambient for overnight. The reaction was then cooled to 0° C. and quenched with saturated sodium bicarbonate. Additional sodium bicarbonate powder was added to saturate the mixture. The reaction was extracted with DCM, washed with brine, dried over sodium sulfate, filtered and concentrated, purified by normal phase chromatography. LCMS-ESI+(m/z): calcd H+ for C30H29F3N4O4, Theoretical: 566.21, Found: 566.99.

Step 7: Synthesis of (1S,10R,13R)-6-benzyloxy-N-[(2,4-difluorophenyl)methyl]-10-(fluoromethyl)-13-methyl-5,8-dioxo-1,2,9-triazatricyclo[7.4.1.02,7]tetradeca-3,6,11-triene-4-carboxamide A solution of 5-benzyloxy-N-[(2,4-difluorophenyl)methyl]-3-[(1R)-1-(fluoromethyl)allyl]-1-(1-methylallyl)-4,6-dioxo-2H-pyrido[2,1-f][1,2,4]triazine-7-carboxamide (370 mg, 0.65 mmol) in DCE (9 mL) at room temperature was sparged with Argon. Hoveyda-Grubbs II catalyst HG-M720 (41 mg, 0.065 mmol) was added. The mixture was sparged for Argon for another 5 minutes and then was sealed and heated at 80° C. under nitrogen balloon for overnight. The reaction was then cooled to room temperature, concentrated and purified by normal phase chromatography. $^1$H NMR (400 MHz, CDCl3) δ 10.38 (t, J=6.0 Hz, 1H), 8.54 (s, 1H), 7.55-7.47 (m, 2H), 7.44-7.29 (m, 4H), 6.89-6.76 (m, 2H), 5.83 (dt, J=10.8, 2.3 Hz, 1H), 5.62-5.45 (m, 3H), 5.25 (d, J=10.5 Hz, 1H), 5.11 (d, J=14.6 Hz, 1H), 4.79-4.65 (m, 1H), 4.65-4.62 (m, 2H), 4.62-4.46 (m, 1H), 4.26 (d, J=14.6 Hz, 1H), 3.77 (tp, J=6.6, 3.3 Hz, 1H), 1.41 (d, J=6.6 Hz, 3H). LCMS-ESI+(m/z): calcd H+ for C28H25F3N4O4, Theoretical: 538.18, Found: 539.09.

Step 8: Synthesis of (1S,10R,13R)—N-[(2,4-difluorophenyl)methyl]-10 (fluoromethyl)-6-hydroxy-13-methyl-5,8-dioxo-1,2,9-triazatricyclo[7.4.1.02,7]tetradeca-3,6,11-triene-4-carboxamide (1S,10R,13R)-6-benzyloxy-N-[(2,4-difluorophenyl)methyl]-10-(fluoromethyl)-13-methyl-5,8-dioxo-1,2,9-triazatricyclo[7.4.1.02,7]tetradeca-3,6,11-triene-4-carboxamide (20 mg, 0.037 mmol) was treated with a mixture of DCM (1.5 mL) and TFA (1.5 mL) at room temperature for 2 hours. The reaction was concentrated, redissolved in DMF and purified by reverse phase prep HPLC. Absolute configuration at C13 is not confirmed. $^1$H NMR (400 MHz, Acetonitrile-d3) δ 10.15 (s, 1H), 8.39 (s, 1H), 7.44 (td, J=9.2, 8.8, 6.5 Hz, 1H), 7.09-6.88 (m, 2H), 5.81 (dt, J=11.5, 2.3 Hz, 1H), 5.66-5.59 (m, 1H), 5.54-5.41 (m, 1H), 5.13 (d, J=14.5 Hz, 1H), 4.80-4.55 (m, 5H), 3.87 (dp, J=10.1, 3.4 Hz, 1H), 1.37 (d, J=6.7 Hz, 3H). LCMS-ESI+(m/z): calcd H+ for C21H19F3N4O4, Theoretical: 448.14, Found: 449.10.

Step 9: Synthesis of (1S,10R,13R)—N-[(2,4-difluorophenyl)methyl]-10 (fluoromethyl) 6 hydroxy 13-methyl-5,8-dioxo-1,2,9-triazatricyclo[7.4.1.02,7]tetradeca-3,6-diene-4-carboxamide (1S,10R,13R)-6-benzyloxy-N-[(2,4-difluorophenyl)methyl]-10-(fluoromethyl)-13-methyl-5,8-dioxo-1,2,9-triazatricyclo[7.4.1.02,7]tetradeca-3,6,11-triene-4-carboxamide (20 mg, 0.037 mmol) was dissolved in EtOH (20 mL) at room temperature. 10% Pd/C (4 mg) was added, the reaction was degassed and flushed with nitrogen three times and then degassed and flushed with hydrogen three times before it was hydrogenated under hydrogen balloon for 1 hr. The reaction was then degassed and flushed with Nitrogen, filtered through Celite, concentrated and purified by reverse phase prep HPLC. Absolute configuration at C13 is not confirmed. $^1$H NMR (400 MHz, Acetonitrile-d3) δ 10.33 (s, 1H), 8.45 (s, 1H), 7.44 (td, J=9.2, 8.8, 6.5 Hz, 1H), 7.06-6.86 (m, 2H), 4.79-4.39 (m, 7H), 3.63-3.58 (m, 1H), 1.95-1.82 (m, 2H), 1.62 (dt, J=7.1, 3.5 Hz, 2H), 1.32 (d, J=7.2 Hz, 3H). LCMS-ESI+(m/z): calcd H+ for C21H21F3N4O4, Theoretical: 450.15, Found: 451.12.

Example 50: Preparation of (1S,2R,5R)-5-(fluoromethyl)-8-hydroxy-2-methyl-7,9-dioxo-N-(2,4,6-trifluorobenzyl)-2,5,7,9-tetrahydro-1,6-methanopyrido[1,2-b][1,2,5]triazonine-10-carboxamide (C50)
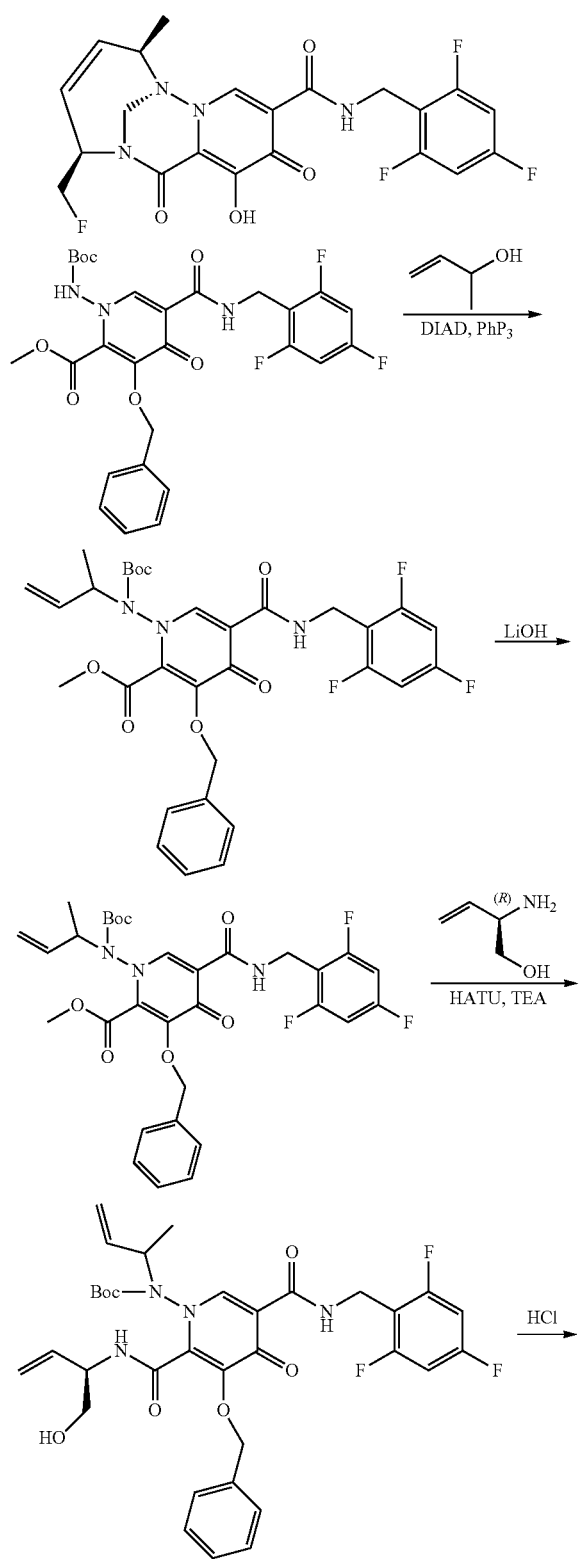
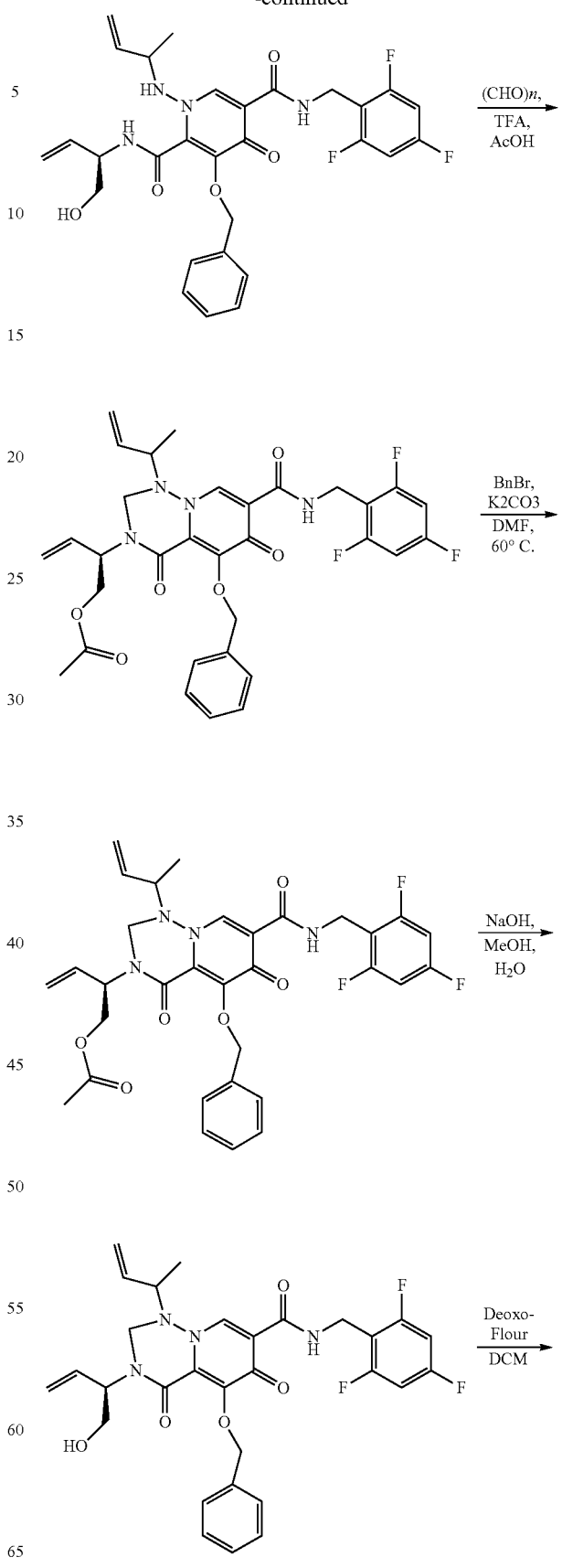

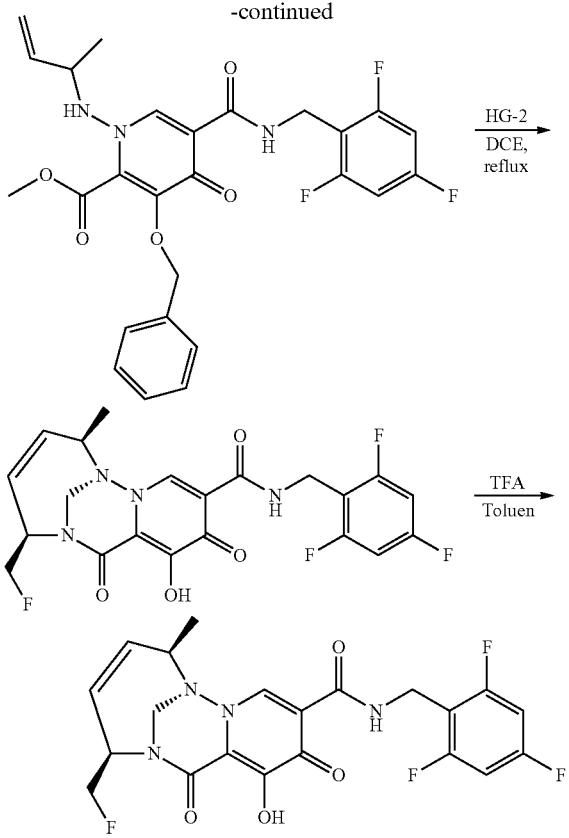

Synthesis of methyl 3-benzyloxy-1-[tert-butoxycarbonyl(1-methylallyl)amino]-4-oxo-5-[(2,4,6-trifluorophenyl)methylcarbamoyl]pyridine-2-carboxylate To methyl 3-benzyloxy-1-(tert-butoxycarbonylamino)-4-oxo-5-[(2,4,6-trifluorophenyl)methylcarbamoyl]pyridine-2-carboxylate (10 g, 17.8 mmol) in THF (200 ml) at 0° C. was added but-3-en-2-ol (1.93 g, 26.7 mmol), followed by the addition of Ph₃P (7.0 g, 26.7 mmol). Then DIAD (5.4 g, 26.7 mmol) was added drop-wise over 5 min. The resulting reaction mixture was stirred at 0° C. for 5 min and then warmed up to room temperature. the reaction was stirred at room temperature for overnight. Solvent was removed under vacuo and the resulting crud material was purified by silica gel column to obtain the title compound. MS (m/z) 615.99 [M+H]⁺

Synthesis of 3-benzyloxy-1-[tert-butoxycarbonyl(1-methylallyl)amino]-4-oxo-5-[(2,4,6-trifluorophenyl)methylcarbamoyl]pyridine-2-carboxylic acid To methyl 3-benzyloxy-1-[tert-butoxycarbonyl(1-methylallyl)amino]-4-oxo-5-[(2,4,6-trifluorophenyl)methylcarbamoyl]pyridine-2-carboxylate (11 g, 17.9 mmol) in MeOH (80 ml) was added aqueous LiOH solution (2.5N) (43 ml, 107 mmol). The reaction mixture was heated to 70° C. for overnight. Reaction mixture was concentrated carefully for removal of MeOH. The residue was diluted and rinsed with some water and was acidified with 1N HCl to pH=3. EtOAc was added for extraction. Organic phase was separated. Aqueous layer was extracted with more EtOAc. The combined organic phases were washed with water and brine, dried over Na₂SO₄, filtered and concentrated to afford the title compound. The crude material was taken forward to next step. MS (m/z) 601.84 [M+H]⁺

Synthesis of tert-butyl N-[3-benzyloxy-2-[[(1R)-1-(hydroxymethyl)allyl]carbamoyl]-4-oxo-5-[(2,4,6-trifluorophenyl)methylcarbamoyl]-1-pyridyl]-N-(1-methylallyl)carbamate To 3-benzyloxy-1-[tert-butoxycarbonyl(1-methylallyl)amino]-4-oxo-5-[(2,4,6-trifluorophenyl)methylcarbamoyl]pyridine-2-carboxylic acid (11.2 g, 18.6 mmol) in DMF (50 ml) was added DIEA (16.2 ml, 93.1 mmol) followed by the addition of HATU (9.2 g, 24.2 mmol). After the reaction mixture was stirred at rt of 1 hour, (2R)-2-aminobut-3-en-1-ol; hydrochloride (2.9 g, 24.2 mmol) was added to the reaction mixture. 2 h later, the reaction mixture was diluted with EtOAc and washed with aqueous LiCl. Aqueous layer was extracted with EtOAc (1×). Combined organic phases were washed with water (1×). Organic phase was dried with MgSO₄ and concentrated to afford the crude which was purified by silica gel chromatography to afford the title compound. MS (m/z) 670.86 [M+H]⁺

Synthesis of 3-benzyloxy-N2-[(R)-1-(hydroxymethyl)allyl]-1-(1-methylallylamino)-4-oxo-N5-[(2,4,6-trifluorophenyl)methyl]pyridine-2,5-dicarboxamide Tert-butyl N-[3-benzyloxy-2-[[(1R)-1-(hydroxymethyl)allyl]carbamoyl]-4-oxo-5-[(2,4,6-trifluorophenyl)methylcarbamoyl]-1-pyridyl]-N-(1-methylallyl)carbamate (XX-3) (10 g, 14.9 mmol) was dissolved in DCM (50 ml) at rt. HCl (4 M in dioxane) (11.2 mL, 44.7 mmol)) was added. The reaction mixture was stirred for 24 h at r.t. LCMS shows reaction was done. So reaction mixture was then concentrated to dryness. The residue was then partitioned between EtOAc and aqueous NaHCO₃ solution. Aqueous layer was extracted with EtOAc. Combined organic phases were washed with water, dried over Na₂SO₄, filtered and concentrated to afford the title compound. MS (m/z) 571.06 [M+H]⁺

Synthesis of 5-hydroxy-3-[(1R)-1-(hydroxymethyl)allyl]-1-(1-methylallyl)-4,6-dioxo-N-[(2,4,6-trifluorophenyl)methyl]-2H-pyrido[2,1-f][1,2,4]triazine-7-carboxamide (2 g, 4.06 mmol) in DMF was added bromomethylbenzene To 3-benzyloxy-N2-[(1R)-1-(hydroxymethyl)allyl]-1-(1-methylallylamino)-4-oxo-N5-[(2,4,6-trifluorophenyl)methyl]pyridine-2,5-dicarboxamide (XX-4) (0.89 g, 1.56 mmol) in 20 ml microwave reaction viral in CAN (5 ml) and DCE (5 ml) was added paraformaldehyde (93.1 mg, 3.04 mmol), AcOH (0.5 mL), followed by the addition of TFA (0.5 mL). the viral was capped after addition and it was heated to 89° C. for overnight. LCMS showed complete reaction. The reaction mixture was diluted with EtOAc and was washed with sat. aqueous NaHCO₃. Organic phase was dried with MgSO4 and solvent was removed under vacuo to afford the crude material of title compound, crude was taken forward to next step. MS (m/z) 535.1 [M+H]⁺

Synthesis of (2R)-2-[5-benzyloxy-1-(1-methylallyl)-4,6-dioxo-7-((2,4,6-trifluorophenyl)methylcarbamoyl]-2H-pyrido[2,1-f][1,2,4]triazin-3-ylbut-3-enyl acetate To 5-hydroxy-3-[(1R)-1-(hydroxymethyl)allyl]-1-(1-methylallyl)-4,6-dioxo-N-[(2,4,6-trifluorophenyl)methyl]-

2H-pyrido[2,1-f][1,2,4]triazine-7-carboxamide (2 g, 4.06 mmol) in DMF was added bromomethylbenzene (XX-5) (2.08 g, 12.2 mmol) and followed by the addition of POTASSIUM CARBONATE (2.93 g, 21.2 mmol). The reaction mixture was stirred at 60° C. for overnight. Lcms showed complete reaction. The reaction mixture was diluted with EtOAc and was washed with sat. aqueous NaHCO$_3$. Organic phase was dried with MgSO4 and solvent was removed under vacuo to afford the crude material. MS (m/z) 625 [M+H]$^+$ Synthesis of 5-benzyloxy-3-[(1R)-1-(hydroxymethyl)allyl]-1-(1-methylallyl)-4,6-dioxo-N-[(2,4,6-trifluorophenyl)methyl]-2H-pyrido[2,1-f][1,2,4]triazine-7-carboxamide To the crude [(2R)-2-[5-benzyloxy-1-(1-methylallyl)-4,6-dioxo-7-[(2,4,6-trifluorophenyl)methylcarbamoyl]-2H-pyrido[2,1-f][1,2,4]triazin-3-yl]but-3-enyl]acetate (7.61 g, 12.2 mmol) in MeOH (100 ml) was added NaOH (1N) (63 ml, 63.3 mmol). The mixture was stirred at rt of 30 minutes. LCMS showed reaction was complete. Solvent was removed under vacuo, the resulting residue was diluted in EtOAc and washed with H$_2$O. Organic phase was dried with MgSO$_4$ and concentrated under vacuo. The resulting crude material was purified by silicone gel column to provide the title compound. MS (m/z) 583.01 [M+H]$^+$ Synthesis of 5-benzyloxy-3-[(1R)-1-(fluoromethyl)allyl]-1-(1-methylallyl)-4,6-dioxo-N-[(2,4,6-tri fluorophenyl)methyl]-2H-pyrido[2,1-f][1,2,4]triazine-7-carboxamide At 0° C., to 5-benzyloxy-3-[(1R)-1-(hydroxymethyl)allyl]-1-(1-methylallyl)-4,6-dioxo-N-[(2,4,6-trifluorophenyl)methyl]-2H-pyrido[2,1-f][1,2,4]triazine-7-carboxamide (XX-7) (0.82 g, 1.41 mmol) in DCM (8 ml) was added deoxo-fluor in toluene (2.7N) (5.21 ml, 14.1 mmol), then the mixture was slowly warmed up to rt and it was stirred for overnight. Reaction mixture was added to iced NaHCO$_3$ aqueous slowly, then extracted with DCM. DCM phase was dried with MgSO$_4$ and crude was purified by silicone gel column to afford the title compound. MS (m/z) 585.03 [M+H]$^+$ Synthesis of (1S,10R,13R)-6-benzyloxy-10-(fluoromethyl)-13-methyl-5,8-dioxo-N-[(2,4,6-tri fluorophenyl)methyl]-1,2,9-triazatricyclo[7.4.1.02,7]tetradeca-3,6,11-triene-4-carboxamide 5-benzyloxy-3-[(1R)-1-(fluoromethyl)allyl]-1-(1-methylallyl)-4,6-dioxo-N-[(2,4,6-trifluorophenyl)methyl]-2H-pyrido[2,1-f][1,2,4]triazine-7-carboxamide (XX-9) (0.41 g, 0.7 mmol) was dissolved in DEC (25 ml) and degassed by vacuum then refilled with N2 (×3) at rt. Then catalyst HG-II was added into the solution and flushed with argon 1.5 h with vented needle at 80° C. Afterwards, vented needle was removed and the reaction was stirred with argon balloon at 80° C. for overnight. LCMS showed complete reaction, solvent was removed under vacuo and the resulting residue was purified by silicone gel column to afford the title compound (XX-9). MS (m/z) 556.94 [M+H]$^+$ Synthesis of (1S,2R,5R)-5-(fluoromethyl)-8-hydroxy-2-methyl-7,9-dioxo-N-(2,4,6-trifluorobenzyl)-2,5,7,9-tetrahydro-1,6-methanopyrido[1,2-b][1,2,5]triazonine-10-carboxamide (C50)

To (1S,10R,13R)-6-benzyloxy-10-(fluoromethyl)-13-methyl-5,8-dioxo-N-[(2,4,6-trifluorophenyl)methyl]-1,2,9-triazatricyclo[7.4.1.02,7]tetradeca-3,6,11-triene-4-carboxamide (80 mg, 0.144 mmol) in Toluene (2 ml) was added TFA (2 ml), the reaction mixture was stirred at room temperature for overnight. LCMS showed complete reaction. Solvent was removed under vacuo and resulting material was purified by prep-HPLC to afford the title compound (51). MS (m/z) 467 [M+H]$^+$. $^1$H NMR (400 MHz, Chloroform-d) δ 10.19 (s, 1H), 8.57 (s, 1H), 6.75-6.68 (m, 3H), 5.88 (dt, J=11.4, 2.3 Hz, 1H), 5.65 (dt, J=11.4, 3.5 Hz, 1H), 5.49 (dd, J=32.6, 3.1 Hz, 1H), 5.26 (d, J=14.6 Hz, 1H), 4.84 (dd, J=9.9, 3.3 Hz, 1H), 4.77-4.66 (m, 3H), 4.67-4.55 (m, 2H), 3.80 (dq, J=6.7, 3.4 Hz, 1H), 1.43 (d, J=6.7 Hz, 3H).

Example 51: Preparation of (1S,2R,5R)-5-(fluoromethyl)-8-hydroxy-2-methyl-7,9-dioxo-N-(2,4,6-trifluorobenzyl)-2,3,4,5,7,9-hexahydro-1,6-methanopyrido[1,2-b][1,2,5]triazonine-10-carboxamide (C51)

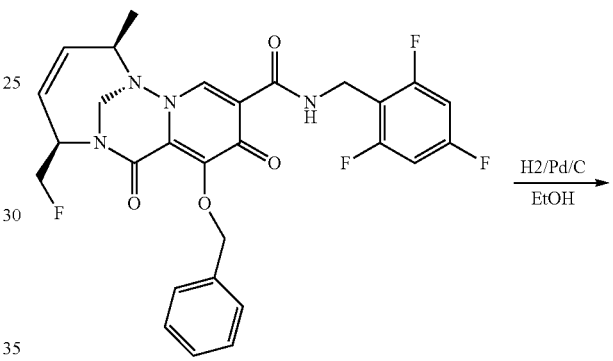

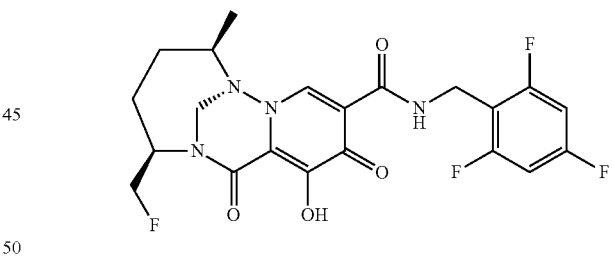

(1S,10R,13R)-6-benzyloxy-10-(fluoromethyl)-13-methyl-5,8-dioxo-N-[(2,4,6-trifluorophenyl)methyl]-1,2,9-triazatricyclo[7.4.1.02,7]tetradeca-3,6,11-triene-4-carboxamide (from Example 50) (520 mg, 0.93 mmol) was dissolved in EtOH (100 ml), then followed by the addition of Pd/C (10% Wt) (7.8 mg, 0.09 mmol). Then the mixture was vacuum and back filled with H$_2$ three times. The reaction was stirred under H$_2$ overnight. LCMS showed complete reaction. Reaction mixture was filtered with Celite to remove Pd/C, and solvent was removed under vacuo. The resulting crude material was purified by prep-HPLC to afford the title compound (XX). MS (m/z) 469.11 [M+H]$^+$ 1H NMR (400 MHz, Chloroform-d) δ 10.37 (s, 1H), 8.61 (s, 1H), 6.82-6.59 (m, 2H), 4.79-4.44 (m, 7H), 3.64-3.39 (m, 1H), 2.35-2.27 (m, 1H), 2.14-1.86 (m, 1H), 1.71-1.61 (m, 2H), 1.38 (d, J=7.1 Hz, 3H).

Example 52: Preparation of (1S,2R,4S,5S)—N-(2,4-difluorobenzyl)-4-fluoro-8-hydroxy-2,5-dimethyl-7,9-dioxo-2,3,4,5,7,9-hexahydro-1,6-methanopyrido[1,2-b][1,2,5]triazonine-10-carboxamide (C52)

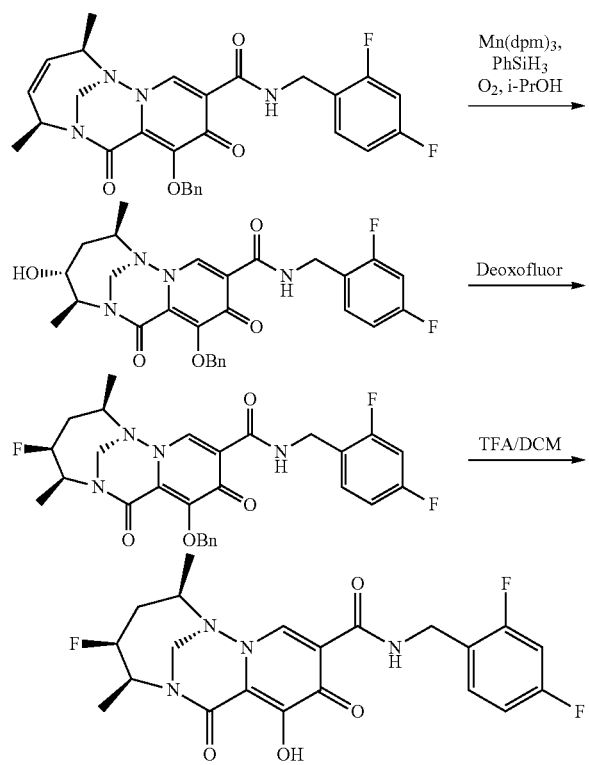

Step 1: Preparation of (1S,2R,4R,5S)-8-(benzyloxy)-N-(2,4-difluorobenzyl)-4-hydroxy-2,5-dimethyl-7,9-dioxo-2,3,4,5,7,9-hexahydro-1,6-methanopyrido[1,2-b][1,2,5]triazonine-10-carboxamide A solution of (1S,2R,5S)-8-(benzyloxy)-N-(2,4-difluorobenzyl)-2,5-dimethyl-7,9-dioxo-2,5,7,9-tetrahydro-1,6-methanopyrido[1,2-b][1,2,5]triazonine-10-carboxamide (455 mg, 0.85 mmol), prepared according to Example 29, in isopropyl alcohol (5 mL) was purged with Argon. To the solution of added phenylsilane (189 mg, 1.75 mmol) and tris(2,2,6,6-tetramethyl-3,5-heptanedionato)manganese(III) (16 mg, 0.026 mmol). The reaction mixture was stirred at rt under oxygen balloon for one day. Then the reaction was quenched by adding 10% sodium thiosulfate solution and the mixture was extracted with EtOAc. The organic phase was separated and dried over MgSO$_4$, filtered, concentrated down and the residue was purified by silica gel chromatography column, eluting with 0-100% hexane/EtOAc to give title product. MS (m/z) 539.03 [M+H]+.

Step 2: Preparation of (1S,2R,4S,5S)-8-(benzyloxy)-N-(2,4-difluorobenzyl)-4-fluoro-2,5-dimethyl-7,9-dioxo-2,3,4,5,7,9-hexahydro-1,6-methanopyrido[1,2-b][1,2,5]triazonine-10-carboxamide To a solution of (1S,2R,4R,5S)-8-(benzyloxy)-N-(2,4-difluorobenzyl)-4-hydroxy-2,5-dimethyl-7,9-dioxo-2,3,4,5,7,9-hexahydro-1,6-methanopyrido[1,2-b][1,2,5]triazonine-10-carboxamide (20 mg, 0.037 mmol) in DCM (2 mL) was added deoxofluor solution in toluene (50%, 0.041 mL, 0.11 mmol) at 0° C. The reaction mixture was stirred at 0° C. for 15 min and the reaction was quenched by adding sat. NaHCO$_3$ solution. The mixture was extracted with DCM, the organic phase was separated and dried over MgSO$_4$, filtered, concentrated down and purified by silica gel chromatography column (eluting with 0-100% hexane/EtOAc) to give the title compound. MS (m/z) 540.92 [M+H]+.

Step 3: Preparation of (S,2R,4S,5S)—N-(2,4-difluorobenzyl)-4-fluoro-8-hydroxy-2,5-dimethyl-7,9-dioxo-2,3,4,5,7,9-hexahydro-1,6-methanopyrido[1,2-b][1,2,5]triazonine-10-carboxamide To a solution of (1S,2R,4S,5S)-8-(benzyloxy)-N-(2,4-difluorobenzyl)-4-fluoro-2,5-dimethyl-7,9-dioxo-2,3,4,5,7,9-hexahydro-1,6-methanopyrido[1,2-b][1,2,5]triazonine-10-carboxamide (13 mg, 0.024 mmol) in DCM (1 mL) was added TFA (1 mL). The reaction mixture was stirred at rt overnight. The reaction mixture was concentrated down, and the residue was purified by reverse phase HPLC, eluting with 5-100% acetonitrile in water to give title compound. MS (m/z) 451.12 [M+H]+. 1H NMR (400 MHz, Methanol-d4) δ 8.50 (s, 1H), 7.45 (td, J=8.5, 6.4 Hz, 1H), 7.04-6.90 (m, 2H), 5.13-5.03 (m, 1H), 5.03-4.91 (m, 2H), 4.73 (d, J=15.0 Hz, 1H), 4.65 (s, 2H), 3.50-3.41 (m, 1H), 2.42 (dt, J=15.8, 7.7 Hz, 1H), 2.01-1.84 (m, 1H), 1.52 (dd, J=7.1, 1.7 Hz, 3H), 1.41 (dd, J=7.1, 2.7 Hz, 3H).

Example 53: Preparation of (1S,2R,4R,5S)—N-(2,4-difluorobenzyl)-4-fluoro-8-hydroxy-2,5-dimethyl-7,9-dioxo-2,3,4,5,7,9-hexahydro-1,6-methanopyrido[1,2-b][1,2,5]triazonine-10-carboxamide (C53)

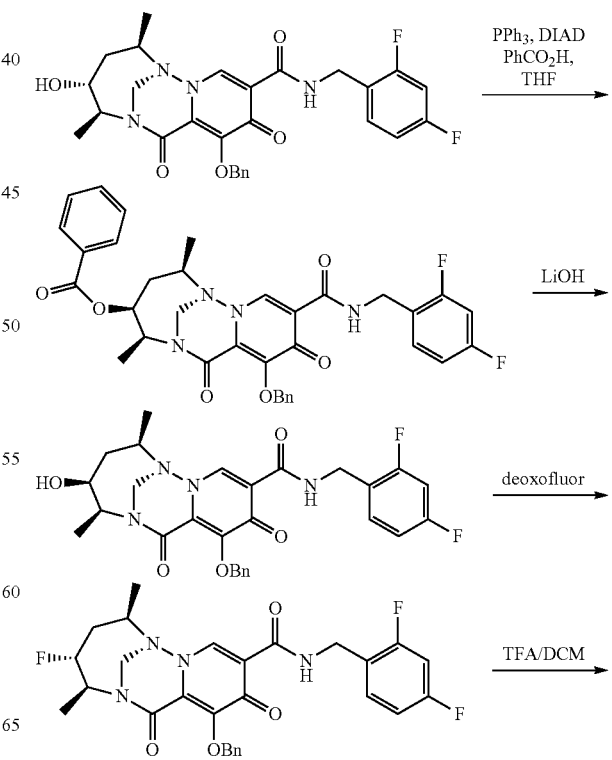

-continued

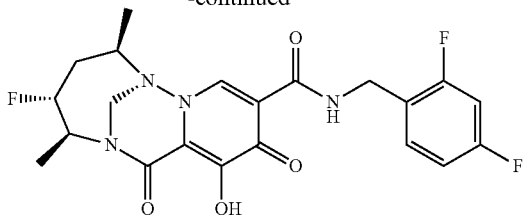

Step 1: Preparation of (1S,2R,4S,5S)-8-(benzyloxy)-10-((2,4-difluorobenzyl)carbamoyl)-2,5-dimethyl-7,9-dioxo-2,3,4,5,7,9-hexahydro-1,6-methanopyrido[1,2-b][1,2,5]triazonin-4-yl benzoate To a solution of (1S,2R,4R,5S)-8-(benzyloxy)-N-(2,4-difluorobenzyl)-4-hydroxy-2,5-dimethyl-7,9-dioxo-2,3,4,5,7,9-hexahydro-1,6-methanopyrido[1,2-b][1,2,5]triazonine-10-carboxamide (36.0 mg, 0.067 mmol), prepared according to Example 52, in THF (2 mL) was added benzoic acid (24.5 mg, 0.201 mmol), diisopropyl azodicarboxylate (40.6 mg, 0.201 mmol) and triphenyl phosphine (53 mg, 0.201 mmol). The reaction mixture was stirred at rt for 3 h. The reaction mixture was diluted with EtOAc, washed with sat. NaHCO₃, and extracted with EtOAc. The organic phase was dried over MgSO₄, filtered, concentrated down and the residue was purified by silica gel chromatography, eluting with 0-100% hexane/EtOAc, to give the title product. MS (m/z) 643.02 [M+H]+.

Step 2: Preparation of (1S,2R,4S,5S)-8-(benzyloxy)-N-(2,4-difluorobenzyl)-4-hydroxy-2,5-dimethyl-7,9-dioxo-2,3,4,5,7,9-hexahydro-1,6-methanopyrido[1,2-b][1,2,5]triazonine-10-carboxamide To a solution of (1S,2R,4S,5S)-8-(benzyloxy)-10-((2,4-difluorobenzyl)carbamoyl)-2,5-dimethyl-7,9-dioxo-2,3,4,5,7,9-hexahydro-1,6-methanopyrido[1,2-b][1,2,5]triazonin-4-yl benzoate (15 mg, 0.023 mmol) in MeOH (2 mL) and water (0.5 mL), was added LiOH·H₂O (2.80 mg, 0.117 mmol). The reaction mixture was stirred at rt overnight. The reaction mixture was concentrated down. The residue was washed with sat. NaHCO₃, extracted with EtOAc, dried over MgSO₄, filtered, concentrated down and used in next step without purification.

Steps 3-4: Preparation of (1S,2R,4R,5S)—N-(2,4-difluorobenzyl)-4-fluoro-8-hydroxy-2,5-dimethyl-7,9-dioxo-2,3,4,5,7,9-hexahydro-1,6-methanopyrido[1,2-b][1,2,5]triazonine-10-carboxamide (1S,2R,4R,5S)—N-(2,4-difluorobenzyl)-4-fluoro-8-hydroxy-2,5-dimethyl-7,9-dioxo-2,3,4,5,7,9-hexahydro-1,6-methanopyrido[1,2-b][1,2,5]triazonine-10-carboxamide was prepared in a similar way as Example 52, except that (1S,2R,4R,5S)-8-(benzyloxy)-N-(2,4-difluorobenzyl)-4-fluoro-2,5-dimethyl-7,9-dioxo-2,3,4,5,7,9-hexahydro-1,6-methanopyrido[1,2-b][1,2,5]triazonine-10-carboxamide was used instead of (1S,2R,4S,5S)-8-(benzyloxy)-N-(2,4-difluorobenzyl)-4-fluoro-2,5-dimethyl-7,9-dioxo-2,3,4,5,7,9-hexahydro-1,6-methanopyrido[1,2-b][1,2,5]triazonine-10-carboxamide. MS (m/z) 451.11 [M+H]⁺. 1H NMR (400 MHz, Methanol-d4) δ 8.50 (s, 1H), 7.46 (dd, J=8.7, 6.4 Hz, 1H), 7.04-6.90 (m, 2H), 5.13-5.03 (m, 1H), 5.03-4.91 (m, 2H), 4.72 (d, J=15.0 Hz, 1H), 4.65 (s, 2H), 3.46 (d, J=8.4 Hz, 1H), 2.42 (dt, J=15.7, 7.9 Hz, 1H), 2.00-1.84 (m, 2H), 1.52 (dd, J=7.0, 1.7 Hz, 3H), 1.41 (dd, J=7.0, 2.7 Hz, 3H).

Example 54: Preparation of (1S,2R,5S)—N-(2,4-difluorobenzyl)-4,4-difluoro-8-hydroxy-2,5-dimethyl-7,9-dioxo-2,3,4,5,7,9-hexahydro-1,6-methanopyrido[1,2-b][1,2,5]triazonine-10-carboxamide (C54)

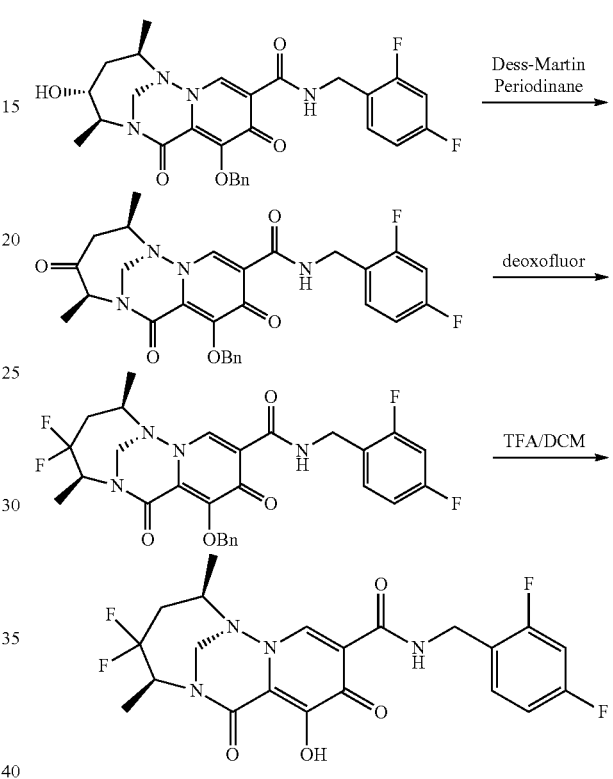

Step 1: Preparation of (1S,2R,5S)-8-(benzyloxy)-N-(2,4-difluorobenzyl)-2,5-dimethyl-4,7,9-trioxo-2,3,4,5,7,9-hexahydro-1,6-methanopyrido[1,2-b][1,2,5]triazonine-10-carboxamide To a solution of (1S,2R,4R,5S)-8-(benzyloxy)-N-(2,4-difluorobenzyl)-4-hydroxy-2,5-dimethyl-7,9-dioxo-2,3,4,5,7,9-hexahydro-1,6-methanopyrido[1,2-b][1,2,5]triazonine-10-carboxamide (60 mg, 0.11 mmol) in DCM (2.0 mL), was added Dess-Martin periodinane (94.5 mg, 0.223 mmol) at 0° C. Then the reaction mixture was stirred at rt for 3 h. The reaction mixture was quenched by adding 1N NaS₂SO₃, the mixture was washed by Sat. NaHCO₃ and extracted with DCM. The organic phase was separated, dried over MgSO₄, filtered, concentrated down and the residue was purified by silica gel chromatography, eluting with 0-100% Hexane/EtOAc to give title compound. MS (m/z) 537.09 [M+H]+.

Step 2: Preparation of (1S,2R,5S)-8-(benzyloxy)-N-(2,4-difluorobenzyl)-4,4-difluoro-2,5-dimethyl-7,9-dioxo-2,3,4,5,7,9-hexahydro-1,6-methanopyrido[1,2-b][1,2,5]triazonine-10-carboxamide To a solution of (1S,2R,5S)-8-(benzyloxy)-N-(2,4-difluorobenzyl)-2,5-dimethyl-4,7,9-trioxo-2,3,4,5,7,9-hexahydro- 1,6-methanopyrido[1,2-b][1,2,5]triazonine-10-carboxamide (35 mg, 0.065 mmol) in DCM (2.0 mL) at 0° C., was added deoxofluor solution in toluene (50%, 0.072 mL, 0.20 mmol). The reaction was stirred at rt overnight. To the reaction mixture was added more deoxofluor solution in toluene (50%, 0.072 mL, 0.20 mmol) and stirred at rt. After one day, to the mixture was added more deoxofluor solution in toluene (50%, 0.072 mL, 0.20 mmol). The reaction mixture was stirred at rt for about 2 weeks. Quench the reaction by adding sat NaHCO₃, extracted with DCM. The organic phase was separated, dried over MgSO₄, filtered, concentrated down and the residue was purified by silica gel the title compound. MS (m/z) 469.26 [M+H]⁺. 1H NMR (400 MHz, Chloroform-d) δ 10.23 (t, J=5.7 Hz, 1H), 8.56 (s, 1H), 7.38 (td, J=8.7, 6.4 Hz, 1H), 6.90-6.78 (m, 2H), 5.06 (dp, J=14.1, 7.1 Hz, 1H), 4.83-4.56 (m, 4H), 3.37 (tt, J=7.9, 5.1 Hz, 1H), 2.42-2.21 (m, 2H), 1.52 (dd, J=7.0, 1.7 Hz, 3H), 1.44 (dd, J=7.3, 2.6 Hz, 3H).

Example 55: Preparation of (1S,2R,5S)-4-fluoro-8-hydroxy-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (C55)

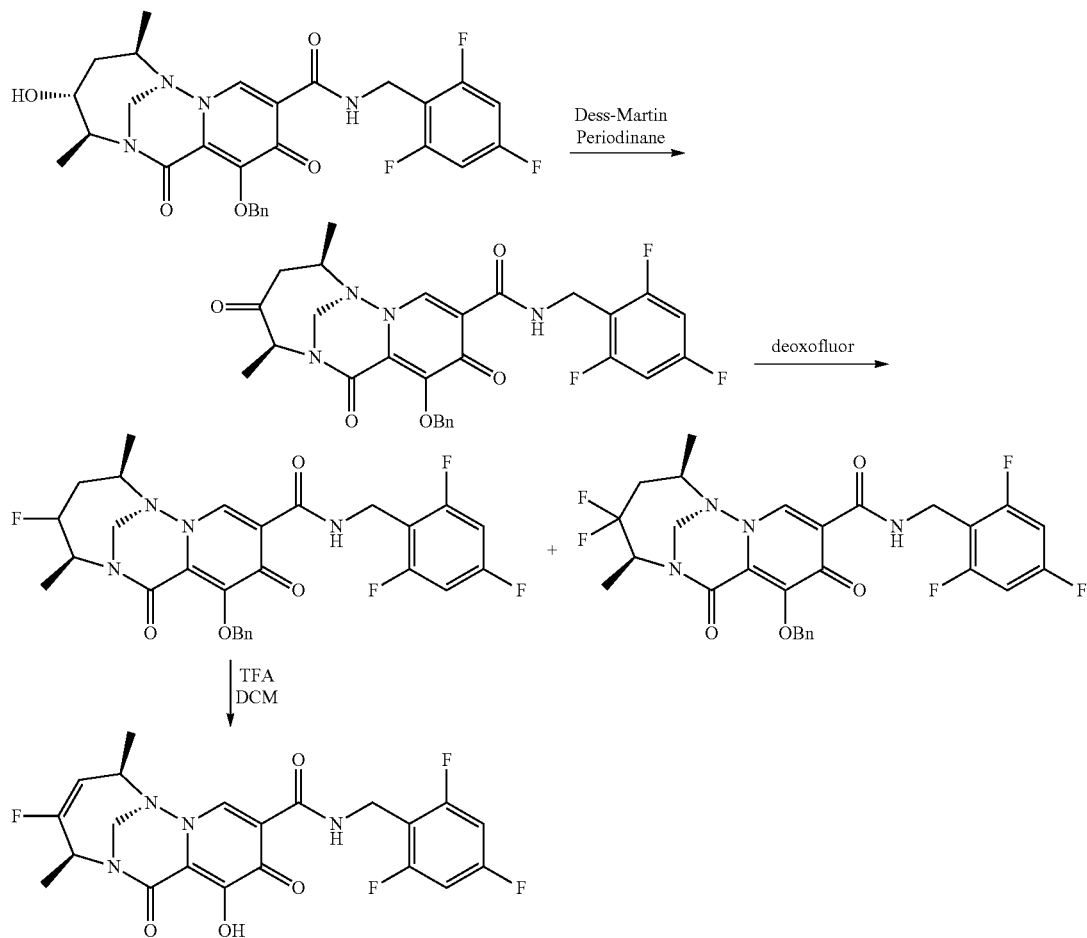

chromatography, eluting with 0-100% hexane/EtOAc to give title compound. MS (m/z) 559.09 [M+H]+.

Step 3: Preparation of (1S,2R,5S)—N-(2,4-difluorobenzyl)-4,4-difluoro-8-hydroxy-2,5-dimethyl-7,9-dioxo-2,3,4,5,7,9-hexahydro-1,6-methanopyrido[1,2-b][1,2,5]triazonine-10-carboxamide The solution of (1S,2R,5S)-8-(benzyloxy)-N-(2,4-difluorobenzyl)-4,4-difluoro-2,5-dimethyl-7,9-dioxo-2,3,4,5,7,9-hexahydro-1,6-methanopyrido[1,2-b][1,2,5]triazonine-10-carboxamide (13 mg, 0.023 mmol) in DCM (1 mL) and TFA (1 mL) was stirred at rt overnight. The reaction mixture was concentrated down, and the residue was purified by reverse phase HPLC, eluting with 5-100% acetonitrile/water to give (1S,2R,5S)-4-fluoro-8-hydroxy-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide was prepared in a similar method to prepare Example 54, except that (1S,2R,4R,5S)-8-(benzyloxy)-4-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide was used instead of (1S,2R,4R,5S)-8-(benzyloxy)-N-(2,4-difluorobenzyl)-4-hydroxy-2,5-dimethyl-7,9-dioxo-2,3,4,5,7,9-hexahydro-1,6-methanopyrido[1,2-b][1,2,5]triazonine-10-carboxamide and (1S,2R,5S)-8-(benzyloxy)-4-fluoro-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide was the minor product of fluorination reaction.

MS (m/z) 467.17 [M+H]⁺. 1H NMR (400 MHz, Methanol-d4) δ 10.47 (s, 1H), 8.45 (s, 1H), 6.92 (t, J=8.4 Hz, 2H), 5.53 (d, J=7.7 Hz, 1H), 5.33-5.14 (m, 2H), 4.79 (d, J=14.6 Hz, 1H), 4.69 (t, J=3.5 Hz, 2H), 3.92 (dq, J=6.9, 3.5 Hz, 1H), 1.49 (dd, J=7.3, 1.8 Hz, 3H), 1.44 (d, J=6.8 Hz, 3H).

Example 56: Preparation of (1S,2R,4R,5S)-4-(difluoromethyl)-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (C56)

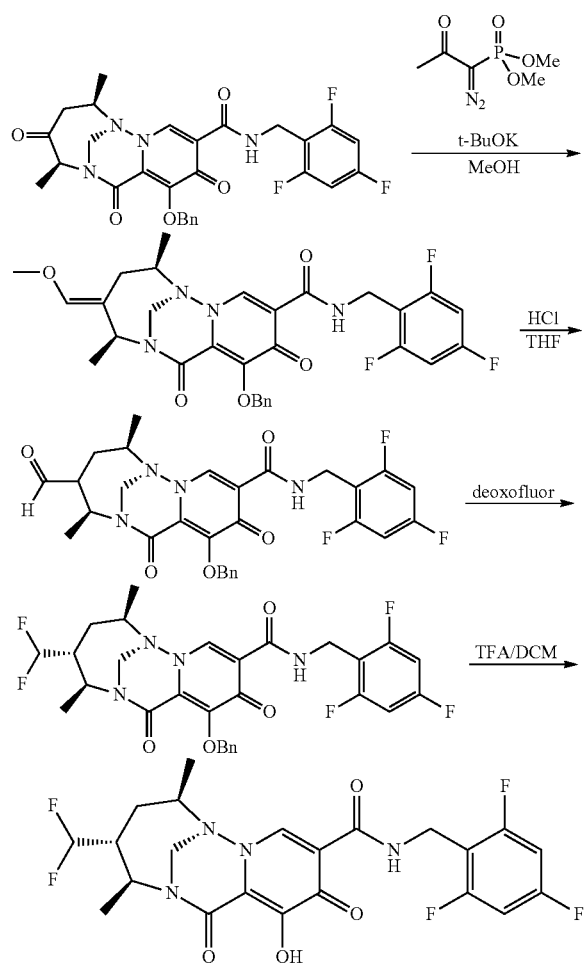

Step 1: Preparation of (1S,2R,5S,E)-8-(benzyloxy)-4-(methoxymethylene)-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide To a solution of (1S,2R,5S)-8-(benzyloxy)-2,5-dimethyl-4,7,9-trioxo-N-(2,4,6-trifluorobenzyl)-2,3,4,5,7,9-hexahydro-1,6-methanopyrido[1,2-b][1,2,5]triazonine-10-carboxamide (120 mg, 0.22 mmol) in methanol (1.5 mL) was added 1-diazo-1-dimethoxyphosphoryl-propan-2-one (96 mg, 0.5 mmol) and potassium tert-butoxide (85 mg, 0.76 mmol) at 0° C. The reaction mixture was stirred at 0° C. for 45 min. The reaction mixture was diluted with EtOAc, washed with sat. NaHCO₃, extracted with EtOAc, the organic phase was separated, dried over MgSO₄, filtered, concentrated down and purified by silica gel column, eluting with 0-100% hexane/EtOAc to give title compound. MS (m/z) 583.06 [M+H]⁺.

Step 2: Preparation of (1S,2R,5S)-8-(benzyloxy)-4-formyl-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (1S,2R,5S,E)-8-(benzyloxy)-4-(methoxymethylene)-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (30 mg, 0.051 mmol) was treated with THF (1.5 mL) and 1N HCl (1.5 mL) in a microwave vial. Then the vial was sealed and heated to 55° C. for 1 day. The reaction was quenched with saturated sodium bicarbonate solution and extracted into EtOAc. The organic phase was washed with brine, dried over sodium sulfate, filtered and concentrated. The residue was purified by silica gel chromatography, eluting 0-100% EtOAc/hexane. MS (m/z) 569.07 [M+H]+.

Step 3: Preparation of (1S,2R,4R,5S)-8-(benzyloxy)-4-(difluoromethyl)-2,5-dimethyl-7,9-dioxo-N-(2,4,6-trifluorobenzyl)-2, 3, 4, 5,7,9-hexahydro-1,6-methanopyrido[1,2-b][1,2,5]triazonine-10-carboxamide To a solution of (1S,2R,5S)-8-(benzyloxy)-4-formyl-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (15 mg, 0.026 mmol) in DCM (2.0 mL), was added deoxofluor in toluene (50%, 23 mg, 0.053 mmol) at 0° C. The reaction mixture was stirred at 0° C. for 1 h. The reaction was quenched by adding sat. NaHCO₃ slowly at 0° C., extracted into DCM. The organic phase was separated, dried over MgSO₄, filtered, concentrated down and the residue was purified by silica gel chromatography, 0-100% EtOAc/hexane to give title compound. MS (m/z) 591.06 [M+H]+.

Step 4: Preparation (1S,2R,4R,5S)-4-(difluoromethyl)-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide The solution of (1S,2R,4R,5S)-8-(benzyloxy)-4-(difluoromethyl)-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (5 mg, 0.0085 mmol) in DCM (0.5 mL) and TFA (0.5 mL) was stirred at rt overnight. The reaction mixture was concentrated down, and the residue was purified by reverse phase HPLC, eluting with 5-100% acetonitrile/water to give title compound. MS (m/z) 501.22 [M+H]⁺. 1H NMR (400 MHz, Methanol-d4) δ 8.49 (s, 1H), 6.98-6.85 (m, 2H), 6.02 (td, J=56.0, 2.8 Hz, 1H), 4.83-4.59 (m, 5H), 3.72 (d, J=7.6 Hz, 1H), 2.47 (td, J=8.3, 7.7, 2.8 Hz, 1H), 1.68 (dd, J=6.1, 3.3 Hz, 2H), 1.47 (d, J=6.8 Hz, 3H), 1.42 (d, J=7.2 Hz, 3H).

Example 57: Preparation of (1S,2R,4R,5S)-4-(fluoromethyl)-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (C57)

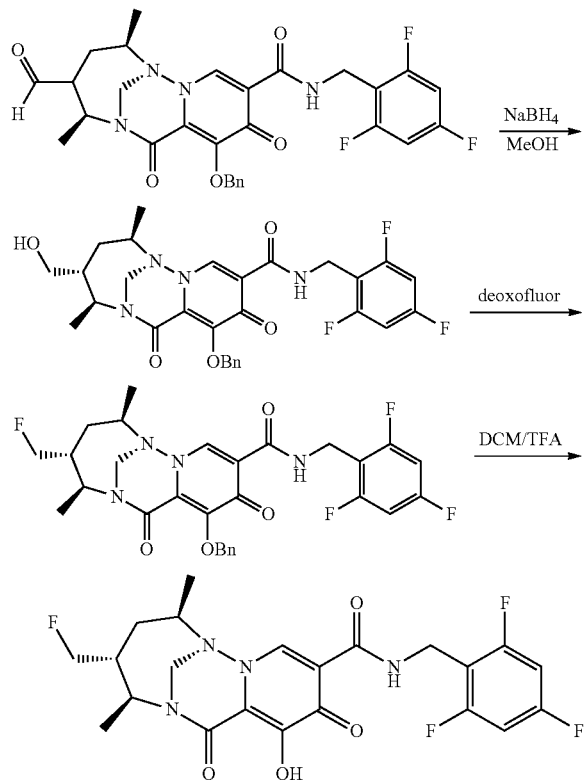

Step 1: Preparation of (1S,2R,4R,5S)-8-(benzyloxy)-4-(hydroxymethyl)-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide To a solution of (1S,2R,5S)-8-(benzyloxy)-4-formyl-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (20 mg, 0.035 mmol) in MeOH (5 mL) at 0° C. was added sodium borohydride (0.65 mg, 0.017 mmol) slowly. The reaction mixture was stirred at 0° C. for 15 min. After the reaction is finished, the reaction was quenched by adding sat. NaHCO$_3$, extracted with DCM. The organic was separated, dried over MgSO$_4$, filtered, concentrated down and the residue was used in next step without purification. MS (m/z) 571.22 [M+H]$^+$.

Steps 2-3: Preparation of (1S,2R,4R,5S)-4-(fluoromethyl)-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (1S,2R,4R,5S)-4-(fluoromethyl)-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide was prepared in the similar method to Example 56, except that (1S,2R,4R,5S)-8-(benzyloxy)-4-(hydroxymethyl)-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide was used instead of (1S,2R,5S)-8-(benzyloxy)-4-formyl-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide. MS (m/z) 483.29 [M+H]$^+$. 1H NMR (400 MHz, Methanol-d4) δ 8.48 (s, 1H), 6.97-6.85 (m, 2H), 4.87-4.72 (m, 2H), 4.69 (d, J=7.3 Hz, 2H), 4.59-4.30 (m, 3H), 3.71-3.63 (m, 1H), 2.28 (dddd, J=21.6, 16.5, 10.9, 5.9 Hz, 1H), 1.73 (ddd, J=14.5, 10.7, 3.4 Hz, 1H), 1.61 (dd, J=15.5, 3.2 Hz, 1H), 1.42 (dd, J=7.0, 4.4 Hz, 6H).

Example 58: Preparation of (1S,2S,4S,5S)—N-(2,4-difluorobenzyl)-4-fluoro-8-hydroxy-2,5-dimethyl-7,9-dioxo-2,3,4,5,7,9-hexahydro-1,6-methanopyrido[1,2-b][1,2,5]triazonine-10-carboxamide (C58)

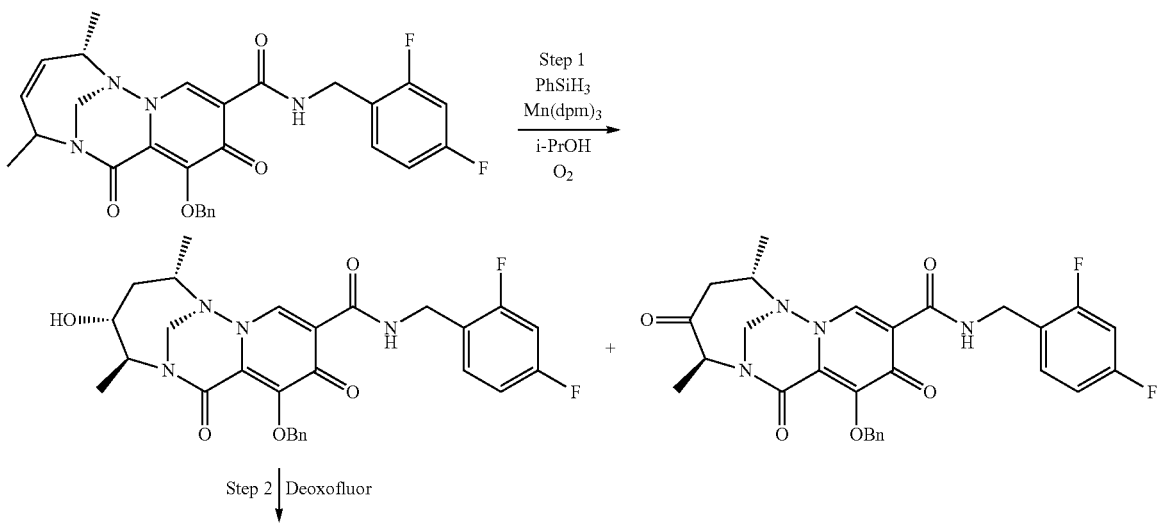

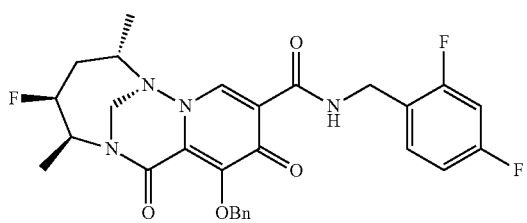

Step 3
TFA
Toluene

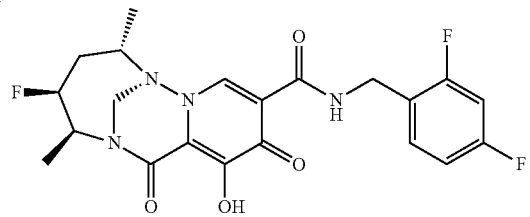

Step 1: Preparation of (1S,2S,4R,5S)-8-(benzyloxy)-N-(2,4-difluorobenzyl)-4-hydroxy-2,5-dimethyl-7,9-dioxo-2,3,4,5,7,9-hexahydro-1,6-methanopyrido[1,2-b][1,2,5]triazonine-10-carboxamide A solution of (1S,2S,5S)-8-(benzyloxy)-N-(2,4-difluorobenzyl)-2,5-dimethyl-7,9-dioxo-2,5,7,9-tetrahydro-1,6-methanopyrido[1,2-b][1,2,5]triazonine-10-carboxamide (0.576 mmol, 300 mg) from Example 30, in i-PrOH (14 mL) was sparged with argon for 10 minutes then treated with phenylsilane (2 equiv, 1.15 mmol, 140 uL) and tris(2,2,6,6-tetramethyl-3,5-heptanedionato)manganese(III) (0.03 equiv, 0.017 mmol, 10.5 mg) and affixed with a balloon of oxygen. The reaction mixture was stirred at room temperature overnight, at which point additional phenylsilane (1 equiv, 0.576 mmol, 70 uL) and tris(2,2,6,6-tetramethyl-3,5-heptanedionato)manganese(III) (0.03 equiv, 0.017 mmol, 10.5 mg) were added. After stirring for an additional 24 hours, the reaction mixture was quenched with 10% sodium thiosulfate and extracted into EtOAc (2×). The combined organic layers were washed with brine, dried with sodium sulfate, filtered and concentrated. The crude residue was purified by silica gel chromatography (0-100% EtOAc in hexanes) to afford (1S,2S,4R,5S)-8-(benzyloxy)-N-(2,4-difluorobenzyl)-4-hydroxy-2,5-dimethyl-7,9-dioxo-2,3,4,5,7,9-hexahydro-1,6-methanopyrido[1,2-b][1,2,5]triazonine-10-carboxamide and (1S,2S,5S)-8-(benzyloxy)-N-(2,4-difluorobenzyl)-2,5-dimethyl-4,7,9-trioxo-2,3,4,5,7,9-hexahydro-1,6-methanopyrido[1,2-b][1,2,5]triazonine-10-carboxamide. Alcohol: MS (m/z) 539.15 [M+H]+. Ketone: MS (m/z) 537.07 [M+H]+.

Step 2: Preparation of (1S,2S,4S,5S)-8-(benzyloxy)-N-(2,4-difluorobenzyl)-4-fluoro-2,5-dimethyl-7,9-dioxo-2,3,4,5,7,9-hexahydro-1,6-methanopyrido[1,2-b][1,2,5]triazonine-10-carboxamide A solution of (1S,2S,4R,5S)-8-(benzyloxy)-N-(2,4-difluorobenzyl)-4-hydroxy-2,5-dimethyl-7,9-dioxo-2,3,4,5,7,9-hexahydro-1,6-methanopyrido[1,2-b][1,2,5]triazonine-10-carboxamide (0.033 mmol, 18 mg) in CH2Cl2 (0.3 mL) in a polypropylene tube was treated with [Bis(2-methoxyethyl)amino]sulfur trifluoride (2.7 M in toluene, 2 equiv, 0.067 mmol, 25 uL) and sealed. After stirring at room temperature for one hour, the reaction mixture was carefully quenched with saturated sodium bicarbonate then extracted into EtOAc (3×). The combined organic layers were washed with brine, dried with sodium sulfate, filtered and concentrated. The crude residue was carried on directly without further purification. MS (m/z) 541.16 [M+H]+.

Step 3: Preparation of (1S,2S,4S,5S)—N-(2,4-difluorobenzyl)-4-fluoro-8-hydroxy-2,5-dimethyl-7,9-dioxo-2,3,4,5,7,9-hexahydro-1,6-methanopyrido[1,2-b][1,2,5]triazonine-10-carboxamide A solution of crude (1S,2S,4S,5S)-8-(benzyloxy)-N-(2,4-difluorobenzyl)-4-fluoro-2,5-dimethyl-7,9-dioxo-2,3,4,5,7, 9-hexahydro-1,6-methanopyrido[1,2-b][1,2,5]triazonine-10-carboxamide was treated with toluene (0.5 mL) and trifluoroacetic acid (0.5 mL) then stirred at room temperature for 7 hours. The reaction mixture was concentrated and purified by preparative HPLC (10-100% MeCN in water, 0.1% TFA) then lyophilized to afford the title compound. MS (m/z) 451.23 [M+H]+. 1H NMR (400 MHz, Methanol-d4) δ 8.47 (s, 1H), 7.44 (td, J=8.4, 6.3 Hz, 1H), 7.01-6.88 (m, 2H), 5.08 (ddd, J=48.4, 6.7, 5.0 Hz, 1H), 4.97-4.89 (m, 1H), 4.89-4.75 (m, 2H), 4.63 (s, 2H), 4.01 (ddt, J=14.6, 7.8, 3.9 Hz, 1H), 2.20 (ddd, J=16.1, 6.7, 1.8 Hz, 1H), 1.67 (ddd, J=35.4, 16.1, 11.7 Hz, 1H), 1.42 (dd, J=7.2, 2.3 Hz, 3H), 1.19 (d, J=7.0 Hz, 3H).

Example 59: Preparation of (1S,2S,5S)—N-(2,4-difluorobenzyl)-4,4-difluoro-8-hydroxy-2,5-dimethyl-7,9-dioxo-2,3,4,5,7,9-hexahydro-1,6-methanopyrido[1,2-b][1,2,5]triazonine-10-carboxamide C (59)

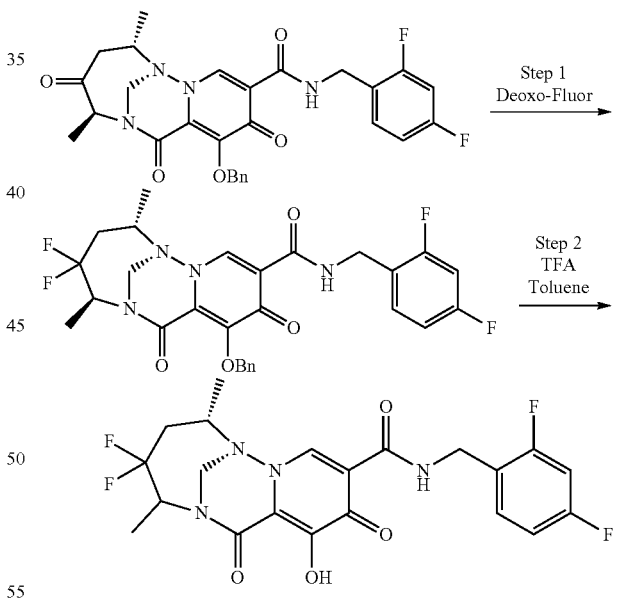

Step 1: Preparation of (1S,2S,5S)-8-(benzyloxy)-N-(2,4-difluorobenzyl)-4,4-difluoro-2,5-dimethyl-7,9-dioxo-2,3,4,5,7,9-hexahydro-1,6-methanopyrido[1,2-b][1,2,5]triazonine-10-carboxamide A solution of (1S,2S,5S)-8-(benzyloxy)-N-(2,4-difluorobenzyl)-2,5-dimethyl-4,7,9-trioxo-2,3,4,5,7,9-hexahydro-1,6-methanopyrido[1,2-b][1,2,5]triazonine-10-carboxamide (0.065 mmol, 35 mg), prepared according to Example 58, in CH2Cl2 (0.65 mL) in a polypropylene tube was treated with [Bis(2-methoxyethyl)amino]sulfur trifluoride (2.7 M in toluene, 2 equiv, 0.13 mmol, 50 uL) and sealed. After stirring at room temperature overnight, an additional portion [Bis(2-methoxyethyl)amino]sulfur trifluoride (2.7 M in toluene, 2 equiv, 0.13 mmol, 50 uL) was added. After an additional 3 hours, the reaction mixture was carefully quenched with saturated sodium bicarbonate then extracted into EtOAc (3×). The combined organic layers were washed with brine, dried with sodium sulfate, filtered and concentrated. The crude residue was carried on directly without further purification. MS (m/z) 559.10 [M+H]+.

Step 2: Preparation of (1S,2S,5S)—N-(2,4-difluorobenzyl)-4,4-difluoro-8-hydroxy-2,5-dimethyl-7,9-dioxo-2,3,4,5,7,9-hexahydro-1,6-methanopyrido[1,2-b][1,2,5]triazonine-10-carboxamide A solution of crude (1S,2S,5S)-8-(benzyloxy)-N-(2,4-difluorobenzyl)-4,4-difluoro-2,5-dimethyl-7,9-dioxo-2,3,4,5,7,9-hexahydro-1,6-methanopyrido[1,2-b][1,2,5]triazonine-10-carboxamide was treated with toluene (1 mL) and trifluoroacetic acid (1 mL) then stirred at room temperature for 7 hours. The reaction mixture was concentrated and purified by preparative HPLC (10-100% MeCN in water, 0.1% TFA) then lyophilized to afford the title compound. MS (m/z) 469.23 [M+H]+. 1H NMR (400 MHz, Methanol-d4) δ 8.45 (s, 1H), 7.50-7.41 (m, 1H), 7.03-6.91 (m, 2H), 5.08-4.96 (m, 1H), 4.97-4.79 (m, 2H), 4.65 (s, 2H), 4.04-3.92 (m, 1H), 2.41-2.10 (m, 2H), 1.45 (dd, J=7.2, 2.0 Hz, 3H), 1.23 (d, J=6.9 Hz, 3H).

Example 60: Preparation of (4R,5S,13S)—N-(2,4-difluorobenzyl)-10-hydroxy-4,13-dimethyl-9,11-dioxo-4,9,11,13-tetrahydro-1H-5,12-methanoimidazo[4,5-g]pyrido[1,2-b][1,2,5]triazonine-8-carboxamide (C60)

Step 1, Preparation of (1S,2R,3R,4S,5S)-8-(benzyloxy)-N-(2,4-difluorobenzyl)-3,4-dihydroxy-2,5-dimethyl-7,9-dioxo-2,3,4,5,7,9-hexahydro-1,6-methanopyrido[1,2-b][1,2,5]triazonine-10-carboxamide A solution of (1S,2R,5S)-8-(benzyloxy)-N-(2,4-difluorobenzyl)-2,5-dimethyl-7,9-dioxo-2,5,7,9-tetrahydro-1,6-methanopyrido[1,2-b][1,2,5]triazonine-10-carboxamide (0.48 mmol, 250 mg), prepared according to Example 29, in acetone (10 mL) and water (1.25 mL) was cooled to 0° C. then treated with a solution of N-methylmorpholine N-oxide (50 wt % in water, 1.1 equiv, 0.528 mmol, 110 uL) and a solution of osmium tetroxide (2.5 wt % in tert-butanol, 0.04 equiv, 0.019 mmol, 195 uL). The reaction mixture was allowed to slowly warm to room temperature and stirred for 4 days then quenched with 10% aqueous sodium sulfite and extracted into 1/1 EtOAc/n-BuOH (2×). The combined organic layers were washed with saturated aqueous sodium bicarbonate and brine then dried with sodium sulfate, filtered and concentrated. The crude material was purified by silica gel chromatography (0-20% MeOH in DCM). MS (m/z) 555.12 [M+H]+.

Step 2: Preparation of (1S,2R,5S)-8-(benzyloxy)-N-(2,4-difluorobenzyl)-2,5-dimethyl-3,4,7,9-tetraoxo-2,3,4,5,7,9-hexahydro-1,6-methanopyrido[1,2-b][1,2,5]triazonine-10-carboxamide A solution of (1S,2R,3R,4S,5S)-8-(benzyloxy)-N-(2,4-difluorobenzyl)-3,4-dihydroxy-2,5-dimethyl-7,9-dioxo-2,3,4,5,7,9-hexahydro-1,6-methanopyrido[1,2-b][1,2,5]triazonine-10-carboxamide (0.283 mmol, 157 mg) in $CH_2Cl_2$ (3 mL) was treated with Dess-Martin periodinane (3 equiv, 0.85 mmol, 360 mg). The reaction mixture was quenched

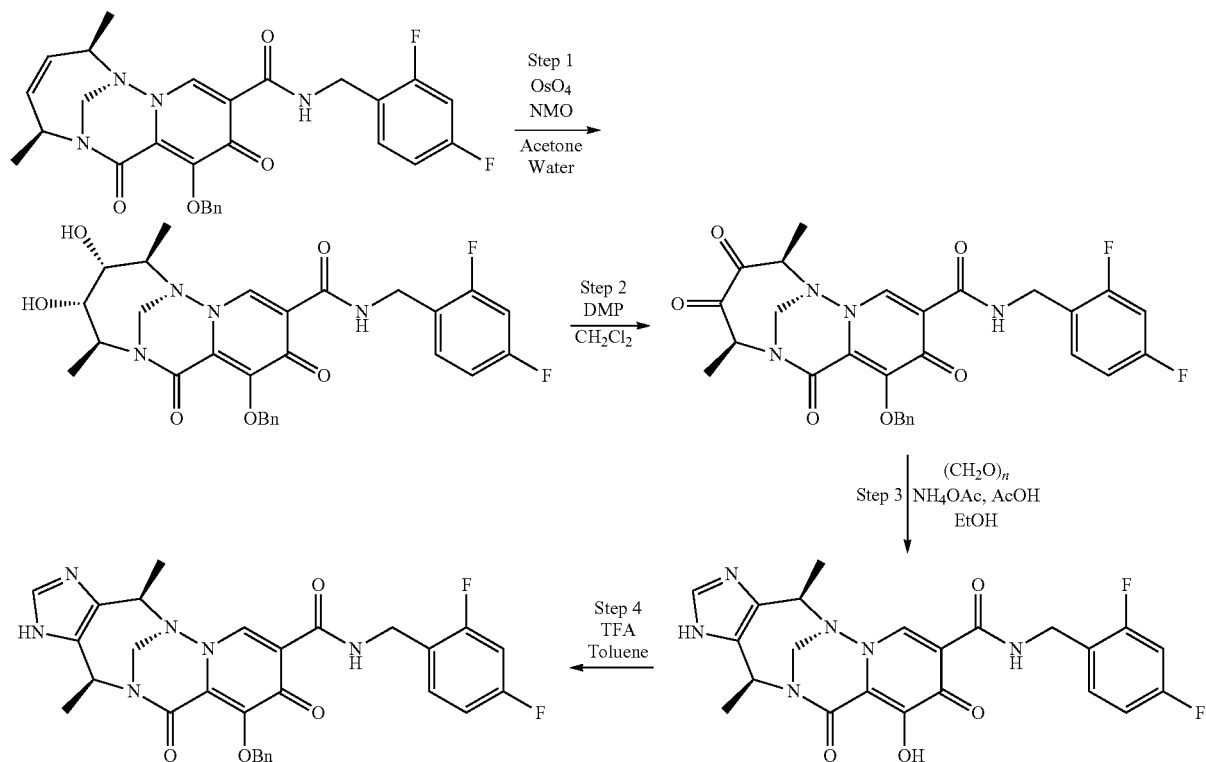

with 10% sodium thiosulfate, extracted into EtOAc, washed with saturated sodium bicarbonate (3×) and brine, then dried with sodium sulfate, filtered and concentrated. The crude material was purified by silica gel chromatography (0-20% MeOH in DCM). MS (m/z) 569.18 [M+H$_3$O]+.

Step 3: Preparation of (4R,5S,13S)-10-(benzyloxy)-N-(2,4-difluorobenzyl)-4,13-dimethyl-9,11-dioxo-4,9,11,13-tetrahydro-1H-5,12-methanoimidazo[4,5-g]pyrido[1,2-b][1,2,5]triazonine-8-carboxamide A solution of (1S,2R,5S)-8-(benzyloxy)-N-(2,4-difluorobenzyl)-2,5-dimethyl-3,4,7,9-tetraoxo-2,3,4,5,7,9-hexahydro-1,6-methanopyrido[1,2-b][1,2,5]triazonine-10-carboxamide (0.054 mmol, 30 mg) in EtOH (0.5 mL) was treated with paraformaldehyde (1.5 equiv, 0.082 mmol, 7.4 mg), ammonium acetate (3 equiv, 0.16 mmol, 12.6 mg) and acetic acid (0.5 equiv, 0.027 mmol, 1.6 uL) then stirred at room temperature for 72 hours. The reaction was then quenched with saturated aqueous sodium bicarbonate and extracted into EtOAc (3×). The combined organic layers were dried with sodium sulfate, filtered and concentrated. The crude residue was carried on to the next step without further purification. MS (m/z) 561.23 [M+H]+.

Step 4: Preparation of (4R,5S,13S)—N-(2,4-difluorobenzyl)-10-hydroxy-4,13-dimethyl-9,11-dioxo-4,9,11,13-tetrahydro-1H-5,12-methanoimidazo[4,5-g]pyrido[1,2-b][1,2,5]triazonine-8-carboxamide A solution of crude (4R,5S,13S)-10-(benzyloxy)-N-(2,4-difluorobenzyl)-4,13-dimethyl-9,11-dioxo-4,9,11,13-tetrahydro-1H-5,12-methanoimidazo[4,5-g]pyrido[1,2-b][1,2,5]triazonine-8-carboxamide was treated with toluene (1 mL) and trifluoroacetic acid (1 mL) then stirred at room temperature overnight. The reaction mixture was concentrated and purified by preparative HPLC (10-100% MeCN in water, 0.1% TFA) then lyophilized to afford the title compound. MS (m/z) 471.21 [M+H]+. $^1$H NMR (400 MHz, Acetonitrile-d3) δ 10.12 (t, J=5.3 Hz, 1H), 8.47 (s, 1H), 8.32 (s, 1H), 7.47-7.37 (m, 1H), 7.01-6.90 (m, 2H), 5.86 (q, J=7.0 Hz, 1H), 5.06 (d, J=14.9 Hz, 1H), 4.79 (d, J=14.9 Hz, 1H), 4.59 (d, J=6.0 Hz, 2H), 4.55-4.45 (m, 1H), 1.65 (d, J=6.8 Hz, 3H), 1.60 (d, J=7.2 Hz, 3H).

Example 61: Preparation of (1S,2R,3S,4R,5S)-8-hydroxy-3,4-dimethoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (C61)

(1S,2R,3S,4R,5S)-8-(benzyloxy)-3,4-dimethoxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (20 mg, 0.033 mmol), prepared in a similar manner as Example 32, was dissolved in CH$_3$CN (1.2 mL) added MgBr$_2$ (18.4 mg, 0.1 mmol) and stirred at 50° C. for 2 h. The reaction was concentrated down and purified via preparative HPLC, eluting 10-100% acetonitrile (0.1% TFA) in water (0.1% TFA) to give to the title compound. MS (m/z): 511.1 [M+H]+. $^1$H NMR (400 MHz, Acetonitrile-d$_3$) δ 10.44 (s, 1H), 8.40 (s, 1H), 6.98-6.73 (m, 2H), 4.67-4.56 (m, 2H), 4.50 (t, J=14.8 Hz, 2H), 4.21-4.16 (m, 1H), 3.80 (d, J=7.1 Hz, 1H), 3.61 (d, J=3.1 Hz, 1H), 3.46 (d, J=8.8 Hz, 1H), 3.36 (s, 3H), 3.09 (s, 3H), 1.37 (t, J=7.6 Hz, 6H).

Example 62: Preparation of (1S,2R,5S)—N-(2,4-difluorobenzyl)-8-hydroxy-2,3,5-trimethyl-7,9-dioxo-2,5,7,9-tetrahydro-1,6-methanopyrido[1,2-b][1,2,5]triazonine-10-carboxamide (C62)

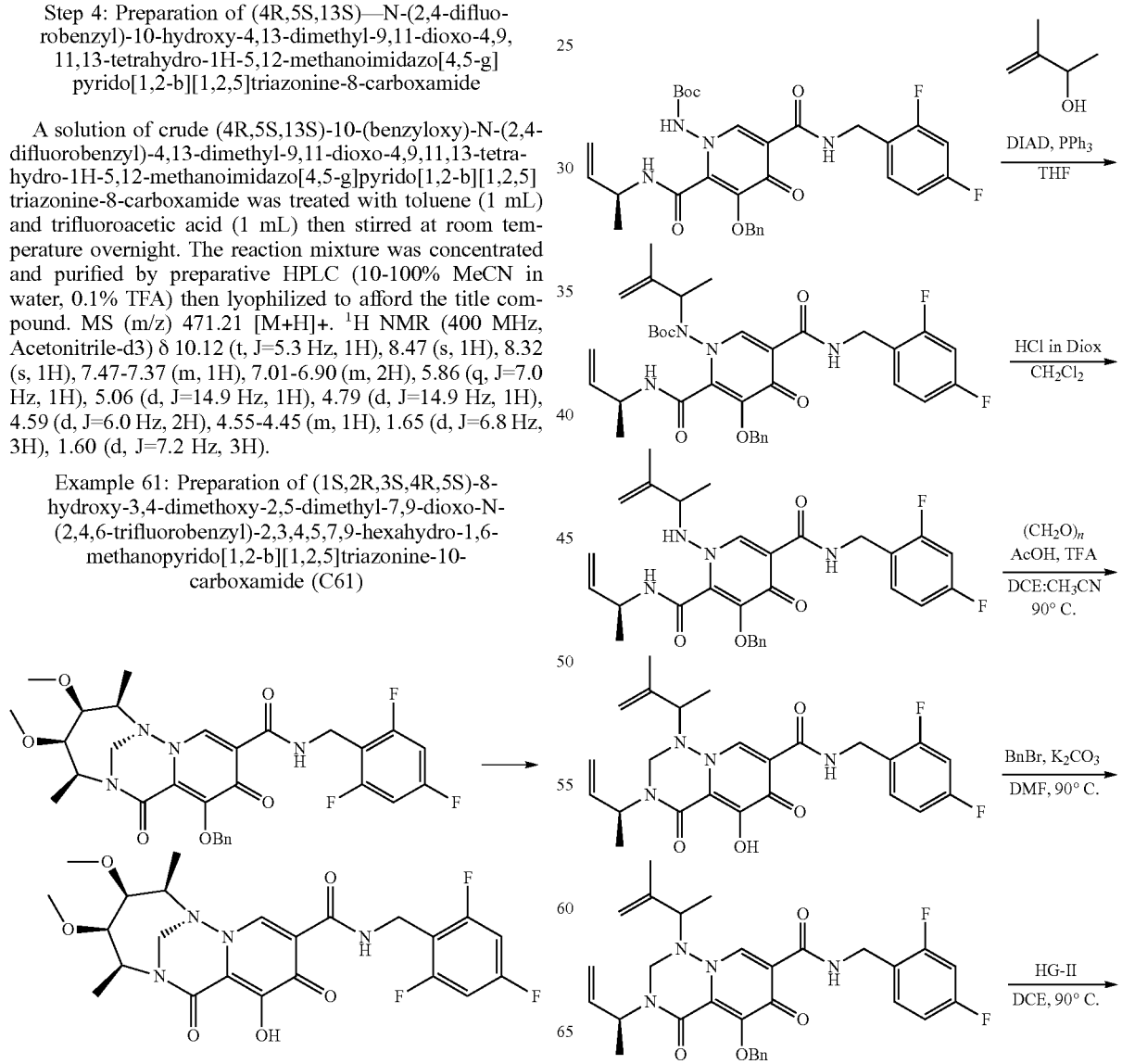

-continued

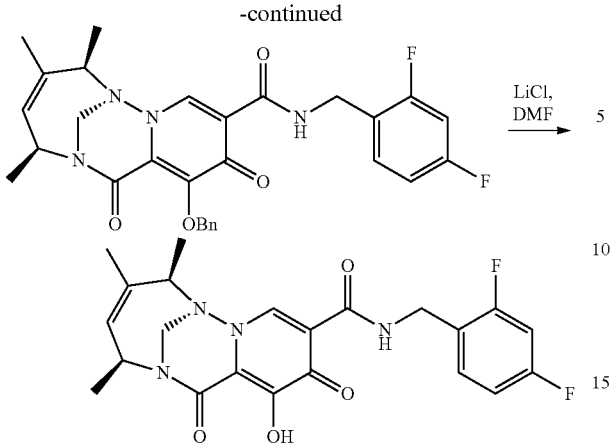

Step 1: Preparation of tert-butyl (3-(benzyloxy)-2-(((S)-but-3-en-2-yl)carbamoyl)-5-((2,4-difluorobenzyl)carbamoyl)-4-oxopyridin-1(4H)-yl)(3-methylbut-3-en-2-yl)carbamate tert-butyl (S)-(3-(benzyloxy)-2-(but-3-en-2-ylcarbamoyl)-5-((2,4-difluorobenzyl)carbamoyl)-4-oxopyridin-1(4H)-yl)carbamate (700 mg, 1.20 mmol), prepared according to Example 29, was dissolved in THF (6.0 mL). 3-Methylbut-3-en-2-ol (186 mg, 2.16 mmol) and triphenyl phosphine (551 mg, 2.10 mmol) were added. Diisopropyl azodicarboxylate (0.423 mL, 2.04 mmol) was added over a few minutes at ambient temperature. After 1 hour the reaction was concentrated by rotary evaporation and the residue was purified by flash chromatography (hexanes:EtOAc) yielding tert-butyl (3-(benzyloxy)-2-(((S)-but-3-en-2-yl)carbamoyl)-5-((2,4-difluorobenzyl)carbamoyl)-4-oxopyridin-1(4H)-yl)(3-methylbut-3-en-2-yl)carbamate. ES/MS: 651.023 (M+H+).

Step 2: Preparation of 3-(benzyloxy)-N2-((S)-but-3-en-2-yl)-N5-(2,4-difluorobenzyl)-1-((3-methylbut-3-en-2-yl)amino)-4-oxo-1,4-dihydropyridine-2,5-dicarboxamide tert-butyl (3-(benzyloxy)-2-(((S)-but-3-en-2-yl)carbamoyl)-5-((2,4-difluorobenzyl)carbamoyl)-4-oxopyridin-1(4H)-yl)(3-methylbut-3-en-2-yl)carbamate (0.780 g, 1.14 mmol) was dissolved in DCM (6.0 mL) and hydrogen chloride in 1,4-dioxane (4.00 mol/L, 1.42 mL, 5.69 mmol) was added. The reaction was stirred at ambient temperature for 21 hours. The reaction was concentrated and purified by flash chromatography (hexanes:EtOAc) yielding 3-(benzyloxy)-N2-((S)-but-3-en-2-yl)-N5-(2,4-difluorobenzyl)-1-((3-methylbut-3-en-2-yl)amino)-4-oxo-1,4-dihydropyridine-2,5-dicarboxamide. ES/MS: 551.183 (M+H+).

Step 3: Preparation of 3-((S)-but-3-en-2-yl)-N-(2,4-difluorobenzyl)-5-hydroxy-1-(3-methylbut-3-en-2-yl)-4,6-dioxo-2,3,4,6-tetrahydro-1H-pyrido[2,1,2,4]triazine-7-carboxamide 3-(benzyloxy)-N2-((S)-but-3-en-2-yl)-N5-(2,4-difluorobenzyl)-1-((3-methylbut-3-en-2-yl)amino)-4-oxo-1,4-dihydropyridine-2,5-dicarboxamide (0.630 g, 1.14 mmol) was dissolved in 1:1 DCE:ACN (3.0 mL). Paraformaldehyde (309 mg, 3.43 mmol), acetic acid (0.463 mL, 8.01 mmol), and trifluoroacetic acid (0.443 mL, 5.72 mmol) were added to the solution. The reaction was heated to 90° C. overnight (~12 hours). The reaction mixture was cooled to ambient temperature and concentrated most of the way by rotary evaporation. The resultant residue was quenched with sat. aq. NaHCO$_3$ and extracted with EtOAc (3×10 mL). The organic layers were combined and washed with brine (1×20 mL) then dried with sodium sulfate before concentration by rotary evaporation. The residue was purified by flash chromatography (hexanes:EtOAc) yielding 3-((S)-but-3-en-2-yl)-N-(2,4-difluorobenzyl)-5-hydroxy-1-(3-methylbut-3-en-2-yl)-4,6-dioxo-2,3,4,6-tetrahydro-1H-pyrido[2,1-f][1,2,4]triazine-7-carboxamide. ES/MS: 473.252 (M+H+).

Step 4: Preparation of 5-(benzyloxy)-3-((S)-but-3-en-2-yl)-N-(2,4-difluorobenzyl)-1-(3-methylbut-3-en-2-yl)-4,6-dioxo-2,3,4,6-tetrahydro-1H-pyrido[2,1-f][1,2,4]triazine-7-carboxamide 3-((S)-but-3-en-2-yl)-N-(2,4-difluorobenzyl)-5-hydroxy-1-(3-methylbut-3-en-2-yl)-4,6-dioxo-2,3,4,6-tetrahydro-1H-pyrido[2,1-f][1,2,4]triazine-7-carboxamide (117 mg, 0.247 mmol) was dissolved in DMF (2.5 mL). Potassium carbonate (0.205 g, 0.00148 mol) was added followed by benzyl bromide (0.106 g, 0.617 mmol). The reaction was heated at 90° C. for 4 hours. The mixture was cooled to ambient temperature and diluted with water (5 mL). The reaction was extracted with EtOAc (3×5 mL). The organic layers were combined and washed with brine (2×10 mL), dried with sodium sulfate and concentrated by rotary evaporation. The residue was purified by flash chromatography (hexanes:EtOAc) yielding 5-(benzyloxy)-3-((S)-but-3-en-2-yl)-N-(2,4-difluorobenzyl)-1-(3-methylbut-3-en-2-yl)-4,6-dioxo-2,3,4,6-tetrahydro-1H-pyrido[2,1-f][1,2,4]triazine-7-carboxamide. ES/MS: 563.183 (M+H+).

Step 5: Preparation of (S,2R,5S)-8-(benzyloxy)-N-(2,4-difluorobenzyl)-2,3,5-trimethyl-7,9-dioxo-2,5,7,9-tetrahydro-1,6-methanopyrido[1,2-b][1,2,5]triazonine-10-carboxamide 5-(benzyloxy)-3-((S)-but-3-en-2-yl)-N-(2,4-difluorobenzyl)-1-(3-methylbut-3-en-2-yl)-4,6-dioxo-2,3,4,6-tetrahydro-1H-pyrido[2,1-f][1,2,4]triazine-7-carboxamide (0.117 g, 0.207 mmol) was dissolved in DCE (6 mL) and Hoveyda-Grubbs Catalyst 2nd Generation (51.9 mg, 0.0828 mmol) was added. The mixture was sparged with Ar three times then heated to 90° C. overnight (~12 h). The mixture was cooled to ambient temperature and concentrated by rotary evaporation. Purification by flash chromatography (Hexanes:EtOAc) yielded (1S,2R,5S)-8-(benzyloxy)-N-(2,4-difluorobenzyl)-2,3,5-trimethyl-7,9-dioxo-2,5,7,9-tetrahydro-1,6-methanopyrido[1,2-b][1,2,5]triazonine-10-carboxamide. ES/MS: 535.102 (M+H+).

Step 6: Preparation of (1S,2R,5S)—N-(2,4-difluorobenzyl)-8-hydroxy-2,3,5-trimethyl-7,9-dioxo-2,5,7,9-tetrahydro-1,6-methanopyrido[1,2-b][1,2,5]triazonine-10-carboxamide (1S,2R,5S)-8-(benzyloxy)-N-(2,4-difluorobenzyl)-2,3,5-trimethyl-7,9-dioxo-2,5,7,9-tetrahydro-1,6-methanopyrido[1,2-b][1,2,5]triazonine-10-carboxamide (3.10 mg, 5.80 µmol) was dissolved in DMF (500 µL) and lithium chloride (7.00 mg, 165 µmol) was added. The reaction was heated overnight at 90° C. The mixture was cooled to ambient temperature, filtered and purified by reverse phase HPLC (water:ACN with 0.1% TFA) to yield (1S,2R,5S)—N-(2,4-difluorobenzyl)-8-hydroxy-2,3,5-trimethyl-7,9-dioxo-2,5,7,9-tetrahydro-1,6-methanopyrido[1,2-b][1,2,5]triazonine-10-carboxamide. ES/MS: 445.213 (M+H+). 1H NMR (400 MHz, Acetonitrile-d3) δ 10.17 (s, 1H), 8.34 (s, 1H), 7.41 (q, J=9.0, 8.3 Hz, 1H), 7.09-6.80 (m, 2H), 5.51 (d, J=2.3 Hz, 1H), 5.15 (d, J=7.1 Hz, 1H), 5.07 (d, J=14.5 Hz, 1H), 4.72-4.40 (m, 3H), 3.83 (d, J=6.9 Hz, 1H), 1.86-1.68 (m, 3H), 1.28 (dd, J=15.0, 7.0 Hz, 6H). 19F NMR (376 MHz, Acetonitrile-d3) δ–114.02 (p, J=7.8, 7.4 Hz), –115.37--118.64 (m).

Example 63: Preparation of (1S,2R,5S)—N-(3-chloro-2,4-difluorobenzyl)-8-hydroxy-2,5-dimethyl-7,9-dioxo-2,5,7,9-tetrahydro-1,6-methanopyrido[1,2-b][1,2,5]triazonine-10-carboxamide (C63)

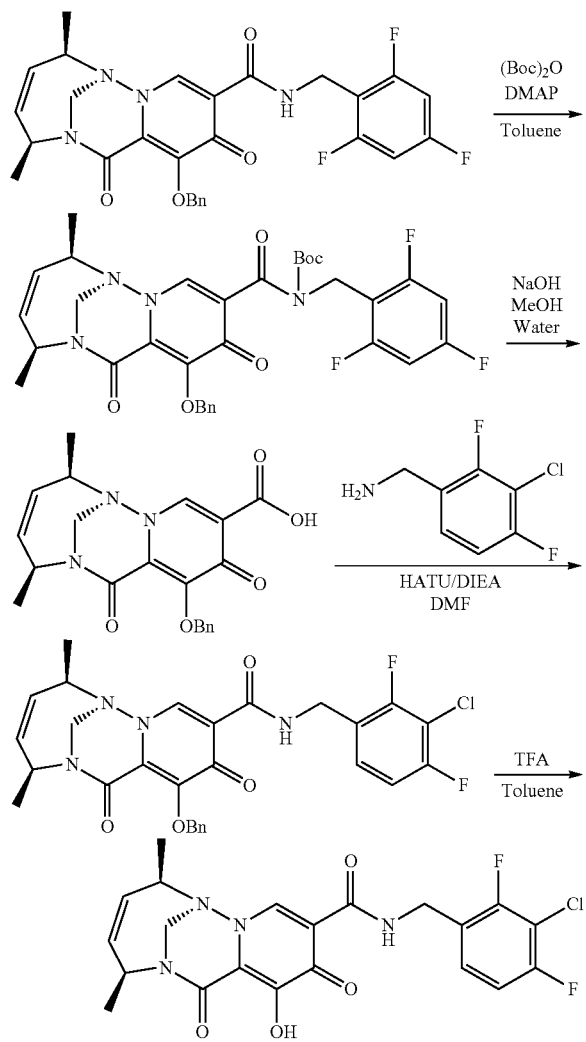

Step 1: Preparation of tert-butyl ((1S,2R,5S)-8-(benzyloxy)-2,5-dimethyl-7,9-dioxo-2,5,7,9-tetrahydro-1,6-methanopyrido[1,2-b][1,2,5]triazonine-10-carbonyl)(2,4,6-trifluorobenzyl)carbamate (1S,2R,5S)-8-(Benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (837 mg, 1.55 mmol) was dissolved in toluene (12 mL) at rt. DMAP (570 mg, 4.66 mmol) and (Boc)2O (1.355 g, 6.22 mmol) were added sequentially. The reaction mixture was heated with stirring at 110° C. for 2 h and was then concentrated to dryness. Residue was purified with silica gel column with 0-100% EtOAc/Hex to afford product. MS (m/z): 639.2 [M+H]+.

Step 2: Preparation of (1S,2R,5S)-8-(benzyloxy)-2,5-dimethyl-7,9-dioxo-2,5,7,9-tetrahydro-1,6-methanopyrido[1,2-b][1,2,5]triazonine-10-carboxylic acid Tert-butyl ((1S,2R,5S)-8-(benzyloxy)-2,5-dimethyl-7,9-dioxo-2,5,7,9-tetrahydro-1,6-methanopyrido[1,2-b][1,2,5]triazonine-10-carbonyl)(2,4,6-trifluorobenzyl)carbamate (635 mg, 0.994 mmol) was dissolved in MeOH (12 mL) and then water (6 mL) was added. Then NaOH (1 M, 3.5 mL, 3.4 mmol) was added dropwise. The resulting reaction mixture was stirred at rt for 17 h. Reaction mixture was then diluted with water (20 mL) and was acidified to pH=3 with 1N HCl. EtOAc (50 mL) was added for extraction. Organic phase was separated and washed with brine (50 mL). Organic phase was separated and dried over Na2SO4. Filtration and concentration afforded a crude product which was purified by reverse phase preparative HPLC with 0-100% acetonitrile in water with 0.1% TFA to afford the desired product. MS (m/z): 396.1 [M+H]+.

Step 3: Preparation of (1S,2R,5S)-8-(Benzyloxy)-N-(3-chloro-2,4-difluorobenzyl)-2,5-dimethyl-7,9-dioxo-2,5,7,9-tetrahydro-1,6-methanopyrido[1,2-b][1,2,5]triazonine-10-carboxamide (1S,2R,5S)-8-(Benzyloxy)-2,5-dimethyl-7,9-dioxo-2,5,7,9-tetrahydro-1,6-methanopyrido[1,2-b][1,2,5]triazonine-10-carboxylic acid (13 mg, 0.0329 mmol) was dissolved in DMF (1 mL) at rt. DIEA (17 mg, 0.132 mmol) was added under argon atmosphere. The resulting reaction mixture was cooled to 0° C. Then HATU (18.8 mg, 0.0493 mmol) was added. The resulting reaction mixture was then warmed up to rt and stirred at rt for 1 h. To this reaction mixture, was added a solution of (3-chloro-2,4-difluorophenyl)methanamine (8.76 mg, 0.0493 mmol) in DMF (0.5 mL). The reaction mixture was then stirred at rt for 17 h. Reaction mixture was diluted with EtOAc (10 mL) and was treated with a mixture of saturated aqueous NH4Cl solution (10 mL) and water (10 mL). Organic phase was then washed with water (10 mL) and saturated brine (10 mL) sequentially. Organic phase was then separated and concentrated. The residue was purified on silica gel column with 0-100% EtOAc/Hex to afford product. MS (m/z): 555.2 [M+H]+.

Step 4: Preparation of (1S,2R,5S)—N-(3-chloro-2,4-difluorobenzyl)-8-hydroxy-2,5-dimethyl-7,9-dioxo-2,5,7,9-tetrahydro-1,6-methanopyrido[1,2-b][1,2,5]triazonine-10-carboxamide (1S,2R,5S)-8-(Benzyloxy)-N-(3-chloro-2,4-difluorobenzyl)-2,5-dimethyl-7,9-dioxo-2,5,7,9-tetrahydro-1,6-methanopyrido[1,2-b][1,2,5]triazonine-10-carboxamide (17 mg, 0.0306 mmol) was dissolved in toluene (2 mL) at rt. TFA (2 mL) was added carefully with stirring. The resulting reaction mixture was stirred at rt for 17 h. Reaction mixture was then concentrated to dryness. The residue was taken up in MeOH and was purified with reverse phase prep-HPLC with 0-100% CH3CN in water with 0.1% TFA to afford the desired product. Lyophilization afforded product. MS (m/z): 465.2 [M+H]+. 1H NMR (400 MHz, CD3CN) δ 10.26 (s, 1H), 8.39 (s, 1H), 7.38 (td, J=8.4, 6.1 Hz, 1H), 7.10 (td, J=8.7, 1.8 Hz, 1H), 5.66 (dt, J=11.4, 2.4 Hz, 1H), 5.46-5.31 (m, 2H), 5.02 (d, J=14.4 Hz, 1H), 4.64 (m, 2H), 4.58 (d, J=14.4 Hz, 1H), 3.84 (tq, J=6.7, 3.6 Hz, 1H), 1.35 (dd, J=7.1, 2.3 Hz, 6H).

Example 64: Preparation of (1S,2R,5R)-8-hydroxy-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (C64)

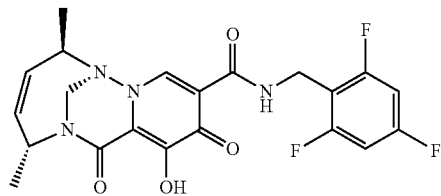

(1S,2R,5R)-8-hydroxy-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide was prepared in a similar manner as Example 24, except using (R)-but-3-en-2-amine hydrochloride instead of (S)-but-3-en-2-amine hydrochloride in Step 4. MS (m/z): 449.2 [M+H]$^+$. 1H NMR (400 MHz, CD3CN) δ 10.31 (s, 1H), 8.39 (s, 1H), 6.93-6.81 (m, 2H), 5.80 (ddd, J=11.7, 2.7, 1.9 Hz, 1H), 5.45 (ddd, J=11.7, 4.1, 2.4 Hz, 1H), 4.82-4.55 (m, 4H), 4.32 (dtt, J=7.4, 5.0, 2.5 Hz, 1H), 4.01 (ddt, J=6.8, 4.5, 2.2 Hz, 1H), 1.79 (d, J=7.5 Hz, 3H), 1.40 (d, J=7.0 Hz, 3H).

Example 65: Preparation of (1S,2R,5R)-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (C65)

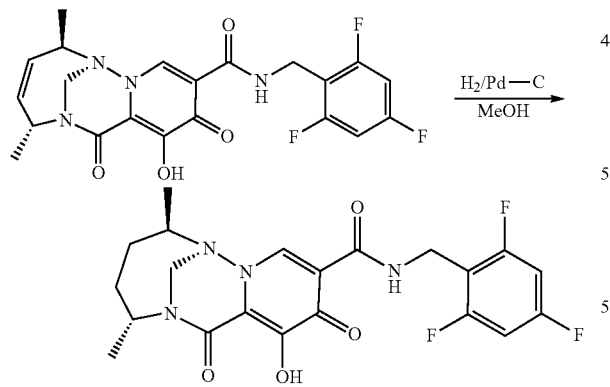

(1S,2R,5R)-8-Hydroxy-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (25 mg, 0.0558 mmol), prepared according to Example 64, was dissolved in MeOH (10 mL). Pd/C (10%) (12 mg) was added. Hydrogenolysis was performed with H$_2$ balloon at rt for 7 h. Reaction mixture was filtered through celite. Filtrate was collected and concentrated to dryness. The residue was taken up in MeOH and was purified with reverse phase prep-HPLC with 0-100% CH$_3$CN in water with 0.1% TFA to afford the desired product. Lyophilization afford product. MS (m/z): 451.2 [M+H]. 1H NMR (400 MHz, CD3CN) δ 10.30 (s, 1H), 8.38 (s, 1H), 6.87 (t, J=8.5 Hz, 2H), 4.75-4.51 (m, 4H), 3.60-3.42 (m, 1H), 3.00 (dq, J=12.2, 6.4 Hz, 1H), 1.59-1.76 (m, 4H), 1.73 (d, J=7.0 Hz, 3H), 1.30 (d, J=6.5 Hz, 3H).

Example 66: Preparation of (1R,2S,5S)-8-hydroxy-2,5-dimethyl-7,9-dioxo-N-(2,4,6-trifluorobenzyl)-2,3,4,5,7,9-hexahydro-1,6-methanopyrido[1,2-b][1,2,5]triazonine-10-carboxamide (C66)

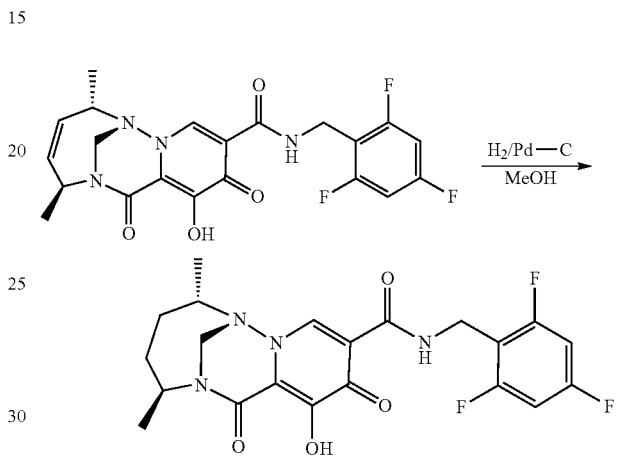

(1R,2S,5S)-8-(benzyloxy)-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (16 mg, 0.0297 mmol), prepared according to Example 24, was dissolved in MeOH (10 mL). Pd—C(10%) (12 mg) was added. Hydrogenolysis was performed with H$_2$ balloon at rt for 7 h. Reaction mixture was filtered through celite. Filtrate was collected and concentrated to dryness. The residue was taken up in MeOH and was purified with reverse phase prep-HPLC with 0-100% CH$_3$CN in water with 0.1% TFA to afford the desired product. Lyophilization afford product. MS (m/z): 451.2 [M+H]. 1H NMR (400 MHz, CD$_3$CN) δ 10.30 (s, 1H), 8.38 (s, 1H), 6.87 (t, J=8.5 Hz, 2H), 4.75-4.51 (m, 4H), 3.60-3.42 (m, 1H), 3.00 (dq, J=12.2, 6.4 Hz, 1H), 1.59-1.76 (m, 4H), 1.73 (d, J=7.0 Hz, 3H), 1.30 (d, J=6.5 Hz, 3H).

Example 67: Preparation of (1S,2R,5R)—N-(2,4-difluorobenzyl)-8-hydroxy-2,5-dimethyl-7,9-dioxo-2,3,4,5,7,9-hexahydro-1,6-methanopyrido[1,2-b][1,2,5]triazonine-10-carboxamide (C67)

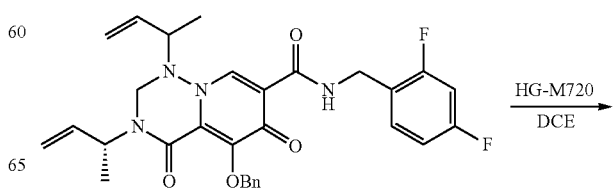

227
-continued

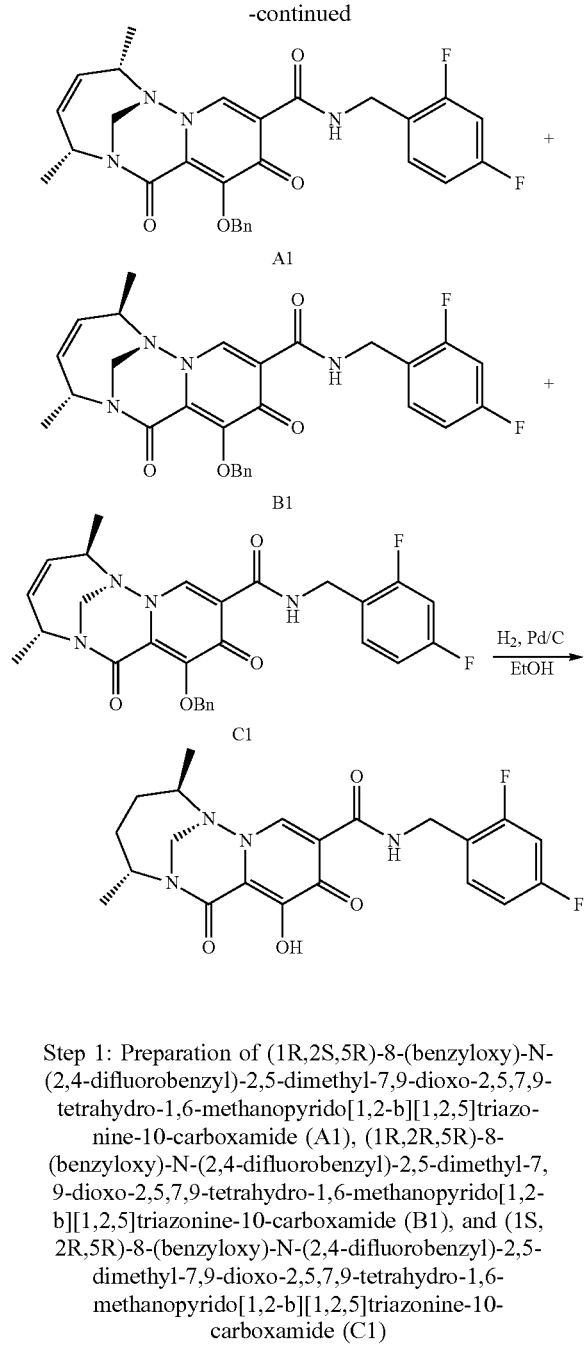

Step 1: Preparation of (1R,2S,5R)-8-(benzyloxy)-N-(2,4-difluorobenzyl)-2,5-dimethyl-7,9-dioxo-2,5,7,9-tetrahydro-1,6-methanopyrido[1,2-b][1,2,5]triazonine-10-carboxamide (A1), (1R,2R,5R)-8-(benzyloxy)-N-(2,4-difluorobenzyl)-2,5-dimethyl-7,9-dioxo-2,5,7,9-tetrahydro-1,6-methanopyrido[1,2-b][1,2,5]triazonine-10-carboxamide (B1), and (1S,2R,5R)-8-(benzyloxy)-N-(2,4-difluorobenzyl)-2,5-dimethyl-7,9-dioxo-2,5,7,9-tetrahydro-1,6-methanopyrido[1,2-b][1,2,5]triazonine-10-carboxamide (C1)

5-(benzyloxy)-3-((R)-but-3-en-2-yl)-1-(but-3-en-2-yl)-N-(2,4-difluorobenzyl)-4,6-dioxo-2,3,4,6-tetrahydro-1H-pyrido[2,1-f][1,2,4]triazine-7-carboxamide (390 mg, 0.711 mmol), prepared in a similar manner as Example 29 except using (R)-but-3-en-2-amine instead of (S)-but-3-en-2-amine, was dissolved in dichloromethane (60 mL) at room temperature. Argon was bubbled through the reaction solution for 20 min. HG-M720 catalyst (44.5 mg, 0.071 mmol) was then added with stirring. The purging with argon was continued for 10 min. The reaction mixture was then heated with reflux condenser under argon atmosphere for 24 hrs. The resulting reaction mixture was then concentrated to dryness. The crude material was purified on silica gel column with 0-100% EtOAc/Hex to afford three diastereomers. MS (m/z): 521.1 [M+H]+.

228

Step 2: Preparation of (1S,2R,5R)—N-(2,4-difluorobenzyl)-8-hydroxy-2,5-dimethyl-7,9-dioxo-2,3,4,5,7,9-hexahydro-1,6-methanopyrido[1,2-b][1,2,5]triazonine-10-carboxamide (1S,2R,5R)-8-(benzyloxy)-N-(2,4-difluorobenzyl)-2,5-dimethyl-7,9-dioxo-2,5,7,9-tetrahydro-1,6-methanopyrido[1,2-b][1,2,5]triazonine-10-carboxamide (10 mg, 0.019 mmol) was dissolved in EtOH (3 mL) and added 10% Pd—C(4 mg, 0.0038 mmol). Hydrogenolysis was performed with H₂ balloon at rt for 7 h. Reaction mixture was filtered through pad of Celite. Filtrate was collected and concentrated to dryness. The residue was taken up in MeOH and was purified with reverse phase prep-HPLC with 50-100% CH₃CN in water with 0.1% TFA to afford the desired product. MS (m/z): 433.2 [M+H]⁺. 1H NMR (400 MHz, Acetonitrile-d3) δ 10.33 (d, J=30.5 Hz, 1H), 8.41 (d, J=19.1 Hz, 1H), 7.43 (td, J=9.2, 8.8, 6.5 Hz, 1H), 7.06-6.85 (m, 2H), 4.71 (d, J=14.9 Hz, 1H), 4.60 (d, J=5.8 Hz, 2H), 4.56 (s, 1H), 3.51 (ddt, J=11.2, 7.1, 3.5 Hz, 1H), 3.31-3.01 (m, 1H), 2.07-1.99 (m, 1H), 1.93-1.66 (m, 6H), 1.30 (p, J=6.6 Hz, 3H).

Example 68: Preparation of (1R,2R,5R)—N-(2,4-difluorobenzyl)-8-hydroxy-2,5-dimethyl-7,9-dioxo-2,5,7,9-tetrahydro-1,6-methanopyrido[1,2-b][1,2,5]triazonine-10-carboxamide (C68)

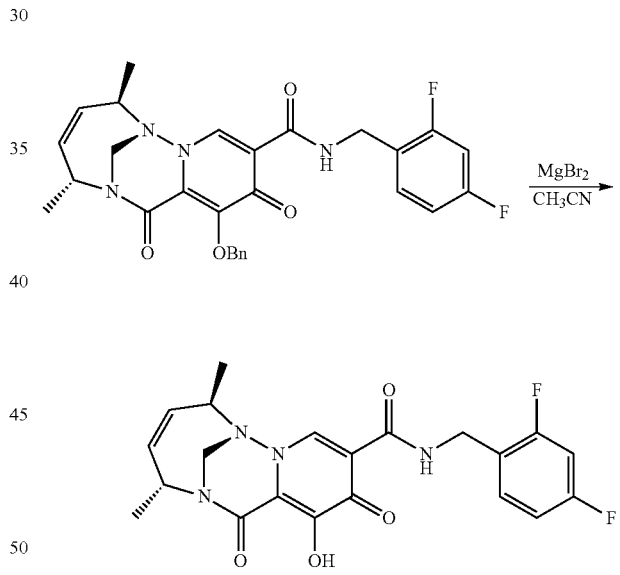

(1R,2R,5R)-8-(benzyloxy)-N-(2,4-difluorobenzyl)-2,5-dimethyl-7,9-dioxo-2,5,7,9-tetrahydro-1,6-methanopyrido[1,2-b][1,2,5]triazonine-10-carboxamide (21 mg, 0.04 mmol), prepared according to Example 67, was dissolved in CH₃CN (2 mL), added MgBr₂ (22.3 mg, 0.22 mmol) and stirred at 50° C. for 2 h. Reaction mixture was quenched with water (1 mL) to form clear solution, filtered and the residue was taken up in MeOH and was purified with reverse phase prep-HPLC with 50-100% CH₃CN in water to afford the desired product. MS (m/z): 431.2 [M+H]+. 1H NMR (400 MHz, Acetonitrile-d3) δ 10.28 (s, 1H), 8.45 (s, 1H), 7.44 (q, J=9.1, 8.4 Hz, 1H), 6.98 (tt, J=10.9, 3.1 Hz, 2H), 5.69-5.54 (m, 1H), 5.47-5.26 (m, 2H), 4.94 (d, J=14.3 Hz, 1H), 4.73 (d, J=14.4 Hz, 1H), 4.61 (d, J=5.7 Hz, 3H), 1.36 (d, J=7.2 Hz, 3H), 1.03 (d, J=7.3 Hz, 3H).

Example 69: Preparation of (1S,2R,5R)—N-(2,4-difluorobenzyl)-8-hydroxy-2,5-dimethyl-7,9-dioxo-2,5,7,9-tetrahydro-1,6-methanopyrido[1,2-b][1,2,5]triazonine-10-carboxamide (C69)

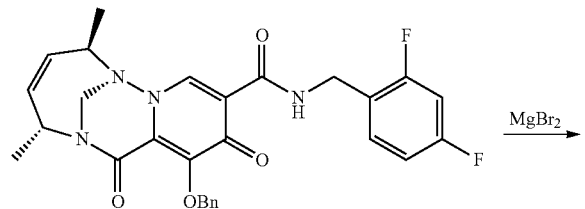

(1S,2R,5R)-8-(benzyloxy)-N-(2,4-difluorobenzyl)-2,5-dimethyl-7,9-dioxo-2,5,7,9-tetrahydro-1,6-methanopyrido[1,2-b][1,2,5]triazonine-10-carboxamide (8 mg, 0.015 mmol), prepared according to Example 67, was dissolved in CH$_3$CN (2 mL), added MgBr$_2$ (6.2 mg, 0.034 mmol) and stirred at 50° C. for 2 h. Reaction mixture was quenched with water (1 mL) to form clear solution, filtered and the residue was taken up in MeOH and was purified with reverse phase prep-HPLC with 50-100% CH$_3$CN in water to afford the desired product. MS (m/z): 431.1 [M+H]+. 1H NMR (400 MHz, Acetonitrile-d3) δ 10.31 (s, 1H), 8.44 (d, J=9.2 Hz, 1H), 7.44 (h, J=6.6 Hz, 1H), 6.98 (dt, J=13.7, 4.9 Hz, 2H), 5.89-5.72 (m, 1H), 5.55-5.33 (m, 1H), 4.83-4.67 (m, 2H), 4.66-4.52 (m, 2H), 4.33 (ddd, J=8.8, 5.6, 3.2 Hz, 1H), 4.23-3.90 (m, 1H), 1.80 (d, J=7.5 Hz, 3H), 1.41 (d, J=7.0 Hz, 3H).

Example 70: Preparation of (1S,2R)-8-hydroxy-2-methyl-7,9-dioxo-N-(2,4,6-trifluorobenzyl)-2,5,7,9-tetrahydro-1,6-methanopyrido[1,2-b][1,2,5]triazonine-10-carboxamide (C70)

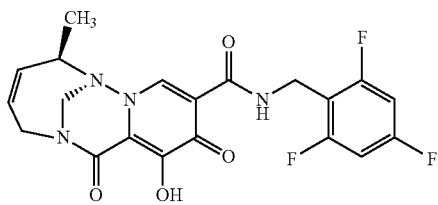

(1S,2R)-8-hydroxy-2-methyl-7,9-dioxo-N-(2,4,6-trifluorobenzyl)-2,5,7,9-tetrahydro-1,6-methanopyrido[1,2-b][1,2,5]triazonine-10-carboxamide was prepared in a similar manner as Example 24, except using allyl ammonium chloride instead of (S)-but-3-en-2-amine hydrochloride in Step 4. ES/MS (m/z): 435.199 [M+H]+, 1H NMR (400 MHz, Acetonitrile-d3) δ 10.19 (s, 1H), 8.37 (s, 1H), 6.85 (t, J=8.6 Hz, 2H), 5.74 (dq, J=11.7, 2.8 Hz, 1H), 5.43 (ddt, J=11.8, 3.6, 2.2 Hz, 1H), 4.95 (dq, J=18.4, 2.9 Hz, 1H), 4.84 (d, J=14.4 Hz, 1H), 4.70 (d, J=14.3 Hz, 1H), 4.64-4.57 (m, 2H), 3.92-3.74 (m, 2H), 1.36 (d, J=6.8 Hz, 3H).

Example 71: Preparation of (1S,2R)-8-hydroxy-2-methyl-7,9-dioxo-N-(2,4,6-trifluorobenzyl)-2,3,4,5,7,9-hexahydro-1,6-methanopyrido[1,2-b][1,2,5]triazonine-10-carboxamide (C71)

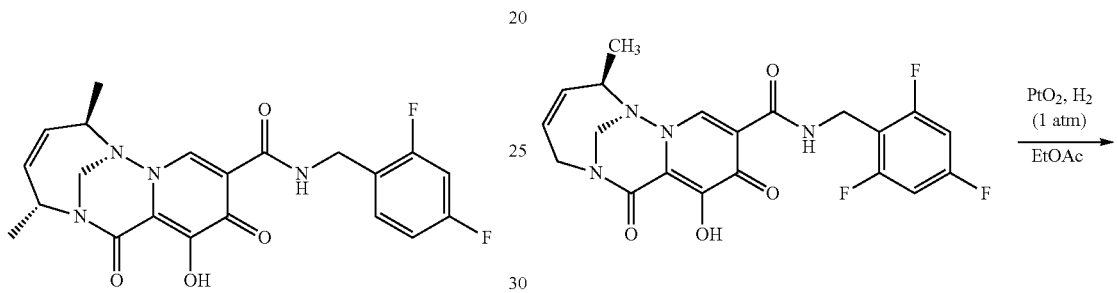

To a vial were added (1S,13R)-6-hydroxy-13-methyl-5,8-dioxo-N-[(2,4,6-trifluorophenyl)methyl]-1,2,9-triazatricyclo[7.4.1.02,7]tetradeca-3,6,11-triene-4-carboxamide (37.6 mg, 0.086 mmol, 1.0 eq), prepared according to Example 70, platinum (IV) oxide (1 mg, 4.3 umol, 5 mol %) and ethyl acetate (1.5 mL). The vial was then fitted with a hydrogen balloon and the hydrogen was bubbled through the reaction mixture for 5 minutes. The reaction was left under a hydrogen atmosphere for 39 hours whereupon the grey suspension was filtered and the volatiles were removed in vacuo and the resultant residue was purified via preparative HPLC (0-100% CH$_3$CN/H$_2$O with 0.1% TFA modifier) affording (1S,2R)-8-hydroxy-2-methyl-7,9-dioxo-N-(2,4,6-trifluorobenzyl)-2,3,4,5,7,9-hexahydro-1,6-methanopyrido[1,2-b][1,2,5]triazonine-10-carboxamide. ES/MS (m/z): 437.168 [M+H]+. 1H NMR (400 MHz, Chloroform-d) δ 10.20 (s, 1H), 8.54 (s, 1H), 6.66 (t, J=8.1 Hz, 2H), 4.76-4.58 (m, 3H), 4.49-4.36 (m, 2H), 3.26-3.16 (m, 1H), 3.05 (dt, J=13.4, 6.5 Hz, 1H), 1.98 (q, J=5.5 Hz, 2H), 1.74 (q, J=5.0 Hz, 2H), 1.35 (d, J=6.8 Hz, 3H).

Example 72: Preparation of (1S,2R,5S)-2-ethyl-8-hydroxy-5-methyl-7,9-dioxo-N-(2,4,6-trifluorobenzyl)-2,5,7,9-tetrahydro-1,6-methanopyrido[1,2-b][1,2,5]triazonine-10-carboxamide (C72)

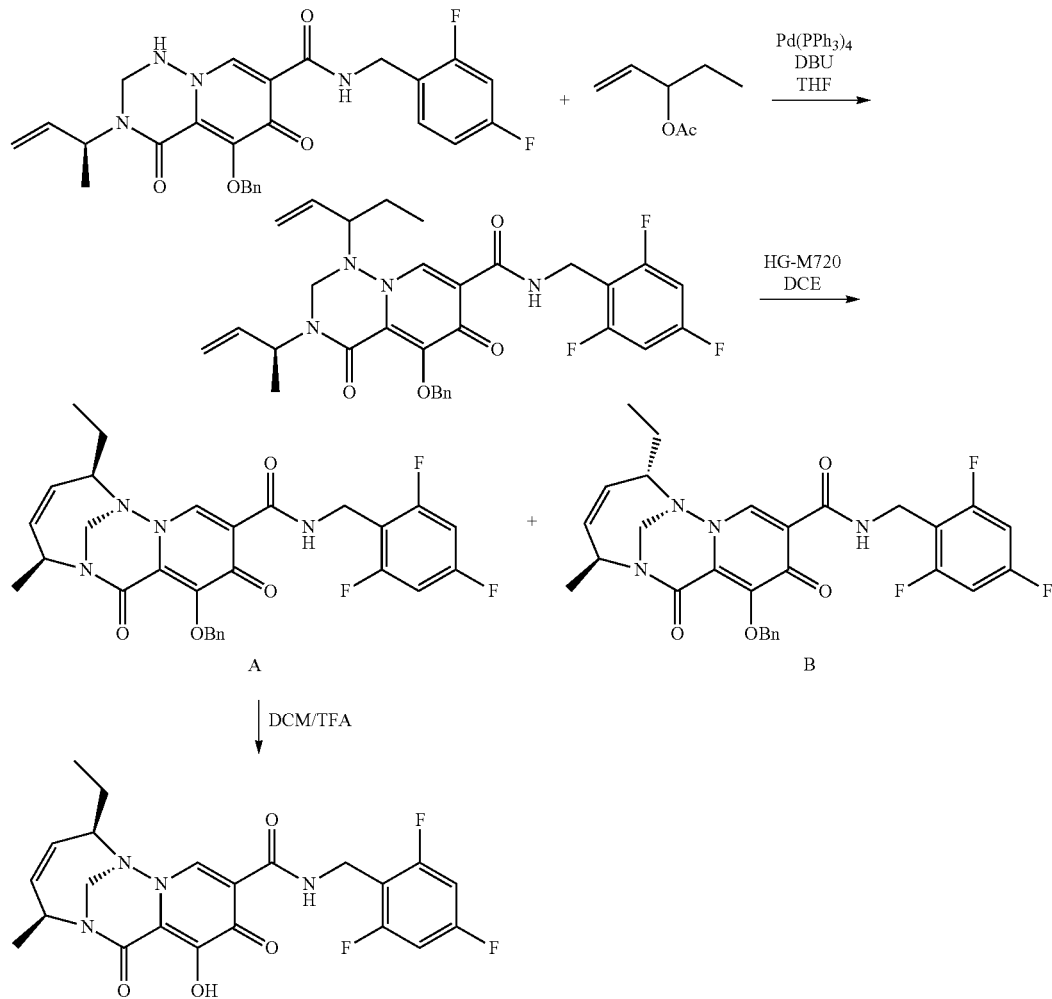

Preparation of 5-(benzyloxy)-3-((S)-but-3-en-2-yl)-4,6-dioxo-1-(pent-1-en-3-yl)-N-(2,4,6-trifluorobenzyl)-2,3,4,6-tetrahydro-1H-pyrido[2,1-f][1,2,4]triazine-7-carboxamide To a solution of (S)-5-(benzyloxy)-3-(but-3-en-2-yl)-4,6-dioxo-N-(2,4,6-trifluorobenzyl)-2,3,4,6-tetrahydro-1H-pyrido[2,1-f][1,2,4]triazine-7-carboxamide (500 mg, 0.976 mmol), prepared according to Example 46, in THF, was added 1-ethylallyl acetate (625 mg, 4.88 mmol), 1,8-diazabicyclo[5.4.0]undec-7-ene (1.5 g, 9.76 mmol) and tetrakis(triphenylphosphine)palladium(0) (225 mg, 0.195 mmol). The reaction mixture was heated at 65° C. After the reaction was finished, the reaction mixture was concentrated down and the residue was purified through silica gel chromatography, eluting with 0-100% hexane/EtOAc. MS (m/z) 581.19 [M+H]+.

Preparation of (1S,2R,5S)-8-(benzyloxy)-2-ethyl-5-methyl-7,9-dioxo-N-(2,4,6-trifluorobenzyl)-2,5,7,9-tetrahydro-1,6-methanopyrido[1,2-b][1,2,5]triazonine-10-carboxamide (A) and (1S,2S,5S)-8-(benzyloxy)-2-ethyl-5-methyl-7,9-dioxo-N-(2,4,6-trifluorobenzyl)-2,5,7,9-tetrahydro-1,6-methanopyrido[1,2-b][1,2,5]triazonine-10-carboxamide (B)

The solution of (S)-5-(benzyloxy)-3-(but-3-en-2-yl)-4,6-dioxo-N-(2,4,6-trifluorobenzyl)-2,3,4,6-tetrahydro-1H-pyrido[2,1-f][1,2,4]triazine-7-carboxamide (60 mg, 0.103 mmol) in DCE (8 mL), was degassing with Ar for 5 min. To the mixture was added cat. Hoverda-Grubbs II catalyst M720 (6.5 mg, 0.013 mmol) and the mixture was sparged with Ar for 10 min. Then the reaction mixture was stirred at 80° C. overnight. The reaction mixture was concentrated down, the residue was purified by silica gel chromatography, eluting with 0-100% hexane/EtOAc to give (1S,2R,5S)-8-(benzyloxy)-2-ethyl-5-methyl-7,9-dioxo-N-(2,4,6-trifluorobenzyl)-2,5,7,9-tetrahydro-1,6-methanopyrido[1,2-b][1,2,5]triazonine-10-carboxamide (A) as the major product and (1S,2S,5S)-8-(benzyloxy)-2-ethyl-5-methyl-7,9-dioxo-N-(2,4,6-trifluorobenzyl)-2,5,7,9-tetrahydro-1,6-methanopyrido[1,2-b][1,2,5]triazonine-10-carboxamide (B) as the minor product.

(1S,2R,5S)-8-(benzyloxy)-2-ethyl-5-methyl-7,9-dioxo-N-(2,4,6-trifluorobenzyl)-2,5,7,9-tetrahydro-1,6-methanopyrido[1,2-b][1,2,5]triazonine-10-carboxamide (A): MS (m/z) 553.06 [M+H]+.

(1S,2S,5S)-8-(benzyloxy)-2-ethyl-5-methyl-7,9-dioxo-N-(2,4,6-trifluorobenzyl)-2,5,7,9-tetrahydro-1,6-methanopyrido[1,2-b][1,2,5]triazonine-10-carboxamide (B): MS (m/z) 553.05 [M+H]+.

Preparation of (1S,2R,5S)-2-ethyl-8-hydroxy-5-methyl-7,9-dioxo-N-(2,4,6-trifluorobenzyl)-2,5,7,9-tetrahydro-1,6-methanopyrido[1,2-bf][,2,5]triazonine-10-carboxamide The solution of (1S,2R,5S)-8-(benzyloxy)-2-ethyl-5-methyl-7,9-dioxo-N-(2,4,6-trifluorobenzyl)-2,5,7,9-tetrahydro-1,6-methanopyrido[1,2-b][1,2,5]triazonine-10-carboxamide (15 mg, 0.0258 mmol) in DCM (1 mL) and TFA (1 mL) was stirred at rt overnight. The mixture was then concentrated down and purified by reverse phase HPLC, 5-100% acetonitrile in water to give the title product. MS (m/z) 462.21 [M+H]+. 1H NMR (400 MHz, Methanol-d4) δ 8.43 (s, 1H), 7.01-6.84 (m, 2H), 5.77 (dt, J=11.6, 2.4 Hz, 1H), 5.58-5.46 (m, 1H), 5.42 (dt, J=7.5, 2.8 Hz, 1H), 5.08 (d, J=14.4 Hz, 1H), 4.75-4.56 (m, 3H), 3.76 (dp, J=6.7, 3.4 Hz, 1H), 1.88-1.59 (m, 2H), 1.39 (d, J=7.3 Hz, 3H), 1.08 (t, J=7.3 Hz, 3H).

Example 73: Preparation of (1S,2R,5S)-2-ethyl-8-hydroxy-5-methyl-7,9-dioxo-N-(2,4,6-trifluorobenzyl)-2,3,4,5,7,9-hexahydro-1,6-methanopyrido[1,2-b][1,2,5]triazonine-10-carboxamide (C73)

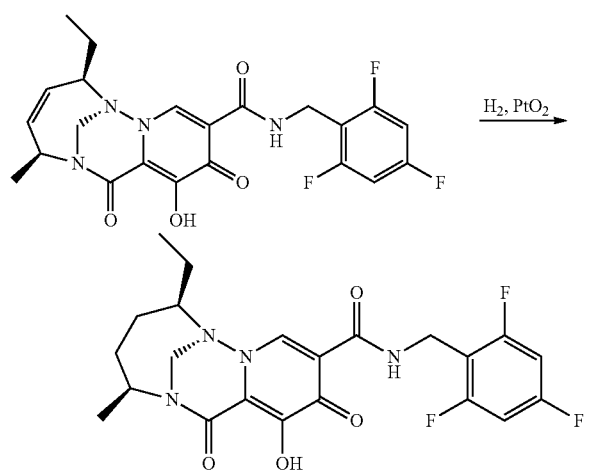

To a solution of (1S,2R,5S)-2-ethyl-8-hydroxy-5-methyl-7,9-dioxo-N-(2,4,6-trifluorobenzyl)-2,5,7,9-tetrahydro-1,6-methanopyrido[1,2-b][1,2,5]triazonine-10-carboxamide (5 mg, 0.011 mmol), prepared according to Example 72, in EtOH (2 ml) was added PtO₂ (1 mg). The reaction mixture was stirred at rt under H₂ balloon for 2 h. The reaction mixture was filtered through celite, concentrated down. The residue was purified by reverse phase HPLC, 5-100% ACN/H2O, containing 0.1% TFA to give title compound. MS (m/z) 465.24 [M+H]+. 1H NMR (400 MHz, Methanol-d4) δ 8.44 (s, 1H), 6.97-6.87 (m, 2H), 4.80-4.52 (m, 5H), 3.24 (t, J=7.1 Hz, 1H), 2.04 (dt, J=14.3, 6.9 Hz, 1H), 1.97-1.66 (m, 3H), 1.63-1.43 (m, 2H), 1.31 (d, J=6.7 Hz, 3H), 1.19 (t, J=7.3 Hz, 3H).

Example 74: Preparation of (1S,2R,5S)-8-hydroxy-2-isopropyl-5-methyl-7,9-dioxo-N-(2,4,6-trifluorobenzyl)-2,5,7,9-tetrahydro-1,6-methanopyrido[1,2-b][1,2,5]triazonine-10-carboxamide (C74)

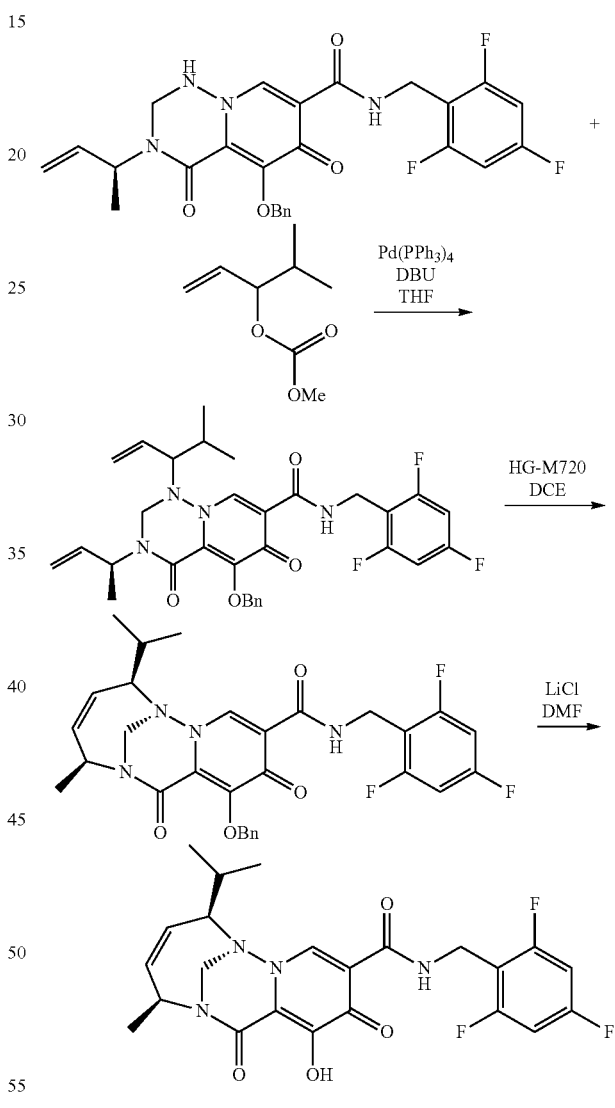

Preparation of (1S,2R,5S)-8-(benzyloxy)-2-isopropyl-5-methyl-7,9-dioxo-N-(2,4,6-trifluorobenzyl)-2,5,7,9-tetrahydro-1,6-methanopyrido[1,2-b][1,2,5]triazonine-10-carboxamide (1S,2R,5S)-8-(benzyloxy)-2-isopropyl-5-methyl-7,9-dioxo-N-(2,4,6-trifluorobenzyl)-2,5,7,9-tetrahydro-1,6-methanopyrido[1,2-b][1,2,5]triazonine-10-carboxamide was prepared in a similar as (1S,2R,5S)-8-(benzyloxy)-2-ethyl-5-methyl-7,9-dioxo-N-(2,4,6-trifluorobenzyl)-2,5,7,9- tetrahydro-1,6-methanopyrido[1,2-b][1,2,5]triazonine-10-carboxamide in Example 72, except that methyl (4-methylpent-1-en-3-yl) carbonate was used instead of pent-1-en-3-yl acetate. MS (m/z) 567.08 [M+H]⁺.

Preparation of (1S,2R,5S)-8-hydroxy-2-isopropyl-5-methyl-7,9-dioxo-N-(2,4,6-trifluorobenzyl)-2,5,7,9-tetrahydro-1,6-methanopyrido[1,2-b][1,2,5]triazonine-10-carboxamide The reaction mixture of (1S,2R,5S)-8-(benzyloxy)-2-isopropyl-5-methyl-7,9-dioxo-N-(2,4,6-trifluorobenzyl)-2,5,7,9-tetrahydro-1,6-methanopyrido[1,2-b][1,2,5]triazonine-10-carboxamide (10 mg, 0.017 mmol) and lithium chloride (7.5 mg, 0.17 mmol) in DMF (1 mL) was heated at 100° C. overnight. The reaction mixture was filtered, the solution was purified by reverse phase HPLC, eluting with 5-100% acetonitrile/water to give title compound. MS (m/z) 477.21 [M+H]⁺. 1H NMR (400 MHz, Methanol-d4) δ 8.42 (s, 1H), 6.95-6.86 (m, 2H), 5.83 (dt, J=11.7, 2.4 Hz, 1H), 5.56 (dt, J=11.8, 3.1 Hz, 1H), 5.42 (dtd, J=9.9, 7.0, 4.1 Hz, 1H), 5.05 (d, J=14.4 Hz, 1H), 4.75-4.62 (m, 3H), 3.67 (p, J=3.3 Hz, 1H), 2.00 (dtq, J=10.4, 7.0, 3.9 Hz, 1H), 1.39 (d, J=7.3 Hz, 3H), 1.17 (d, J=6.7 Hz, 3H), 0.92 (d, J=7.0 Hz, 3H).

Example 75: Preparation of (1S,2S,5S)-8-hydroxy-2-isopropyl-5-methyl-7,9-dioxo-N-(2,4,6-trifluorobenzyl)-2,3,4,5,7,9-hexahydro-1,6-methanopyrido[1,2-b][1,2,5]triazonine-10-carboxamide (C75)

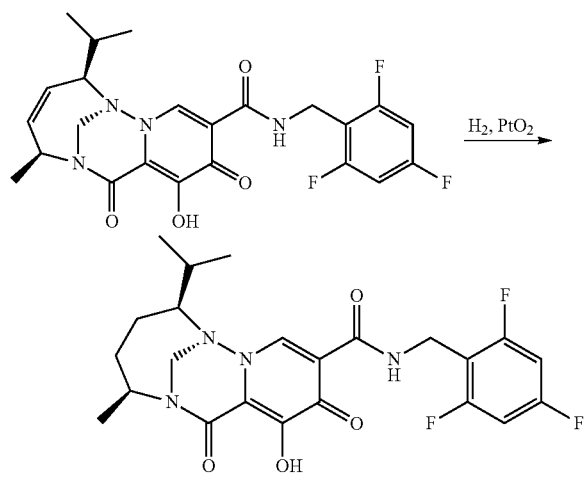

(1S,2S,5S)-8-hydroxy-2-isopropyl-5-methyl-7,9-dioxo-N-(2,4,6-trifluorobenzyl)-2,3,4,5,7,9-hexahydro-1,6-methanopyrido[1,2-b][1,2,5]triazonine-10-carboxamide was synthesized in similar method as Example 73, except that (1S,2R,5S)-8-hydroxy-2-isopropyl-5-methyl-7,9-dioxo-N-(2,4,6-trifluorobenzyl)-2,5,7,9-tetrahydro-1,6-methanopyrido[1,2-b][1,2,5]triazonine-10-carboxamide was used instead of (1S,2R,5S)-2-ethyl-8-hydroxy-5-methyl-7,9-dioxo-N-(2,4,6-trifluorobenzyl)-2,5,7,9-tetrahydro-1,6-methanopyrido[1,2-b][1,2,5]triazonine-10-carboxamide. MS (m/z) 479.21 [M+H]⁺. 1H NMR (400 MHz, Methanol-d4) δ 8.43 (s, 1H), 6.91 (t, J=8.4 Hz, 2H), 4.82-4.53 (m, 5H), 2.89 (d, J=10.0 Hz, 1H), 2.11-1.98 (m, 2H), 1.94 (dp, J=16.1, 4.4, 3.9 Hz, 1H), 1.73 (dt, J=14.7, 10.2 Hz, 1H), 1.44 (ddd, J=14.8, 11.0, 3.1 Hz, 1H), 1.30 (dd, J=10.4, 6.6 Hz, 6H), 0.97 (s, 3H).

Example 76: Preparation of (1S,2S,5S)-2-(fluoromethyl)-8-hydroxy-5-methyl-7,9-dioxo-N-(2,4,6-trifluorobenzyl)-2,5,7,9-tetrahydro-1,6-methanopyrido[1,2-b][1,2,5]triazonine-10-carboxamide (C76)

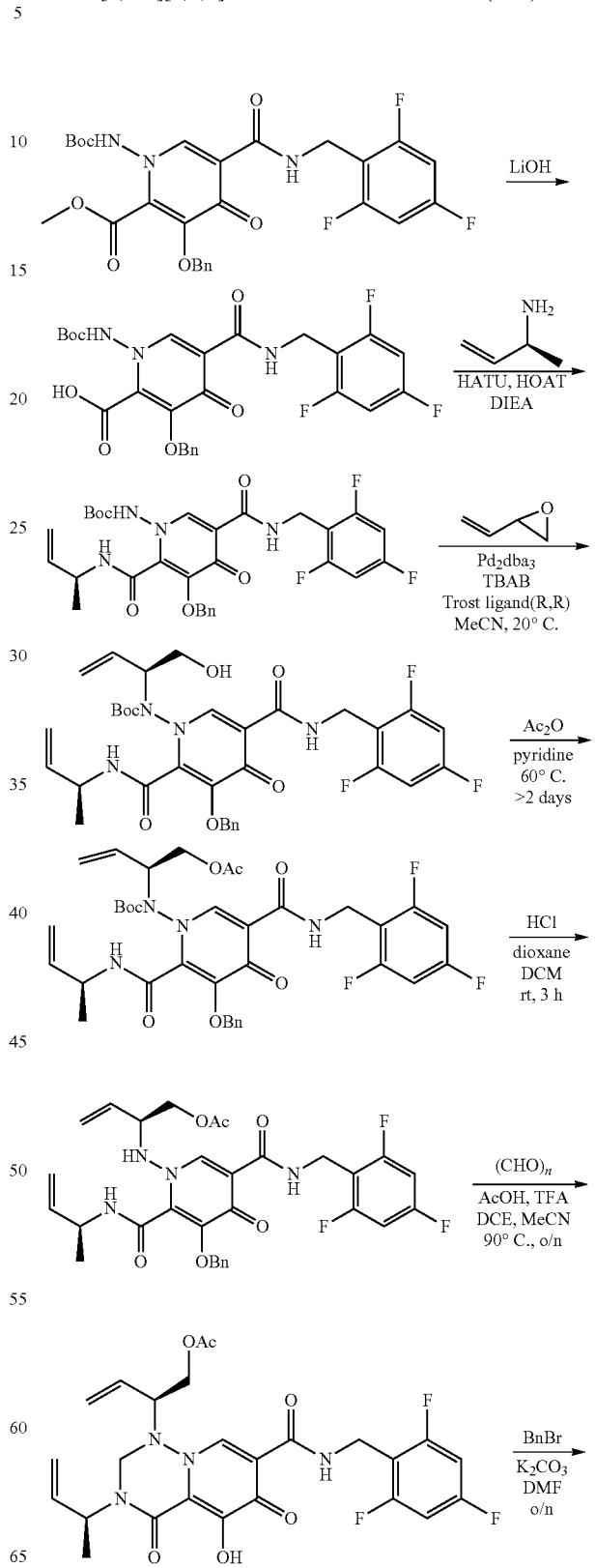

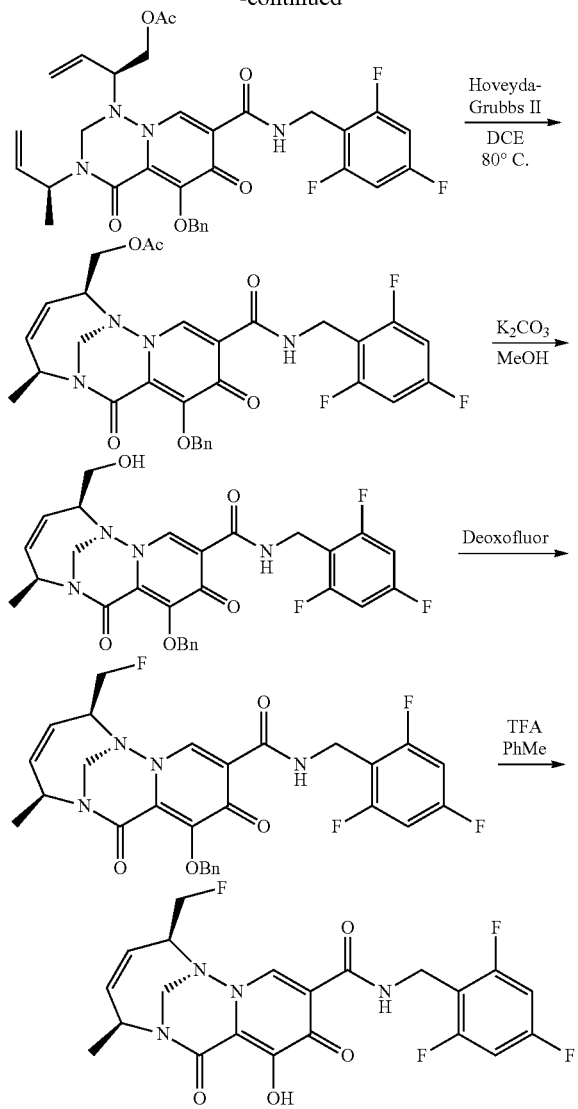

Step 1: Synthesis of 3-(benzyloxy)-1-((tert-butoxycarbonyl)amino)-4-oxo-5-((2,4,6-trifluorobenzyl)carbamoyl)-1,4-dihydropyridine-2-carboxylic acid Methyl 3-(benzyloxy)-1-((tert-butoxycarbonyl)amino)-4-oxo-5-((2,4,6-trifluorobenzyl)carbamoyl)-1,4-dihydropyridine-2-carboxylate (5.9 g, 10.5 mmol) was dissolved in 100 mL MeOH and 20 mL water, lithium hydroxide (1.26 g, 52.5 mmol) was added at room temperature, then heat to 60° C. overnight, then 70° C. for 8 hours. The reaction was cooled to 0° C., 2N HCl was added to adjust pH to 3. The reaction crude was concentrated down. 100 mL EtOAc was added. The precipitate was filtered and washed with water (30 mL 2×). The solid was dried on vacuum to give 4.82 g 3-(benzyloxy)-1-((tert-butoxycarbonyl)amino)-4-oxo-5-((2,4,6-trifluorobenzyl)carbamoyl)-1,4-dihydropyridine-2-carboxylic acid.

Step 2: Synthesis tert-butyl (S)-(3-(benzyloxy)-2-(but-3-en-2-ylcarbamoyl)-4-oxo-5-((2,4,6-trifluorobenzyl)carbamoyl)pyridin-1(4H)-yl)carbamate 3-(benzyloxy)-1-((tert-butoxycarbonyl)amino)-4-oxo-5-((2,4,6-trifluorobenzyl)carbamoyl)-1,4-dihydropyridine-2-carboxylic acid (5.2 g, 9.5 mmol) and (2S)-but-3-en-2-amine HCl salt (1.23 g, 11.4 mmol) were dissolved in anhydrous DMF (500 mL), cooled to 0° C. HATU (4.3 g, 11.4 mmol) and 1-hydroxy-7-azabenzotriazole (388 mg, 2.85 mmol) were added, followed by DIEA (4.96 mL, 28.5 mmol). The reaction was kept at 0° C. 10 minutes, the reaction was complete. Poured the reaction mixture into ice-water, extract with EtOAc (400 mL 2×). The organic layers were concentrated down and purified by silica column, elute with EtOAc/hexane (20-70%) to give tert-butyl (S)-(3-(benzyloxy)-2-(but-3-en-2-ylcarbamoyl)-4-oxo-5-((2,4,6-trifluorobenzyl)carbamoyl)pyridin-1(4H)-yl)carbamate. MS (m/z) 601.2 [M+H]+.

Step 3: Synthesis of tert-butyl (3-(benzyloxy)-2-(((S)-but-3-en-2-yl)carbamoyl)-4-oxo-5-((2,4,6-trifluorobenzyl)carbamoyl)pyridin-1(4H)-yl)((S)-1-hydroxybut-3-en-2-yl)carbamate Tert-butyl (S)-(3-(benzyloxy)-2-(but-3-en-2-ylcarbamoyl)-4-oxo-5-((2,4,6-trifluorobenzyl)carbamoyl)pyridin-1(4H)-yl)carbamate (5.09 g, 8.48 mmol) was dissolved in 500 mL anhydrous MeCN, Tetrabutylammonium bromide (5.46 g. 17 mmol) was added, followed by (R,R)-DACH naphthyl Trost ligand (804 mg, 1.02 mmol) and tris(dibenzylideneacetone) dipalladium (439 mg, 0.424 mmol). Purge Ar for 10 minutes, then butadiene monoxide (1.71 mL, 21.2 mmol) was added dropwise to the reaction. The reaction was stirred at room temperature for 3 hours. The reaction crude was concentrated down and purified by silica column, elute with EtOAc/hexane (30-70%) to give tert-butyl (3-(benzyloxy)-2-(((S)-but-3-en-2-yl)carbamoyl)-4-oxo-5-((2,4,6-trifluorobenzyl)carbamoyl)pyridin-1(4H)-yl)((S)-1-hydroxybut-3-en-2-yl)carbamate. MS (m/z) 671.3 [M+H]+.

Step 4: Synthesis of (S)-2-((3-(benzyloxy)-2-(((S)-but-3-en-2-yl)carbamoyl)-4-oxo-5-((2,4,6-trifluorobenzyl)carbamoyl)pyridin-1(4H)-yl)(tert-butoxycarbonyl)amino)but-3-en-1-yl acetate Tert-butyl (3-(benzyloxy)-2-(((S)-but-3-en-2-yl)carbamoyl)-4-oxo-5-((2,4,6-trifluorobenzyl)carbamoyl)pyridin-1(4H)-yl)((S)-1-hydroxybut-3-en-2-yl)carbamate (1.54 g, 2.29 mmol) was dissolved in pyridine (30 mL) and acetic anhydride (3.25 mL, 34.4 mmol) and 1-hydroxy-7-azabenzotriazole (388 mg, 2.85 mmol) were added, followed by DMAP (560 mg, 4.59 mmol). The reaction was heated at 50° C. for 4 days. The reaction crude was concentrated down and purified by silica column, elute with EtOAc/hexane (40-70%) to give (S)-2-((3-(benzyloxy)-2-(((S)-but-3-en-2-yl)carbamoyl)-4-oxo-5-((2,4,6-trifluorobenzyl)carbamoyl)pyridin-1(4H)-yl)(tert-butoxycarbonyl)amino)but-3-en-1-yl acetate. MS (m/z) 713.4 [M+H]+.

Step 5: Synthesis of (S)-2-((3-(benzyloxy)-2-(((S)-but-3-en-2-yl)carbamoyl)-4-oxo-5-((2,4,6-trifluorobenzyl)carbamoyl)pyridin-1(4H)-yl)amino)but-3-en-1-yl acetate (S)-2-((3-(benzyloxy)-2-(((S)-but-3-en-2-yl)carbamoyl)-4-oxo-5-((2,4,6-trifluorobenzyl)carbamoyl)pyridin-1(4H)-yl)(tert-butoxycarbonyl)amino)but-3-en-1-yl acetate (1.13 g, 2.29 mmol) was dissolved in dichloromethane (3 mL), 4N HCl in dioxane (4 mL) was added at room temperature. The reaction was stirred at room temperature for one hour. Reaction was complete. The crude reaction was concentrated down and purified by silica column, elute with EtOAc/ hexane (40-80%) to give (S)-2-((3-(benzyloxy)-2-(((S)-but-3-en-2-yl)carbamoyl)-4-oxo-5-((2,4,6-trifluorobenzyl)carbamoyl)pyridin-1(4H)-yl)amino)but-3-en-1-yl acetate. MS (m/z) 613.3 [M+H]$^+$.

Step 6: Synthesis of (S)-2-(3-((S)-but-3-en-2-yl)-5-hydroxy-4,6-dioxo-7-((2,4,6-trifluorobenzyl)carbamoyl)-2,3,4,6-tetrahydro-1H-pyrido[2,1-f][1,2,4]triazin-1-yl)but-3-en-1-yl acetate (S)-2-((3-(benzyloxy)-2-(((S)-but-3-en-2-yl)carbamoyl)-4-oxo-5-((2,4,6-trifluorobenzyl)carbamoyl)pyridin-1(4H)-yl)amino)but-3-en-1-yl acetate (405 mg, 0.66 mmol) was dissolved in 12-dichlorethane (17 mL) and acetonitrile (17 mL), paraformaldehyde (60 mg, 1.98 mmol) was added. Then acetic acid (0.265 mL, 4.63 mmol) and TFA (0.253 mL, 3.31 mmol) were added to the reaction at the same time. The reaction was heated at 90° C. for 20 hours. The crude reaction was concentrated down and purified by silica column, elute with EtOAc/hexane (40-100%) to give (S)-2-(3-((S)-but-3-en-2-yl)-5-hydroxy-4,6-dioxo-7-((2,4,6-trifluorobenzyl)carbamoyl)-2,3,4,6-tetrahydro-1H-pyrido[2,1-f][1,2,4]triazin-1-yl)but-3-en-1-yl acetate. MS (m/z) 535.2 [M+H]$^+$.

Step 7: Synthesis of (S)-2-(5-(benzyloxy)-3-((S)-but-3-en-2-yl)-4,6-dioxo-7-((2,4,6-trifluorobenzyl)carbamoyl)-2,3,4,6-tetrahydro-1H-pyrido[2,1-f][1,2,4]triazin-1-yl)but-3-en-1-yl acetate (S)-2-(3-((S)-but-3-en-2-yl)-5-hydroxy-4,6-dioxo-7-((2,4,6-trifluorobenzyl)carbamoyl)-2,3,4,6-tetrahydro-1H-pyrido[2,1-f][1,2,4]triazin-1-yl)but-3-en-1-yl acetate (163 mg, 0.3 mmol) was dissolved in DMF (3 mL), K$_2$CO$_3$ (208 mg, 1.5 mmol) was added, followed by bromomethylbenzene (0.072 mL, 0.6 mmol). The reaction was stirred at room temperature overnight. The crude reaction was extracted using EtOAc and sat. NaHCO$_3$ solution. The organic layers were concentrated down and purified by silica column, elute with EtOAc/hexane (40-100%) to (S)-2-(5-(benzyloxy)-3-((S)-but-3-en-2-yl)-4,6-dioxo-7-((2,4,6-trifluorobenzyl)carbamoyl)-2,3,4,6-tetrahydro-1H-pyrido[2,1-f][1,2,4]triazin-1-yl)but-3-en-1-yl acetate. MS (m/z) 625.3 [M+H]$^+$.

Step 8: Synthesis of ((S,2S,5S)-8-(benzyloxy)-5-methyl-7,9-dioxo-10-((2,4,6-trifluorobenzyl)carbamoyl)-2,5,7,9-tetrahydro-1,6-methanopyrido[1,2-b][1,2,5]triazonin-2-yl)methyl acetate (S)-2-(5-(benzyloxy)-3-((S)-but-3-en-2-yl)-4,6-dioxo-7-((2,4,6-trifluorobenzyl)carbamoyl)-2,3,4,6-tetrahydro-1H-pyrido[2,1-f][1,2,4]triazin-1-yl)but-3-en-1-yl acetate (210 mg, 0.336 mmol) was dissolved in 1,2-dichloroethane (17 mL), Hoveyda-Grubbs Catalyst 2nd Generation (42 mg, 0.067 mmol) was added. The reaction was heated at 80° C. for 6 hours. The crude reaction was concentrated down and purified by silica column, elute with EtOAc/hexane (40-100%) to give ((1S,2S,5S)-8-(benzyloxy)-5-methyl-7,9-dioxo-10-((2,4,6-trifluorobenzyl)carbamoyl)-2,5,7,9-tetrahydro-1,6-methanopyrido[1,2-b][1,2,5]triazonin-2-yl)methyl acetate. MS (m/z) 597.3 [M+H]$^+$.

Step 9: Synthesis of (1S,2S,5S)-8-(benzyloxy)-2-(hydroxymethyl)-5-methyl-7,9-dioxo-N-(2,4,6-trifluorobenzyl)-2,5,7,9-tetrahydro-1,6-methanopyrido[1,2-b][1,2,5]triazonine-10-carboxamide ((1S,2S,5S)-8-(benzyloxy)-5-methyl-7,9-dioxo-10-((2,4,6-trifluorobenzyl)carbamoyl)-2,5,7,9-tetrahydro-1,6-methanopyrido[1,2-b][1,2,5]triazonin-2-yl)methyl acetate (135 mg, 0.226 mmol) was dissolved in MeOH_(3 mL), K$_2$CO$_3$ (93.8 mg, 0.679 mmol) was added. The reaction was stirred at room temperature for 15 minutes. EtOAc was added to the crude reaction. Transfer to a separate funnel, water was added to wash the organic layer twice. The organic layer was concentrated down and purified by silica column, elute with EtOAc/hexane (60-100%) to give (1S,2S,5S)-8-(benzyloxy)-2-(hydroxymethyl)-5-methyl-7,9-dioxo-N-(2,4,6-trifluorobenzyl)-2,5,7,9-tetrahydro-1,6-methanopyrido[1,2-b][1,2,5]triazonine-10-carboxamide. MS (m/z) 555.3 [M+H]$^+$.

Step 10: Synthesis of (1S,2S,5S)-8-(benzyloxy)-2-(fluoromethyl)-5-methyl-7,9-dioxo-N-(2,4,6-trifluorobenzyl)-2,5,7,9-tetrahydro-1,6-methanopyrido[1,2-b][1,2,5]triazonine-10-carboxamide (1S,2S,5S)-8-(benzyloxy)-2-(hydroxymethyl)-5-methyl-7,9-dioxo-N-(2,4,6-trifluorobenzyl)-2,5,7,9-tetrahydro-1,6-methanopyrido[1,2-b][1,2,5]triazonine-10-carboxamide (24 mg, 0.05 mmol) was dissolved in DCM (1.5 mL), cooled to ice bath. Deoxofluor (50% in toluene, 2.7 M, 0.39 mL) was added. The reaction was stirred at 0° C., then warm up to room temperature for 2 hours. Sat. NaHCO$_3$ solution was added to quench the reaction. Extract using DCM. The organic layer was concentrated down and purified via preparative HPLC, eluting 10-60% acetonitrile (0.1% TFA) in water (0.1% TFA) to give (1S,2S,5S)-8-(benzyloxy)-2-(fluoromethyl)-5-methyl-7,9-dioxo-N-(2,4,6-trifluorobenzyl)-2,5,7,9-tetrahydro-1,6-methanopyrido[1,2-b][1,2,5]triazonine-10-carboxamide. MS (m/z) 557.2 [M+H]$^+$.

Step 11: Synthesis of (1S,2S,5S)-2-(fluoromethyl)-8-hydroxy-5-methyl-7,9-dioxo-N-(2,4,6-trifluorobenzyl)-2,5,7,9-tetrahydro-1,6-methanopyrido[1,2-b][1,2,5]triazonine-10-carboxamide (1S,2S,5S)-8-(benzyloxy)-2-(fluoromethyl)-5-methyl-7,9-dioxo-N-(2,4,6-trifluorobenzyl)-2,5,7,9-tetrahydro-1,6-methanopyrido[1,2-b][1,2,5]triazonine-10-carboxamide (15 mg, 0.027 mmol) was dissolved in toluene (0.5 mL), TFA (0.5 mL) was added. The reaction was stirred at room temperature for 4 hours. The reaction was concentrated down and purified via preparative HPLC, eluting 10-60% acetonitrile (0.1% TFA) in water (0.1% TFA) to give (1S,2S,5S)-2-(fluoromethyl)-8-hydroxy-5-methyl-7,9-dioxo-N-(2,4,6-trifluorobenzyl)-2,5,7,9-tetrahydro-1,6-methanopyrido[1,2-b][1,2,5]triazonine-10-carboxamide. MS (m/z) 467.2 [M+H]$^+$. $^1$H NMR (400 MHz, Acetonitrile-d$_3$) δ 10.21 (s, 1H), 8.46 (d, J=1.1 Hz, 1H), 6.87 (t, J=8.5 Hz, 2H), 5.82 (dt, J=11.7, 2.8 Hz, 1H), 5.39 (ddt, J=14.7, 12.0, 3.4 Hz, 2H), 4.95 (d, J=14.5 Hz, 1H), 4.70-4.59 (m, 4H), 4.54-4.49 (m, 1H), 4.09 (ddd, J=18.4, 5.9, 3.0 Hz, 1H), 1.35 (d, J=7.3 Hz, 3H).

Example 77: Preparation of (1S,2S,5S)-2-(fluoromethyl)-8-hydroxy-5-methyl-7,9-dioxo-N-(2,4,6-trifluorobenzyl)-2,3,4,5,7,9-hexahydro-1,6-methanopyrido[1,2-b][1,2,5]triazonine-10-carboxamide (C77)

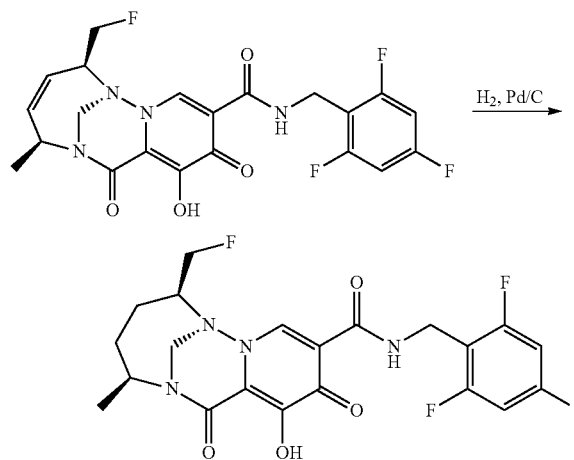

(1S,2S,5S)-2-(fluoromethyl)-8-hydroxy-5-methyl-7,9-dioxo-N-(2,4,6-trifluorobenzyl)-2,5,7,9-tetrahydro-1,6-methanopyrido[1,2-b][1,2,5]triazonine-10-carboxamide (6 mg, 0.013 mmol), prepared according to Example 76, was dissolved in EtOH (5 mL) and EtOAc (5 mL). 10% Pd/C (3 mg) was added and a hydrogen balloon was applied. The reaction was stirred at room temperature for 2 hours. The reaction was filtered through celite, the filtrate was concentrated down and purified via preparative HPLC, eluting 10-60% acetonitrile (0.1% TFA) in water (0.1% TFA) to give (1S,2S,5S)-2-(fluoromethyl)-8-hydroxy-5-methyl-7,9-dioxo-N-(2,4,6-trifluorobenzyl)-2,3,4,5,7,9-hexahydro-1,6-methanopyrido[1,2-b][1,2,5]triazonine-10-carboxamide. MS (m/z) 469.2 [M+H]$^+$. 1H NMR (400 MHz, Acetonitrile-d3) δ 10.31 (s, 1H), 8.40 (s, 1H), 7.01-6.80 (m, 2H), 4.77-4.68 (m, 1H), 4.65-4.56 (m, 4H), 4.47 (dd, J=9.9, 5.4 Hz, 1H), 3.67-3.45 (m, 2H), 2.06 (dt, J=13.2, 7.0 Hz, 1H), 1.84 (ddd, J=15.5, 7.9, 3.9 Hz, 1H), 1.75-1.60 (m, 2H), 1.26 (d, J=6.7 Hz, 3H).

Example 78: Preparation of (1S,2S,5S)-2-(difluoromethyl)-8-hydroxy-5-methyl-7,9-dioxo-N-(2,4,6-trifluorobenzyl)-2,3,4,5,7,9-hexahydro-1,6-methanopyrido[1,2-b][1,2,5]triazonine-10-carboxamide (C78)

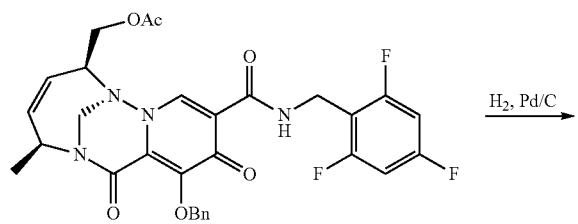

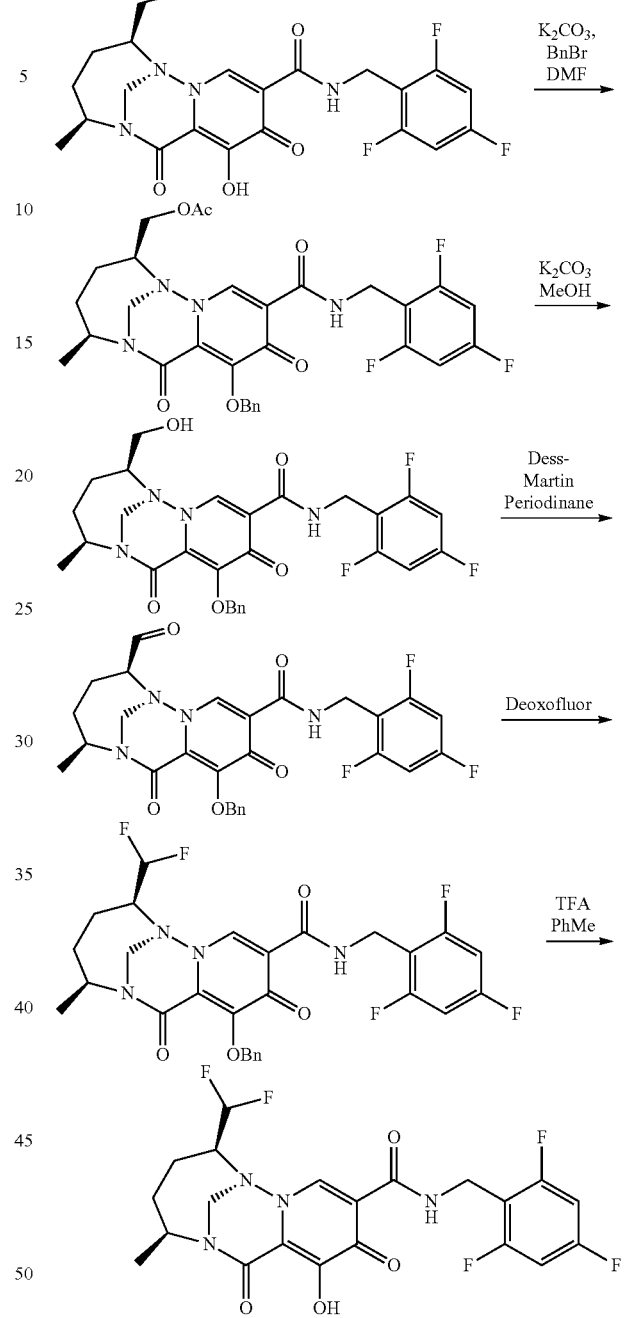

Step 1: Synthesis of ((1S,2S,5S)-8-hydroxy-5-methyl-7,9-dioxo-10-((2,4,6-trifluorobenzyl)carbamoyl)-2,3,4,5,7,9-hexahydro-1,6-methanopyrido[1,2-b][1,2,5]triazonin-2-yl)methyl acetate ((1S,2S,5S)-8-(benzyloxy)-5-methyl-7,9-dioxo-10-((2,4,6-trifluorobenzyl)carbamoyl)-2,5,7,9-tetrahydro-1,6-methanopyrido[1,2-b][1,2,5]triazonin-2-yl)methyl acetate (48 mg, 0.08 mmol) was dissolved in EtOH (5 mL) and EtOAc (5 mL), 10% Pd/C (16 mg) was added, hydrogen balloon was applied. The reaction was stirred at room temperature for 2 hours. The reaction was filtered through celite, the filtrate was concentrated down to give ((1S,2S,5S)-8-hydroxy-5- methyl-7,9-dioxo-10-((2,4,6-trifluorobenzyl)carbamoyl)-2,3,4,5,7,9-hexahydro-1,6-methanopyrido[1,2-b][1,2,5]triazonin-2-yl)methyl acetate which was used directly in next step. MS (m/z) 509.2 [M+H]+.

Step 2: Synthesis of ((1S,2S,5S)-8-(benzyloxy)-5-methyl-7,9-dioxo-10-((2,4,6-trifluorobenzyl)carbamoyl)-2,3,4,5,7,9-hexahydro-1,6-methanopyrido[1,2-b][1,2,5]triazonin-2-yl)methyl acetate The crude of ((1S,2S,5S)-8-hydroxy-5-methyl-7,9-dioxo-10-((2,4,6-trifluorobenzyl)carbamoyl)-2,3,4,5,7,9-hexahydro-1,6-methanopyrido[1,2-b][1,2,5]triazonin-2-yl) methyl acetate was dissolved in DMF (3 mL), K₂CO₃ (22 mg, 0.16 mmol) was added, followed by BnBr (0.014 mL, 0.12 mmol). The reaction was stirred at room temperature for 2 hours. The reaction was extracted using EtOAc/sat. NaHCO₃, the organic layer was concentrated down, purified by silica column, elute with EtOAc/hexane (60-100%) to give ((1S,2S,5S)-8-(benzyloxy)-5-methyl-7,9-dioxo-10-((2,4,6-trifluorobenzyl)carbamoyl)-2,3,4,5,7,9-hexahydro-1,6-methanopyrido[1,2-b][1,2,5]triazonin-2-yl)methyl acetate. MS (m/z) 599.3 [M+H]+.

Step 3: Synthesis of (1S,2S,5S)-8-(benzyloxy)-2-(hydroxymethyl)-5-methyl-7,9-dioxo-N-(2,4,6-trifluorobenzyl)-2,3,4,5,7,9-hexahydro-1,6-methanopyrido[1,2-b][1,2,5]triazonine-10-carboxamide ((1S,2S,5S)-8-(benzyloxy)-5-methyl-7,9-dioxo-10-((2,4,6-trifluorobenzyl)carbamoyl)-2,3,4,5,7,9-hexahydro-1,6-methanopyrido[1,2-b][1,2,5]triazonin-2-yl)methyl acetate (33 mg, 0.06 mmol) dissolved was in MeOH (1 mL), K2CO3 (24 mg, 0.18 mmol) was added. The reaction was stirred at room temperature for 15 minutes. EtOAc was added to the reaction crude. Transfer to a separate funnel, water was added to wash the organic layer twice. The organic layer was concentrated down and purified by silica column, elute with EtOAc/hexane (60-100%) to give (1S,2S,5S)-8-(benzyloxy)-2-(hydroxymethyl)-5-methyl-7,9-dioxo-N-(2,4,6-trifluorobenzyl)-2,3,4,5,7,9-hexahydro-1,6-methanopyrido[1,2-b][1,2,5]triazonine-10-carboxamide. MS (m/z) 557.3 [M+H]+.

Step 4: Synthesis of (S,2S,5S)-8-(benzyloxy)-2-formyl-5-methyl-7,9-dioxo-N-(2,4,6-trifluorobenzyl)-2,3,4,5,7,9-hexahydro-1,6-methanopyrido[1,2-b][1,2,5]triazonine-10-carboxamide (1S,2S,5S)-8-(benzyloxy)-2-(hydroxymethyl)-5-methyl-7,9-dioxo-N-(2,4,6-trifluorobenzyl)-2,3,4,5,7,9-hexahydro-1,6-methanopyrido[1,2-b][1,2,5]triazonine-10-carboxamide (22 mg, 0.039 mmol) was dissolved in DCM (2 mL), Dess-Martin Periodinane (50 mg, 0.12 mmol) was added. The reaction was stirred at room temperature, later another 50 mg Dess-Martin Periodinane was added. The reaction was complete after 4 hours. 10% Na₂S₂O₃ solution was added to quench. The crude was extracted using DCM. The organic layer was concentrated down and used in next step directly. MS (m/z) 555.3 [M+H]+.

Step 5: Synthesis of (1S,2S,5S)-8-(benzyloxy)-2-(difluoromethyl)-5-methyl-7,9-dioxo-N-(2,4,6-trifluorobenzyl)-2,3,4,5,7,9-hexahydro-1,6-methanopyrido[1,2-b][1,2,5]triazonine-10-carboxamide The crude (1S,2S,5S)-8-(benzyloxy)-2-formyl-5-methyl-7,9-dioxo-N-(2,4,6-trifluorobenzyl)-2,3,4,5,7,9-hexahydro-1,6-methanopyrido[1,2-b][1,2,5]triazonine-10-carboxamide was dissolved in DCM (1.5 mL), Deoxofluor (50% in toluene, 2.7 M, 0.043 mL) was added. The reaction was stirred at room temperature, and another 0.043 mL of deoxofluor (50% in toluene, 2.7 M) was added. The reaction was stirred at room temperature overnight. Sat. NaHCO₃ solution was added to quench the reaction. Extract using DCM. The organic layer was concentrated down and purified via preparative HPLC, eluting 10-60% acetonitrile (0.1% TFA) in water (0.1% TFA) to give (1S,2S,5S)-8-(benzyloxy)-2-(difluoromethyl)-5-methyl-7,9-dioxo-N-(2,4,6-trifluorobenzyl)-2,3,4,5,7,9-hexahydro-1,6-methanopyrido[1,2-b][1,2,5]triazonine-10-carboxamide. MS (m/z) 577.3 [M+H]+.

Step 6: Synthesis of (S,2S,5S)-2-(difluoromethyl)-8-hydroxy-5-methyl-7,9-dioxo-N-(2,4,6-trifluorobenzyl)-2,3,4,5,7,9-hexahydro-1,6-methanopyrido[1,2-b][1,2,5]triazonine-10-carboxamide (1S,2S,5S)-8-(benzyloxy)-2-(difluoromethyl)-5-methyl-7,9-dioxo-N-(2,4,6-trifluorobenzyl)-2,3,4,5,7,9-hexahydro-1,6-methanopyrido[1,2-b][1,2,5]triazonine-10-carboxamide (15 mg, 0.026 mmol) was dissolved in toluene (0.5 mL), TFA (0.5 mL) was added. The reaction was stirred at room temperature for 4 hours. The reaction was concentrated down and purified via preparative HPLC, eluting 10-60% acetonitrile (0.1% TFA) in water (0.1% TFA) to give (1S, 2S,5S)-2-(difluoromethyl)-8-hydroxy-5-methyl-7,9-dioxo-N-(2,4,6-trifluorobenzyl)-2,3,4,5,7,9-hexahydro-1,6-methanopyrido[1,2-b][1,2,5]triazonine-10-carboxamide. MS (m/z) 487.2 [M+H]+. 1H NMR (400 MHz, Acetonitrile-d3) δ 10.26 (s, 1H), 8.44 (s, 1H), 6.87 (t, J=8.5 Hz, 2H), 6.11 (td, J=55.1, 3.5 Hz, 1H), 4.72-4.54 (m, 5H), 3.55 (td, J=14.9, 4.1 Hz, 1H), 2.23-2.01 (m, 2H), 1.85 (ddd, J=13.9, 10.5, 7.7 Hz, 1H), 1.79-1.59 (m, 1H), 1.26 (d, J=6.9 Hz, 3H).

Example 79: Preparation of (1S,2S,5S)-8-hydroxy-2-(methoxymethyl)-5-methyl-7,9-dioxo-N-(2,4,6-trifluorobenzyl)-2,5,7,9-tetrahydro-1,6-methanopyrido[1,2-b][1,2,5]triazonine-10-carboxamide (C79)

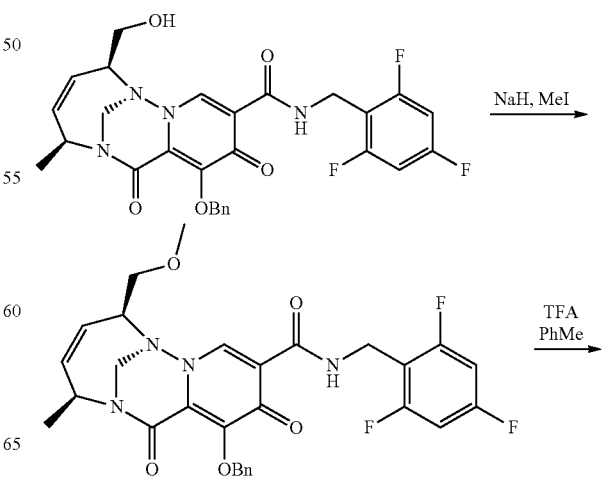

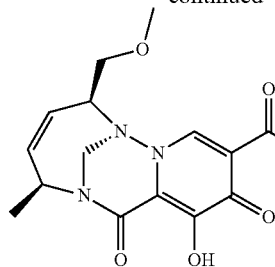

Step 1: Synthesis of (1S,2S,5S)-8-(benzyloxy)-2-(methoxymethyl)-5-methyl-7,9-dioxo-N-(2,4,6-trifluorobenzyl)-2,5,7,9-tetrahydro-1,6-methanopyrido[1,2-b][1,2,5]triazonine-10-carboxamide (1S,2S,5S)-8-(benzyloxy)-2-(hydroxymethyl)-5-methyl-7,9-dioxo-N-(2,4,6-trifluorobenzyl)-2,5,7,9-tetrahydro-1,6-methanopyrido[1,2-b][1,2,5]triazonine-10-carboxamide (46 mg, 0.083 mmol), prepared according to Example 76, was dissolved in anhydrous DMF (2 mL), cooled to 0° C., and NaH (60%, 6 mg, 0.014 mL) was added. The reaction was kept at 0° C. for 10 minutes. Diluted MeI (1.2 eq) was added. The reaction was kept at 0° C. for 10 minutes, then warmed up to room temperature for 30 minutes. A drop of water was added to quench the reaction. The crude reaction was extracted using EtOAc/sat. NaHCO₃ solution. The organic layer was concentrated and purified by silica column, eluting with EtOAc/hexane (60-100%), to give (1S,2S,5S)-8-(benzyloxy)-2-(methoxymethyl)-5-methyl-7,9-dioxo-N-(2,4,6-trifluorobenzyl)-2,5,7,9-tetrahydro-1,6-methanopyrido[1,2-b][1,2,5]triazonine-10-carboxamide. MS (m/z) 569.3 [M+H]⁺.

Step 2: Synthesis of (1S,2S,5S)-8-hydroxy-2-(methoxymethyl)-5-methyl-7,9-dioxo-N-(2,4,6-trifluorobenzyl)-2,5,7,9-tetrahydro-1,6-methanopyrido[1,2-b][1,2,5]triazonine-10-carboxamide (1S,2S,5S)-8-(benzyloxy)-2-(methoxymethyl)-5-methyl-7,9-dioxo-N-(2,4,6-trifluorobenzyl)-2,5,7,9-tetrahydro-1,6-methanopyrido[1,2-b][1,2,5]triazonine-10-carboxamide (2 mg, 0.004 mmol) was dissolved in toluene (0.5 mL), TFA (0.5 mL) was added. The reaction was stirred at room temperature for 4 hours. The reaction was concentrated down and purified via preparative HPLC, eluting 10-60% acetonitrile (0.1% TFA) in water (0.1% TFA) to give (1S,2S,5S)-8-hydroxy-2-(methoxymethyl)-5-methyl-7,9-dioxo-N-(2,4,6-trifluorobenzyl)-2,5,7,9-tetrahydro-1,6-methanopyrido[1,2-b][1,2,5]triazonine-10-carboxamide. MS (m/z) 479.2 [M+H]⁺. 1H NMR (400 MHz, Acetonitrile-d3) δ 8.59 (s, 1H), 6.84 (s, 1H), 6.70 (s, 1H), 5.77 (d, J=12.5 Hz, 1H), 5.41 (d, J=41.9 Hz, 2H), 4.96 (m, 1H), 4.67 (d, J=28.6 Hz, 3H), 3.95 (m, 1H), 3.66-3.53 (m, 2H), 3.36 (s, 3H), 1.47-1.15 (m, 3H).

Example 80: Preparation of (1R,2R,5S)-2-(fluoromethyl)-8-hydroxy-5-methyl-7,9-dioxo-N-(2,4,6-trifluorobenzyl)-2,5,7,9-tetrahydro-1,6-methanopyrido[1,2-b][1,2,5]triazonine-10-carboxamide (C80)

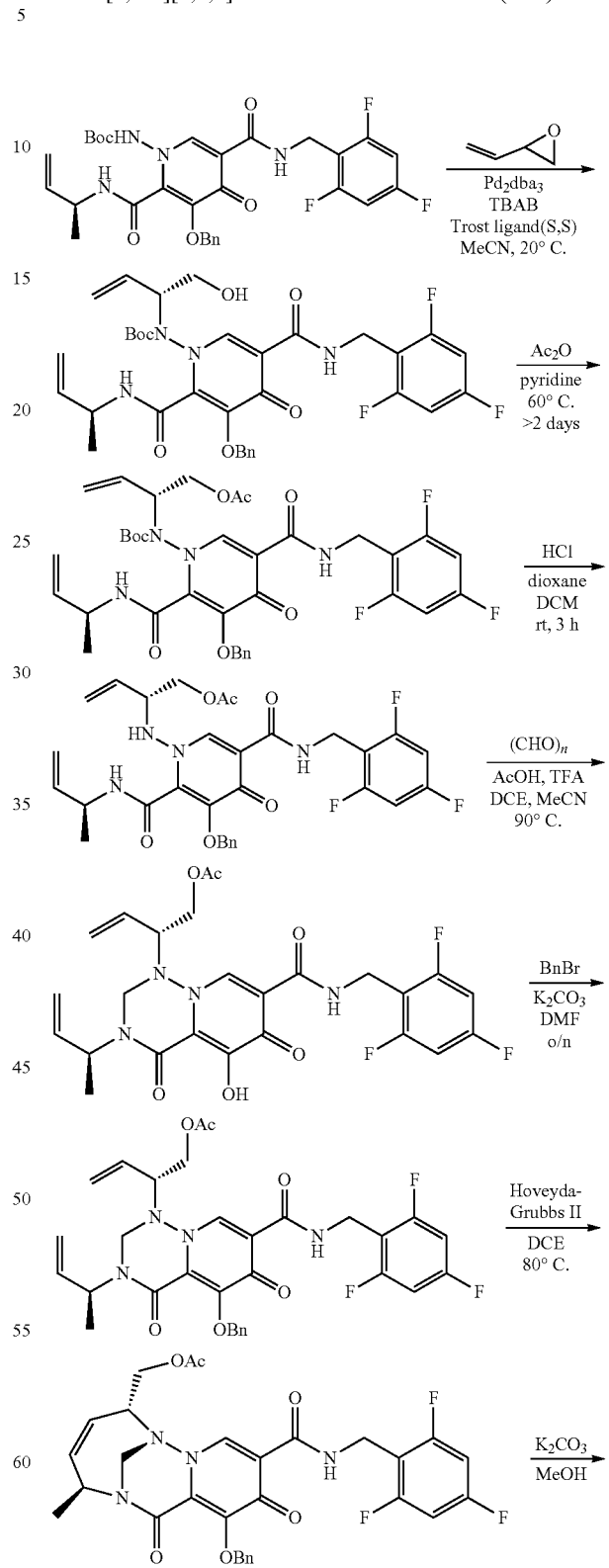

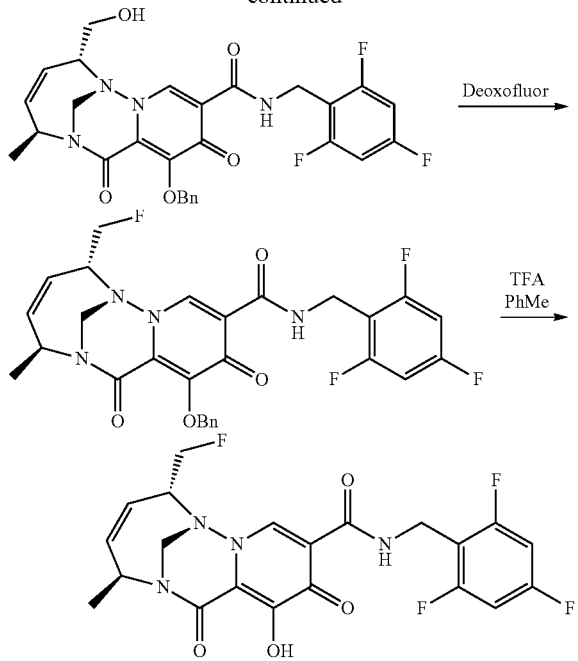

(1R,2R,5S)-2-(fluoromethyl)-8-hydroxy-5-methyl-7,9-dioxo-N-(2,4,6-trifluorobenzyl)-2,5,7,9-tetrahydro-1,6-methanopyrido[1,2-b][1,2,5]triazonine-10-carboxamide was prepared in a similar manner as (1S,2S,5S)-2-(fluoromethyl)-8-hydroxy-5-methyl-7,9-dioxo-N-(2,4,6-trifluorobenzyl)-2,5,7,9-tetrahydro-1,6-methanopyrido[1,2-b][1,2,5]triazonine-10-carboxamide in Example 76, except using (S,S)-DACH naphthyl Trost ligand instead of (R,R)-DACH naphthyl Trost ligand in Step 3. MS (m/z) 467.2 [M+H]+. 1H NMR (400 MHz, Acetonitrile-d3) δ 10.25 (s, 1H), 8.45 (d, J=5.4 Hz, 1H), 6.99-6.80 (m, 2H), 6.03-5.93 (m, 1H), 5.41 (ddd, J=12.0, 3.6, 2.5 Hz, 1H), 4.94-4.78 (m, 1H), 4.78-4.57 (m, 5H), 4.37-4.15 (m, 2H), 1.88-1.71 (m, 3H).

Example 81: Preparation of (1S,2S,5S)—N-(2,4-difluorobenzyl)-2-(difluoromethyl)-8-hydroxy-5-methyl-7,9-dioxo-2,3,4,5,7,9-hexahydro-1,6-methanopyrido[1,2-b][1,2,5]triazonine-10-carboxamide (C81)

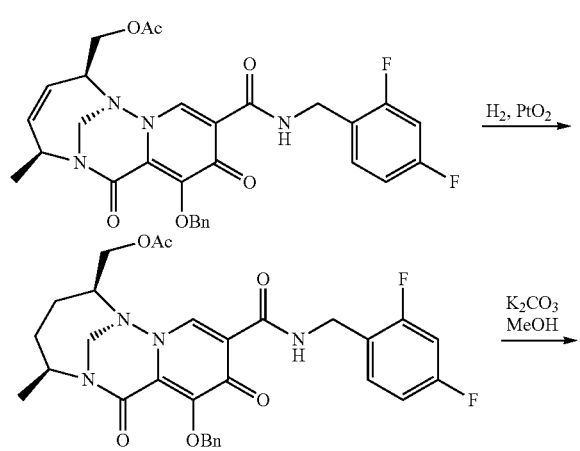

Step 1: Synthesis of ((1S,2S,5S)-8-(benzyloxy)-10-((2,4-difluorobenzyl)carbamoyl)-5-methyl-7,9-dioxo-2,3,4,5,7,9-hexahydro-1,6-methanopyrido[1,2-b][1,2,5]triazonin-2-yl)methyl acetate ((1S,2S,5S)-8-(benzyloxy)-10-((2,4-difluorobenzyl)carbamoyl)-5-methyl-7,9-dioxo-2,5,7,9-tetrahydro-1,6-methanopyrido[1,2-b][1,2,5]triazonin-2-yl)methyl acetate (170 mg, 0.294 mmol), prepared in a manner similar to Example 76, was dissolved in 5 ml of ethanol and 5 ml of ethyl acetate and was sparged under an argon atmosphere. Platinum(IV) oxide (34 mg, 0.15 mmol) was added and the mixture was sparged under a hydrogen atmosphere (1 atm, balloon). The mixture was stirred for 20 minutes. After sparged with argon, it was filtered through a pad of Celite®, and washed with absolute ethanol. The filtrate was concentrated to dryness and directly used for next step. MS (m/z): 581.300 [M+H]+.

Step 2: Synthesis of (1S,2S,5S)-8-(benzyloxy)-N-(2,4-difluorobenzyl)-2-(hydroxymethyl)-5-methyl-7,9-dioxo-2,3,4,5,7,9-hexahydro-1,6-methanopyrido[1,2-b][1,2,5]triazonine-10-carboxamide ((1S,2S,5S)-8-(benzyloxy)-10-((2,4-difluorobenzyl)carbamoyl)-5-methyl-7,9-dioxo-2,3,4,5,7,9-hexahydro-1,6-methanopyrido[1,2-b][1,2,5]triazonin-2-yl)methyl acetate (170 mg, 0.293 mmol) was dissolved in 10 ml of methanol. To it was added potassium carbonate (80.9 mg, 0.589 mmol). The reaction mixture was stirred at room temperature for 10 minutes, partitioned between ethyl acetate and water. The organic layer was separated, washed with brine, dried over magnesium sulfate and concentrated to dryness. The residue was dried under high vacuum to afford the title product. MS (m/z): 539.300 [M+H]+.

Step 3: Synthesis of (1S,2S,5S)-8-(benzyloxy)-N-(2,4-difluorobenzyl)-2-formyl-5-methyl-7,9-dioxo-2,3,4,5,7,9-hexahydro-1,6-methanopyrido[1,2-b][1,2,5]triazonine-10-carboxamide To a solution of (1S,2S,5S)-8-(benzyloxy)-N-(2,4-difluorobenzyl)-2-(hydroxymethyl)-7,9-dioxo-2,3,4,5,7,

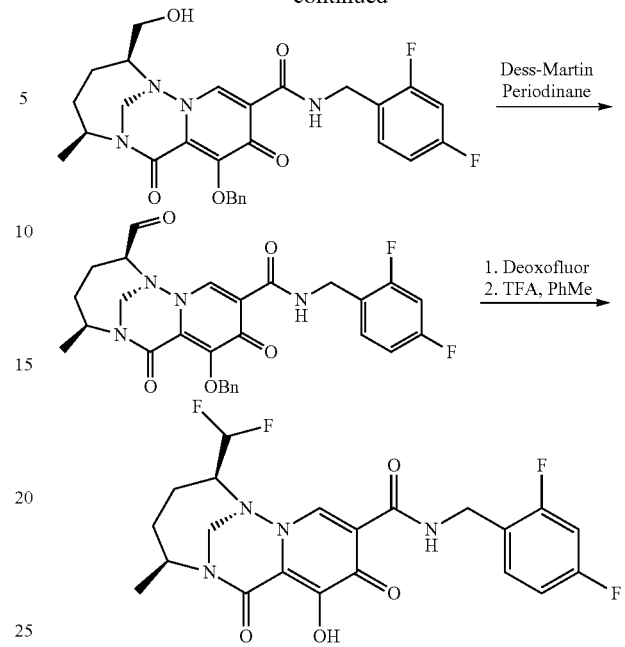

9-hexahydro-1,6-methanopyrido[1,2-b][1,2,5]triazonine-10-carboxamide (68 mg, 0.126 mmol) in dry DCM (7 ml) was added Dess-Martin Periodinane (80.3 mg, 0.189 mmol) and the mixture was stirred for 30 minutes at room temperature. DCM was added and the organic phase was washed twice with 10% sodium thiosulphate solution and once with brine. The organic phase was dried, evaporated to dryness, and used directly for next step. MS (m/z): 537.288 [M+H]⁺.

Steps 4-5: Synthesis of (1S,2S,5S)—N-(2,4-difluorobenzyl)-2-(difluoromethyl)-8-hydroxy-5-methyl-7,9-dioxo-2,3,4,5,7,9-hexahydro-1,6-methanopyrido[1,2-b][1,2,5]triazonine-10-carboxamide (1S,2S,5S)-8-(benzyloxy)-N-(2,4-difluorobenzyl)-2-formyl-5-methyl-7,9-dioxo-2,3,4,5,7,9-hexahydro-1,6-methanopyrido[1,2-b][1,2,5]triazonine-10-carboxamide (30 mg, 0.0559 mmol) in DCM (2 mL) was cooled at 0° C. under argon. To it was added Deoxofluor (50% in toluene, 0.103 ml, 0.280 mmol) under argon. The resulting mixture was stirred at 0° C. for 1 hour. The reaction mixture was diluted with DCM, cooled in an ice/water bath and quenched by dropwise addition of saturated aqueous NaHCO3. The resulting mixture was stirred for 20 minutes. Added more saturated aqueous NaHCO3 until no more bubbling. The organic layer was separated, dried over Na2SO4 and the solvent removed under reduced pressure. The residue was purified by RP-HPLC eluting with ACN/water (w/0.1% TFA) to afford (1S,2S,5S)-8-(benzyloxy)-N-(2,4-difluorobenzyl)-2-(difluoromethyl)-5-methyl-7,9-dioxo-2,3,4,5,7,9-hexahydro-1,6-methanopyrido[1,2-b][1,2,5]triazonine-10-carboxamide. The residue was dissolved in 1 ml of toluene and 1 ml of TFA, stirred at room temperature for one hour. Solvent was removed and the residue was purified by RP-HPLC eluting with ACN/water (w/0.1% TFA) to afford the title product. MS (m/z): 469.200 [M+H]⁺. ¹H NMR (400 MHz, Acetonitrile-d3) δ 10.26 (s, 1H), 8.45 (s, 1H), 7.49-7.38 (m, 1H), 7.03-6.92 (m, 2H), 6.11 (td, J=55.1, 3.6 Hz, 1H), 4.72-4.57 (m, 5H), 3.62-3.49 (m, 1H), 2.18-1.99 (m, 2H), 1.88-1.72 (m, 2H), 1.27 (d, J=6.9 Hz, 3H).

Example 82: Preparation of (1S,2S,5S)—N-(2,4-difluorobenzyl)-8-hydroxy-2-(methoxymethyl)-5-methyl-7,9-dioxo-2,5,7,9-tetrahydro-1,6-methanopyrido[1,2-b][1,2,5]triazonine-10-carboxamide (C82)

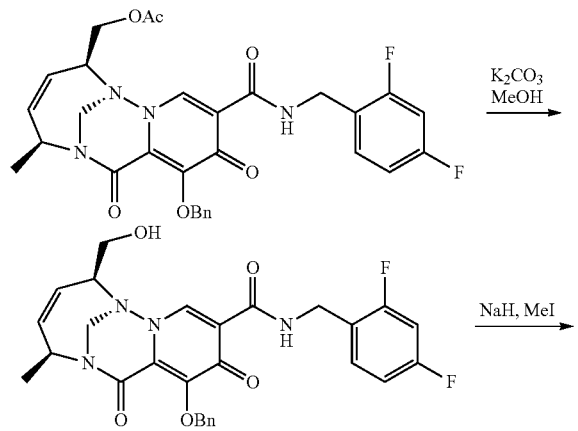

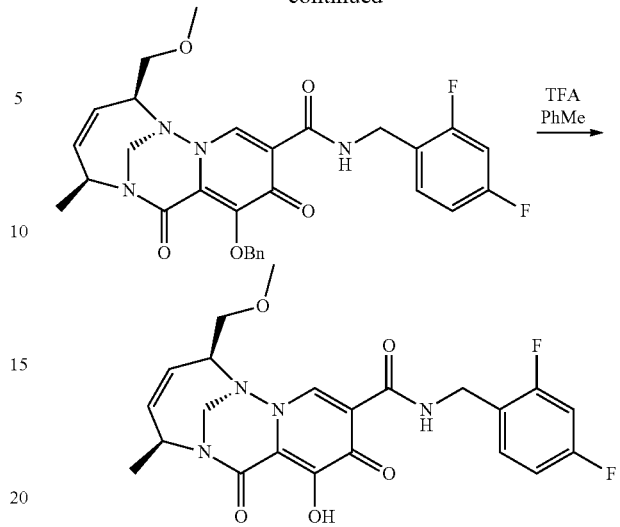

Step 1: Synthesis of (1S,2S,5S)-8-(benzyloxy)-N-(2,4-difluorobenzyl)-2-(hydroxymethyl)-5-methyl-7,9-dioxo-2,5,7,9-tetrahydro-1,6-methanopyrido[1,2-b][1,2,5]triazonine-10-carboxamide (1S,2S,5S)-8-(benzyloxy)-N-(2,4-difluorobenzyl)-2-(hydroxymethyl)-5-methyl-7,9-dioxo-2,5,7,9-tetrahydro-1,6-methanopyrido[1,2-b][1,2,5]triazonine-10-carboxamide was prepared in a manner similar to Step 2 of Example 81, except using ((1S,2S,5S)-8-(benzyloxy)-10-((2,4-difluorobenzyl)carbamoyl)-5-methyl-7,9-dioxo-2,5,7,9-tetrahydro-1,6-methanopyrido[1,2-b][1,2,5]triazonin-2-yl) methyl acetate instead of ((1S,2S,5S)-8-(benzyloxy)-10-((2,4-difluorobenzyl)carbamoyl)-5-methyl-7,9-dioxo-2,3,4,5,7,9-hexahydro-1,6-methanopyrido[1,2-b][1,2,5]triazonin-2-yl)methyl acetate. MS (m/z): 537.300[M+H]⁺.

Step 2: Synthesis of (1S,2S,5S)-8-(benzyloxy)-N-(2,4-difluorobenzyl)-2-(methoxymethyl)-5-methyl-7,9-dioxo-2,5,7,9-tetrahydro-1,6-methanopyrido[1,2-b][1,2,5]triazonine-10-carboxamide To glass vial charged with (1S,2S,5S)-8-(benzyloxy)-N-(2,4-difluorobenzyl)-2-(hydroxymethyl)-5-methyl-7,9-dioxo-2,5,7,9-tetrahydro-1,6-methanopyrido[1,2-b][1,2,5]triazonine-10-carboxamide (25 mg, 0.0466 mmol) under argon was added DMF (2.5 ml) and cooled to 0° C. Sodium hydride (60% dispersion in mineral oil, 2.42 mg, 0.0606 mmol) was added and stirred at 0° C. for 20 minutes. Iodomethane (0.0029 ml, 0.0466 mmol) was added and stirred for 20 minutes. The reaction was quenched with saturated ammonium chloride solution, extracted into ethyl acetate. Washed organic phase with water, then brine. Back extracted the combined aqueous phases with more ethyl acetate. Dried combined organic phases over magnesium sulfate, filtered, concentrated in vacuo. The residue was purified by silica gel flash column chromatography to afford the title product. MS (m/z): 551.300[M+H]+.

Step 3: Synthesis of (1S,2S,5S)—N-(2,4-difluorobenzyl)-8-hydroxy-2-(methoxymethyl)-5-methyl-7,9-dioxo-2,5,7,9-tetrahydro-1,6-methanopyrido[1,2-b][1,2,5]triazonine-10-carboxamide (1S,2S,5S)-8-(benzyloxy)-N-(2,4-difluorobenzyl)-2-(methoxymethyl)-5-methyl-7,9-dioxo-2,5,7,9-tetrahydro-1, 6-methanopyrido[1,2-b][1,2,5]triazonine-10-carboxamide (12 mg, 0.0218 mmol) was dissolved in 1 ml of toluene and 1 ml of TFA, stirred at room temperature for three hours. Solvent was removed and the residue was purified by RP-HPLC to afford the title product. MS (m/z) 461.200[M+H]$^+$. 1H NMR (400 MHz, Acetonitrile-d3) δ 10.23 (s, 1H), 8.55 (s, 1H), 7.54-7.38 (m, 1H), 6.98 (ddt, J=13.0, 8.4, 3.1 Hz, 2H), 5.75 (dt, J=11.7, 2.7 Hz, 1H), 5.38 (dt, J=12.1, 2.8 Hz, 2H), 4.95 (d, J=14.4 Hz, 1H), 4.65-4.57 (m, 3H), 3.91 (dt, J=7.8, 4.3 Hz, 1H), 3.63-3.48 (m, 2H), 3.36 (s, 3H), 1.35 (d, J=7.4 Hz, 3H).

Example 83: Preparation of (1S,2S,5S)—N-(2,4-difluorobenzyl)-8-hydroxy-2-(methoxymethyl)-5-methyl-7,9-dioxo-2,3,4,5,7,9-hexahydro-1,6-methanopyrido[1,2-b][1,2,5]triazonine-10-carboxamide (C83)

(1S,2S,5S)-8-(benzyloxy)-N-(2,4-difluorobenzyl)-2-(methoxymethyl)-5-methyl-7,9-dioxo-2,5,7,9-tetrahydro-1,6-methanopyrido[1,2-b][1,2,5]triazonine-10-carboxamide (9 mg, 0.0163 mmol), prepared according to Example 82, was dissolved in 3 ml of ethanol and 3 ml of ethyl acetate, and was sparged under an argon atmosphere. Palladium on carbon (10 wt %, 2 mg) was added and the mixture was sparged under a hydrogen atmosphere (1 atm, balloon). The mixture was stirred vigorously for one hour and then sparged under an argon atmosphere. It was filtered through a pad of Celite® and washed with absolute ethanol. The filtrate was concentrated to dryness. The residue was purified by RP-HPLC to afford the title product. MS (m/z) 463.200[M+H]$^+$. 1H NMR (400 MHz, Acetonitrile-d3) δ 10.33 (s, 1H), 8.41 (s, 1H), 7.44 (td, J=8.8, 6.7 Hz, 1H), 7.03-6.91 (m, 2H), 4.66 (d, J=14.9 Hz, 1H), 4.64-4.50 (m, 4H), 3.65 (dd, J=9.9, 7.0 Hz, 1H), 3.51-3.34 (m, 2H), 3.38 (s, 3H), 2.03 (dd, J=14.7, 7.4 Hz, 1H), 1.90-1.64 (m, 2H), 1.56 (ddd, J=15.2, 10.9, 3.3 Hz, 1H), 1.26 (d, J=6.8 Hz, 3H).

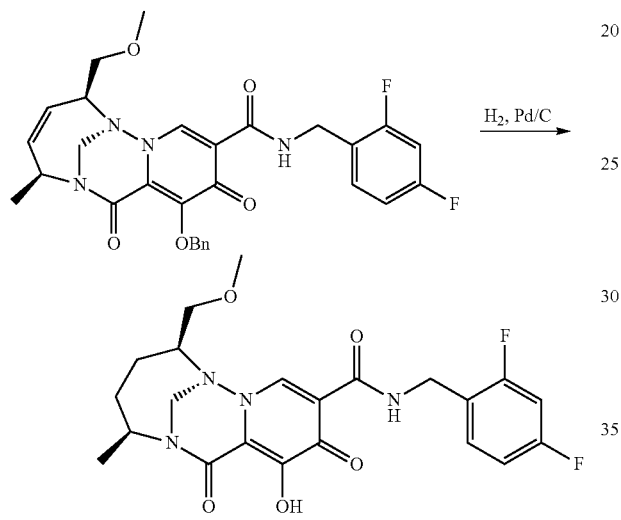

Examples 84 and 85: Preparation of (1'S,3S,5'S)-8'-hydroxy-5'-methyl-7',9'-dioxo-N-(2,4,6-trifluorobenzyl)-4,5,7',9'-tetrahydro-2H,5'H-spiro[furan-3,2'-[1,6]methanopyrido[1,2-b][1,2,5]triazonine]-10'-carboxamide and (1'S,3R,5'S)-8'-hydroxy-5'-methyl-7',9'-dioxo-N-(2,4,6-trifluorobenzyl)-4,5,7',9'-tetrahydro-2H,5'H-spiro[furan-3,2'-[1,6]methanopyrido[1,2-b][1,2,5]triazonine]-10'-carboxamide (C84 and C85)

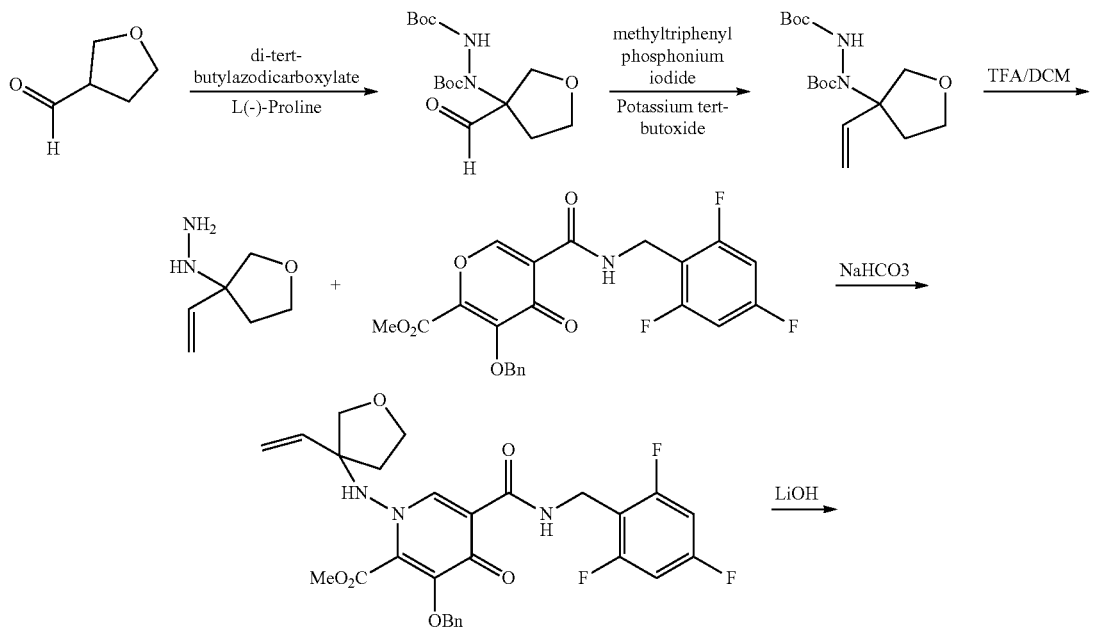

-continued
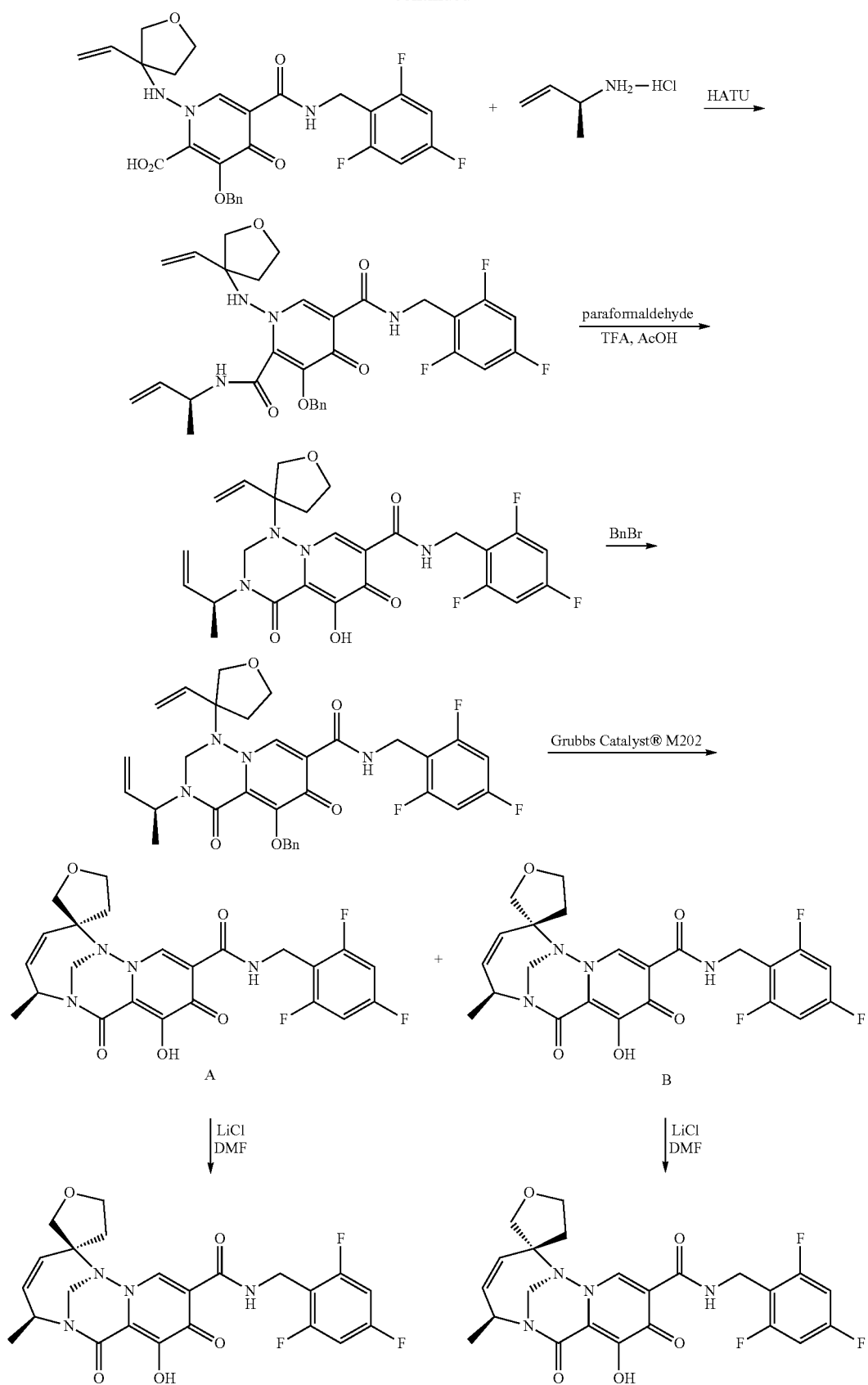

Step 1: Preparation of di-tert-butyl 1-(3-formyltetrahydrofuran-3-yl)hydrazine-1,2-dicarboxylate A mixture of tetrahydrofuran-3-carbaldehyde (2.04 g, 0.02 mol), di-tert-butylazodicarboxylate (3.13 g, 0.014 mol) and L(−)-Proline (0.626 g, 0.54 mmol) in DCE (50 mL) was stirred at 65° C. for 3 days. The reaction mixture was concentrated down, the residue was purified by silica gel chromatography, eluting with 0-60% hexane/EtOAc to give title compound.

Step 2: Preparation of di-tert-butyl 1-(3-vinyltetrahydrofuran-3-yl)hydrazine-1,2-dicarboxylate To a suspension of methyltriphenylphosphonium iodide (4.77 g, 11.8 mmol) in THF (50 mL), was added potassium tert-butoxide (1.32 g, 11.8 mmol) at 0° C. The reaction mixture was stirred at 0° C. for 5 min. The to the mixture was added a solution of di-tert-butyl 1-(3-formyltetrahydrofuran-3-yl)hydrazine-1,2-dicarboxylate tert-butyl N-(tert-butoxycarbonylamino)-N-(3-formyltetrahydrofuran-3-yl)carbamate (1.3 g, 3.93 mmol) in THF (5 mL) at 0° C. Then the reaction mixture was stirred at rt for 1 h. The reaction was quenched with aq. NH$_4$Cl at 0° C., extracted with EtOAc and dried over anhyd. Na$_2$SO$_4$. The combined organic layer was concentrated under reduced pressure to get the crude product which was then purified by silica column chromatography with hexane/acetate (0-60%) as eluents to give title compound.

Step 3: Preparation of (3-vinyltetrahydrofuran-3-yl)hydrazine

The reaction mixture of di-tert-butyl 1-(3-vinyltetrahydrofuran-3-yl)hydrazine-1,2-dicarboxylate (820 mg, 3.59 mmol) in DCM (3 mL) and TFA (3 mL) was stirred at rt for 1 h. The reaction mixture was concentrated down and used in next step without purification.

Step 4: Preparation of methyl 3-(benzyloxy)-4-oxo-5-((2,4,6-trifluorobenzyl)carbamoyl)-1-((3-vinyltetrahydrofuran-3-yl)amino)-1,4-dihydropyridine-2-carboxylate To a solution of (3-vinyltetrahydrofuran-3-yl)hydrazine (460 mg, 3.59 mmol) in MeOH (6 mL) and water (1 mL) was added methyl 3-benzyloxy-4-oxo-5-[(2,4,6-trifluorophenyl)methylcarbamoyl]pyran-2-carboxylate (1.6 g, 3.59 mmol) and sodium bicarbonate (1.64 g, 19.6 mmol). The reaction mixture was stirred at 60° C. overnight. The reaction mixture was cooled down and the solvent was removed under vacuum. The residue was washed with water, extracted with EtOAc, the organic phase was separated, dried over MgSO$_4$, filtered, concentrated down and purified by silica gel chromatography, eluting with 0-100% hexane/EtOAc to give title compound. MS (m/z) 558.04 [M+H]+.

Step 5: Preparation of 3-(benzyloxy)-4-oxo-5-((2,4,6-trifluorobenzyl)carbamoyl)-1-((3-vinyltetrahydrofuran-3-yl)amino)-1,4-dihydropyridine-2-carboxylic acid The reaction mixture of methyl 3-(benzyloxy)-4-oxo-5-((2,4,6-trifluorobenzyl)carbamoyl)-1-((3-vinyltetrahydrofuran-3-yl)amino)-1,4-dihydropyridine-2-carboxylate (760 mg, 1.36 mmol) and lithium hydroxide monohydrate (286 mg, 6.82 mmol) in THF (6 mL), MeOH (6 mL) and water (2 mL) was stirred at 60° C. for 4.5 h. Solvent was removed under vacuum. The residue was washed with 1N HCl, extracted with DCM. The organic was dried over MgSO$_4$, filtered, concentrated down. Material was used in next step without purification. MS (m/z) 544.11 [M+H]+.

Step 6: Preparation of 3-(benzyloxy)-N2-((S)-but-3-en-2-yl)-4-oxo-N5-(2,4,6-trifluorobenzyl)-1-((3-vinyltetrahydrofuran-3-yl)amino)-1,4-dihydropyridine-2,5-dicarboxamide To a solution of 3-(benzyloxy)-4-oxo-5-((2,4,6-trifluorobenzyl)carbamoyl)-1-((3-vinyltetrahydrofuran-3-yl)amino)-1,4-dihydropyridine-2-carboxylic acid (530 mg, 0.975 mmol) in DMF (3 mL) was added HATU (1.0 g, 2.53 mmol) and DIEA (786 mg, 6.09 mmol) at 0° C. Then reaction mixture was stirred at rt for 1 h. Then the (S)-but-3-en-2-amine HCl salt (315 mg, 2.92 mmol) was added at rt in one portion. Reaction mixture was stirred at rt for 5 hr. The reaction mixture was washed with sat. NH$_4$Cl, extracted with EtOAc. The organic phase was separated, dried over MgSO$_4$, filtered, concentrated down. The residue was purified by silica gel chromatography, eluting with 0-80% hexane/EtOAc to give title compound. MS (m/z) 597.10 [M+H]+.

Step 7: Preparation of 3-((S)-but-3-en-2-yl)-5-hydroxy-4,6-dioxo-N-(2,4,6-trifluorobenzyl)-1-(3-vinyltetrahydrofuran-3-yl)-2,3,4,6-tetrahydro-1H-pyrido[2,1-f][1,2,4]triazine-7-carboxamide To a solution of 5-(benzyloxy)-3-((S)-but-3-en-2-yl)-4,6-dioxo-N-(2,4,6-trifluorobenzyl)-1-(3-vinyltetrahydrofuran-3-yl)-2,3,4,6-tetrahydro-1H-pyrido[2,1-f][1,2,4]triazine-7-carboxamide (791 mg, 1.33 mmol) in DCE (10 mL)/ACN (10 mL), was added paraformaldehyde (139 mg, 4.64 mmol), acetic acid (557 mg, 9.28 mmol) and TFA (756 mg, 6.63 mmol). Then the reaction mixture first stirred at rt and then allowed the temp to raise to 82° C. The reaction mixture was stirred at 82° C. for one day. Then to the mixture was added more paraformaldehyde (99 mg, 3.31 mmol), acetic acid (557 mg, 9.28 mmol) and TFA (756 mg, 6.63 mmol). The mixture was heated at 82° C. for one more day. The reaction was cooled down. The reaction mixture was concentrated down, and the residue was purified by silica gel chromatography, eluting with 0-100% hexane/EtOAc to afford the title compound. MS (m/z) 519.22 [M+H]+.

Step 8: Preparation of 5-(benzyloxy)-3-((S)-but-3-en-2-yl)-4,6-dioxo-N-(2,4,6-trifluorobenzyl)-1-(3-vinyltetrahydrofuran-3-yl)-2,3,4,6-tetrahydro-1H-pyrido[2,1-f][1,2,4]triazine-7-carboxamide To a solution of 3-((S)-but-3-en-2-yl)-5-hydroxy-4,6-dioxo-N-(2,4,6-trifluorobenzyl)-1-(3-vinyltetrahydrofuran-3-yl)-2,3,4,6-tetrahydro-1H-pyrido[2,1-f][1,2,4]triazine-7-carboxamide (690 mg, 1.33 mmol) in DMF (10 mL) was added potassium carbonate (920 mg, 6.65 mmol) and benzyl bromide (683 mg, 3.99 mmol). The reaction mixture was stirred at 65° C. for 3 h. The reaction was cooled down. The reaction mixture was washed with water, extracted with EtOAc. The organic phase was dried over MgSO$_4$, filtered, concentrated down. The residue was purified by silica gel chromatography, eluting with 0-100% hexane/EtOAc to give the title compound. MS (m/z) 609.12 [M+H]+.

Step 9: Preparation (1'S,3S,5'S)-8'-(benzyloxy)-5'-methyl-7',9'-dioxo-N-(2,4,6-trifluorobenzyl)-4, 5, 7' 9'-tetrahydro-2H, 5'H-spiro[furan-3,2'-[1,6]methanopyrido[1,2-b][1,2,5]triazonine]-10'-carboxamide (A) and (1'S,3R,5'S)-8'-(benzyloxy)-5'-methyl-7' 9'-dioxo-N-(2,4,6-trifluorobenzyl)-4, 5, 7' 9'-tetrahydro-2H, 5'H-spiro[furan-3,2'-[1,6]methanopyrido[1,2-b][1,2,5]triazonine]-10'-carboxamide (B)

The solution of 5-(benzyloxy)-3-((S)-but-3-en-2-yl)-4,6-dioxo-N-(2,4,6-trifluorobenzyl)-1-(3-vinyltetrahydrofuran-3-yl)-2,3,4,6-tetrahydro-1H-pyrido[2,1-f][1,2,4]triazine-7-carboxamide (370 mg, 0.608 mmol) in DCE (10 mL) was sparged with Argon for 5 min. Then to the mixture was added dichloro[1,3-bis(2,4,6-trimethylphenyl)-2-imidazolidinylidene](3-phenyl-1H-inden-1-ylidene)(tricyclohexylphosphine)ruthenium(II) (86.5 mg, 0.091 mmol) and the mixture was sparged under Argon for 5 min. The mixture was stirred at 80° C. for one day. To the mixture was added more dichloro[1,3-bis(2,4,6-trimethylphenyl)-2-imidazolidinylidene](3-phenyl-1H-inden-1-ylidene)(tricyclohexylphosphine)ruthenium(II) (86.5 mg, 0.091 mmol), sparged with Argon and the reaction mixture was stirred at 80° C. for one week. The reaction mixture was concentrated down and purified by silica gel chromatography, eluting with 0-100% hexane/EtOAc. Two desired compounds formed in the reaction. The major product can be isolated pure as single diastereomer through silica gel chromatography using 0-100% hexane/EtOAc. The minor product was isolated pure as diastereomer through SFC chiral separation.
Major diastereomer: MS (m/z) 581.13 [M+H]+.
Minor diastereomer: MS (m/z) 581.09 [M+H]+.

Step 10: Preparation of ('S,3S,5'S)-8'-hydroxy-5'-methyl-7',9'-dioxo-N-(2,4,6-trifluorobenzyl)-4, 5, 7' 9'-tetrahydro-2H, 5'H-spiro[furan-3,2'-[1,6]methanopyrido[1,2-b][1,2,5]triazonine]-10'-carboxamide and (1'S, 3R,5'S)-8'-hydroxy-5'-methyl-7' 9'-dioxo-N-(2,4,6-trifluorobenzyl)-4,5,7',9'-tetrahydro-2H, 5'H-spiro[furan-3,2'-[1,6]methanopyrido[1,2-b][1,2,5]triazonine]-10'-carboxamide To a solution of (1'S,3S,5'S)-8'-(benzyloxy)-5'-methyl-7',9'-dioxo-N-(2,4,6-trifluorobenzyl)-4,5,7',9'-tetrahydro-2H, 5'H-spiro[furan-3,2'-[1,6]methanopyrido[1,2-b][1,2,5]triazonine]-10'-carboxamide (A) in DMF was added LiCl (10 eq). The reaction mixture was heated at 100° C. overnight. The reaction mixture was filtered, and the solution was purified by reverse phase HPLC, eluting with 5-100% acetonitrile/water. (1'S,3R,5'S)-8'-hydroxy-5'-methyl-7',9'-dioxo-N-(2,4,6-trifluorobenzyl)-4,5,7',9'-tetrahydro-2H, 5'H-spiro[furan-3,2'-[1,6]methanopyrido[1,2-b][1,2,5]triazonine]-10'-carboxamide was synthesized in similar method, except that (1'S,3R,5'S)-8'-(benzyloxy)-5'-methyl-7',9'-dioxo-N-(2,4,6-trifluorobenzyl)-4,5,7',9'-tetrahydro-2H,5'H-spiro[furan-3,2'-[1,6]methanopyrido[1,2-b][1,2,5]triazonine]-10'-carboxamide (B) was used instead of (1'S, 3S,5'S)-8'-(benzyloxy)-5'-methyl-7',9'-dioxo-N-(2,4,6-trifluorobenzyl)-4,5,7',9'-tetrahydro-2H,5'H-spiro[furan-3,2'-[1,6]methanopyrido[1,2-b][1,2,5]triazonine]-10'-carboxamide (A).
Major diastereomer: MS (m/z) 491.19 [M+H]+. 1H NMR (400 MHz, Methanol-d4) δ 8.53 (s, 1H), 6.92 (t, J=8.4 Hz, 2H), 5.68 (dd, J=12.3, 2.7 Hz, 1H), 5.53 (dd, J=12.3, 2.2 Hz, 1H), 5.50-5.38 (m, 1H), 5.19 (d, J=14.5 Hz, 1H), 4.77 (d, J=14.5 Hz, 1H), 4.68 (s, 2H), 4.09 (dd, J=8.7, 1.3 Hz, 1H), 3.79 (pd, J=8.9, 6.0 Hz, 2H), 3.67 (d, J=8.7 Hz, 1H), 1.94 (ddd, J=14.8, 9.3, 5.8 Hz, 1H), 1.51 (dt, J=14.5, 7.4 Hz, 1H), 1.40 (d, J=7.3 Hz, 3H).
Minor diastereomer: MS (m/z) 491.16 [M+H]+. 1H NMR (400 MHz, Methanol-d4) δ 8.52 (s, 1H), 6.91 (t, J=8.4 Hz, 2H), 5.80 (dd, J=12.5, 3.7 Hz, 1H), 5.48-5.38 (m, 1H), 5.34 (dd, J=12.5, 1.7 Hz, 1H), 5.13 (s, 1H), 4.86 (s, 1H), 4.67 (s, 2H), 4.31-4.21 (m, 1H), 4.11 (td, J=8.9, 2.6 Hz, 1H), 3.49 (d, J=11.0 Hz, 1H), 3.32-3.26 (m, 1H), 2.58 (dd, J=13.2, 7.0 Hz, 1H), 2.25 (dt, J=13.2, 9.3 Hz, 1H), 1.43 (d, J=7.3 Hz, 3H).

Example 86: Preparation of (1'S,5'S)-8'-hydroxy-5'-methyl-7',9'-dioxo-N-(2,4,6-trifluorobenzyl)-4,4',5,5',7',9'-hexahydro-2H,3'H-spiro[furan-3,2'-[1,6]methanopyrido[1,2-b][1,2,5]triazonine]-10'-carboxamide (C86)

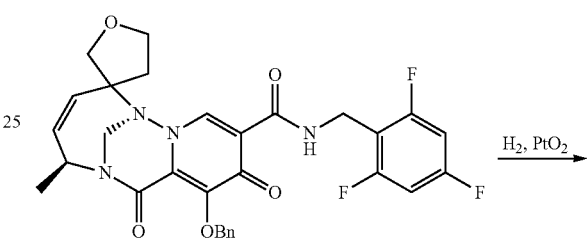

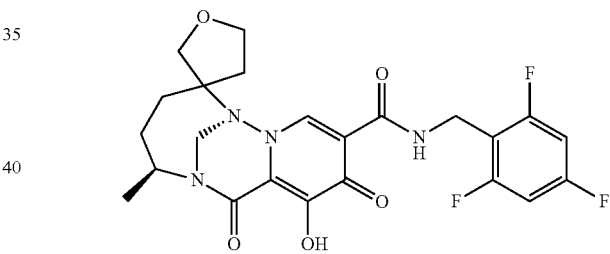

To a solution of (1'S,5'S)-8'-(benzyloxy)-5'-methyl-7',9'-dioxo-N-(2,4,6-trifluorobenzyl)-4,5,7',9'-tetrahydro-2H, 5'H-spiro[furan-3,2'-[1,6]methanopyrido[1,2-b][1,2,5]triazonine]-10'-carboxamide (10 mg, 0.017 mmol), the major diastereomer prepared according to Step 9 of Examples 84 and 85, in EtOH (1 mL) was added platinum dioxide (2 mg). The reaction mixture was stirred at rt under H2 balloon overnight. The reaction mixture was filtered through celite, the filtrate was concentrated down and the residue was purified by reverse phase HPLC, eluting with 5-100% acetonitrile/water to give title compound. MS (m/z) 493.17 [M+H]+. 1H NMR (400 MHz, Methanol-d4) δ 8.44 (s, 1H), 6.97-6.87 (m, 2H), 4.81 (d, J=14.9 Hz, 1H), 4.75-4.60 (m, 3H), 4.16 (q, J=7.7 Hz, 2H), 3.95 (td, J=8.9, 5.0 Hz, 1H), 3.68 (d, J=9.4 Hz, 1H), 2.18 (dt, J=14.6, 6.5 Hz, 1H), 1.92-1.56 (m, 6H), 1.30 (d, J=6.8 Hz, 3H).

Example 87: Preparation of (1S,5S)-8-hydroxy-2,2,5-trimethyl-7,9-dioxo-N-(2,4,6-trifluorobenzyl)-2,3,4,5,7,9-hexahydro-1,6-methanopyrido[1,2-b][1,2,5]triazonine-10-carboxamide (C87)

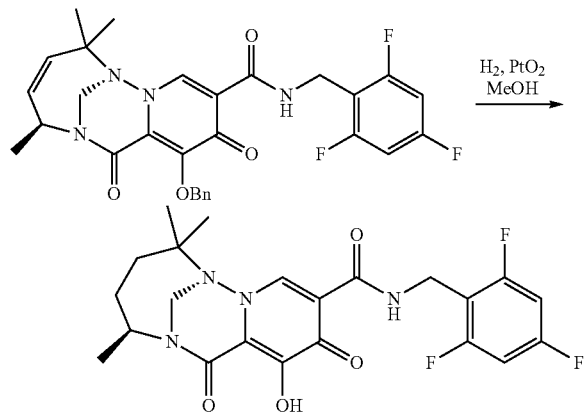

Synthesis of (1S,5S)-8-hydroxy-2,2,5-trimethyl-7,9-dioxo-N-(2,4,6-trifluorobenzyl)-2,3,4,5,7,9-hexahydro-1,6-methanopyrido[1,2-b][1,2,5]triazonine-10-carboxamide (1S,5S)-8-(benzyloxy)-2,2,5-trimethyl-7,9-dioxo-N-(2,4,6-trifluorobenzyl)-2,5,7,9-tetrahydro-1,6-methanopyrido[1,2-b][1,2,5]triazonine-10-carboxamide (0.005 g, 0.009 mmol, 1 equiv.), prepared according to Example 48, was dissolved in methanol (1 mL) and platinum(IV) oxide (0.2 mg, 0.001 mmol, 0.1 equiv.) was added. The vial was sealed, evacuated then backfilled with hydrogen gas (repeated 2 times). The reaction mixture was sparged with hydrogen gas for 5 min and left to stir under 1 atm of hydrogen gas for 4 h. The reaction mixture was filtered and concentrated to afford a crude residue, which was dissolved in MeCN, filtered, and purified by preparative HPLC (column, Gemini 10μ C18 110A, AXI/; 250×21.2 mm) eluting 5-100% acetonitrile (0.1% TFA) in water (0.1% TFA) over 20 minutes. Combined fractions were lyophilized to afford (1S,5S)-8-hydroxy-2,2,5-trimethyl-7,9-dioxo-N-(2,4,6-trifluorobenzyl)-2,3,4,5,7,9-hexahydro-1,6-methanopyrido[1,2-b][1,2,5]triazonine-10-carboxamide. MS (m/z) 465.21 [M+H]. $^1$H NMR (400 MHz, DMSO-$d_6$) δ 10.34 (t, J=6.0 Hz, 1H), 8.28 (s, 1H), 7.21 (t, J=8.7 Hz, 2H), 4.79 (d, J=14.8 Hz, 1H), 4.65 (d, J=14.8 Hz, 1H), 4.56 (d, J=5.7 Hz, 2H), 4.53-4.44 (m, 1H), 1.96-1.84 (m, 1H), 1.71-1.58 (m, 1H), 1.49 (dd, J=15.4, 6.7 Hz, 1H), 1.32 (s, 3H), 1.26-1.22 (m, 1H), 1.20 (d, J=6.8 Hz, 3H), 0.92 (s, 3H). $^{19}$F NMR (376 MHz, DMSO-$d_6$) δ −109.16−−109.37 (m), −112.53 (t, J=7.3 Hz).

Examples 88 and 89: Preparation of (1aS,2R,3S,11S,11aR)-8-hydroxy-2,11-dimethyl-7,9-dioxo-N-(2,4,6-trifluorobenzyl)-1a,2,7,9,11,11a-hexahydro-1H-3,10-methanocyclopropa[g]pyrido[1,2-b][1,2,5]triazonine-6-carboxamide and (1aS,2R,3R,11S,11aR)-8-hydroxy-2,11-dimethyl-7,9-dioxo-N-(2,4,6-trifluorobenzyl)-1a,2,7,9,11,11a-hexahydro-1H-3,10-methanocyclopropa[g]pyrido[1,2-b][1,2,5]triazonine-6-carboxamide (C88 and C89)

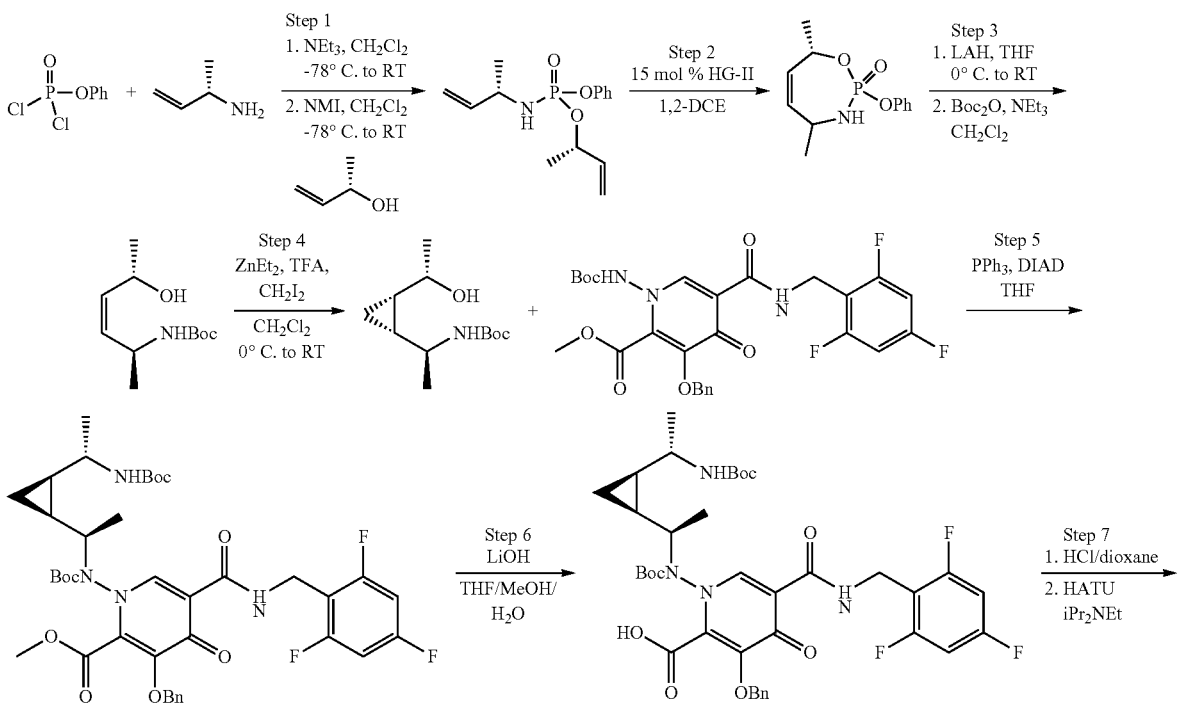

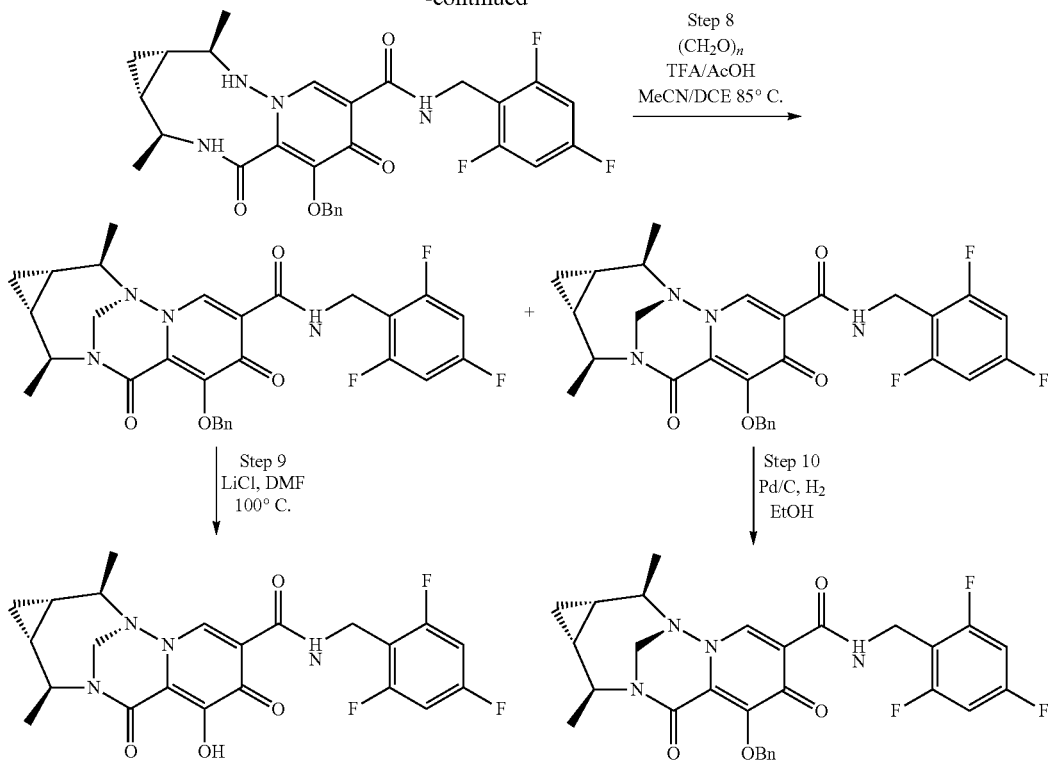

Step 1: Preparation of (S)-but-3-en-2-yl phenyl ((S)-but-3-en-2-yl)phosphoramidate A suspension of (S)-but-3-en-2-amine hydrochloride (1 equiv, 23.2 mmol, 2.5 g) and phenyl phosphorodichloridate (1 equiv, 23.2 mmol, 3.47 mL) in 40 mL DCM was cooled to −78° C. under argon, treated dropwise with triethylamine (2 equiv, 46.5 mmol, 6.5 mL), and allowed to slowly warm to room temperature overnight. The reaction mixture was then cooled again to −78° C., treated with (S)-but-3-en-2-ol (1.5 equiv, 34.9 mmol, 2.5 g) followed by the dropwise addition of NMI (2 equiv, 46.5 mmol, 3.7 mL) in 10 mL DCM and allowed to slowly warm to room temperature overnight. The reaction was quenched with water and extracted into EtOAc (3×). The combined organic layers were dried with sodium sulfate, filtered and concentrated. The crude mixture was purified by silica gel chromatography (0-100% EtOAc in hexanes) to afford the desired product as a ~1:1 mixture of phosphorous diastereomers. MS (m/z) 281.9 [M+H]+. $^1$H NMR (400 MHz, Chloroform-d) δ 7.36-7.18 (m, 4H), 7.17-7.09 (m, 1H), 5.96-5.74 (m, 2H), 5.37-4.92 (m, 4H), 4.01-3.81 (m, 1H), 2.75-2.60 (m, 1H), 1.46 (d, J=6.4 Hz, 1.5H), 1.38 (d, J=6.4 Hz, 1.5H), 1.25 (d, J=6.9 Hz, 1.5H), 1.23 (d, J=6.8 Hz, 1.5H). $^{31}$P NMR (162 MHz, Chloroform-d) δ 2.63-1.96 (m).

Step 2: Preparation of (4S,7S)-4,7-dimethyl-2-phenoxy-3,4,7-trihydro-1,3,2-oxaza phosphepine 2-oxide A solution of (S)-but-3-en-2-yl phenyl ((S)-but-3-en-2-yl) phosphoramidate (11.7 mmol, 3.29 g) in 1,2-DCE (470 mL) was sparged with argon for 20 minutes, treated with Hoveyda-Grubbs Catalyst 2nd Generation (0.05 equiv, 366 mg), sparged for an additional 5 minutes then stirred at room temperature. An additional portion of catalyst was added in the same manner per above at approximately 24 and 48 hours. After 72 hours, the reaction mixture was absorbed onto silica gel and purified by silica gel chromatography (0-100% EtOAc in hexanes). The diastereomers eluted in distinct bands but were combined and concentrated to afford the desired product as a ~1:1 mixture of phosphorous diastereomers. Diastereomer 1 (LCMS Rt=1.14 min): MS (m/z) 254.19 [M+H]+. Diastereomer 2 (LCMS Rt=1.20 min): MS (m/z) 254.18 [M+H]+. $^1$H NMR (400 MHz, Chloroform-d) δ 7.37-7.11 (m, 5H), 5.55-5.35 (m, 2.5H), 5.24-5.13 (m, 0.5H), 4.24 (h, J=7.2 Hz, 0.5H), 4.13-4.01 (m, 0.5H), 3.30 (dd, J=11.8, 7.0 Hz, 0.5H), 3.11 (t, J=6.7 Hz, 0.5H), 1.45 (dt, J=6.9, 1.6 Hz, 3H), 1.33 (dd, J=7.1, 2.2 Hz, 1.5H), 1.25 (dd, J=7.1, 2.4 Hz, 1.5H). $^{31}$P NMR (162 MHz, Chloroform-d) δ 6.08 (s), 4.93 (d, J=8.8 Hz).

Step 3: Preparation of tert-butyl ((2S,5S,Z)-5-hydroxyhex-3-en-2-yl)carbamate A solution of (4S,7S)-4,7-dimethyl-2-phenoxy-3,4,7-trihydro-1,3,2-oxazaphosphepine 2-oxide (6.32 mmol, 1.6 g) in 60 mL THF was cooled to −78° C. under argon. A solution of lithium aluminum hydride (2 M THF, 3.75 equiv, 23.7 mmol, 11 mL) was added dropwise then the reaction mixture was slowly allowed to warm to room temperature overnight. The reaction was cooled to 0° C. then carefully quenched with 1 mL water, 1 mL 10% aqueous NaOH, and 1.5 mL water, warmed to room temperature, treated with magnesium sulfate and filtered across Celite with additional CH$_2$Cl$_2$. The filtrate was concentrated to afford (2S,5S,Z)-5-aminohex-3-en-2-ol as a clear oil. $^1$H NMR (400 MHz, Chloroform-d) δ 5.48-5.31 (m, 2H), 4.66-4.57 (m, 1H), 3.91 (p, J=6.7 Hz, 1H), 1.28 (d, J=6.5 Hz, 3H), 1.22 (d, J=6.5 Hz, 3H).

The crude reaction mixture containing (2S,5S,Z)-5-aminohex-3-en-2-ol was dissolved in 65 mL DCM and cooled to 0° C. under argon then treated with triethylamine (2 equiv, 12.6 mmol, 1.76 mL) and di-tert-butyl dicarbonate (1.5 equiv, 9.48 mmol, 2.07 g) and allowed to slowly warm to room temperature overnight. The reaction mixture was concentrated then dissolved again in EtOAc and washed with half-saturated aqueous sodium bicarbonate and brine, dried over sodium sulfate, filtered and concentrated. The crude residue was purified by silica gel chromatography (0-100% EtOAc in hexanes) to afford the desired product as a white solid. MS (m/z) 215.76 [M+H]$^+$. $^1$H NMR (400 MHz, Chloroform-d) δ 5.46 (ddd, J=11.1, 7.3, 1.0 Hz, 1H), 5.20 (t, J=10.3 Hz, 1H), 4.83-4.61 (m, 2H), 4.45 (bs, 1H), 1.43 (s, 9H), 1.28 (d, J=6.4 Hz, 3H), 1.20 (d, J=6.7 Hz, 3H).

Step 4: Preparation of tert-butyl ((S)-1-((1R,2S)-2-((S)-1-hydroxyethyl)cyclopropyl)ethyl)carbamate)

A solution of diethylzinc (1 M in hexanes, 5 equiv, 9.41 mmol, 9.4 mL) in CH$_2$Cl$_2$ (4 mL) was cooled to 0° C. under argon, treated dropwise with trifluoroacetic acid (4.8 equiv, 9.0 mmol, 690 uL) and stirred for 15 minutes. Diiodomethane (5 equiv, 9.41 mmol, 760 uL) was added dropwise and the reaction mixture was stirred for an additional 20 minutes. A solution of tert-butyl ((2S,5S,Z)-5-hydroxyhex-3-en-2-yl)carbamate (1 equiv, 1.88 mmol, 405 mg) in CH$_2$Cl$_2$ (2 mL) was added dropwise and the reaction mixture was allowed to slowly warm to room temperature overnight then quenched with saturated ammonium chloride and extracted into EtOAc (3×). The combined organic layers were washed with brine, dried with sodium sulfate, filtered and concentrated. The crude residue was purified by silica gel chromatography (0-100% EtOAc in hexanes) to afford the title compound. MS (m/z) 229.73 [M+H]$^+$. $^1$H NMR (400 MHz, Chloroform-d) δ 4.57 (s, 1H), 3.80-3.66 (m, 1H), 3.50-3.33 (m, 1H), 1.43 (s, 9H), 1.30 (d, J=6.2 Hz, 3H), 1.25 (d, J=6.3 Hz, 3H), 0.99-0.79 (m, 2H), 0.74 (td, J=8.5, 4.5 Hz, 1H), 0.34 (d, J=5.7 Hz, 1H).

Step 5: Preparation of methyl 3-(benzyloxy)-1-((tert-butoxycarbonyl)((R)-1-((S,2R)-2-((S)-1-((tert-butoxycarbonyl)amino)ethyl)cyclopropyl)ethyl)amino)-4-oxo-5-((2,4,6-trifluorobenzyl)carbamoyl)-1,4-dihydropyridine-2-carboxylate A solution of tert-butyl ((S)-1-((1R,2S)-2-((S)-1-hydroxyethyl)cyclopropyl)ethyl)carbamate (1.2 equiv, 0.427 mmol, 98 mg), methyl 3-(benzyloxy)-1-((tert-butoxycarbonyl)amino)-4-oxo-5-((2,4,6-trifluorobenzyl)carbamoyl)-1,4-dihydropyridine-2-carboxylate (1 equiv, 0.356 mmol, 200 mg), prepared according to Example 6, and triphenylphosphine (1.2 equiv, 0.427 mmol, 106 mg) in THF (3.5 mL) was cooled to 0° C. under argon then treated dropwise with diisopropyl azodicarboxylate (1.2 equiv, 0.427 mmol, 85 uL) and allowed to slowly warm to room temperature overnight. The reaction mixture was then treated with an additional portion of triphenylphosphine and diisopropyl azodicarboxylate at 0° C. and again warmed to room temperature overnight then concentrated and purified by silica gel chromatography (0-100% EtOAc in hexanes) followed by reversed-phase C18 chromatography (0-100% MeCN in water). The combined clean fractions were concentrated then dissolved again in CH$_2$Cl$_2$, dried with sodium sulfate, filtered and concentrated to afford the title product. MS (m/z) 773.01 [M+H]+.

Step 6: Preparation of 3-(benzyloxy)-1-((tert-butoxycarbonyl)((R)-1-((1S,2R)-2-((S)-1-((tert-butoxycarbonyl)amino)ethyl)cyclopropyl)ethyl)amino)-4-oxo-5-((2,4,6-trifluorobenzyl)carbamoyl)-1,4-dihydropyridine-2-carboxylic acid A solution of methyl 3-(benzyloxy)-1-((tert-butoxycarbonyl)((R)-1-((1R,2S)-2-((S)-1-((tert-butoxycarbonyl)amino)ethyl)cyclopropyl)ethyl)amino)-4-oxo-5-((2,4,6-trifluorobenzyl)carbamoyl)-1,4-dihydropyridine-2-carboxylate (0.113 mmol, 87 mg) in 3/2/1 THF/MeOH/water (4 mL) was treated with lithium hydroxide (4 equiv, 0.45 mmol, 19 mg) and stirred at room temperature overnight. The reaction mixture was treated with an additional portion lithium hydroxide and further stirred at room temperature, then carefully acidified to pH~3 with 1N HCl and extracted into EtOAc (3×). The combined organic layers were washed with brine, dried with sodium sulfate, filtered and concentrated to afford the title compound that was carried forward to Step 7 without further purification. MS (m/z) 759.02 [M+H]$^+$.

Step 7: Preparation of (1aS,2R,11S,11aR)-8-(benzyloxy)-2,11-dimethyl-7,9-dioxo-N-(2,4,6-trifluorobenzyl)-1a,2,3,7,9,10,11,11a-octahydro-1H-cyclopropa[g]pyrido[1,2-b][1,2,5]triazonine-6-carboxamide The crude reaction mixture from Step 6 containing 3-(benzyloxy)-1-((tert-butoxycarbonyl)((R)-1-((1R,2S)-2-((S)-1-((tert-butoxycarbonyl)amino)ethyl)cyclopropyl)ethyl)amino)-4-oxo-5-((2,4,6-trifluorobenzyl)carbamoyl)-1,4-dihydropyridine-2-carboxylic acid was dissolved in CH$_2$Cl$_2$ (200 uL) and 4N HCl/dioxane (70 uL), stirred at room temperature for 3 hours, then concentrated, redissolved in CH$_2$Cl$_2$ and concentrated again (3×) to afford 1-(((R)-1-((1R,2S)-2-((S)-1-aminoethyl)cyclopropyl)ethyl)amino)-3-(benzyloxy)-4-oxo-5-((2,4,6-trifluorobenzyl)carbamoyl)-1,4-dihydropyridine-2-carboxylic acid. MS (m/z) 559.28 [M+H]+. The crude residue was dissolved in CH$_2$Cl$_2$ (1 mL), treated with N,N-diisopropylethylamine (5 equiv, 0.079 mmol, 14 uL) and 2-(7-Aza-1H-benzotriazole-1-yl)-1,1,3,3-tetramethyluronium hexafluorophosphate (HATU, 1.5 equiv, 0.024 mmol, 9.0 mg) then stirred at room temperature overnight. The reaction mixture was diluted with EtOAc, washed with saturated aqueous sodium bicarbonate then further extracted with EtOAc (2×). The combined organic layers were dried with sodium sulfate, filtered and concentrated. The crude residue was purified by silica gel chromatography (0-100% EtOAc in hexanes) to afford the title compound. MS (m/z) 541.10 [M+H]+.

Step 8: Preparation of (1aS,2R,3S,11S,11aR)-8-(benzyloxy)-2,11-dimethyl-7,9-dioxo-N-(2,4,6-trifluorobenzyl)-1a,2,7,9,11,11a-hexahydro-1H-3,10-methanocyclopropa[g]pyrido[1,2-b][1,2,5]triazonine-6-carboxamide and (1aS,2R,3R,11S,11aR)-8-(benzyloxy)-2,11-dimethyl-7,9-dioxo-N-(2,4,6-trifluorobenzyl)-1a,2,7,9,11,11a-hexahydro-1H-3,10-methanocyclopropa[g]pyrido[1,2-b][1,2,5]triazonine-6-carboxamide A solution of (1aS,2R,11S,11aR)-8-(benzyloxy)-2,11-dimethyl-7,9-dioxo-N-(2,4,6-trifluorobenzyl)-1a,2,3,7,9,10,11,11a-octahydro-1H-cyclopropa[g]pyrido[1,2-b][1,2,5]triazonine-6-carboxamide (0.044 mmol, 23.7 mg) in 1/1 MeCN/1,2-DCE (0.8 mL) was treated with paraformaldehyde (3 equiv, 0.13 mmol, 12 mg), acetic acid (7 equiv, 0.31 mmol, 18 uL), and trifluoroacetic acid (5 equiv, 0.22 mmol, 17 uL) then heated to 85° C. for 90 minutes. The reaction mixture was concentrated then dissolved again in EtOAc and washed with saturated aqueous sodium bicarbonate and the aqueous layer was further extracted with EtOAc (2×). The combined organic layers were dried with sodium sulfate, filtered and concentrated. The crude residue was purified by silica gel chromatography (0-100% EtOAc in hexanes) followed by preparative TLC (EtOAc) to afford the title compound as separated diastereomers. Minor diastereomer (LCMS Rt=1.51 min): MS (m/z) 553.07 [M+H]+. Major diastereomer (LCMS Rt=1.55 min): MS (m/z) 553.09 [M+H]+.

Step 9: Preparation of (1aS,2R,3S,11S,11aR)-8-hydroxy-2,11-dimethyl-7,9-dioxo-N-(2,4,6-trifluorobenzyl)-1a,2,7,9,11,11a-hexahydro-JH-3,10-methanocyclopropa[g]pyrido[1,2-b][1,2,5]triazonine-6-carboxamide (C88)

A solution of (1aS,2R,3S,11S,11aR)-8-(benzyloxy)-2,11-dimethyl-7,9-dioxo-N-(2,4,6-trifluorobenzyl)-1a,2,7,9,11,11a-hexahydro-1H-3,10-methanocyclopropa[g]pyrido[1,2-b][1,2,5]triazonine-6-carboxamide (0.0081 mmol, 4.5 mg), the minor diastereomer from Step 8, in DMF (0.15 mL) was treated with lithium chloride (10 equiv, 0.081 mmol, 3.5 mg) and heated to 100° C. for 6 hours. The reaction mixture was cooled to room temperature, diluted with MeOH/MeCN/TFA, filtered, purified by preparative HPLC (10-100% MeCN in water, 0.1% TFA) and lyophilized to afford the title compound. MS (m/z) 463.29 [M+H]⁺. ¹H NMR (400 MHz, Chloroform-d) δ 10.35 (t, J=4.9 Hz, 1H), 8.48 (s, 1H), 6.73-6.60 (m, 2H), 5.13 (q, J=7.1 Hz, 1H), 4.67 (s, 2H), 4.64 (d, J=8.9 Hz, 1H), 4.49 (d, J=14.3 Hz, 1H), 4.29 (p, J=6.9 Hz, 1H), 1.50 (d, J=7.1 Hz, 3H), 1.23-1.17 (m, 2H), 1.18 (d, J=7.0 Hz, 3H), 1.12 (q, J=8.0 Hz, 1H), 0.17 (q, J=6.9 Hz, 1H).

Step 10: Preparation of (aS,2R,3R,11S,11aR)-8-hydroxy-2,11-dimethyl-7,9-dioxo-N-(2,4,6-trifluorobenzyl)-1a,2,7,9,11,11a-hexahydro-1H-3,10-methanocyclopropa[g]pyrido[1,2-b][1,2,5]triazonine-6-carboxamide (C89)

A solution of (1aS,2R,3R,11S,11aR)-8-(benzyloxy)-2,11-dimethyl-7,9-dioxo-N-(2,4,6-trifluorobenzyl)-1a,2,7,9,11,11a-hexahydro-1H-3,10-methanocyclopropa[g]pyrido[1,2-b][1,2,5]triazonine-6-carboxamide (0.01 mmol, 5.5 mg), the major diastereomer from Step 8, in EtOH (0.2 mL) was purged with argon then treated with 10% palladium on carbon (2 mg), affixed with a hydrogen balloon and purged with hydrogen (3×). After 30 minutes, the reaction mixture was filtered across Celite, concentrated, purified by preparative HPLC (10-100% MeCN in water, 0.1% TFA) and lyophilized to afford the title compound. MS (m/z) 463.21 [M+H]+. ¹H NMR (400 MHz, Chloroform-d) δ 10.40 (t, J=5.1 Hz, 1H), 8.62 (s, 1H), 6.71-6.62 (m, 2H), 4.77-4.59 (m, 3H), 4.44 (d, J=15.0 Hz, 1H), 4.44-4.34 (m, 1H), 3.01 (dq, J=10.0, 6.8 Hz, 1H), 1.94-1.86 (m, 1H), 1.85 (d, J=6.7 Hz, 3H), 1.39 (d, J=7.5 Hz, 3H), 1.12 (td, J=8.8, 5.4 Hz, 1H), 1.00 (q, J=5.7 Hz, 1H), 0.91 (qd, J=8.7, 5.6 Hz, 1H).

Example 90: Preparation of (1S,2R)—N-(2,4-difluorobenzyl)-8-hydroxy-2,5,5-trimethyl-7,9-dioxo-2,5,7,9-tetrahydro-1,6-methanopyrido[1,2-b][1,2,5]triazonine-10-carboxamide (C90)

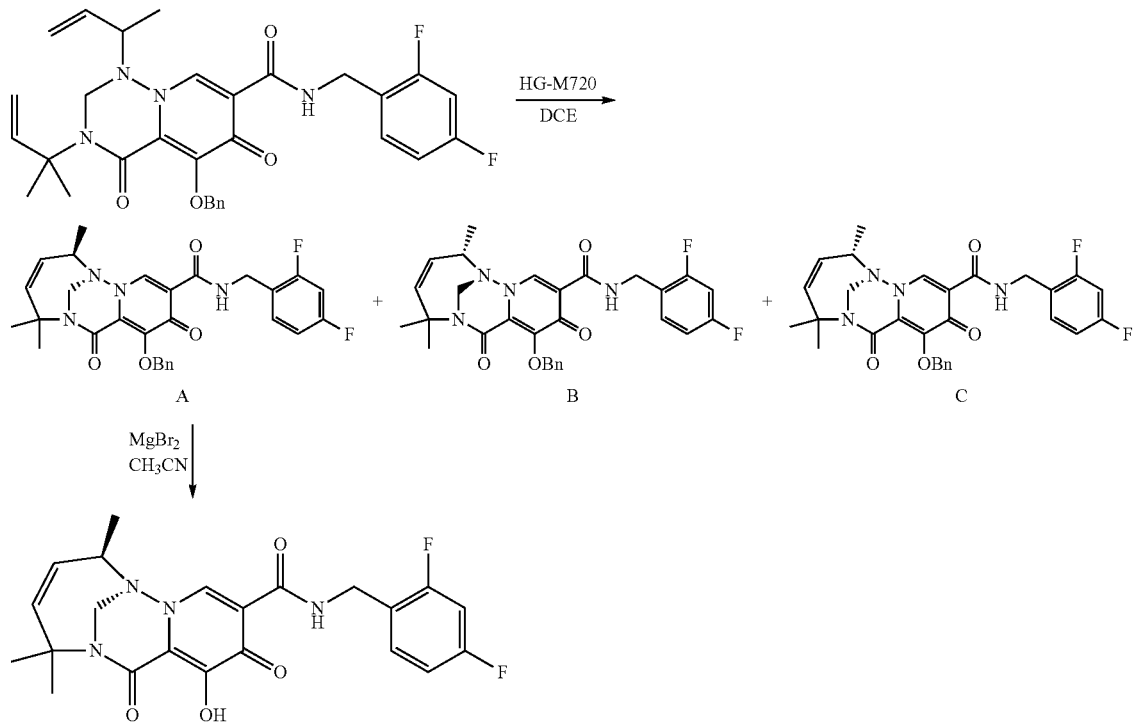

Step 1: Preparation of (1S,2R)-8-(benzyloxy)-N-(2,4-difluorobenzyl)-2,5,5-trimethyl-7,9-dioxo-2,5,7,9-tetrahydro-1,6-methanopyrido[1,2-b][1,2,5]triazonine-10-carboxamide (A), (1R,2S)-8-(benzyloxy)-N-(2,4-difluorobenzyl)-2,5,5-trimethyl-7,9-dioxo-2,5,7,9-tetrahydro-1,6-methanopyrido[1,2-b][1,2,5]triazonine-10-carboxamide (B), and (1S,2S)-8-(benzyloxy)-N-(2,4-difluorobenzyl)-2,5,5-trimethyl-7,9-dioxo-2,5,7,9-tetrahydro-1,6-methanopyrido[1,2-b][1,2,5]triazonine-10-carboxamide (C)

5-(benzyloxy)-1-(but-3-en-2-yl)-N-(2,4-difluorobenzyl)-3-(2-methylbut-3-en-2-yl)-4,6-dioxo-2,3,4,6-tetrahydro-1H-pyrido[2,1-f][1,2,4]triazine-7-carboxamide (400 mg, 0.711 mmol), prepared in a manner similar to Example 29 except using 2-methylbut-3-en-2-amine instead of (S)-but-3-en-2-amine, was dissolved in dichloromethane (60 mL) at room temperature. Argon was bubbled through the reaction solution for 20 min. HG-M720 catalyst (44.5 mg, 0.071 mmol) was then added with stirring. The purging with argon was continued for 10 min. The reaction mixture connected with reflux condenser (Vacuuming, flushing with argon three times) then heated with stirring under argon atmosphere for 24 hrs. The resulting reaction mixture was then concentrated to dryness. The crude material was purified on silica gel column with 0-100% EtOAc/Hex to afford three diastereomers. (1S,2R)-8-(benzyloxy)-N-(2,4-difluorobenzyl)-2,5,5-trimethyl-7,9-dioxo-2,5,7,9-tetrahydro-1,6-methanopyrido[1,2-b][1,2,5]triazonine-10-carboxamide (A): MS (m/z): 535.1 [M+H]+. (1R,2S)-8-(benzyloxy)-N-(2,4-difluorobenzyl)-2,5,5-trimethyl-7,9-dioxo-2,5,7,9-tetrahydro-1,6-methanopyrido[1,2-b][1,2,5]triazonine-10-carboxamide (B): MS (m/z): 535.0 [M+H]+. (1S,2S)-8-(benzyloxy)-N-(2,4-difluorobenzyl)-2,5,5-trimethyl-7,9-dioxo-2,5,7,9-tetrahydro-1,6-methanopyrido[1,2-b][1,2,5]triazonine-10-carboxamide (C): MS (m/z): 535.1 [M+H]+.

Step 2: Preparation of (1S,2R)—N-(2,4-difluorobenzyl)-8-hydroxy-2,5,5-trimethyl-7,9-dioxo-2,5,7,9-tetrahydro-1,6-methanopyrido[1,2-b][1,2,5]triazonine-10-carboxamide (1S,2R)-8-(benzyloxy)-N-(2,4-difluorobenzyl)-2,5,5-trimethyl-7,9-dioxo-2,5,7,9-tetrahydro-1,6-methanopyrido[1,2-b][1,2,5]triazonine-10-carboxamide (25 mg, 0.0.56 mmol) was dissolved in CH$_3$CN (3 mL) added MgBr$_2$ (38 mg, 0.206 mmol) and stirred at 50° C. for 2 h. Reaction mixture was quenched with water (1 mL) to form clear solution, filtered and the residue was taken up in MeOH and was purified with reverse phase prep-HPLC with 50-100% CH$_3$CN in water to afford the desired product. MS (m/z): 445.1 [M+H]$^+$. 1H NMR (400 MHz, Acetonitrile-d3) δ 10.39 (s, 1H), 8.41 (s, 1H), 7.44 (td, J=9.2, 8.8, 6.5 Hz, 1H), 7.03-6.90 (m, 2H), 5.70-5.45 (m, 2H), 5.13 (d, J=14.5 Hz, 1H), 4.59 (dd, J=13.6, 5.4 Hz, 4H), 1.83 (s, 3H), 1.45 (s, 3H), 1.03 (d, J=7.3 Hz, 3H).

Examples 91 and 92: Preparation of (1R,2S)—N-(2,4-difluorobenzyl)-8-hydroxy-2,5,5-trimethyl-7,9-dioxo-2,5,7,9-tetrahydro-1,6-methanopyrido[1,2-b][1,2,5]triazonine-10-carboxamide and (1S,2S)—N-(2,4-difluorobenzyl)-8-hydroxy-2,5,5-trimethyl-7,9-dioxo-2,5,7,9-tetrahydro-1,6-methanopyrido[1,2-b][1,2,5]triazonine-10-carboxamide (C91 and C92)

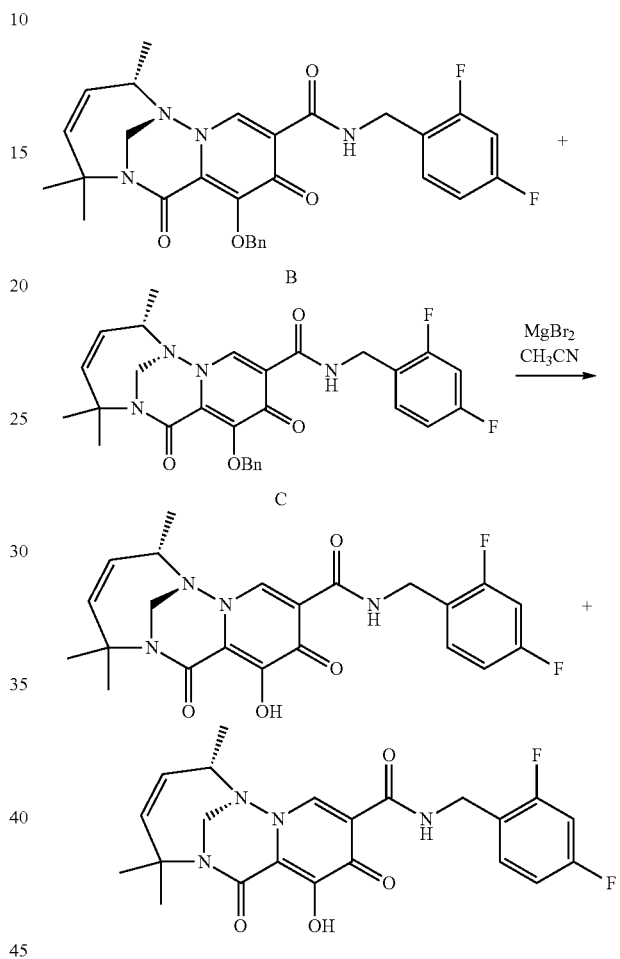

A mixture of (1R,2S)-8-(benzyloxy)-N-(2,4-difluorobenzyl)-2,5,5-trimethyl-7,9-dioxo-2,5,7,9-tetrahydro-1,6-methanopyrido[1,2-b][1,2,5]triazonine-10-carboxamide (B) and (1S,2S)-8-(benzyloxy)-N-(2,4-difluorobenzyl)-2,5,5-trimethyl-7,9-dioxo-2,5,7,9-tetrahydro-1,6-methanopyrido[1,2-b][1,2,5]triazonine-10-carboxamide (C) (25 mg, 0.0.56 mmol), prepared according to Example 90, was dissolved in CH$_3$CN (3 mL) and added MgBr2 (38 mg, 0.206 mmol) and stirred at 50° C. for 2 h. Reaction mixture was quenched with water (1 mL) to form clear solution, filtered and the residue was taken up in MeOH. The crude product was purified by reverse phase prep-HPLC with 50-100% CH$_3$CN in water to afford the desired products, (1R,2S)—N-(2,4-difluorobenzyl)-8-hydroxy-2,5,5-trimethyl-7,9-dioxo-2,5,7,9-tetrahydro-1,6-methanopyrido[1,2-b][1,2,5]triazonine-10-carboxamide and (1S,2S)—N-(2,4-difluorobenzyl)-8-hydroxy-2,5,5-trimethyl-7,9-dioxo-2,5,7,9-tetrahydro-1,6-methanopyrido[1,2-b][1,2,5]triazonine-10-carboxamide.

(1R,2S)—N-(2,4-difluorobenzyl)-8-hydroxy-2,5,5-trimethyl-7,9-dioxo-2,5,7,9-tetrahydro-1,6-methanopyrido[1,2-b][1,2,5]triazonine-10-carboxamide (C91): MS (m/z): 445.1

[M+H]+. 1H NMR (400 MHz, Acetonitrile-d3) δ 10.35 (s, 1H), 8.37 (s, 1H), 7.44 (td, J=9.2, 8.8, 6.5 Hz, 1H), 6.97 (ddt, J=13.0, 8.5, 3.0 Hz, 2H), 5.67 (dd, J=11.2, 2.5 Hz, 1H), 5.39 (dd, J=11.2, 4.1 Hz, 1H), 5.11 (d, J=14.3 Hz, 1H), 4.60 (d, J=6.0 Hz, 2H), 4.51 (d, J=14.2 Hz, 1H), 3.93 (ddd, J=6.7, 4.1, 2.6 Hz, 1H), 1.76 (s, 3H), 1.42 (s, 3H), 1.33 (d, J=6.6 Hz, 3H).

(1S,2S)—N-(2,4-difluorobenzyl)-8-hydroxy-2,5,5-trimethyl-7,9-dioxo-2,5,7,9-tetrahydro-1,6-methanopyrido[1,2-b][1,2,5]triazonine-10-carboxamide (C92): MS (m/z): 445.1 [M+H]+. 1H NMR (400 MHz, Acetonitrile-d3) δ 10.35 (s, 1H), 8.37 (s, 1H), 7.52-7.32 (m, 1H), 6.97 (ddt, J=11.2, 8.6, 3.0 Hz, 2H), 5.67 (dd, J=11.2, 2.5 Hz, 1H), 5.39 (dd, J=11.2, 4.1 Hz, 1H), 5.11 (d, J=14.2 Hz, 1H), 4.60 (d, J=5.9 Hz, 2H), 4.51 (d, J=14.3 Hz, 1H), 3.93 (ddd, J=6.6, 4.1, 2.5 Hz, 1H), 1.76 (s, 3H), 1.42 (s, 3H), 1.33 (d, J=6.6 Hz, 3H).

Examples 93 and 94: Preparation of (1S,2R)—N-(2,4-difluorobenzyl)-8-hydroxy-2,5,5-trimethyl-7,9-dioxo-2,3,4,5,7,9-hexahydro-1,6-methanopyrido[1,2-b][1,2,5]triazonine-10-carboxamide and (1R,2S)—N-(2,4-difluorobenzyl)-8-hydroxy-2,5,5-trimethyl-7,9-dioxo-2,3,4,5,7,9-hexahydro-1,6-methanopyrido[1,2-b][1,2,5]triazonine-10-carboxamide (C93 and C94)

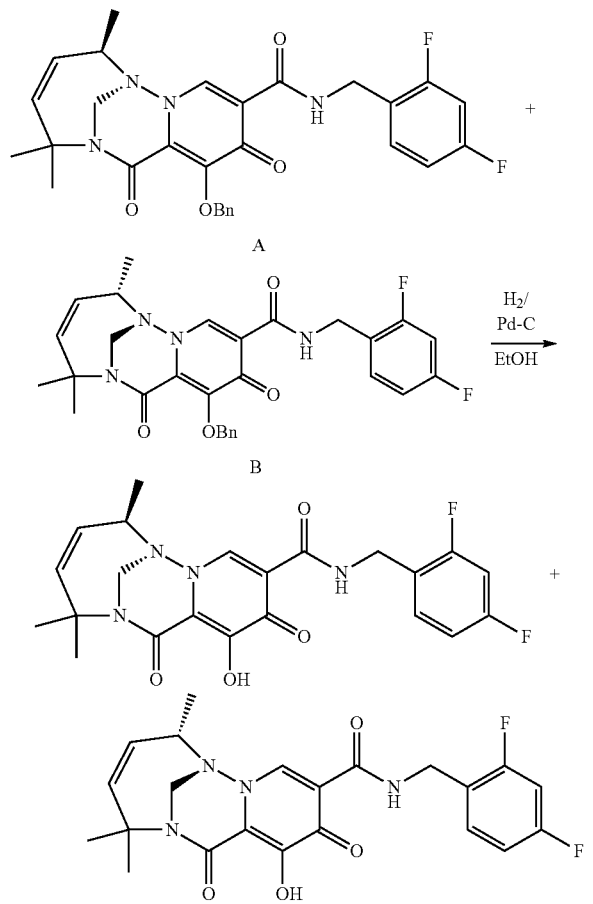

A mixture of (1S,2R)-8-(benzyloxy)-N-(2,4-difluorobenzyl)-2,5,5-trimethyl-7,9-dioxo-2,5,7,9-tetrahydro-1,6-methanopyrido[1,2-b][1,2,5]triazonine-10-carboxamide (A) and (1R,2S)-8-(benzyloxy)-N-(2,4-difluorobenzyl)-2,5,5-trimethyl-7,9-dioxo-2,5,7,9-tetrahydro-1,6-methanopyrido[1,2-b][1,2,5]triazonine-10-carboxamide (15 mg, 0.028 mmol), prepared according to Example 90, was dissolved in EtOH (3 mL) and added 10% Pd—C(6 mg, 0.006 mmol). Hydrogenolysis was performed with H₂ balloon at rt for 7 hrs. Reaction mixture was filtered through pad of Celite. Filtrate was collected and concentrated to dryness. The residue was taken up in MeOH and was purified with reverse phase prep-HPLC with 50-100% CH₃CN in water with 0.1% TFA to afford the desired product (1S,2R)—N-(2,4-difluorobenzyl)-8-hydroxy-2,5,5-trimethyl-7,9-dioxo-2,3,4,5,7,9-hexahydro-1,6-methanopyrido[1,2-b][1,2,5]triazonine-10-carboxamide and (1R,2S)—N-(2,4-difluorobenzyl)-8-hydroxy-2,5,5-trimethyl-7,9-dioxo-2,3,4,5,7,9-hexahydro-1,6-methanopyrido[1,2-b][1,2,5]triazonine-10-carboxamide.

(1S,2R)—N-(2,4-difluorobenzyl)-8-hydroxy-2,5,5-trimethyl-7,9-dioxo-2,3,4,5,7,9-hexahydro-1,6-methanopyrido[1,2-b][1,2,5]triazonine-10-carboxamide (C93): MS (m/z): 447.2 [M+H]⁺. ¹H NMR (400 MHz, Acetonitrile-d₃) δ 10.45 (s, 1H), 8.32 (s, 1H), 7.44 (d, J=7.6 Hz, 1H), 6.97 (t, J=9.9 Hz, 3H), 5.00-4.43 (m, 4H), 1.88-1.77 (m, 3H), 1.68 (s, 2H), 1.64-1.47 (m, 2H), 1.39 (s, 3H), 1.12 (d, J=6.9 Hz, 3H).

(1R,2S)—N-(2,4-difluorobenzyl)-8-hydroxy-2,5,5-trimethyl-7,9-dioxo-2,3,4,5,7,9-hexahydro-1,6-methanopyrido[1,2-b][1,2,5]triazonine-10-carboxamide (C94): MS (m/z): 447.1 [M+H]⁺. ¹H NMR (400 MHz, Acetonitrile-d₃) δ 10.45 (s, 1H), 8.32 (s, 1H), 7.44 (q, J=9.3, 8.5 Hz, 1H), 6.97 (t, J=10.0 Hz, 2H), 4.83 (d, J=14.6 Hz, 1H), 4.66 (d, J=14.6 Hz, 1H), 4.60 (d, J=5.9 Hz, 2H), 3.74-3.30 (m, 1H), 1.74-1.52 (m, 4H), 1.39 (s, 3H), 1.30 (s, 3H), 1.12 (d, J=6.9 Hz, 3H).

Example 95: Preparation of (1S,2S)—N-(2,4-difluorobenzyl)-8-hydroxy-2,5,5-trimethyl-7,9-dioxo-2,3,4,5,7,9-hexahydro-1,6-methanopyrido[1,2-b][1,2,5]triazonine-10-carboxamide (C95)

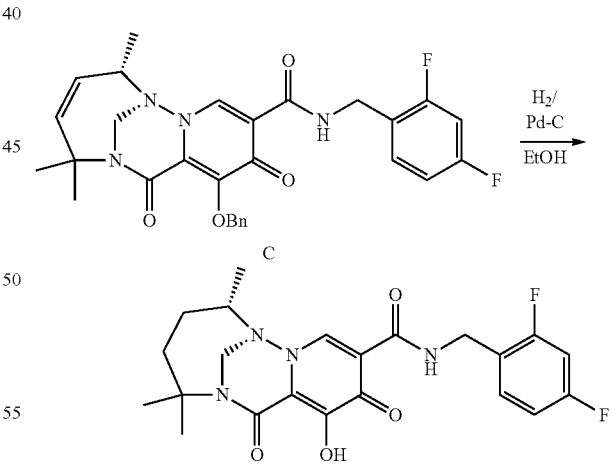

(1S,2S)-8-(benzyloxy)-N-(2,4-difluorobenzyl)-2,5,5-trimethyl-7,9-dioxo-2,5,7,9-tetrahydro-1,6-methanopyrido[1,2-b][1,2,5]triazonine-10-carboxamide (C) (20 mg, 0.037 mmol), prepared according to Example 90, was dissolved in EtOH (3 mL) and added 10% Pd—C (8 mg, 0.0075 mmol). Hydrogenolysis was performed with H2 balloon at rt for 7 hrs. Reaction mixture was filtered through pad of Celite. Filtrate was collected and concentrated to dryness. The residue was taken up in MeOH and was purified with reverse phase prep-HPLC with 50-100% CH₃CN in water with 0.1% TFA to afford the desired product (1S,2S)—N-(2,4-difluorobenzyl)-8-hydroxy-2,5,5-trimethyl-7,9-dioxo-2,3,4,5,7,9-hexahydro-1,6-methanopyrido[1,2-b][1,2,5]triazonine-10-carboxamide. MS (m/z): 447.1 [M+H]⁺. 1H NMR (400 MHz, Acetonitrile-d3) δ 8.57-8.18 (m, 1H), 7.45 (s, 1H), 7.01 (d, J=22.1 Hz, 2H), 6.77 (s, 1H), 5.78-5.26 (m, 1H), 5.19-4.14 (m, 4H), 3.97 (s, 1H), 1.87 (s, 4H), 1.82-1.67 (m, 3H), 1.46-1.31 (m, 3H), 1.30 (s, 3H).

Example 96: Preparation of (1R,2S,5S)—N-(2,4-difluorobenzyl)-5-(fluoromethyl)-8-hydroxy-2-methyl-7,9-dioxo-2,3,4,5,7,9-hexahydro-1,6-methanopyrido[1,2-b][1,2,5]triazonine-10-carboxamide (C96)

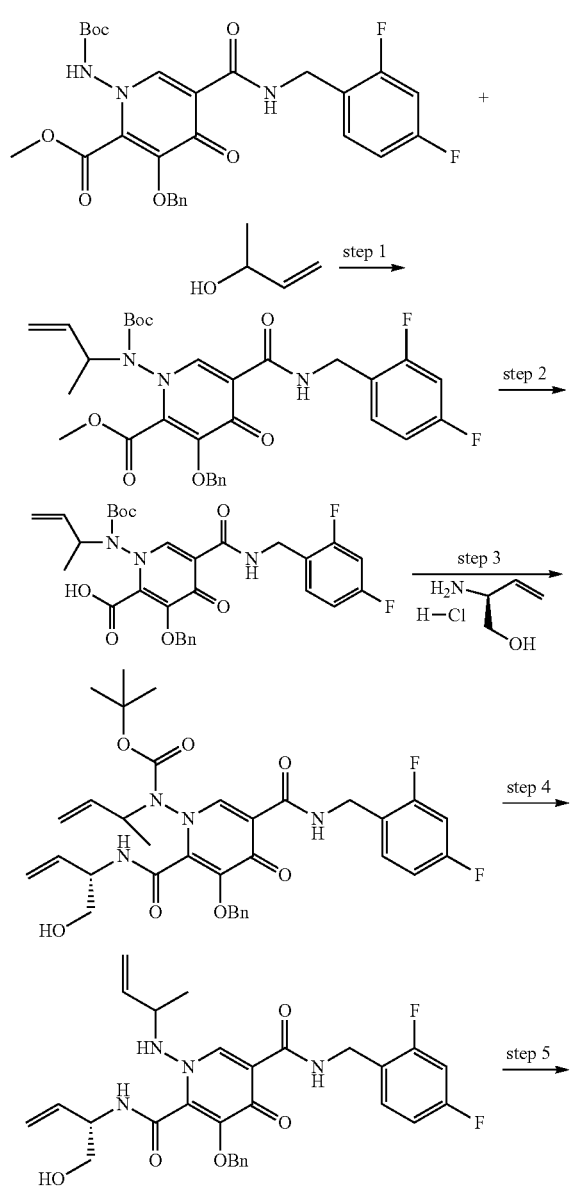

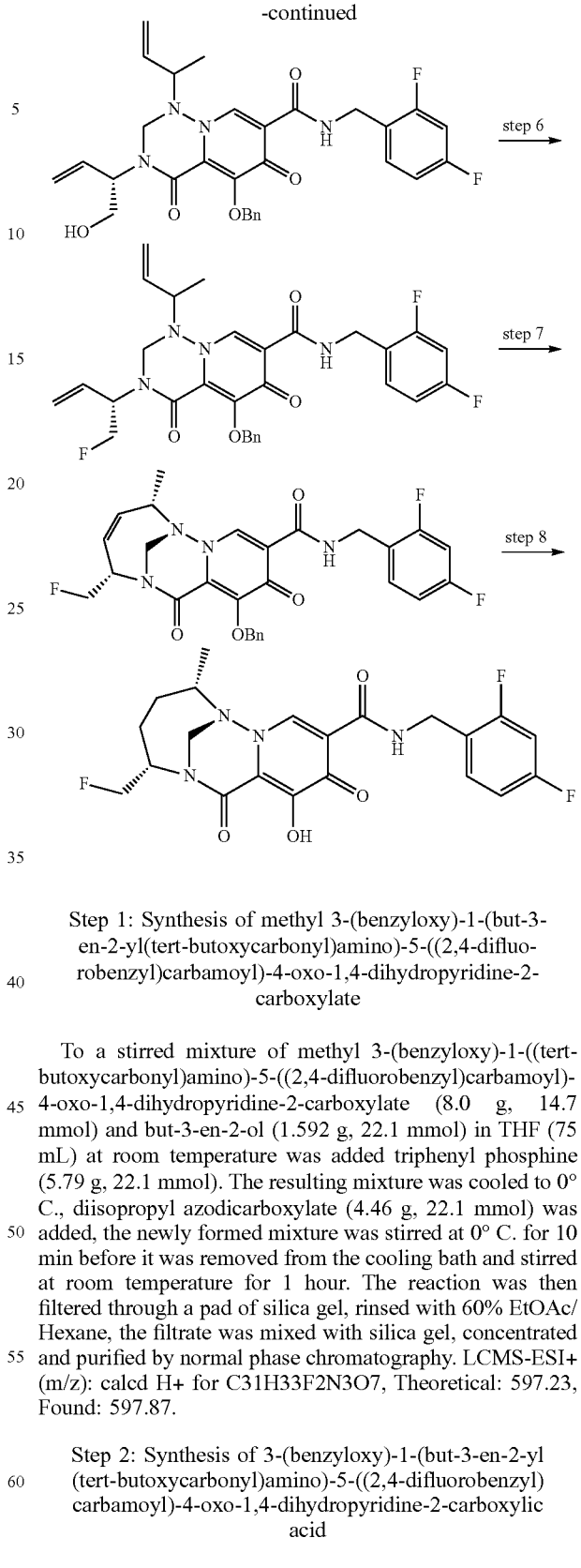

Step 1: Synthesis of methyl 3-(benzyloxy)-1-(but-3-en-2-yl(tert-butoxycarbonyl)amino)-5-((2,4-difluorobenzyl)carbamoyl)-4-oxo-1,4-dihydropyridine-2-carboxylate To a stirred mixture of methyl 3-(benzyloxy)-1-((tert-butoxycarbonyl)amino)-5-((2,4-difluorobenzyl)carbamoyl)-4-oxo-1,4-dihydropyridine-2-carboxylate (8.0 g, 14.7 mmol) and but-3-en-2-ol (1.592 g, 22.1 mmol) in THF (75 mL) at room temperature was added triphenyl phosphine (5.79 g, 22.1 mmol). The resulting mixture was cooled to 0° C., diisopropyl azodicarboxylate (4.46 g, 22.1 mmol) was added, the newly formed mixture was stirred at 0° C. for 10 min before it was removed from the cooling bath and stirred at room temperature for 1 hour. The reaction was then filtered through a pad of silica gel, rinsed with 60% EtOAc/Hexane, the filtrate was mixed with silica gel, concentrated and purified by normal phase chromatography. LCMS-ESI+ (m/z): calcd H+ for C31H33F2N3O7, Theoretical: 597.23, Found: 597.87.

Step 2: Synthesis of 3-(benzyloxy)-1-(but-3-en-2-yl(tert-butoxycarbonyl)amino)-5-((2,4-difluorobenzyl)carbamoyl)-4-oxo-1,4-dihydropyridine-2-carboxylic acid Methyl 3-(benzyloxy)-1-(but-3-en-2-yl(tert-butoxycarbonyl)amino)-5-((2,4-difluorobenzyl)carbamoyl)-4-oxo-1,4-dihydropyridine-2-carboxylate (10.0 g, 16.7 mmol) was dissolved in a mixture of MeOH (96 mL), THF (48 mL) and water (48 mL). To this stirred mixture was added LiOH—H$_2$O (4.21 g, 100 mmol). The resulting mixture was heated to 60° C. for 6 hours. The reaction was then cooled to room temperature, concentrated, the residue was diluted with EtOAc, acidified to pH-4 with 1N HCl, layers were separated, the organic layer was washed with brine, dried over sodium sulfate, filtered and concentrated. LCMS-ESI+(m/z): calcd H+ for C30H31F2N3O7, Theoretical: 583.21, Found: 583.868.

Step 3: Synthesis of tert-butyl (3-(benzyloxy)-5-((2,4-difluorobenzyl)carbamoyl)-2-(((S)-1-hydroxybut-3-en-2-yl)carbamoyl)-4-oxopyridin-1(4H)-yl)(but-3-en-2-yl)carbamate To a mixture of 3-(benzyloxy)-1-(but-3-en-2-yl(tert-butoxycarbonyl)amino)-5-((2,4-difluorobenzyl)carbamoyl)-4-oxo-1,4-dihydropyridine-2-carboxylic acid (1.5 g, 2.57 mmol) and (2S)-2-aminobut-3-en-1-ol; hydrochloride (381 mg, 3.08 mmol) in DCM (12.0 mL) at room temperature was added 1-ethyl-3-(3-dimethylaminopropyl)carbodiimide HCl (736 mg, 3.86 mmol) followed by 1-hydroxy-7-azabenzotriazole (525 mg, 3.86 mmol) and DIEA (1.329 g, 10.3 mmol). The resulting mixture was stirred at room temperature for overnight. The reaction was then diluted with DCM, washed with 10% citric acid, brine, dried over sodium sulfate, filtered and concentrated. Purified by normal phase chromatography.

Step 4: Synthesis of 3-(benzyloxy)-1-(but-3-en-2-ylamino)-N$^5$-(2,4-difluorobenzyl)-N$^2$—((S)-1-hydroxybut-3-en-2-yl)-4-oxo-1,4-dihydropyridine-2,5-dicarboxamide tert-butyl (3-(benzyloxy)-5-((2,4-difluorobenzyl)carbamoyl)-2-(((S)-1-hydroxybut-3-en-2-yl)carbamoyl)-4-oxopyridin-1(4H)-yl)(but-3-en-2-yl)carbamate (700 mg, 1.07 mmol) was dissolved in DCM (10 mL) at room temperature and treated with 4N HCl in 1,4-dioxane (10 mL) for 90 minutes. The reaction was concentrated, coevaporated with ethyl acetate (×5) and then coevaporated with acetonitrile (×5). Used directly in next step.

Step 5: Synthesis of 5-(benzyloxy)-1-(but-3-en-2-yl)-N-(2,4-difluorobenzyl)-3-((S)-1-hydroxybut-3-en-2-yl)-4,6-dioxo-2,3,4,6-tetrahydro-1H-pyrido[2,1-f][1,2,4]triazine-7-carboxamide 3-(benzyloxy)-1-(but-3-en-2-ylamino)-N5-(2,4-difluorobenzyl)-N2-((S)-1-hydroxybut-3-en-2-yl)-4-oxo-1,4-dihydropyridine-2,5-dicarboxamide (300 mg, 0.543 mmol) was dissolved in acetonitrile (1 mL). The resulting mixture was heated to 88° C. To this hot mixture was added paraformaldehyde (42.9 mg, 1.36 mmol) followed by TFA (0.15 mL). Heating continued for 15 hours. The reaction was then cooled to room temperature and concentrated. The resulting residue was then dissolved in DMF (2 mL), Benzyl bromide (111 mg, 0.652 mmol) and potassium carbonate (600 mg, 4.34 mmol) were added sequentially. The resulting mixture was heated to 70° C. for 2 hours. Then it was cooled to room temperature, partitioned between ethyl acetate and water, the organic layer was washed with brine, dried over sodium sulfate, filtered and concentrated, purified by normal phase chromatography. LCMS-ESI+(m/z): calcd H+ for C30H30F2N4O5, Theoretical: 564.22, Found: 565.102.

Step 6: Synthesis of 5-(benzyloxy)-1-(but-3-en-2-yl)-N-(2,4-difluorobenzyl)-3-((S)-1-fluorobut-3-en-2-yl)-4,6-dioxo-2,3,4,6-tetrahydro-1H-pyrido[2,1-f][1,2,4]triazine-7-carboxamide 5-(benzyloxy)-1-(but-3-en-2-yl)-N-(2,4-difluorobenzyl)-3-((S)-1-hydroxybut-3-en-2-yl)-4,6-dioxo-2,3,4,6-tetrahydro-1H-pyrido[2,1-f][1,2,4]triazine-7-carboxamide (180 mg, 0.32 mmol) was dissolved in DCM (3 mL) and cooled to 0° C. To this cold mixture was added bis(2-methoxyethyl)aminosulfur trifluoride (423 mg, 1.91 mmol) dropwise. The reaction was removed from the cooling bath after addition and allowed to warm up to room temperature and stirred at that temperature for overnight. The reaction was then cooled back to 0° C., quenched with saturated sodium bicarbonate dropwise with vigorous stirring. The mixture was extracted with DCM. Organic layer was washed with brine, dried over sodium sulfate, filtered and concentrated, purified by normal phase chromatography. LCMS-ESI+(m/z): calcd H+ for C30H29F3N4O4, Theoretical: 566.21, Found: 567.120.

Step 7: Synthesis of (R,2S,5S)-8-(benzyloxy)-N-(2,4-difluorobenzyl)-5-(fluoromethyl)-2-methyl-7,9-dioxo-2,5,7,9-tetrahydro-1,6-methanopyrido[1,2-b][1,2,5]triazonine-10-carboxamide 5-(benzyloxy)-1-(but-3-en-2-yl)-N-(2,4-difluorobenzyl)-3-((S)-1-fluorobut-3-en-2-yl)-4,6-dioxo-2,3,4,6-tetrahydro-1H-pyrido[2,1-f][1,2,4]triazine-7-carboxamide (100 mg, 0.177 mmol) was dissolved in DCE (3 ml). Hoveyda-Grubbs II catalyst (11.1 mg, 0.0177 mmol) was added. The resulting mixture was purged with Argon for 5 minutes, then it was sealed and heated at 80° C. for overnight. The reaction was cooled to room temperature, concentrated, purified by normal phase chromatography. LCMS-ESI+(m/z): calcd H+ for C28H25F3N4O4, Theoretical: 538.18, Found: 539.105.

Step 8: Synthesis of (1R,2S,5S)—N-(2,4-difluorobenzyl)-5-(fluoromethyl)-8-hydroxy-2-methyl-7,9-dioxo-2,3,4,5,7,9-hexahydro-1,6-methanopyrido[1,2-b][1,2,5]triazonine-10-carboxamide (1R,2S,5S)-8-(benzyloxy)-N-(2,4-difluorobenzyl)-5-(fluoromethyl)-2-methyl-7,9-dioxo-2,5,7,9-tetrahydro-1,6-methanopyrido[1,2-b][1,2,5]triazonine-10-carboxamide (20 mg, 0.0371 mmol) was dissolved in EtOH (20 mL) at room temperature. To this stirred mixture was added 10% Pd/C (4 mg). The resulting mixture was degassed and flushed with nitrogen three times, degassed and flushed with hydrogen three times and then it was hydrogenated under hydrogen balloon for 1 hour. The reaction was degassed and flushed with nitrogen, filtered through Celite. The filtrate was concentrated, purified by reverse phase prep HPLC. LCMS-ESI+(m/z): calcd H+ for C21H21F3N4O4, Theoretical: 450.15, Found: 451.224. 1H NMR (400 MHz, DMSO-d6) δ 10.34 (t, J=5.9 Hz, 1H), 8.34 (s, 1H), 7.42 (td, J=8.6, 6.6 Hz, 1H), 7.25 (ddd, J=10.5, 9.3, 2.6 Hz, 1H), 7.07 (td, J=8.6, 2.6 Hz, 1H), 4.74 (s, 2H), 4.71-4.43 (m, 6H), 1.94-1.81 (m, 1H), 1.77-1.65 (m, 1H), 1.61-1.39 (m, 2H), 1.28 (d, J=7.1 Hz, 3H).

Example 97: Preparation of (1R,2S,5S)—N-(2,4-difluorobenzyl)-5-(fluoromethyl)-8-hydroxy-2-methyl-7,9-dioxo-2,5,7,9-tetrahydro-1,6-methanopyrido[1,2-b][1,2,5]triazonine-10-carboxamide (C97)

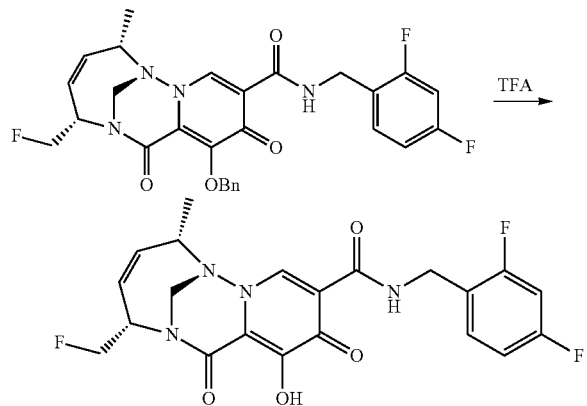

(1R,2S,5S)-8-(benzyloxy)-N-(2,4-difluorobenzyl)-5-(fluoromethyl)-2-methyl-7,9-dioxo-2,5,7,9-tetrahydro-1,6-methanopyrido[1,2-b][1,2,5]triazonine-10-carboxamide (20 mg, 0.0371 mmol), prepared according to Example 96, was treated with a mixture of DCM (1.5 mL) and TFA (1.5 mL) at room temperature for 2 hours. The reaction was concentrated and purified by reverse phase prep HPLC. LCMS-ESI+(m/z): calcd H+ for C21H19F3N4O4, Theoretical: 448.14, Found: 449.179. 1H NMR (400 MHz, Acetonitrile-d3) δ 10.19-10.11 (m, 1H), 8.39 (s, 1H), 7.50-7.38 (m, 1H), 7.02-6.92 (m, 2H), 5.81 (dt, J=11.4, 2.3 Hz, 1H), 5.66-5.59 (m, 1H), 5.54-5.39 (m, 1H), 5.13 (d, J=14.6 Hz, 1H), 4.80-4.55 (m, 5H), 3.92-3.82 (m, 1H), 1.37 (d, J=6.7 Hz, 3H).

Example 98: Preparation of (1S,2R,5R)—N-(2,4-difluorobenzyl)-5-(fluoromethyl)-8-hydroxy-2-methyl-7,9-dioxo-2,3,4,5,7,9-hexahydro-1,6-methanopyrido[1,2-b][1,2,5]triazonine-10-carboxamide (C98)

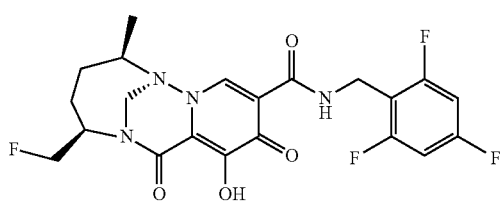

(1S,2R,5R)—N-(2,4-difluorobenzyl)-5-(fluoromethyl)-8-hydroxy-2-methyl-7,9-dioxo-2,3,4,5,7,9-hexahydro-1,6-methanopyrido[1,2-b][1,2,5]triazonine-10-carboxamide was made according to Example 96 except (2R)-2-aminobut-3-en-1-ol was used instead of (2S)-2-aminobut-3-en-1-ol hydrochloride in Step 3. LCMS-ESI+(m/z): calcd H+ for C21H21F3N4O4, Theoretical: 450.15, Found: 451.12. 1H NMR (400 MHz, Acetonitrile-d3) δ 10.33 (s, 1H), 8.45 (s, 1H), 7.44 (td, J=9.2, 8.8, 6.5 Hz, 1H), 7.06-6.86 (m, 2H), 4.79-4.39 (m, 7H), 3.63-3.58 (m, 1H), 1.95-1.82 (m, 2H), 1.62 (dt, J=7.1, 3.5 Hz, 2H), 1.32 (d, J=7.2 Hz, 3H).

Example 99: Preparation of (1S,2R,4S,5S)-4-fluoro-5-(fluoromethyl)-8-hydroxy-2-methyl-7,9-dioxo-N-(2,4,6-trifluorobenzyl)-2,3,4,5,7,9-hexahydro-1,6-methanopyrido[1,2-b][1,2,5]triazonine-10-carboxamide (C99)

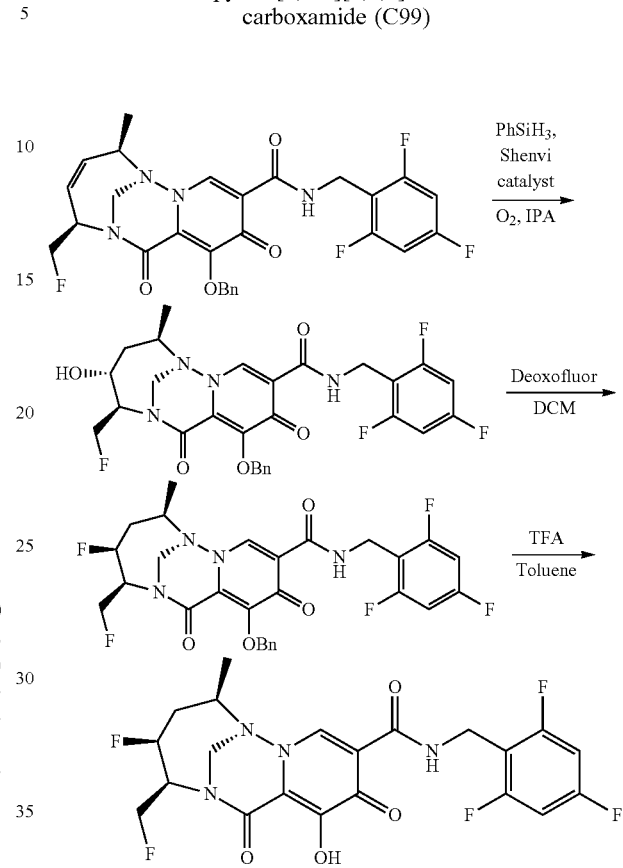

Step 1: Synthesis of (1S,2R,4R,5R)-8-(benzyloxy)-5-(fluoromethyl)-4-hydroxy-2-methyl-7,9-dioxo-N-(2,4,6-trifluorobenzyl)-2,3,4,5,7,9-hexahydro-1,6-methanopyrido[1,2-b][1,2,5]triazonine-10-carboxamide To (1S,2R,5R)-8-(benzyloxy)-5-(fluoromethyl)-2-methyl-7,9-dioxo-N-(2,4,6-trifluorobenzyl)-2,5,7,9-tetrahydro-1,6-methanopyrido[1,2-b][1,2,5]triazonine-10-carboxamide (116 mg, 0.208 mmol), prepared according to Example 50, in IPA (3 ml) was added PhSiH₃ (45.1 mg, 0.417 mmol), followed by Shenvi cat. (7.56 mg, 0.0012 mmol), then the mixture was stirred under O₂ for 24 h at room temperature. The reaction was quenched by adding 10% sodium thiosulfate, then it was extracted with EtOAc. The organic phase was washed with brine and dried with MgSO₄. Solvent was removed under vacuo. Crude material was purified by silica gel column to obtain the title compound. MS (m/z) [M+H]⁺ 574.98.

Step 2: Synthesis of (1S,2R,4S,5S)-8-(benzyloxy)-4-fluoro-5-(fluoromethyl)-2-methyl-7,9-dioxo-N-(2,4,6-trifluorobenzyl)-2,3,4,5,7,9-hexahydro-1,6-methanopyrido[1,2-b][1,2,5]triazonine-10-carboxamide To (1S,2R,4R,5R)-8-(benzyloxy)-5-(fluoromethyl)-4-hydroxy-2-methyl-7,9-dioxo-N-(2,4,6-trifluorobenzyl)-2,3,4, 5,7,9-hexahydro-1,6-methanopyrido[1,2-b][1,2,5]triazonine-10-carboxamide (30 mg, 0.0522 mmol) at 0° C. was added deoxofluor (2.7N in toluene) (0.193 ml, 0.522 mmol) in DCM (1 ml) in a plastic vial. Then the reaction was stirred at room temperature for overnight. Reaction was quenched with sat. NaHCO$_3$ at 0° C. and was extracted with DCM three times. The organic phase was washed with brine and dried with MgSO$_4$. The crude material was purified by silica gel column to obtain the title compound. MS (m/z) [M+H]$^+$ 577.4.

Step 3: Synthesis of (1S,2R,4S,5S)-4-fluoro-5-(fluoromethyl)-8-hydroxy-2-methyl-7,9-dioxo-N-(2,4,6-trifluorobenzyl)-2,3,4,5,7,9-hexahydro-1,6-methanopyrido[1,2-b][1,2,5]triazonine-10-carboxamide To (1S,2R,4S,5S)-8-(benzyloxy)-4-fluoro-5-(fluoromethyl)-2-methyl-7,9-dioxo-N-(2,4,6-trifluorobenzyl)-2,3,4,5,7,9-hexahydro-1,6-methanopyrido[1,2-b][1,2,5]triazonine-10-carboxamide (66.2 mg, 0.115 mmol) was added TFA (0.5 ml) in toluene (0.5 ml) at room temperature. The reaction mixture was stirred at room temperature for overnight. Solvent was removed under vacuo and the crude material was purified by prep-HPLC to obtain the title compound. MS (m/z) [M+H]$^+$ 487.05. 1H NMR (400 MHz, Chloroform-d) δ 10.18 (d, J=5.1 Hz, 1H), 8.59 (s, 1H), 6.80-6.56 (m, 2H), 5.41-5.21 (m, 1H), 5.12-4.88 (m, 2H), 4.86-4.55 (m, 4H), 3.49 (s, 1H), 2.46-2.26 (m, 1H), 2.10-1.86 (m, 1H), 1.56 (dd, J=7.3, 2.3 Hz, 3H), 1.54-1.14 (m, 1H).

Example 100: Preparation of (1S,2R,5S)-8-hydroxy-2,5,13-trimethyl-7,9-dioxo-N-(2,4,6-trifluorobenzyl)-2,5,7,9-tetrahydro-1,6-methanopyrido[1,2-b][1,2,5]triazonine-10-carboxamide (C100)

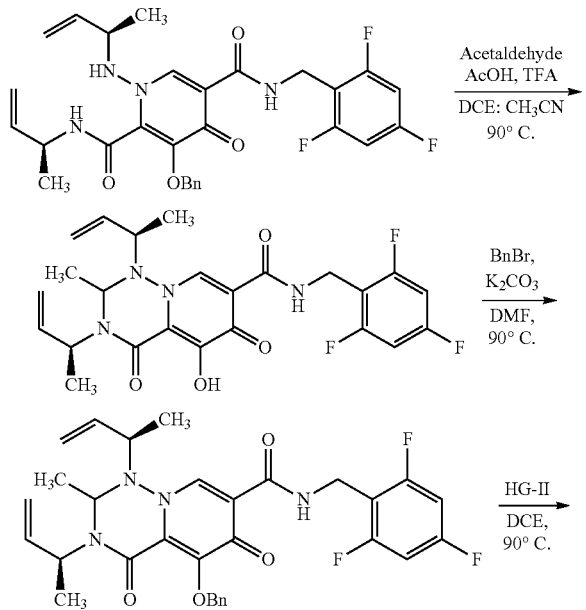

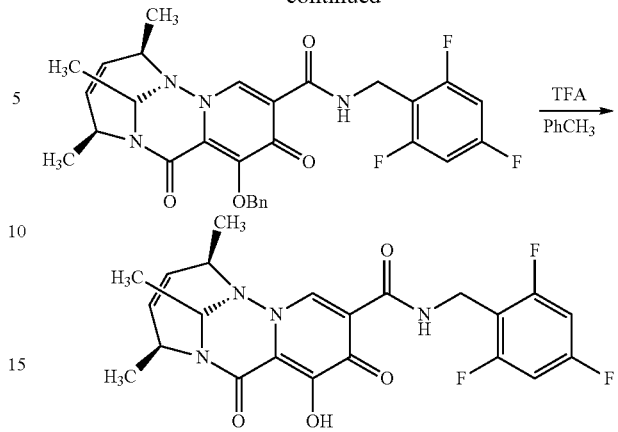

Step 1: Synthesis of 1-((R)-but-3-en-2-yl)-3-((S)-but-3-en-2-yl)-5-hydroxy-2-methyl-4,6-dioxo-N-(2,4,6-trifluorobenzyl)-2,3,4,6-tetrahydro-1H-pyrido[2,1-f][1,2,4]triazine-7-carboxamide To a 20 mL microwave vial, 3-(benzyloxy)-N2-((S)-but-3-en-2-yl)-1-(((R)-but-3-en-2-yl)amino)-4-oxo-N5-(2,4,6-trifluorobenzyl)-1,4-dihydropyridine-2,5-dicarboxamide (500 mg, 0.90 mmol, 1.0 eq), prepared in a manner similar to Example 24 except using (S)-but-3-en-2-ol instead of but-3-en-2-ol in Step 2, acetaldehyde (0.5 mL, 8.97 mmol, 10 eq), dichloroethane (3.2 mL), and acetonitrile (3.2 mL), glacial acetic acid (354 μL, 6.14 mmol, 6.8 eq) and trifluoroacetic acid (354 μL, 4.58 mmol, 5.1 eq) were added sequentially and the vials were immediately sealed and moved to a hot plate preheated to 90° C. The solutions were left to stir 90° C. for 16.5 hours whereupon the vials were removed from heat allowed to cool to ambient temperature. The contents of the vials were combined in a 100 mL Erlenmeyer flask and saturated sodium bicarbonate (30 mL) and ethyl acetate (20 mL) were added and let stir for 30 minutes. The layers were then separated, the aqueous layer was extracted into ethyl acetate (2×20 mL), and the combined organic extracts were dried over magnesium sulfate, filtered, and concentrated. The resultant residue was purified via flash column chromatography (0-100% EtOAc/Hexanes) affording 1-((R)-but-3-en-2-yl)-3-((S)-but-3-en-2-yl)-5-hydroxy-2-methyl-4,6-dioxo-N-(2,4,6-trifluorobenzyl)-2,3,4,6-tetrahydro-1H-pyrido[2,1-f][1,2,4]triazine-7-carboxamide. ES/MS: 491.171 [M+H]+.

Step 2: Synthesis of 5-(benzyloxy)-1-((R)-but-3-en-2-yl)-3-((S)-but-3-en-2-yl)-2-methyl-4,6-dioxo-N-(2,4,6-trifluorobenzyl)-2,3,4,6-tetrahydro-1H-pyrido[2,1-f][1,2,4]triazine-7-carboxamide To a 20 mL vial, 1-((R)-but-3-en-2-yl)-3-((S)-but-3-en-2-yl)-5-hydroxy-2-methyl-4,6-dioxo-N-(2,4,6-trifluorobenzyl)-2,3,4,6-tetrahydro-1H-pyrido[2,1-f][1,2,4]triazine-7-carboxamide (123 mg, 0.25 mmol, 1.0 eq), potassium carbonate (178 mg, 1.3 mmol, 5.1 eq), and dimethylformamide (6 mL) were added. To the suspension, benzyl bromide (89 μL, 0.75 mmol, 3.0 eq) was added and the suspension was then heated to 90° C. for 23 hours whereupon the reaction was removed from heat allowed to cool to ambient temperature. The reaction mixture was quenched with aqueous lithium chloride (10% w/w, 10 mL) and the layers were separated. The aqueous layer was extracted into CH₂Cl₂ (2×15 mL), and the combined organic extracts were washed with water (2×15 mL), brine (15 mL), dried over magnesium sulfate, filtered, and concentrated. The resultant residue was purified via flash column chromatography (0-100% EtOAc/Hexanes) affording 5-(benzyloxy)-1-((R)-but-3-en-2-yl)-3-((S)-but-3-en-2-yl)-2-methyl-4,6-dioxo-N-(2,4,6-trifluorobenzyl)-2,3,4,6-tetrahydro-1H-pyrido[2,1-f][1,2,4]triazine-7-carboxamide. ES/MS: 581.182 [M+H]+.

Step 3: Synthesis of (1S,2R,5S)-8-(benzyloxy)-2,5,13-trimethyl-7,9-dioxo-N-(2,4,6-trifluorobenzyl)-2,5,7,9-tetrahydro-1,6-methanopyrido[1,2-b][1,2,5]triazonine-10-carboxamide To a 20 mL vial, 5-(benzyloxy)-1-((R)-but-3-en-2-yl)-3-((S)-but-3-en-2-yl)-2-methyl-4,6-dioxo-N-(2,4,6-trifluorobenzyl)-2,3,4,6-tetrahydro-1H-pyrido[2,1-f][1,2,4]triazine-7-carboxamide (76 mg, 0.13 mmol, 1.0 eq), Hoyveda-Grubbs' catalyst second generation (8.3 mg, 0.013 mmol, 10 mol %), and dichloroethane (5 mL) were added. The solution was degassed and placed under an argon atmosphere (this was done in triplicate). The flask was then equipped with an air condenser and heated 80° C. for 21 hours whereupon it was removed from heat and allowed to cool to ambient temperature. The solids were removed via filtration, the volatiles were removed in vacuo and the resultant residue was purified via flash column chromatography (0-100% EtOAc/Hexanes) affording (1S,2R,5S)-8-(benzyloxy)-2,5,13-trimethyl-7,9-dioxo-N-(2,4,6-trifluorobenzyl)-2,5,7,9-tetrahydro-1,6-methanopyrido[1,2-b][1,2,5]triazonine-10-carboxamide. ES/MS: 553.183 [M+H]+.

Step 4: Synthesis of (1S,2R,5S)-8-hydroxy-2,5,13-trimethyl-7,9-dioxo-N-(2,4,6-trifluorobenzyl)-2,5,7,9-tetrahydro-1,6-methanopyrido[1,2-b][1,2,5]triazonine-10-carboxamide To 1 dram vial, (1S,2R,5S)-8-(benzyloxy)-2,5,13-trimethyl-7,9-dioxo-N-(2,4,6-trifluorobenzyl)-2,5,7,9-tetrahydro-1,6-methanopyrido[1,2-b][1,2,5]triazonine-10-carboxamide (43 mg, 0.077 mmol, 1.0 eq), toluene (0.7 mL) and trifluoroacetic acid (0.7 mL) were added. The reaction was stirred as ambient temperature for 4.5 hours whereupon the volatiles were removed in vacuo and the resultant residue was purified via preparative HPLC (0-100% CH₃CN/H₂O with 0.1% TFA modifier) affording (1S,2R,5S)-8-hydroxy-2,5,13-trimethyl-7,9-dioxo-N-(2,4,6-trifluorobenzyl)-2,5,7,9-tetrahydro-1,6-methanopyrido[1,2-b][1,2,5]triazonine-10-carboxamide. ES/MS: 463.215 [M+H]+. ¹H NMR (400 MHz, Chloroform-d) δ 10.25 (s, 1H), 8.50 (d, J=1.1 Hz, 1H), 6.67 (t, J=8.1 Hz, 2H), 5.59 (d, J=11.5 Hz, 1H), 5.50-5.39 (m, 1H), 5.35 (dt, J=11.6, 3.0 Hz, 1H), 5.18 (q, J=6.7 Hz, 1H), 4.75-4.59 (m, 2H), 3.66 (dt, J=6.8, 3.3 Hz, 1H), 1.38 (dd, J=7.1, 5.9 Hz, 6H), 1.28 (d, J=6.6 Hz, 3H).

Example 101: Preparation of (1S,2R,5S)-13-ethyl-8-hydroxy-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide (C101)

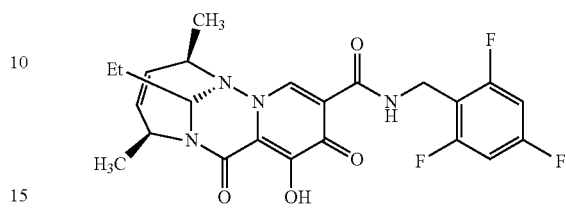

(1S,2R,5S)-13-ethyl-8-hydroxy-2,5-dimethyl-7,9-dioxo-N-(2,4,6-trifluorobenzyl)-2,5,7,9-tetrahydro-1,6-methanopyrido[1,2-b][1,2,5]triazonine-10-carboxamide was prepared in a manner similar to Example 100, except using propanal instead of acetaldehyde in Step 1. ES/MS: 477.186 [M+H]+. ¹H NMR (400 MHz, Chloroform-d) δ 10.24 (s, 1H), 8.49 (s, 1H), 6.67 (t, J=8.1 Hz, 2H), 5.66-5.50 (m, 1H), 5.50-5.42 (m, 1H), 5.34 (dt, J=11.6, 3.0 Hz, 1H), 4.83 (t, J=7.3 Hz, 1H), 4.74-4.58 (m, 2H), 3.68 (dd, J=6.6, 3.3 Hz, 1H), 1.52 (ddp, J=21.9, 14.5, 7.5 Hz, 2H), 1.38 (dd, J=10.5, 7.1 Hz, 6H), 0.96 (t, J=7.4 Hz, 3H).

Example 102: Preparation of (1S,2R,5S)—N-((4-chloro-3,5-difluoropyridin-2-yl)methyl)-8-hydroxy-2,5-dimethyl-7,9-dioxo-2,5,7,9-tetrahydro-1,6-methanopyrido[1,2-b][1,2,5]triazonine-10-carboxamide (C102)

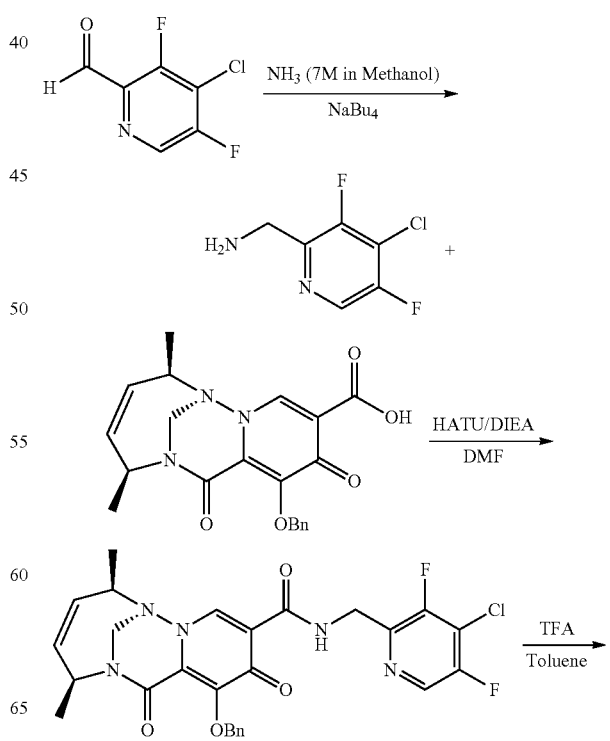

-continued

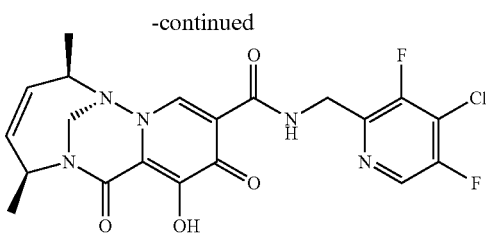

Step 1: Synthesis of (4-chloro-3,5-difluoropyridin-2-yl)methanamine

4 Å molecular sieve (1 g) was added to 4 mL 7N $NH_3$ in MeOH. Stir for 2 hours. Molecular sieve was removed by filtration. The filtrate was treated with 4-chloro-3,5-difluoropicolinaldehyde (202 mg, 1.14 mmol) at room temperature. The reaction mixture was stirred at r.t. overnight. Reaction mixture was cooled to 0° C. $NaBH_4$ (65 mg, 1.71 mmol) was added at 0° C. Reaction mixture was then warmed to r.t. In 2 hrs the reaction was quenched by sat. $NaHCO_3$ (10 mL). EtOAc (2×10 mL) was added for extraction of crude product. The organic layer was then treated with TN HCl (10 mL). Aqueous layer was collected and was treated with $NaHCO_3$ (sat) to make pH=8. Me-THF (1×10 mL) was used for extraction of product. The organic phase was separated and concentrated to dryness to afford product, which can be used directly without further purification. MS (m/z): 179.0 [M+H]+.

Step 2: Synthesis of (1S,2R,5S)-8-(benzyloxy)-N-((4-chloro-3,5-difluoropyridin-2-yl)methyl)-2,5-dimethyl-7,9-dioxo-2,5,7,9-tetrahydro-1,6-methanopyrido[1,2-b][1,2,5]triazonine-10-carboxamide (1S,2R,5S)-8-(benzyloxy)-2,5-dimethyl-7,9-dioxo-2,5,7,9-tetrahydro-1,6-methanopyrido[1,2-b][1,2,5]triazonine-10-carboxylic acid (150 mg, 0.379 mmol), prepared according to Example 63, was dissolved in DMF (1 mL) at rt. DIEA (0.264 mL, 1.52 mmol) was added under argon atmosphere. The resulting reaction mixture was cooled to 0° C. Then HATU (216 mg, 0.569 mmol) was added. The resulting reaction mixture was then warmed up to rt and stirred at rt for 1 hr. To this reaction mixture, was added a solution of (3-chloro-2,4-difluorophenyl)methanamine (102 mg, 0.569 mmol) in DMF (0.5 mL). The reaction mixture was then stirred at rt for 17 hrs. Reaction mixture was diluted with EtOAc (10 mL) and was treated with a mixture of saturated aqueous $NH_4Cl$ solution (10 mL) and water (10 mL). Organic phase was then washed with water (10 mL) and saturated brine (10 mL) sequentially. Organic phase was then separated and concentrated. The residue was purified on silica gel column with 0-100% EtOAc/Hex to afford product. MS (m/z): 556.1 [M+H]+.

Step 3: Synthesis of (1S,2R,5S)—N-((4-chloro-3,5-difluoropyridin-2-yl)methyl)-8-hydroxy-2,5-dimethyl-7,9-dioxo-2,5,7,9-tetrahydro-1,6-methanopyrido[1,2-b][1,2,5]triazonine-10-carboxamide (1S,2R,5S)-8-(benzyloxy)-N-((4-chloro-3,5-difluoropyridin-2-yl)methyl)-2,5-dimethyl-7,9-dioxo-2,5,7,9-tetrahydro-1,6-methanopyrido[1,2-b][1,2,5]triazonine-10-carboxamide (100 mg, 0.180 mmol) was dissolved in toluene (2 mL) at rt. TFA (2 mL) was added carefully with stirring. The resulting reaction mixture was stirred at rt for 17 hrs. Reaction mixture was then concentrated to dryness. The residue was taken up in MeOH and was purified with reverse phase prep-HPLC with 0-100% $CH_3CN$ in water with 0.1% TFA to afford the desired product. Lyophilization afforded product. MS (m/z): 466.2 [M+H]+; $^1$H NMR (400 MHz, Acetonitrile-d3) δ 10.43 (s, 1H), 8.44 (s, 1H), 8.39 (s, 1H), 5.67 (dt, J=11.4, 2.5 Hz, 1H), 5.40 (ddt, J=16.9, 10.3, 5.3 Hz, 2H), 5.02 (d, J=14.3 Hz, 1H), 4.78 (dd, J=5.7, 1.8 Hz, 2H), 4.58 (d, J=14.3 Hz, 1H), 3.84 (tt, J=6.7, 3.4 Hz, 1H), 1.35 (dd, J=7.1, 2.9 Hz, 6H).

Example 103: Preparation of (1S,2R,5S)—N-(3-chloro-2,4,6-trifluorobenzyl)-8-hydroxy-2,5-dimethyl-7,9-dioxo-2,5,7,9-tetrahydro-1,6-methanopyrido[1,2-b][1,2,5]triazonine-10-carboxamide (C103)

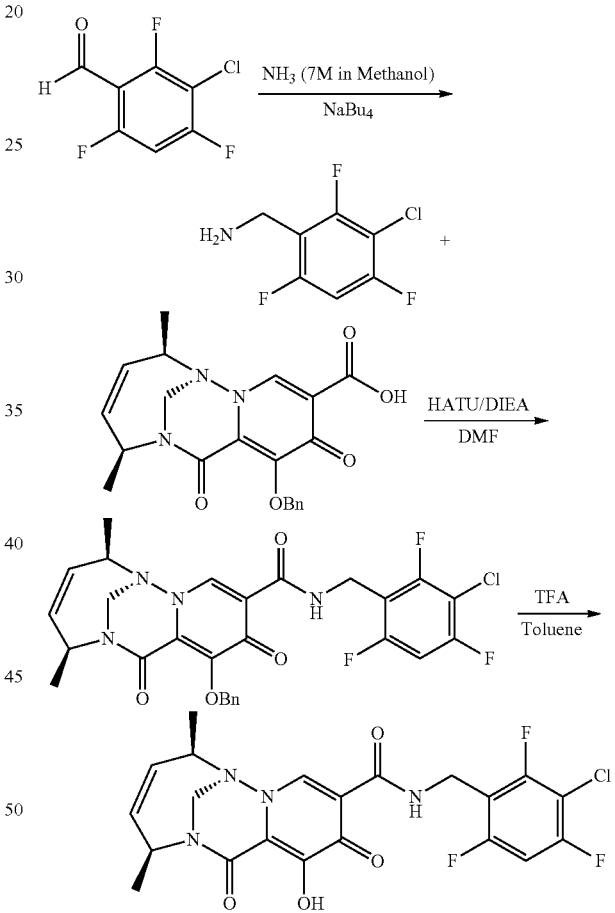

Step 1: Synthesis of (3-chloro-2,4,6-trifluorophenyl)methanamine

4 Å molecular sieve (1 g) was added to 4 mL 7N $NH_3$ in MeOH. Stir for 2 hours. Molecular sieve was removed by filtration. The filtrate was treated with 3-chloro-2,4,6-trifluorobenzaldehyde (1000 mg, 5.14 mmol) at room temperature. The reaction mixture was stirred at r.t. overnight. Reaction mixture was cooled to 0° C. $NaBH_4$ (292 mg, 7.71 mmol) was added at 0° C. Reaction mixture was then warmed to r.t. In 2 hrs the reaction was quenched by sat.

NaHCO₃ (10 mL). EtOAc (2×10 mL) was added for extraction of crude product. The organic layer was then treated with 1N HCl (10 mL). Aqueous layer was collected and was treated with NaHCO₃ (sat) to make pH=8. Me-THF (1×10 mL) was used for extraction of product. The organic phase was separated and concentrated to dryness to afford product, which can be used directly without further purification. MS (m/z): 196.0 [M+H]⁺.

Step 2: Synthesis of (1S,2R,5S)-8-(benzyloxy)-N-(3-chloro-2,4,6-trifluorobenzyl)-2,5-dimethyl-7,9-dioxo-2,5,7,9-tetrahydro-1,6-methanopyrido[1,2-b][1,2,5]triazonine-10-carboxamide (1S,2R,5S)-8-(Benzyloxy)-2,5-dimethyl-7,9-dioxo-2,5,7,9-tetrahydro-1,6-methanopyrido[1,2-b][1,2,5]triazonine-10-carboxylic acid (200 mg, 0.506 mmol), prepared according to Example 63, was dissolved in DMF (1 mL) at rt. DIEA (0.35 mL, 2.02 mmol) was added under argon atmosphere. The resulting reaction mixture was cooled to 0° C. Then HATU (250 mg, 0.658 mmol) was added. The resulting reaction mixture was then warmed up to rt and stirred at rt for 1 hr. To this reaction mixture, was added a solution of (3-chloro-2,4,6-trifluorophenyl)methanamine (148 mg, 0.759 mmol) in DMF (0.5 mL). The reaction mixture was then stirred at rt for 17 hrs. Reaction mixture was diluted with EtOAc (10 mL) and was treated with a mixture of saturated aqueous NH₄Cl solution (10 mL) and water (10 mL). Organic phase was then washed with water (10 mL) and saturated brine (10 mL) sequentially. Organic phase was then separated and concentrated. The residue was purified on silica gel column with 0-100% EtOAc/Hex to afford product. MS (m/z): 572.9 [M+H]+.

Step 3: Synthesis of (S,2R,5S)—N-(3-chloro-2,4,6-trifluorobenzyl)-8-hydroxy-2,5-dimethyl-7,9-dioxo-2,5,7,9-tetrahydro-1,6-methanopyrido[1,2-b][1,2,5]triazonine-10-carboxamide (1S,2R,5S)-8-(Benzyloxy)-N-(3-chloro-2,4,6-trifluorobenzyl)-2,5-dimethyl-7,9-dioxo-2,5,7,9-tetrahydro-1,6-methanopyrido[1,2-b][1,2,5]triazonine-10-carboxamide (130 mg, 0.227 mmol) was dissolved in DMF (2 mL) at rt. LiCl (58 mg, 1.36 mmol) was added. The resulting reaction mixture was heated with stirring at 100° C. for 6 hrs. Reaction mixture was then diluted with EtOAc (10 mL) and was treated with NH₄Cl (saturated aq) (10 mL) and 1N HCl (10 mL). The organic phase was separated and washed with water (10 mL) and brine (10 mL). Concentration of organic extraction afforded the crude product. Further purification with silica gel column (0-100% EtOAc/Hex) afforded the product. MS (m/z): 483.2 [M+H]+; 1H NMR (400 MHz, Acetonitrile-d3) δ 10.26 (s, 1H), 8.37 (s, 1H), 7.05 (td, J=9.5, 2.2 Hz, 1H), 5.66 (dt, J=11.4, 2.4 Hz, 1H), 5.46-5.32 (m, 2H), 5.01 (d, J=14.4 Hz, 1H), 4.65 (d, J=6.0 Hz, 2H), 4.56 (d, J=14.4 Hz, 1H), 3.83 (tt, J=7.0, 3.6 Hz, 1H), 1.37-1.28 (m, 6H).

Example 104: Preparation of (1'S,5'S)-8'-hydroxy-5'-methyl-7',9'-dioxo-N-(2,4,6-trifluorobenzyl)-7',9'-dihydro-5'H-spiro[cyclobutane-1,2'-[1,6]methanopyrido[1,2-b][1,2,5]triazonine]-10'-carboxamid (C104)

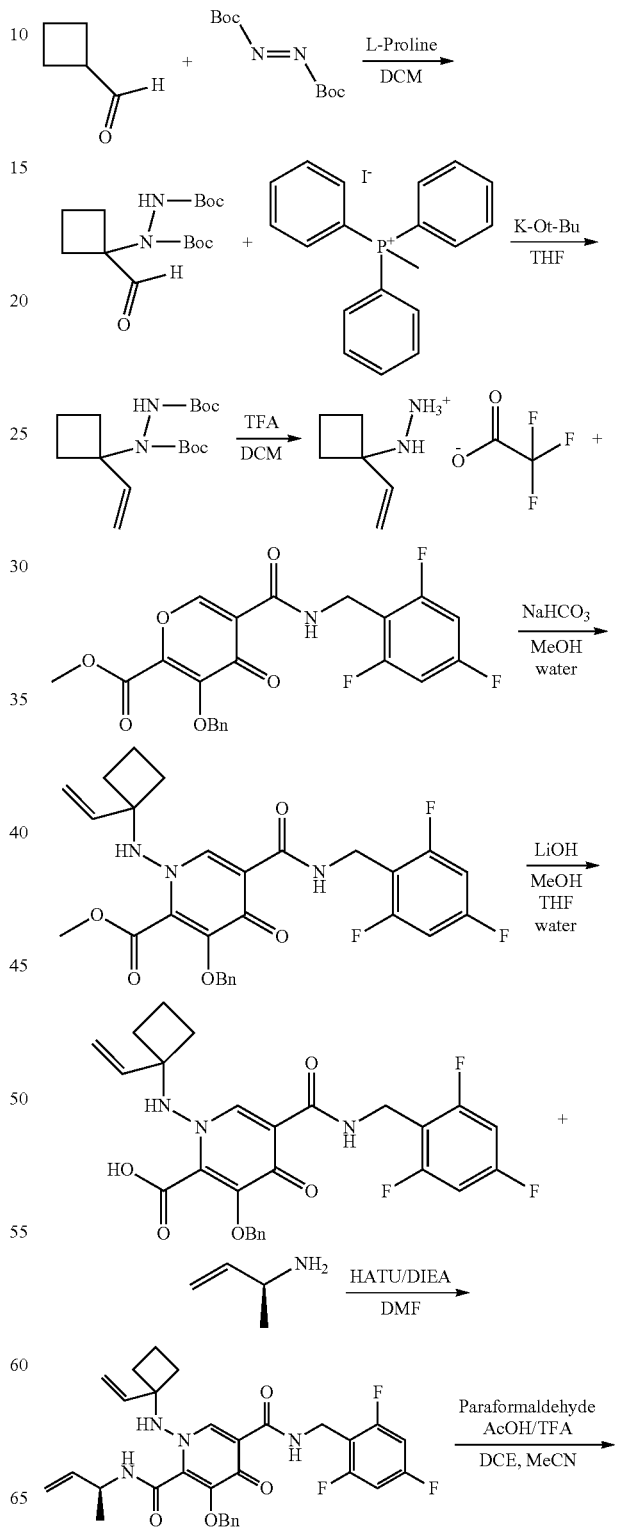

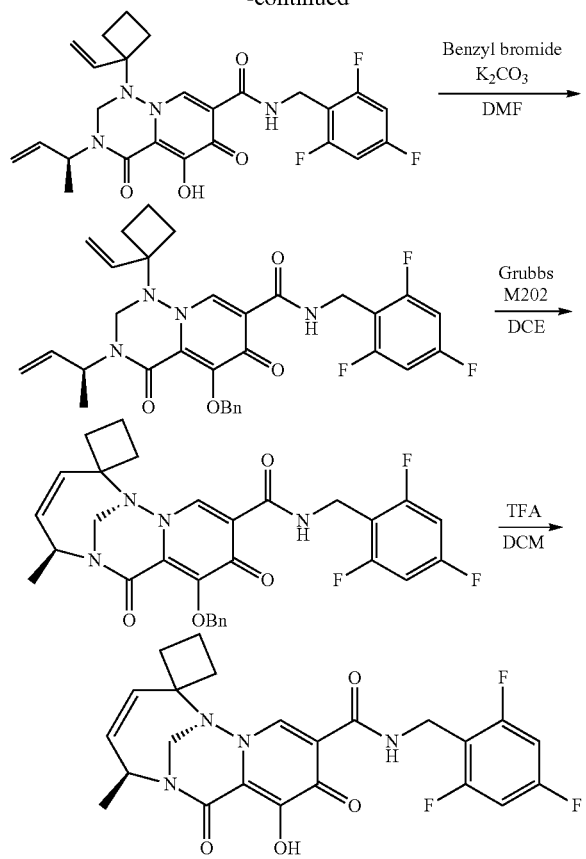

Step 1: Synthesis of di-tert-butyl 1-(1-formylcyclobutyl)hydrazine-1,2-dicarboxylate Cyclobutanecarbaldehyde (1.64 g, 19.5 mmol) and di-tert-butyl-diazene-1,2-dicarboxylate (3 g, 13 mmol) were dissolved in DCM. Then L-Proline (0.15 g, 1.3 mmol) was added. The slurry was stirred at rt for 2 hr and then was heated at 40° C. for 5 hr. Solvent was removed via rotovap. The residue was partitioned between EtOAc (50 mL) and water (50 mL). Brine was added to facilitate the separation. Organic phase was separated and washed with water and brine. Organic phase was separated and concentrated to afford pale yellow solid. Purification on silica gel column with 0-100% EtOAc in Hex afforded product. 1H NMR (400 MHz, CD3CN) δ 9.99-9.39 (br, 1H), 7.69-6.55 (br, 1H), 2.48-2.20 (m, 4H), 1.82 (d, J=15.2 Hz, 2H), 1.61-1.34 (m, 18H).

Step 2: Synthesis of di-tert-butyl 1-(1-vinylcyclobutyl)hydrazine-1,2-dicarboxylate To a suspension of methyltriphenylphosphonium iodide (5.56 g, 13.5 mmol) in THF (25 mL) at 0° C. was added KOtBu (1.51 g, 13.5 mmol). The mixture was stirred for 30 min. A solution of di-tert-butyl 1-(1-formylcyclobutyl)hydrazine-1,2-dicarboxylate (2.12 g, 6.74 mmol) in THF (10 mL) was added dropwise over 10 min. The reaction mixture was warmed to rt. After being stirring 17 h, the reaction mixture was cooled to 0° C. EtOAc (20 mL) was added. The resulting reaction mixture was treated with saturated NH4Cl aqueous solution (10 mL) and water (10 mL). The organic phase was separated and the aqueous phase was extracted with EtOAc (2×10 mL). The combined organic phases were concentrated. Purification by silica gel column chromatography (0-50% EtOAc/hexanes) afforded product. 1H NMR (400 MHz, CD3CN) δ 7.01 (br, 1H), 6.14 (dd, J=17.4, 10.6 Hz, 1H), 5.31-4.97 (m, 2H), 2.53-2.22 (m, 2H), 2.17-1.99 (m, 2H), 1.83-1.64 (m, 2H), 1.44 (d, J=16.0 Hz, 18H).

Step 3: Synthesis of 2-(1-vinylcyclobutyl)hydrazin-1-ium 2,2,2-trifluoroacetate Di-tert-butyl 1-(1-vinylcyclobutyl)hydrazine-1,2-dicarboxylate (1.25 g, 4 mmol) was dissolved in DCM (15 mL) at rt and was cooled down with ice-water bath under argon. TFA (15 mL) was added. The resulting reaction mixture was allowed to warm to rt and stir for 17 hr. Reaction mixture was then concentrated to dryness. The residue was place under high vac for 5 hrs to afford the product. MS (m/z): 113.0 [M+H]+.

Step 4: Synthesis of methyl 3-(benzyloxy)-4-oxo-5-((2,4,6-trifluorobenzyl)carbamoyl)-1-((1-vinylcyclobutyl)amino)-1,4-dihydropyridine-2-carboxylate 2-(1-Vinylcyclobutyl)hydrazin-1-ium 2,2,2-trifluoroacetate (900 mg, 4 mmol) was dissolved in MeOH (20 mL). Then NaHCO3 (1.4 g, 16.8 mmol) was added as solid. Then methyl 3-(benzyloxy)-4-oxo-5-((2,4,6-trifluorobenzyl)carbamoyl)-4H-pyran-2-carboxylate (1.5 g, 3.35 mmol) was added as solid in one portion. Water (10 mL) was added. The resulting reaction mixture was heated at 55° C. for 17 hr. Then reaction mixture was diluted with EtOAc (20 mL) and was treated with brine (20 mL) and water (20 mL). Organic phase was separated and concentrated to afford the product. MS (m/z): 542.0 [M+H]+.

Step 5: Synthesis of 3-(benzyloxy)-4-oxo-5-((2,4,6-trifluorobenzyl)carbamoyl)-1-((1-vinylcyclobutyl)amino)-1,4-dihydropyridine-2-carboxylic acid Methyl 3-(benzyloxy)-4-oxo-5-((2,4,6-trifluorobenzyl)carbamoyl)-1-((1-vinylcyclobutyl)amino)-1,4-dihydropyridine-2-carboxylate (1.82 g, 3.36 mmol) was dissolved in MeOH (30 mL), water (15 mL) and THF (10 mL) at rt. LiOH (5 M in water, 5.38 mL) was added. Reaction mixture was stirred at rt for 20 hr. Reaction mixture was concentrated carefully for removal of MeOH. The residue was diluted and rinsed with some water (30 mL) and was acidified with 1N HCl to pH=3. EtOAc (50 mL) was added for extraction. Organic phase was separated. Aqueous layer was extracted with more EtOAc (30 mL). The combined organic phases were washed with water and brine. The separated organic phase was dried over Na2SO4, filtered and concentrated to afford the acid product. MS (m/z): 527.9 [M+H]+.

Step 6: Synthesis of (S)-3-(benzyloxy)-N2-(but-3-en-2-yl)-4-oxo-N5-(2,4,6-trifluorobenzyl)-1-((1-vinylcyclobutyl)amino)-1,4-dihydropyridine-2,5-dicarboxamide 3-(benzyloxy)-4-oxo-5-((2,4,6-trifluorobenzyl)carbamoyl)-1-((1-vinylcyclobutyl)amino)-1,4-dihydropyridine-2-carboxylic acid (1.71 g, 3.24 mmol) was dissolved in DMF (20 mL) at rt under argon. DIEA (2.82 mL, 16.2 mmol) was added. Reaction mixture was cooled down with ice-water bath. HATU (1.946 g, 4.86 mmol) was then added. Let reaction mixture be stirred at low temp for 5 min then the cold bath is removed. Reaction mixture was stirred at rt for 1 h. Then (S)-but-3-en-2-amine HCl salt (0.816 g, 7.59 mmol) was added at rt in one portion. Reaction mixture was stirred at rt for 17 hr. Reaction mixture was then diluted with EtOAc (50 ml) and washed sequentially with NaHCO$_3$ (sat) (20 mL)/water (20 mL), NH4Cl (20 mL), water (20 mL) and brine (20 mL). Organic phase was dried over Na$_2$SO$_4$ and filtered. The filtrate was concentrated to afford product. MS (m/z): 581.0 [M+H]$^+$.

Step 7: Synthesis of (S)-3-(but-3-en-2-yl)-5-hydroxy-4,6-dioxo-N-(2,4,6-trifluorobenzyl)-1-(1-vinylcyclobutyl)-2,3,4,6-tetrahydro-1H-pyrido[2,1-f][1,2,4]triazine-7-carboxamide (S)-3-(benzyloxy)-N2-(but-3-en-2-yl)-4-oxo-N5-(2,4,6-trifluorobenzyl)-1-((1-vinylcyclobutyl)amino)-1,4-dihydropyridine-2,5-dicarboxamide (1.8 g, 3.1 mmol) was dissolved in ACN (6 mL) and DCE (6 mL). Paraformaldehyde (245 mg, 7.75 mmol) was added. AcOH (0.86 mL) and TFA (0.86 mL) were added dropwise sequentially without stirring. Reaction was heated under argon to 85° C. with stirring and kept under that condition for 24 hrs. Reaction mixture was then concentrated to dryness. The residue was purified on silica gel column with 0-100% EtOAc/Hex to afford product. MS(m/z): 503.2 [M+H]$^+$.

Step 8: Synthesis of (S)-5-(benzyloxy)-3-(but-3-en-2-yl)-4,6-dioxo-N-(2,4,6-trifluorobenzyl)-1-(1-vinylcyclobutyl)-2,3,4,6-tetrahydro-1H-pyrido[2,1-f][1,2,4]triazine-7-carboxamide (S)-3-(but-3-en-2-yl)-5-hydroxy-4,6-dioxo-N-(2,4,6-trifluorobenzyl)-1-(1-vinylcyclobutyl)-2,3,4,6-tetrahydro-1H-pyrido[2,1-f][1,2,4]triazine-7-carboxamide (1.16 g, 2.31 mmol) was dissolved in DMF (5 mL) at rt. K$_2$CO$_3$ (2.44 g, 17.7 mmol) was added. Then BnBr (1.38 g, 8.08 mmol) was added. Reaction mixture was heated to 73° C. (bath temp) for 5 hrs. Reaction mixture was diluted with EtOAc (50 mL) and was treated with water (20 mL). Organic phase was separated. Aqueous layer was extracted with EtOAc (20 mL). The combined organic phases were washed with water and brine. Concentration of organic phase gave the crude product. Further purification on silica gel column with 0-100% EtOAc/Hex afforded product. MS (m/z): 593.1 [M+H]+.

Step 9: Synthesis of (1'S,5'S)-8'-(benzyloxy)-5'-methyl-7' 9'-dioxo-N-(2,4,6-trifluorobenzyl)-7',9'-dihydro-5'H-spiro[cyclobutane-1,2'-[1,6]methanopyrido[1,2-b][1,2,5]triazonine]-10'-carboxamide (S)-5-(benzyloxy)-3-(but-3-en-2-yl)-4,6-dioxo-N-(2,4,6-trifluorobenzyl)-1-(1-vinylcyclobutyl)-2,3,4,6-tetrahydro-TH-pyrido[2,1-f][1,2,4]triazine-7-carboxamide (0.5 g, 0.85 mmol) was dissolved in dichloroethane (15 mL). The solution was bubbled with argon gas for 10 min. Grubbs catalyst M202 (211 mg, 0.22 mmol) was added. Then the purging with argon was applied again for 10 min. The reaction mixture was heated at 80° C. under argon for 24 hrs. Another round of addition of Grubbs M202 (211 mg, 0.22) was applied, followed by purging with argon gas for 10 min. Reaction mixture was heated again at 80° C. for 24 hrs. Reaction mixture was then concentrated to dryness. The residue was purified on silica gel column with 0-100% EtOAc/Hex to afford product. MS (m/z): 565.1 [M+H]+.

Step 10: Synthesis of (1'S,5'S)-8'-hydroxy-5'-methyl-7',9'-dioxo-N-(2,4,6-trifluorobenzyl)-7',9'-dihydro-5'H-spiro[cyclobutane-1,2'-[1,6]methanopyrido[1,2-b][1,2,5]triazonine]-10'-carboxamide (1'S,5'S)-8'-(benzyloxy)-5'-methyl-7',9'-dioxo-N-(2,4,6-trifluorobenzyl)-7',9'-dihydro-5'H-spiro[cyclobutane-1,2'-[1,6]methanopyrido[1,2-b][1,2,5]triazonine]-10'-carboxamide (12 mg, 0.0213 mmol) was dissolved in toluene (8 mL). TFA (9 mL) was added at rt. The resulting reaction mixture was stirred at rt for 17 hr. Reaction mixture was then concentrated to dryness. The residue was purified with reverse phase prep-HPLC with 0-100% CH$_3$CN in water with 0.1% TFA to afford the desired product. Lyophilization afforded product. MS (m/z): 475.2 [M+H]$^+$. $^1$H NMR (400 MHz, CD3CN) δ 10.23 (s, 1H), 8.48 (s, 1H), 7.05-6.82 (m, 2H), 6.05 (dd, J=11.8, 2.6 Hz, 1H), 5.64 (dd, J=11.8, 2.3 Hz, 1H), 5.43-5.23 (m, 1H), 5.00 (d, J=14.4 Hz, 1H), 4.73-4.59 (m, 2H), 4.55 (d, J=14.4 Hz, 1H), 2.45-2.32 (m, 1H), 2.32-2.22 (m, 1H), 1.86-1.57 (m, 4H), 1.32 (d, J=7.3 Hz, 3H).

Example 105: Preparation of (1'S,5'S)-8'-hydroxy-5'-methyl-7',9'-dioxo-N-(2,4,6-trifluorobenzyl)-4',5',7',9'-tetrahydro-3'H-spiro[cyclobutane-1,2'-[1,6]methanopyrido[1,2-b][1,2,5]triazonine]-10'-carboxamide (C105)

(1'S,5'S)-8'-(benzyloxy)-5'-methyl-7',9'-dioxo-N-(2,4,6-trifluorobenzyl)-7',9'-dihydro-5'H-spiro[cyclobutane-1,2'-[1,6]methanopyrido[1,2-b][1,2,5]triazonine]-10'-carboxamide (10 mg, 0.0177 mmol), prepared according to Example 104, was dissolved in MeOH (10 mL). Pd/C (10%) (12 mg) was added. The reaction mixture was stirred under a H$_2$ balloon atmosphere for 6 hrs. Reaction mixture was then filtered to remove the catalyst. The filtrate was concentrated to dryness. The residue was purified with reverse phase prep-HPLC with 0-100% CH$_3$CN in water with 0.1% TFA to afford the desired product. Lyophilization afforded product. MS (m/z): 477.1 [M+H]$^+$. 1H NMR (400 MHz, CD3CN) δ 10.35 (s, 1H), 8.50 (s, 1H), 6.87 (t, J=8.5 Hz, 2H), 4.64-4.57 (m, 4H), 4.45 (d, J=14.6 Hz, 1H), 2.21-2.00 (m, 4H), 1.85 (dt, J=15.4, 5.0 Hz, 2H), 1.74-1.39 (m, 4H), 1.23 (d, J=6.7 Hz, 3H).

Example 106: Preparation of (1S,2S,5S)-2-ethyl-8-hydroxy-5-methyl-7,9-dioxo-N-(2,4,6-trifluorobenzyl)-2,5,7,9-tetrahydro-1,6-methanopyrido[1,2-b][1,2,5]triazonine-10-carboxamide (C106)

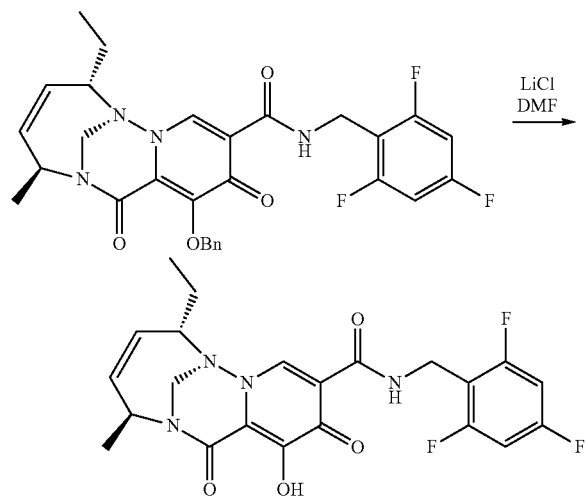

The reaction mixture of (1S,2S,5S)-8-(benzyloxy)-2-ethyl-5-methyl-7,9-dioxo-N-(2,4,6-trifluorobenzyl)-2,5,7,9-tetrahydro-1,6-methanopyrido[1,2-b][1,2,5]triazonine-10-carboxamide (8 mg, 0.0145 mmol), prepared as the minor product (B) according to Step 2 of Example 72, and lithium chloride (6.1 mg, 0.145 mmol) in DMF (1 mL) was stirred at 100° C. overnight. The reaction mixture was filtered, loaded on reverse phase HPLC, eluting with 5-100% acetonitrile in water to give the title product. MS (m/z) 463.20 [M+H]⁺. 1H NMR (400 MHz, Methanol-d4) δ 8.51 (s, 1H), 6.98-6.86 (m, 2H), 5.74 (ddd, J=12.3, 3.1, 1.8 Hz, 1H), 5.57 (ddd, J=12.4, 4.7, 2.1 Hz, 1H), 5.45-5.38 (m, 1H), 5.11 (d, J=14.4 Hz, 1H), 4.78 (d, J=14.4 Hz, 1H), 4.69 (d, J=2.3 Hz, 2H), 4.47 (dd, J=6.6, 3.1 Hz, 1H), 1.61 (tt, J=12.3, 7.3 Hz, 1H), 1.41 (d, J=7.3 Hz, 3H), 1.24 (ddd, J=13.3, 9.4, 7.0 Hz, 1H), 0.82 (t, J=7.3 Hz, 3H).

Example 107: Preparation of (1S,2R,5S)-8-hydroxy-5-methyl-7,9-dioxo-N-(2,4,6-trifluorobenzyl)-2-(2,2,2-trifluoroethyl)-2,5,7,9-tetrahydro-1,6-methanopyrido[1,2-b][1,2,5]triazonine-10-carboxamide (C107)

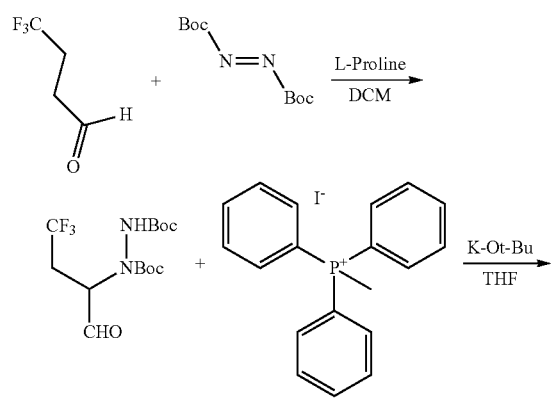

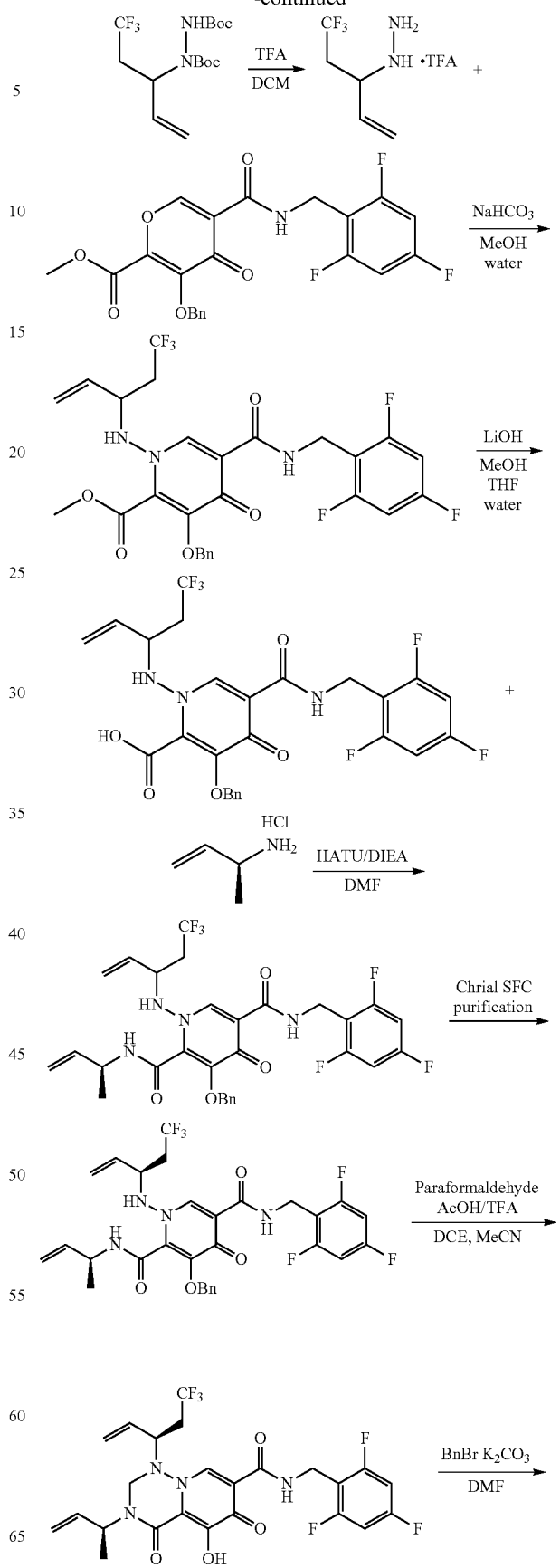

-continued

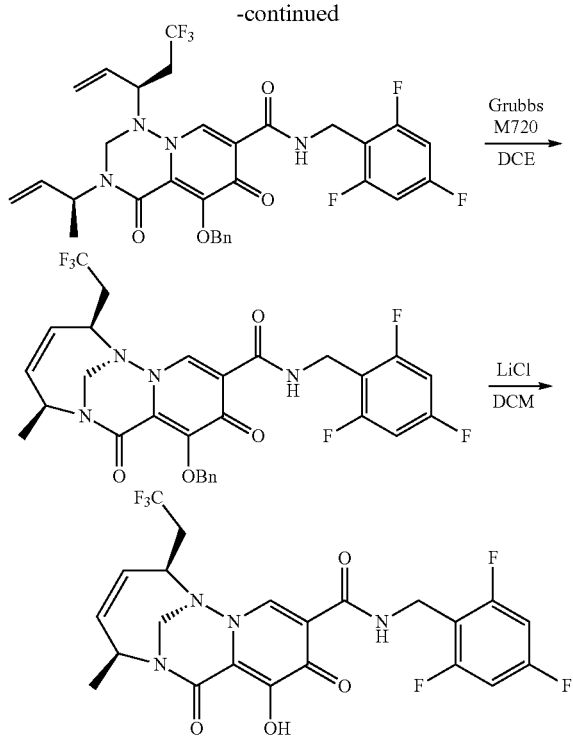

Step 1: Synthesis of di-tert-butyl 1-(4,4,4-trifluoro-1-oxobutan-2-yl)hydrazine-1,2-dicarboxylate 4,4,4-Trifluorobutanol (2.46 g, 19.5 mmol) and di-tert-butyl-diazene-1,2-dicarboxylate (3 g, 13 mmol) were dissolved in DCM (100 mL). Then L-proline (0.15 g, 1.3 mmol) was added. The slurry was stirred at rt for 2 h and then was heated at 40° C. for 17 h. Solvent was removed. The residue was purified on silica gel column with 0-100% EtOAc in hex to afford product. 1H NMR (400 MHz, CD3CN) δ 9.66 (d, J=12.9 Hz, 1H), 7.70-7.37 (m, 1H), 4.67-4.62 (m, 1H), 2.87 (dtt, J=15.5, 12.0, 5.8 Hz, 1H), 2.63-2.44 (m, 1H), 1.51-1.40 (m, 18H).

Step 2: Synthesis of di-tert-butyl 1-(5,5,5-trifluoropent-1-en-3-yl)hydrazine-1,2-dicarboxylate To a suspension of methyltriphenylphosphonium iodide (7.03 g, 17 mmol) in THF (100 mL) at 0° C. was added KOtBu (2.0 g, 17.8 mmol). The mixture became a yellow suspension and was stirred for 30 min. A solution of di-tert-butyl 1-(4,4,4-trifluoro-1-oxobutan-2-yl)hydrazine-1,2-dicarboxylate (2.5 g, 7.02 mmol) in THF (27 mL) was added dropwise over 10 min. The reaction mixture was warmed to rt. After being stirring 17 h, the reaction mixture was cooled to 0° C. and EtOAc (20 mL) was added. The resulting reaction mixture was treated with saturated NH4Cl aqueous solution (10 mL) and water (10 mL). The organic phase was separated and the aqueous phase was extracted with EtOAc (2×10 mL). The combined organic phases were concentrated to afford an orange foamy oil. Purification by silica gel column chromatography (0-50% EtOAc/hexanes) afforded product. 1H NMR (400 MHz, CD3CN) δ 7.31-6.47 (m, 1H), 6.05-5.78 (m, 1H), 5.38-5.12 (m, 2H), 4.94 (s, 1H), 2.83-2.36 (m, 2H), 1.45 (d, J=3.4 Hz, 18H).

Step 3: Synthesis of (5,5,5-trifluoropent-1-en-3-yl)hydrazine trifluoroacetic acid salt Di-tert-butyl 1-(5,5,5-trifluoropent-1-en-3-yl)hydrazine-1,2-dicarboxylate (1.76 g, 4.97 mmol) was dissolved in DCM (40 mL) at rt and was cooled down with ice-water bath under argon. TFA (20 mL) was added. The resulting reaction mixture was allowed to warm to rt and stirred for 17 h. Reaction mixture was then concentrated to dryness and the residue was placed under high vac for 5 h to afford the product. MS (m/z) 155.1 [M+H]+.

Step 4: Synthesis of methyl 3-(benzyloxy)-4-oxo-5-((2,4,6-trifluorobenzyl)carbamoyl)-1-((5,5,5-trifluoropent-1-en-3-yl)amino)-1,4-dihydropyridine-2-carboxylate (5,5,5-trifluoropent-1-en-3-yl)hydrazine trifluoroacetic acid salt (1.32 g, 4.96 mmol) was dissolved in MeOH (30 mL). Then NaHCO3 (3.474 g, 41.4 mmol) was added as solid and some bubbles appeared. Methyl 3-(benzyloxy)-4-oxo-5-((2,4,6-trifluorobenzyl)carbamoyl)-4H-pyran-2-carboxylate (1.85 g, 4.14 mmol) was added as solid in one portion. Water (15 mL) was added. The resulting reaction mixture was heated at 55° C. for 17 h. Then reaction mixture was diluted with EtOAc (20 mL) and was treated with brine (20 mL) and water (20 mL). Organic phase was separated and concentrated to afford the product. MS (m/z) 584.3 [M+H]+.

Step 5: Synthesis of 3-(benzyloxy)-4-oxo-5-((2,4,6-trifluorobenzyl)carbamoyl)-1-((5,5,5-trifluoropent-1-en-3-yl)amino)-1,4-dihydropyridine-2-carboxylic acid Methyl 3-(benzyloxy)-4-oxo-5-((2,4,6-trifluorobenzyl)carbamoyl)-1-((5,5,5-trifluoropent-1-en-3-yl)amino)-1,4-dihydropyridine-2-carboxylate (2.41 g, 4.13 mmol) was dissolved in MeOH (30 mL), water (10 mL) and THF (15 mL) at rt. LiOH (5 M in water) (6.61 mL, 33.05 mmol) was added. Reaction mixture was stirred at rt for 20 hr. Reaction mixture was concentrated carefully for removal of MeOH. The residue was diluted and rinsed with some water (30 mL), then acidified with 1N HCl to pH=3. EtOAc (50 mL) was added and the organic phase was extracted with EtOAc (2×30 mL). The combined organic phases were washed with water and brine. The separated organic phase was dried over Na2SO4, filtered and concentrated to afford the product. MS (m/z) 570.2 [M+H]+.

Step 6: Synthesis of 3-(benzyloxy)-N2-((S)-but-3-en-2-yl)-4-oxo-N5-(2,4,6-trifluorobenzyl)-1-((5,5,5-tri fluoropent-1-en-3-yl)amino)-1,4-dihydropyridine-2,5-dicarboxamide 3-(Benzyloxy)-4-oxo-5-((2,4,6-trifluorobenzyl)carbamoyl)-1-((5,5,5-trifluoropent-1-en-3-yl)amino)-1,4-dihydropyridine-2-carboxylic acid (2.35 g, 4.13 mmol) was dissolved in DMF (20 mL) at rt under argon. DIEA (3.59 mL, 20.6 mmol) was added and the reaction mixture was cooled to 0° C. HATU (2.478 g, 6.19 mmol) was then added and the reaction mixture was stirred at this temperature for 5 min before the cold bath was removed. Reaction mixture was stirred at rt for 1 h. Then the (S)-methyl allylamine HCl salt (1.05 g, 9.78 mmol) was added at rt in one portion. Reaction mixture was stirred at rt for 17 h. Reaction mixture was then diluted with EtOAc (50 mL) and washed sequentially with NaHCO₃ (sat) (20 mL), water (20 mL), NH4Cl (20 mL), water (20 mL) and brine (20 mL). Organic phase was dried over Na₂SO₄ and filtered. The filtrate was concentrated to afford product. MS (m/z) 623.3 [M+H]+.

Step 7: Synthesis of 3-(benzyloxy)-N2-((S)-but-3-en-2-yl)-4-oxo-N5-(2,4,6-trifluorobenzyl)-1-(((R)-5,5,5-trifluoropent-1-en-3-yl)amino)-1,4-dihydropyridine-2,5-dicarboxamide A mixture of two diastereomers of 3-(benzyloxy)-N2-((S)-but-3-en-2-yl)-4-oxo-N5-(2,4,6-trifluorobenzyl)-1-((5,5,5-trifluoropent-1-en-3-yl)amino)-1,4-dihydropyridine-2,5-dicarboxamide was subject to chiral SFC with ADH-25 and elution with IPA-NH3 to afford 3-(benzyloxy)-N2-((S)-but-3-en-2-yl)-4-oxo-N5-(2,4,6-trifluorobenzyl)-1-(((R)-5,5,5-trifluoropent-1-en-3-yl)amino)-1,4-dihydropyridine-2,5-dicarboxamide as the first peak. MS (m/z) 623.3 [M+H]⁺.

Step 8: Synthesis of 3-((S)-but-3-en-2-yl)-5-hydroxy-4,6-dioxo-N-(2,4,6-trifluorobenzyl)-1-((R)-5,5,5-tri fluoropent-1-en-3-yl)-2,3,4,6-tetrahydro-1H-pyrido[2,1-f][1,2,4]triazine-7-carboxamide 3-(Benzyloxy)-N2-((S)-but-3-en-2-yl)-4-oxo-N5-(2,4,6-trifluorobenzyl)-1-(((R)-5,5,5-trifluoropent-1-en-3-yl)amino)-1,4-dihydropyridine-2,5-dicarboxamide (0.5 g, 0.803 mmol) was dissolved in ACN (3 mL) and DCE (3 mL). Paraformaldehyde (63.4 mg, 2.01 mmol) was added. AcOH (0.223 mL) and TFA (0.223 mL) were added dropwise sequentially without stirring. Reaction was heated under argon to 85° C. with stirring and kept under that condition for 24 h. Reaction mixture was then concentrated to dryness. The residue was purified on silica gel column with 0-100% EtOAc/Hex to afford product. MS (m/z) 545.1 [M+H]+.

Step 9: Synthesis of 5-(benzyloxy)-3-((S)-but-3-en-2-yl)-4,6-dioxo-N-(2,4,6-trifluorobenzyl)-1-((R)-5,5,5-tri fluoropent-1-en-3-yl)-2,3,4,6-tetrahydro-1H-pyrido[2,1-f][1,2,4]triazine-7-carboxamide 3-((S)-But-3-en-2-yl)-5-hydroxy-4,6-dioxo-N-(2,4,6-trifluorobenzyl)-1-((R)-5,5,5-trifluoropent-1-en-3-yl)-2,3,4,6-tetrahydro-1H-pyrido[2,1-f][1,2,4]triazine-7-carboxamide (70 mg, 0.129 mmol) was dissolved in DMF (5 mL) at rt. K2CO3 (136 mg, 0.98 mmol) was added. Then benzyl bromide (77 mg, 0.45 mmol) was added. The reaction mixture was heated to 73° C. (bath temp) for 5 h. Reaction mixture was diluted with EtOAc (50 mL) and was treated with water (20 mL). Organic phase was separated and the aqueous layer was extracted with EtOAc (20 mL). The combined organic phases were washed with water and brine. Concentration of organic phase gave the crude product. Further purification on silica gel column with 0-100% EtOAc/Hex afforded product. MS (m/z) 635.0 [M+H]⁺.

Step 10: Synthesis of (1S,2R,5S)-8-(benzyloxy)-5-methyl-7,9-dioxo-N-(2,4,6-trifluorobenzyl)-2-(2,2,2-tri fluoroethyl)-2,5,7,9-tetrahydro-1,6-methanopyrido[1,2-b][1,2,5]triazonine-10-carboxamide 5-(Benzyloxy)-3-((S)-but-3-en-2-yl)-4,6-dioxo-N-(2,4,6-trifluorobenzyl)-1-((R)-5,5,5-trifluoropent-1-en-3-yl)-2,3,4,6-tetrahydro-1H-pyrido[2,1-f][1,2,4]triazine-7-carboxamide (40 mg, 0.063 mmol) was dissolved in dichloroethane (5 mL). Grubbs catalyst M720 (8.14 mg, 0.0124 mmol) was added. Then purging with argon was applied for 10 min. The reaction mixture was heated at 80° C. under argon for 24 h. Reaction mixture was then concentrated to dryness. The residue was purified on silica gel column with 0-100% EtOAc/Hex to afford product. MS (m/z) 607.0 [M+H]+.

Step 11: Synthesis of (1S,2R,5S)-8-hydroxy-5-methyl-7,9-dioxo-N-(2,4,6-trifluorobenzyl)-2-(2,2,2-tri fluoroethyl)-2,5,7,9-tetrahydro-1,6-methanopyrido[1,2-b][1,2,5]triazonine-10-carboxamide (1R,2R,5S)-8-(Benzyloxy)-5-methyl-7,9-dioxo-N-(2,4,6-trifluorobenzyl)-2-(2,2,2-trifluoroethyl)-2,5,7,9-tetrahydro-1,6-methanopyrido[1,2-b][1,2,5]triazonine-10-carboxamide (38 mg, 0.0627 mmol) was dissolved in DMF (3 mL). LiCl (34.2 mg, 0.807 mmol) was added at rt. The resulting reaction mixture was heated at 100° C. with stirring for 7 h. Reaction mixture was then diluted with EtOAc (10 mL) and then treated with 1N HCl (10 mL). The organic phase was separated and washed with water (10 mL) and brine (10 mL). The organic phase was concentrated to afford a residue, which was purified by reverse phase prep-HPLC with 0-100% CH3CN in water with 0.1% TFA to afford the desired product. Lyophilization afforded desired product. MS (m/z) 517.2 [M+H]+. 1H NMR (400 MHz, CD3CN) δ 10.18 (s, 1H), 8.43 (s, 1H), 6.88 (t, J=8.5 Hz, 2H), 5.79 (dt, J=11.8, 2.6 Hz, 1H), 5.50 (dt, J=11.6, 3.1 Hz, 1H), 5.38 (h, J=6.9 Hz, 1H), 4.98 (d, J=14.6 Hz, 1H), 4.71-4.56 (m, 3H), 4.17 (tq, J=6.1, 3.0 Hz, 1H), 2.68 (dddd, J=15.8, 13.2, 10.3, 5.4 Hz, 2H), 1.36 (d, J=7.4 Hz, 3H).

Examples 108 and 109: Preparation of (1R)-8-hydroxy-7,9-dioxo-N-(2,4,6-trifluorobenzyl)-2,3,4,5,7,9-hexahydro-1,6-methanopyrido[1,2-b][1,2,5]triazonine-10-carboxamide and (1S)-8-hydroxy-7,9-dioxo-N-(2,4,6-trifluorobenzyl)-2,3,4,5,7,9-hexahydro-1,6-methanopyrido[1,2-b][1,2,5]triazonine-10-carboxamide (C108 and C109)

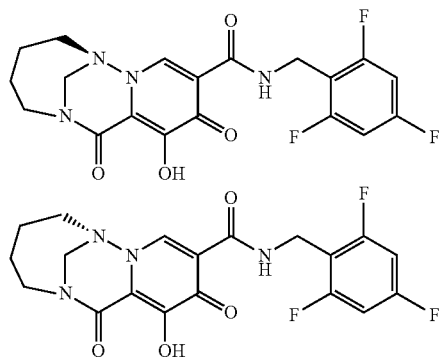

Prepared according to Example 2 of WO2019160783 using (2,4,6-trifluorophenyl)methanamine instead of (2,4-difluorophenyl)methanamine in Step 3. Separated by chiral SFC using 40% methanol to give Peak 1 and Peak 2.

Peak 1: MS-ESI (m/z) 423.1 [M+H]⁺. 1H NMR (400 MHz, CDCl3) δ 10.23 (br s, 1H), 8.55 (s, 1H), 6.66 (t, J=8.0 Hz, 2H), 4.82-4.61 (m, 3H), 4.42-4.36 (m, 2H), 3.37 (s, 2H), 3.22-3.17 (m, 1H), 2.23-2.20 (m, 1H), 1.95-1.89 (m, 1H), 1.77-1.74 (m, 1H), 1.60-1.57 (m, 1H).

Peak 2: MS-ESI (m/z) 423.1 [M+H]⁺. 1H NMR (400 MHz, CDCl3) δ 10.25 (br s, 1H), 8.58 (s, 1H), 6.66 (t, J=8.0 Hz, 2H), 4.82-4.61 (m, 3H), 4.44-4.36 (m, 2H), 3.39 (s, 2H), 3.22-3.18 (m, 1H), 2.23-2.20 (m, 1H), 1.95-1.89 (m, 1H), 1.76-1.74 (m, 1H), 1.61-1.57 (m, 1H).

Example 110: HIV MT-4 Antiviral and Cytotoxicity Assay

Antiviral Assay in MT-4 Cells

Compounds were tested in a high-throughput 384-well assay format for their ability to inhibit the replication of HIV-1 (IIIB) in MT-4 cells. Compounds were serially diluted (1:3) in DMSO on 384-well polypropylene plates and further diluted 200-fold into complete RPMI media (10% FBS, 1% P/S) using the Biotek Micro Flow and Labcyte ECHO acoustic dispenser. Each plate contained up to 8 test compounds, with negative (No Drug Control) and 5 µM AZT positive controls. MT-4 cells were pre-infected with 10 µL of either RPMI (mock-infected) or a fresh 1:250 dilution of HIV-1 IIIB concentrated virus stock. Infected and uninfected MT-4 cells were further diluted in complete RPMI media and added to each plate using a Micro Flow dispenser. After 5 days incubation in a humidified and temperature controlled incubator (37° C.), Cell Titer Glo (Promega) was added to the assay plates and chemiluminescence read using an Envision plate-reader. $EC_{50}$ values were defined as the compound concentration that causes a 50% decrease in luminescence signal, and were calculated using a sigmoidal dose-response model to generate curve fits.

Cytotoxicity Assay in MT-4 Cells

Assays were performed as above except uninfected MT-4 cells were added to each well containing test compound. In addition, 10 µM puromycin was added to the last column of each assay plate to assess a base level of cytotoxicity.

Example 111: HIV MT-4 Serum Shift Antiviral Reporter Assay

To quantify the amount of protein binding to human serum, compounds were serially diluted (1:3) in DMSO and acoustically transferred onto 384-well assay plates via a Labcyte ECHO robot. Each plate contained up to 8 test compounds, including negative and positive controls, (DMSO, 5 µM AZT respectively). Assay plates were prepared in duplicate, and tested in either CCM (cell culture media) or HS/CCM (human serum/cell culture media). MT-4 cells were first pre-infected with pLai RLuc reporter virus for 2 h at 37° C., then further diluted in either CCM (RPMI media, 10% FBS, 1% P/S) or HS/CCM (RPMI media, 10% FBS, 50% HS, 1% P/S), and subsequently added to each plate using a Biotek Micro Flow dispenser. After a 72-h incubation in a humidified and temperature controlled incubator (37° C.), Renilla Glo (Promega) was added to all assay plates and chemiluminescence read using an Envision plate-reader. $EC_{50}$ values were defined as the compound concentration that causes a 50% decrease in luminescence signal, and were calculated using a sigmoidal dose-response model to generate curve fits. To determine the amount of protein binding, $EC_{50}$ fold shifts (or $EC_{50}$ shifts) were calculated by dividing $EC_{50}$ (HS/CCM)/$EC_{50}$ ((CCM).

Compounds of the present disclosure demonstrate antiviral activity in this assay as depicted in Table 1 below. Accordingly, the compounds of the embodiments disclosed herein may be useful for treating the proliferation of the HIV virus, treating AIDS, or delaying the onset of AIDS or ARC symptoms.

TABLE 1

| Example No. | MT4 $EC_{50}$ (nM) | $CC_{50}$ (nM) | RLUC CCM (nM) | RLUC 50% HS (nM) | RLUC Shift |
|---|---|---|---|---|---|
| C1 | 20 | 10057 | 3.18 | 30.2 | 9 |
| C2 | 18 | 12797 | 2.86 | 47.9 | 17 |
| C3 | 1.7 | 13396 | 0.39 | 2.72 | 7 |
| C4 | 1.2 | 11965 | 0.54 | 6.08 | 11 |
| C5 | 3.4 | 14173 | 0.42 | 40.4 | 96 |
| C6 | 7.5 | 9880 | 3.5 | 23.1 | 7 |
| C7 | 2.1 | 9188 | 0.35 | 172 | 485 |
| C8 | 1.8 | 4717 | 0.55 | 16.4 | 30 |
| C9 | | 25327 | | | |
| C10 | 1.8 | 7572 | 0.4 | 339 | 854 |
| C11 | 1.1 | 9929 | 0.27 | 7.32 | 27 |
| C12 | 3.4 | 10845 | 0.77 | 273 | 356 |
| C13 | 1.3 | 8872 | 0.25 | 4.07 | 16 |
| C14 | 2.0 | 8056 | 0.71 | 31.1 | 44 |
| C15 | 1.9 | 9972 | | | |
| C16 | 1.1 | 11436 | 0.32 | 19.4 | 60 |
| C17 | 0.91 | 11186 | 0.16 | 7.12 | 44 |
| C18 | 4.3 | 13377 | | | |
| C19 | 1.1 | 10209 | 0.41 | 60.3 | 148 |
| C20 | 3.5 | 16591 | | | |
| C21 | 1.7 | 11696 | 0.23 | 98.1 | 425 |
| C22 | 2.2 | 16331 | | | |
| C23 | 2.5 | 50000 | 0.29 | 14.5 | 51 |
| C24 | 0.98 | 11413 | 0.44 | 328 | 747 |
| C25 | 1.0 | 17448 | 0.47 | 68 | 147 |
| C26 | 2.4 | 28143 | 0.63 | 349 | 552 |
| C27 | 1.3 | 9549 | 0.55 | 594 | 1072 |
| C28 | 1.4 | 6872 | 0.33 | 319 | 979 |
| C29 | 0.71 | 18657 | 0.31 | 169 | 543 |
| C30 | 1.3 | 35827 | 0.32 | 29 | 89 |
| C31 | 0.9 | 7854 | 0.41 | 328 | 798 |
| C32 | 2.4 | 28033 | 0.55 | 1.039 | 1.9 |
| C33 | 4.0 | 32884 | 1.8 | 4.3 | 2.3 |
| C34 | 1.4 | 8361 | 0.59 | 938 | 1587 |
| C35 | 1.6 | 29913 | 1.3 | 188 | 149 |
| C36 | 1.6 | 16563 | | | |
| C37 | 1.3 | 8567 | 0.87 | 325 | 375 |
| C38 | 1.5 | 13570 | 1.1 | 17 | 14 |
| C39 | 3.5 | 20277 | 0.93 | 4.7 | 5 |
| C40 | 2.1 | 15990 | 1.3 | 139 | 103 |
| C41 | 1.2 | 14235 | 0.71 | 68.6 | 97 |
| C42 | 2.2 | 7033 | 2.47 | 1881 | 761 |
| C43 | 5.3 | 6106 | 1.68 | 544 | 324 |
| C44 | 1.2 | 14955 | | | |
| C45 | 1.8 | 11014 | | | |
| C46 | 1.6 | 27042 | 0.44 | 468 | 1071 |
| C47 | 1.8 | 11488 | 1.71 | 196 | 114 |
| C48 | 1.5 | 50000 | | | |
| C49a | 1.2 | 11320 | 0.64 | 140 | 220 |
| C49b | 1.9 | 8926 | 1.0 | 462 | 450 |
| C50 | 0.85 | 13332 | 0.37 | 850 | 2322 |
| C51 | 1.3 | 9811 | 2.3 | 408 | 180 |
| C52 | 1.5 | 9215 | 0.77 | 472.6 | 614 |
| C53 | 1.3 | 9013 | 0.55 | 350.1 | 642 |
| C54 | 2.3 | 47389 | 0.63 | 72.36 | 114 |
| C55 | 1.3 | 29525 | 0.71 | 515.1 | 730 |
| C56 | 1.1 | 10116 | 0.52 | 24.9 | 48 |
| C57 | 1.2 | 8931 | 0.27 | 11.6 | 44 |
| C58 | 1.5 | 11251 | 0.28 | 293.6 | 1034 |
| C59 | 2.8 | 50000 | | | |
| C60 | 95.7 | 50000 | 42.64 | 103.6 | 2 |
| C61 | 2.8 | 50000 | 0.76 | 1.6 | 2 |
| C62 | 1.4 | 50000 | | | |
| C63 | | | | | |
| C64 | 0.8 | 11354 | 0.27 | 150.3 | 549 |
| C65 | 1.8 | 15419 | 0.44 | 63.8 | 146 |
| C66 | 1.4 | 10440 | 0.5 | 178.7 | 357 |
| C67 | 1.9 | 25509 | 0.51 | 35.3 | 69 |
| C68 | 1.6 | 17269 | 0.82 | 291.3 | 356 |
| C69 | 1.5 | 38937 | 0.55 | 145.5 | 264 |
| C70 | 1.2 | 11567 | 0.54 | 11.5 | 21 |

TABLE 1-continued

| Example No. | MT4 EC$_{50}$ (nM) | CC$_{50}$ (nM) | RLUC CCM (nM) | RLUC 50% HS (nM) | RLUC Shift |
|---|---|---|---|---|---|
| C71 | | | | | |
| C72 | 0.5 | 13830 | 0.33 | 250.9 | 772 |
| C73 | 0.8 | 7645 | 0.63 | 275.7 | 440 |
| C74 | 0.9 | 6813 | 0.47 | 325.3 | 695 |
| C75 | 2.0 | 10868 | 1.02 | 277.2 | 273 |
| C76 | 1.0 | 16378 | 0.42 | 265.2 | 632 |
| C77 | 2.0 | 15741 | 1.14 | 295.9 | 260 |
| C78 | 1.6 | 13658 | 0.42 | 1037.5 | 2470 |
| C79 | 4.6 | 50000 | 1.81 | 638.3 | 352 |
| C80 | 8.1 | 25356 | 1.24 | 809.7 | 652 |
| C81 | 1.5 | 13709 | 0.48 | 723.0 | 1509 |
| C82 | 1.3 | 16836 | 0.73 | 75.0 | 102 |
| C83 | 3.6 | 30477 | 1.97 | 260.9 | 132 |
| C84 | 0.6 | 20471 | 0.26 | 24.9 | 95 |
| C85 | | 29000 | | | |
| C86 | 0.5 | 26017 | 0.27 | 14.1 | 53 |
| C87 | | | 0.68 | 197.9 | 289 |
| C88 | 1.1 | 34277 | | | |
| C89 | 1.1 | 37238 | 1.09 | 36.5 | 34 |
| C90 | 2.0 | 47114 | 0.35 | 91.9 | 262 |
| C91 | 1.9 | 31009 | 0.67 | 195.3 | 291 |
| C92 | 1.5 | 17527 | 0.67 | 245.9 | 368 |
| C93 | 16.9 | 50000 | 1.15 | 96.8 | 84 |
| C94 | 25.1 | 50000 | 6.21 | 360.7 | 58 |
| C95 | 12.3 | 50000 | 2.52 | 460.6 | 183 |
| C96 | 11.2 | 5372 | 8.27 | 958.0 | 116 |
| C97 | 34.9 | 9548 | 14.66 | 1733.9 | 118 |
| C98 | 2.0 | 8926 | 1.03 | 462.2 | 450 |
| C99 | 1.7 | 9444 | 0.52 | 349 | 669 |
| C100 | 0.8 | 16230 | | | |
| C101 | 19.7 | 33530 | | | |
| C102 | | | | | |
| C103 | | | | | |
| C104 | 1.4 | 19699 | 0.44 | 140.0 | |
| C105 | 3.0 | 13649 | 1.38 | 998.2 | |
| C106 | 1.7 | 18413 | 0.22 | 106.8 | |
| C107 | | | | | |
| C108 | 3.3 | 22906 | 0.98 | 207.8 | 212 |
| C109 | 1.2 | 15169 | 0.62 | 11.4 | 18 |

The data in Table 1 represents an average over time of each assay for each compound. For certain compounds, multiple assays have been conducted.

Example 112: Half-Life of Exemplary Compounds

Nonclinical In Vivo Studies

All nonclinical studies were conducted in accordance with the Guide for the Care and Use of Laboratory Animals as adopted and promulgated by the U.S. National Institutes of Health, and were approved by the Institution's Animal Care and Use Committee or local equivalent.

Test compound PK was determined in monkeys (Labcorp, Madison, WI) following a single-dose intravenous infusion for 30 minutes. The dosing vehicle was 10% N-methylpyrrolidone; 50% polyethylene glycol 300 and 40% water (pH 8.3) for intravenous administration in monkeys. Serial blood samples were collected at predose, 0.25, 0.48 (before end of infusion), 0.58, 0.75, 1, 1.5, 2, 4, 8, 12, 24, 48, 72, 96, 120, 144, and 168 hours postdose (based on start of infusion) and plasma test compound concentrations were quantified using an LC-MS/MS method.

Plasma Bioanalysis

Nonclinical plasma samples were prepared by addition of 200 µl cold acetonitrile/internal standard solution to 96-well plates containing 50 µl aliquots of each plasma sample. After protein precipitation, each of the supernatants (50 µl) were transferred to clean 96-well plates and diluted with 450 µl of water. The sample injection volume was 2 µl. Samples were analyzed by a multiple reaction monitoring LC-MS/MS method. LC-MS system consisted of a Cohesive LX-2 multiplex with two identical DIONEX UltiMate 3000 RS pumps, Hypersil Gold C18 HPLC column (50×2.1 mm, 1.9 µm particle size; Thermo Fisher Scientific), and the ABSciex QTRAP5500 Mass Spectrometer LC-MS/MS system. Chromatography was performed using 0.1% formic acid and 1% isopropyl alcohol in aqueous solution (MP A), and 0.1% formic acid and 1% isopropyl alcohol in acetonitrile (MP B). The flow rate was maintained at 0.5 mL/min (gradient: 0-0.5 minutes, 5% MP B; 1.83 minutes, 30% MP B; 2.83-3.50 minutes, 95% MP B; 3.5-5 minutes, 5% MP B).

Pharmacokinetic Analysis

Plasma PK parameters for test compounds in monkeys were estimated via noncompartmental analysis using the software program Phoenix WinNonlin, version 6.3 (Pharsight Corporation, Mountain View, CA). The following plasma PK parameters were estimated in nonclinical species (as appropriate): observed peak plasma concentration ($C_{max}$), time to reach $C_{max}$ ($T_{max}$), last quantifiable plasma concentration ($C_{last}$), $t_{1/2}$, time of $C_{last}$ ($T_{last}$), area under the plasma concentration-time curve (AUC) from time 0 to $C_{last}$ (AUC$_{last}$), AUC from time 0 to infinity (AUC$_{inf}$), CL, mean residence time (MRT), and volume of distribution at steady state ($V_{ss}$).

Abbreviations

AUC: area under the plasma concentration-time curve;
AUCinf: area under the plasma concentration-time curve from time 0 to infinity;
CL: clearance;
Cmax: observed peak plasma concentration;
HPLC: high-performance liquid chromatography;
LC-MS/MS: liquid chromatography-tandem mass spectrometry;
PK: pharmacokinetic(s);
Tmax: time to reach peak plasma concentration;
Vss: volume of distribution at steady state;

| Example No. | Structure | Cyno half-life (h) |
|---|---|---|
| C109 | 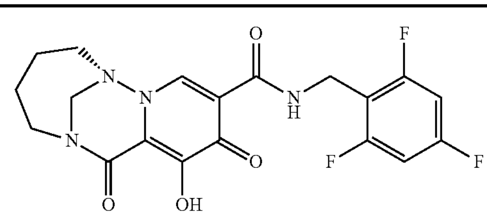 | 4.7 |

-continued
| Example No. | Structure | Cyno half-life (h) |
|---|---|---|
| C24 | 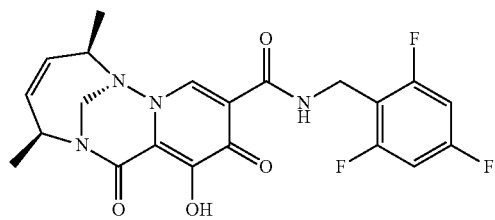 | 57 |
| C25 | 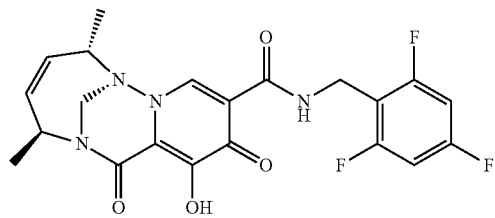 | 55 |
| C27 | 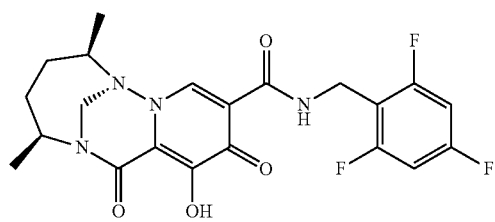 | 48 |
| C29 | 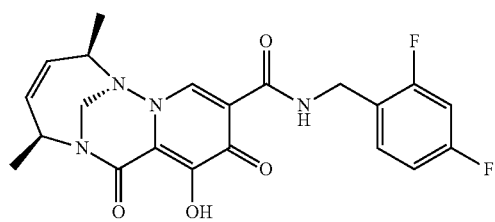 | 32 |
| C30 | 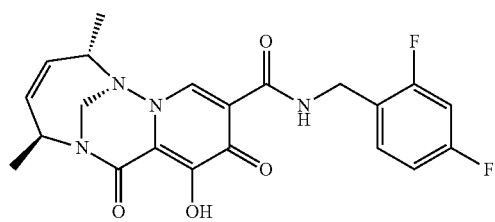 | 6 |
| C31 | 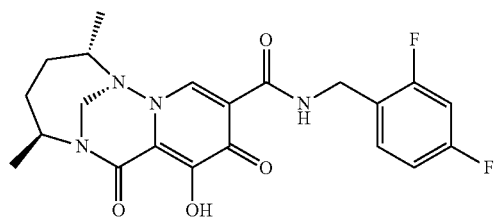 | 9 |

-continued

| Example No. | Structure | Cyno half-life (h) |
|---|---|---|
| C37 | 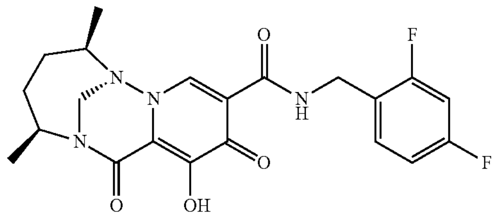 | 22 |
| C44 | 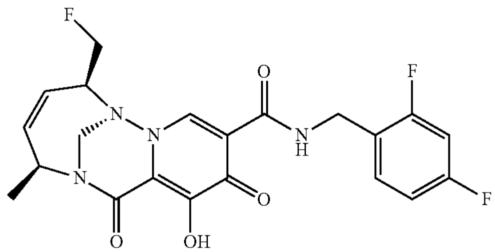 | 29 |
| C63 | 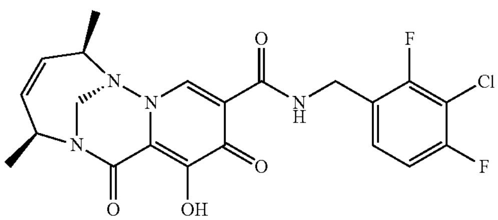 | 110 |
| C72 | 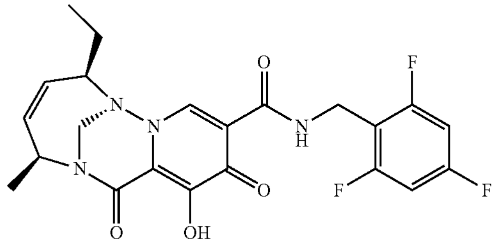 | 51 |
| C76 | 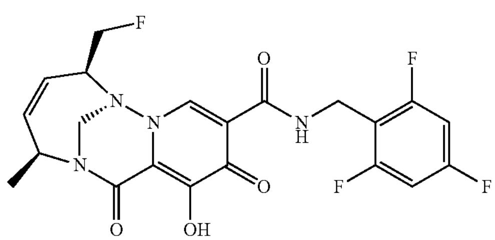 | 60 |

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments have been described herein for purposes of illustration, various modifications may be made without deviating from the spirit and scope of the disclosure. Accordingly, the disclosure is not limited except as by the appended claims.

What is claimed:

1. A compound selected from the group consisting of:

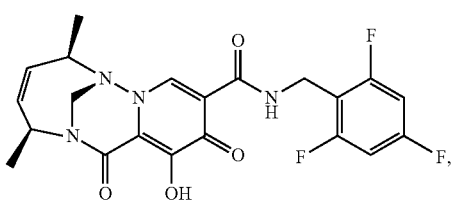

-continued

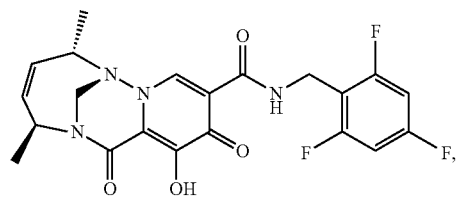

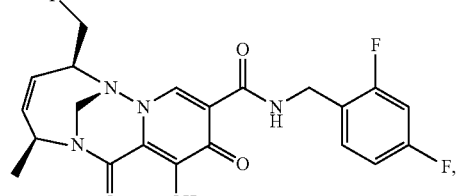

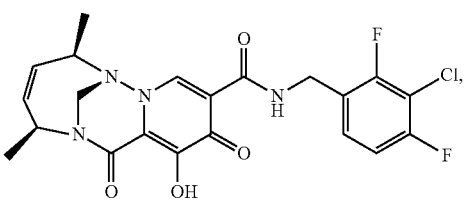

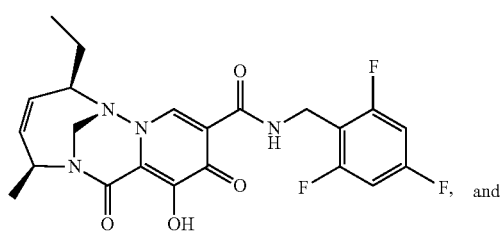

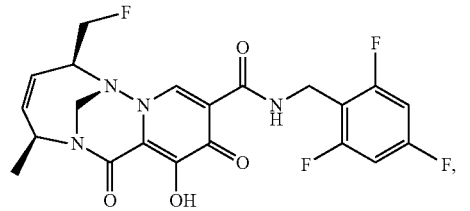

or a pharmaceutically acceptable salt thereof.

2. The compound of claim 1, wherein the compound is:

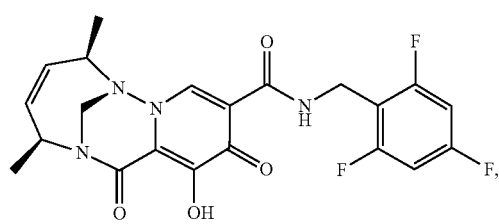

or a pharmaceutically acceptable salt thereof.

3. The compound of claim 1, wherein the compound is:

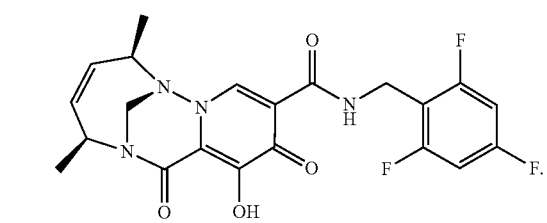

4. The compound of claim 1, wherein the compound is:

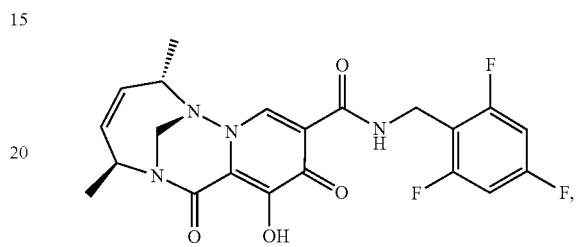

or a pharmaceutically acceptable salt thereof.

5. The compound of claim 1, wherein the compound is:

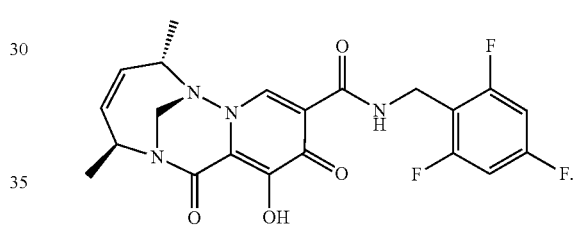

6. The compound of claim 1, wherein the compound is:

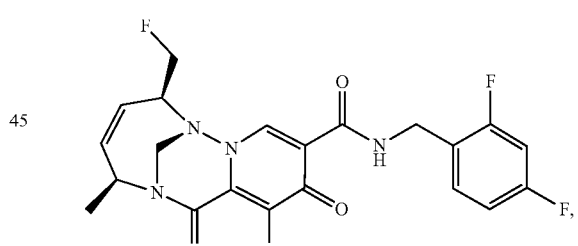

or a pharmaceutically acceptable salt thereof.

7. The compound of claim 1, wherein the compound is:

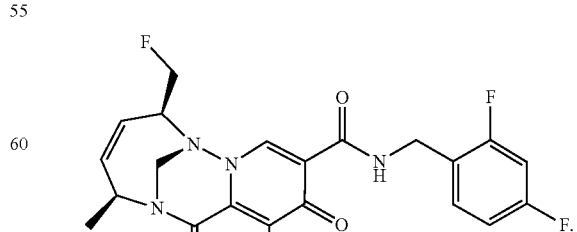

8. The compound of claim 1, wherein the compound is:

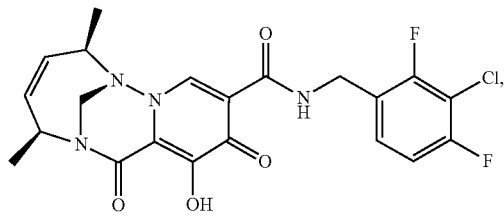

or a pharmaceutically acceptable salt thereof.

9. The compound of claim 1, wherein the compound is:

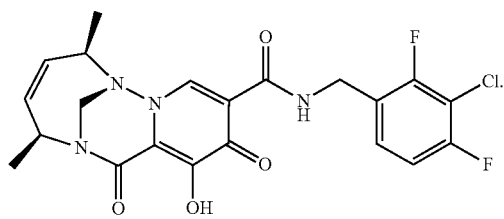

10. The compound of claim 1 wherein the compound is:

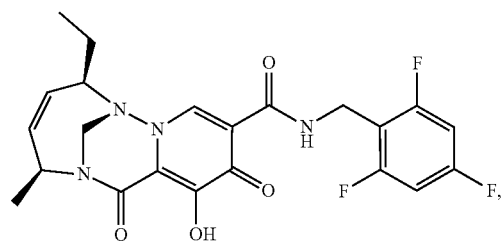

or a pharmaceutically acceptable salt thereof.

11. The compound of claim 1, wherein the compound is:

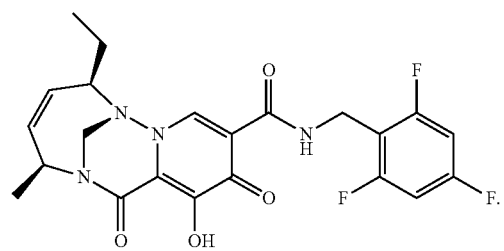

12. The compound of claim 1, wherein the compound is:

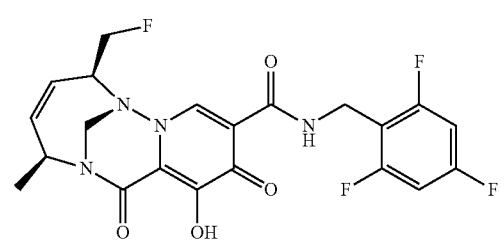

or a pharmaceutically acceptable salt thereof.

13. The compound of claim 1, wherein the compound is:

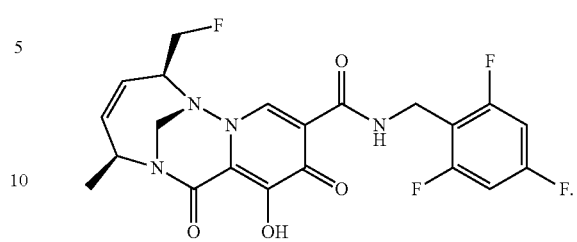

14. A pharmaceutical composition comprising a therapeutically effective amount of a compound of claim 1, or a pharmaceutically acceptable salt thereof, and a pharmaceutically acceptable excipient.

15. The pharmaceutical composition of claim 14, wherein the pharmaceutical composition comprises the compound:

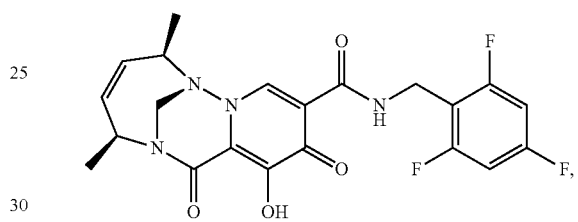

or a pharmaceutically acceptable salt thereof.

16. The pharmaceutical composition of claim 14, wherein the pharmaceutical composition comprises the compound:

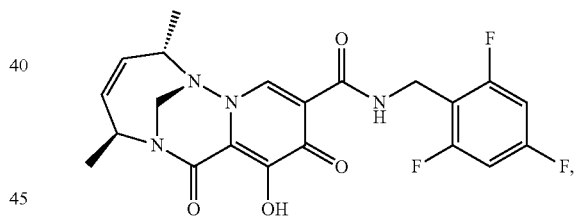

or the pharmaceutically acceptable salt thereof.

17. The pharmaceutical composition of claim 14, wherein the pharmaceutical composition comprises the compound:

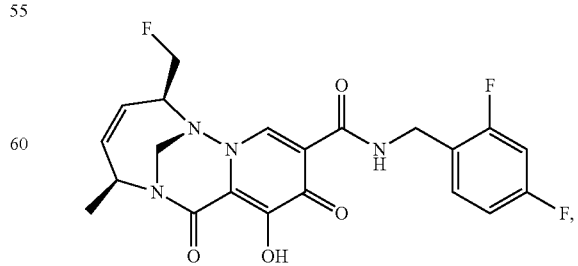

or the pharmaceutically acceptable salt thereof.

18. The pharmaceutical composition of claim 14, wherein the pharmaceutical composition comprises the compound:

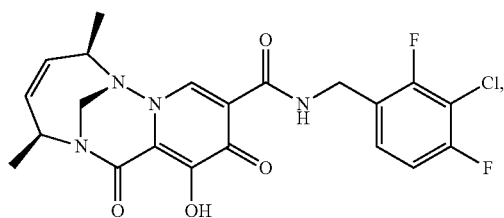

or the pharmaceutically acceptable salt thereof.

19. The pharmaceutical composition of claim 14, wherein the pharmaceutical composition comprises the compound:

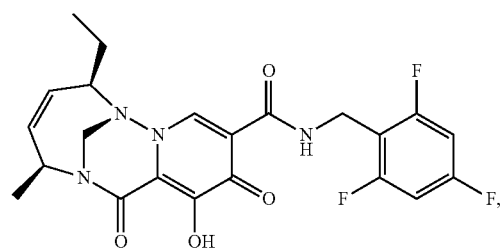

or the pharmaceutically acceptable salt thereof.

20. The pharmaceutical composition of claim 14, wherein the pharmaceutical composition comprises the compound:

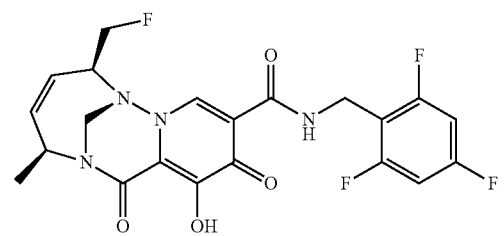

or the pharmaceutically acceptable salt thereof.

21. A method of treating an HIV infection in a human having or at risk of having the infection, comprising administering to the human a therapeutically effective amount of a compound of claim 1, or a pharmaceutically acceptable salt thereof.

22. The method of claim 21, comprising administering to the human a therapeutically effective amount of the compound:

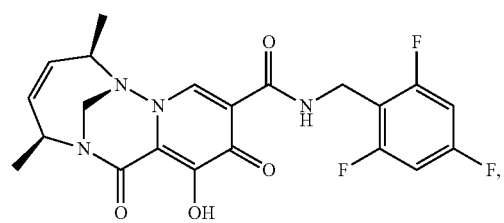

or a pharmaceutically acceptable salt thereof.

23. The method of claim 21, comprising administering to the human a therapeutically effective amount of the compound:

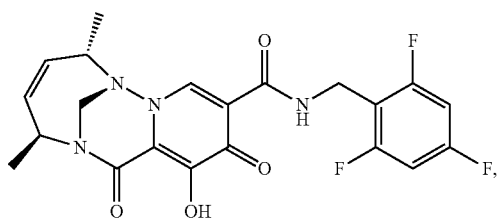

or a pharmaceutically acceptable salt thereof.

24. The method of claim 21, comprising administering to the human a therapeutically effective amount of the compound:

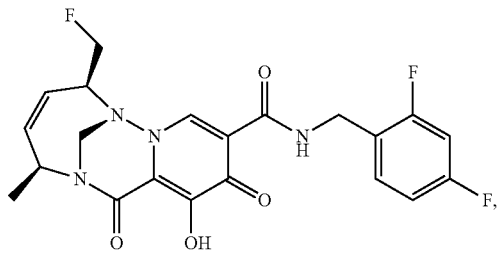

or a pharmaceutically acceptable salt thereof.

25. The method of claim 21, comprising administering to the human a therapeutically effective amount of the compound:

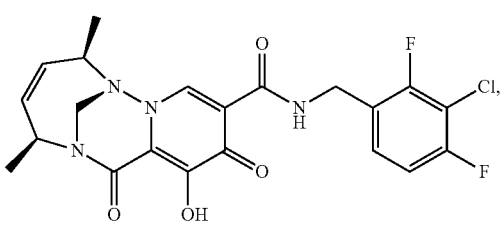

or a pharmaceutically acceptable salt thereof.

26. The method of claim 21, comprising administering to the human a therapeutically effective amount of the compound:

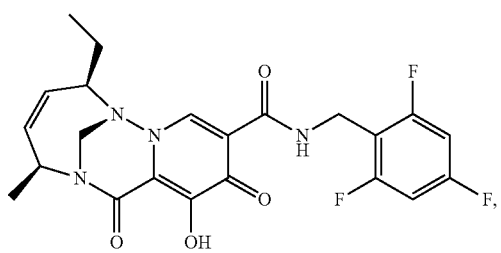

or a pharmaceutically acceptable salt thereof.

27. The method of claim 21, comprising administering to the human a therapeutically effective amount of the compound:
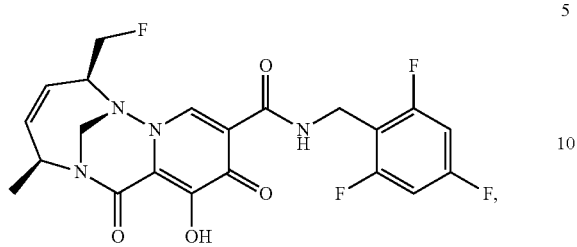
or a pharmaceutically acceptable salt thereof.
* * * * *